US011746355B2

(12) United States Patent
Jin

(10) Patent No.: US 11,746,355 B2
(45) Date of Patent: Sep. 5, 2023

(54) CONTROLLING FUNGAL PATHOGENS USING RNAI-BASED STRATEGY

(71) Applicant: The Regents of the University of California, Oakland, CA (US)

(72) Inventor: Hailing Jin, Oakland, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 16/756,020

(22) PCT Filed: Oct. 4, 2018

(86) PCT No.: PCT/US2018/054412
§ 371 (c)(1),
(2) Date: Apr. 14, 2020

(87) PCT Pub. No.: WO2019/079044
PCT Pub. Date: Apr. 25, 2019

(65) Prior Publication Data

US 2020/0340003 A1 Oct. 29, 2020

Related U.S. Application Data

(60) Provisional application No. 62/573,546, filed on Oct. 17, 2017.

(51) Int. Cl.
*C12N 15/82* (2006.01)

(52) U.S. Cl.
CPC ..... *C12N 15/8218* (2013.01); *C12N 15/8282* (2013.01)

(58) Field of Classification Search
None
See application file for complete search history.

(56) References Cited

U.S. PATENT DOCUMENTS

2007/0009530 A1* 1/2007 Altaba .............. A61K 31/4745 424/155.1
2009/0188006 A1 7/2009 Schmidt
2011/0061129 A1* 3/2011 Tumer .............. C12N 15/8282 800/279
2015/0203865 A1 7/2015 Jin
2016/0032314 A1 2/2016 Jin
2016/0152994 A1* 6/2016 Ren ...................... C12N 15/79 435/348

FOREIGN PATENT DOCUMENTS

EP 2298915 A1 3/2011
WO 2016/176324 A1 11/2016

OTHER PUBLICATIONS

Koch et al 2016 PLOS Pathogens 1-22, provided by Applicant (Year: 2016).*
Jurick and Rollins Fungal Genetics and Biology 44:521-530 (Year: 2007).*
Koch, et al. "An RNAi-based control of Fusarium graminearum infections through spraying of long dsRNAs involves a plant passage and is controlled by the fungal silencing machinery." PLoS pathogens 12, No. 10 (2016): e1005901.
Wang, et al. "Bidirectional cross-kingdom RNAi and fungal uptake of external RNAs confer plant protection." Nature plants 2, No. 10 (2016): 1-10.
Supplementary Partial European Search Report for European Patent Application No. 18867401.4, dated Jul. 21, 2021.
Li et al., "MoEnd3 regulates appressorium formation and virulence through mediating endocytosis in rice blast fungus *Magnaporthe oryzae*," PLoS Pathog, 13(6), Jun. 19, 2017, pp. 1-31.

* cited by examiner

*Primary Examiner* — Brent T Page
(74) *Attorney, Agent, or Firm* — Kilpatrick Townsend & Stockton LLP

(57) ABSTRACT

The present invention relates to pathogen-resistant plants. In one aspect, plants comprising a heterologous expression cassette are provided, wherein the expression cassette comprises a polynucleotide that inhibits expression of a fungal pathogen gene and wherein the plant has increased resistance to a fungal pathogen or multiple pathogens compared to a control plant lacking the expression cassette. In another aspect, contacting a plant or a plant part with double stranded RNAs or small RNAs that inhibit expression of a fungal target gene or genes from multiple pathogens, wherein the plant has increased resistance to a pathogen or multiple pathogens compared to control plants that has not been contacted with the RNAs. Methods of making and cultivating pathogen-resistant plants are also provided.

26 Claims, 37 Drawing Sheets

Specification includes a Sequence Listing.

ZOOSPORES

SPORANGIA

MYCELIA

SEQUENCE LISTING

<160> NUMBER OF SEQ ID NOS: 468

<210> SEQ ID NO 1
<211> LENGTH: 3437
<212> TYPE: DNA
<213> ORGANISM: Botrytis cinerea

<400> SEQUENCE: 1
gcaggggtcg gatcaacatg tctataaaca aacatatgta ccggcgttga tctctcctgc 60
agactgcatt tgcacttgct tccctcttcc tcctcccgtt tcctggtctt cttctacaag 120
ctgcaggcga gagagataac ttctacgcac cttccatatc cctcacctct tctctcccca 180
caagttcgtt cataatcctt tcgtcctgtt gttttgtcta gcattacctt gcaattctta 240
acaacggccg atcgtggaca tcaatcaata aaaaggacga caaatcatct tataattatt 300
atcccaaact ttcattgcac aaatttgaat tggatactca tttggcttta ttcggagcga 360
taaacgtaga aattaatcgt ataggggctt ttatcagaca atcaagaacg gtgattggct 420
cacagcggtg aattgtgagg ggtggtaata cagaaaacaa atagtatagg gagtattttt 480
gggtggattg ttaccaatgt ctaccacaag aatctcaaca ccgaaaaggt cccccaaaaa 540
atcgactttt gtcaaaactg gaatcttgac caccaaatca acgcccaatc tcaacgcctc 600

```
ctataatttg gcattactac aagcttcagg agctacaccc gttcctgcat atccttccaa    660
taacggtcaa agttttgccc taaataatcc taggtcgcaa ccgtctcgac aagtctcact    720
cgcttccctt acctcgaatt cacttgcgac aatcccggat gcaagcaaga gataccctct    780
ttctacagtc tttgatgagg atatgccaac agtaggcaac atgccgccat acacacctgc    840
tcgagttggc ggtggaccgg aagaactaga ggttggtgat atagtcgatg tgccaggtaa    900
catgtatggt atcgtcaaat ttgttggcag tgtgcaaggc aaaaagggtg tatttgctgg    960
ggtagaatta agtgaaacgt ttgcttcgaa agggaaaaac aatggcgatg tcgaaggaat   1020
tcaatacttt gacacaacca tcgatggtgc tgggattttt cttccagtca acagggcgaa   1080
gagacgtagc accccttcgt cgcatgatga gtcatttccc ctttcaccgg cgtctccatc   1140
gatgggcaat agggctggga gattaggatc tgaattaaat ggtcagccaa cacctttgtt   1200
accaaaattc ggtcaatctg ttggtccagg cagagcggca aacccatatg tccaaaaaac   1260
acgtccatcc atggctacac ctaccacctc aagaccggaa tcaccagttc gaagagcagc   1320
caatgccaac ccatcattaa atacacctgc acaaagagtc ccatctcgat atgcaagccc   1380
tgcgcaggca aactttggac agagcgttag aggaacacaa gattctagag atccaagtaa   1440
gaaagttggc tacaccccc gaaatggcat gaaaacacca atacctccac gaagtgtttc   1500
tgcacttgga acggggaata gacctgcacc aatgaactcg atgaatttca gtgatgaaga   1560
gacacctcct gcagagattg cacgtacggc aacaaacgga agcgtaggct cagtctcttc   1620
tttcaacgcg aaattacgtc cagcatcaag atccgcatcg cgtacaactt ccagggctac   1680
cgacgacgaa tttgagcgat tgagaagttt gttagaagat cgcgataggg aaataaaaga   1740
acaggcttct attatagaag acatggagaa aactctcagt gaagcacaat cgttgatgga   1800
gaacaataac gagaacgcaa gtggtagaca tagtcaggga agtgtggatg acaaggacgc   1860
aacacagttg agagcaataa tacgtgaaaa gaacgacaaa atcgccatgc tgactgccga   1920
gtttgatcag catcgagctg atttcagaag cacgatagac acgctcgaaa tggccggtgc   1980
ggaaaccgag cgagtgtacg acgagcgcat gcgtgttctc gtaatggagc tcgatacaat   2040
gcacgagaat agtcatgatg taaagcacgt tgctgtacaa ctgaaacagc tagaagagct   2100
cgttcaggag ctcgaggaag gtcttgaaga tgcacgacgt ggtgaagccg aagctcgggg   2160
agaagttgag ttcttgcgtg gagaggttga aagaactcga tctgaactcc gccgcgagcg   2220
agagaagact gccgaagctc ttagcaacgc aaattctcct acgagcgcaa gtgcggaaac   2280
acattccaaa gagattgctc agagagatga cgagattcgt ggattgaaag ccatcatcca   2340
ctcgctcagc agagatgcca tacctgatgg gaatttctcg gatcatgagg caacaccaaa   2400
tattctacga cctggactaa accgaagtcg aacagaaagt gcttcggttt ctgaggagga   2460
gcgccgtact cgggaaaagc tagagcgaga agtgagtgag cttcgtgctc tcgtcgaaag   2520
caaagacaat aaagaagaac aaatggagcg cgagttggag ggattgcgaa gaggaagtgt   2580
tagcaatcct actacgcatc gtactagtgc catgagcagc ggaactgtga ctcaggatag   2640
gaattctctc caagacaata agagcacagt tgtaagctgg cgagaacgtg gtgcctcaga   2700
tgctcgccgc tacaatctgg attcaatgcc agagaatgac agctactcct ctgcagctga   2760
ggatttctgt gaattatgcg aaacctcagg tcatgatgtt ctacattgcc cgatgtttgg   2820
ccccaatggt aacagcagca attctaagga tgagtcacct aaacagcaac gaacaggaaa   2880
agacgttgtc atggagggac ttaaattatc acccaaacct tctcaagaag aatacaaacc   2940
```

ggcgccgtta gcgccagcta agaagtcgcc tgatgcgtcg cctatcaaga ctgttcccaa 3000
ccttatggaa ccaggacctg ccccaggaaa ggaaagtgga gtaatcaaca tggataaatg 3060
gtgcggtgta tgtgaaagag atggacatga cagtattgat tgtccttttg aagatgcttt 3120
ttaggagact actgctttcg atgtttcagg ataagcagtc acaacgacga ctttttttcat 3180 agattttctt tgttaatcat aggcaaggcc gcattgcatt gcaggagcgt aatccgtctg 3240
cgatataccc tttcggttct ctgtttgaag tatgcttttc aagcgataag tttagagggg 3300
aagatgatgt ttttacgagg attgaatgag atggatgaat gcaggctaaa tcggggaagg 3360
gggagggaag acaaacatga gttgaacgga cgtaatgatc atgtagtata ctttgtcaaa 3420
ttaatgatcc aaatgca 3437

<210> SEQ ID NO 2
<211> LENGTH: 2406
<212> TYPE: DNA
<213> ORGANISM: Sclerotinia sclerotiorum

<400> SEQUENCE: 2
atgtcgacta caagaatctc aactccaaaa aggtctccaa aaaaatcgac attcactaaa 60
acaggaattc aagtcacaaa atcaactccc aatctcggtg cctcctacaa tttggcttta 120
ttacaagctt caggagcttc accggttctt gcacattttt ccaataacgg tcagggtttt 180
ggtctaaaca atcctaggtc gaagccatct cgacaagtct cactcgcatc ccttacctca 240
aattcactgg cggcaatacc ggatgctagt aaaagatacc ctctttcaac cgtttttgat 300
gaggatatgc caccagcagg caacatgtat acaccttctc gagttggtgg tgggcccgat 360
gagttggagg tgggtgacat agttgatgtt cctggtaaca tgtatggtac tgtcagattt 420
gtcggcagtg tgcaaggcaa gaagggggtc tttgccggag tggaattgga tgagatgttt 480
gcttccaaag ggaagaacaa tggtgatgtt gaaggtcaat cagttggccc aggtagaatt 540
caaaaaaccc gaccatcgat agccacacca accacatcac gaccagagtc tccagtacga 600
agagcagccg ctgctaggac atcaataaat gcacccgggc agagagtccc atctcgatat 660
ggaagtcctg cagcggcgaa ctttgggcag aacattagag gagtgcaaga tgctagagac 720
ccaagcaaga aagtcggtta cgccccaaca aatggcatga agacaccagt ccctccacga 780
agtgtttcgg cacttggcac agggagtaga cctgcagcaa tgaacctcag tgatgaagat 840
acaccttctg ctggaattac acggacggca acaaacggga gtgtgagctc aatctcttcc 900
ttcaacgcaa agttacgacc tgcatcaaga tccgcctcgc gtgcgtcccg agctactgac 960
gacgaggtcg agcgattgag aggtctactg gaggagcgcg atcgggaaat aaaagcacaa 1020
gcttcaatca tagaagacat ggaaaagact cttagtgaag ctcagtcact gatggaggac 1080
aacaatgaga acgcgggcgg tcatagagat agccggggaa gcatggagga caaagacgca 1140
gcacaattga gagcaataat tcgtgaaaag aatgaaaaaa tcgccatgct gactgctgag 1200
tttgatcagc atcgagctga tttcagaagt acaatagaca cacttgagat ggctggtgct 1260
gaaaccgaaa gagtctacga tgagcgcatg agtaatcttg taatggagct caggacgatg 1320
catgagaaca gtcatgatgt gaagcatgtt gctgtacaac tgaaacagct agaagagctt 1380
gttcaggagc ttgaggaagg tcttgaagat gcgcggcgtg gtgaagccga ggctcgcggt 1440
gaggtcgagt tcttgcgtgg agaggttgaa agaactcgat ctgagcttcg tcgtgagcgg 1500
gagaaaactg ctgaagctct cagtaacgca aatcctgcta cgggtgtggg tgcagcaaca 1560
ctttctaaag agattgcaca aagagatgac gagatccgcg gtttgaaagc tatcattcac 1620
tcgcttagcc gagatgccat acctgatggg aatttctcgg atcatgaaaa gacaccaagt 1680
gttacacgac cagggctaca tcgaagccgt acggaaagcg cttcagcttc agaggaggag 1740
cgtcttagcc gggagaagtt ggaacgagaa gtgagcgaac ttcgtgccgt cgtagaaagt 1800
aaagacagca aggaagaaga aatggagcgt gagctagagg ggctacgaag gggaagtgtc 1860
agcaattcta ctacgcagcg tactagtgcc attagcagtg gaactgcaac ccaggataga 1920
aactctgtcc gagattccaa aggcacagtt ggaagctggc gggaccgcga aggaacatcg 1980
gatgttcacc accacaactt ggagtcaatg ccagagattg acggttactc ttcagcagcg 2040
gaggatttct gtgaattgtg cgaggcatca ggtcatgatg ttctacattg ccccatgttc 2100
ggtcctaatg gtaatagtgg caactctaga gaggagtctc ctaaagagca acgaacagga 2160
aaagacgttg tcatggaagg actcaaacta tcacccaaac tagcgcaaga agaatacgaa 2220
ccagcacctt tagcaccagc caagaagtcg tctgatgact cgcctattaa aaccatccct 2280
aacctcatgg acccaggtgc tgctccagga aaagcaagtg gagtcatcaa tatggacaaa 2340
tggtgcggtg tatgtgaacg agatggacat gacagcattg actgtccgtt tgaagatgca 2400
ttttag 2406

<210> SEQ ID NO 3
<211> LENGTH: 2601
<212> TYPE: DNA
<213> ORGANISM: Botrytis cinerea

<400> SEQUENCE: 3
gacacatgcg atatgcaaag tctagaacct cgaatactga ttcgaaaaag actggcaatt 60
ccataaatct acagtatatt ttaatccgca actcatgaat gactacattt aatacgaatt 120
acaaacattc cctaacgcca aaatggcagc tacgattccc ctctccacta caacatgctt 180
gacctcctca gaagctttca aatatcctct tccacagatt cgtcaattcc accgcgatct 240
cactacagag cttgacgaga aaaatgcacg tctgcggaca ctggtcggag ggagttatag 300
acaattactt ggaaccgccg agcaaatctt acagatgcga caggatatta gtggagtaga 360
ggaaaagtta ggcaaagtag gagaaggatg tgggagaaat gtgttggttg gaatggttgg 420
cggattggga aaattacagg gagaaatgaa gaatggaaag aagggcgagg aaatgcgggt 480
tgtggctaag atgaaggtat tgggtatgtg tgggattgtg gttgggaagc tcttgaggag 540
accagggcga atggatgggg atggtgggag agggaaggaa ttagtagttg ctgcgaaagt 600
cttagttttg agccgattgt tggcgaagag cttggagaat actggagata aggaattcgt 660
tgaagaagcg aagaagaaga ggtcggcttt gacgaagcga ttgttacgcg cagttgaaaa 720
gacattggtt tccgtcaagg atgctgaaga tagagacgat ttggtacaga cactttgtgc 780
atacagtcta gctactagtt ctggcaccaa agacgtcttg cgacatttct taaatgttcg 840
tggtgaagca atggctttag cgtttgacga tgaagaggag tcgaacaagc agacctcagg 900
tgtcctacgc gctttggaaa tatatacgag aactttacta gatgtacagg ctctagtgcc 960
aaggaggctg agcgaagcgt tggctgtgct gaagacgaaa cctttactga aagatgacag 1020
cattcgggaa atggagggat tgaggttgga tgtatgtgag cggtggtttg gcgatgagat 1080
tatttacttc acaccttatg tccggcatga tgatttggaa gggtcattgg cggttgaaac 1140
actacgaggt tgggcgaaga aagcgtcaga agtgttactg gaaggtttta cgaagactct 1200
tcaaggggga ttagacttta aagtagttgt tgaactacga acaaagattc tggaggtgtg 1260

```
ggttagagat ggaggcaaag caaggggatt cgatccctct atacttctaa atggcttacg   1320

agacgttata aacaaacgac tcgtagagtt attagaaact agagttggca aacttcatct   1380

agtggggaca gagatagagt ccacattagc aacatggcaa gaaggaatca ccgacataca   1440

tgcaagtctt tgggacgaag atatgatggc aaccgagctc agcaatggtg gtaacatttt   1500

caagcaagac atacttgctc gcacgttcgg acggaacgat gctgtttcaa gagttgttaa   1560

cagttttcac acttggagac atctcatcga ggaaattggt acttatattg atgaactgaa   1620

gaaacaaaga tgggatgatg atttggaaga tatggaagat gatgaaagtc tcgaatcacg   1680

acaaaacctt cttagcaagg aagatccaca aatgctacaa gatcatctcg attcaagctt   1740

agaaaattcg ttccaggagt tacacgcaaa gatcacttca ctggtggacc agcaaaaaga   1800

tagtaaacat atcgggaaaa tatcgatata tattctccga attctacgag atatcagagc   1860

agaattacct agtaaccctg cactacaaaa gtttggactc tcacttgtct catcactgca   1920

cgaaaatctc gcaggtatgg tctcagaaaa cgccatctta gcccttgcaa aatctctcaa   1980

gaagaagaag gttgcgggca gagcattatg ggagggtaca ccggaacttc ctgttcagcc   2040

ctccccagca acattcaaat ttttgagagg tttatcgact gctatggctg atgctggagc   2100

cgatctatgg agccctgttg ccgtcaaagt gttgaaagcg cgtctggaca cccaagttga   2160

agaccaatgg agtaaggctc taaaagaaaa agaggaagag cctagcaatg gaatctctgg   2220

ttctcccacc aatgctcccg aagcagatgc cgaggaaaaa gaaggggacg cttctgctcc   2280

taatcctgct gctgctgtag aagtagatga agaaaaacaa aaggatttac taaagcaatc   2340

actgttcgat atatctgtct tgcagcaagc tttagaatca cagtcagaca ataaggagaa   2400

caaacttaag aacttagcgg atgaggtggg aggaaaacta gatctcgagg cgagggaaag   2460

gaaacgtatg gttaatggcg cggcggagta ttggaagagg tgcagtcttt tgtttggact   2520

tttagcgtag attccagatg gatgaattag tgagaggctt ataatgaatt atattacgaa   2580

tactttactt ttgagtattc a                                              2601
```

```
<210> SEQ ID NO 4
<211> LENGTH: 2424
<212> TYPE: DNA
<213> ORGANISM: Sclerotinia sclerotiorum

<400> SEQUENCE: 4

atggcatcta caaccctctc cacaacaaca tgcttcactt cctcggaagc atttaaacat     60

cctctccctc aaatccggca attccaccgc gatctcacca ccgaacttga tgagaaaaac    120

gcacgtctac gtacacttgt cggaggtagt tatagacaat tactgggaac cgctgaacaa    180

atcctacaaa tgcgcaagga tatccgtgaa gtggaggaaa agttggggga agtaggggaa    240

ggatgtggaa gaaatgtatt agttgggatg gcttctggat taggtaaatt acagggagaa    300

atgaagaatg ggaagaaagg ggaggaaata aggggattgg ctagaatgaa gggtttgggt    360

atgtgtggga ttgtggttgg gaaacttttg aggaggcagg gaagagtgga tggggagggg    420

agagggaaaa gtttagtgat tgctgcgaaa gttttggttt tgagtcggtt gttggcgaag    480

agtttggagg gttgtgtgaa tagtgcggat agagaatttg ttgaggaggc aaagaagaag    540

agggtggttt tgacgaaacg attgttacgg gcggttgaga agacattagt ctcgaccaag    600

gatggtgaag atagagaaga cctggtacag gctctttgcg cgtatagtct tgctactagc    660

tctggtgcga aagacgtttt acgacatttt ctaaatgtcc gaggggaagc aatggcatta    720

gcattcgaag acgaagagga atcgaaccag gagacatcag gtgttttgcg ggcattggaa    780
```

```
atatatacga ggactttact tgatgtacaa gcattggtac cgagtagact tagccaagca    840

ttggctgcgc tgaagacgaa acctttattg aaagatgaaa gtattcgaga tttggaggga    900

ttgagattag atgtatgtga gcggtggttt ggtgatgaaa ttctttactt tacaccttat    960

gttcgacacg atgatttgga aggatcatta gccgttgaga cattaagagg ttgggcgaag   1020

aaagcatcag aggtactact ggaaggattc acaaagactc ttcaaggtgg cttggacttc   1080

aaggtagtag tcgaattacg gacaaagata ttggaggtat ggatacggga tggaggaaag   1140

gcaagagggt ttgatccgtc tatacttcga gatggactgc gaggtgttgt taacgaacga   1200

cttgtagagt tattggaaac tcgagttggc aaacttcatc tagtgggaac agaaatagaa   1260

tccacattgg ctacatggga gaaatggatt actgatcatc atgctagtct atgggatgaa   1320

gatatgatgg caacggaact cagcaatgga ggtaatatgt tcaaacaaga cattcttgct   1380

cgtacctttg gacgtaatga tgctgtttca agagtagtca acagttttca gacttggaga   1440

catctcatca aggaaatagg tactgttatt gatgaattga agaaacaaag atgggatgat   1500

gatttagaag atatcgaaga tgaagaaagt cttgagtcgc gacaaaatct tcttagtaag   1560

aaagatccac aaatgttgca agatcatctt gattcaagct tagaaaaagc ttttcaggag   1620

ttacatacga aaatcacgac acttgtggag caatacaaag atagcgagca tatcggaaag   1680

atatcaatgt atattttacg aattttacga gatatccgag cagagctacc gacaaatcca   1740

tcactacaac aattcggtct ttcactgatc ccattactac acgagagcct tgccagcaca   1800

gtttctgaaa accctatctc ttctctagca aaatcgctca agaaaaaaaa agttgcagga   1860

agagcattat gggaaggaac accggaactt ccaattcaac cttcacctgc tacatttaaa   1920

tttcttcgtg ctttatcaaa tgctatggct gatgctggag cagatctttg gagtcctatt   1980

gctattaaga ctttgaaagt acatctcgat tcccaaatta atgagaaatg gagcatagcc   2040

ttgtcagaga agatggctag taataaaaca actacttctt ccagcaatcc acccgatact   2100

gaaaaatccg cggaaacaga agaaccaaaa aatgaagttc aatccccgtt ggataaagaa   2160

gtagaagaag aaaaagaaaa aaatctacta aaacaatatt tattcgatat cttcgtctta   2220

caacaagctt tagcgctaca atctatacaa tttggggata aggaaaagga aaaggaaaaa   2280

gggattatgg ggatgaaaat caagaatttg agtgatgaga ttgaattgga attgaagctt   2340

gagatgcagg agaggaagag ggtggggaat ggtgcgaggg agtattggaa gaggacgggg   2400

cttttgtttg ggtttttggt gtag                                          2424
```

<210> SEQ ID NO 5
<211> LENGTH: 3180
<212> TYPE: DNA
<213> ORGANISM: Botrytis cinerea

<400> SEQUENCE: 5

```
gatccaccca catccttcct catatgactt cgatgataat tacatagaca ctgccagtat     60

gcctggcctc gttcgcaaac tccttatctt tgccgccatc gatgggttga ttttgcaacc    120

agcagcgcca aaaggccaac gccccgcccc cgcaacgaag atcgcataca aagataagca    180

tatcgggcca gtattgagtg atttgcagga tctggagggg tcgtctgcga aaagtttcga    240

ggcatttggt attgtcggtc tcttgacggt ttccaaaagc tccttcctga tatcgattac    300

gaaaagagag caagtcgcac aaatacaagg gaaacctata tatgttatta ctgaagtggc    360

tttgacccca ttaagttcca agaacgaagc agagatctcg attgatagta cgaaagcggg    420
```

-continued

```
gttattgaag agtaatatcg aggggcagca tggcttggac gagagtgata gcgaggatga    480
tgtcgttagc gatgaagtgg aggacgatac agcagtagaa gcacacaaaa gaacgagtag    540
cgtagctgaa gatgtgatct cgaagaaggg gggatatgga agatttgctc aaaaatggtt    600
ctcgaagaaa ggatgggccg tggaccagaa gaagaacctg ggatgagcg ctgagccgta    660
ttccacagtg gagcaagctt ccaaggccac cgatgtacca gctacgattt caggagtcac    720
tgaaggaaaa tctgatatct caattcccga taagggcaag gaaattgagg acattgaaac    780
tcctgaaaat attagcgaca ttgcagagag catgctgcca aaattactac gaacatcgca    840
gatattgttt ggggcctctc ggagttacta cttttcttac gaccatgata tcacaagaag    900
tttggcaaat aagaggaata caaattctga attgccattg cacaaggaag ttgatccact    960
cttcttctgg aatcggcatc ttactttacc atttattgat gctggccagt cttctcttgc   1020
cttgcctctt atgcagggct ttgtaggaca gcgtgcattt tcaatggata gtaatccacc   1080
aaaccctgct ataggttcag acactggaaa gacttccgtg cagatgaagg atattacaac   1140
aagtagttcg gatgagcaaa tttacacagc acgtgctggt acagacaagt cgtatctatt   1200
gacgttaata tctagaaggt cagtcaaacg tgccgggctt agatatttac gccggggtgt   1260
ggatgaggac ggcaatacag ccaatggcgt ggaaacagag caaatcttat cggattctgc   1320
ttggggccct tcgagtaaga catattcgtt cgttcagata cgtggcagca ttcccatatt   1380
cttctcccag tcaccttact cttttaaacc tgtacctcaa gttcaccact ctaccgaaac   1440
aaattatgaa gctttcaaga agcattttga taatataagt gatcgctacg gggccattca   1500
agtggcttcc ttggtggaga agcatggaaa cgaggcaata gtcggtggag agtacgagaa   1560
attgatgact ctccttaatg tctcccgagc tagcgagctt aggaaatcca ttgggtttga   1620
atggtttgat ttccatgcta tttgcaaagg tatgaaattt gagaatgtca gcctgctcat   1680
ggaaatactg gacaagaagc ttgactcgtt ttcgcacact gttgaaaccg atgggaaact   1740
tgtatcgaaa cagaatggcg ttttaaggac taactgtatg gattgtctgg atcgaacaaa   1800
cgttgttcaa agtgcagtgg caaagcgagc acttgaaatg cagttaaaga atgagggact   1860
agatgtcact ctacaaattg atcaaactca acaatggttc aatactttgt gggccgacaa   1920
tggtgacgcc atttctaagc aatacgcttc tacagcagca ttgaagggag actttactcg   1980
tactaggaag cgggattata agggggccat cacagatatg ggctttcta tctccagatt    2040
ttatagcggc attgtaaatg actacttcag tcaagctgcc attgatttcc tgcttggaaa   2100
tgtgagctat cttgtttttg aagacttcga ggcaaacatg atgagcggtg atcctggcgt   2160
ttcgatgcaa aaaatgaggc aacaagccat tgatgtttct cagaaactcg ttgttgctga   2220
cgaccgtgaa gaatttattg gaggatggac atttctcact ccgcaggtac ccaatacgat   2280
caaatctagt ccttttgagg aatccgtcct cctattgaca gatgctgcat tgtatatgtg   2340
caattttgat tggaatatcg agaaagtatc atctttcgtg agagtggact tgaaccaggt   2400
gaacggcatc aagtttggaa catacatcac gagtactttg tcacaagccc aggcagatga   2460
gaagaggaat gtgggctttg taataactta taaggctggt tcaaacgaca ttattcgcgt   2520
gaacacgaga tctatggcta cggaatttcc ttcttcgaaa ctctctctcg aagacaaaac   2580
atccacgccc gcttctacat ctaccaccaa ctctgtcgtc gccccaattg ccgccgggtt   2640
tgcaaaccta atctcaggtt tacaaaatca aagtatagcg gaacctaaag atctcgtgaa   2700
ggttctcgca ttcaaggctc taccctccag atctgcggta tcagatgaag gagttagtga   2760
ggccgagcaa gtgaagagtg tctgtggaga gattagaaga atggttgaga ttggaagtat   2820
```

```
aagagaggct ggagaggaga gaaaggatat tgtagaggag ggtactatca ttagtttggc   2880

cgaggccaag aaaagcacgg gactattcga tgtgctggga catcaggtga agaaactggt   2940

ttgggcttaa tgaaagtgta tcgatactcg tgctagtaat gcttagagca aaagaagcac   3000

ttcttgaagg atttacgaat ggaattgtgg aagttggcag ggaggttagc gatcgtcaag   3060

aacgggtatg tggaattcaa ttccatattg aagctgcgaa actcattaac ttcaatagaa   3120

gtggatgtgt agatagaccc gagtatatgg tattggccag ataagtaatt ttaatgggga   3180
```

<210> SEQ ID NO 6
<211> LENGTH: 1292
<212> TYPE: DNA
<213> ORGANISM: Sclerotinia sclerotiorum

<400> SEQUENCE: 6

```
atgcctggcc tcgttcgaaa gcttcttatc tttgccgcca ttgatggctt gattctgcaa     60

ccaacggcgc aaaaaggcca gcgccccgcc cccgcaacga agatcacgta taaagataag    120

catgtcggac cagcatctta tgattctcac gattacgagg ggccgtctgc caaaggcttt    180

gaagcattcg ggattgtcgg tctcttgacg gtttctaaaa gctccttctt aatatcgatt    240

acgaaaaggg aacaagtcgc acaaatacaa ggaaaaccta tatatgttat tactgaagta    300

gctttgaccc ctctagcttc caggatagaa gcagagaact cgatcaacaa aacaagagcg    360

ggattgttaa agagtagtat tgaagatcat ggattggacg acagtgatag tgaggatgac    420

gaagtcaatg ttagtgacga agtggaggac gatacagcaa tagaaacaca tacaagaacg    480

agcagtgtgg ccgaagatgt aatttcgaag aagggagggt atgggagatt cgctcaaaaa    540

tggttctcga agaaaggatg ggctgtggac cagaagagga acctgggaat gagcactgaa    600

ccgtatgctg cacgagagca agatgccagg tctgccgacg tagcagctac cacttcaaag    660

gatgctgaag tggaacctga ggttttgatt tccgatgagg tcagggacat tgaaaatgtt    720

ggaaagtctg acaaggttaa gaacgttcag gatattgctg agagcatgct gccaaagtta    780

ctgcgtacga cacaaatatt gtttgggacc tcccggagtt actatttttc ttacgatcat    840

gatatcacaa gaagtttggc caataaaagg aacacaaact ctgaattgcc attgcataag    900

gagtcgatcc actcttcttc tggaaccgac accttctgtt accatttatt gatgctgggc    960

aagcttcact tgccttgcct attatgcagg gcttcgtagg acaacgagca tttgtaatgg   1020

atagcaatcc gccaaagcct gttgtaggtt cggacactga gaagacctcc atggaactga   1080

atgagatcac aacagatagt tcggatgaac aaatctccac agcacgtgtt agtgcagata   1140

agccatatct attgacatta gtgtctagaa gatcggttaa gcgtgccggg cttagatatc   1200

ttcgtcgagg tgtggatgag gacggcaata ccgccaatgg tgtggagacg gagcaaattt   1260

taatcagatt ctacttgggc tccttcaagt aa                                 1292
```

<210> SEQ ID NO 7
<211> LENGTH: 2429
<212> TYPE: DNA
<213> ORGANISM: Botrytis cinerea

<400> SEQUENCE: 7

```
gatacaaaag ctttcgaaag ccgcttgagt aagtaagaag gcaataagag aggtcctcgt     60

ccgtgtcgag atgtgatgct tgagtcattt tcctggtata gcttctgcaa tcgagttcac    120

actctactac ttgattcaga ttacaccagg agtaacacct caagtattcc atattaaata    180
```

```
caaacctttc ccatcttaat ctattgttgg cgcatgggga gaggaattaa ttgctttgct    240
ttttggccat caggatgtgg tcattagatc gattatccgg acacacaaca ccttctgcct    300
ctccacctcc cccgttaaat aggatcccaa atctccctcg tcgtccgagt catcttgtgc    360
catccccagt tggtggtaga cctcctttca acccaagatc gtcttccctg tcgttaatct    420
ccaatgactc taattcatcg ttgctatcat cacggagacc caatggttcg aatctcaaac    480
aagcagtcac atctccgaat gtgccagatc ctttggaggt tttgggaaca ctactgaata    540
atggggaaga gacaaaattg ccatcagcga aaagcccggg ggcgacaaat gggacagttg    600
ctcccattga agaggaagac gatgaaggcg aatgggattt cggaggttta agtctgcaag    660
acattgtagc aggagaacct ctcgatgttg aggatgagca tgtgtataaa tctcaaacgc    720
tggaagaata tgagcgcgag aaagagaagt ttgaagacct ccatcgatca attcgcgcct    780
gcgatgacgt tcttaattca gtcgagataa acctcacaag ctttcaaaac gaccttgcta    840
tggtatctgc ggagattgaa actctgcaag cacgatcgac ggctttgagt gtaaggttgg    900
aaaatcgcaa agtagtagag aacggacttg ggcctatagt ggaggagatc agtgtctctc    960
cagctgtcgt taaaaaaatt gtggatggag ctatagatga agcttgggtt cgagcattgg   1020
cggaagttga gaaacgatca aaagcaatgg atgctaaatc gaaggagcaa cgtactataa   1080
agggcgtgaa cgatcttaag cctttactgg agaatctagt ttccaaggca ttggaaagaa   1140
tcagagattt cctcgttgct caagtgaaag cattgcgatc gcccaatata aatgcacaga   1200
tcattcagca acagcacttt cttcgctata aggatttata tgcattcttg catagacatc   1260
acccaaagtt ggctgaggag cttggtcaag catatatgaa tacaatgcga tggtacttcc   1320
ttaatcagtt cacgaggtat ttgaaggcgt tggaaaagat caagcttcat gtgttggaca   1380
gatacgatgt gctcggatca gatgacgggt ctcgtaaggc cactcttctt tcaggatcca   1440
aacagacagg tccaccacac gacgcattca atctaggtcg acgaatcgac cttctcaaga   1500
cgccaaacca aactgcactt ccctctttct tagccgaaga agacaaacaa acccactata   1560
tggaatttcc tttccgtaac ttcaacctcg cactgattga taacgcttcc gccgaatact   1620
cctttcttac ctctttcttc tctccctctc taagctacgc taccatttcc cgacacttca   1680
actacatctt cgaacccact ttttccctcg gccaatctct caccaaatcc ctcatccacg   1740
agtcccatga ttgtctcggc ctcctcctat gtgtgcgctt gaatcaacac tttgcatttt   1800
cccttcaacg ccgcaagatc cccgctgtag attcctacat aaatgcaaca tccatgctcc   1860
tctggccacg cttccaactc acaatggata tccactgcga atccgtccgc accctaacat   1920
ccgctctccc tacccgcaaa ccctcagctt cggaacaagc taaacaatct gcagctccac   1980
acttcatgac ccaacgtttc ggtcaattcc tacagggtat cttagaattg agtacggaag   2040
cgggagatga tgaacctgta gcgagtagtt tggcaagatt gagaggcgag atggaagcat   2100
ttttgacaaa gtgcgcgggg gttatgccgg ataagaggaa gaaggaacga tttttgttta   2160
ataattattc gttgatttg acaattgtag gggacgtaga gggtaaatta gccggggaac    2220
aaagggcgca ttttgaggag ctgaagaaag cttttggaga tggtgtctga tccttcactt   2280
cattttgata cttaattgga agtttttgag cgtgtacact tatcaaagcg tattatttga   2340
tcatgtattt tgtatttgtg aagagaaaca aagaactttt attatggtag aaatagagcc   2400
ggaaataatc tatgctgtgg aagaaacca                                     2429
```

<210> SEQ ID NO 8
<211> LENGTH: 2016

<212> TYPE: DNA
<213> ORGANISM: Sclerotinia sclerotiorum

<400> SEQUENCE: 8

```
atgtggtcat tagaccgatt atctggacat acaacacctt ctgcttctcc acctccacca     60
ttaaatagga accccagtct acctcgtcgt ccgactcatc ttgcgccatt accagtcggc    120
ggtagacctc catttaatcc gagatcctct tccctatcat tagtctccaa tgactccagt    180
acatccttgc taccatcgcg gagacccaac gggtcgaacc ccaaacaagc agctacacca    240
cccaatgtgc cagatccttt agaggtttta ggaagaatat taaacaatgg agaagaggca    300
aaatcaccac ctgcgaaggg cttgggagcc ataaatggaa cagccgctcc cataagagag    360
aaagatgatg aaggcgaatg ggacttcgaa ggtttaagtc tacaagatat cgtggcagag    420
gaaccttctg tcactgagga tgagcatgta tataaatcac aaacacttga agaatatgag    480
cgtgatatgg ataagtttga agatctccac agatcgattc gcgcttgcga tgatgtccta    540
aattccgtcg aaataaacct caccagcttt cagaacgatc ttgctatggt ttctgcggag    600
atcgaaactc tacaagcacg atcaacggcg ttgagtgtac ggttggaaaa tcgaaaggtg    660
gtagagaatg gacttggacc tatagtggag gagatcagcg tctccccagc cgtcgttaag    720
aagattgtgg atggagctat agatgaagct tgggttcgag cattggcgga aatcgagaag    780
cgatcaaagg ctatcgatgc aaaatcaaag gaacaacaga atataaaggg ggttaatgat    840
ctcaagcctc tattggagaa tctagtgtct aaggcactgg aaagaatccg agatttcctc    900
gttgctcaag tgaaagcttt gcgatccccc aatataaatg cccagattat tcaacagcag    960
cacttcctac gttacaaaga tctctatgct ttcttgcata gacatcaccc aaaattggcc   1020
gaggaacttg gtcaagcata tatgaatacg atgcgatggt actttctcaa tcaatttaca   1080
cggtacgcaa aagcattgga aaagatcaag ctccatgtgt tggacagaca cgatgttctc   1140
gggtcagatg atggatctcg caagaccacg ctcctctccg cgtctaaaca aacaggtcca   1200
ccacatgatg cattcaattt aagtcgacga atcgatcttc tcaaaacctc caacgaaatt   1260
gcactgccgt cctttctagc agaagaagac aaacaaactc attacatgga attccccttc   1320
cggaatttca acctcgccct aatcgacaac gcttccgccg aatactcctt cctaacctca   1380
ttcttctccc cgtcactaac ctacgcaacc atctctcgct acttcaccta tatcttcgaa   1440
cccaccttct ccctcggcca atcgatcacc aaatccctcg tccatgagtc acacgattgt   1500
cttggtctcc tcctgtgcgt gcgtcttaac caacattttg cattttctct ccagcgccgg   1560
aaaatccctg tcgtagattc atatatcaac gcaacatcca tgctcctctg gccgcgcttc   1620
caactcacaa tggacacaca ctgcgactcg gtccgcaccc tgacctcggc cctccccacc   1680
cgaaaaccat cggcttcaga acaagcgaaa caatccgccg ccccccattt catgactcaa   1740
cgtttcggcc aatttcttca gggcattttg gaactaagca cggaagctgg agatgatgaa   1800
cccgtggcga gtagtctagc gagactgaga agcgagatgg aagcgttttt gtcaaagtgt   1860
gcggcgatta tgccggataa gagaaagaag gaacgatttt tgtataataa ttattcgttg   1920
atattgacca ttgtggggga tgtggagggg aaattggctg gggaacagag ggcgcatttt   1980
gagggattaa agaacgcttt tggggagggc atttaa                             2016
```

<210> SEQ ID NO 9
<211> LENGTH: 2861
<212> TYPE: DNA
<213> ORGANISM: Botrytis cinerea

<400> SEQUENCE: 9

```
gagtattctc gattagacaa ttagaattct cgaacaatag aagccggagc tcgagttcct     60
cgatctttac ctacctgaag tctctcgatc agaagagtgt caaattccta tgatatcaat    120
gattattgag gatatattta caaaatcaaa tctcttcaat gaatctctat ctacctaagc    180
aagtcaatta tgattgatta caattatcgt tgttgcacgg aatccagtcg catttggtcc    240
cggtcactcg taacagcaac cacatcggta tttcgtagat tcccgagtat tgcctttaca    300
tacctaagga actttaaatc cccccaacaa cagaattgac gacagaatta ctaccattac    360
aagtgaaaac actccatggt acccaaatac aacagtctca tatagccatt tgatcgcaac    420
tcgcatcttt catctacaaa atgtcgtttg gaggggacat cggactcgat acaacatcgt    480
cgtccaatgc tgctggtaat ggcggcaacc agggcgagac aactggaaga cctgccaccc    540
ctcaagatgc aaccgcaaaa gcagttcaag atgtcacaag ctcggagatt ggaatatcaa    600
ccttgttaac ccgactgaaa caaagtattg cttccgcaaa ggaattcgca cttttcctca    660
agaaacggtc catcatggaa gaggaacatt cgaacggttt aaaaaagctg tgtaaggcaa    720
ccggggataa tattcgcaga ccagagcatc gacacggatc gtttctacag tcatacgaag    780
aggtcctcat tatacacgag cgaatggccg agaatggggc tcaatttggc gtgtctctac    840
atcagatgca tgaggatctt atcgaaatgg cttcgaacat agagaagggc agaaagcatt    900
ggaagaatac tgggttggca gcagaacaac gtgctgctga taccgaagct gccatgaaga    960
agtcgaaggc gaagtacgac tctctggcag acgagtatga tagagctcgc actggggaca   1020
ggcaaccagg aaagattttt ggcctcaagg gccccaaatc ggcagcgcaa catgaagagg   1080
accttcttcg caaagtccag gctgccgatg cagattatgc gtccaaggta caagctgcgc   1140
aaagccaacg aaccgagctc tggtcaaaat caagacctga ggctgtgaaa gctctagaag   1200
atctcattca agaatgcgac tctgcattga cattgcagat gcagaagttt gcatccttta   1260
acgaaaagct acttttgagc aatggcttga atataagccc tatcaaagga aaagagcaag   1320
ggacattaaa tcgcagtctc cgtgaagttg ttcacgcaat tgataatgtt aaagacctga   1380
gcaactacat cagtagcttc tctggtaaca tgcagtcccg gatcacggaa atcaaatatg   1440
agcgtaatcc ggttttgcaa cccgcacaaa ataccgctca gcgacaatcg gatcccaacg   1500
ctctccaagc tcgacaagga cccgtaatac caccacagcc atctcaccaa gttcatatga   1560
gccaaccttt taatcaaagc agtcccccaa ctcaccagcg cgaaagaagc tttagccatg   1620
gcccatctct ttcgcaacac atcgttgcac ctgttgtatc gcccactaac ccaatatcca   1680
cctctcccga cttcaatacc tggtcacctc gtgcagatgg cccccccag atatcaacct   1740
tgccatttca gccacaacct caaaacgaga caccaataca acagacacca caaaacccta   1800
caacgcatgc accagtgtcc catggcccat cctcggcacc actattcgga gcgggatcgg   1860
ctccagctcc aggcaacagc actcatctag cacctttgaa accagtgttt ggactcagcc   1920
tcgaggaact ctttgacaga gatggctctg ctgttccaat gattgtctac cagtgtattc   1980
aagcagttga cctctttggg ctcgaggtcg aaggaatata ccggctatct ggtaccgcat   2040
ctcatataat gaagatcaag gcaatgttcg ataacgacgc atctaaggtg gacttccgta   2100
acccggaaag cttctttcac gatgtcaata gtgtggctgg tcttctcaaa cagttcttcc   2160
gcgaactccc agaccccttta ttgactatcg agcaatatcc tgcatttatc gaggctgcaa   2220
agcatgatga tgaaatagtc cgtcgcgact ctctacatgc gatcatcaat ggccttcctg   2280
atcccaatta cgctactctt cgagccttga ctttacattt aaatagagta caggagagtt   2340
```

cggcatctaa caggatgact gcaagcaact tggccatagt atttggccct acactcatgg 2400
gtgctaattc aggaccgaac atgtcagatg ctgggtggca ggttcgtgtc gttgacacta 2460
ttttgaaaaa cacttatcag atatttgacg acgactgagg cgaagaagat tgtcgattga 2520
cttgaagagt tcttaacgag ataccatagc tgctcatatt atgaacctgc ctttggaaca 2580
gaaacaaggg cagggaattc ctagcatcag acctctattt gccgacaaga cattctaaag 2640
aaagtacatg ccactgtatt tcgaatacta ttattgtaag gcacgggcct gttgacaaat 2700
atttacggtc tatcaagcga gtgtacgtca gggggtggtc tacaccacga tcgattttgt 2760
agggtcatgt gctcagctct gatgccagta ttggtgcaac tattgaatca aaagggtacc 2820
aaggtttcaa tactcgttaa ttttggatca cgaaaagatc a 2861

<210> SEQ ID NO 10
<211> LENGTH: 2082
<212> TYPE: DNA
<213> ORGANISM: Sclerotinia sclerotiorum

<400> SEQUENCE: 10
atgtcatttg gaggggacac cggacttgat tcatcatcgt cgcccaatat cgtcggcaat 60
ggcaacaatg gcgagacaat cggaaggcct gcaactcctc aagatgcagc cacgaaagcg 120
gttcacgatg ttacaagctc cgaggtgatt gagtcaacca attggaatat caaccttgtt 180
gaaccggttg aaacagagca ttgcttccgc aaaggcagtc ccccccgaac tttcaacgtc 240
tgcatagata tggagctgac ttcttcgaaa caggagttcg cacttttcct caaaaaaagg 300
tccataatgg aagaggaaca ttcgaatgga ttaaaaaagc tgtgtaaagc aactggagat 360
aatattcgca aaccagagca tcgccatggt tcattcctgc agtcatatga agagattctt 420
attatacacg agcgaatggc cgaaaacggg gctcaatttg gcgtgtctct acatcagatg 480
catgaagacc ttattgaaat ggcttcgaat atagagaagg gtaggaagca ctggaaaaat 540
actggcttgg cagcagagca gcgtgctgct gacacggaag ccgccatgag aaagtcaaag 600
gcgaaatatg atagcttggc ggatgagtac gacagagctc gcaccggaga taggcaaccg 660
ggcaagatat ttggcctcaa gggacctaaa tcggcagcgc aacatgaaga ggaccttctc 720
cgtaaggttc aggctgcaga tgcagattat gcagcgaagg tacaagctgc acaaagccag 780
cgctctgagc tctggtcaaa gtcaagaccc gaggcggtga aagcgctaga agatctcatt 840
caggagtgtg actctgcatt gacattacaa atgcagaaat ttgcgtcctt caacgaaaag 900
ttacttctta gcaatggttt gaacataagc cctatcaaag ccaaagaaca aggcacctcg 960
aatcgtagtc tgcgtgaagc tgttcatgcc atcgataacg ttaaagacct gagcaactac 1020
atcagtagct ttgccggtaa ggtaccatca cgggtcacgg aaataagata cgagcgtaac 1080
acggtcttgc aacctgcagc aaatattgcc caacgacaat cagaccccaa cgctctcaac 1140
tctcgacaag gaccaggaat atcatctcag caacctcatc aggtgcatgt aagccaaacc 1200
tttaaccaag gcactccgca aacacaccag cacgaaagaa gttttagtca cggcccctct 1260
ctttcgcaac acatcgttcc aactgttgca tcgcccacgg cgccaacatc cacctcccct 1320
gacttcacca cctggtcacc tcgtacagat gggcctcctc aaatctcaac attgccgttt 1380
cagccactgc ctcagaacga gacagttttg caacaaacac caccaaatcc tacgactcat 1440
gctccagcat cccatggacc accttcggca ctattatctg gaccaggacc tccggcttca 1500
ggcaataata cacatctagc gcctttgaaa ccagtatttg ggcttagcct cgaggagctc 1560

```
tttgagagag atggctctgc tgttcctatg attgtctatc aatgtattca agcagttgac   1620
ctctttgggc tcgaggttga agggatatac cgactatctg acgcatctaa ggtggacttt   1680
cgtaaccctg aaagcttctt ccacgacgtt aatagtgtcg ctggcctttt gaagcagttt   1740
tttcgagagc tcccagaccc tctactgact agtgaacaat accccgcatt catcgaggcc   1800
gcaaagcatg atgatgaaac agtccgtcgc gactctcttc atgccatcat taatggcctc   1860
cccgatccta actatgctac tttgcgcgcc ttaaccttac atttaaatcg agtgcaggaa   1920
agttcggcgt ctaacaggat gactgcaagc aacctggcta ttgtatttgg acctactctc   1980
atgggagcta attctggacc aaacatacaa gatgctgggt ggcaggttcg cgtcattgac   2040
accattttga acaacaccta tcagatattt gatgacgact ga                     2082
```

<210> SEQ ID NO 11
<211> LENGTH: 2795
<212> TYPE: DNA
<213> ORGANISM: Botrytis cinerea

<400> SEQUENCE: 11

```
gtttccaagt acagtacagt accacttcaa gtacataaac tcagcgctct tcttgagata     60
aaaggttaaa gggttgcaag atttctttga tacatatcat tggaaataaa gtattccgga    120
ttacattaga ggaagctcac tgtaacaggt ttctgctttg ttgttcatgg acatgatggc    180
agcaactcca gacatttctt tgacctggtc atcagtctat aaagtcgccc caaaagacaa    240
cgtctcgctg cccggggaca agatactact acctcaatca gcgctggaac aactactatc    300
ggcatctaca gttacggtga attctaacac tcgccccagc aatgttgcat ttgatccatt    360
caatccatat tcattggcag ccgctcgcat agaacagtcg caatggagag atacccaaca    420
acaactgccc catcctctca cctttaggct ggtcaactcg aagaacggaa atgtagtata    480
tgcaggaatt cgagagttct cggcagatga aggagaagtt gtcttaagcc catttttgct    540
agaggcatta gggatcactg cgcccttacg aaatccaaca ccaccaagtt caaaggttga    600
aagcaggaga gggtcgccgg atacgcctat agatcttaca gataaccctg caatcgatct    660
tacgggtgac gagatgatag accttacaga cgaaaccgaa gaaccggcgc agatcactgt    720
acatgcgaaa caattaccta aaggcacata cgtgaggcta aggccattgg aggctggtta    780
taatcccgag gattggaaat cattgctcga aaaacacatg cgagaaaatt tcacaacttt    840
aacgaaagga gaaatattga cggttcgagg ttcaaagtcg gaggaattcc gatttctgat    900
tgataagttt gcaccggaag gagatgcagt ttgcgttgtt gatacagatc tagaggtcga    960
tattgaggct ttgaatgaag agcaggctcg ggaaaccttg aagcaaatca tgtcaaaggc   1020
acaaaaagct ccaggaacgg ctcaagggag ttcaattggc ggagaattag atctttggaa   1080
tgctttgcag ggacaggtcg cagaaggtga ttatgtcgac tatactttac cttcatggga   1140
tcgatcaaat ggtcttgata ttgagctttc acttgaggac gatggtgatg gtgatgtgga   1200
gatattcatt agtcctcaat cagcccatca aagagcaaaa ccacgggagg atgaacatgt   1260
tctcggagat ttctcaagtg acaaaatcaa gagaataacc atacaacaat caaatgtgga   1320
attagacgga gctgatgcta tattaatttc tttatactgt cgaggaactg gagcaggctc   1380
tgagccacca catggaccac ggaagtattc cattagagta aaatcgcttg aaaagggggc   1440
aagcaatggg gccccaagca acccaatctc gctcgaagaa gatgccgaaa tgcatggatc   1500
tgatgaggag caatgtaaaa attgtcatca atgggtgcca aagcggacaa tgatgcttca   1560
tgagaacttt tgtctccgca ataatatctc atgccctcat tgcaatggcg tctttcagaa   1620
```

-continued

```
gaaatcttca gaatggctga atcattggca ttgtcctcat gattcagccc atggaaattc   1680

ctcagaaagc aaaactaaac acgactctat ttttcacgaa gctcgacaat gtcccaattg   1740

cccttacgaa gcaacaaata tgagggatct tgccactcac cgtacgtcta tttgtcctgg   1800

caagatcatt ctatgtcaat tttgccatct tgaagttcct caagagggcg acccctcga   1860

tccgtctcca gaaagtctta tttccggact tacagcacac gagcttgcag atggggctcg   1920

aactacggaa tgtcacctgt gcagcaaaat tgttcgactt cgggatatga ccacccatct   1980

taaacatcac gaactcgaaa agaatagccg atttaaacca gccatctgta gaaatgcaat   2040

ctgcggtaga actctggagg gcgttggtaa gaatggggaa gtgggcgctg gatcgagaat   2100

gggccaagga cctggtaatg atttgggtct ttgcagtatc tgcttcggtc cactatacgc   2160

tagtatgcac gacccattag gaaaagcaat gaaacgccgc gtggaacgaa ggtatctgag   2220

ccagatgatc acgggatgcg gcaagaaatg gtgtacaaac atctattgca agactgcaag   2280

ggcgaaagaa gcgaatgggc ctcaggcaat actagcgatg aaagatgccc ttcctcttat   2340

tcagccatta gtagcccaag tagaggataa gaccgaaccg atgcatttct gtgtcgatga   2400

aggaaaccag aagagaagaa atctggctga aatgttagct atggagcctg gaggttggga   2460

attggagtgg tgtgttgcgg cttgtgaagc agaaggtgca aatcttgata aggccaggac   2520

atggttatct aattgggctc ccaagaaagc ttgatgtggt tcagatctgg aagatatttt   2580

ggtatggatg aaagggatgg agcatggcgt ggtaccgatt gcataagtaa gggagttctg   2640

gtggctgatg acgatatgat atgatatgat accaatttat agacccgatt ttgttgtgcg   2700

tacataaata tacatggttg gcgtcgcatt agctagagat agatcgaaca gattaagaat   2760

ttactgctaa tacataaaca tatatacatt cttca                             2795


<210> SEQ ID NO 12
<211> LENGTH: 2364
<212> TYPE: DNA
<213> ORGANISM: Sclerotinia sclerotiorum

<400> SEQUENCE: 12

atggcggcga ctccagatat ctctttgaaa tggtcatcag tctataaagt tgcctcaaaa     60

gacagcatat ctctgcctgg tgataagata ctgttaccgc agtctgctct ggaacagcta    120

ttagcagcat ctacggttac ggtcaattct aacagccgcc caaataatgt cgcattcgat    180

ccatttaatc catattcttt agcagcagct cgcatagaac agtcgcaatg gagagatact    240

caacagcaac tacctcatcc tctcacattt aggctcgtca attcaaagaa tgggaatgtg    300

gtacatgcag gaatccgaga gttctctgca gatgagggag aagttgtcct gagcccattc    360

ttgcttgagg cattgggaat ctctgcgccc acacgaaaat ctacgccaag tcccaaagtt    420

gagagcgaga gaggatcccc tagtgcgcct atagacctta cagataaccc ttcgattgac    480

cttacacgcg atgagacgat agatcttaca gatgaaattg aagaatctgc gcaaatcacc    540

gtacatgcga aacagctatc taaaggtaca tatgtgaggt taaggccgtt ggaagctggg    600

tataatcctg aggactggaa atcgttacta gaaagacatt tgcgggaaaa ttttacaact    660

ttaacaaatg gagaaatatt aacggttcga gggtcaaagt cagaggaatt tcgatttttg    720

attgacaaac tcgcgcctga aggagatggg atttgtgttg ttgacaccga tttagaggtc    780

gatatagaag ctttgaatga ggaacaagcc cgagaaacct tgaagcaaat catggcaaag    840

gcacaaaaag ctccaggaac ggcccaagga agttctatcg gtggagaatt agacctatgg    900
```

-continued

```
aaagcttcgc aaggacagat tgctgaagga gattacgtgg attatacttt accttcatgg    960
gatcgatcaa atgaccttga gattgagctg tcgctcgagg atgatggcga tgtggagatt   1020
tttattagcc ctcaatcagc tcatcaaaga gcaaaaccgc gagaagatga gcatgttttt   1080
ggagatttct cagaaaataa aaccaagagg ctcgtcatac aacaatcaga cgtggaatta   1140
ataggagctg atgcaatact aatttccata tacttccgag ggtctggaag tgagtcatca   1200
caggggttac ggaaatactc tcttagagtg aaatcgcttg agaaaggggc aagcaatgga   1260
tcttcaagta atccagtttc gcccgaagaa gatactgaaa tgcatggatc tgatgaggag   1320
caatgtaaaa attgccatca atgggtaccg aagcggacaa tgatgcttca tgaaaacttc   1380
tgtcttcgta ataatgtctc atgtcctcat tgtaacaacg tgtttcagaa aaaatcccaa   1440
gaatggcagg atcattggca ttgtccttat gattcttcct acggaaatac accagcaagc   1500
aaaaccaaac acgattctgt atttcacgaa tcccgccaat gtcccaattg tccctatgaa   1560
gcaacaaatc tcagagatct tgctacccat cgtacgtctg tatgtcccgg caaggttatt   1620
ctttgtcaat tctgccatct cgaagtcccc caagaaggcg accccttcga tccgtcccct   1680
gaaagtctca tatctgggct cacagcccac gagctcgctg atggagctcg aactacggaa   1740
tgtcaccttt gcagcaggat cgttcgactt cgcgatatgt ccacgcatct caagcaccac   1800
gaacttgaga agaacaatcg attcaaacca gacatctgta ggaatgtcaa ctgtggtaga   1860
actttggacg gtgttggtaa gaacggggaa gtaggagcag gttcgaggat gggtcaagga   1920
ccaggtaatg atttgggtct ttgtagtatt tgcttcggcc cactatacgc tagtatgcac   1980
gacccgttag gaaaggcgat gaagcgtcgt gtggaacgaa gatacttgag ccaaataatt   2040
acgggatgtg gcaagaaatg gtgtacaaat ctctattgta agactgcaaa gactaaagac   2100
gccaatgggc cccaggtggc attatcggta aaagatgcac ttcccctcat tcaaccatta   2160
ctagcccaat tagaggataa gaccgaacca atgtatttct gtgtggatga agcaaatcag   2220
aagaggagaa atctggcgga aatgttggcc atggaaccag gaggttggga tctagagtgg   2280
tgtgttgcgg cttgcgaagc agaaggtcca aatcttgata aagtcaggac atggttaagt   2340
aattgggctc caagaaaagc atga                                          2364
```

<210> SEQ ID NO 13
<211> LENGTH: 801
<212> TYPE: DNA
<213> ORGANISM: Botrytis cinerea

<400> SEQUENCE: 13

```
ggatcgcaac taactcttct ggaaggttct tgtggcaata tcaaccacat ggatcttcag     60
taccaccgcc gtcaaattgg ctgtgcttgg gttatatatg cgaatcttca ccacgcccgt    120
tttcaagcga tgggccgtct ctttgatgac catagacgtt tgtttcggta tcaccttctt    180
cgtcgtgttt ttaactcatt gcaacccagt ctctcaagaa tggaaccctg ttccacgggg    240
ttcatgcaga tctctaacat tgtccgagtt ttcctccatc gctctcaatc tggctctcga    300
cacggcaatc atcattctcc ctatgccatg gctatacaag cttcaaatcg cattaaatca    360
caagcttttt gtgatggtca tgttcagttt cggctttgca actattgcca tcatgtgcta    420
tcgtcttgaa ttgacagccc gaagcccttc tgatcccatg attgccattg caagagtcgg    480
agtgctgagc aatctcgagc tttggattgg tattattgtt gcctgcttac ctactatgaa    540
accttttgtt agagtatatc tcagacccag cctatcaaag ctctcccaaa aactttatgg    600
cagccccaca gtgtcaacaa aagacgaaaa tccacaactt cagctaagga acttcggggg    660
```

```
ttccggacct tcacgccccc aaaaaaaaca gtaactacac tgaactttct gaagctccat    720

ctgtgcagac agatactgac gagttgcatc tcgttccaaa tgaatcatcc aattttgatg    780

caaattgtga atctagcaac a                                              801


<210> SEQ ID NO 14
<211> LENGTH: 1840
<212> TYPE: DNA
<213> ORGANISM: Botrytis cinerea

<400> SEQUENCE: 14

gaagctttaa aacatacgat tatttgatcc tgtttgaaca cgttttcttg aaatttcaag     60

cttgaatgaa acacaacacc aagtctatcg gccaaaggac ccctttgaga ttgcattgag    120

cgttgtccca tctcaagatt taacaactgt tattcacgaa atcatgcctc caccaccacc    180

acctcctcct ccgccgcctc ctccgcctgg aggagctcca ggaggtatgc catccagacc    240

acctgcgaaa gttgctgcaa atagaggcgc acttttgtcg gatatcacga agggaagagc    300

actcaagaaa gctgtaacta acgatcgatc ggcaccggta gtaggcaaag tatctaatgg    360

ttctggacct gcgccaatag gaggtgctcc tccagtaccg ggaatggcaa aacctcccgg    420

tggatttggc gcaccgccag taccaggagg aaatagagct cgaagtgata gtaaccaagg    480

gagcaataat gcggtttcgg ggatggaaca agctccacag ttaggaggaa tattcgcagg    540

cggcatgccc aagttgaaga aacgaggtgg aggagtagat actggcgcaa accgcgactc    600

atcgactgca tcggaaccag aattctctgc tcccagaccg ccaggtatgg ctgctcccag    660

acctccaaca aatgcagctc cgcctttgcc atcagtccgg cctcctcctc aacctagcgc    720

tagtactccc gcatttgcgc cctcggttgc aaatctgaga aagaccggcg ggccatctat    780

ttctcgtcct gcatcctcaa cctctctcaa ggggccacca ccccctattg gcaaaaaacc    840

tcctccaccc cctggaactc gaaagccatc atcagcgcta tcaaccccac caccaccacc    900

gcctccagca ttcgcccctc cacctccttc ttcagcacct ccgccacctg ttgcacctcc    960

accaccacct tccccagctc cacgccctcc gagtaaccca cctcgatcac atgcaccacc   1020

gccaccacca ccaccaccac caccaacatc tccaccttcg actaacggag gtaacccaag   1080

tcttgctata caagcaacaa ttcgtgctgc tggccaagca tcaccaatgg gtgcaccacc   1140

accaccacca ccgcctcctc ctccatctaa tgggcctccc tctctctcgt cgcacagaac   1200

gccatctccg cccgcggcac ccccagcggc acccccagcg gcaccaatat caagaagtca   1260

aagtcaacaa ggaagaactc acacaatgga ttccagttct tatacccttt catcaaacgg   1320

cagtttaccg caagcctcta gttctagcag aagaatcatg atcaatgatc ctcgatggaa   1380

atttacagat gaatcggtat tcccaaaacc tcgagatttt attggtgggc ccaaaaaata   1440

ccgggctggt cgtggaagta gtgttccgtt ggatctgagt gcttaccatt aagaatttcg   1500

cttaccaaaa agaatataac tcttcggatc gtattcatgt gttaccatta tgatttaagg   1560

cgttatagcg ggatatcatt tagaatccgg taaggcggca tcaagctatc tgaattggga   1620

gttatacatc aggacactaa agatcgtcaa aaaatttccc ctgaatcgcg agatggagat   1680

tgacgagaga catcagctca ctacccaggg taccgaggag gaaatcgcag ctataaatat   1740

cacgggtgat gggcaaattc cacagtggaa ccttaaaaga atgagtacgg agaatattaa   1800

acttttgaga tttatctttc tcttcctgtg attttaacca                         1840


<210> SEQ ID NO 15
```

<211> LENGTH: 1311
<212> TYPE: DNA
<213> ORGANISM: Sclerotinia sclerotiorum

<400> SEQUENCE: 15

```
atgcctcctc cacctcctcc accacctcct cctccaccgg gatttggtgg tcctcctccc     60

cctccacctc ctggaggagc cccaggatcg atgccatcaa ggccacctgc gaaggtcgct    120

gccaatagag gcgcactttt gtcagatatc acaaaaggaa gaacactcaa aaaggctgta    180

accaacgaca gatcggcacc aatagtaggc aaagtatccg gtggctctgg gcaaatgcca    240

ataggaggtg ctccaccagt acctggaatg gcaaaacctc ctgggggttt cggcgcacca    300

cccgtacctg ggggaaacag agctcgaagt gacagtgaac atgggaacgg cgtgtctgca    360

ggaatggaac aacctccaca gttaggagga attttcgcag gtggcatgcc caagttaaag    420

aaacgaggcg gaggagtaga cactggcgca aatcgagatt catcattcac atcagaaccc    480

gaattttctg cgcctaaacc accaggtatg gcagctccta gacctccaat aaatgcagct    540

cctccgttac catcagcccg gcctcctcct cagcccagtc cttcggcacc tacattcgcg    600

ccatcgattg ccaatttgcg aaaaactgct gggccatcaa tttctcgacc tgcttcttca    660

acttctctca agggaccacc acctcctatt ggcaagaaac ctcctccacc tcctgggact    720

cgaaagccat cagctttatc agccccacca ccgccatcat cattcgcacc tccacctcct    780

tcttcggccc ctccaccgcc tgctgcaccg ccgccaccac cttctccagc tccgcgccct    840

cccagtaacc cacctcgagc acatgcgccc cctcctccac caacgtctcc accttcggct    900

aatggaggtg gtcagagtct tgctatgcaa gcagcaattc gtgctgccgg tcaagcatca    960

ccaatgggtg cacccccctcc accgccgcca cccccatcta gtggaccacc ctctatatcg   1020

tcacacagag cgccatctcc gcctgcaccg ccagctgcac caatatcaag aagtcaaagt   1080

caacaacaag gaagaactca cccaatggat tctagctcat atactctatc gtcgaacggt   1140

accttaccga aaaccgccag ctctgatagg agagttacaa tcaacgattc tagatggaaa   1200

ttcaccgacg aatcagtatt tcccaaacct cgggagttta ttggtggacc caagaaatat   1260

cgggctggcc gtgggagcag tgttccgttg gatcttagtg ctttccattg a             1311
```

<210> SEQ ID NO 16
<211> LENGTH: 3607
<212> TYPE: DNA
<213> ORGANISM: Botrytis cinerea

<400> SEQUENCE: 16

```
gatattgtac acgagcctct tcctgcattg attgattgat tgctcttaca catatccagt     60

tcatctccca caaaatacca agcggccgca tttggatgca acatacatac tcactacctt    120

ccacttcacc tacctaccta ctgacttaat ataccttctt gtcatctttg atggcactga    180

ataaagtacc ttcctattaa aactacctca accagtccag tcattactac ccaccttaca    240

tctcgagaag cctccttcct cgatatacat tcttctctta tattaatgca aagatgtcgg    300

agcacgaaca tcaaaaacat ctttccgatt ctgaagaaga ttccataatg gaagagagag    360

aggagaaaaa gggaaaagac gagatagagg agaaagacaa aaaagacgag aaagacgaga    420

tagaggagaa agaggagaaa gaggagaagg agaaagacaa aaaagacgag gaagagagag    480

aggagagaga ggagagagaa gagagagaag agagagagga tacagttgat cagagttctg    540

atcatgagag tgacaccttc gaggatgcca atgatgttga agacattgca gacactctta    600

cctccccagt tgaaaggaca agatctttaa cgaaacgaag atcatcatcc attaagagca    660
```

-continued

```
atacacaaga cctcagtacc gatatcccat cggtcccaac agtaccactt ccagaaacga    720
atggcgaaac gaatgacgaa caaatagaat ccgataatcc actacctaaa tctcccettt    780
taacatctca tcgcatgtcc actacatccc tacataatgt gaatctcgaa gacggtgatg    840
attttggatc acctccacca cctcctcccg tttcgaaagt agcaccagaa gatcaaccac    900
ccgaattacc tccaaagccc aatacaataa ttccaatgca gggcctttct ggagcccttc    960
cagatgtgcc attctcaccg ccccctcctc ctcctcccgc tcctcccgct cctgcaaacc   1020
tcgctgcgcc agcacctgtc accagaaaat taaccagccc attctcatgg ctgtcgagaa   1080
atacctcggc tccaaaagag aacgtcaagt caccgccatt accttcatct cacgcaaccg   1140
agcgtagaca taccgcttct tcgatagcga ccattagcag caatcctgaa atgatggtaa   1200
acaaattgga ggagggtaat gatacagatg ccgcgaatgg agttagacga cctgggagga   1260
atagtttacg ggacaggttt aagctcgtga gaatgcgaga agaggctgga ataacagaat   1320
tgcctgaaga aaaggatgaa gcaggcaaca cagcatttgg gggtctcatt aggcagagta   1380
caagtcttgg tttgggattt accgcctcaa atgatgacaa agacccttct cccgtatctc   1440
ctggtccgcc tacgagtccc aacccaatta gtgtcaaccc tgcattagcc cccggtacgg   1500
catctggagt ttctgcaggc ccttctgcat tgggtgaatc agaagcacca gtcgattggg   1560
atttgtggca aaatgtcgtc tgggaaggac cagctgcggt agcaagaaca agtgcagaag   1620
agctgaatca cgctattgca actggtatac cacatgctat cagaggcgtg gtatggcaag   1680
tattggcgga gagtaagaat gaagagctcg aggttgtcta tcggaatttg gtcaatcggg   1740
gcacagacaa ggacaaggac aggatgagta catctagtgg gacacaaagc aatggatcaa   1800
tcaaggagat tgtggtttca tcagcatcat caatacattc agagaaatct acacccgcta   1860
cgacaatcac caatggaatg agatctcctt ctccccctag tgaaaaggat gtagcccagt   1920
ctttggctga aaagaaaaag aaagctaagg aggatgcggc ggcattgaca aaactcgaga   1980
gagccataaa gcgggacttg ggtgctcgaa caagttattc aaaattcgct gcaagtgctg   2040
gactacaaga tggattattc ggtttatgca aagcatatgc tctttatgat gaaggtgttg   2100
gttatgcaca aggcatgaat ttcttagtta tgcctttgct tttcaacatg cccgaagaag   2160
aagcattctg tctattagta cgacttatga atcagtatca ccttcgagat ctttttattc   2220
aggatatgcc aggtctacat aaacatcttt atcagtttga gagattatta gaagattttg   2280
aaccagcatt gtattgtcat ctccatcgac gtcaggtcac acctcactta tatgctacgc   2340
aatggttcct aactcttttc gcctatcgat ttccattaca gcttgtgctt cgaatttacg   2400
atctcatttt aagcgagggt ctcgaggcta ttctcaaatt tggaattgta ctcatgcaaa   2460
agaatgcagc tcatctactc accctccatg atatggctgc attgactacg ttcctgaaag   2520
atcgactttt cgatgtttac attgatgctt caccttcagc aggatcaatt ctagaatctg   2580
gtttctttgg aaattcagga gcgactatcg ataaggaagt ttatcgagca gatcatatga   2640
ttcaagatgc ttgtgccgtc aaaattacac ccaaaatgct ggaaacttac gcattagaat   2700
gggaggaaaa gaccaagata gaaaaggatc gtgaagcaga attagaacac ttgaaatcaa   2760
caaatgtcgc ccttacacac aaagttcgac gtctggaaga aagagtcgaa tctcacgata   2820
cggagcacgc agctttggca actgaacttg ttcggactaa ggtcgaaaat caagagattc   2880
atgaagaaac agaagttctt aaagaacaag ttaaagaact gaaaaaagta attgataagc   2940
taccggaaga aattgaagcg aaattacaga gtgagatgga tagattgatg aagagaaatc   3000
```

aagaagttca tgaagaaaat caaaaattgg aggatgaaat gaatgaaatg gaacaaaact 3060
tggtggaaac aaaaatgaaa tatgctgaga tgaatgcggc ccatgaagct ctaactcgta 3120
aatggacgga tttgagaaaa gctttgggtg attaatatcg ttactttgag atatcctaaa 3180
ttattaaata cgacttgtac agttcttctc aattgatacc gatgcctttg aagtttttgg 3240
ggggtagggg agagaggcgt aaatgcctat attggggaac gaaggaacaa tgctctcgtt 3300
tggaagcttg ctggatttct tgctaggtgg aggggatgat tgggaatcaa tcagattata 3360
caggtactgc tgcattggta cgcaaatggt ataggaattg gcgtgggttg taaaagtacc 3420
ggagaaatac tttgggtgct tgcttgtctt gtttctctct cttttttta gtcgttttag 3480 cgagttgtga tgttggtagg aaagaaatta agaaattatg gacgggtagg gggagtggag 3540
agaggaaggg agggggtgaa agagggtggg gggaggggaa gaaataaaaa ttaagaataa 3600
atgatca 3607

<210> SEQ ID NO 17
<211> LENGTH: 2714
<212> TYPE: DNA
<213> ORGANISM: Sclerotinia sclerotiorum

<400> SEQUENCE: 17
atgtctgatc acgagcatca acagcatcat tccgatgcag aaaaagattc aataatggaa 60
gaaacagaga agagggttga gcagagttcg gatcatgaga gtgacatgtt cgaagatgcc 120
aacgatgttg aagacctcac agatactcct acttccccaa ttgagagaac taggtctttg 180
acgaaacgaa gatcatcatc tattaagagc agtacacaag atatcagtag cgatattcca 240
tcggtcccaa cagtaccact tccagaatca aatggcgaaa cgaatgacga acaattagaa 300
tccgatattc caccacctaa atcccccctt ttgacatccc atcgcatgtc cgcttcttcc 360
ctccataatg taaatctcga agacggtgat gattttggtt cacctccacc acctcctcca 420
ctttcgaaag tagcaccaga ggaaatgaca cctgatcaac cacccgaatt accaccaaaa 480
cccagcataa ttactccaat gcaaggtctt tctggaatcc ttccagatgt gccattctca 540
ccgccaccac cccctcctcc tgctcccgcg cctgcgaatc ttcctgcgcc cgcacccgtt 600
acaagaaaat taactagtcc attttcatgg ctttcaagaa atacctcggc tccaaaagag 660
aacgtaaaat cgtcaccatt gccctcacct catgcgaatg agcgaagaca taccgcttcc 720
tcgatagcaa ccgtcggcag cagttcagaa atgatgctaa ataaattgga ggagggcaat 780
gaaacagata ccacgaatgg ggtcagacgg cctgggagga atagtctgcg ggacagattt 840
aagctcgtga gaatgcgtga ggaggccggt attacagagt tgcctgaaga acaggacgag 900
gcaggcaata tagcatttgg aggactcatt agacagagta caactcttgg tatgggcttt 960
acaggctctc acgacgacaa agaccactca cccaacggag gtgttccacc tgcgactcat 1020
aacccagtca gtgtcaatcc agcattggcc ccaggtacgg cgtctggggt ttctgcgggc 1080
ccttctgcga tgggtgatcc agaagcaccg gtcgactggg atttgtggca gaatgttgtg 1140
tacgaagggc cagccgcggt agcaaggaca agtgcagaag aactcaatca agctatcgca 1200
actggtatac cgcatgctat cagaggtgtg gtatggcaag ttttggcaga aagtaagaac 1260
gaagagctcg aggttctcta tagaagcttg gtaaatcgag gtacagacaa ggacaaggac 1320
aggatgagta catctagcgg agtacaaagc aatggatcaa taaaggagac tgtggtttca 1380
tcggcatcgt cgatacattc cgagaaatct accccggcaa ctactgtcac caatggaatg 1440
agatctccct ctccgccgag cgagaaagat gtagcattgt cgttagctga gaagaaaaag 1500

-continued aaagcgaagg aagatgcagc ggctctgaca aaactcgaga gagccatcaa gcgagacttg 1560
ggtgctcgaa cgagttattc aaaatttgct gcaagtgctg gacttcaaga tggattattc 1620
ggtttatgca aggcatatgc tctttatgat gaaggtgttg gctacgcgca aggcatgaac 1680
tttttagtta tgcctctgct gtttaacatg cctgaagaag aagcattctg tctattagta 1740
cgacttatga atcagtatca ccttagagat ctttttattc aggatatgcc aggtcttcat 1800
aagcatcttt atcaattcga gagattatta gaagatttcg aaccggcgtt gtattgccac 1860
ctccatcgac gtcaagttac acctcattta tacgcaacac aatggttcct tactcttttc 1920
gcctatcgtt tcccattaca acttgtgctt cgaatttatg atctcattct tagcgaaggt 1980
cttgaggcaa ttcttaaatt tggcatcgta ctcatgcaaa agaatgcggc ccaccttctt 2040
acactcactg atatggctgc attaaccaca ttccttaagg atcgactttt cgatgtttat 2100
attgatgctt ctccttcagc aggatcaata ctggaaaatg gtttcttcgg aaattctggt 2160
gcgagtattg ataaagaagt ttatcgagcg gatcatatga ttcaagatgc ttgtgctgtc 2220
aagataactc caaagatgtt agaaacgtac gcattagaat gggaagaaaa aaccaaattg 2280
gagaaagaac gagaagcaga gttagaaaac ttaaattgac gaatatctct ctcacacaca 2340
aagttcgacg tctagaagaa agagtcgaat ctcatgatac cgagcacgcg gccttggcta 2400
ctgagcttgt tcgtactaaa gtcgaaaatc aggaaattca tgaagagatc gagactttga 2460
gggaacaagt taaggagtta aaaaatgtga ttgaaaagca acctgacgaa atcgaagcaa 2520
aattacagag tgagatggat cgattaatga agagaaatca agaagtacat gaagaaaatc 2580
aaaaactcga ggatgaaatg aatgaaatgg aacaaaattt ggtggaaaca aagatgaaat 2640
acgccgagat taatgcagct catgaagctt tgaatcggaa atggacggat ttgaggaaag 2700
cattgggcga ttaa 2714

<210> SEQ ID NO 18
<211> LENGTH: 4841
<212> TYPE: DNA
<213> ORGANISM: Botrytis cinerea

<400> SEQUENCE: 18
ggcttcaatt gacgttgaaa catgaatgct gaatgatgat acgatacact ttacttcagc 60
ccctttaaca ttttgtcgca aaatcggtga aacttgggtt gtatgtattt gtatattaaa 120
gatcgctaag cccagcctct atggtaacag attacctgag cttcgtcatt tcgacccccg 180
gaccgtgatc ttctaccaac ctcgaaccca ttccttcaaa taaatgtcac aaatctatct 240
ttcttcatac ctatttcttt tttgttcata ctcataatgt tttcgggttc gaactcgtac 300
cttggtggta acaccggccg ccaaccacca cagcaaccgc aacaacaata tggtggtttc 360
cagccaaacc aaggtttcca accacagcag actggtttcc agccacaaca gactggtttt 420
caacctcaac ccacaggata tggtaatgcg gctcctttac aacccaattt caccggttat 480
ccacttcaac cacagcctac gggatattct cagccctctc aagcaggctt ccctggaggc 540
cagcagcaac agcagcagtt caacaatgct cctcaacagc agaacttcca aacgggagct 600
cccccaatcc cgcagattcc gcagcaattc cagcagcctc aacaaacgca acaggctcaa 660
ccacctcctg cacctcctgt gcagcaaccg caagcgaccg gatttgctgc aatggcagat 720
tcatttaaac ctgctgctgc agagccatcg aagccaagag gacgcagagc ctccaagggg 780
ggagcaaaga tacctagtat acgactttcc ttcattacag cccaagatca agcaaagttc 840
gaaactcttt tcaaatccgc tgttggggat gggcaaacac tttctgggga gaaatcgagg 900
gatcttttac tacgctcaaa actagacggg aactcactgt cgcaaatatg gacgctcgca 960
gacactacaa gatctggaca gctacatttt cccgaattcg cattggctat gtacctctgt 1020
aatctcaagc tagtcggcaa gcagttacca tccgtgcttc ccgatgttat caaaaatgaa 1080
gtttctagca tggtggatat cataaacttc gctatagatg atgatgcacc agcggcaacg 1140
aatgcgccca gttttgatgg tcgacaaaac accgcgacac ctccgactat ccaacaacca 1200
cagccaatgg cgtctaattc cgcccttctc actgcgcaaa tgacaggtta ccctggacag 1260
cagaataact tttcgggtgg atttcaacca caacaaacag gcttccaggg ccaaatgcaa 1320
actggctttt ctggacagca aggcggattg caacctcagc caactggata taatcagatg 1380
tcaaaccctc aagcaacggg ctataatgga ccgcgccctc caatgcctcc tatgccatct 1440
aacttcagtt ctcatttatc tccggctcag acgggtatgc aaggtggaat gatcgcgcca 1500
ttgaatagcc agcctacagg agtcgatggc caatggggct tggtaaatgc gccagccccc 1560
aatatcgatc tattacattc ccggatgatg ccgcaacagg gtcgagaaca aggcaacttc 1620
accacggctg gtataacagg caatgctgaa attccatggg gaattacgaa agacgagaag 1680
accagatatg attccgtttt caaagcttgg gatgggtttg gtaaaggata tattagcggt 1740
gatgtcgcta ttgaagtttt tgggcagagt ggtctcccga agcctgacct ggagcgcgta 1800
tggaccttag cagatcacgg caacaaggga aagctcaaca tggatgaatt cgcggttgcc 1860
atgcatttga tttatcgaaa gcttaatgga tatcctctac cagcccaact acctccggcg 1920
ctcatacccc cttccactcg taacttcaat gattcgattg ggctgtcaa atctttactt 1980 catcaagaat ctaatttccg caagaactct ggtgctaccc ttttgccaca aaagactgga 2040
gtgagctacc tcaaaaatca ttctttccgt ggtgatgcta ccccaggtcg cacaggccgt 2100
aaagacgcta cagtatacaa aaataacgac gatgatgttg ggtataaatc tagtgctcgt 2160
cgcagactcg ggcctcttc tccacgacct tcgtctccgg gatcaacaac ttccaacgat 2220
gacctttcac tagaccagct tagaaagaaa atcgcggaga gacaagtgat actggatgca 2280
attgatttca aggccgaaaa tgctgcagat gaagatgatg ctcttgatcg taaagatcgt 2340
cgtgaagcag aggatcttta tcaccgcatt cgtcgtattc aagaggatat cgatgcgcat 2400
ccagacgcat cgttgcgtaa tgttgattcc ggcgccgagc gtcgtgcttt gaaaagacag 2460
ttgcagacat tgacagataa acttccagat attgcttcgc gtgtccgaag aacggaaaga 2520
agcattgctg atgccaagct tgaactattc cgtctaaagg atgccaaagc tcaccctgga 2580
agtgcctcta gcattgttgg aactggtcct ggcggcgcta tcaccgaatc agatagactc 2640
aaagcaagag ccaaggctat gatgcaacaa cgttctgctg ctctcactgg taagaagatt 2700
gaggcgagta atgatgactt ggatgcgcca aaacgcctcg aagaagaaaa tctcaagatt 2760
cgaactgaga aggaaaacaa cgagcgcatg gttcaagatg ttgaagagag tgtccgtgac 2820
ttttcacgag gactggagga tagtctcaaa gatggtggtg agagctcgtc cagtgagcat 2880
gagaagagac gttgggagga tgggctaggt gttgaggatg aagtgaagga cttcatcttc 2940
gatttgcaaa ggagcagcag gagtgccaga gttcgaactg atgatcgcag cagagagact 3000
cctcgtactg aagcgtctca tgctagccct gctccagcag ctcgtagcga aactccatcg 3060
tcacagccat catctacacc aacccctgct ggaggttcat actcacaata caagactcct 3120
gaagatagag cagcttatat caagcaacag gccgagaagc gcatggctga acgtctagct 3180
gctcttggta tcaaggcacc atctaaatct ggagaaacaa cacaacagag actggaacgt 3240
gaaaagaatg agcgtgcagc caaactcaga caagcagaag aggaagatgc taaacgtgaa 3300
gctgagaggc aagctaggat cgctgaagag cagggtgcac caccacctgc ccccgagcaa 3360
ccaaaggaaa ccgcgaaaaa gccacctcca ccccccttcaa ggaaggccgc aagaagtgac 3420
gctagtgagc gcaaggccga agaggagaga atcattaacg agcaaaaggc acaaattatt 3480
gccacaaatg agctagagga cgatgctcaa cgacaagagg ccgagcttgc aaaggaacgc 3540
gaggcggctc aggctcgtgt caaggccttg gaagaccaaa tgaaggccgg gaaattgaag 3600
aaagaagagg agaaaaagaa gagaaaggct ctccaagctg agaccaaaca acaagaagct 3660
cgtctcgcag ctcaacgcgc agagattgaa gccgcacaag cacgtgagcg agaattgcaa 3720
cgtcaacttg aagctattga cgattcagat tcatctgatg atgacgaagg tcctgagcaa 3780
gttacccctc aagcatcaac gcccactcaa ggaagtcaag agcttgagcg caaagaacct 3840
tctccaccac ctcctccacc ttcaattcca gttgttgtat caccagtccc tgctattgca 3900
acaacaacta gtcttccatc accaacccca caagttacta gccctgttgt cagccctcca 3960
gtcgatacag agacccgcaa tcctttcttg aagaaaatgg cccaatccgg tgacgcatct 4020
accgcatcta ctgcatctaa caatccattc catcgtcttc ctgctcaaga gctttctaca 4080
cctgcaccaa ttcaagttca accaacaggt aacaggccat ctcgtgttcg tccagaagaa 4140
gatgattggg atgtcgtcgg atctgacaaa gaggatgatt cctctgacga tgaaggacca 4200
ggtgcaggtg gtgcgcgtca tttggcatcg atccttttcg gaaccatggc acctcctcgc 4260
ccattgtcat ccatgggtaa cgaagctaca tctgcgcctg aatctcctgc tgtagcatct 4320
ccaccagcgg caaccccccc acctccacca gtacctaact tcaatgcacc gccacctcct 4380
ccaatgccat cagccggtgc gccaggtggt cctccaccac cacctcctcc tccaccaggg 4440
atgggtgctc cacctccacc accaatgcca ccaatgggag gcgctcctgc tccaccagca 4500
ggtgtacgac cagctggtct cttgggtgaa atccagatgg ggcgatcgtt gaaaaagaca 4560
caaactaaag acaagagttc agctgctgtt gctggaaggg ttttggatta aatacctttc 4620
aaatcattga gaagagacaa gatgaaatgg aggtttgtgg ttagcgagcc taagaacatg 4680
gattgtatta taaattactt ttggttcata gtattgggca agggggctta ggtgtggaag 4740
gtgcgaaaca ggaaagataa gagacgagca taatttgtag tcgaagtagc aatttgaaaa 4800
tattcgttcg ttttgatagt catttgatgc acttatcacc a 4841

<210> SEQ ID NO 19
<211> LENGTH: 4122
<212> TYPE: DNA
<213> ORGANISM: Sclerotinia sclerotiorum
<400> SEQUENCE: 19
atgttttcgg gttcgaactc gtatctaggt ggtaatagtg gccggcaacc gccacaacaa 60
caaccacagc aacagcaaca gtatggcggt tttcagccaa atcaaggttt ccaaccacaa 120
cagactggct tccagccaca acagactggt ttccaacctc aacccactgg gtacggaaac 180
gtcgctcctt tgcaacccaa tttcacaggt tatcctcttc aagcacaacc tacaggatat 240
tctcagccgc ctcaatcagg gtttcccgga ggccagcagc agttcaacaa tgctcctcaa 300
cagcagagct tccagacggg agctccgcca atgccgcaga ttccacaaca attccagcag 360
cagcctcaac aaatacagca agcccagcca tctccagcag ctcccgtgca gcaaccgcaa 420
gccacgggat ttgcagcgat ggcagattca ttcaaatctg cttcagaacc atcgaagcca 480

-continued agaggacgca gagcctctaa gggtggagca aagataccca gtataagact ttcgttcatt 540
acagcccaag atcaagcgaa gtttgaaacc cttttcaagt ccgcagtcgg agacggccaa 600
acattgtctg gcgagaaatc gagggatctc ttactgcgct caaagttaga tgggaactca 660
ttgtcgcaaa tatggacgct cgcagacact acaagatctg gacaattaca tttccccgag 720
ttcgcattgg caatgtacct ttgcaatctt aagctcgtcg gcaagtcact accctcggta 780
cttcccgatc agatcaagaa tgaagtttct agcatggtag atatcataaa ttttgctata 840
gaagatgatg ggccagcagg aacgaatgcg ccgagttttg atagtcgaca gagtactgca 900
acgcctccga ctatccagca gccacagcca atgccgtcaa attctgcttt actcactgcg 960
caaatgactg gtttccctgg acagcaaaat aacttctccg gtgggtttca atcgcaaccg 1020
acaggtttcc agagctcaat gcaaactggc tttcctgggc agcaaggagg attgcagcct 1080
cagccaactg gattcagtca gaatatgtca aaccctcaag caacgggata tactggaccg 1140
cgccctccaa tgccccctat gccatcaaac ttcagttcca atctgtctcc tgctcagacg 1200
ggtatgcaag gcggcatgat tgctccgctg aatagccaac ctacaggagt cccaggtcaa 1260
tggggattgg tcaatgcgcc tgcaactggt ttgcctaaca tcgatctact acaatctcgg 1320
atgatgccgc agcaaggccg agaacaaggc aattttacta cagctggcat aacaggcaat 1380
gccgtcattc catgggcagt tacaaaggaa gagaagacta ggtacgattc cgtcttcaaa 1440
gcttgggatg gatttggaaa aggattcatt ggtggtgatg tcgctatcga ggtcttcggg 1500
cagagtggcc ttgaaaagcc cgacttggaa cgcatctgga ccttatcgga tcacggcaac 1560
aagggaaagc ttaacatgga tgaatttgcg gttgccatgc atttgatcta tcgaaagctt 1620
aatggatatc ctctaccagc tcaattacct cccgagcttg tacccccctc cactcgtaac 1680
ttcaatgatt caattggagc cgtcaaatcg ttgcttcatc aagaatcaga tttccgaaag 1740
aattctggcg cgacactttt gccccaaaag actggactga agaagaaagt cagagagaag 1800
caagtgttat tggacgcgat tgatttcaag gacgaaaatg ctgcggatga agacgatgcc 1860
cttgatcgta aggatcgtcg tgaagcagaa gatttgtatc gtcgcattcg tcgtatccaa 1920
gaggacattg atgcgcaccc agacgcttca ttgcgtaacg ttgactccgg cgccgagcgt 1980
cgtgccatga agagacagtt gcagacattg acagataaac ttccggatat tgcgtcgcgt 2040
gttcgacgaa cagaaagaag cattgccgat gcaaagcttg aactctttcg tctaaaggat 2100
gcaaaagctc accctggaag tgcttccagc attgttggaa ctggtccagg tggcgcggtt 2160
accgaatcag atagactcaa agcaagagct aaggccatga tgcaacaacg ctctgctgct 2220
ctcactggca agaagattga gataagtaat gatgatttgg atgcaccaaa acgcctcgag 2280
gaagaaaacc ttaagatcag aaccgagaag gaaaataatg agcgaatggt tcaagatgtc 2340
gaagaaagtg tccgcgattt ttcacggggt ctggaggata gtctcaaaga tggtggcgag 2400
agttcatcta gcgagcatga aaaaagacgc tgggaggatg ggctcggtgt tgaagatgaa 2460
gtcaaggact tcatctttga tttgcaaagg agcagtagaa gtgcaaaagt taggactgac 2520
gatcgcagta gggaggctcc cactgagacg tctcgtgtta gctccgctcc agcagctcgt 2580
agtgaaactc catcgtcgca gccttcatct acaccaaccc cttctgcagg tacatattca 2640
caatataaga cagcagaaga tagagcagcg tacatcaagc aacaggcaga gcagcgcatg 2700
gctgagcgtc tagctgctct tggcattagg gcaccttcta aacctggaga gacaacacaa 2760
cagagattgg agcgtgagaa gaatgagcgt gctgctaaac tcaagcaagc ggaagaggaa 2820
gatgctagac gtgaggccga aaggcaagct agaattgctg aagagcaggg agtggcccca 2880
catacaccgg atcaaccaaa agaaattacg aaaaagccac ctccgccgcc ttcgaggaag 2940
gctgcaagaa gcgacgctag tgaacgtaaa ttcgaagagg atagaatcct caaggagcaa 3000
aagtcacaaa ttattgccac aaatgagcta gaggacgatg ctcaacgaca agaaaatgag 3060
cttgcaaaag agcgcgaggc agctcaagct cgtgtgaagg cattggaaga gcaaatgaag 3120
gctgggaaat tgaagaaaga agaggaaaag aagaagagaa aggctctaca agccgagacg 3180
aagcaacaag aagctcgtct tgcagctcaa cgtgcggaga tcgaagccgc ccaagcacgt 3240
gagcgggaat tgcaacgtca actggaagct attgatgatt cagactcatc agatgatgat 3300
gaaggtccag agcaagttac tcctcaagcg tcaacaccaa ctcaggggag ccaagaattt 3360
gagcgcaaag aagcctctcc accccctcct cctccctcag tcccagtcat tgtatcaccc 3420
gtccctgcgg cagcaacaac aaccagcctt cccccaccaa ccccacaagt tactagccct 3480
gttgtcagcc ctccagctga aacagaaacc cgcaatcctt tcctgaagaa aatggctcaa 3540
tctggtgatg cttctgccgc atctactgca tctaacaacc cattccatcg tcttccttct 3600
caagaacttc ccgctcctgc gccaattcag gttcagccaa caggtaacag accatctcgt 3660
gtccgtccag aagaggatga ttgggacgtt gttggatctg acaaggagga tgattcctct 3720
gatgatgaag gacctggtgc aggcggcgcg cgtcacttgg catcgattct ttttggaacc 3780
atgggacctc ctcgtccttt gtcggctatg ggcaacgaag ctacatccgc acctcattcg 3840
cctgctgcgg catctccacc agtggcatct ccaccacctc caccacccat gccatcagcc 3900
ggtgcaccag gcggtccacc tccaccacct cctcctccgc caccaggaat gggtgctcca 3960
cctccaccac caatgcctcc catgggaggg gctcctgcgg ccccacctgc gggtggacga 4020
ccagctggat tcttgggtga aatccagatg ggaaagctt tgaagaagac acaaactaag 4080
gacaagagtg cagctgctac ggctgggcga gttttggatt aa 4122

<210> SEQ ID NO 20
<211> LENGTH: 2415
<212> TYPE: DNA
<213> ORGANISM: Botrytis cinerea

<400> SEQUENCE: 20
gggtgtgggt gtagatgaat taaatgaaga acatcagcgt tccaaggtaa tccgtatcca 60
tcatatcaca tcacatctct tcacatcact ccaatattct ctcttctatc ctctctctct 120
ctctctctcc ctctccctct ctgtcttcct ccccctcgcc gtcgtcgctt cattgtagga 180
gacctctttc tcgtcgctcc ataccagtcc cgcaaatcga tagcttcttc catttgcctg 240
ctaattacca ttccatatta cattatttat atgcgtaatt agcaaccttt tgcctccttc 300
cccttgcatt agcaccacga aacatcgaga accagacagc tccattccct caaacaacct 360
cctattcgat cgatcattcc ttcttcaaca agactttgga acaactactg cacttcaata 420
tgtctcaaca acctgaagct gtaaataata tgcataattt gactacgctc ataaaacgac 480
tcgaagccgc aacctctcgt cttgaagata tagcttcctc taccattcca ccacctgctt 540
catcatccat ccctctaatt tctcctccgg ccgaagctgc gaaaacaaat ggcacaactc 600
cgccgccgcc aacgatccaa acaccagata tcaaaaagat catcgaggat ccaatcccag 660
gagtagtctc agagttcgat aattttattc agggggcggt taagaaatat gttaacttga 720
gtgatgagat tggaggggtt gttgcgcagc aggcatctag tgtattgaag gcatatgtcg 780
gacaacgaag atatattttg atcactacaa agtcaaagaa acctggcatg caagatgaac 840

```
cattccaaaa gctcatcaaa cctcttcagg attcatttac tgccgttgat gatatccgaa    900
agtccaatcg tgcatctcca ttcttcaatc atctcagtgc tgtttctgaa agtattggtg    960
tacttgcctg ggttacaatg gacaacaaac catttaaaca tgtcgatgaa tcattgggat   1020
ctgctcaata ttacggaaac agagtattga aggaatttaa ggagaaagac ccaaaacaag   1080
tcgaatggat tcaagcattc tatcaaatct ttaaagatct cagcgaatat gctaaggata   1140
acttcccaaa cggtattcca tggaatccaa agggtgaaga tttggaagtt gcgattaagg   1200
atgtagatga aaaggctcca gcccctcctg ctcctcatcc aaaggctgca actgctggag   1260
gtgccgcacc accaccaccc cctccacctc ctcctccacc agtcttcgat gacattccat   1320
caaagccagc accaaaccaa gcagattcag gtgctggact aggagccgtt ttctctgaac   1380
tgaataaagg agcagacgtt acaaaaggat tgcgcaaagt gaatgctgat caaatgacac   1440
ataaaaatcc ttctttgaga gcaggtgcta cagttcccac cagaagtgat agtcaatcca   1500
gtattaattc gaaccgagga aagagtcctg ctcctggtaa aaagcccaag ccagagagta   1560
tgagaactaa gaaaccccct gttaaaaaat tggagggtaa caagtggttt attgaaaact   1620
acgaaaacga gtctgagcca atcacaattg aagcatctat ttcacactcg atcctcattt   1680
cccgctgctc aaaaaccact attatcatta aaggaaaagc aaacgctatt tctattgaca   1740
actcccctcg tcttgccttg gtaattgata gtctcgtctc atcgattgat gttatcaaag   1800
caccaaactt cgcacttcaa gtactgggca cattgccaac gattatgatg gatcaagttg   1860
atggtgctca aatttacttg ggaaggaga gtttgaacac ggaagtcttc acgagtaaat   1920
gtagtagtgt caatgtgcta cttccagatt tggagagtgc agacggggaa ggagattaca   1980
aggaggtgcc gttgcccgaa cagttgagga cttgggtgga gaatggaaag gtcaagagtg   2040
agattgttga acatgctgga tagattggtt gagatggatt gtggagtttg gggagaggct   2100
ctggcgaaaa cttgttgggg gtgaggggta atgagatgtg atggagaatc tgggtagatt   2160
tgatattata gagatagttg agtgaagttt tatatcatcg catgttagtt gaagttttca   2220
ggcagagtag aagtcaaagt tgaattgtac atatctatgt atatgtatat ccgaggcttg   2280
tctcgctttg ttgtttagta gatttcaaac cgaagatttt ctactcatca tatcgtgccg   2340
tgtgttttat attgggcgat gtgtcgttgt gctttttctc tctctatctc ttttactttc   2400
agggaaataa atata                                                    2415
```

```
<210> SEQ ID NO 21
<211> LENGTH: 1617
<212> TYPE: DNA
<213> ORGANISM: Sclerotinia sclerotiorum

<400> SEQUENCE: 21
```

```
atggctacaa ataatatgca taatttgacg acgctcataa aacgactcga agccgcgacc     60
tcacgcttag aagatatagc ctcatcaact attccccctc ccagtactcc caaaacaaat    120
ggtacaacaa gcgtcgcatc tcctaccgta caagccgcta ctcctacagt tgtagccccg    180
actattcaaa ccattatcga agatccagtt cctgaatcaa tcagcgaatt cgatgctcta    240
attcaggggc ctgtgaagaa atatgttaat cttagtgatg agattggtgg ggtcgttgcg    300
gaacaggcat ccggtgtatt gaaagcattt gtcgggcagc gaagatacat tttaattacc    360
acgaagtcga agaaacccgc tatgcaagat gaaccattca aaaaactcat caaacctact    420
caagattcat tctctgctgt tgacaaaatt cgaaagtcta atcgtgattc accgtatttc    480
attaatctca gtgttgtttc ggaaagtatt ggtgtacttg cttgggttac aatggataat    540
```

```
aaaccatata aacatgttga tgaatcattg gcatcggctc aatactttgg aaatagatta    600

ttgaaggaat tcaaggagaa agatcccaaa caagttgaat ggcttcaagc attttatcaa    660

atcttcaaag aacttagcga atatgctaag aataactacc caaatggtat tccgtggaat    720

ccgaagggag cagatttaga agatgctatc aacgaagtag attcgaacgc tccagcccct    780

cctgctcctc acccaacagc gactagtgga ggagccgcgg caccaccacc acctcctcct    840

cctcctcctc caccagtttt cgacgacatt ccaacaaaat ctgcaccaaa gccaggagat    900

gcaagtgctg gactaggagc tgttttctct gagttgaata agggagcaga tgttacgaag    960

ggattgcgca aagtcaatgc tgaacaaatg acacataaga atccatcttt aagagcaggt   1020

gctactgttc ctactagaag tgatagtcaa tctagtatta gttcgaaccg tggaaagagt   1080

cctgctcctg gtaagaaacc taagccagag agtatgagaa ctaagaaacc tcctgttaag   1140

aagttggagg gtaacaagtg gtttattgag aactacgaaa atgaatcatc gccaattgaa   1200

atcgaagctt caatttcgca ttcgatcctc atttcccgtt gctcaaaaac tacaatcatg   1260

attaaaggaa aagcaaacgc catttccatt gataattccc ctcgtctttc cctaattatc   1320

gagagtctcg tttcatcaat tgatgttatt aaagcacaaa gttttgcgct tcaggtattg   1380

gggacattgc caacaattat gatggatcag gttgatggtg cacaaattta ccttgggaag   1440

gaaagtttga acacggaagt tttcacgagt aaatgtagta gtgttaatgt actattaccg   1500

gatctggaaa gtgaagaggg tgagggtgat tacaaggagg tgccattgcc ggagcaattg   1560

aggacttgga ttgaagatgg gaaggttaga agtgagattg tggaacatgc cggttag      1617
```

<210> SEQ ID NO 22
<211> LENGTH: 2601
<212> TYPE: DNA
<213> ORGANISM: Botrytis cinerea

<400> SEQUENCE: 22

```
gacacatgcg atatgcaaag tctagaacct cgaatactga ttcgaaaaag actggcaatt     60

ccataaatct acagtatatt ttaatccgca actcatgaat gactacattt aatacgaatt    120

acaaacattc cctaacgcca aaatggcagc tacgattccc ctctccacta caacatgctt    180

gacctcctca gaagctttca aatatcctct tccacagatt cgtcaattcc accgcgatct    240

cactacagag cttgacgaga aaaatgcacg tctgcggaca ctggtcggag ggagttatag    300

acaattactt ggaaccgccg agcaaatctt acagatgcga caggatatta gtggagtaga    360

ggaaaagtta ggcaaagtag gagaaggatg tgggagaaat gtgttggttg gaatggttgg    420

cggattggga aaattacagg gagaaatgaa gaatggaaag aagggcgagg aaatgcgggt    480

tgtggctaag atgaaggtat tgggtatgtg tgggattgtg gttgggaagc tcttgaggag    540

accagggcga atggatgggg atggtgggag agggaaggaa ttagtagttg ctgcgaaagt    600

cttagttttg agccgattgt tggcgaagag cttggagaat actggagata aggaattcgt    660

tgaagaagcg aagaagaaga ggtcggcttt gacgaagcga ttgttacgcg cagttgaaaa    720

gacattggtt tccgtcaagg atgctgaaga tagagacgat ttggtacaga cactttgtgc    780

atacagtcta gctactagtt ctggcaccaa agacgtcttg cgacatttct taaatgttcg    840

tggtgaagca atggctttag cgtttgacga tgaagaggag tcgaacaagc agacctcagg    900

tgtcctacgc gctttggaaa tatatacgag aactttacta gatgtacagg ctctagtgcc    960

aaggaggctg agcgaagcgt tggctgtgct gaagacgaaa cctttactga aagatgacag   1020
```

cattcgggaa atggagggat tgaggttgga tgtatgtgag cggtggtttg gcgatgagat 1080
tatttacttc acaccttatg tccggcatga tgatttggaa gggtcattgg cggttgaaac 1140
actacgaggt tgggcgaaga aagcgtcaga agtgttactg gaaggtttta cgaagactct 1200
tcaaggggga ttagacttta aagtagttgt tgaactacga acaaagattc tggaggtgtg 1260
ggttagagat ggaggcaaag caaggggatt cgatccctct atacttctaa atggcttacg 1320
agacgttata aacaaacgac tcgtagagtt attagaaact agagttggca aacttcatct 1380
agtggggaca gagatagagt ccacattagc aacatggcaa gaaggaatca ccgacataca 1440
tgcaagtctt tgggacgaag atatgatggc aaccgagctc agcaatggtg gtaacatttt 1500
caagcaagac atacttgctc gcacgttcgg acggaacgat gctgtttcaa gagttgttaa 1560
cagttttcac acttggagac atctcatcga ggaaattggt acttatattg atgaactgaa 1620
gaaacaaaga tgggatgatg atttggaaga tatggaagat gatgaaagtc tcgaatcacg 1680
acaaaacctt cttagcaagg aagatccaca aatgctacaa gatcatctcg attcaagctt 1740
agaaaattcg ttccaggagt tacacgcaaa gatcacttca ctggtggacc agcaaaaaga 1800
tagtaaacat atcgggaaaa tatcgatata tattctccga attctacgag atatcagagc 1860
agaattacct agtaaccctg cactacaaaa gtttggactc tcacttgtct catcactgca 1920
cgaaaatctc gcaggtatgg tctcagaaaa cgccatctta gcccttgcaa aatctctcaa 1980
gaagaagaag gttgcgggca gagcattatg ggagggtaca ccggaacttc ctgttcagcc 2040
ctccccagca acattcaaat ttttgagagg tttatcgact gctatggctg atgctggagc 2100
cgatctatgg agccctgttg ccgtcaaagt gttgaaagcg cgtctggaca cccaagttga 2160
agaccaatgg agtaaggctc taaaagaaaa agaggaagag cctagcaatg gaatctctgg 2220
ttctcccacc aatgctcccg aagcagatgc cgaggaaaaa gaaggggacg cttctgctcc 2280
taatcctgct gctgctgtag aagtagatga agaaaaacaa aaggatttac taaagcaatc 2340
actgttcgat atatctgtct tgcagcaagc tttagaatca cagtcagaca ataaggagaa 2400
caaacttaag aacttagcgg atgaggtggg aggaaaacta gatctcgagg cgagggaaag 2460
gaaacgtatg gttaatggcg cggcggagta ttggaagagg tgcagtcttt tgtttggact 2520
tttagcgtag attccagatg gatgaattag tgagaggctt ataatgaatt atattacgaa 2580
tactttactt ttgagtattc a 2601

<210> SEQ ID NO 23
<211> LENGTH: 3437
<212> TYPE: DNA
<213> ORGANISM: Botrytis cinerea

<400> SEQUENCE: 23
gcaggggtcg gatcaacatg tctataaaca aacatatgta ccggcgttga tctctcctgc 60
agactgcatt tgcacttgct tccctcttcc tcctcccgtt tcctggtctt cttctacaag 120
ctgcaggcga gagagataac ttctacgcac cttccatatc cctcacctct tctctcccca 180
caagttcgtt cataatcctt tcgtcctgtt gttttgtcta gcattacctt gcaattctta 240
acaacggccg atcgtggaca tcaatcaata aaaaggacga caaatcatct tataattatt 300
atcccaaact ttcattgcac aaatttgaat tggatactca tttggcttta ttcggagcga 360
taaacgtaga aattaatcgt ataggggctt ttatcagaca atcaagaacg gtgattggct 420
cacagcggtg aattgtgagg ggtggtaata cagaaaacaa atagtatagg gagtattttt 480
gggtggattg ttaccaatgt ctaccacaag aatctcaaca ccgaaaaggt cccccaaaaa 540

-continued

```
atcgactttt gtcaaaactg gaatcttgac caccaaatca acgcccaatc tcaacgcctc    600
ctataatttg gcattactac aagcttcagg agctacaccc gttcctgcat atccttccaa    660
taacggtcaa agttttgccc taaataatcc taggtcgcaa ccgtctcgac aagtctcact    720
cgcttccctt acctcgaatt cacttgcgac aatcccggat gcaagcaaga gataccctct    780
ttctacagtc tttgatgagg atatgccaac agtaggcaac atgccgccat acacacctgc    840
tcgagttggc ggtggaccgg aagaactaga ggttggtgat atagtcgatg tgccaggtaa    900
catgtatggt atcgtcaaat ttgttggcag tgtgcaaggc aaaaagggtg tatttgctgg    960
ggtagaatta agtgaaacgt ttgcttcgaa agggaaaaac aatggcgatg tcgaaggaat   1020
tcaatacttt gacacaacca tcgatggtgc tgggattttt cttccagtca acagggcgaa   1080
gagacgtagc accccttcgt cgcatgatga gtcatttccc ctttcaccgg cgtctccatc   1140
gatgggcaat agggctggga gattaggatc tgaattaaat ggtcagccaa cacctttgtt   1200
accaaaattc ggtcaatctg ttggtccagg cagagcggca aacccatatg tccaaaaaac   1260
acgtccatcc atggctacac ctaccacctc aagaccggaa tcaccagttc gaagagcagc   1320
caatgccaac ccatcattaa atacacctgc acaaagagtc ccatctcgat atgcaagccc   1380
tgcgcaggca aactttggac agagcgttag aggaacacaa gattctagag atccaagtaa   1440
gaaagttggc tacacccccc gaaatggcat gaaaacacca atacctccac gaagtgtttc   1500
tgcacttgga acggggaata gacctgcacc aatgaactcg atgaatttca gtgatgaaga   1560
gacacctcct gcagagattg cacgtacggc aacaaacgga agcgtaggct cagtctcttc   1620
tttcaacgcg aaattacgtc cagcatcaag atccgcatcg cgtacaactt ccagggctac   1680
cgacgacgaa tttgagcgat tgagaagttt gttagaagat cgcgataggg aaataaaaga   1740
acaggcttct attatagaag acatggagaa aactctcagt gaagcacaat cgttgatgga   1800
gaacaataac gagaacgcaa gtggtagaca tagtcaggga agtgtggatg acaaggacgc   1860
aacacagttg agagcaataa tacgtgaaaa gaacgacaaa atcgccatgc tgactgccga   1920
gtttgatcag catcgagctg atttcagaag cacgatagac acgctcgaaa tggccggtgc   1980
ggaaaccgag cgagtgtacg acgagcgcat gcgtgttctc gtaatggagc tcgatacaat   2040
gcacgagaat agtcatgatg taaagcacgt tgctgtacaa ctgaaacagc tagaagagct   2100
cgttcaggag ctcgaggaag gtcttgaaga tgcacgacgt ggtgaagccg aagctcgggg   2160
agaagttgag ttcttgcgtg gagaggttga aagaactcga tctgaactcc gccgcgagcg   2220
agagaagact gccgaagctc ttagcaacgc aaattctcct acgagcgcaa gtgcggaaac   2280
acattccaaa gagattgctc agagagatga cgagattcgt ggattgaaag ccatcatcca   2340
ctcgctcagc agagatgcca tacctgatgg gaatttctcg gatcatgagg caacaccaaa   2400
tattctacga cctggactaa accgaagtcg aacagaaagt gcttcggttt ctgaggagga   2460
gcgccgtact cgggaaaagc tagagcgaga agtgagtgag cttcgtgctc tcgtcgaaag   2520
caaagacaat aaagaagaac aaatggagcg cgagttggag ggattgcgaa gaggaagtgt   2580
tagcaatcct actacgcatc gtactagtgc catgagcagc ggaactgtga ctcaggatag   2640
gaattctctc caagacaata agagcacagt tgtaagctgg cgagaacgtg gtgcctcaga   2700
tgctcgccgc tacaatctgg attcaatgcc agagaatgac agctactcct ctgcagctga   2760
ggatttctgt gaattatgcg aaacctcagg tcatgatgtt ctacattgcc cgatgtttgg   2820
ccccaatggt aacagcagca attctaagga tgagtcacct aaacagcaac gaacaggaaa   2880
```

agacgttgtc atggagggac ttaaattatc acccaaacct tctcaagaag aatacaaacc 2940
ggcgccgtta gcgccagcta agaagtcgcc tgatgcgtcg cctatcaaga ctgttcccaa 3000
ccttatggaa ccaggacctg ccccaggaaa ggaaagtgga gtaatcaaca tggataaatg 3060
gtgcggtgta tgtgaaagag atggacatga cagtattgat tgtccttttg aagatgcttt 3120
ttaggagact actgctttcg atgtttcagg ataagcagtc acaacgacga ctttttttcat 3180 agatttttctt tgttaatcat aggcaaggcc gcattgcatt gcaggagcgt aatccgtctg 3240
cgatataccc tttcggttct ctgtttgaag tatgcttttc aagcgataag tttagagggg 3300
aagatgatgt ttttacgagg attgaatgag atggatgaat gcaggctaaa tcggggaagg 3360
gggagggaag acaaacatga gttgaacgga cgtaatgatc atgtagtata ctttgtcaaa 3420
ttaatgatcc aaatgca 3437

<210> SEQ ID NO 24
<211> LENGTH: 3180
<212> TYPE: DNA
<213> ORGANISM: Botrytis cinerea

<400> SEQUENCE: 24
gatccaccca catccttcct catatgactt cgatgataat tacatagaca ctgccagtat 60
gcctggcctc gttcgcaaac tccttatctt tgccgccatc gatgggttga ttttgcaacc 120
agcagcgcca aaaggccaac gccccgcccc cgcaacgaag atcgcataca aagataagca 180
tatcgggcca gtattgagtg atttgcagga tctggagggg tcgtctgcga aaagtttcga 240
ggcatttggt attgtcggtc tcttgacggt ttccaaaagc tccttcctga tatcgattac 300
gaaaagagag caagtcgcac aaatacaagg gaaacctata tatgttatta ctgaagtggc 360
tttgacccca ttaagttcca agaacgaagc agagatctcg attgatagta cgaaagcggg 420
gttattgaag agtaatatcg aggggcagca tggcttggac gagagtgata gcgaggatga 480
tgtcgttagc gatgaagtgg aggacgatac agcagtagaa gcacacaaaa gaacgagtag 540
cgtagctgaa gatgtgatct cgaagaaggg gggatatgga agatttgctc aaaaatggtt 600
ctcgaagaaa ggatgggccg tggaccagaa gaagaacctg gggatgagcg ctgagccgta 660
ttccacagtg gagcaagctt ccaaggccac cgatgtacca gctacgattt caggagtcac 720
tgaaggaaaa tctgatatct caattcccga taagggcaag gaaattgagg acattgaaac 780
tcctgaaaat attagcgaca ttgcagagag catgctgcca aaattactac gaacatcgca 840
gatattgttt ggggcctctc ggagttacta cttttcttac gaccatgata tcacaagaag 900
tttggcaaat aagaggaata caaattctga attgccattg cacaaggaag ttgatccact 960
cttcttctgg aatcggcatc ttactttacc atttattgat gctggccagt cttctcttgc 1020
cttgcctctt atgcagggct ttgtaggaca gcgtgcattt tcaatggata gtaatccacc 1080
aaaccctgct ataggttcag acactggaaa gacttccgtg cagatgaagg atattacaac 1140
aagtagttcg gatgagcaaa tttacacagc acgtgctggt acagacaagt cgtatctatt 1200
gacgttaata tctagaaggt cagtcaaacg tgccgggctt agatatttac gccggggtgt 1260
ggatgaggac ggcaatacag ccaatggcgt ggaaacagag caaatcttat cggattctgc 1320
ttggggccct tcgagtaaga catattcgtt cgttcagata cgtggcagca ttcccatatt 1380
cttctcccag tcaccttact cttttaaacc tgtacctcaa gttcaccact ctaccgaaac 1440
aaattatgaa gctttcaaga agcattttga taatataagt gatcgctacg gggccattca 1500
agtggcttcc ttggtggaga agcatggaaa cgaggcaata gtcggtggag agtacgagaa 1560
attgatgact ctccttaatg tctcccgagc tagcgagctt aggaaatcca ttgggtttga 1620
atggtttgat ttccatgcta tttgcaaagg tatgaaattt gagaatgtca gcctgctcat 1680
ggaaatactg gacaagaagc ttgactcgtt ttcgcacact gttgaaaccg atgggaaact 1740
tgtatcgaaa cagaatggcg ttttaaggac taactgtatg gattgtctgg atcgaacaaa 1800
cgttgttcaa agtgcagtgg caaagcgagc acttgaaatg cagttaaaga atgagggact 1860
agatgtcact ctacaaattg atcaaactca acaatggttc aatactttgt gggccgacaa 1920
tggtgacgcc atttctaagc aatacgcttc tacagcagca ttgaagggag actttactcg 1980
tactaggaag cgggattata agggggccat cacagatatg gggctttcta tctccagatt 2040
ttatagcggc attgtaaatg actacttcag tcaagctgcc attgatttcc tgcttggaaa 2100
tgtgagctat cttgtttttg aagacttcga ggcaaacatg atgagcggtg atcctggcgt 2160
ttcgatgcaa aaaatgaggc aacaagccat tgatgtttct cagaaactcg ttgttgctga 2220
cgaccgtgaa gaatttattg gaggatggac atttctcact ccgcaggtac ccaatacgat 2280
caaatctagt ccttttgagg aatccgtcct cctattgaca gatgctgcat tgtatatgtg 2340
caattttgat tggaatatcg agaaagtatc atctttcgtg agagtggact tgaaccaggt 2400
gaacggcatc aagtttggaa catacatcac gagtactttg tcacaagccc aggcagatga 2460
gaagaggaat gtgggctttg taataactta taaggctggt tcaaacgaca ttattcgcgt 2520
gaacacgaga tctatggcta cggaatttcc ttcttcgaaa ctctctctcg aagacaaaac 2580
atccacgccc gcttctacat ctaccaccaa ctctgtcgtc gccccaattg ccgccgggtt 2640
tgcaaaccta atctcaggtt tacaaaatca aagtatagcg gaacctaaag atctcgtgaa 2700
ggttctcgca ttcaaggctc taccctccag atctgcggta tcagatgaag gagttagtga 2760
ggccgagcaa gtgaagagtg tctgtggaga gattagaaga atggttgaga ttggaagtat 2820
aagagaggct ggagaggaga gaaaggatat tgtagaggag ggtactatca ttagtttggc 2880
cgaggccaag aaaagcacgg gactattcga tgtgctggga catcaggtga agaaactggt 2940
ttgggcttaa tgaaagtgta tcgatactcg tgctagtaat gcttagagca aaagaagcac 3000
ttcttgaagg atttacgaat ggaattgtgg aagttggcag ggaggttagc gatcgtcaag 3060
aacgggtatg tggaattcaa ttccatattg aagctgcgaa actcattaac ttcaatagaa 3120
gtggatgtgt agatagaccc gagtatatgg tattggccag ataagtaatt ttaatgggga 3180

<210> SEQ ID NO 25
<211> LENGTH: 2861
<212> TYPE: DNA
<213> ORGANISM: Botrytis cinerea

<400> SEQUENCE: 25
gagtattctc gattagacaa ttagaattct cgaacaatag aagccggagc tcgagttcct 60
cgatctttac ctacctgaag tctctcgatc agaagagtgt caaattccta tgatatcaat 120
gattattgag gatatattta caaaatcaaa tctcttcaat gaatctctat ctacctaagc 180
aagtcaatta tgattgatta caattatcgt tgttgcacgg aatccagtcg catttggtcc 240
cggtcactcg taacagcaac cacatcggta tttcgtagat tcccgagtat tgcctttaca 300
tacctaagga actttaaatc cccccaacaa cagaattgac gacagaatta ctaccattac 360
aagtgaaaac actccatggt acccaaatac aacagtctca tatagccatt tgatcgcaac 420
tcgcatcttt catctacaaa atgtcgtttg gaggggacat cggactcgat acaacatcgt 480

-continued

```
cgtccaatgc tgctggtaat ggcggcaacc agggcgagac aactggaaga cctgccaccc    540
ctcaagatgc aaccgcaaaa gcagttcaag atgtcacaag ctcggagatt ggaatatcaa    600
ccttgttaac ccgactgaaa caaagtattg cttccgcaaa ggaattcgca cttttcctca    660
agaaacggtc catcatggaa gaggaacatt cgaacggttt aaaaaagctg tgtaaggcaa    720
ccggggataa tattcgcaga ccagagcatc gacacggatc gtttctacag tcatacgaag    780
aggtcctcat tatacacgag cgaatggccg agaatggggc tcaatttggc gtgtctctac    840
atcagatgca tgaggatctt atcgaaatgg cttcgaacat agagaagggc agaaagcatt    900
ggaagaatac tgggttggca gcagaacaac gtgctgctga taccgaagct gccatgaaga    960
agtcgaaggc gaagtacgac tctctggcag acgagtatga tagagctcgc actggggaca   1020
ggcaaccagg aaagattttt ggcctcaagg gccccaaatc ggcagcgcaa catgaagagg   1080
accttcttcg caaagtccag gctgccgatg cagattatgc gtccaaggta caagctgcgc   1140
aaagccaacg aaccgagctc tggtcaaaat caagacctga ggctgtgaaa gctctagaag   1200
atctcattca agaatgcgac tctgcattga cattgcagat gcagaagttt gcatccttta   1260
acgaaaagct acttttgagc aatggcttga atataagccc tatcaaagga aaagagcaag   1320
ggacattaaa tcgcagtctc cgtgaagttg ttcacgcaat tgataatgtt aaagacctga   1380
gcaactacat cagtagcttc tctggtaaca tgcagtcccg gatcacggaa atcaaatatg   1440
agcgtaatcc ggttttgcaa cccgcacaaa ataccgctca gcgacaatcg gatcccaacg   1500
ctctccaagc tcgacaagga cccgtaatac caccacagcc atctcaccaa gttcatatga   1560
gccaaccttt taatcaaagc agtcccccaa ctcaccagcg cgaaagaagc tttagccatg   1620
gcccatctct ttcgcaacac atcgttgcac ctgttgtatc gcccactaac ccaatatcca   1680
cctctcccga cttcaatacc tggtcacctc gtgcagatgg cccccccag atatcaacct    1740
tgccatttca gccacaacct caaaacgaga caccaataca acagacacca caaaaccccta  1800
caacgcatgc accagtgtcc catggcccat cctcggcacc actattcgga gcgggatcgg   1860
ctccagctcc aggcaacagc actcatctag cacctttgaa accagtgttt ggactcagcc   1920
tcgaggaact ctttgacaga gatggctctg ctgttccaat gattgtctac cagtgtattc   1980
aagcagttga cctctttggg ctcgaggtcg aaggaatata ccggctatct ggtaccgcat   2040
ctcatataat gaagatcaag gcaatgttcg ataacgacgc atctaaggtg gacttccgta   2100
acccggaaag cttctttcac gatgtcaata gtgtggctgg tcttctcaaa cagttcttcc   2160
gcgaactccc agacccttta ttgactatcg agcaatatcc tgcatttatc gaggctgcaa   2220
agcatgatga tgaaatagtc cgtcgcgact ctctacatgc gatcatcaat ggccttcctg   2280
atcccaatta cgctactctt cgagccttga ctttacattt aaatagagta caggagagtt   2340
cggcatctaa caggatgact gcaagcaact tggccatagt atttggccct acactcatgg   2400
gtgctaattc aggaccgaac atgtcagatg ctgggtggca ggttcgtgtc gttgacacta   2460
ttttgaaaaa cacttatcag atatttgacg acgactgagg cgaagaagat tgtcgattga   2520
cttgaagagt tcttaacgag ataccatagc tgctcatatt atgaacctgc ctttggaaca   2580
gaaacaaggg cagggaattc ctagcatcag acctctattt gccgacaaga cattctaaag   2640
aaagtacatg ccactgtatt tcgaatacta ttattgtaag gcacgggcct gttgacaaat   2700
atttacggtc tatcaagcga gtgtacgtca gggggtggtc tacaccacga tcgattttgt   2760
agggtcatgt gctcagctct gatgccagta ttggtgcaac tattgaatca aaagggtacc   2820
aaggtttcaa tactcgttaa ttttggatca cgaaaagatc a                       2861
```

<210> SEQ ID NO 26
<211> LENGTH: 2429
<212> TYPE: DNA
<213> ORGANISM: Botrytis cinerea

<400> SEQUENCE: 26

```
gatacaaaag ctttcgaaag ccgcttgagt aagtaagaag gcaataagag aggtcctcgt      60
ccgtgtcgag atgtgatgct tgagtcattt tcctggtata gcttctgcaa tcgagttcac     120
actctactac ttgattcaga ttacaccagg agtaacacct caagtattcc atattaaata     180
caaacctttc ccatcttaat ctattgttgg cgcatgggga gaggaattaa ttgctttgct     240
ttttggccat caggatgtgg tcattagatc gattatccgg acacacaaca ccttctgcct     300
ctccacctcc cccgttaaat aggatcccaa atctccctcg tcgtccgagt catcttgtgc     360
catccccagt tggtggtaga cctcctttca acccaagatc gtcttccctg tcgttaatct     420
ccaatgactc taattcatcg ttgctatcat cacggagacc caatggttcg aatctcaaac     480
aagcagtcac atctccgaat gtgccagatc ctttggaggt tttgggaaca ctactgaata     540
atggggaaga gacaaaattg ccatcagcga aaagcccggg ggcgacaaat gggacagttg     600
ctcccattga agaggaagac gatgaaggcg aatgggattt cggaggttta agtctgcaag     660
acattgtagc aggagaacct ctcgatgttg aggatgagca tgtgtataaa tctcaaacgc     720
tggaagaata tgagcgcgag aaagagaagt ttgaagacct ccatcgatca attcgcgcct     780
gcgatgacgt tcttaattca gtcgagataa acctcacaag ctttcaaaac gaccttgcta     840
tggtatctgc ggagattgaa actctgcaag cacgatcgac ggctttgagt gtaaggttgg     900
aaaatcgcaa agtagtagag aacggacttg ggcctatagt ggaggagatc agtgtctctc     960
cagctgtcgt taaaaaaatt gtggatggag ctatagatga agcttgggtt cgagcattgg    1020
cggaagttga gaaacgatca aaagcaatgg atgctaaatc gaaggagcaa cgtactataa    1080
agggcgtgaa cgatcttaag cctttactgg agaatctagt ttccaaggca ttggaaagaa    1140
tcagagattt cctcgttgct caagtgaaag cattgcgatc gcccaatata aatgcacaga    1200
tcattcagca acagcacttt cttcgctata aggatttata tgcattcttg catagacatc    1260
acccaaagtt ggctgaggag cttggtcaag catatatgaa tacaatgcga tggtacttcc    1320
ttaatcagtt cacgaggtat ttgaaggcgt tggaaaagat caagcttcat gtgttggaca    1380
gatacgatgt gctcggatca gatgacgggt ctcgtaaggc cactcttctt tcaggatcca    1440
aacagacagg tccaccacac gacgcattca atctaggtcg acgaatcgac cttctcaaga    1500
cgccaaacca aactgcactt ccctctttct tagccgaaga agacaaacaa acccactata    1560
tggaatttcc tttccgtaac ttcaacctcg cactgattga taacgcttcc gccgaatact    1620
cctttcttac ctctttcttc tctccctctc taagctacgc taccatttcc cgacacttca    1680
actacatctt cgaacccact ttttccctcg gccaatctct caccaaatcc ctcatccacg    1740
agtcccatga ttgtctcggc ctcctcctat gtgtgcgctt gaatcaacac tttgcatttt    1800
cccttcaacg ccgcaagatc cccgctgtag attcctacat aaatgcaaca tccatgctcc    1860
tctggccacg cttccaactc acaatggata tccactgcga atccgtccgc accctaacat    1920
ccgctctccc tacccgcaaa ccctcagctt cggaacaagc taaacaatct gcagctccac    1980
acttcatgac ccaacgtttc ggtcaattcc tacagggtat cttagaattg agtacggaag    2040
cgggagatga tgaacctgta gcgagtagtt tggcaagatt gagaggcgag atggaagcat    2100
```

-continued ttttgacaaa gtgcgcgggg gttatgccgg ataagaggaa gaaggaacga tttttgttta 2160
ataattattc gttgattttg acaattgtag gggacgtaga gggtaaatta gccggggaac 2220
aaagggcgca ttttgaggag ctgaagaaag cttttggaga tggtgtctga tccttcactt 2280
cattttgata cttaattgga agtttttgag cgtgtacact tatcaaagcg tattatttga 2340
tcatgtattt tgtatttgtg aagagaaaca aagaactttt attatggtag aaatagagcc 2400
ggaaataatc tatgctgtgg aagaaacca 2429

<210> SEQ ID NO 27
<211> LENGTH: 4391
<212> TYPE: DNA
<213> ORGANISM: Botrytis cinerea

<400> SEQUENCE: 27
gggtctattc acacctctcc ctcgatcaat acgacgtctg cggcttctgc aacccattga 60
gaaaggtaga aaagaggttc aaaaagtcga gattccccgt gcctattctt ccttcttctt 120
cctgttctcc tcccactttc ctccgtgtga tacttcgtct atatctacct cacccccctcc 180 ccctcgaacg cagattgtac cgataccccca agtgattccg ccgtaccgtg tacgcgtttt 240
cattaattta ccatatcgta ttacctacct attacctact acctattacc cattacctac 300
tccctcccac cactactcga ctctacctgg gtgcgttgcg attatattct tcttcttagt 360
agctcgtttt actagaaagc tttcccaccc acccagcttg aacccctcca ttaccaagaa 420
ctttaaacgc tacccatcca tccttgggcc gaacctagac cgaaaacccc tccgtccgtt 480
gtgataaatc caacgagcac agaagctcaa caaataccat caccgtccaa atcccaatct 540
tctcaaacgt tcagtcatgg ctcaccacga tgagaaaggt cctcatggag atggagctta 600
cagtgaggtt tttgaggagg gttccgacat caaacaccca cataccgtcc atcgtatcag 660
agccaactcc tctattatgc aactgaagaa gattcttgtt gccaatcgtg gagaaattcc 720
tattcgtatc ttccgtacag cccacgagct ttctctccaa acagtcgcag tctttagtta 780
tgaggaccgt cttagtatgc acaggcagaa ggccgatgaa gcatatgtta ttggaaagcg 840
gggtcaatac acaccagtcg gtgcttactt ggctggagat gaaatcatca agattgctct 900
cgaacatggc gttcaaatga ttcatcctgg ttatggtttc ctttctgaaa atgccgagtt 960
tgcaagaaac gttgagaagg ctggacttat cttcgttggt ccttcgccaa ccgttatcga 1020
tgcccttgga gacaaggtat ctgccagaga aatcgccatc aaggccggtg taccagtcgt 1080
tccaggtacc gaaggagctg tcgaaaaatt cgaggatgta aagaaattca ccgatgaata 1140
tggtttccca attatcatca aggcagcata tggaggtggt ggacgtggta tgcgtgttgt 1200
ccgacaacaa gcagaactcg aagattcttt caaccgtgcc acatccgaag ccaagtcggc 1260
ttttggtaat ggaactgttt tcgtcgaaag atttctcgac aaaccaaagc acattgaggt 1320
acaacttttg ggagataacc acggaaacat tgttcacttg tacgaacgtg attgttccgt 1380
acaacgtaga catcaaaagg tggtagaaat cgcaccagct aaggatcttc cccaatcagt 1440
tagagataac ctcttggccg atgctgtcag acttgccaag tcggtcaact accgcaacgc 1500
aggaacggct gaattcttgg ttgatcaaca aaaccgttac tactttatcg aaatcaaccc 1560
acgtattcaa gtcgaacata ctatcaccga agagatcact ggaattgatc ttattgcagc 1620
acaaattcaa atcgctgcag gtgcaaccct tgctcaattg ggtcttacac aagatcgcat 1680
ttccaccaga ggttttgcta ttcaatgtcg tatcaccaca gaagatccat cccagggatt 1740
ctcaccagat actggaaaga ttgaagtcta tcgttcagct ggtggtaacg gagttcgtct 1800

-continued

```
tgatggtggt aatggattcg ctggcgcagt tattactcct cattatgata gtatgttggt   1860
caaatgtact tgccaaggat ctacttatga aattgctcga agaaaggtcc ttcgtgcttt   1920
gatcgaattc cgtattcgtg gtgtcaagac caacattcct ttcttggcta ctttactcac   1980
tcatcctacc tttattgacg gtaactgctg gaccacattc atcgacgata cccctgaact   2040
gttcgatttg gtcggtagtc aaaaccgtgc tcaaaaattg ttggcatacc ttggagatgt   2100
tgccgtaaac ggaagtagca tcaaaggtca aatgggagaa ccaaaattca agggtgaaat   2160
catcatgcca gaactctttg atgagagtgg agccaagatt gatacctctg taccatgcaa   2220
aaagggatgg agaaacattc ttcttgagga aggtcctgag ggattcgcca aggctgtcag   2280
agcaaacaaa ggatgtcttc tcatggacac aacatggcgt gatgctcatc aatcgcttct   2340
tgctacacgt gttcgaacag ttgatctttt gaacattgca aaggagacaa gtcacgctta   2400
cagcaacttg tacagtttgg aatgttgggg tggagctact ttcgatgttg ccatgcgttt   2460
cctttatgaa gatccatggg acagactcag aaagatgaga aagcttgttc caaacattcc   2520
gttccaaatg ttgttgcgtg gagctaacgg tgttgcttac tcttcattgc ctgataatgc   2580
tatctatcac ttctgtgagc aagcaaagaa acatggtgtt gatattttca gagtttttga   2640
tgctttgaac gatattgatc aacttgaggt tggtatcaag gctgtacaca aggctggtgg   2700
tgttgttgag ggtacaattt gctactcagg tgacatgttg aacccagcca agaaatacaa   2760
cttggagtac tacttgtctt tggctgagaa gcttgttgct cttaaaattc acatcttggg   2820
tgttaaggat atggctggtg ttcttagacc aagagctgct acattgttga ttggagctct   2880
tcgcaagaag tatcccgatc ttccaatcca cgttcatact cacgactctg ccggaactgg   2940
tgtcgcatct atggttgctt gcgctcaagc aggtgctgat gctgtcgaca ctgctactga   3000
tagtttgtct ggtatgacat ctcaaccaag tgttggagct gtccttgctt cattggaagg   3060
atcagagctt gacccaggct tgaacgttca ccatgttcga gctatcgata cctactggtc   3120
tcaacttcgt ctcatgtact caccgtttga ggctggttta cacggaccag acccagacgt   3180
gtacgagcat gagataccccg gtggtcaatt gaccaacatg atgttccaag catctcaact   3240
tggtctcggt gctcaatggg ccgagacaaa gaaagcttat gagcaggcca atgacttact   3300
gggtgatatc gtcaaggtca ctccaacatc taaggttgtt ggtgacttgg cacaattcat   3360
ggtttccaac aaacttgact tcgattccgt tcaagctaga gccagtgaat tggatttccc   3420
aggttccgtt ttggaattct ttgaaggttt gatgggtcaa ccatacggtg gtttccctga   3480
accattgaga accaatgctc tccgtggccg acccaagctc gacaagcgcc ctggtctcac   3540
tcttgcgcca cttgatttgg ctcagatcaa gaaagacatc catgctaaat ggggcagcgt   3600
tactgagtgc gatgtttcaa gttatgccat gtaccctaag gtctttgatg agtaccgaaa   3660
gttcgttcag aagtacggtg atttgagtgt tcttccaact agatatttcc tctcgagacc   3720
agaaattgga gaggaattcc atgttgagtt ggagaagggt aaggttttga tcttgaagct   3780
tcttgctgtt ggtccattgt cagataccac cggacaaaga gaggtcttct acgagatgaa   3840
cggagaagtt cgacaagtca caattgatga caacaaggca gctgttgaga acacaagcag   3900
accaaaggcc gatccaggag attccagcca agttggagct cctatgtcag gtgttgtcgt   3960
tgagttgaga gtcaaggatg gtggtgaggt taagaagggt gatccacttg ctgtcttgag   4020
tgccatgaag atggaaatgg ttatctctgc accacatgct ggtaaggtca gcagtatgca   4080
aatcaaggag ggagattcag ttggaggttc tgatctcatc tgtaaaattg tcaaggcagg   4140
```

```
agagtaaata gcaaatttca gtgtgaatgc aagttttgga gcggttatta tgatatcaga   4200

tgttgcaagt attgatggga tgaatggatt atgattgaca ggtttaaagg ttattgcttg   4260

acctactttt tatagaatta tgaataagct tttatcaatt tctggtgttt ttagtgtcct   4320

catgaattgt atgtaaccta acatgatgtg aaaattgaga gccaatgatg taatactgcc   4380

tctcgtatac a                                                        4391
```

<210> SEQ ID NO 28
<211> LENGTH: 3277
<212> TYPE: DNA
<213> ORGANISM: Botrytis cinerea

<400> SEQUENCE: 28

```
ggagaggcga gggagggatt acttgaagat tatttatacg aaatgatttt ccctatgttt     60

tgttcccgag attgttttcc tccattgctt tcttcattct tgtaaaacca agttttttttt   120

cttgttctac tttgagaaac tttcttcaga tatacctggc gcttaaatct gcaatccaac    180

aactacccca ccggctcttc acatttgcca acctcgcata tctcgcatct accccctgca    240

tatcatacca agtatataga aggtcgaggt cacactgact ctcaccataa cgagtcacaa    300

tgatctccca tcattttgaa agtctccctg ttcctcccct agagaatctc agcacagaat    360

atatactcca agaaattatc gaccacattg gaaaactcgc cgatgatctc ccacacacca    420

agctcaattt gtttcgcaaa caactctggg acattagaaa tcggaatgtg gatccaaaaa    480

cacatttgcg aggtttattg agagtgtttg aaaatacaca tacattcaaa catgcatttg    540

aggaactaga acccggtttg caagcgcaga ttcgtgcgtt tatggatgat gaaaaggatg    600

tgaaggagga ggagattatg ggcatgggga aagtcaaagg ggaatttttc attccgccat    660

cgccggcagt gaaacatcat ttcaaggaga tggtcaagga gacggtgagg gaaaaggctc    720

acgagaagaa gatgaagttg gtgcagagta aagtgatgaa gaagattcaa gaagcgaaag    780

aggagattga aagagagatt gtggaggagg tgggaggcca tatcgagatg attcagaagg    840

ttgaggacca tgtgggggag ttttgggggga gacatggtca cttgggagcg ttgctgaaga   900

gcaatgatgt tgtctctttg acttcaaaac tagatgcttc gatgcttgga agtgggaaat    960

ctccaaagat ctgggaagat gagagaggag agaggatcat ggaagtccac aaaaatgccc   1020

cgtttcataa ttgggggaac agcgtgaaga atactcctct ttataccttt gttcctacca   1080

cagttctggg cctgtcgaat ctggtcaagt gggctaaagt cgagggttat agagtgagat   1140

gtagtgggta cagacactcg tggagtaata ctttctcgca agacaaacag attttggtca   1200

gtatgttgaa cttggagagt gtggaaaaaa tcccggatgt catgagcatt acgaaggaga   1260

aaggagatgt ggatttgaat ggagatggag tgatagatgt caatgaatta aagacgattg   1320

agttggcgcc gaaaattgag ggattgagtt tggcgggggga tgaaaaaggg aaaatgctct   1380

gtagagttgg agcggcggtt acgaatgaac agtttaggag gtgggccgtg ggtcatggca   1440

aatgggcctt gccggtggat gttattcttg ttgaggtcac agcaggtggc gtcaacggtc   1500

ccatttgtca cggcgccggt cgtcgtcatc aaacagtatc agattatgtt cgtgccatcg   1560

aatacatcga tgcaaatggt gtgcaccgca ccgtgacaaa accagcccat ctccgcgccg   1620

cagctggttg tttcggactc ctcggtatcg taacccacat aacactcctc ctctccccca   1680

tgacatacgc cgttctccgc cccaccaaac ccgacattgc acttgccatc ccccctctct   1740

cccctaccga tatccccatc gcgctccgca aatcgtggac cccagcccaa tacgccgatg   1800

cgctgaaaga gtttgaagat aaagccaata atgactatta cagcgaatgg ttttggttta   1860
```

cgcgcagtca gcaggcgtgg gtcaatacgt ggaatgatac ggcggatgct gagggcgcag 1920
tcgagtatcc gagcccgttt gatacgtttg tgcagtgggt tcaggggtgg gtggggagtg 1980
tgttgacggg gagtgaggtt tttggtttgt tgccggggag gtggcaggct tgtatcttga 2040
gttcttttgg gatggtcgca ctcccccct ttgaattcaa cgaattcgaa caaaagaaaa 2100
cggtcgaata caaaaccgct cttcccaacg gtctccattt ccgtcgcggc atccaaaaca 2160
tgcgagtccg cgacctcgaa ttccaaatcc ccatcccctg tctccccaac gcaacgcccg 2220
attacaccat cgtccgacgc gcctggtggg atatcatcaa cctctgctat cgcgattcgg 2280
aaacgccgat gcggctcacg ctcgagttac ggatcatggg ggattcgaat ctgattatgg 2340
cgcctcagag agggaatcgc tggggcacgg cgagtattga gattctgagt gtgcccgatg 2400
cggtgaggga tgaggagtgg ttgccgtttt gtcaggaggt ggtggatttg tgggcggggt 2460
ataaagggag gatgagtgtt gatggggaag agcggttgtt gaatgtgagg ccccattggg 2520
cgaaggagtg ggaggggtg aagattagag ggaggaaggc gagggagtat gtgagagagg 2580
tggggtatag agaggaagtg ggcgagtttc gagcggtgct gggtgagatt gggagggagc 2640
aggggtgggg gttggaggat ttgaagggga ggtttagtaa tgagttgtgg gattatgtgg 2700
tttttgatgg gatggagggg gggaaggtaa aggggggaga gggggtgcag aatgttaaga 2760
tggggaaggg aaaccctgtt gtgatggatg tcggtgtgga tgttaaagag aacaaagaga 2820
ctaaacctct tggaggggtg gatggtacaa aaaccactag tccggagaat ttaacagata 2880
acttgatgtt ggagaggaag gggaaggga aggaacagga acaggaacgg aaacgggaaa 2940
tcaagatcaa cgaggtggaa agtgtcgagt cgaagggagt agctaataac gtaagcgagg 3000
tgaagagttt gagtagttct gctgtgcagg tgcaggggaa ggtggttggg attcagggag 3060
ggagtcacgc gtgtggggtt ttgcctgtta ggttggggcg gtagatgatt ggattttttg 3120
gggggggggg ggttcttgtt tttcttttct tggaggagaa gggaagggtg ggatggattc 3180
tttggtttgg gggtttgggg acttgggact tggggttggg gtagggaggg aaggaaggaa 3240
agggaatgag aaagggaatt ggaaggggtg tttatta 3277

<210> SEQ ID NO 29
<211> LENGTH: 1355
<212> TYPE: DNA
<213> ORGANISM: Botrytis cinerea

<400> SEQUENCE: 29
gaaacgtgat gatgaaatta attcgaattt caccaaatgc tatggagctt tccaaaaatc 60
cgatttcatc atgtctttct tcgttctcct cacctctatt cttatccttc ttttgtctat 120
acctctcttc taccgtacaa aatggtggag ggatgggctc gagcaagtgt gtttcagacg 180
gattccaatc aatgcgctat caatatcaag tctcccctcg aacttctcca tgctattaac 240
tccagtgctc agaatatctc tttcaagacc tatttccaca atgtcattct tcttaaatca 300
tttgaaatca cacaccctag ttaccttacc cattcctgaa aagaagttta cggggaaaac 360
aatcattgtc acagggagta atagtggatt gggactagag gccgcgaggt ggtttgtccg 420
tctcgatgcc caaaaagtca tccttgccgt ccgctccctc tcaaaaggtg aagctgcacg 480
tcaatccatc ataagcagta cctcctgctc tccagacacc ctcgaagtat ggaatctcga 540
tctttgctct caatcttctg tcagagaatt cgcgcatcga gcaaatgcgc tcccgagact 600
tgatgttttg gtatcgaatg ctggaatcta tgtttttgat ttcgaagtag cagaggaaaa 660
tgaagagacg atttgtgtaa atgtaattaa tacgtttttg ttggctttgc ttttgttgcc 720
taaactgagg gaaactagta tagaatatga tacgaggggg gtaatgacat tcacgggaag 780
tttcgtgcat catcttacta cgttcccgga acggcgagcc gggaacgtat ttgaagaatt 840
gcgagtggag gaaagagcag atatgaaaga tcgatataat gtgagtaaac tcatctctct 900
gctattttcc cgagaactcg cgtttgctct tcgcgaatct gagaggcgcg ggagggaggg 960
acatgttgtt gcgaatattg ttaatcccgg gttggtggat acggagatta tgagacatgc 1020
gacgggagct acgaaacatt tggtgagggg agcgatgaaa ttgatggcga gaagtgttga 1080
ggaggggagt aggactttag tgcatgctgc tggaggagag gaggaaacga atggaatgta 1140
tttggatgat tgtaagattg ggaaagtatc accatggaca acatcactcg atgggatagc 1200
aacccaaaaa gacatttgga tggaattatc gcaggaattg gagaaggtag aaccaggtat 1260
catggggaat gtatgagaga tttagatcga aatttatact gccttttgta atcaattccc 1320
atgccattgt gttaaaattt tgggcataag taaca 1355

<210> SEQ ID NO 30
<211> LENGTH: 3252
<212> TYPE: DNA
<213> ORGANISM: Botrytis cinerea

<400> SEQUENCE: 30
gaactttaag gcggaacccg tatctcaatc ggcactagcc ccagcaagaa cgaacacact 60
ccaatccaat tggctttcgc tgctcacaat gatatttcat ggtggtctcg gtgtattgtc 120
gcaattcaat tcacctcata ctcaaactaa tcaccaagag cgactcaatc gacaattcga 180
tttggtcaat ccttacacca atgctttatg gcaatttcac ggatcgctca taggagaatc 240
caacagtgac aaagtatcgg cggacaatat aattgagaac cgacagaagc gacggattgg 300
gtgtccaacg gcttcttcca cctcactaca tgatacggcg ttttccggcg cattagttgc 360
gacgatgcct ccaaaacgaa atgcttctgg tgagccaaac ggttcgaatg cgcccgttgc 420
taagcacatt aaatcggaac aacatccaga agaattctca aataccgtga agaagaaact 480
gctggcatcc acgagaactg gccaagcttg cgaccgttgt aaggttcgca agatacgatg 540
cgatggattg gctggcggtt gttcgccatg tatccaaaac cacaacgagt gtaaaacgac 600
agatagaata acaggtcgtg cgacatcgcg gggttatgtg gagggaatcg aacaacaaaa 660
tcgagatctg catcttcgca ttcaggaatt ggagcatcga ttgatgcaag gcggtgcgga 720
tatcaaaccg gcgaatggtt atcaggattc gggatcgggc caatatggtt atgctcaatc 780
ctcaaatggc atgcaatcaa catggagctc gacaggtcca gcatatactt cacccacttc 840
aactacgtcg aacaatggcc agcagcaaga aactaatatg tttcgcgcat tgcctgccta 900
tcgcgctgga tgtatgggcg ataattatct cggagtatcg cctggcagtt ctcacttgag 960
cgcaatcaaa gggacggctt tgtcgatttt gggtatggaa attgatattg cggacttccg 1020
ttcaacggat atggatgaac cagatccttc gattttccat ccccagctat acaataaatc 1080
atatcagtct tttatgcaat cggcttggaa tgtaaatcca aggattgaaa aggttgaatt 1140
gcccgcacgc tcagaggctc tcatttatgc ggagtggtat tttcgtgtta ttaacccata 1200
ctgtcctcta cttcacagag gcactttcat gagattgtta actcgcatgt acgacgatcc 1260
caactttcgc ccccacgactg ctgagaatgt tattgttcat atgctgttcg ccatcatgtt 1320
ctttcaatac gcgaccagaa attgggaaga tgccgaacaa caagccagtt tgaattctca 1380
atcaaataca cattatcatt actgtcttgg aatgttctat caactggcat gtagtcacac 1440
agcacaagat gttcaagcat tggccttgat ctgcttgcac cttcgaaact ttcctaagcc 1500
gggagccagt tgggtgcttg caagaatggc aatgactctt gctattgagc ttggccttca 1560
ccgatcaatg aagagatggg cacctgaatc gaacacgctt agtgagctcg acattgaaat 1620
gcgccgacga acattttggg tcatccttgc tgtcaatgtc actcttagcg gcaagcttgg 1680
ccgtccaatg ccccttcgaa atgaagatta cgacgtcgaa tgtccatcac aaattgatga 1740
cgattacatt cccggagagg gtatagatcc acccaatcca ataaaatgta accatgagat 1800
tggaattcaa ggtttcaaat tgataccatg ctatttggag ctttattcga ctatctattc 1860
gatttctcgt caaccaagta cctatattgc aactgttaac cgattggagg caaagattcg 1920
tgcttggaaa gatgacttgc ccccagagct tgtgaacgga gagttgggac acaatgaaca 1980
agaaggacgg gtatttgctc tttatgctca atcttggtct caagaattcc gtcttcttct 2040
tcgccatcct tcagtttcta tgaccacaga tccagatttc aacgcggaga gtatgagaat 2100
ttgtgtagag tcttcccgcc aaatgttagg agttgttcgt caactgcaga agtataagag 2160
ccttgatacg acttggtaca atacctcagt ttttgttatg gcacttacta ctacactttt 2220
tgcccaatgg gaaaagcgtg gagggacttc atcagctgat ttggctgcat tgagagaaga 2280
gatggatatt tggttggata ttatgggtga tataggttca cttcttggtt cgggaacacg 2340
gcttaagaaa gctgtgcaag ttgtcaccga tgggacactc ggattactaa gtcgaaattt 2400
acctgctaag aatgacaaga gctacgcttc caataataat gcccaggaag aagtcagacc 2460
ttcggagcaa acatcgaata ccaatggaaa taatggttat ccggtcaatg ctcaaaactt 2520
taattataat gaaccaactt ctgctacggg gactgcgcct acacctaact attcaccctc 2580
cgaaggtcaa atgtctcatc aacaaacacc ctatccagca gcaacccaat attcaccata 2640
tcttgaatcg gcttctggta cttcggattt gacatatgcg caaccagaga atcaaggtta 2700
tggaggatat tcggccccaa ctagtgattc tgtagaagca ccattaattg ctgcgttagc 2760
tgctcaggca acgcaggtcg cccctaatac atggcacaga aacccgatcc aggtcaacac 2820
agcgccaaca caagcctggc aacattggac atctaccgtc acaggtaacc ttgagccaca 2880
agaatgttac tcggcaagtg ctctaatgca attaggagga agagatatga gtaatggcga 2940
cacaacacaa ttgaatacat cgatgggcga tgttcaaagc ggaggagtta gtgagccagg 3000
acatttgggt ggtcaagttt cgggagccat cgcgggtact tggccgctta atctttttga 3060
tattggtgtg aatggttcga cgggttgatc cttttggctt ttctgcttgt gattaatttt 3120
cttgtgcata ttatgatggt ggatggagat aaccggcgtc ttaaggatgg atggggaaag 3180
atagaaaggc atggtgcaat ggacgggccg gtcggcttac ttggagttat caggcggtgg 3240
aaggggacta ca 3252

<210> SEQ ID NO 31
<211> LENGTH: 3848
<212> TYPE: DNA
<213> ORGANISM: Botrytis cinerea

<400> SEQUENCE: 31
gagcaattat tagcaattat caactacttt gggggctgaa agccatttca attcatgagt 60
agtgatatgt gagcattggg gcagaggaat ttaagagttt ggtctttgca atatgttgca 120
gaggtgaaat tggaggttca gccgtcgcat ttccattact tcgctcccat ctcaatccat 180
cctcccgtcc aacttttcca cgtcccacat tcattcaccg tggcaaacaa gatctttatg 240

-continued

```
ctcttgccag cagaaactcg accatattta cgtctgcgaa gcaatatcga cctcgccagc    300
taatatttcg cgaccttgca tgcaagctat tcgcgttttg ccatccaggc gcaaccactt    360
tcttgacttt caggtgtgcg cgcaacaaac aagaattaat tgcttgcaaa gtcaaggggg    420
ctttataact accaacatca ttaatacggc gttgtgttct accgccgttg ggtacttcac    480
gtctgccacc actagtaagg gaacaaaagg ccgcttcgaa cacattaata aatagttcgg    540
cttccccttc gcctcaacac acaaaaacaa agtaatcgca ccacaacctt acaaagtctc    600
ctgctcacga tggaggatga cattcgggag ctccagccag aagctgtaga tgctgcgatt    660
ggtgaaatga agattgagga ggggattgag gtccaggatt ttgccaatgg cttaaatgga    720
tatatttcta ctcctacaga aatcaagaga tctcactcca gcacaccggg tcttgtaaat    780
tctcgctctc agacaccgcc cagaaagcaa agcaccagcc aaacaccaaa atccggagat    840
gaagaggaag aagaggttat tggcggtgat atcaccgtca ccgtcgaacc tggcaaggca    900
ccgaagctat cgagaaaatc gtcacaaaaa gtaatccctc gaccaccccc tctcttcaac    960
gatcttccag attctacaga ggaggcagct tcggtatttc aggtaatcaa ggattgtatt   1020
tatggagcta agcacatggg agcttcagat cacgatgcgt tggattgtga ttgtcccgag   1080
gaattcagcg atggaaaaaa ttatgcctgc ggagaggatt ctgattgcat taatcgactg   1140
accaaaatgg aatgtggtgg aggtcataaa gattgcaatt gtggtttgga ttgtcagaat   1200
caacgctttc aacgcaaaca gtatgccaaa gtttcagtga tcaagacaga taaaaagggt   1260
tacggtttac gcgcaaatac tgatctacag cctgatgatt tcattttcga gtatatcgga   1320
gaagttatta acgaaccaac gtttcgacga cgtactgtcc aatatgatca ggaggggatc   1380
aagcatttct atttcatgtc tctcacgaag catgaattcg tggatgcaac gaaaaaaggg   1440
aatctaggtc gattttgcaa tcattcttgt aatccaaatt gctatgtcga taagtgggtg   1500
gtcggagaaa agttgcgcat gggcattttt gccgagcgtg caatcaaagc cggagaagag   1560
ttggtcttca attataatgt tgatcgatac ggtgccgacc ctcaaccttg ctattgcggc   1620
gaaccgaatt gtaccggatt cattggaggc aagactcaaa ctgagcgtgc tactaaactt   1680
cctcatgcta ccattgaagc tcttggtatc gatgatggtg atggttggga cacagctgtt   1740
gccaagaaac ctcggaaaaa gaagacaggt gaggatgatg aagaatatgt caacaacgtt   1800
caacccaagg ggctcgatga aaatggagtg cggaaggtta tggcaactct tatgcaatgc   1860
aaagaaaaat ggattgctgt caagttgctt ggtcgaatcc aacgttgcga tgatgataaa   1920
gttcgaaaca gagttataca aatgcacggt tatcaaattc ttcgtacgac cttgactact   1980
tggaaggaag acaacaacgt gatcctccaa gttctcgacg tcctttacaa atttccacga   2040
cttactcgaa acaaaattgt tgattccaaa atcgaaacag ttctagaaga attcacaact   2100
tccgagcatg aagatgttgc tttcgagtca aagaggctat tggaagcatg gagcaaattg   2160
gagcatgcgt atcgaatccc aagaagagcc ccaactcttg ttgcacaagt atttgagcgg   2220
cgtccagacc aagtagaaaa ggtcactcca tcgccatccc ctgttattgt cgcccctact   2280
ggcccccgaa gtggtgttcc tcaacgcaac gccaatttcg ttgccaatcg ctcaatttct   2340
cggcgcccgt tcgtccccat ggtattacca cctggctggt ttactgcgat ggaccaaaac   2400
ggaaatgctt attattacag taagacggga caaacaacat gggagaggcc atttatgcca   2460
gcaggggtat cgccaccacc tccaccaccc aaggcagctc caaagagtgt gcaaacacaa   2520
aaagctcttc aagatattat cgacagtatt acaaaggagc cctcgacgac tccggcactt   2580
tcctcccatt ccgccgaggg tacacccaag gagaagaaga agaagcctgt ggaaaagtgg   2640
```

cgctcattgc ctatcgagaa gcagatgaaa ctgtacgaaa atactttatt tcctcacatc 2700
aaacacgtaa tgcaaaaata ttctggcaaa cttcccaagg atgatcttaa aaaattcgcc 2760
aaggaatgtg gaaagaagct cgtggcttct gatttcaaaa acaatcgcat tgaagatccc 2820
acaaagatat ctgacagaaa tcaaaggaaa gtaaagcaat atgtgtttga atattttaag 2880
aaggctgtgg aaaagaaaag ggagatggac gccaagcgag cagagaggaa aagacgcgaa 2940
gcgcaggcta aaatcaatgg aaacggcacg agtgaaaagg ggataaagcg agagaatgta 3000
aatttgatca gtagtccgga tgtgattgat aatgaggacg tagaagttaa cataccaagt 3060
ccaaccgcat cgcctagtgg acaactcgag atggagttgt tgaagaggaa gagggaagat 3120
gacgaggaaa gtccatcgga gaacaagagg gtaaaagagg atgatactga gagtgcaaca 3180
ccaacggatt catctacgcc tcctccgcct cctccgccgc cgcccgcgga agggatgcct 3240
atggcagagt cggaagatcc ggagatggct aatggcgagg gagaggtgaa agaagaaacg 3300
gaagaggaaa gagagttaag gatgcaggaa gaagatttaa tgagggagaa tgaagaggct 3360
atgaagatgg aaatggaagt agatactgat ggaaggttaa aggggaataa tggttgtagt 3420
gagcatatca atggtggaaa tagttgtggg gaagtctcaa cggagggatg atatttattg 3480
ccaatggagg gacacaaaat tgggaaccgc ctgtatcaac atcatcatta tcttcattca 3540
aaaaaaatca tcggcatcgc atcgcatcgc atcgcatcag ggtcggttta tatcatattt 3600
attatatgga taggggagcg aactaagtga gtttggcgtt tacaatttct tcatctcgta 3660
ttggagatcg agagatgaac atcatcttag atcaaaagga tagttggaag ggatagtcac 3720
agaacaaata caccctgcta ttcctcatgc attaaaggaa agtaggctat ttagatacta 3780
ggcagtaaat ggaaatcaag tgaagtgtaa tgataattat taatcaaatg gcatttgtga 3840
aaactcca 3848

<210> SEQ ID NO 32
<211> LENGTH: 1989
<212> TYPE: DNA
<213> ORGANISM: Botrytis cinerea

<400> SEQUENCE: 32
gagtcgtgcc tgtctgcaag actttattat tagtcttcat taaatttaac tctttcaaga 60
tatacactac atacactaca tacttcaatt ttcacttcgc ccagccgttt atacccatct 120
tgaagttaca gcgaaaacat attttaatct atcattttat tgcatcttac aaatagtcca 180
atatttgttt atacttttgt tcttgttctc aaaatctgca ggaatgagct tgaattttgg 240
actgaccaat attaaacctg tggcgccaaa atttaaatcc gaaaaggttc caaaacagag 300
gccgactcta tctagtagga catccagtaa tggccttcga attggaacac ctgtatccaa 360
agtcactgat gctcgtggca gactagccgt cccaagccct ccccccgagg caggaaagaa 420
gaggaaagaa agagaaatca gcggaagccg caacactaaa agaaacacaa ctctaaccct 480
tcgaaaaagc cccagtcaac agccgttgac gagtgatagc gaggaagatg aagagatcgc 540
cgtgtcttcc aaacgggcca agccggaaaa catcgagcct gatttgaaga ggaatttgaa 600
ggacaaaaaa gccttttcga ctgaacccga taatacgcaa ggctctacat gcagaatgat 660
ccatgcggcg gatgtcatga tgacgaaacg cacggctaag agcggcgaga aagtttgcga 720
taggaagaag gaagacggcg acgcggtcct tctaagatat cccagtgtca gtcgcagaga 780
aagataccaa cttatctccg aaggcgaagt tattgatccc gcaggagaag atttgatcaa 840

-continued

```
cccttatgac gagataccga agattgtgga aattgtcaag gatgaatatt tgaccgatga    900

acaagcagcg gagttcgcac atccggaaac gggtataatt cgaaaaatca acaaagcgac    960

gaacaatatt acctggactc tttccagcgc aaaaaagccc cacgacaaag agaaaatgaa   1020

ggggctgttg cttgagttca ggaatgctgt gggagcttac aatgacgcgc tcagcactct   1080

cactaaaaat ggatcgctgg cgaaaaatct agaaaacaag cattcactgt cgtctaagct   1140

tctcaaaatg gttctccagc aagtttacga ccgagcagtg tctccccaag ttgacttgac   1200

taataaatac caaaatggca cggattatgt ttacggcgag ctcacattcc cgttcatatc   1260

ccgaatcctc agggaggata ctcgcatgaa atccgatcaa gttttcatag atcttggttc   1320

gggagtagga aatgtcgtcg tgcatgccgc gctacaagtt ggttgcgaaa gttggggttg   1380

cgaaataatg cctaactgct gtaagctggc ttccttacaa cagacagaat tttccgcacg   1440

ctgtagggcg tggggcctca gcgccgggtc agtcaacctc gaggaaggga atttcttgaa   1500

taacgaaaac attctcaaag ttatgaagag ggctgatgtt atcttggtta acaatcaagt   1560

tttcgcacct gctttgaacc aaagtcttgt gaacctattc ttggatttaa aagagggttg   1620

caagattgta agtttaaaaa ctttcgtacc ggatggtcac gttataaatt cttacaatga   1680

acacaatccc atcaatttat tgcgggtgga aaaaaagacg tacgcggaag gcgacgttag   1740

ttggcattct aatggagggg attactacgt tactacgaag gacagcacta tcgtagctaa   1800

gtatcaccag accccaaagg atagaaagac acgggggagt cgggttagat gatttttgaa   1860

tttgaatata cggtttcctt gcacagttga taccattggg aaggttatta ttgggtactt   1920

gagcacgaag cgatatcaca gcgaggcagc atagagtaga tgtatggata aatgtatgta   1980

tttgtaaca                                                           1989
```

```
<210> SEQ ID NO 33
<211> LENGTH: 3037
<212> TYPE: DNA
<213> ORGANISM: Botrytis cinerea

<400> SEQUENCE: 33
```

```
gatgctgtga agctagctcg acatatcttg atctctttca aaagaattat cctccacctg     60

cattgactcc accctgagta ccacagcatt agcacgaaat ggccccagct aacataataa    120

gcattctgag gctctgcgct agcagagacg acgggcgcgg tattgtcact tatccactgg    180

gaagcagaaa cagtgtgaag acgttataca aagatttaga gttccaagtg atccacaacg    240

caagattcct gtcacgtatc tccaacttca gaccaagatc aatcgtttta cttcatttca    300

cggatcacct tgataacatc gtatggtttt ggtccgtaat tgctgctgga ggcattcctg    360

cactatcaac accattcagt aatgttgaaa cccagcgcct gaaacatatt gcacatttac    420

acaatctctt gaaggctccc ctctgcataa cgagacgttc cttgttagat cagttctcgg    480

atcaggatat actgagacca tacgttatcg aagacatctt ctccgctcaa gtcgccttag    540

aaaatgataa tatagacgaa cttggtcaag ttgcaagaga agagcatccg gaagacttag    600

ctatattaat gcttacctct ggcagcacgg gaaacgcaaa agccgtctgc ttgactcatg    660

gccaaatttt tgcctcaatg gctggaaagt cttcagttcg gaaggatatc cccaaggatt    720

tctctgccct gaactggata ggctttgacc atgtcgccaa cttgacagag atacaccttg    780

aagccatgta ccttaatata gaccaagttc acgtacaggc tccagatgtc atttctaacc    840

ctctgttttt actggaactc atacacaagc atcgtgtggg atggacattt gcaccaaact    900

ttttcttggg aaaattgagg aaacagctag acacagttat tgtggacaca agtctctacc    960
```

```
tagacttaag ctgtctccgt cttttggttt ccggtggcga ggcaaatgtc gtggagacat   1020
gtgatgttct ttcccgccat ctagaaaaat acggagcacc atcaaatgtg atctctgcag   1080
cctttggtat gacagaaacc tgcgctgggt ctatctataa tctcgattgc cctagatacg   1140
atgttcataa tatgcagcag ttctgttctc ttgggcgttg cgtaccggga atagagatgc   1200
gagttacaat ccctcaggct ggcgatgaaa ttgtccgggc ttcagccaac gaacttggcc   1260
ttcttgaact tcgtggacct atcgtgttca agtcctattt caataataag tccgccacaa   1320
cagcttcctt cactccagat ggctggttta gaacaggaga tcacgccacg atcgatcgag   1380
ctggaatgct ccatctggca gggaggacaa acgataccat gaacatcaat ggcgttaagt   1440
atctcccgaa cgagctagag gctgctatcg aagaggttgg aattgagggt gtgacaccga   1500
gttacacagt atgtttttcc tttcgtccac ttggtgcgga atcagagcaa atcgaagttg   1560
tttacttgcc ctcctttgga ccccaaaatg tcgatgctcg aattgcagct cgagacgcca   1620
ttattcaagt cacaatgttg caaactggct ctcgaccttc agttctgcca ttgaacgatg   1680
ctttgctgca gaaaacgaca ctcggaaaac tctctcgcgc caaaatcaga gctgcatttg   1740
aacgtggtga ctataagaaa tgcctggaat ttgataagat gcagatcgaa atatataatt   1800
catcccatat gcaacaacct tgtactgaga gtgaacgcat cattcaagaa gtattttgcg   1860
aggatctaga tctccatccg caagagtttg gcgtcaatac acatgtgttt gagattggca   1920
ttacctccat ccatttaatc cgattgaagc agaaacttca aagccgcttc tctatcccag   1980
agattcccat tcgcatgatg atgcaaaatt cgaccgttcg agagttagcc acggctttgg   2040
agaacctcgg taaaccacga aactatgaac ccatcatatc acttcagaat atcggacaaa   2100
aggctcctct atggctcttt cacccaggag ttggcgaagt tctcgtattt ctcaatctcg   2160
caaagtatct tcctgatcgc ccagtatttg ctcttcgtgc tcgaggcttc gaaaaggggg   2220
aaacattttt cacagatatt aaagaagcag taaacacata tttcgaagcc ataaagagca   2280
agcaaccgaa aggtccatat cttctcgcag gttattcgta tggtacaatg ctcgcatttg   2340
aaaccgcgaa actgctagaa gcgagcggtg atgagatttc cttccttgga tccttcaacc   2400
tgcccccaca tatcaaattc agaatgagac aacttgattg gaccgaatgc ttgctgcatc   2460
tggcctactt ccttagtctc atcgatgtcg agcattgcga gataatggca ccacagctcc   2520
gacaatattc caaaaagcaa gccatccaat gcatcagcaa agtcgcaaac ccaaaccgtc   2580
ttcttgagct ttcactcaat gaagagatgc ttggaaattg ggtcgacctt tcatataggc   2640
tgcagagcat ggcaaataac tatgacccct cgggaacagt tgcgatgata gatatatttg   2700
ttgcagatcc cttgcaagct gtggcagcga atagagagga ttggaggaaa aattgcttaa   2760
gcaaatgggc ggattttagc agatcgaaac caagatttca cgatgtaatg ggcgagcatt   2820
acacaatgat tggggcggac catgttttca gtttccagca gactttccgt aaggcattag   2880
aagcaagggg atgttgaaat tttcgcaaga tataataata ttatgcgaac catacctact   2940
gcaggtagca gtgtttggag caatgaaggc aatatactat gaactgtccg aacattatgc   3000
taatatttat aattgttaga tagcacgtgt attttca                            3037
```

<210> SEQ ID NO 34
<211> LENGTH: 2168
<212> TYPE: DNA
<213> ORGANISM: Botrytis cinerea

<400> SEQUENCE: 34

-continued

```
gtttaaccat caagataata actgaaaaat cctatccaca tctgaagctc ctgagcctcg     60
agatattttc aaaagctcga gagcattaaa ctacaccaca atctaatcgg tttgacctta    120
tcgttcaata tggcggacgc aattaccgaa ggaacggcca agctccagct tgatgaggag    180
acaggtgaga tggtctcgaa ggccgaactg aagaagagat tggcaaaacg tgcgaagaaa    240
gcagcacaag caaaagcaaa atcagcagca ccacctaaag aagctgctgc aactaaacct    300
aagaagccag aagagaccaa agcagcagag ccatcaaatg tattcgccca aggatttctc    360
tcagaagtgt acaaggagcg tcctgtcaaa ccagtcttta cccgatttcc acctgaaccc    420
aatggatact tgcatatcgg tcatgcaaaa gctattgctg tcaatttcgg atttgctaag    480
tatcatggcg gtcagtgtta tctgagattt gatgacacca atcccgaagc agaggaagag    540
aaatatttta cagcgataaa agaaatggtt tcgtggttgg gcttcacacc ttacaagatt    600
acacattcca gcgataattt cgataaactt tatgagaagg cagaggagct tatcaactta    660
ggggggggctt atgtttgcca ctgtggtgat gctgaaatca aagctcagag aggaggtgaa   720
gcacggggtc cgagatttag atgcgagcat gcgaaccaat cgatcgaaga aaatttgaga    780
aagtttagag ccatgcgaga tggcgaatac aaacctaggg aggcattctt gcgcatgaag    840
cagaacattg aagatggaaa ccctcaaatg tgggatttgg cagcatatcg agtcttggat    900
gctaaacatc atctaacggg agataaatgg aagatttatc caacatacga cttcactcat    960
tgtctttgcg atagttttga gaacatcaca cactcgcttt gcacgaccga gttcattcta   1020
tcaagagtat cgtacgaatg gttgaatagt acactgaaag tatacgagcc catgcagaga   1080
gaatatggtc gcctaagcat tacgggtact gtcctttcta agcgaaagct caagaaactt   1140
gtggacgaca actatgttag aggatgggat gatccaagac tatatacatt gattggaatc   1200
aaaagacgtg gtgtacctcc tggagcaatc cttgagttca tcaacgaact aggagtgacg   1260
actgctccta ccaacattca actttctcgt tttgatcaaa ctgttcgtaa gtacttggag   1320
ctcacagttc ccagacttat gttagttctg gatcctgtac ctgtcgtcat cgaggatgcc   1380
gaagagcttg aacttgacat tccattctca cctaaagtac cggcaatggg cagccacaag   1440
gtcaagttga ctagaactgt ttacattgag agaagtgatt tcagagaagt tgatagcaaa   1500
gattacttcc gtctcgcccc tggaaaatct gtcggtctac tacacgttcc atacccagtc   1560
aaggcagtct cattctctaa ggatggagat aaggtcacag agattcgtgc cgtctacgat   1620
aaggagagca agaagcccaa aacttacatt cattgggttg cagatggttc aaaaaaatgtc  1680
gaagttagaa ttttcaacag tctcttcaag agtgaaaagc cagacgatgc tgaaggtggt   1740
ttcttaaatg acatcaaccc tgatagcgaa gaagtttggc ccaatgctgt tatcgagtct   1800
ggatttgacg aggtacgaaa acgagctcca tggccagaag ctgctggaga atcggagctc   1860
ggcaagggag gtcctgaatc tgtcagattc caggccatgc gtgtagcata catggcaatg   1920
gattcggact caacggatga taagattata ttgaatcgca ttgttagttt gaaggaggat   1980
gctggaaagt agggaattag gggccattat gcaagggtcc aaagaactca tcaattgaga   2040
agtgcatggg atatcatgaa tgaatgattt gttgcaaaga agtttacgtc tagtcaagaa   2100
tatactggcc ttgaaaagca gattcatgcg caaacaattg aagggaatac tgagtgaaca   2160
gcgtatca                                                            2168
```

<210> SEQ ID NO 35
<211> LENGTH: 5954
<212> TYPE: DNA
<213> ORGANISM: Botrytis cinerea -continued

<400> SEQUENCE: 35
gagcaaaaag aaaagacact gcccttcctg cggacagact gtgcataccg tacacactac 60
gtcctacacg ctacttgcta cttgctactc actactcgta cataaacaca acggtgctaa 120
aggcagagga ccccagtctt ctattcttcc agtccagtcg tccagtcgtc cagtcgccca 180
gtcgcccagt cgcccagccc agtcagtctc ccagcccatt ctcccactcg tcccagtgct 240
ccctcgcacc ctcgcaccct cacaccctca caccctcagt cactcacacg cagtcactct 300
catcagtcag tacagaatct agatccactt tttgtttcta taggcaacgg aaaagacctt 360
ggtcataaac ccccaaccct gaccaccctg actttcctga gccacctcga atctcgaaaa 420
ggtacgggaa acatcaagct tttatcccat tcgcagcacc agcaaccagt aacgggaacg 480
tacaggtaca ggcttgcaat ccattccccc aaatattgtt caactcctct tagtctatct 540
gcagccgcaa agagactgac tctccataca ataaaaaaaa tacaacatcc accgctatct 600
tcatttcacc actaaacaca atccacgagc cattcctcga gatatcttcc aaacttcgaa 660
tgcaaaaaga ggagaccgtc aattgacgcg cttgatttct gtggagaaga gaaaaaaaaa 720
agatattgac tctcgagaga cgcagataca gatagctttc cgctgcattt tactgggttc 780
ctatttacaa cgacttccct gtttactagt tataccctac gacggccatt tgaaatgaga 840
tagtctatcg acaaactcgg cccttaaacg gactgagctc aaggaaaagc aaaatccttt 900
actcgagatt aatttctgtc gctggctttc cccagtgact ttggttcctt attcatgatt 960
cgggaacaga gggctccatc aggtccacgg cctgaccttt cacccacaag acaaaggatt 1020
gctgagaatt atcctcccag tgtaggcacc ggaggatcgc gtctgatagc cgggacagag 1080
cctacactgc atgctccgca acgaaacaat catactttat ttacatttgg ggctcacaac 1140
gacgatagtt cgacgtctta cgacttcttg ccttctccca gttttgacga cctgcaaacc 1200
agcatctcca atgaactaca gcttgcagct caatatccgg caacaggtgg gggagattca 1260
atgccgagag agaagccttc aatgggggaa atcaaagcat ctatgaacaa tgggcgggga 1320
ataggttctg cgcgtggagt gtctggacca cgaccggcga gaacctcctc ttttcaacgt 1380
aggcagagtg tgagcaatcg tcaaggtagc atatcttcaa caacttcttc aactgcatcg 1440
gggaatatgg acccaccatc tgctcctcta gctgttcgaa cccgacgaaa tcaatatcct 1500
ccgatatctg gaagtgctgc ctccaatgcg cctgctgcta gaataccgcg cagatctgtc 1560
ggaggcgctg agtcggatag ctcgagcaag gcggggacca cacaaagacg acgtccgagt 1620
cttgctccaa gtacatcatt acaatctttg tcggatgctg ccaatgcatc tgcaagaatg 1680
aataatacag ggggttccaag ttatatggac ggagcaagag gtacaacggc ctcgagagca 1740
gcgaaaacta aatcattgca acctccgagt aaagggcaac cccaagtttc tattcagcct 1800
ggcacaccag atcacagcag atcatcatcc cttgctgcaa agtcaccagg gaggcccagt 1860
gcaacaggaa tacctgcaac cacaccatca tcaacctcga agcggatgtc agttttgcca 1920
ggtacttccc atgcaagtgg gcttggggct agaaccatca gccctacgga tactcgaaga 1980
gccaaacgtt tatcgactca tcaaggaaac ccaaccgttt cgccgggtac accgccaact 2040
ccacaacctg actcttatcc cgcatttact cctcgagggt cttcaagatc tccttccatg 2100
ttacctagaa aggtgcctac accttcatca tctcgaacta ccccggatag taaccgtaag 2160
tacaattctg ctatttcagc tgcgtcgagt tcaagctgta acacatctcg aaatactgca 2220
ggttccttac agcctcgagt atcgtcactt gcccccacag catcaaggtt accaacacct 2280

-continued

```
aagtcacgaa atgttcatag ctccgctggc aataatgagg aggaggatgt tccgccagtt   2340
cccgcgattc ccaaagcgta tgaatccccc aaagattcac ctatcgaaac tccatttttc   2400
accaagagga aatcaagtat gccttttgat gctagtagta ttaacagtac ttcaacaaat   2460
agcatttctg gtaggaattc tgcacgtgag ccaactaagg ttgaacgaga gccaaagagg   2520
tcaaggcatg caccacccag ctcgaattcg gatcttgaac agcaaaaaca gaataccacg   2580
actcccaaga aaaagaacct tcaaccactt cgtctgccac ccttgaattt gttaccattg   2640
agtgcccccca cggctgcaaa ggctgcggcc atatccaatc ctgagccctt accaaatggt   2700
gccattactc ctccgcctaa gcggacaaat acaaaaactc caagttcacc catgacagct   2760
tccaagacct cattcttttc ccgtcgcaac gaagacaaat cagagcatca tatgcccaaa   2820
atgcggagca atagctctat tcatcataga ccaacggagt cttcgcaagt atttggaagt   2880
aacggtggga caaagcctat acctatagct aataaccgtc caccgccgcc tagggaaacc   2940
tccccatatt tgtcctcatc tctccctaag aataacgctg gccaacatct tatgcctcga   3000
tccaaaacta gtggtgattt cactacgatg gacacctcga cgactgaaaa caagccggca   3060
aggttgactg gaccacgtgc cttaaaggtg aatagattag ctaaaacgga tactcctgcg   3120
gaagtctcaa gtccagaaga acccccaaca ccatcttcaa caacttcatt gcgaagaaag   3180
ttgagtctag gctggaagcg atctggatcg aagaacaccg ccagtgctgc tcaagcaaca   3240
ggcggaagag aagccaatca gcctcctcct cccccaaaac atgacaatat gccaccacct   3300
agattgcctg cttcttctac catgaataat atgagtagca ataataagga aatacctagt   3360
cctagtccct cggtcaagtc aaccactact acttatctca attccagtcg aagaaagagc   3420
tcagtttcaa gcctcaatat gatcacaggt cacgacagaa caaagagtga tagctggggt   3480
ttgaatcgaa acagtccgaa gaaagagaca tcaaccgact ctatggcttc tgaaaggaat   3540
atcccaaccg cgacttctcg aactacatct tcggttatgc atagaatgct gaatccaaag   3600
gcttccagta ccagtattag acatcaggat cactggacag cggaattgga caaggatgat   3660
cttctggcag aagatgagat gaagaagctc gggaataaac gaaaggaaac agagacggca   3720
gctcgtcaat tggatgctct aagaaaacgt gctactccta aggatcgagc gaaccctcaa   3780
caggccctca aacttgtctc gcatctcaac atttatgaga agggggaaat tgtcgattac   3840
aaggacattt acttctgtgg aacatctagt gcagctaaac acgttggtca gcttcaatct   3900
gatgctgcca atttcgggta tgatgatgaa agaggagatt atcaaatcgc cactggagat   3960
catctctcat atcgttatga aatcatcgat gttcttggca agggaagttt tggtcaagtc   4020
gtaagatgta ttgatcacaa gactggagga ttagtagcta taaagatcat tcggaacaag   4080
aagagattcc atcagcaagc tttggtagag gttaacatcc tccaaaagtt acgcgaatgg   4140
gatcccaaaa acaagcacag catggtcaac tttgttcaaa gcttttactt ccgtggtcat   4200
ctttgtatct ctactgaact tttagatatg aatctttatg agctcatcaa agctcattct   4260
ttcagaggtt tctcactgaa gatcgttcgg cgatttacaa agcaaatgct tagcagtttg   4320
ttgcttttga aatcaaagaa ggtcattcat tgtgatttga agcccgaaaa tattctcctc   4380
gcacatcctc ttcattcgga gattaaggtt attgactttg gatcaagttg tttcgagaat   4440
gagaaggtat atacatacat tcaatcccga ttctaccgat cgcctgaagt cattctcggt   4500
atgacatatg gtatgccaat agatatgtgg agtcttggat gtatcttggc ggaacttttt   4560
actggagtac cgatctttcc tggtgaaaac gaacaggaac aactcgcctg catcatggaa   4620
gtgtttggtc caccggaaaa gcatttgatt gagaagagta ctcgcaaaaa gctcttcttt   4680
```

-continued gattctctcg gaaaaccacg tcttacggta tcttcaaagg gacgtagacg tcgaccatcc 4740
tcaagatcgc ttcaacaaac catcaaatgc gatgacgaag ttttccttga ctttttggcg 4800
cgttgtctca ggtgggatcc tgaaaagcgt ctgaaacctg atgaagctgt tagacatgaa 4860
ttcatcactg gccaaaaacc tactgctcca cctcgtatca atactcgaat cgactcgcca 4920
ataaagcgac acaataccac cgctgcacct gcctccaata ggcctcttcc agaaccacct 4980
gctactagtt acaagagtgg ttcatctgtt cggccacccg cagctgggac aagcccaagt 5040
aaagctcttc cacctcgaag acaatccaat gccacaacat taactggacc tcctgggccg 5100
aaacgtacaa gtactggaac cgtggcaatt tctggtggta gcagcttacc ccgagttaca 5160
cgaagcgtca gctcgaaaca ggatttagca tcagcggggg catcggcagc tatgagtagt 5220
cggcgagcat tatagaatat gtaatgtatg aaacgaaaag tgttgagagt gaataaatca 5280
ttcatatcac tcattgggta cataaggagc ggattatacg aatagacgag tttttattac 5340
ttcactgcca ttttcttcct ttccttcgtt tgaagttgtc ctttattgca tagcagcgag 5400
gtcaaccgga gcatttttct tttcacattt tttttcttgt ccatgatgca tacccactgc 5460
gcaacaacta tacatacctc attcgtttaa aaacacaatg cgaatcgtat aaatctagcc 5520
gaagtctttc atttgataca ctgaaagtta atcaggcgtt cttgtggcag cagggctgtg 5580
agctggaaca gtctggagta tcctttttgc ggaccgaccg cgcattcatt gatacgcata 5640
taaacactac tataatttaa tttgacgtct ttcattcacg aacttattta ctgggagttt 5700
gggagttttt tttaattaag aaaagatggg ttggagggga agatgaagga ggggaaaaac 5760
atttgtgggg atgaggaggc tcgttcgaaa tagcttgttc gaggaagctt gtttgcatgt 5820
agggagcttg tttgtatgga gactttggtc gcagtaaatg caatgcatag caaaaggaag 5880
gaagcgggta cggattggaa ttgaatgata gggaattgac gaatagcatt gagatgaata 5940
agatgaataa atta 5954

<210> SEQ ID NO 36
<211> LENGTH: 3124
<212> TYPE: DNA
<213> ORGANISM: Botrytis cinerea

<400> SEQUENCE: 36
ggccagcaca atcaatcaat ctcttgattt gatttcctaa taatctgatg atgcactttg 60
gagattcttg agatctcctg tatgtgaaca tcgacttttt atcccgacca taccaaccca 120
gttatcacat attcaagcaa acttttaccg gtgtattgat acccaagact tatctgggaa 180
gggaaaatag tttgtcggta ataggagtat cggcgtatca attatctttg aaggaagtgg 240
gttgtaccaa aaaccacatc aggtattcca ccagacaatt cggtaccgca aaacgaatct 300
tctaaaagga cggaaacctt caattcacat tactatttta caaaagcttg tcggcccaac 360
gacaatgacc agatgtctat tctttccatt gaacgctttt gttaatctac ttccttaatc 420
tacaccactt ccaaaagtat ccattcttcg acgacccctc tgccaacctg ggatttcgac 480
attgtccaat ctggacatat acgctcattt ccgcgatttg atttacaatt aacgcatacc 540
tttcatggct actgcgccaa tgacgacaga tccatcgagg ctgtcattcg caaaggttgc 600
cgcttcagct gggaaggata atgtagctct cgcttcgttc gcaaaaattg ctgcttcttc 660
aacttctgta cgagatacga gatctgaaaa catagctcca actgtacata aaaacaaaga 720
cacaaatatg cctagtgcta cacgcaatga tactggcagt atggccactc tcaaagagac 780

-continued

```
gggcacatcg acaaacgatc aatcctcaaa gaagaggaca attaccgaga gcaaacctac    840
ggctgctaag aaggaatcgg atttggcaga tgcggttaaa gcgatgcaca ttcgtgatat    900
cacaccaagc cttgttgtaa atggttcagg gattgcacct ccaacccaca aaagagattt    960
gggagaagga ttcccagaag atccatttca gagaacagaa tctgggtccg acctaggaac   1020
gaagcctcca agtttggatg gaaagagcat tacctcaggc acaacgttcg ctttggacga   1080
gaaggagtct ttacgtcccg atgacagcgc gagcgtaaaa gcagccgaag atgatgatac   1140
attttctggt cgcggttcca ttgttgctgg ttctagaatt ggatctgaag cagctgcaag   1200
agcttatcgt gcacagttct atgaggctcc tgatcgacgt agtatacaac tcatgcagga   1260
gcgtcaaact cagggcattg ttactcctca aagtggttcc tctgggcagc aaaccacgga   1320
tgataaatcc aagccgcttg taggcccatc aggatcaact gaagcagcat ttacactctt   1380
ctatcgccag actcccgacg aaaagctttt ggaggcatta gagtcgccaa aagaccgcat   1440
ctttctcctt cgtctcgaga aggatgttat cgagtttgtg aaggactcca aggaaccttt   1500
cattgatctc ccaccgtgta actccttttg cagaatgctg actcacaagt tggcggatta   1560
ctaccacatg acacatcaag tcgatgctgt agttggagca gtccgtattt tccgaacacc   1620
attttgcagg attccgccat cactaacaag catttccaat cctcctacta ctggaaatac   1680
cccacctccc aatctacctg caatgaagat catgcgtaga ggtggtgatg gtgacactgg   1740
accgagcccc tcaaaagcta cttccgagac tggaagcgat ggcaaggaaa aggcacagtc   1800
cgctaaagag aaactttcgc gagaggagcg agaagccgtt tatcttgcgg ctcgagaaag   1860
aattttcggc aaagaagaca aatctggcga ggctacacca gaaaccgacg agggtaacga   1920
gatgtcacgt tccagctctg tttctacaaa ggataaaggc aagaggggta aagttggaaa   1980
acagcgtcgt gatgactctg aaagcttcga cgttcgatct caatacactc cctactttcc   2040
acaacaacaa aatcagccgg cctggatccc cacccagaat ttcggcgcaa tgggagttca   2100
gcaatacaat ggcgtcatgc caaacaatta tcaaaaccag atgcaacctc aatatgctcc   2160
acctccgcaa ccatttaatc ctgctatgat gagcaatgga aacatgcaac catacaataa   2220
tatgacacca ccgcaatttc ctcagcaaag tcagccacgt taccaaccac atagcgctcc   2280
aattacgact tacggcacac ctgcacagtc ccctcaacct ccccaacaat ggattccaca   2340
gaatcaatac ccaggaggcc agtatcagtc acgaggacct gttgcaggag gaccacctaa   2400
cactatccct tacgcttttg gacaactacc cagcacggta aacccagccg atcccaaaag   2460
tcaacacccg attccgggaa gtttcattaa tagacatgcc ttcaatccaa agacgcagtc   2520
gtttgttcct ggcagtcaag gtcttcctat cccgcagccc atgtctcatc atggatctcc   2580
tcaccatggt tccccacacc atggatctcc tcatctctct tacagcaact tctctccacc   2640
tcagcaacaa tacggggctg gaatgggtta tagcatggcg agacaagggt ctaatagctc   2700
tttaccctcg tatcatgcat ctccacacat ggcacataga ccaatgatgc atcagaatat   2760
gccgcaaggt cttcctcaag gcctttccca aggtcacctt caaggcttac cacaaggttt   2820
gccacaagct atgccacatg gtatgccacc aggaatgcca cagggcatgg ttccaaatgg   2880
tcaagttgga agccaccttc ctaactttgg caacccggca actttacctc caaagcctcc   2940
aactggtgtt taggtgtctt ttgaggaatt gcggatacat tctgtgatga ataaacggtg   3000
gcgtatggta gcattggtgg agttagtggg aaatgtgggc attaaaacga aagtcatttt   3060
aagtacctgg tttatattgg ctgatagacc tatgattaca aatacaatac atttgattac   3120
acca                                                                3124
```

<210> SEQ ID NO 37
<211> LENGTH: 1877
<212> TYPE: DNA
<213> ORGANISM: Botrytis cinerea

<400> SEQUENCE: 37

```
gacagtcatt cttcccttcc tgagaatttc tccatatcaa tcttctcatc atcacatgcg     60
cacatggact cgcaaatgcg aatgacaggg ctgagtgaat tctgagtagt gcatgactcg    120
attcgaagtt ctataatagt tgaatcagga ttcaggactt gatagtacat cccgcccaat    180
caacctcttt ggtaaaaaga gggggagata ttctcgctga gtatcacatc accgcaaaag    240
ttgacacatt cttctcagcc ccttttccac tgatcgaaat tctgcatact aaattctatc    300
tttccctagt tcacttacac acgagtgcac cactgggata tcttatgtgt ttcggattga    360
gcaggaagtg aataatatta gtgtgtaatt tcctagttcg aggcaatgcg gaattttaga    420
tgacttcgtg tagaatccaa actccaattc ataaagcttt ataatcctgc acagctgtct    480
cttttctcac acaactaact atatttcatc cccacgaacc agtctcggag agtcaaataa    540
atatacctgt tcgcatcatg gttgataaag cccaagatga ggcggaaaag gccgctttga    600
acccatctcc agaagaaggc gccgttccca aggagaaagt tgttgagcga agaggtatgc    660
cagggatttg gaagtcagga agaaactgcg tttcgtactt cgctagtctc agcatcttca    720
cgatcaccac tctcctgatg attccgggcc tcgctcttgc gtgctatcat cagagagcac    780
ttcaactcct tacgcttact accatatcta ctgctcctgg taagactatt ggaggtttga    840
atgcaacaaa tggaagtgga gacaatctca cctacaagat ttatctatgg tattattgta    900
tcttgggcgt tgctgctgga actggcaatt ttgtgaccat aacggatgtt tgtcatcaat    960
caagacaagc attgacctat cacattctcc cttccctcaa ttcaactttc ataccccctc   1020
ttcctggata cgatgcctct ggtcctatca tgacaataaa tggtctcttt cagaactacg   1080
catacccggc tttcgcttca tatgtcgccg ccatttttct cttgataatt tttgcaagtt   1140
tcttcaactt gtggttcggt gctaccgcca cgccacataa gaagatactt atgctcgtac   1200
tttccatctt tacaggttgt ttcgctaccc ttgcagcact ccaaacctat ctctgctacc   1260
aaaccgtcta cgtgctcaac caaatcatga aatattccaa atccactcta aaaatatccg   1320
tcacacccgg ttttctctac ctcatcatca ttcatctctt ctggatcatc cttcttctca   1380
acgtcctcat cattcccatc acaacttgca ccaagcgtcg ccgcgctaag cgacaacttc   1440
aagccctaga agccgatgca caagagctca aagaaaaaga gactctaggc ggcgacacga   1500
atgtacgtag tagtccagcg aagtctgctg attcagattc tagtgacgat gatcacgata   1560
tgtctcctcg tggtgtgcct cagtatggta tgcctcctta tggtatgtcc gcatatcctc   1620
atcccggtat gcaaaatgaa ggatactatg gtcatggcta tgatatgccg atgcctatgc   1680
aaccacagtc tggagagcgc aagaacaagg ggaagcgaga gcaaggaaga gacagcgaac   1740
gacgacaact cagagaatct gatgtttgaa aattgcatat ctgcaatatc atgatttttt   1800
ataccatttt agttgaattc ctagatttag gatgacttgg aggagttggg cgggccaaat   1860
aaatttcaca actttca                                                  1877
```

<210> SEQ ID NO 38
<211> LENGTH: 3703
<212> TYPE: DNA
<213> ORGANISM: Botrytis cinerea

<400> SEQUENCE: 38
gacgcgcaag caattccttt tgatcaataa gttgaatgaa aactcactgt ccccaatacc 60
tccttctgtg tcaaacatct ttactccatc tcttgtgagg aagaaacatc aaagttgtcg 120
caattgcttt aacacgattg attccccagc cgcatacatt ccacagcgag agcgcagata 180
cggatacgat acccacacat cttacttatc gataccatcc atagtctttc gagctttgga 240
agttctattt agacagttgc tagtagtttc cacgatcaaa ccctttggaa ggccttgggg 300
aggagctcga ttgcgtcctt ctacaaaact gaaagctgta taagacaatt tgaaaagcag 360
agctgtggtt ggatgctgtt atcgacttgt tttgaattgc ttatgacctc atggttctct 420
gataccgata tttgaggaat ccaagatatc aatcttaccc cggatattca ttcgacagga 480
acaaagcttc gtcccgctcc aaataatacc tcttgccata caaaaatcgt cattcacgat 540
ggtcactcga aagcccgttc cccaatctag catcccttcc aacaacacct cattgccgcc 600
ataccccata tccccagttt cttccgatcc acatcatatt tcacaccccg aaaggaacca 660
caatgcgatt tatgatagct ctacaaatga cctagagcct aatgtttgga atgaagagga 720
gcattctcat cctgatccca aaagcctacc taacgcttta agagttggcc catcgacaat 780
ccctcccagg ccttctcagg atatgttaaa acccagtccc tcaaccacga acccattttt 840
aaggaggcag caatcgcaga gttcgcaaag tgcagcatcc gatgggaagg aaagtagcgc 900
agatatctgg aatgagctca cagagaaacc cacacagccg gcttatccac cccctcctcc 960
tcctgtatct caagtaactc aacaattttc gaccatggga gtgtctggcc aagacacgaa 1020
cccttggcaa cccaccgcga acgaaaagcc gccattacaa acacccagtc ttcaacgcga 1080
agattcggga aacgaagcct ggtcaggcgc aaatcctcca aatatcgtta cctcttctgg 1140
cttgtctcaa aattcgcaac atccagtttt agtagatatt gatgaacctg aatctccagc 1200
atgggatgag gatgattatg acgatggtga agaggaagaa ggaacgccag tcagccccaa 1260
gaagtctacg ctacctacgc acgaaacgca ggagatacta gaagaccaac atgcatggga 1320
ttctactcct ggtcaaagtt cggatcaatc gcaaacaatg ccagttcagt cctctggaaa 1380
tacacaatat tcgaaccctc ctacggaagg gtggaatttg attgatcatg atcctatacc 1440
ggggaatttt cagcaaagcg gagtagtcgg agcagatggc acagagattt ccagaatgac 1500
ccctgaagaa gttgctccag cacttccacc gcgaaactct caagaacatc ctcctcctca 1560
gcctccgcgg ccagtcttag tcgcgacaaa cacaagtaca acaccggcta tgacacctga 1620
tttatcagcg gctgctctaa gacagaagaa agagacgtac gagatcaaaa aaatatcttg 1680
gcatgacatc aacgcccaac acaaccccag aatttcacct gttctagtgc aaaatgcaaa 1740
tggaccttgc cctctgttgg ctcttgtgaa tgctctgact ttatcgacac ccgcaaatgt 1800
ggaaactgct ttagtggaga cactccggtc gcgagagcag gtaagcctcg ggttactgct 1860
tgatgcagtt tttgatgaac tcatgtccgg gcgacgtgga gatgctgcac aagagcttcc 1920
agacgtgggt gatctctatt cctttctcct aacgcttcat acgggaatga acgtgaaccc 1980
tctcttcttt cctgttgatc ctatcctatc agtgaatgat cccaggaact caatgccaca 2040
cattcatcct gcgcagcgtg agagctcact tccaggcaca tttgaggaga ctcgtgaaat 2100
gaaattatat ggtactttct ctgtgccttt gattcatggt tggctccccg aggaagaatc 2160
gcctgcatac atggcactca aaagatccgc caagtcgtat gaagatgcac agaacttgat 2220
gttccatgaa gaggtattgg aagagaagtt agccgctgaa ggcctcagtt tcgaggaaca 2280
agggattcta gaggacattt cgactataaa agcgtttttt atctccgcag caactcagct 2340

```
tacagctcat ggcttagatc tcataactaa atctatgagt ccaggtgctg tagccattct   2400
atttcgaaat gaccacttct ccacaatctt caaacacccc acaacacttc aactattgca   2460
gctcgtgaca gattctggtt atgcaggaca tgcagaagtt gtatgggaag gccttattga   2520
tgttaatgga gaaagggccg agttctattc tggtgacttt cgtttagtcg gcggatcctc   2580
tacattacac cagggaaatg aagaaggcaa ctggaccaca gtcactggtc gtagaaataa   2640
taaccgtgtt gaaaattcac atgatgcacc attagggaat caacaagaat cgcagaatca   2700
cgagcaaggt acgaatgcag aacaggagga tcacgatttt gccttagcac tgcaactaca   2760
ggaagaagag gacgagcgga accgaaatga gaccgcccga aggcgaagag aatcagagct   2820
ctcacagcag tacatcgagc aacagggtag tagcaacgac actggtaatg cccctgtcag   2880
tcagcgaggc ggcaatggac gaggtagtac cagaggccgt ggagtcaatg taccagttcg   2940
aggagggtca attcgtggta gtgctagtac ccgaggtcgt cccgcgattc cacctcgcaa   3000
caataatgtt gccactcctg ccgccgaccc agaagcaggc atcgatgcac cgcctcctac   3060
atacgagcaa gccgctactg aaccggctta ccaacctcca gataatcatc ctgcacatcc   3120
aaacgcagat ccaagtcgga gaacaagtgc ttacacggca accgctaata gtcaacaacg   3180
tcctccagct aatgccgcag gtcgccgtaa tacgacttcc catagtggca ttggaagggg   3240
cagtcagaca ctcatagatc aggttcctgg gcgcaggatc caagccccaa atcaagggct   3300
accgaactcc cagcagccag aaaggcagaa ggattgtatt gttatgtgat tattgcgttt   3360
tatgaatata tggcaacgat ggatatgcaa ttggggcaca ttagttgagc ggaatttgaa   3420
gctaggcgtt taggcaatgg gtatattgat ttataagaag aaacatatca cgagctacgg   3480
tcgatgaggg gacttttcat catgtactca tacgcttttt tcaaatggtt aatttgcggg   3540
cgataaatag gaggatagac ttggagggtg gtttggtggt taataatcaa tttattagta   3600
tactttgaaa tttatggact tcattttatg gcagtatgcc tctctcctgt tcagaccata   3660
tctttaattg atcgagattg gcaaatcaga cgtattcctt cca                      3703
```

<210> SEQ ID NO 39
<211> LENGTH: 2119
<212> TYPE: DNA
<213> ORGANISM: Botrytis cinerea

<400> SEQUENCE: 39

```
gctcttactt ctcaaattat ttgtttagta cattaattat cattatggta gattccacgg     60
acttttctca ttaccatctt acaggatgga atatagacga cgactcctta tcttatattg    120
atcatgatta ttgggaaggc gtgctaaatc aaatagtcga atcagaaatg ggtagaaaat    180
tatcggatct ggatcgagac aaactgttcc acaaaggctt tggcctcatc aacaacccac    240
cgcatggcga tcgttcagga ctaagacgtt acagcaaata ctcagagagt cgaaggttca    300
aatttgtgat aaaatgttta tgggatatca ctgctggtcg ggatcgtggt tgtacattag    360
accttgaagg taagagacgt aagactcgcg attcagcaga taatacacca tgtggaaagg    420
atttcggcaa caccatatgc aacatgccgg tttctactag gggtttcttt tcctttgtag    480
tggcaacatt acacgctgcc aaagaatacg cgtcgaagcg cagtcaaatt ccagctcttc    540
atcagtcaat tgaagttgat tcagaagaaa gactatcaaa agagacttct ccacctctgc    600
taaaagaaac ctcgagcaac caggaagaac caacaatgga tcaaccaatg tccagttcat    660
caaatggatt agaccattca agtgtggaac aatcagatga cgatctttca gcgtcgatat    720
```

```
caattgcatc tgaacagtcg gaacattcga ctgggcaggg ggaagttgtt gaaccgttag     780
caaattcatc atgtggattg ggacacctgg gtgaagaaca gttagaagtc gatcgtccag     840
catcaatgtc aattgcatcg gactcttcgg aaaatccaga tgttggtcat ccagagacaa     900
tagcagttac accaggctcg tcagaaaaat cagacagtga tcgttcagcg acaatatcaa     960
ttgcatcgaa cccttcggaa caatcaaaca gtgttcgtcc agcaccagtg tcaattgaat    1020
cagactcatc ggaacattca attcagtcgg aggaagttac tgatctgata gcacttgcac    1080
caaacggatt gggtcattca attgggcctt accatccacc actagttggc attgatatta    1140
caggtcatgg aagtctcctt atcaagaaag ccttcttaga caaaaggacg gaatcgcaaa    1200
atgcccttcg agtttctttg aacgttcttt gtacacagtc caaggactac atcctatgtg    1260
gactaagatc ttgggaggaa ggaggccatg tcgagggcca attggctctt gatattgttg    1320
gcgtgtggct tgagaaatca atgcgtcaat attcttgtca aaccttcata tgtttcatac    1380
acgacctcgg tgcaggacaa caattggatt tggagcaact ttatagggct gctggtggat    1440
tttcccttgt ggctagccga agtaaattcg atttagttcc aaaagacgca gtagtttcaa    1500
accagtctca gaacgtttcg cataattctt cttctcatcg gcacgtattg caaattacga    1560
accagaacgt tactagtaag ttcattggtc atgacggagc cagcgcaaga gaagtcgagg    1620
aaattctagg attatccatg tctatcgagc attttgatgg aaaagagtac attgtgtgta    1680
agccacacgc aaatcaaatt cttgatcgac aggaacatgt caatcatgaa aggtgccgga    1740
ttgggttgga aattattagt atatggcttt gggaacattg ggacgcaaaa aatgactaca    1800
tagatttgcc ggggttcctt gtttgtctga aagcatcaaa cgataagatg gctttggagg    1860
aaatctatga agccgcaata cagtctatga ggcgaacaag gctgccatat acccaaaaag    1920
ctttcttcaa ttcaaattat accatagaag cagaatcagg agcttagaaa gatggatatt    1980
tgaatcaatg tcaatcaggt ggagcaagca actcatcagt gatgtatctt ttggacatgc    2040
ccaatattag aaaagcatga caatcatcac aaggaaaaga atcaatggcc gaataaactt    2100
tgaactgtgg cgcttgaga                                                 2119
```

<210> SEQ ID NO 40
<211> LENGTH: 1329
<212> TYPE: DNA
<213> ORGANISM: Botrytis cinerea

<400> SEQUENCE: 40

```
gagaaagcat tgaatttcat aacaaaatat acttttacaa gagaaggtta tatttcagaa      60
gaacgattat cctgtcacta cggcgatgga aaacaaatta ggttagtgtc tactacgctt     120
tttgttaccc tgtactgccg tatcaaagaa attacaaggt atcatagaaa tgcatccaca     180
aacctttgat ctgctccgga tggagactag tcttcgcaaa atgcaactat tcgagcctca     240
cgatcctgtc gtcatcggcg tcgaccacaa tttggatcct tatttcaaat cccagcattc     300
attttgcctc tttcccagat tcccgccgga gcttcagctt atgatctggg ctgcggctgc     360
cgatgatcga cagattgttc ggattaaacc ttgcgccgag gatggatcag gagaggaagg     420
gttccggggt gattatacca tgccggtggc tctgcgcgtt tgtcgcgact ctagaaaaga     480
agcgcttaaa agatacacgg ttatattcaa aggtatcctt cgcaatccta tttatttcaa     540
ttatcagcaa gattacctga gtcttgttgg tagtagcgca catgagcatt tccaaattct     600
atctggagaa gaccatatca tttcagaaga gatccaaaag gtcgaaaatg tgttttcgat     660
gattgctggt tgtggaagtg gtgagagcga ggaagatgtt ttgactgaga tattgggcat     720
```

```
ctgggatggt atcaagcgtc tagtcattgc agaaagatcg ccaacctggt ggggcacatt    780

caaggagatc tggtccgaca aggaggtgaa gaggcttgct cgagacgcca aagctgaccg    840

tatcagggaa ggaactgcga ctccagaatt ccctcaagtt cgcattgtca agtttgatga    900

tgttctagat gccgtagcac gaggtgagca acaatcaatg agcagtacga acgcgacgct    960

ttcttttttc gactcgatat ttgaagcaga ttctacatat aacattaaga aacagtctaa   1020

gaaagctttg gaatcagcat aggcaaagaa acaatgtagc ttgctttggt aactgttgga   1080

ataatgcttt attcatagaa acccatggaa atagatggcg gtgtcaatga aaggaaggtt   1140

gaagctctag ttatctcatg tgtggggcat tggatggctt ttggttcaag aattatgtaa   1200

catagatcag ctttcatttc aaaggttgtc tacatatcat gtattttcat gataatgaaa   1260

ttacctctat atttcaaggt tccaggcggt cttccgtgta aaatcgaaaa aaaaaaattc   1320

tacacatca                                                           1329
```

<210> SEQ ID NO 41
<211> LENGTH: 2403
<212> TYPE: DNA
<213> ORGANISM: Botrytis cinerea

<400> SEQUENCE: 41

```
gcttctattt ccaccaccat catatttcac gatctataat actgcgttcg ctgattctat     60

tcaatcttcc aactttgcga tcaaactgtc agatacgatt tccaaaacaa ccccgcagcc    120

ttggagatta caacaatatg ggctcttcaa atatagctcg aaaggagcgg cgcaaaaaac    180

aaacacgctt gacattcgat ccgatctcca ccgaagtgcc ttcagattta gatttacctg    240

ccaaaagcca aggaccgtcg cctgcgaagg ttagatatga gagaacaaat gacggcacat    300

ctgctggaag tggaggaaga attacgcgca gtggattgtc ttcaggatcg ccctcgaaag    360

taactttgga taggaaagga aaatctgggg gcaaaggaaa gaatgcgaga gatggaaaaa    420

tcgattttgg aacattacca acgcctgcga aaagctcgca gaaagaggat attattgttg    480

cagatgcaga agtgactagc ggatcacgtc gaagcacacg aagttcaaaa acgactccat    540

cgaagactac gccaaagaaa agatcggtaa ctttatcgga tacaagtgat gatggcgtat    600

tcacatcaaa ctcaagacct tcacaacgct ctggcctatt tagtcagaaa tcagctgcgc    660

caatagaaag tagtgatgaa tctggcgagg aagctgacga agattctgag gatgatatac    720

tgccatcttc tactacgcgt cgacaagcaa cacggatcgt tccgcaagtt gcacttgaga    780

ttgattccga agacccggat gatgagcctc caacctcacc catgaagaga aagcgaccca    840

ccataatttc tgacgatgag gatagcgttg ttaggtcgcc tgcaaagaga gcgagggttg    900

tggatgagag tgattcggat gatgatttgc cgcatatgac taagctatct aagaccaccc    960

cccctgaatc tgatagccca gctccttccc cacaagttaa acgaaaagga ccgcctagga   1020

agcacagaac tgctaagcag aagcaattag agattctcaa acgcaagcgt gctggagaaa   1080

gtaaccccat tcttacagaa tccgagtctg atgaagaaga ggttggcggt ttatatgatt   1140

cgggtagtga tgcattgact acatttgagg atgaagaaga ggaggaggtg gaagaggagg   1200

ttcaagaaac gcgcaaacga aaatcgccaa agaagactgt acgagagaat gaggatgagt   1260

acgattcgga ctttgttgat gacgacgatg ttggccttct tggagtaccg gattatgcta   1320

tgattcccct acatctcacg gccgcagccc acaaacctct cagagaacac tttgtcgaag   1380

cggttgaatg gtgtgttcaa aacaagatca atccaggttt caaccaaaat ctcatgccca   1440
```

```
tttacaaggc ggcgtggaat aagctcgaag acgcatacag tggattatct ggtagcaaat   1500
ttgtttctac ttcatggact cgtgatttta ccaaaggcct ttatgcccgt cccgaattca   1560
tcaccaggag actcgcccca ggagaagcaa ttgatctatt aggcgaagct aaatgtgagg   1620
catgtaatcg taggaagcat ataccaactt ttggtatcac attaagggga tctgcatacc   1680
acaaggatag cttagccgag gtagagaaag atgatagtga tactgaggaa gacgacgagg   1740
aagattctga tgatgagaag gacacgcgga gtttgaacag cagggatgaa cctctaccac   1800
ctcaagacaa agagtacatg gtcggctctg tctgtaaaga aaatgccgaa aacgcacaca   1860
ttcttattca tttgaagtat gcactcaacc aatgggtcat aggcagtcta gaaagtcaag   1920
ggcatcttac gattgagaag cttgccaaga gagacaagat gagtgcaaag aagagacaga   1980
aggaagtcaa cgggattgtc gataagtgga aggaggagaa agaaatcaaa gaattgtatg   2040
gcatctggaa acaacaattg gagacggcac agaatgccag tacaacggga agacgataag   2100
ataccacgtg gtagctgaag gtgtgaattc ggagacgaac atgagaggaa tgggatttat   2160
ggcacataat ggtagagaac tgggaagatt ttaatgatgc tgggtaaagg atcaggtatt   2220
tgggagcgaa atatggaagc agctagcgat gattttggaa tcatgacttt gattcttctt   2280
cactttattt cagagtcagt aattagggat gactgggaac agaattttat taaaatcaga   2340
gatacggcct gattttagat ttagatatat atccacatcc aatagcaaat tattaacaat   2400
tca                                                                2403
```

<210> SEQ ID NO 42
<211> LENGTH: 3770
<212> TYPE: DNA
<213> ORGANISM: Botrytis cinerea

<400> SEQUENCE: 42

```
gatcttttca acaaacaaac cactttaggt tcataatggt ggctctctga ttaatacggt     60
tcgctatcga ttattccact cgaggaacgc ttgttgcaga cttgcgacat cttacttttc    120
ttctgaaccc ctattgaccc tacgatatgg atctctaaag tcttcgcatt actctctgca    180
tatctagtgt ctttattata aggttgacga aattcacctt tccgcgcttt actattaggc    240
ccgaattgat ttccatccgt tcgaaaacaa tcctctcgat aacacaaatc ttggagggtt    300
tgtggttact ctgatcaaac aaatcaatca ttgttctttt ttaaacacgt gcacttcacg    360
tgggccatag atcgaatgcc tccaatacgt cttgacgaga gtgacgacga ctctgagctt    420
tcggacgttg acgtagctga gatcgccagt gtagctctct cggatacccc aggatctaca    480
gtaattccaa ctgccacagg cttacctgga cacgatgaga tgaataggaa tgtgtctcct    540
cctagatctc agaccattgc agcatcatca aacccagaag aagatggtgg aatgattggt    600
cttgccaccc ggccactgtt ccatgacaaa ggcgatccac gaaatagtgt aaaggcggaa    660
tctgagtctc ccaaacatac tcgattgacc atacaaaatt cgggacgtcg aggcaagaag    720
ttattgttat ccaccgaacg ggagtctgga aataatccat ccgaacaacc accgaatacc    780
ctgaagagaa aatcatttcc aagtgactct cctaataatg cttccacgag tcccacagca    840
cacagacagc ttcgtcgttc agatcttgtt acgccaacgc taagacaacc ttccatagcg    900
acctctgaac gtcagtccat ccgccaccac gaatcaccat ccaatgccaa gatccaagaa    960
gaaactgctc atttaaggga agttttattg catgtgtcaa ctgaagcgac tcaagaaata   1020
ttgaaggagc agtggagaaa ctttcttttc acgaatgcaa aagagtcaca catcacattc   1080
attcttcgag ctggattgaa gaatgctact cctaatgttc ttggacgaat ctacaacgac   1140
```

```
tctggtgtca tgaaagatgc cttcttggag actatcacct ctaaacagcc cgttgtcgct   1200
agggttctca agagtgcatc tgcaaatcaa cttgcagatc ttgtgcccag taaagttctg   1260
gatcaggcgt tatctgaacg gttaaagagt gttccagcaa aaacgctcat acgatggcta   1320
gctgaggctg acagacttgg ttacagtctt gatgacatcc tggatgagag cgatgagact   1380
gtcgtaccaa acataccgag tagggcgcaa agtcatgacg ctgatgatgg tgatgataat   1440
gatacagaaa tgatagatga tggacaaaag aaattggaag ccccttcttt ggatccactt   1500
gttgctgaac aggaacgaat cagcgccctg caaaagtctc aaaacgatgc ccaagcaaat   1560
cctccacgcg agttaagatg ccccacatgc acctataagt ttgataccgt tagaggtcat   1620
aatttccatc gacagaagaa tatctgtact agaactcagc ctccgggatt aaagttctat   1680
tgtggtaatt gtgctcaagg ctttacgacc aagcaaggaa tgctatatca tgaaaagaag   1740
cgtgtttgtc ttggggaaga aggaagtgca gacgacgaaa ccatttatca agactaccga   1800
gacgttgttt cgaattcgcc aaatgctcaa tacggacagc accctgatca cccacagact   1860
acatcatttg gcaatatccc tcgcccacct ctccacactc cagcatcgcg ttccaaacat   1920
atcgaggcga ttattgcttc atctccctgg gacggcgagg ctcgtcattc accatctgaa   1980
ttgccacccg agaaacgtgc tgctttagaa gatgctcttc agaaaatcga agagaaatat   2040
ctcgaggatc aaagcaagat tcccgaggac tggactcccg aaagacgaga agcacgtctt   2100
atctctctca agaatggaaa cgcatcccgc aaatctcaaa tccgcaaaca atttggtgtt   2160
actcttcgta tgcgcgacag agataaagag gcaaagaaga ttcgcgaggt tttgggagct   2220
aactctccaa tggtgcctac tggcatgaac cgagctgaat accgtaattc accaacggtt   2280
gctggctatc cagtaaatcc tcagcagcaa atgcaaccga atcaaacacc ggccagcata   2340
agaatggaga tggtggatgt gagacctgct acaggattct cgccaatcaa tgccccgccg   2400
caaaaccagc aacaccagca acatcagcaa caccagcaat atccgcaagc accaccaggt   2460
caccacccaa tgcaatattc aggtccacct caagctcaag gtttccaaca aagtattccg   2520
cctgtatcac aacttctgtc gcagcaacga cctagccagg accaccaaat gagccccctt   2580
gggtatcaag gagctccgga gcaagcatac agaggaccag aagatcacgc aaacaaaaga   2640
ctcaagcgtg gatcaagtgc aggactgtca cgatcagatg aagaaagaag taggcatttt   2700
gcatcagctg attcgactcc aatgggtgtg aatgagacaa gggtttcagg gggaagaact   2760
caggcttata acggtgcggg aatgctctct gtggaaaatc aaagatctgt ttctgcagga   2820
gcaaatggtg ctatgattga aggtgagagt agaccaaact ctgcaggctc aagtactgtg   2880
cgaaagaggg tgccagttgg tgcgttgcag aggcaatggg aagcgttgaa tggcaagggg   2940
ccgggtagga agtcggaggt tgaaaataag gcggggaatg tattaatgag tagtgtggac   3000
gggaatgaga aagcaaatgg acgggctgag ggtggaaagt tggttatggg tggtaaaggt   3060
aaggagccaa tgcacgaggg agttaggaat gtggtcgatt tgattagtga tgatagttcg   3120
agtgagcgtg gaattaggag acccagtgga ggaggaaaat agactcctgg gaggggcagt   3180
gagatcctga agagatcata catttgttcg atggaagcat ggattttcat tttcattcaa   3240
ggctacttgc cttttctttt atacctgttt ttgtcacaca agcttttttt tttctttctt   3300
cattcggaga ccaagcaaag gaaaagaaac agcgagatag gagacttatt ggaatctaca   3360
ttacagaaat ggatagatgg gagaagtgtc aagaaacgta ttgtattcta aatacctcgg   3420
tctgcttttt tccctttttc ttttttttcaa aacagttttg atgcgactcg atgcgattcg   3480
```

ataaaataca atacgatagt tgatgatgtc cttggcctac aagatcgtgg ctttaaatat 3540
cgtattttga tgaagatgca gaagaagaag atgatgatga tgattactta gttagttaat 3600
acgatgaaat tactggatgt tgattttcga gaacattaca ggagttttta ttggatggat 3660
ggatggatgg atggatggat tgtatttgat agtgtaggta gtgtataata ggtcattaga 3720
tagtacctac ctaggtaggt tgattgatta attgatcacc tcttccacca 3770

<210> SEQ ID NO 43
<211> LENGTH: 1873
<212> TYPE: DNA
<213> ORGANISM: Botrytis cinerea

<400> SEQUENCE: 43
caggaactat gcatcttatc ggtgacttca ttcagtaaga aatccgagaa tgaaatgatt 60
ttgagcctca tgaattgtgt attaatggtg attccgtttg ccgcgccgta atcaatattt 120
agtcatttta agtcgttgag tttatcatgg acaaattttt attcgaccaa catttgcgag 180
attgcaccat agtgcaagaa aaaacaacat gcttcgaaac ttttctctat gctgatccag 240
aataccgaac cacagtgacc gaagagaccc ttcttgaggc cgaagagttt gatgattttt 300
tgaatcaaaa gggcagattc gaaaacagaa atcaagggtg catcggagga attagactta 360
tcttacaaag aaatgcaatc catccccata cattcgaacc caagttttta tctttaccta 420
atggctttca taaaaagatt gtggacgcaa tgcatctccc tcactcatgg attgagactc 480
taagcgcagt gggcccattt tactggtctg gatatgagca aaacgataac gatctttatc 540
ttcagataat ataccgcaag agcgacgtaa aaaagccatc caatgctcga aactgggaat 600
tggttctttc acactcccctc aagactggta tcacgaatgc ctttttcaag ggtacgcctc 660
gggctgatgt tactcaatgt attacatgtc ttcgtcaatg catcagtgag atcgatcacc 720
ctttattcct gcctgctctg gtcttttctt gtgacattga ttttggagaa gataaacgtc 780
accgagacaa tcgagagcga gtccggatct tagaaaaaca agtagtcgat gcatcccaca 840
tatatgcaca tccagacttt accaagcgag ataaagtcaa cctttcacaa atcaatagtg 900
acttggtaga ttgccataag aatgtgttgt ggaagcggcc ggaagggtat atcactattg 960
tacaaaaaat ggagaaaaca ttatacgagt tcaaaacttt gtggccggtt gaaagaaagg 1020
aaagattaaa aaagcttcaa acaatgatgg aagggaggct tgaactgctt cagtctaagc 1080
ttcagggaat aagcacccat cgtgaagtta caatctcgag attgaagtta attggggagg 1140
tgttggaaaa tttggtctcg ctggatatct acaagcaaga gaaacagcgg caattcagta 1200
aattgctgag tcgaaaaacg gcacttctag aggaaacaaa acaagaagag agaagagaaa 1260
tggagaaaac acagagagat ctagaagtaa tgctagaaac aaggaaacag acgactatgt 1320
cattactagg cattttgttt ctacctggta catttttttgc agcaattttc agtaccacat 1380
tcttcaactt ccaacatggt gattatgcgg gaatcgtctc taagaaattt tatatttact 1440
gggcagctac ggttccgacc actgtaactt tgttaggcat gtggctcctc tggcaaagaa 1500
gaactaagaa aatgctagag aagagagatg ataaatttcg ggaccttgaa gcaaagagca 1560
agaaggcacg aaacgatatc tttaaagagg aagaaaaaca ttttagacca gtttgattcc 1620
acagctcttg aatatgtatt tttcaacttg gggttttgtt tgctataatt tgaagaagcg 1680
ggtcgcgatt cgtccaaaca catagtcggt gtcgaagaaa gatagcatta cacccgatgt 1740
aacagctttt ggggattgtg ggaaagatag tccaatacat gatctttcgc tggaaaattg 1800
cagtactgac tacacgcaaa gttgacgatg gttcatgagt tgtaacagga acttattaaa 1860
atgatcgagc cca 1873

<210> SEQ ID NO 44
<211> LENGTH: 4087
<212> TYPE: DNA
<213> ORGANISM: Botrytis cinerea

<400> SEQUENCE: 44
ggcctcaatc tctcctttc acatatcgtg tcttgtcttc tgttgaaagt cggcattcac 60 aattttttg gttcaatcaa cttttggtta atacatgcat gcatgtaata gctgtatcac 120
gcatttaatt tcgattcatt caaaattacc tccttttgta agcattccat aaaggacatg 180
ctccgtcgaa atagttctag tcgacctgtt cgaagcaaat caacattatc aacctatcca 240
aaacacgatt ttgtcgaccc tgaagagtct cgtatgcatg ctcatgctgc agcaatgcat 300
gctttcaata gggcccaaga gaggaatggc actagttatg gaaacaggaa cggtctttca 360
cgaagcaaca ctacaagtca agaaagtcaa tggcggccga gtcaacaaaa tagttctaca 420
agtcttgata acccagggct caagcgtcag cagagtgttc gatttgcagg cccaaatgcg 480
gtaaagaggc gccaatcagc ggggaaaagg acggacccgc cagcactgaa ccagaaacta 540
agtactgcta ctttgggacc tgttgtgatg accacaaata ctccagtccc agcagtgtat 600
cgtccaccca gtcgttcttc ttcaattggc aaagcttcac ttaacaaatc agtcgttcga 660
gactactctg ctcataatta cgttaccaac ttagatttcg atgaatacta tacgcaagag 720
aacgatgtgg cctcgacgcc atcttcatat cggcgaatca gaaagtcgag gtctatgttc 780
agccccttgt cagcgccaac caacatcttc tacagcaatg gcagccctga tcgcaccaat 840
tgttcatcca ctccgcggac gctagagaat aatgctccat tacgggctcc aaaatcaatg 900
agcttcctcc gagggggcg ggactatttc aaatctacat cgtcttgcga aagaaatgac 960
gatgccgtcc aaatggccag agatagattt tttgttcaag ccaatcaaca aagacttcgg 1020
gagcagccat cttttctctt cagatcgaag gcacaacggc aagagaagcc ttttcgaaag 1080
tcggttcgaa gcagcagcgg aaagtctgca gcgacatatg attcggccga atctatgaga 1140
gagggtggcc taagagccaa agctcgcaag gtatcccaag gattaaagag caaactccga 1200
aaagtttttg gccgcagcaa agacgaaccc gtcgctatcc ctaatcaaca ggtggatgcc 1260
attgaaactc acgttcgaga atacgctgga caattagcgt cagatcatga gtcgttcgat 1320
gatattccta tacccgatga ggccgcattt gctcatgtgg cagctagagt cccatcatta 1380
cgtgctattg cttcaagcca gagactcaga tcacaaagtg gtagtattcg tagcttacga 1440
agtgatcata gtgatgaaaa gtccagagta acaagctgga ccaatagtac agctaacaat 1500
actgttacca gtcaaggatt gcgtcctccg cctagcagag accaaagact ttctataatc 1560
aatgaatcag gcacgcatat ctctaaagca gcatttcatc gcccaaatgt aaagaatcaa 1620
catccagctt atcctgcatt tcatcgtcct ggctatatcc aatcaattcg accaggaggt 1680
gtagatagcg ccagactttg ctctgctttg atgaagcgtc tcgacgagaa tagcccagaa 1740
gcaatactcg caaagtcaaa gaaagccagc actgaaactc tcggacttga gaaagtacct 1800
agacaaagta gctcctttac caatactctt tcacggccca agccatggat tagacaggta 1860
cctcctgact gtgacccagg aaatcagagc caaaatcaac ttcctaacgt atactgttcg 1920
aacaacgctg gcccaatacc cgtcacgagc ggcgaggaac tacctggtca ggcaatcgac 1980
tctgagtatc aattcaaatc tgcaggttta ccattacata atccacaact tcaaagccaa 2040

```
gacgatgtgt tttcctcact cccaggatct agtcatggca actcctttca ccacggtagc   2100
tcatttcatg aagacaactc atttcatcaa cgtgctcacc agcgtaattc aaagtctgca   2160
cacagacgcc acttatccga tattgatgcc gcatatgacc ctgtgcaaga cccttcaggt   2220
ctcactccgc agcaagtcgc acagcgggac gatcctatag ttcccaaacc aaaagttatc   2280
cgcgaggcaa ggtctgcatt tttcggaggc acgacatttg caattgacag agtcggaaat   2340
acaagtccgt atcgtcgcgc tttggcggaa agcgacaatt ctgctgccta caacgaagtg   2400
agtatggcac cggtaaatga tgacgtttat agtgagagtg tttactctcg aagtattggc   2460
cgtaatcttt cggaggctat gagtagtgat acatcggtac cgctcccaaa tgtccgtatg   2520
ccgtcattgc ccgtcgatgg ctcaactccc aatggtggcg ctgtcattat caacagcaca   2580
acctatcgtc caactcatcc aagacagcga ggtgacaatt ccggtggttc tattgagtgg   2640
caaacatgga tgtcgtctga agtggcaaag ttggaaagac catctgaaaa cgatcgcgta   2700
agcgtcagca acatcgaaca atcactatca cccacgccta cgatgtcaaa ctcctttcac   2760
attgtgcaca gaagagaaaa ggctcagatg gctgatgatg atacggatat cgctcagaag   2820
aaacttcctg ctggtaaaca gccgcttggt ctcattcaac agaatcttaa tgcccaagtt   2880
cttctgaagc cgattttgaa aaatcgctcg acgacatctt tgcctgaaga tgatttcatt   2940
gataactcta agccgtttaa tattccttct gcaccaccac ttcctcttag atcgatatta   3000
agaccagcac aaagcaaaac gagtctgaaa agtacctcga actctcaaca cgcaccaacc   3060
ccaaatcccg tcactcaaac ccagaatcca aataccagcg ctcgcaacgt cttgcgcaaa   3120
cgtctctcat ctacaaccct aagaagcgca ccaacaacac ctaatcatgg tgtagaaaaa   3180
caatccccga gtacgcgtaa tgtactccac aaacgaaacg tatcggaagc cacgatgaaa   3240
agcggcaaga gtattagaag cgtgaagagt ttcgatacga gtggaagtca aagccgtagc   3300
tttaccacta gtccggcgaa attggtcaag aggagtggga gaccggtgta taattttacg   3360
ccgcagagta gtccgggtac gggtattggg gccgcggtgg agagacagtt tgggagtgcg   3420
aacgcgaagc cgaatgcgaa tacgagtgga ggtttgtatg gaacggggag atcgagagtg   3480
agggctgggg gcagggaaaa tgaaagggtc ggtggaggcg gcacggatga tgtttatggg   3540
gttgagggaa gtggggtggg ggattcgaat gggttggggt tggggttgga tcaacaacag   3600
gtgggtagta aacagatggt ggatatgttt ttgagtagta gacgaaagag aattgctagt   3660
gtagggacga tcgcgggggg gagtatgggg ggtgatgggg gtgggaggag tgatggtgga   3720
atggatgatg gtgcggtgtt tctttaggcg tggggattgg tgtatgagta ttgggaatag   3780
atgagagggt aacgaagtca tgacttatgg atttgggtgc ttgagaccag gattaggatt   3840
aggattatgt atatattttt agcgggtata tcatgtatta tacttggtga ctcggttact   3900
ggggattgga gaatagaaca ataaagcgct tgtgagaggg ctgatatagt atggattagg   3960
gtcgatgaca ttacttttgc ttttcttttc ttttttagaa aattagagtt tagtgtaagt   4020
agacagctgg tagagtagtg tagtgtagtg ccagtatgaa tggtagttga ggtatggaaa   4080
atattag                                                             4087
```

<210> SEQ ID NO 45
<211> LENGTH: 2795
<212> TYPE: DNA
<213> ORGANISM: Botrytis cinerea

<400> SEQUENCE: 45

```
gtttccaagt acagtacagt accacttcaa gtacataaac tcagcgctct tcttgagata     60
```

-continued

```
aaaggttaaa gggttgcaag atttctttga tacatatcat tggaaataaa gtattccgga    120
ttacattaga ggaagctcac tgtaacaggt ttctgctttg ttgttcatgg acatgatggc    180
agcaactcca gacatttctt tgacctggtc atcagtctat aaagtcgccc caaaagacaa    240
cgtctcgctg cccggggaca agatactact acctcaatca gcgctggaac aactactatc    300
ggcatctaca gttacggtga attctaacac tcgccccagc aatgttgcat ttgatccatt    360
caatccatat tcattggcag ccgctcgcat agaacagtcg caatggagag atacccaaca    420
acaactgccc catcctctca cctttaggct ggtcaactcg aagaacggaa atgtagtata    480
tgcaggaatt cgagagttct cggcagatga aggagaagtt gtcttaagcc catttttgct    540
agaggcatta gggatcactg cgcccttacg aaatccaaca ccaccaagtt caaaggttga    600
aagcaggaga gggtcgccgg atacgcctat agatcttaca gataaccctg caatcgatct    660
tacgggtgac gagatgatag accttacaga cgaaaccgaa gaaccggcgc agatcactgt    720
acatgcgaaa caattaccta aaggcacata cgtgaggcta aggccattgg aggctggtta    780
taatcccgag gattggaaat cattgctcga aaaacacatg cgagaaaatt tcacaacttt    840
aacgaaagga gaaatattga cggttcgagg ttcaaagtcg gaggaattcc gatttctgat    900
tgataagttt gcaccggaag gagatgcagt ttgcgttgtt gatacagatc tagaggtcga    960
tattgaggct ttgaatgaag agcaggctcg ggaaaccttg aagcaaatca tgtcaaaggc   1020
acaaaaagct ccaggaacgg ctcaagggag ttcaattggc ggagaattag atctttggaa   1080
tgctttgcag ggacaggtcg cagaaggtga ttatgtcgac tatactttac cttcatggga   1140
tcgatcaaat ggtcttgata ttgagctttc acttgaggac gatggtgatg gtgatgtgga   1200
gatattcatt agtcctcaat cagcccatca aagagcaaaa ccacgggagg atgaacatgt   1260
tctcggagat ttctcaagtg acaaaatcaa gagaataacc atacaacaat caaatgtgga   1320
attagacgga gctgatgcta tattaatttc tttatactgt cgaggaactg gagcaggctc   1380
tgagccacca catggaccac ggaagtattc cattagagta aaatcgcttg aaaagggggc   1440
aagcaatggg gccccaagca acccaatctc gctcgaagaa gatgccgaaa tgcatggatc   1500
tgatgaggag caatgtaaaa attgtcatca atgggtgcca aagcggacaa tgatgcttca   1560
tgagaacttt tgtctccgca ataatatctc atgccctcat tgcaatggcg tctttcagaa   1620
gaaatcttca gaatggctga atcattggca ttgtcctcat gattcagccc atggaaattc   1680
ctcagaaagc aaaactaaac acgactctat ttttcacgaa gctcgacaat gtcccaattg   1740
cccttacgaa gcaacaaata tgagggatct tgccactcac cgtacgtcta tttgtcctgg   1800
caagatcatt ctatgtcaat tttgccatct tgaagttcct caagagggcg accccttcga   1860
tccgtctcca gaaagtctta tttccggact tacagcacac gagcttgcag atggggctcg   1920
aactacggaa tgtcacctgt gcagcaaaat tgttcgactt cgggatatga ccacccatct   1980
taaacatcac gaactcgaaa agaatagccg atttaaacca gccatctgta gaaatgcaat   2040
ctgcggtaga actctggagg gcgttggtaa gaatggggaa gtgggcgctg gatcgagaat   2100
gggccaagga cctggtaatg atttgggtct ttgcagtatc tgcttcggtc cactatacgc   2160
tagtatgcac gacccattag gaaaagcaat gaaacgccgc gtggaacgaa ggtatctgag   2220
ccagatgatc acgggatgcg gcaagaaatg gtgtacaaac atctattgca agactgcaag   2280
ggcgaaagaa gcgaatgggc ctcaggcaat actagcgatg aaagatgccc ttcctcttat   2340
tcagccatta gtagcccaag tagaggataa gaccgaaccg atgcatttct gtgtcgatga   2400
```

aggaaaccag aagagaagaa atctggctga aatgttagct atggagcctg gaggttggga 2460
attggagtgg tgtgttgcgg cttgtgaagc agaaggtgca aatcttgata aggccaggac 2520
atggttatct aattgggctc ccaagaaagc ttgatgtggt tcagatctgg aagatatttt 2580
ggtatggatg aaagggatgg agcatggcgt ggtaccgatt gcataagtaa gggagttctg 2640
gtggctgatg acgatatgat atgatatgat accaatttat agacccgatt ttgttgtgcg 2700
tacataaata tacatggttg gcgtcgcatt agctagagat agatcgaaca gattaagaat 2760
ttactgctaa tacataaaca tatatacatt cttca 2795

<210> SEQ ID NO 46
<211> LENGTH: 801
<212> TYPE: DNA
<213> ORGANISM: Botrytis cinerea

<400> SEQUENCE: 46
ggatcgcaac taactcttct ggaaggttct tgtggcaata tcaaccacat ggatcttcag 60
taccaccgcc gtcaaattgg ctgtgcttgg gttatatatg cgaatcttca ccacgcccgt 120
tttcaagcga tgggccgtct ctttgatgac catagacgtt tgtttcggta tcaccttctt 180
cgtcgtgttt ttaactcatt gcaacccagt ctctcaagaa tggaaccctg ttccacgggg 240
ttcatgcaga tctctaacat tgtccgagtt ttcctccatc gctctcaatc tggctctcga 300
cacggcaatc atcattctcc ctatgccatg gctatacaag cttcaaatcg cattaaatca 360
caagcttttt gtgatggtca tgttcagttt cggctttgca actattgcca tcatgtgcta 420
tcgtcttgaa ttgacagccc gaagcccttc tgatcccatg attgccattg caagagtcgg 480
agtgctgagc aatctcgagc tttggattgg tattattgtt gcctgcttac ctactatgaa 540
accttttgtt agagtatatc tcagacccag cctatcaaag ctctcccaaa aactttatgg 600
cagccccaca gtgtcaacaa aagacgaaaa tccacaactt cagctaagga acttcggggg 660
ttccggacct tcacgccccc aaaaaaaaca gtaactacac tgaactttct gaagctccat 720
ctgtgcagac agatactgac gagttgcatc tcgttccaaa tgaatcatcc aattttgatg 780
caaattgtga atctagcaac a 801

<210> SEQ ID NO 47
<211> LENGTH: 1584
<212> TYPE: DNA
<213> ORGANISM: Botrytis cinerea

<400> SEQUENCE: 47
gcacggttgg cttgccaaga ctttcccacc cacagaaagt gcgatactgg agaatacccc 60
tgtcagaggt acctccggaa ccgggcagga aaatttccta gctactgttg cccacaacaa 120
aaagacgaag agtcacatct acaacttttt gatttaaacc tcaaaatacc catctgttat 180
tcttcctttt tttttgaact ccactcactt cttccttcaa aatggccgcc cgtacatttt 240
ccagagtcgc tagaccagtt gcacgtcaat tgactgcacc agcacgcaga acttttgtct 300
ctgctatcaa tgcctcagcc agaccttccg ctgctcgtgc tgttgttgga gcttcccaac 360
aagtcagagg tgtaaagacc attgactttg ctggcacaaa ggagaaggtt tacgagagag 420
ccgactggcc agttgagaga ctccaggaat acttcaagaa tgacacaatg gccattattg 480
gttacggttc ccaaggacat gctcaatctt tgaacatgcg tgataacggt cttaacgtcg 540
tggtcggtgt acgaaagaac ggtcaatcat ggaaggatgc tcaacaagat ggttgggttc 600
caggaaagaa cctcttcgag gtcgatgagg ctatctcaaa gggtaccatc atcatgaact 660

```
tgctttctga tgctgctcaa agtgaaactt ggccagcact taagccccag atcaccaagg    720

gaaagactct ttacttctcc cacggtttct ccccagtctt caaggaccaa accaaggtcg    780

atgtcccaac tgacgttgat gtcatcctcg ttgcaccaaa gggatctgga cgtaccgtcc    840

gaactctctt ccgtgagggt cgtggtatca actcttccat cgccgttttc caagatgtta    900

ccggtaaggc acaagagaag gctatcgctc tcggtgtcgg tgttggatct ggatacctct    960

acgagaccac cttcgagaag gaggtttact ccgacttgta cggtgagcgt ggttgcttga   1020

tgggtggtat ccacggcatg ttcctcgcac aatacgaggt tctccgtgag caaggtcaca   1080

gcccaagtga agctttcaac gagactgttg aggaggctac tcaatctttg tacccattga   1140

ttggtgccaa cggtatggac tggatgtacg aggcttgctc taccactgct cgtcgtggtg   1200

ctatcgattg gtccggaaag ttcaaggatg ctttgaagcc agtcttcaac gacttgtatg   1260

actccgtcaa gaccggaaag gagactcaaa gatcccttga gttcaactcc caaaaggatt   1320

accgtgagaa gtatgaggct gagatgaagg agatccgtga tttggagatc tggagagcag   1380

gaaaggctgt ccgttccctc cgtcctgaaa acaactaagt ggatagttaa tggggccttt   1440

ggggctggag ttgcatattt gaaattgggc caattgtatc atactctcat gactttccgt   1500

tttttaatc aacggtatct ggaattaaaa gtttaagcca ttgaattcaa aaaaattata   1560

tttccaattg tttttataat tgac                                         1584
```

<210> SEQ ID NO 48
<211> LENGTH: 1495
<212> TYPE: DNA
<213> ORGANISM: Botrytis cinerea

<400> SEQUENCE: 48

```
gagcacaccc actttcaaaa tttcttccaa gttttggata cctcgaagtt acatttctgg     60

ttattctaat aagtatggcg ccttctccgg tgacagtaag tctaaaagat ttgcaaagtg    120

gcaatgtttc cttctcaaca ctcgaagagg cttttggccc cgagtcttta ggtattatac    180

tcgtcaaaga tgttccagag ccattcgtag agttaagaca tagtctactc tcatattcat    240

cttatcttgg aaacttgcct gaagccagac tagagaaaat cgaaaacgcg gctgcaaaat    300

atcttaccgg ctggtctcgt ggtaaagaaa ctctaaaaaa tggccaagtg gacacactca    360

aaggatcata ctatgcgaat tgtgccttct acgtcgaccc atctttagca tgtgcgattc    420

ctactcctga cttttcaccc gaaaatttc ccgaatatct cagtccaaat ttatggcctg    480

gagaaatcgt gttgcctggc ttcaagagca catttgagag attgtgtcga attattattg    540

acaccggagt actggtcgct cgggcttgtg acagatatgc agagaaggag attccagact    600

acaaacctgg atatcttgag cacgttgtaa aaacttcgac aaccactaaa gcacgattgc    660

tacattattt tccagcagaa gccaaggact cttctgatgc tctagacgat gattggtgtg    720

caacccattt ggatcatggc tgcttaactg gactcacatc agctatgttc attaacgaga    780

ctcgcaatcc acccgtgatt ccagtatcct actcataccg tccaactacc cttagccctc    840

ttaaggagct tcctacatct ccggacccaa ctgcgggact ttacattcaa tctcggagtg    900

gcgagactgt tcaagttaaa attcccaaag actgcattgc tttccaaacg gggaggccc     960

tcgagagaat caccaaaggt aaattcaagg cagttcctca ctatgtgaga ggtgtacgac   1020

caggagttgc agatggcgag aatgaaggag gaaggattgc gagaaatact attgccgtct   1080

ttactcaacc caacttggac gagattgtag actcagagat ggggattact tttggagagt   1140
```

-continued

```
tcgcgagagg ggtagttgcg aaaaatacaa cgaagtgagg ttattctaac aaattattca   1200
caagttcata caaaataccc agtacagctt tgtttttatc taaatatatt tcatgatgct   1260
caatgtttta gcgagggggt attgggggaa atattgaggt ggcgaagcgc ataactttcc   1320
agtatctcag cccaaaggcc cccatttgcc cccccaattt attgtatcgg attggaattc   1380
ttccgtccga gtgaaaaaaa aagcaataac atccaaggat ggcggcggta cggggacatt   1440
ggaaggacgt tccaagacta ggatctttat tttattctgg tggcaataac cccta        1495
```

<210> SEQ ID NO 49
<211> LENGTH: 2264
<212> TYPE: DNA
<213> ORGANISM: Botrytis cinerea

<400> SEQUENCE: 49

```
gcttgtctta tctgatcgat tgatcggatt tcattggttt tcattcgaca atagccatgc     60
ggtcccggat gtgacaacta ttttcgaagt gtgagttcgt atgaaaaggt gggcaggcat    120
ggtatgaagt aactgtgctc cgtatctatg gggaaggacg aggcgtagag gtggtccgtt    180
ctttcttgtc atatcctgat ataaatatgt actccacgga agtcgtgata tgtagtcttt    240
gaatactttg ccattcggtg tgttcttttc cattttggct aacgttgcac atctctttct    300
ttctcttgga actttgagat tcgttttgat tttactgtat tcgtacaaac agtcgggaac    360
acaattcgct tgacttaaga agatcagtgt cttccaattc cccaaactat ggctccctcc    420
atcgcagaac ttccgtcttc cccctcgact actgtcaagg aagctcctat atctaccact    480
tctgggcgcg gcatcttcaa tgcagaagta caacctccgg aagcctctgc agttccaata    540
tggcaatcca tcgctactcg tcgccagcaa gaaatcaact cttctattcc ttcggaatgg    600
cttcttccaa caggcctcct ccaatctaaa cgtcctctcg atctagtaaa aacatgcggt    660
ttgttggatg aaagagaggt gaagattgtg tacagtgctg ctgtggattt gctcgagaaa    720
atgagaacga gagagtatac agctgtggaa gttacaacgg cgttttgtaa agcgagcgct    780
gttgcccatc aagcgacaaa ctgtctcgct tggacgatgt accccagcgc cctctcccac    840
gccgccaaac tcgacgctca catgtcccta accgggactc ccatcgggcc cctccatggt    900
cttcccatct ccgtaaaaga acacgtctac ctcatcgaca caccttccac atctggtttc    960
gtaggctggg ccgataactt ctgtacttcc tctgcccaag aaggaatgtg catccaagtc   1020
ctccgcgaca gcggcgcagt ctttcacgtc aagactacta atccccaagg gctcatggct   1080
ctcgaaacac aatcaaatct ctattcaacc actaccaatc ctctcaatac cttcctctcc   1140
ccaggtggtt catcaggtgg tgaatccgcc ctggtagcca tgcacgggtc gattctcgga   1200
attggcaccg acatcggagg gagcattcga aatcccgccc tgagttgcgg tatctacgga   1260
ctcaaaccca gtgtggcgcg acttccacat tccggactct ccggcgcaca cgacggaatg   1320
gaaagtgtga ttggggttgt gggacccatt gctacatgtt tggcagatat ggaactgttt   1380
tgcaaaacgc tcttggatgc gcagccctgg agacaggaag ttggattact acccattcca   1440
tggggaagtc gcgaagctat cgctgccgag aaagaagaga acaggaaatt gaaaatcggt   1500
atcatataca ctgatggagt acatactcct catccaccca ttacccgtgt tctgcactct   1560
acggagtcag cactcaaaga tgcaggacat gaaatcattc ccttcccaac acatctgcac   1620
tctcctatcg tctctactgt caatgcatta tacctcctag acagcggcgc cgaatatctt   1680
tcccacctct ctctaacctc tgagcctccc acctcattac tccaatggct tttagaagaa   1740
gagaccacga aaaatcgtag cattcccgaa caatggaagt tacataagga gagaaacagg   1800
```

```
cttcaagacg catatgcgaa attgatgttg gaaacgggtg tagattgtat catagcgcca   1860

gggggtgtga cggtagcgaa tgcacatgaa gaggcgaagt actggggata cacgaatgtg   1920

tataacgggt tagatctacc ggttgcctgt ttgcctgctg gagaggtgga ggagggagat   1980

gcgtggggcg atgaaaatga aaataaaatt gcaaaaacgc atatggaagc tctgtggggc   2040

cctggaaaag aaggagcgca aaaatatgaa ggaggaagtg taggattaca gattgttgga   2100

aggaggttgg aggaggaaaa gctattgaag atgaccaaaa taattgagag ggacttggga   2160

ttatctgggc ccaactagaa gaaagaactc gaaggtaatg tgaaaatgaa gattagagat   2220

caaatctgag atatcgaagt gattcagatt tttttagaag aaca                    2264
```

<210> SEQ ID NO 50
<211> LENGTH: 3657
<212> TYPE: DNA
<213> ORGANISM: Botrytis cinerea

<400> SEQUENCE: 50

```
ggccccgaat ctttcatctt tttcctgcag gttccaagtt ttaaggttct gtcgaatcaa     60

acgcggttta attatacagc cgtgagattt tggttaatca gccataatcc attatccttc    120

acccattcat tacccatcat ccccatcccc atccccatcc ccatcgccat tcagagcctt    180

tcattaccgg gccgttattt cgtacttact gcgcaccggt ggttgattga ttgattgatt    240

gtgtacagcg ctggttacaa tctccatttt ctgttccatc acagccacgg ccacgtcttt    300

tttcccatcg ttgtattatt agatatcgta ccggatcctc acatcgccat caccactctc    360

accactcacc actcaccact cagctacact cgggtcaaag aatacaacat ttaaaccgtc    420

cattcttttc aactgcctcg agtttctcca cctatcgacc gttcactctc gagcccatac    480

ctaccgacct acatatccat atacacacgc ctacatatat tggtacacca tcgtcccaaa    540

cgccatacat aggtcccata ccacagcctt caattacgaa aagaattgcc acgatcgttg    600

ccaatgagat cacagtgtgt ctgataaaac gaaaagagga tcatcccata accccataaa    660

cccattttgg tctttccaag tgcaaaaggt acaaacgaaa gagacaataa agtttgattg    720

atttggagag atatcttact ttttctcgac tcgaccacca cgcatctcgt cacccatctc    780

ggcatttccc tcgcagaacg gattacctct tgtatactac ttatatcatc accttgcctg    840

tctcctttca ttacatttgt ttgtttgttt atttaccaac caagcactga ctggtataaa    900

aagaagtgaa gcacgaagtg aaagaagaag tgatcttatt attattatta tcattattat    960

tactattact attactgtag ctctgctgaa gcttgttagc gcaatccaat ctcgctaatt   1020

caaaggtcct gaatgtccca tcctattatc gacactcatc tcgtccaatc ttcattcaaa   1080

agtcattctt tcaatttctc tccttcagga gcgtcgagat ttgttgattg gacatcaact   1140

taaatcattc gacgcgtttt gaagataaaa gtccttggat tcgattcgac agatctttat   1200

aaagatttag tcctctgata atcttgtttt ttcttaatca atatcgaatt gccctcgatg   1260

agtaatgagg tagctcagcc gactgagcaa gatcctagcc gctcaacttc attggaagga   1320

acgaaaggag ccaaaccacc taccctcgac acttccaact tcaccgcagt ttcccaacca   1380

cccagctcat ctacacagca gtcaactacc caaaacactt tgacaggaga ttccgataac   1440

ggtttgaatt cgaccacaaa cgttgataac gatcaaggac gaaccagcga aactttgact   1500

gaaactccca agaagaataa agacctactt aaagttccat cgagatcctc ttccaacaaa   1560

attcagcatt cgccaacttc tacaggtttg agtggagcga cggcgagcga gggaagagag   1620
```

-continued agcataggtg ggcgatccaa ggaatcgaag ggtagttttc ttgggcgaag gcggaatggg 1680
agtgcagcaa gcagcaaaat gtcgataaaa tcacctggaa atcccacggg cgctgcaggt 1740
gcttcgcaac cagcagttcc agacgcacct tcagttcgtc agccgaaaaa gaagaagagc 1800
tttctctctc tcctttgttg cggtactccg gaccacgcca attctttgga tgcacctgtt 1860
ccggccaaca aggtctcaaa atttagttta agtcgcccta caacagctaa gcaacccgac 1920
gcgagtaaga tgggacaaca agccagtgtt cccgcggtac cacaagtgga gaaagagaat 1980
ttgctgcaac cacaacaggc gcctcaagtc gagagtggag aggagaagca tgacgcaaca 2040
agctctcaag aaaccgccaa ggctacctct tcttcggatg ccaatgggga gctgaatcgt 2100
ccaatcagca acgctcgcga tcaacctttg ccagacttgc ccactgtcgt agaatcagag 2160
cccacgctac ccgagaccgc aaacccaaca gtatctgttg acaccccagc gcaatctgaa 2220
acggcaattg gagctgtatc tccaagttcg gatctgggac agcaagatgg tggggatgag 2280
aagatcgcaa acttggatcc aggaactacg gaaatcgaag aggccccatt accactccca 2340
aaagacgaac cattggctgg tcaaactctc ccccctcctc cgcccgttcc tcaaattcca 2400
actaccgagg atgatgccga agtagaatcg atagatcaaa aacaacaatg gctcttacca 2460
ccaattgcac caagattcaa agggaaaaaa tgtctggttc ttgatctcga cgagactttg 2520
gtacatagta gttttaagat cttgcaccaa gcagatttca ccattcctgt ggagattgaa 2580
gggcaatttc acaacgtata cgtgatcaag cgtcctggtg ttgatcaatt tatgaagcga 2640
gtcggggagc tctacgaggt tgtggtcttc acagcttcag tttccaagta tggtgaccca 2700
cttctcgacc aactagacat tcatcacgtt gttcaccata gacttttccg tgaaagttgt 2760
tacaaccatc aaggaaatta cgtaaaggat ctttctcaag tcggtcgcga tttgagagaa 2820
accatcatca ttgacaattc accaacctct tacatcttcc acccgcaaca tgctgttcct 2880
atcagcagtt ggttctcaga tgctcacgac aatgagcttt tggatctaat cccagttctt 2940
gaggacttgg ccggctcgca ggtccgagat gtcagtttag ttcttgatgt tgcgctctaa 3000
gaagggggca aaatcttctt gcaattcgct tgatatcata gcggaaggcg tttcggttga 3060
tacctttggt ttcgttgtag agtgtactgt ttaatctata taatgggcca gcgtgctggg 3120
tcagccttgg tgcaggaagg tatgcgagtg ggagtgatgg aggaaaattg ctagaaggcg 3180
cgagattgaa taagaccaac gggtcaaaat ctccgcgatt gagatgtgaa aaaaatcaca 3240
tcatctcagt ggaacaacga acagcaaaac agcaagcatc atacgatgca caccgtacaa 3300
caacagatcg gcctgtcaca ttcttttcct gcccagcaag atctgaggca ctttgggcag 3360
acgcttatcc gacattttca tttgtccaac tctttttttt ttactttcct actttattaa 3420
aacttctcgg ggctttgcgc atggcgcaga ctcttcatgt atcaaacact ctatccaccg 3480
tctgtgaatg ctttggagat agcattcatc aaataccaaa aatgaaacga ttccatacga 3540
ccttctactt tacttacact ccaattacac ctttcttgta aataattact gggtaaataa 3600
aaacttaata ataatactaa gatgcatttt tgggtggcta tttcttattg gtttcca 3657

<210> SEQ ID NO 51
<211> LENGTH: 2456
<212> TYPE: DNA
<213> ORGANISM: Botrytis cinerea

<400> SEQUENCE: 51
gagcattcga caatctggaa tttctaccta ttctacaact ttatttaaca tcttccattt 60
tgtcaatgaa atatcggtag taattgtgga agctctaggg attctgaaat catcctctag 120

```
cagcaacaaa aatcatgtct aaatccaaac atgcggttga gctttgctca ctgctagttg    180
atgatattta tggcgaacta tcgtctcgca tttttactat tttgctcaga cggggaaggt    240
tacctatgaa tgcgctcaaa cgacacactc aactcacaac gcgacaattg aagcttggat    300
taacggtctt agtacgacaa aatttggttt accataactc agaaggcagt gacacccatt    360
atgaagcgaa tatcgatgcc gcatatgcgt tggttagatc tgggaaaatc ttagaaattg    420
cggaagaacg atttgggtct gttgcggccg agattatggg acaattggta cttttgggcc    480
acgccaaaat atccgacata atcgcagagt taaacaagaa ccatgaacca cacgccaatg    540
gcaacagcaa cgaaaccaac ggcgcgacaa atggcaatgg tgttcattca tatccctcag    600
ggcaattgaa ccatacattg atccaattat tggaggaagg atttattcaa cctgttggcc    660
agaatatgtt tcgaagtccg acagatagtt ataacgcggt tgaaaaggcg cttcttcaag    720
atagttatgg gggagccacg agaggcacga agcaaaaaga cgagttgagg atgagaatcc    780
gaggacagct ccaagaactg agagctcagg ttccaaattg gaaacctgtc ggttacaatc    840
gctcatctac caatggccat acgaacgaca ttgcctcgaa acgaagaaga ctctctcaca    900
gcgggggtgc aactaatggg tatgactttg gcgacgacga aagtagcaag cttgacggaa    960
atttggtttt acgaatcaac catgagaaat gcactgtctt tatgagaaat cgacgacttg   1020
ttgagcttgc aaattcccgg attggcgtaa ccacatcgta tatctatgcg gagcttcttc   1080
gactcatggc agagcaaatt cctaggtgtc gacccgatcc tagaattgac gatgctgtgg   1140
acgacgctga tgggccttca atcataataa caacacaaga gttgactgat gctttaagta   1200
agacaatcaa cgtatccact ggaatcggca aagctacgag ccaaaagatc gacacttcca   1260
gacttgacaa actgcagaac ggcagaaaga gaaaggctca ggatgaagca gaagtagaag   1320
gtgtggcaag ttctgacgag gagtcagaag atgatcacaa gcctttcacg aatggaaacg   1380
gccatgcaat ggatgttgac gaagatgatc cattttcgga tcaacccggg gctaacacca   1440
gcaaacgagc cgtcactttt aaagaccggg acagaactcc tcctccaaca gagagtcgcc   1500
aggcccgaat gatgcatgta atgagccatc tccagttgtt agccgctgat gattgccaac   1560
tactacgaaa gtgcggtgct cggcaaatgg gcgagtggac ggtagatttt gagcgtgtga   1620
ttgaccgact tcgagaatcc gaacttgact ccatcattta tgagaatttt ggccaaattg   1680
gtcatcgact tgtacgagtc atgaggaaga tggggaagct tgaagaaaag catattgcca   1740
agctggcgtt gatcaagcag caggactccc gtactacact tgtgaacatg caaatgcatg   1800
gtatggttga tatccaggaa gtccccaggg atactggtcg tatgattgtg cgtactatac   1860
acttgtggtt ttgtgatgaa gaccgggtta cctcactttt gttggatcga acttacaagg   1920
ccatgtcaag atgtctccag cgactcgatg tagagaagcg acgcaaagca aatatcattg   1980
cattgtcaga gcgtacagat gttcaaggtc aagaagaggc ttttcttcga ccagaacaga   2040
tgaaccagtt gcgtgagatc cggcgaaggg aggaagattt attaggacag atttgtagac   2100
tcgacgaatt ggtcggcata tttcaagatt attaactcat atggagggaa ggttttggtt   2160
cggggcttta gcgttcttga tttttcacac tggggcggcg ccatctactg cataaagaaa   2220
ggcgttctag tatagtcgag cagcaatggt tatttccagt tgactcatta ctttgagata   2280
ccataggttt atttcgtagc ctagattagt tgctcaggca aatattctcc aaatttacag   2340
attgtaaagt aggtatgaag cttttaatgc cattgtttcg cttctgatta tctccccttg   2400
aatagataca atattactta attacctaat attctccagt caatacataa aactca       2456
```

<210> SEQ ID NO 52
<211> LENGTH: 14888
<212> TYPE: DNA
<213> ORGANISM: Botrytis cinerea

<400> SEQUENCE: 52
gacatataag acgaccacat gcacttacag cagtccagat tatgaggatc gacctgcatg 60
atccaaaatg gattcaaaga tttcgacttt gaatgaccct ccaagacttt tgtccgggcc 120
acaacttcta catgatttga tccgatggaa tgaatacgaa aattcttgtg caattgactt 180
cactagtcac gatagacgag agaggtaccg ttatcgagac atacaagctt gtgtgacatc 240
tctcgttaca cgaatccaat caacgattaa agtttgtcaa acatctcaac agcagcacat 300
tgtcccaata ttgttaccgc aatgtcctgg gttatatatc tctcaaatcg caatcctgca 360
gtcgggaggg gccttctgcc ctatcaacct cgatgcgccg agagatagga tacgattcgt 420
cgtgggcgac gtttctgcga gtatcataat tacgacatcg gagtttcgag actcggtttc 480
ttgggaaaat ggacccagag ttattgtcgt cgacgaattt cccattgccc ccacggaact 540
ggatgaatca actgaatcac gtgaacctac tagcaatgat cttgcatatg ttatgtatac 600
ttctggttca agcggaaccc caaaaggagt tgcagtcagt catctcgctg cttcacagtc 660
tctcttggct cacgagagtc ttattcccaa atttaaacga tttctccagt ttgccgcacc 720
atctttcgat gtctccgtat tcgagatttt cttccctctg actagaggtc aaacattggt 780
tggatgtgat cgtagtcagc tacttaacga tttaccaggc atgatcaaca atttggatat 840
tgatgctgcc gaacttactc caaccgttgt gggcgcttta ttacagaaga gatcctatgt 900
tcctaaatta agattgctga tgacgattgg tgaaatgatg acgaggccaa tcgtggagga 960
atttggtgga tctgatacaa aagagagcat tctttatggg atgtatggac cgactgaagc 1020
agccattcat tgcacaattc accccaaaat ggaagcaagt gctaagccgg gtaatattgg 1080
agtacccttt gagacagtat ctgcgttcat agcggaagcg gcttctgggt ctgaaaatga 1140
gcaggatctc aaatttctcc cacagggcga gctcggagag cttattttag gaggcccgca 1200
actagcaaat ggttatctta acagagaaga gcagaacagg gctgcttttc tggcagtggc 1260
agataaaaac tactatagga ctggtgataa aggtcggatt cttgaagatg gaagtataga 1320
aatccatggc cgtatgagcg gtggacaagt taaactacgt ggccaacgtg tcgaacttgg 1380
agagatagaa gatgctgtct acaaacatcc ggggatcaga gctgttgtag cagtcgtgat 1440
acgcggggta ctggttgtgt tcgctctcac aagtgaagaa gaaactcatt ccgaacaagt 1500
tctgaatact tgctcacagt ggcttccgag tttcatggta cccagtgaga tcattatcct 1560
gcaagagttt ccttatctac cgtctggaaa ggtagataaa aggaagttgg aagcgggcta 1620
ccagcaagaa tgtgaagaag gggacgagca atcagacttt acacaaaatg aagtaatagt 1680
gagagagtta ctgcgcgaga tacttggtcc atttccccca aatatacgtt tggcagctgc 1740
aggtcttgac tcgctcgttt ctatcaaagt atctagagaa cttcgattgc gaggatttaa 1800
cgttgcgact ttagatgttt tgaaagccga aacattaacg tcgcttgcga ggctttgtga 1860
aaattgcccc gaggtttcaa gttcagccaa ggctcaattg ggccctacca agtcagaaat 1920
gcacgctatg ctgaatggca atgcacatgc cgttgaaagt tctttccctt gcactccgct 1980
tcaaaatgca atgcttgctg aaactgccct cgacgggaga gcttaccgca actggatcga 2040
gttagattta cctggactta gcgacaccga aaatcttcgt acgaagctac acgacctcgc 2100
tgattgcaat ccaatcttga gaactggctt tgcagagtct tctgataata gcggatatat 2160

-continued

```
gcagtttgta tggaaatcat ttcccgactc gaacattaaa attgtggacg tattgaccta   2220
cgatctcgaa gttgaaaatg catcacttca tcgcccgatt gttttcgaga ttctacctac   2280
taagccctgc ctaaaactct tgattcacat ccatcacgct ctgtatgatg cctggtcgtt   2340
agatcttctg cttgatgatt tgaattgtct gttgcaagat gagattccaa ttccacgtcc   2400
ctcatttgcg gatgttgtgg ggggttatct cgacggcagc atctcttctg attctcgagt   2460
ctctaaagat tactggaaag atcatatggc aaacctcgag cttagacatt tacctaattt   2520
tcacacaagc aacgttgctt ccgctagatt ggctgtggcg catcactcga ctcagctctc   2580
aactttagat gttgaagtag ccgcgaaaca attagcttcg agttcgcaag ctatttttca   2640
agcggcatat gctctaatct tatcctctta cttaggaaca acagacgttt gctttggcac   2700
tgtttttct ggcagaacca tccccattgt tggaatagaa gaaattatcg gaccatgtct   2760
ctcaaccttg ccgattcgta tagatacctc catagcctct actctccaag atcttgtaga   2820
agaattaaac agtataaata ggaaacatct caatcatagc accctcccac ttcgcgagat   2880
caaatcggtc aatggtttcg agcctcgaca gccattattt gatacacttc tgatatggca   2940
acaaactctc catagttatg accagagcag aagcaacgtc cttcttatcg accagcttga   3000
tcaactggag tttaatctaa ctcttgaaat aactcctaca tctaatacca ttcaattcaa   3060
agcaaattat caacagtcga tattccccga aagccagata aacatgcttc tgtgtcaaat   3120
tgaagatgtc gcgaaaacaa tcatccagca tgcaggatct tcacctataa atgtcttcaa   3180
tgaaagtatc tctgaattat tatctttgga gaaccataca cctagcgttg cccttggacc   3240
cgagactctg atatcttcag tggaacagat cgcagaagaa gatcccgatc gtccggcaat   3300
tgcgtttgct agcagaatcg aagacgtcag ttcagacatt cgatacatga gttatggtac   3360
tttgaatagt cgtgcaaacc agctgggaca ctatctatcc agtaatggtg ttctgccgaa   3420
tgatattgtt tgcgtttgtc tagaaaaaag tcatgatttt tatgcctcag tattggctat   3480
cacgaaactc ggtgcaggct atctcccagt aacccctgat attccacata gccggttgca   3540
ccatatcttg atggaagcca aggtaaaggt attggttgga cattcttcat cccggaaact   3600
gctggaacaa tttacggaac aaaaagttgt tcaaatcgat gagactgaac tgggtcaaca   3660
atctacgaaa aacctttcta ttgccttcaa gccagaaaat atctcatatt gtgtgttcac   3720
ttcggggagc actggaactc caaaaggagt gcttgtcaca caaggcaatc ttctaagtaa   3780
cctcgacgtg ttagtagaga tctatccagc aaccagcgat tctagacttc tccagtcatg   3840
ttcacaggcc tttgacgtat ctgtcttcga aattttcttc acttggagaa ttgggggatg   3900
cctgtgttct gccgtgaaag acgttttgtt tcgagacata gaacttgcga ttcgtgttct   3960
ggaagtgact catctcagct tgacacctac tgttgctgct cttatcgatc cacttaatgt   4020
acctaaagta aagttcttgg tcactgccgg agaggctgtg acacaaaagg ttttcaacac   4080
atgggctggc catgggcttt accagggtta tggtcccagt gagacaacca atatttgcac   4140
tgtcaagtca caggtcaccc tagatgatcg tattgacaat attggtcctc ctttcaagaa   4200
tacgtcagct tttgtaattg ctcgcaactc agaattctcc ttggtaccaa gaggtggcga   4260
gggtgagttt tgctttggtg gctctcaggt cttcagaggg tacatgaatc gagctcaaga   4320
tgagggaaag attattaatc atcccgaata tgggcgtcta tataaaagtg gcgactttgg   4380
gcgtctgatg tcagacggat cccttgtttt tacaggacga aaagatgacc aagtcaaggt   4440
caggggccaa cgagttgaac ttggcgaaat caacaatatc ttgatctctt taccagatgt   4500
```

-continued

```
cgaagattgt gtaacaatgg ttatcaatgg acaaggaagt tcgcaacgcc tagtttgctt   4560
tttcacgcca cagtcattaa catctggaaa tattcttcct cttcaagttg atccaattat   4620
tattagcgaa ctctatcgaa tactggagtc gaagctcccg agctatatgg taccttcaaa   4680
tctcattccg gtttcaaacc ttccatcgac atcgcaaggc aagattgaca agcgtcgact   4740
aattagcttg tatgaaaact ttgagcttgc gtatcttgac tctactacta aatcttcaac   4800
gtcttctgta gatcatcagt ggacagaact tgagcttgag atccgctcct cattgagtga   4860
aatctcaaaa gtttcagtag atgatatcgg tccagataca tcattcttta gctttggtat   4920
cgactcgatt tcggcaattg cattctcccg gaagctacgt caaacaattg caaaaccaat   4980
tgatatttct gatattttga agcatacttc tgtagtcaga cttgcagaac atttatcaag   5040
atccgatgag cttagaaacg acgacatctc gatggttgat acaaacttag gactcagcga   5100
tgaattttta gagtctactt tgtctcagtt taccaccccg gaaaaagttg cgataagcgt   5160
ttcaccttgt acgcctttac aagaagctat gctgtccgcg gttgagtctt cctcgggcgt   5220
atcatataac aaccatgtca tgttcaatat atttggtgat ctcgaacgaa ttcgtggctg   5280
ttggcaagaa atggtccgga gacatgaaat tcttcgaact tgttttcttg ctactgaaat   5340
gcaaaaacac ccttacgtcc aagtcgtgtt tcaagaattt gaactcaaat tcggctctct   5400
tgattctaac actctggagg ctgccattct tgaagtagag acaaatttaa cacacaacga   5460
tgatagcccg ccttacaagg ttaacgtttt gcacttcaat ggccagcagc atcttttggt   5520
ctcaatgcat cacgcacttt atgatggagt cgccctggca attctttacg atgaaattga   5580
aaggctgtac aatgatttgc ctctacttcc ccaggtttcc tttactccat ttctagagca   5640
cataagctca atgaatcttg attcttctga taaattttgg ggatctacct tacgaggata   5700
ttatccactt cacttcgaag atatgccaaa tttgactagc caagttgaag tggacagcac   5760
ccgcattcag aagctgatat cgaaaattcc tcttagtagc gtcgaaaata atatcaagaa   5820
gcatagtacc acccctctcg ctgcgcttca tgcggtctgg gctggcatca tttctgaact   5880
tttcaaaagc actgatattt gttttggcaa tgtagtcagt ggtcgcactg ccccagttaa   5940
tggtatagaa agactggtcg cgccatgttt caacacggtt ccaatccgtt tggaaaacat   6000
tcacaagtcc acttacctcg aggcattcag aaaattacaa aatgcaaatg ccaactcctt   6060
gccataccaa tttactcctt tacgacgact tcagtcaaag ttcagtcctg atggaactcg   6120
tctatttgat acccttttca ttttacaaca gccgtcgaag gaactcgact cttctatatg   6180
gtccattgcg gaagaaaacg gtgccatgga ttttcctta gtctgcgaaa ttatacccaa   6240
accaagcaac gatacccttg aaattgttct tcatacatct actttaatgt tttccgatta   6300
cgatgcaaat aatttaattc agagattcga ggatttacta caagtcgccc tggagaaccc   6360
tcggcgccag attatttcct cttcggcaag agcgcagatc ctcgctgttg acgaggaaag   6420
agagagaaaa agggtgcgaa ttttggaccc ggaacaccag gacaaaacca tgagtccatt   6480
ggaactagaa attcgaaata tagttgcagg atttacagac gttcccccag acaagatctc   6540
tcgggatacc agtattttca ggttgggtct cgatagtatc agtacagttc aggttgcttc   6600
tcgcttgaga gctcaagggc ataacctcct tgcgagtgat atcctacagc accctaccat   6660
cgctcaagtt gctttgcatc ttgaacaaaa taagtcttca gtgaaacaaa aaagcgttca   6720
gtatgatttc gctgcttttg accaaaaaca tcgcgagcca atctgttcga aaattggagt   6780
tttatctcat aatgttgaag ctatcagacc ttgcacagct gtacaacaag gcatgcttgc   6840
tcaaagtttg cattctggag gtcatgaata tatcaacagc gtgtctctgg agattttacc   6900
```

cgatcactcg ttggaagaaa ttaaacattc ttggactaaa gtctgtaaag ttcatgacat 6960
gcttcgtaca gcatttgctc agattgaaga cccaaagcat ccgttcgcaa tgataacatt 7020
cacagaacac tcctttgttc tcccgtggtt tgaaagtggc gtccaaacat tctctgagga 7080
taatgatcgt ctccgaaacc catgggacat gacgatgtac aagaacgggg acggaactat 7140
actcactttc actgcacatc atgcacttta cgatgctcaa tctatggaaa tgatattttc 7200
ggactttaca aagttatatc atcgtcaaga attggccagt cgacctagca tgaacacatt 7260
gttgggttca gttcttcaag catccgaagg agcccaagat gagaagaaga cattttggca 7320
actgcctgaa aatcgaattg tggtcaataa gttccctgat ttgactcccc tccgtgtcgc 7380
agcacctagt aatgcagttc gtgagataaa atcttctgct tcactgaaag accttgagaa 7440
tagatgtcga gaacttggag tcactatgca agcagctggg caagctactt gggcgaggtt 7500
gttgatggca tatactggag agaacgctac gacttttgga atgaccctct ctggtcgatc 7560
tgttcgtgat gatgccaatt tagtcgcctt tccaactatc gtcacacttc cggttaattg 7620
caacgtgatg ggcagtaacg gcgatctgtt gtccaggact atgtcaacca atgcacaact 7680
tcataatcat caatttacgc cgctgacatc aattcaaaag tggtctgggt accccgaggg 7740
acggatattc gacactttat ttgcgtatca aaaactacct gaagatggag aaactctgaa 7800
ttctccatgg aaagtagtca aagaggaggc tacagtggac tacgtcatat ctctagaagt 7860
ccaaccctca tcatcgggtg aaatcacaat tcgattatca ttcagagaag atgtcgtacc 7920
cgcagctcat gctgagctaa ttgtcaaaca atttgatgcg ctactgctgg atacgctcca 7980
aaacccagat catccctgca atgtagcgcc tgatattgga gttgagttgc tgtccattac 8040
tcctgcacag gatcctgttc ttccggactc cgtagccctt ctgcatcaat acgtcgaaag 8100
aggggccaag acatggccag ataaggtcgc attagagttt gcaacttgcc ttcaaccagg 8160
caattatcaa agccaaaaat ggacatacct acaattggac gaagaatcca acagggtggc 8220
tcagatgctc catgcacgtg gaactactcc gggtgagata attgcagttt gttttgacaa 8280
gtgtgccgag gcttctttcg caattattgg tatcatgaag gctggctgtg gttatgttgc 8340
actggatcct aatgctcctg ccgatcgctt aaagtttatc gtggaggatt ctgctgcgag 8400
attaaccatc agtgcaggaa gcccagccca gaatttgaaa actttcgtag acgggaagat 8460
tatcgatctg actgatccga ccacacttcg cgaatttgcc cctgaagccc cggaactttc 8520
cagagaaatc accccctgacg acatatccta ttgtttgtac acgtctggaa caacaggaac 8580
accgaaagga tgcctgctta ctcatgaaaa tgcgattcaa gcgatgcttg catttcaaag 8640
actgttctct ggacattgga ccaccgactc gaagtggcta cagtttgctt cttttcactt 8700
tgacgtgagc gtcttggaac aattttggag ttggagtgtt ggaatttgtg tagctacagc 8760
tcctcgagat ctgatatttg aggatattcc agttgcgatt caacaactag gtatcacgca 8820
cattgattta acaccgagtc ttgcacgctt gttacaccca gacgacgtcc cgtcattatg 8880
caaaggtgtt ttcattacgg gtggtgaaca actaaagcaa gaaattcttg atgtatgggg 8940
cgagcatgct tgcatttaca atggatatgg gccaaccgaa gctactattg gtgtgactat 9000
gtatcctcga gtaccgagaa atggcaaacc ttccaacatt ggtcctcagt ttgacaacgt 9060
cggatcgttc gttctgaagc caggaactga gctacccgtt ctaagaggag gcattggtga 9120
actttgcgtt tctggaaaac tagtcggaaa aggatatctc aatcgctcag aacttacgac 9180
tgagaaattc cctacgctta ctaatttcaa tgagcgagtg tatcgcaccg gagatcttgt 9240

-continued

```
tcgaatcttg cacgatggca ccttcctctt tcttggtcgt gctgatgacc aagtcaaact   9300
tcgtggacaa cgtttggagt taagcgaaat caatgaggta atcaagaaaa gcagaaacga   9360
tctagaagag gtagtcacat tagttctaaa acacaaagca caagctaaag agcagctcgt   9420
cacgtttttt gtcgtgtcag gaaagagcca gttgaaagat agtgaagtaa ttcccttcat   9480
cagagatgcc tgcagctcgc gacttccagg atatatggtc ccaacacatt tcatccccat   9540
caaagcactt cctctcaacg caaacaacaa agcggattcg aaacaactcg cagcaaaatt   9600
cgacgatttg agtatggagg atcttcaaaa catgagtatt caggtgcaga accatgcgga   9660
atggacaaac agagaggaga aggtggtaga taccatcgtt aaggtatttc ccatcgatgt   9720
tcccgagtta acgcgcagct cgaatatttt ccaactcggt ctcgactcca ttaccatgac   9780
tgccttttca agctccttga gaactgcggg atacaataac gccaccaatg ccaccgtcag   9840
aagcaatccc acgatcggga agttggttga agcacttctt gctgccaaaa tgaatgatac   9900
cagagaaaac tcatatcttg ttacagctca actgagaatt gccggctttt cacagcagca   9960
tacagtcacc atttgcaaag acttagcggt ttcacccgag catattgaga gcatcgcacc  10020
ttgcactcct gtgcaggaag caatgatcta caggttactt gagagtgatg gaagattgta  10080
ttataatcac ttcgagtaca aattggcacc cggagttaat tctaaacacg tttccgatgc  10140
gtgggatcgt gtagtttcta atcttcagat cttgcgaacc agatttgcct tgacagacga  10200
tggctatgcc caggtggttc tcaaacccca ggcatcttcg aagcattggg agtcgggcat  10260
cgtattagaa accttggaaa ttctcaataa cccgtggtgt ttcgatatca aacatcatgg  10320
agacgaagat accgtatcgt taaatatttt tcatggcctt tatgatggga gcagtctagg  10380
aatgatcttg aatcatcttt gcgacgaatc tcgccaatta ccgaacattc agtatggacc  10440
ggctttccat tcatcgttgg cttatgggcc gctgtcgata gttcccggaa aggaggaatt  10500
ctggaaatcc catctaaaga catggactcc ctattattta cctcatgact acgcagatcc  10560
gggaactcgg atattttctc gtacacttga cctgcaagat tttgaaatca gacggaaagc  10620
cttatctgtt gcgccgcagg ccataatcca agcagcatgg atctcagcca ttcaaaagat  10680
catttctacc aaattgacca caattggcat tgtcacatcc ggcagagcaa ttgatttcga  10740
aggagtagaa aaagttgttg gaccccttttt caacaccgtg cccttccatc ttcctgtaca  10800
ggctggcatt caaatttcct caataataaa ggagtgccac cgaataaata tggaaatgca  10860
agaattccaa cacacgccat tgaatgatat aaataaatta gtttctgctg cagtcacagg  10920
tccgctcttc gaggcactat tcgtgttcca acgtccggat gctaacgaag agcaattatc  10980
ggatctaatg ggaaatatta tctctcctga ggaggatagg aatgcagatt atcctatagc  11040
actcgaagct actctgagcc acgatagtac taagcttatt ttggagatgg tcgtgaagag  11100
ctcagctgtg acggaagaaa tggcacgcct tgtgctcatt gagatgaata ataccettag  11160
aactattctt cccggtaacg acaatgcgac aagaacagtt gggattgatc ttcaccatca  11220
agcccactca agacttctcc caaacccctt tcactggctg aacttaattg acgattcaag  11280
tcacctaaag caatcttcgg gagctttaca tcaatctgcg cgctcaggcc aaatacctct  11340
aaccaaagaa aagggtgatg ttgtttgcaa ggaggttgca aatttggcca aaattgacaa  11400
aatagatatt gatgatcata gatctatctt cgaacttgga cttgatagca tcgatgtgat  11460
caagttgtct tcacgtctgc ggaagaacga gattgtgata tctgtcagcg aaattatcaa  11520
atgtcaaacg atcactaaga ttgtagaagc cgcgacactc tccaaagaaa ttgtatccga  11580
cgcattgtct accaagaaac tcgcgagact tagtcacaag cttcacgggt atctaaagcc  11640
```

-continued

```
taggcttcct gcagacttcg aatccattct accggctaca cctttacaag agagcatgtt  11700
aaaagaaatg gttgattcca atttcaaaag ctatttgacc ctccaggttt tcgaactgag  11760
tgaaaacacc caggagggaa gattgttgga tgctgtggat atggttatcg aaaattcgcc  11820
aattttaaga accaccttcc ttgaagttca agacccgcaa tctcccgtca actatgcaca  11880
gattgttcac aaaaaatgga acagggtggc cggaaagtat ctacctaatt ttgatgatca  11940
tgggtgcccc gaagaccttt tacaattagc agaaaacaaa ctaagagcgg acatgtcgtc  12000
gatagagagc caattgtttg gaatacttcc tgtacatttc gaaaacagga gatttatcgt  12060
aatgggaatt tcacatgctc tttacgatgg gaaatcactg ccgatgatac acgacgatat  12120
cagcaaagct tataggtacc aaacaattgc tagtcgtcca gactatagac cgtgccttgc  12180
agagatcttc aattctgata ctcatgaagc gaatgacttc tggaaagcta ccctgtggaa  12240
ctcgccacct gcaatatttc caaagcagga accatcatca attggcgaga ctacgacgta  12300
ccgatatgag aagcattctg agttctctct aaaaaaaatc aggagcttct gccgctcttc  12360
caacattaca ctacaaactc tgggacaagc atgctgggct ttagttctcg cagaactcat  12420
gggccaattt gatgttgtgt ttggaactgt acttgcctgt cgtgatacag gtgacacagc  12480
caatgaagta aacttcccac tgttcaatac tgtggcagtt cgatcagtac ttcgcggaac  12540
tgtgggtcaa atgcttcgag atatgcaaga gaagagcgat atgattcgtc aatttcaaca  12600
attccccctt aggaaagctc aagccctcgc acttggctct cgagaccatt caaccaaaga  12660
taccacattg ttcgacacat tgttcacata tcaaggctct cgacctgaga aggaatctga  12720
tccattatat ttgtcatttg gtggttcttc ggatgttcag ttcgcaatct gtgtcgagat  12780
ggaggttgaa gataaatctg atcgtcttta ctggacaaca gcttgtaaat ctgtggctag  12840
aaatcacttc caaaccaacg aaattcttga aaaattagac aaggttcttg ggaaaatcat  12900
ggcagacaaa gaggaacaga tcattaaaat ttacagcgac ggagtctctg tatgcggatc  12960
tcccaaattt caacttcgag aaagtcccca tcagaaaaac ttccaagtac cttctccttg  13020
tgaaagttgg tctaaaacag aaatggagat tcgaaaatca atatcattca tttcaggtgt  13080
cccagagaaa gatatcctca aagactccac aatctttcaa ttgggcttgg attcagttac  13140
agtcctcaag cttccagcac atctcaaaaa ctacaacctt catctgactg tttcggaaat  13200
catgagacat ctcacaattc aggatatggc tgatcattta gctgagaaac aagactcaca  13260
gtcgaatact cctgccaacg tcgacgttga cgtcgatgtt gatctcatcc tggctcaatc  13320
tacaccatcg attgatgaga cccagatcaa gcaattgaat gaatcttttg gcgagataga  13380
ctacattatg cccgcaactg caggacaaat gtatatgatt agacattggc aaaactctca  13440
aggatctctc ttccaagcaa cttttgagtt cagattatcc agcggttacg acccacaact  13500
actcgatttt gcttggtata atttgctact tcagcacgac attctacgaa ctggtttcat  13560
tgacttggac tcaactatcg ttcaagttgt ttacaaagaa ccaacaagta tggtaaaata  13620
tgttgaggag ctacctaatc ttcaacaaga atgtagcctt caagatccac caataagtct  13680
ttttgtcatc acgccacaga acacttcaaa acaggtcgat atgcatcttg ttattcacca  13740
tgctctttac gatggaatca gcatctcttt gttgcttaag gaattgatgg cttggtataa  13800
tgacccgaac accatggcca agtccacgtc tacaatcgcc aaaaatgaat ggaagaaatt  13860
tgttgcgacg acaatcgagg aaaagaataa accgtccgtg agggatcaat ggattgagta  13920
tcttggcact gttccctcta aacaatcaag ccctgattca aatgtcgaat tcgaagtaat  13980
```

-continued

```
aggaccggga atcaggaagc ctaatcgagt cgaagttttc gaacccaatg tgccagcaaa  14040
aggtgtaaaa aaatatgcac gaaatacagg tgtttctatt gaccacatac ttatcgtttt  14100
ggcatcgaca gtcttgggtg atcaacaatt taagaatgtt gtggatcttg atggaaattt  14160
catcgttggc ctgtatctag ccaatcgctt tccattttca caggaccttt cttccatgat  14220
ggcacctacg ctcaacatat tgccaatcag aatcgggcca agtaatcgga atgaagatga  14280
tggttttgcg ataccagagt tggccaagaa tgtgcagaag ggtttggcta agattggtag  14340
aggcggaatg gctaacgcgg ggctggacga aatctatcag tggactggcg tgaaagtaca  14400
tggatgtatc aatattgtta aagaggtttc tgatcatagt gagaagatgg atgaggcaag  14460
ctccgaggag atatcggatt gggaagttgt tgaagacttg aacggagata cggcgaagga  14520
gcataagaaa cctcgcgagg aggtcggttt acagcctgtg aagaatgagg aaaaggatac  14580
gaccaagcga gttcttttcg aatcgttgga agatatgaaa ggatatgcga gagtggtgaa  14640
gccgaagagg gatcagacta tgtttgttag gaaggattcg ggcgcgtatc cttcgtcaat  14700
cgatatagaa attcgctatc atcctgagag tgaaaccatc gatgttggca ttttcgggcc  14760
ggatgatatg ttgagtcttg aggaggctga ggaatcgatt agaatgctta aaagtttttg  14820
cttctgaaag gaggtgatgg aattttttat tgtcgttggg gaaataacgg agcgagggat  14880
tctgttca                                                           14888
```

<210> SEQ ID NO 53
<211> LENGTH: 2400
<212> TYPE: DNA
<213> ORGANISM: Botrytis cinerea

<400> SEQUENCE: 53

```
gatttactta ttcaattaaa ctaagctcac cttccgcagt gactgcgggc agtctaaacc    60
atgggaaaga tagcaacaaa actacgggag atcaaggaag gaatcagaaa cgatgaaaac   120
ttaactcgag gaagaaaggg atttgttcga ggaataaaag ggttaccgtc atcaacaggg   180
aaatatttgg ttcggaagat tcctttcgta cattggttcc cgaactatgc tccaagatgg   240
cttgtggacg atatgattgc tggggtaaca gtcgcattgg tcttgattcc ccaggctctg   300
gcatctgcag cgctagctgg cataccattg cagcaaggac tctttgctag ctggctacca   360
tcggttatat acttcttcat gggtacatcg aaagatattg ctacaggacc cacaacatct   420
ttgagtctac ttaccaatgc cgttgtgtta tcgattactg ccgaaggatt tccagtacca   480
ccagctctca ttgcctccgg tctctctttc tcgataggta ccttttctct attattcgga   540
ctcctgaacc ttggatggat cttgaacttc gtcactgttc ctatgctagt tgggttccaa   600
atgtcagccg cgttgatcat tgttcaaggt cagattccat taattttagg agaatcgggc   660
gtgggccaaa actttacgct acaagggatg caaataccca aaaacattgc aactactcaa   720
ccgttgtctt tggctgttgg cgtagcttca atagtgatta tcattttatt gaagctcatg   780
ggcaaaaagt gggggcacaa gagtagcatc atcaggatct tatcaaattt acggaacgct   840
tttgtgattg ctatttccac tacgatatcc tttattatca acaaagatct cgtcattcca   900
caattcccca ttgctgggac ggtagcatta accctacaat ctccacaact tccgactaaa   960
cttgttctac ttgtcgccaa gaaatccttc cccgttttta tagctgccat agctcagcat  1020
ttgatattcg ccaagtcatt tgctcgtgag cacaactatg aaattgatga atcgcaagaa  1080
cttgtttttt tgggtaccgc aaatatcgtg aatagctttt ttggtgggat gccagtatcc  1140
ggatctcttt ctctatcggc agtaaattca acaactggag tgagatcacc acttagtgga  1200
```

ctttctctg ccgggtttgt ttttcttgcc atcaatatgt tgacggaaac attccagtgg 1260
ataccaactg cagcaaccag tgcgattata ctagtcgctg taggagaaac attacctcca 1320
aacagtattc cactcacata ctggaaggga tcatttgccg atttcatagg cttttttgtt 1380
gtcatgaatg tggcgttagt tacaagtcta gagcttgctc ttggacttgg gatagtctac 1440
atagcgctct acactctcct acgcacattg ttctcctcaa ttagtccact aaagccccat 1500
gatatcgaaa acagatacag ctttgaaagt gtaaacagaa tgagcatacc tcttcaggga 1560
gggcgcctag taccccaagg cacgcaactc attacgttag aaactcccct catctacttg 1620
aacgccgaga gagttaagaa agatatctta gaagctattt ggacctatca tgagccaact 1680
ccgtatgggc cgacggaacg aaatggatgg agcgactacc gagttcgaag aactgccgct 1740
ctccgtcgca ggagtaacat taatacacca actagattcc ttccaaggct tgaagttatc 1800
gtattcaatt tcacacgagt cacatttatc gataccaccg gactcaccta tcttcaagat 1860
ctcaaagacg aaattatggc atatagtggt gacgctgtag agttacgttt cgtaggtatg 1920
attgactctg tacagaagaa attcaaaaga gtaggatggc cgttgggcac ttatcaagaa 1980
tcacaaatcg gcctagtcgc gggaattgat attatattcg aagatctaca cgatgcagtt 2040
gcagcacctc gaagtgtaag agcatctatg aatggactgg attttgggtt tgcaaatcca 2100
aggaatgata tggaacaatt tggagatgag gaggcttttg aaaagggcag gatgaatgtc 2160
atagttacga atgttgtaac aaaggatggg agggcatata aggagaaaat gtaaatatac 2220
ctttgggtgc tttggagtat tttgggagcg atctttgctg tctttattgg gagaataaga 2280
attgtacaaa tatatatgcg gagaatcaat gcgggaggat gctttcttgg actgcatagt 2340
caaaacgatg aaaggcgttg agacagtcac catatcaact cacaaattcc aaccgaaaca 2400

<210> SEQ ID NO 54
<211> LENGTH: 2415
<212> TYPE: DNA
<213> ORGANISM: Botrytis cinerea

<400> SEQUENCE: 54
gggtgtgggt gtagatgaat taaatgaaga acatcagcgt tccaaggtaa tccgtatcca 60
tcatatcaca tcacatctct tcacatcact ccaatattct ctcttctatc ctctctctct 120
ctctctctcc ctctccctct ctgtcttcct ccccctcgcc gtcgtcgctt cattgtagga 180
gacctctttc tcgtcgctcc ataccagtcc cgcaaatcga tagcttcttc catttgcctg 240
ctaattacca ttccatatta cattatttat atgcgtaatt agcaaccttt tgcctccttc 300
cccttgcatt agcaccacga aacatcgaga accagacagc tccattccct caaacaacct 360
cctattcgat cgatcattcc ttcttcaaca agactttgga acaactactg cacttcaata 420
tgtctcaaca acctgaagct gtaaataata tgcataattt gactacgctc ataaaacgac 480
tcgaagccgc aacctctcgt cttgaagata tagcttcctc taccattcca ccacctgctt 540
catcatccat ccctctaatt tctcctccgg ccgaagctgc gaaaacaaat ggcacaactc 600
cgccgccgcc aacgatccaa acaccagata tcaaaaagat catcgaggat ccaatcccag 660
gagtagtctc agagttcgat aattttattc agggggcggt taagaaatat gttaacttga 720
gtgatgagat tggaggggtt gttgcgcagc aggcatctag tgtattgaag gcatatgtcg 780
gacaacgaag atatattttg atcactacaa agtcaaagaa acctggcatg caagatgaac 840
cattccaaaa gctcatcaaa cctcttcagg attcatttac tgccgttgat gatatccgaa 900

-continued

```
agtccaatcg tgcatctcca ttcttcaatc atctcagtgc tgtttctgaa agtattggtg     960

tacttgcctg ggttacaatg gacaacaaac catttaaaca tgtcgatgaa tcattgggat    1020

ctgctcaata ttacggaaac agagtattga aggaatttaa ggagaaagac ccaaaacaag    1080

tcgaatggat tcaagcattc tatcaaatct ttaaagatct cagcgaatat gctaaggata    1140

acttcccaaa cggtattcca tggaatccaa agggtgaaga tttggaagtt gcgattaagg    1200

atgtagatga aaaggctcca gcccctcctg ctcctcatcc aaaggctgca actgctggag    1260

gtgccgcacc accaccaccc cctccacctc ctcctccacc agtcttcgat gacattccat    1320

caaagccagc accaaaccaa gcagattcag gtgctggact aggagccgtt ttctctgaac    1380

tgaataaagg agcagacgtt acaaaaggat tgcgcaaagt gaatgctgat caaatgacac    1440

ataaaaatcc ttctttgaga gcaggtgcta cagttcccac cagaagtgat agtcaatcca    1500

gtattaattc gaaccgagga aagagtcctg ctcctggtaa aaagcccaag ccagagagta    1560

tgagaactaa gaaacccccct gttaaaaaat tggagggtaa caagtggttt attgaaaact    1620

acgaaaacga gtctgagcca atcacaattg aagcatctat ttcacactcg atcctcattt    1680

cccgctgctc aaaaaccact attatcatta aaggaaaagc aaacgctatt tctattgaca    1740

actcccctcg tcttgccttg gtaattgata gtctcgtctc atcgattgat gttatcaaag    1800

caccaaactt cgcacttcaa gtactgggca cattgccaac gattatgatg gatcaagttg    1860

atggtgctca aatttacttg gggaaggaga gtttgaacac ggaagtcttc acgagtaaat    1920

gtagtagtgt caatgtgcta cttccagatt tggagagtgc agacggggaa ggagattaca    1980

aggaggtgcc gttgcccgaa cagttgagga cttgggtgga gaatggaaag gtcaagagtg    2040

agattgttga acatgctgga tagattggtt gagatggatt gtggagtttg gggagaggct    2100

ctggcgaaaa cttgttgggg gtgaggggta atgagatgtg atggagaatc tgggtagatt    2160

tgatattata gagatagttg agtgaagttt tatatcatcg catgttagtt gaagttttca    2220

ggcagagtag aagtcaaagt tgaattgtac atatctatgt atatgtatat ccgaggcttg    2280

tctcgctttg ttgtttagta gatttcaaac cgaagatttt ctactcatca tatcgtgccg    2340

tgtgttttat attgggcgat gtgtcgttgt gctttttctc tctctatctc ttttactttc    2400

agggaaataa atata                                                     2415
```

<210> SEQ ID NO 55
<211> LENGTH: 4841
<212> TYPE: DNA
<213> ORGANISM: Botrytis cinerea

<400> SEQUENCE: 55

```
ggcttcaatt gacgttgaaa catgaatgct gaatgatgat acgatacact ttacttcagc      60

ccctttaaca ttttgtcgca aaatcggtga aacttgggtt gtatgtattt gtatattaaa     120

gatcgctaag cccagcctct atggtaacag attacctgag cttcgtcatt tcgacccccg     180

gaccgtgatc ttctaccaac ctcgaaccca ttccttcaaa taaatgtcac aaatctatct     240

ttcttcatac ctatttcttt tttgttcata ctcataatgt tttcgggttc gaactcgtac     300

cttggtggta acaccggccg ccaaccacca cagcaaccgc aacaacaata tggtggtttc     360

cagccaaacc aaggtttcca accacagcag actggtttcc agccacaaca gactggtttt     420

caacctcaac ccacaggata tggtaatgcg gctcctttac aacccaattt caccggttat     480

ccacttcaac cacagcctac gggatattct cagccctctc aagcaggctt ccctggaggc     540

cagcagcaac agcagcagtt caacaatgct cctcaacagc agaacttcca aacgggagct     600
```

-continued

```
cccccaatcc cgcagattcc gcagcaattc cagcagcctc aacaaacgca acaggctcaa    660
ccacctcctg cacctcctgt gcagcaaccg caagcgaccg gatttgctgc aatggcagat    720
tcatttaaac ctgctgctgc agagccatcg aagccaagag gacgcagagc ctccaagggg    780
ggagcaaaga tacctagtat acgactttcc ttcattacag cccaagatca agcaaagttc    840
gaaactcttt tcaaatccgc tgttggggat gggcaaacac tttctgggga gaaatcgagg    900
gatcttttac tacgctcaaa actagacggg aactcactgt cgcaaatatg gacgctcgca    960
gacactacaa gatctggaca gctacatttt cccgaattcg cattggctat gtacctctgt   1020
aatctcaagc tagtcggcaa gcagttacca tccgtgcttc ccgatgttat caaaaatgaa   1080
gtttctagca tggtggatat cataaacttc gctatagatg atgatgcacc agcggcaacg   1140
aatgcgccca gttttgatgg tcgacaaaac accgcgacac ctccgactat ccaacaacca   1200
cagccaatgg cgtctaattc cgcccttctc actgcgcaaa tgacaggtta ccctggacag   1260
cagaataact tttcgggtgg atttcaacca caacaaacag gcttccaggg ccaaatgcaa   1320
actggctttt ctggacagca aggcggattg caacctcagc caactggata taatcagatg   1380
tcaaaccctc aagcaacggg ctataatgga ccgcgccctc caatgcctcc tatgccatct   1440
aacttcagtt ctcatttatc tccggctcag acgggtatgc aaggtggaat gatcgcgcca   1500
ttgaatagcc agcctacagg agtcgatggc caatggggct tggtaaatgc gccagccccc   1560
aatatcgatc tattacattc ccggatgatg ccgcaacagg gtcgagaaca aggcaacttc   1620
accacggctg gtataacagg caatgctgaa attccatggg gaattacgaa agacgagaag   1680
accagatatg attccgtttt caaagcttgg gatgggtttg gtaaaggata tattagcggt   1740
gatgtcgcta ttgaagtttt tgggcagagt ggtctcccga agcctgacct ggagcgcgta   1800
tggaccttag cagatcacgg caacaaggga aagctcaaca tggatgaatt cgcggttgcc   1860
atgcatttga tttatcgaaa gcttaatgga tatcctctac cagcccaact acctccggcg   1920
ctcatacccc cttccactcg taacttcaat gattcgattg ggctgtcaa atctttactt    1980
catcaagaat ctaatttccg caagaactct ggtgctaccc ttttgccaca aaagactgga   2040
gtgagctacc tcaaaaatca ttctttccgt ggtgatgcta ccccaggtcg cacaggccgt   2100
aaagacgcta cagtatacaa aaataacgac gatgatgttg ggtataaatc tagtgctcgt   2160
cgcagactcg gggcctcttc tccacgacct tcgtctccgg gatcaacaac ttccaacgat   2220
gacctttcac tagaccagct tagaaagaaa atcgcggaga gacaagtgat actggatgca   2280
attgatttca aggccgaaaa tgctgcagat gaagatgatg ctcttgatcg taaagatcgt   2340
cgtgaagcag aggatcttta tcaccgcatt cgtcgtattc aagaggatat cgatgcgcat   2400
ccagacgcat cgttgcgtaa tgttgattcc ggcgccgagc gtcgtgcttt gaaaagacag   2460
ttgcagacat tgacagataa acttccagat attgcttcgc gtgtccgaag aacggaaaga   2520
agcattgctg atgccaagct tgaactattc cgtctaaagg atgccaaagc tcaccctgga   2580
agtgcctcta gcattgttgg aactggtcct ggcggcgcta tcaccgaatc agatagactc   2640
aaagcaagag ccaaggctat gatgcaacaa cgttctgctg ctctcactgg taagaagatt   2700
gaggcgagta atgatgactt ggatgcgcca aaacgcctcg aagaagaaaa tctcaagatt   2760
cgaactgaga aggaaaacaa cgagcgcatg gttcaagatg ttgaagagag tgtccgtgac   2820
ttttcacgag gactggagga tagtctcaaa gatggtggtg agagctcgtc cagtgagcat   2880
gagaagagac gttgggagga tgggctaggt gttgaggatg aagtgaagga cttcatcttc   2940
```

-continued

```
gatttgcaaa ggagcagcag gagtgccaga gttcgaactg atgatcgcag cagagagact   3000

cctcgtactg aagcgtctca tgctagccct gctccagcag ctcgtagcga aactccatcg   3060

tcacagccat catctacacc aacccctgct ggaggttcat actcacaata caagactcct   3120

gaagatagag cagcttatat caagcaacag gccgagaagc gcatggctga acgtctagct   3180

gctcttggta tcaaggcacc atctaaatct ggagaaacaa cacaacagag actggaacgt   3240

gaaaagaatg agcgtgcagc caaactcaga caagcagaag aggaagatgc taaacgtgaa   3300

gctgagaggc aagctaggat cgctgaagag cagggtgcac caccacctgc cccgagcaa    3360

ccaaaggaaa ccgcgaaaaa gccacctcca ccccccttcaa ggaaggccgc aagaagtgac  3420

gctagtgagc gcaaggccga agaggagaga atcattaacg agcaaaaggc acaaattatt   3480

gccacaaatg agctagagga cgatgctcaa cgacaagagg ccgagcttgc aaaggaacgc   3540

gaggcggctc aggctcgtgt caaggccttg gaagaccaaa tgaaggccgg gaaattgaag   3600

aaagaagagg agaaaaagaa gagaaaggct ctccaagctg agaccaaaca acaagaagct   3660

cgtctcgcag ctcaacgcgc agagattgaa gccgcacaag cacgtgagcg agaattgcaa   3720

cgtcaacttg aagctattga cgattcagat tcatctgatg atgacgaagg tcctgagcaa   3780

gttaccccctc aagcatcaac gcccactcaa ggaagtcaag agcttgagcg caaagaacct  3840

tctccaccac ctcctccacc ttcaattcca gttgttgtat caccagtccc tgctattgca   3900

acaacaacta gtcttccatc accaacccca caagttacta gccctgttgt cagccctcca   3960

gtcgatacag agacccgcaa tcctttcttg aagaaaatgg cccaatccgg tgacgcatct   4020

accgcatcta ctgcatctaa caatccattc catcgtcttc ctgctcaaga gctttctaca   4080

cctgcaccaa ttcaagttca accaacaggt aacaggccat ctcgtgttcg tccagaagaa   4140

gatgattggg atgtcgtcgg atctgacaaa gaggatgatt cctctgacga tgaaggacca   4200

ggtgcaggtg gtgcgcgtca tttggcatcg atcctttttcg gaaccatggc acctcctcgc  4260

ccattgtcat ccatgggtaa cgaagctaca tctgcgcctg aatctcctgc tgtagcatct   4320

ccaccagcgg caaccccccc acctccacca gtacctaact tcaatgcacc gccacctcct   4380

ccaatgccat cagccggtgc gccaggtggt cctccaccac cacctcctcc tccaccaggg   4440

atgggtgctc cacctccacc accaatgcca ccaatgggag gcgctcctgc tccaccagca   4500

ggtgtacgac cagctggtct cttgggtgaa atccagatgg ggcgatcgtt gaaaaagaca   4560

caaactaaag acaagagttc agctgctgtt gctggaaggg ttttggatta aatacctttc   4620

aaatcattga gaagagacaa gatgaaatgg aggtttgtgg ttagcgagcc taagaacatg   4680

gattgtatta taaattactt ttggttcata gtattgggca agggggctta ggtgtggaag   4740

gtgcgaaaca ggaaagataa gagacgagca taatttgtag tcgaagtagc aatttgaaaa   4800

tattcgttcg ttttgatagt catttgatgc acttatcacc a                       4841
```

<210> SEQ ID NO 56
<211> LENGTH: 3607
<212> TYPE: DNA
<213> ORGANISM: Botrytis cinerea

<400> SEQUENCE: 56

```
gatattgtac acgagcctct tcctgcattg attgattgat tgctcttaca catatccagt     60

tcatctccca caaaatacca agcggccgca tttggatgca acatacatac tcactacctt    120

ccacttcacc tacctaccta ctgacttaat ataccttctt gtcatctttg atggcactga    180

ataaagtacc ttcctattaa aactacctca accagtccag tcattactac ccaccttaca    240
```

-continued

```
tctcgagaag cctccttcct cgatatacat tcttctctta tattaatgca aagatgtcgg    300
agcacgaaca tcaaaaacat ctttccgatt ctgaagaaga ttccataatg gaagagagag    360
aggagaaaaa gggaaaagac gagatagagg agaaagacaa aaaagacgag aaagacgaga    420
tagaggagaa agaggagaaa gaggagaagg agaaagacaa aaaagacgag gaagagagag    480
aggagagaga ggagagagaa gagagagaag agagagagga tacagttgat cagagttctg    540
atcatgagag tgacaccttc gaggatgcca atgatgttga agacattgca gacactctta    600
cctccccagt tgaaaggaca agatctttaa cgaaacgaag atcatcatcc attaagagca    660
atacacaaga cctcagtacc gatatcccat cggtcccaac agtaccactt ccagaaacga    720
atggcgaaac gaatgacgaa caaatagaat ccgataatcc actacctaaa tctccccttt    780
taacatctca tcgcatgtcc actacatccc tacataatgt gaatctcgaa gacggtgatg    840
attttggatc acctccacca cctcctcccg tttcgaaagt agcaccagaa gatcaaccac    900
ccgaattacc tccaaagccc aatacaataa ttccaatgca gggcctttct ggagcccttc    960
cagatgtgcc attctcaccg ccccctcctc ctcctcccgc tcctcccgct cctgcaaacc   1020
tcgctgcgcc agcacctgtc accagaaaat taaccagccc attctcatgg ctgtcgagaa   1080
atacctcggc tccaaaagag aacgtcaagt caccgccatt accttcatct cacgcaaccg   1140
agcgtagaca taccgcttct tcgatagcga ccattagcag caatcctgaa atgatggtaa   1200
acaaattgga ggagggtaat gatacagatg ccgcgaatgg agttagacga cctgggagga   1260
atagtttacg ggacaggttt aagctcgtga gaatgcgaga agaggctgga ataacagaat   1320
tgcctgaaga aaaggatgaa gcaggcaaca cagcatttgg gggtctcatt aggcagagta   1380
caagtcttgg tttgggattt accgcctcaa atgatgacaa agacccttct cccgtatctc   1440
ctggtccgcc tacgagtccc aacccaatta gtgtcaaccc tgcattagcc cccggtacgg   1500
catctggagt ttctgcaggc ccttctgcat tgggtgaatc agaagcacca gtcgattggg   1560
atttgtggca aaatgtcgtc tgggaaggac cagctgcggt agcaagaaca agtgcagaag   1620
agctgaatca cgctattgca actggtatac cacatgctat cagaggcgtg gtatggcaag   1680
tattggcgga gagtaagaat gaagagctcg aggttgtcta tcggaatttg gtcaatcggg   1740
gcacagacaa ggacaaggac aggatgagta catctagtgg gacacaaagc aatggatcaa   1800
tcaaggagat tgtggtttca tcagcatcat caatacattc agagaaatct acacccgcta   1860
cgacaatcac caatggaatg agatctcctt ctccccctag tgaaaaggat gtagcccagt   1920
ctttggctga aaagaaaaag aaagctaagg aggatgcggc ggcattgaca aaactcgaga   1980
gagccataaa gcgggacttg ggtgctcgaa caagttattc aaaattcgct gcaagtgctg   2040
gactacaaga tggattattc ggtttatgca aagcatatgc tctttatgat gaaggtgttg   2100
gttatgcaca aggcatgaat ttcttagtta tgcctttgct tttcaacatg cccgaagaag   2160
aagcattctg tctattagta cgacttatga atcagtatca ccttcgagat ctttttattc   2220
aggatatgcc aggtctacat aaacatcttt atcagtttga gagattatta gaagattttg   2280
aaccagcatt gtattgtcat ctccatcgac gtcaggtcac acctcactta tatgctacgc   2340
aatggttcct aactcttttc gcctatcgat ttccattaca gcttgtgctt cgaatttacg   2400
atctcatttt aagcgagggt ctcgaggcta ttctcaaatt tggaattgta ctcatgcaaa   2460
agaatgcagc tcatctactc accctccatg atatggctgc attgactacg ttcctgaaag   2520
atcgactttt cgatgtttac attgatgctt caccttcagc aggatcaatt ctagaatctg   2580
```

-continued

```
gtttctttgg aaattcagga gcgactatcg ataaggaagt ttatcgagca gatcatatga   2640
ttcaagatgc ttgtgccgtc aaaattacac ccaaaatgct ggaaacttac gcattagaat   2700
gggaggaaaa gaccaagata gaaaaggatc gtgaagcaga attagaacac ttgaaatcaa   2760
caaatgtcgc ccttacacac aaagttcgac gtctggaaga aagagtcgaa tctcacgata   2820
cggagcacgc agctttggca actgaacttg ttcggactaa ggtcgaaaat caagagattc   2880
atgaagaaac agaagttctt aaagaacaag ttaaagaact gaaaaaagta attgataagc   2940
taccggaaga aattgaagcg aaattacaga gtgagatgga tagattgatg aagagaaatc   3000
aagaagttca tgaagaaaat caaaaattgg aggatgaaat gaatgaaatg gaacaaaact   3060
tggtggaaac aaaaatgaaa tatgctgaga tgaatgcggc ccatgaagct ctaactcgta   3120
aatggacgga tttgagaaaa gctttgggtg attaatatcg ttactttgag atatcctaaa   3180
ttattaaata cgacttgtac agttcttctc aattgatacc gatgcctttg aagtttttgg   3240
ggggtagggg agagaggcgt aaatgcctat attggggaac gaaggaacaa tgctctcgtt   3300
tggaagcttg ctggatttct tgctaggtgg aggggatgat tgggaatcaa tcagattata   3360
caggtactgc tgcattggta cgcaaatggt ataggaattg gcgtgggttg taaaagtacc   3420
ggagaaatac tttgggtgct tgcttgtctt gtttctctct cttttttta gtcgttttag   3480
cgagttgtga tgttggtagg aaagaaatta agaaattatg gacgggtagg gggagtggag   3540
agaggaaggg agggggtgaa agagggtggg gggaggggaa gaaataaaaa ttaagaataa   3600
atgatca                                                             3607
```

<210> SEQ ID NO 57
<211> LENGTH: 1840
<212> TYPE: DNA
<213> ORGANISM: Botrytis cinerea

<400> SEQUENCE: 57

```
gaagctttaa aacatacgat tatttgatcc tgtttgaaca cgttttcttg aaatttcaag     60
cttgaatgaa acacaacacc aagtctatcg gccaaaggac ccctttgaga ttgcattgag    120
cgttgtccca tctcaagatt taacaactgt tattcacgaa atcatgcctc caccaccacc    180
acctcctcct ccgccgcctc ctccgcctgg aggagctcca ggaggtatgc catccagacc    240
acctgcgaaa gttgctgcaa atagaggcgc actttttgtcg gatatcacga agggaagagc    300
actcaagaaa gctgtaacta acgatcgatc ggcaccggta gtaggcaaag tatctaatgg    360
ttctggacct gcgccaatag gaggtgctcc tccagtaccg ggaatggcaa aacctcccgg    420
tggatttggc gcaccgccag taccaggagg aaatagagct cgaagtgata gtaaccaagg    480
gagcaataat gcggtttcgg ggatggaaca agctccacag ttaggaggaa tattcgcagg    540
cggcatgccc aagttgaaga aacgaggtgg aggagtagat actggcgcaa accgcgactc    600
atcgactgca tcggaaccag aattctctgc tcccagaccg ccaggtatgg ctgctcccag    660
acctccaaca aatgcagctc cgcctttgcc atcagtccgg cctcctcctc aacctagcgc    720
tagtactccc gcatttgcgc cctcggttgc aaatctgaga aagaccggcg ggccatctat    780
ttctcgtcct gcatcctcaa cctctctcaa ggggccacca ccccctattg gcaaaaaacc    840
tcctccaccc cctggaactc gaaagccatc atcagcgcta tcaaccccac caccaccacc    900
gcctccagca ttcgcccctc cacctccttc ttcagcacct ccgccacctg ttgcacctcc    960
accaccacct tccccagctc cacgccctcc gagtaaccca cctcgatcac atgcaccacc   1020
gccaccacca ccaccaccac caccaacatc tccaccttcg actaacggag gtaacccaag   1080
```

-continued tcttgctata caagcaacaa ttcgtgctgc tggccaagca tcaccaatgg gtgcaccacc 1140
accaccacca ccgcctcctc ctccatctaa tgggcctccc tctctctcgt cgcacagaac 1200
gccatctccg cccgcggcac ccccagcggc acccccagcg gcaccaatat caagaagtca 1260
aagtcaacaa ggaagaactc acacaatgga ttccagttct tatacccttt catcaaacgg 1320
cagtttaccg caagcctcta gttctagcag aagaatcatg atcaatgatc ctcgatggaa 1380
atttacagat gaatcggtat tcccaaaacc tcgagatttt attggtgggc ccaaaaaata 1440
ccgggctggt cgtggaagta gtgttccgtt ggatctgagt gcttaccatt aagaatttcg 1500
cttaccaaaa agaatataac tcttcggatc gtattcatgt gttaccatta tgatttaagg 1560
cgttatagcg ggatatcatt tagaatccgg taaggcggca tcaagctatc tgaattggga 1620
gttatacatc aggacactaa agatcgtcaa aaaatttccc ctgaatcgcg agatggagat 1680
tgacgagaga catcagctca ctacccaggg taccgaggag gaaatcgcag ctataaatat 1740
cacgggtgat gggcaaattc cacagtggaa ccttaaaaga atgagtacgg agaatattaa 1800
acttttgaga tttatctttc tcttcctgtg attttaacca 1840

<210> SEQ ID NO 58
<211> LENGTH: 11117
<212> TYPE: DNA
<213> ORGANISM: Botrytis cinerea

<400> SEQUENCE: 58
ggtaagatta attgtaaggc aactctctaa tattatttct tgaacgtcaa tcgtcccaag 60
tgttcatctt taagtttatt tcgttcgttt taccatttgt ttaatttttt caatgccagt 120
taatcttcaa ccttctgttg gtacttctgg tagtctcagg aaagaaaatt caagaggaga 180
gggcacgaga aggatgccga ccaattcgcg acctccccta tcgcatcgga tacgggcatc 240
atttgaagga aggaaatctc atgattctac cagtcctaaa catgcgagct tctccggtag 300
cagtccaaca gatccggaac tcctccgacg gataatcgat gaagctatct ctggagaggt 360
cttccaggct ggacttgctt cacatatagc caaattgctc aagcccgaga tcaaaacggc 420
tttagataca attgagccag ttgtcaatgc agttctacaa catgagctac tcttgaagag 480
aaccaacaac agcgtggatc atgttttatt gaagttggag tcaatggcag atgacgaggg 540
agcaatgact ccaggccaag cacgacttag ttttcacggc gccctgactt cacacccgat 600
agcagaagaa gggtcactgc caatatcaga gaattcggtc tctggaactg gtacacctgt 660
ttccgtttcc aatcaggaat caagacccct cttcaaccga ggcctcacat acacagccgg 720
aaaattaaat gaaatatcgg actctttgga cttgaataac cataaactag ggaaggtggt 780
cgaaggaata gcggaaataa ataatctatt gacatcgaac gaacgcttgg atagtttgaa 840
ggaaagctca gacaagaatg ataccaagac ttcggtaata caaacgcaaa tagatcaact 900
gcaggagaat gttagggtag tcattactcg aattggtccg gatctaggaa taaatgtaaa 960
ggctatcaat gatcatctga ctggagaaac gacgattcaa gagacgaggg cggtggcttc 1020
caatggcagt gggggtgatg ttgagcttct tcaagccata tcttccaaat tagaagcctt 1080
gaaggatagc ttggagacag gaacttcgtc acataatgat aacttgggac tattgaagga 1140
acaaatcaat gctctacagt caacactcga cgcgcagaaa gagatattag gggagattaa 1200
ggaagctgat aatagcactg aagttttggc tggtatacac aaatcaaacg agtcacatga 1260
agcgcatgcc acaattttgg gcgagctcaa agagagaagt acaacacttg cggatttatc 1320

-continued aactcaaccg gctcccacat cagcagacgc ggaaacactc caaacaatct tgatagaagt 1380
acagaaatcc aacgaggcac atgagaaaca tacagctgcg ctcgagagtt tgaaggaatc 1440
ggatacaaat gcagtcatat tagcggaagt tcaaaagtcg aacgacttgc atctttcgca 1500
tgcatctgct ctagaaagtc tcaaaagttc cactccacca ctagaacaaa ccaccgcaat 1560
cgatctagga agtttcgaaa ctaagatggg cagcttaata gaaacaagca cagcaattct 1620
tacggaagtt caaaaatcaa acgagtcaca tgtttcacac gcagctgcat tggaaaatat 1680
caaggcccta ccaactccac cttctgaaac tgaaactgca agtgcaagtg ttgatttggg 1740
aggcttggag aaggatatgg gaactattat tgaaaagttg gacttgcacg ctgctgttct 1800
agaagaaatc aagacaaagg atactcccgg agccggagtg attgatgcta ctgcctttga 1860
tggccatttt ggttccatta atactctctt ggaaagacac acagcggcat tggatgagat 1920
taaatcgata gatgcaggag gtagtacgga ttttagtcca ataactgcct tgttagaagc 1980
tcacagcgca acattggagg atatcaaatc gagagattta aaacctgctg attttggtcc 2040
aatcgtatcg atgcttgaag cacatactgt ggctttggaa gaaatcaagt cgaaagatcc 2100
gggatgtaat ccagatttca gtccaataag tgccttgttg gaagctcata ctgcaacctt 2160
agatgaaatc aaggccaagg aaactacaaa cagtattgat ttaagtccaa taactgcatt 2220
gctagacgct catactgcca gcttggatga aatcaaatcg aaagatatga cagctgctga 2280
tttcagccca ataactgcat tgttggaagc tcatactaca accttggagg atatcaaggc 2340
caaggacagt gcaaacaacg ttgatttaag tccaattact tcgactctgg attctcaccg 2400
tgcagtttta gatgagattg tatcaaagga tgtccaatct agtggtgtac ctgcgacaat 2460
caacatggat gccttcgata cacatttcgg ttcaatcaca ggtatactag cagcacacac 2520
agccgcattg gacgagatca agtccaaaga tagtccttcc aatgcttcgc tgcctgcaga 2580
aaataccatt gaaatcctcg acaaacattt tggttctatc attaacatgt tggaagcaca 2640
cactgcagca ctggaagaaa ttaaggcaaa ggattgcacg gcgactacag gacaaacgga 2700
gttgaacaca gcagcatttg atgatcactt tagttctctg gcacgcatgc tagattcaca 2760
cacagaagct ttggatgaaa tcaaatcaaa gaacaatgat tccactccgc ctacaatatc 2820
aagagataat attggcctcg aatcattcga accacatgtt acggcgatta agagtgcact 2880
cgatgctcat atggttgtgc tgcaagacat aaagtccgag gcccttgcca aaaatgatat 2940
ggatgcaatg gtggtagaca atttgctgga accacacatc atagctatca aaaatacatt 3000
gaatgcacac acagaaactc tggaagaact taaatccaaa attcctacta acaccacaaa 3060
ttcattcgaa attgccaacg atgctttacc taggatcttg gataccctta atagccacac 3120
cgatctactc acagaaatca agaattcaga tgttagtgac gagattttga cagcattgca 3180
tgagctgcag gaaggcaatt cttcagcttt caataccctc aaggaatcag atgtcagtga 3240
tgagatactt actgcgttgc atacatgcaa tgattcacaa gaaaagctgg atagatcact 3300
acttgaactc caaacagtag tgaataactc tatttcctcc gaacagaata ggaacaagtc 3360
cattgatact gctgaagtag tccaagcacc gattgctgct gtagatttga gtggattgga 3420
gactcagatt agtgccatta ttgcaactct cgaaggccaa aatgtggttt taggtgagat 3480
caaggatact actaatgctg gaatggaagc acatggcttg catatcacga ctctaggtga 3540
gatcaaggat gccactagtg cctcaaatga ttctcacgca gcccatgtgg cagctcttgg 3600
agaaatcaga gatgcagcta atgcttcaaa cgaatcccat gacgcccata cttctacact 3660
aggagtcatc agagatgcag cagcctcctt gagtactgca catgccgccc aaattgctgc 3720

-continued

```
tttgattgaa ttgaagcaag caataaacgc ctctaatgaa tctcacaata ctcacaccag   3780
taccttagca acgatacgag atgcagcagt cagctcgaat gacgcaattc tctctcacac   3840
gactactctt agtgagctca aagaagcaat caatgcatcg aatgactctc acacttctca   3900
cgccgccgct ttgacagatc tgaaatccat tcatccaaca cagtcaccgc cagatgatac   3960
gtctgagtcg acatcaccac cattccttga tacaagtgca ctagacaccc agctcacaac   4020
tatcattaca acgcttgaat ctcaaaattc tactctggga gagatgaaag gtgctcatga   4080
atctcacaca acaactttga atgaaatcaa ggacgcaaca gcagcatcaa acgtgtcaca   4140
tacttcacac acgacaattt tgagcgaaat caaagaaaca attgctccta ttcgtggcat   4200
caatgaggtc ataagcacac acacaggtct attggaaggt ctgaaagaag acactggatc   4260
acaacataat gaggtgagaa gtgatatcga tggtttaagg aaccttgtag acgaaaattc   4320
caataaacac gaggaaagtc tgtcaaaatt tggggattta atcagggagc atggcgactt   4380
ggttaaagac agccatgatg ggttgaaggg aacgatcgcc ggacttgctt tgggtggaat   4440
tgccggagcg gggatcatga aagctgtgga tgatggggaa gataacgatg gcgaggtaag   4500
tgatgtagta gagcgggatg tgaaagtgcc ggaagctcca gtcgaagaag acaaggttat   4560
tgaggaagaa tcaccagcat tggagcccga agcacctgcg gtggaagatc cagctccaga   4620
gtctacagaa caaactccgg aacttccagt cgaagaacaa gttctgcctg aaccagaagc   4680
acagttagag cccgaagtgt ctatggaaga agagaagacc gccagtgagg aaacgctagt   4740
agagccagag ctagaaccga aagttatctt gccagatcct gaggagacgg tcgacgtcaa   4800
cgaagattcg gaccctgcac cagtagacca ggaaccgggg ccagaagcta ttgacaagga   4860
atttccagcc gaggagccga caccaatcga aacggaggct ccaacgcagg aggctgtcgt   4920
tgaagagctg attccaacag aggaaaagcc ggaaccagct accttggaaa ccacggaaga   4980
aacaccagct atcgaatccc aatatactga aaaagatctc cctggcgaag aaacaatccc   5040
tcaaggggaa gctgagccca tagcaacccc cgaagattcc tctgaaccaa accaaggaat   5100
tgaagttcca gcaagtattg aaaatcggga gcccgaagct cttgagaagg aacaagaaat   5160
tgaagttacc acgccaaatt cggttgaaca atcggatttg gtccaagata ctaccgaaga   5220
ggaagcgcct caaatacaag aaatagaagg agaaccaata cctggagagg acgatgtcac   5280
agaactgtct aaggacgaat tggatcccga aagagagctt gccgttgagg agatacctgg   5340
tgaggaagag gctgttgcga tggaagggtc tgaggaggaa gcagttgatg agggcgagag   5400
agctaaagta caggaaattg aagatctagg cgatgatgat ttgaaatcca ctgaagaaat   5460
agtgccggat gctgtggagg aagagaaatc aacagaagac atagctccag aaaatgtagt   5520
cgagtatgtg aacccaagcg aggaagctct acaggccgga gaagataaac ctgtcgatga   5580
accaatttca caggagtcag atgtgaattt gactaccgac ttacaacata cacttcctgc   5640
agacgaagaa gaaaagctgc ccgaaatcaa ggaatctaat gagccaagtt tggaggaaac   5700
aaacatcgaa aatgctagcc cagaggtttt gatagacaaa ccgacggact tggaggcgac   5760
tccacctttg gaaataaacg aacctgttcc ggagactgag ccagccaacg tatctggttt   5820
tgcagatccg tcagtggaaa ccgaagaaat acccattgtt ccagatcacg atgtcgatag   5880
tcatactcaa gtacccgaag caagcggtga agtttccgcg gatgacttag aaattcctac   5940
agattctgaa gtcattgagc cgttcaatga agagcaaaaa gttgatgaag aaaccgagaa   6000
tgaacgactg gctgaacatc cgatcgatcc ccaagaaaca aatctgaaaa atgaggatcg   6060
```

```
agagcctaac aatgaggata ttcctatcga gaacgcggag agtgttgctg aaccatcgaa   6120
agaggataag tcttcagaat cagttgcgga gatcgagaca ccgcacttgg attcaaacga   6180
tcaaaatgaa ggttctgccg aggtagatac aaaggatttg gaaacagaag ctttgtatcc   6240
cagcaaggaa gagacaccag accagacaga ggaagctgta gagctctcta atgatcaaag   6300
taatcccagc cctatttttg aaaccgatgt acccgtttcg gagatagacg accaagatga   6360
aaagcctgtt gaagttgagg cgagggattt ggaaatggaa gatggggaac atcacagcga   6420
tgaggtacct gaaaaatctg cggagaaacc ctcacaaacc ttacaggaag aaagcgattc   6480
tgaaccggtt gtcgaaaccg agacatatgt tcctgaatca aactctcatg atcaaaatcc   6540
aattgaaagc gaagagaaac tagcggaact tcctgttaat caacttgtca ctgaggagat   6600
ctctagcgag cccagagaag actctgagac cttacaaggg aaaaacattt cacaatcacc   6660
tgtcgaaact gaggaacata ttcccgagtt gaacacttac gtcgaacctt cagttgagaa   6720
cgagcaaccc cctaaggagc ctgaggacag cgaatttgtt gtcaaggaac ctgaaaactt   6780
cgaagacttg acccgatctg tcgaaaatga agaagagact ttcgaaccag aaaaccaggt   6840
atctaggagt gagaacacac cactcgaaac cgaacaaacg gttcctcgag aaaagactcc   6900
agttttaaat gctgaatccg agataccggc gtttgagtca gatgatcaaa tgcaaatccc   6960
tgctgagaat gaagagaagt ctatggaacc cgctcttagt gagccagaag ccgcaggttt   7020
ggaaattaca gagccacaag tgaataatga agctcagatc actgaaacat cgccgcaaga   7080
tactgttgag gagccggtgg ttgagaatca aattcctgtt gttccagaat tgagcaatga   7140
gactagaggg gtcaccgaag atcatgaaac tcttgaaaca gcagagcaac aagctgtcga   7200
ggtacctgtc gaaaaatcag tcattgagag ccaacttgaa ctctccaacg aagataaaag   7260
tattgaggac aatgcatcaa cagaaaatac ccccgagcca gatgtcgtgg acaaacatat   7320
ttctgatggg tttggatcaa gcgaagaagg acaaatcgta accgaccatg gagacgaacc   7380
tctatcaaat gagaaagaga ttcttgataa ttatcaagaa gaatcggttc ctgaaaacgg   7440
atcaacttct gagagtgtaa ttcatgaata ttccagagat atcagagatg cagaccaacc   7500
aatggaaatt gatgaacagg ttgcggatac aagcggtcaa gattcaaatc ctcaaagcca   7560
accaacatca gaggtagcca tctatgaaga tcctgaagat atcaaagccc gtgaggaaat   7620
tgctgctttg aacgcggaga tggctaaaat attagctgaa gctgaggagg aggaaaggag   7680
aaatgttccg gtagagacgg aaacaatttc cgaggatgaa cctatggagc cggaggtcga   7740
atatcatgtc gaagaaccta ttgatgtctc ggatacacag ccactggtcg aaagccacga   7800
aatccccgaa gaccgaactg agaatgagca tgcgcaggaa gaagtgactg aaccggaaga   7860
agagcagaag tttgctgtta ctgatgagga gcgctcaaac gacactagca cagaagaacc   7920
tctggaaagc catgttgtgt cctctaccga ttctgaagag catatcatgc ccatattacc   7980
agaaaccaac gccatcgagt ctaccaatat tttacctgca gataaattgc atcacgtcga   8040
ggatactatt ccggtcaact acgaggatct taacgagagc caaaatcaga ttacagagga   8100
tggaaatata gatgaaaagc cttccgtgtt ctcttccgaa gatgagaaaa tagatcttgg   8160
aataccgtcc atagccgagc aacctgagat ggaagttgtg agcaatgaaa gtgcacctat   8220
gcaagataaa gctttatcta gagaagaagt aaaaattccg gacatggaat tgctaccctc   8280
tgaatctcac atggagcccg agacggaaaa ccttgagggc gcacacttag gtgaccatgt   8340
tgtacttcct ttggacagcg aggaagacaa atctttgtct atccaaactg aatttgaatc   8400
agatcctagg gagatagcac cagagggaca aaatctggag ggagaaatca atcctgaaca   8460
```

-continued

```
atctttcgta gaatccgaac aggaaaatcc aaaagatgaa atgacattcg aagattaccc   8520
tgtcgaagaa agttcgattc cgaagttgga ttccattaag gaaagcacag aggatccaga   8580
aagtggaaac gaggaaatag agaatggcag tccttcagta gagcatctcg aggttgtaga   8640
aacagagcca agtcctgagg agcacctaaa agagctcgaa tccatagatg acggagattt   8700
ctaccccgta gagcctgaaa ctgaccgaga agatttcgaa gaccacaaag aattagaagc   8760
taatactgtg gttcctggaa gtcttgaatt cgaaacgatc gacaatagcg agccggatga   8820
agtacatgat atttccgatg gaagattgca agaattagag catgcagcgg aagctcaatc   8880
aactacgtct aatcacggag aagctgcaga taccgaagaa aattatcatg acagcgagcc   8940
gagtcaagaa gaaatcgctt ccgagattcc tctcccaggc ccatcagttc aagaagggca   9000
atctatccta gaggaagaga aaaatcctgc tattaaacaa cttccagccc aaaatgacat   9060
ggaacccgaa agccatcaaa tgtctgatga tgtctttcca gtcaataatg aaggtgtcaa   9120
taacagcttc catgttccag atgaagatga gctagagttg acggacgagc caaactctag   9180
agaagttcca gtttcgtttg acaccaagca cacaacagag aatattgttc cttccggagt   9240
cacagataac ttaaaactca aggataccga atcaatctat tcccaagaaa atgagccaat   9300
gatcgcaaca gggcactaca gacaagagag agaagagttt tctgacccga cagccacagg   9360
tcaacatgtg gctgccgagc aagtagaacc ggaacaagag ttagaagcta gacactttgt   9420
tcccgaaact accccaactc acgagaccca gctcagtcag ccagaaactt cagcggagca   9480
aaggtacaca ggttatggct acgactatga agagcctact ctaaatacac aaacttactc   9540
cgactcggaa gatgatatcg agccaattca gtcggaacaa acgagttctc gctatgaatc   9600
aaggggctct tacccctacc aaggaaccag ctttagtaga tctataccac aaccaagata   9660
ttcaagctat gaagagcccc ctcacgattc acgaactttc ttcaacgacc aagatgacaa   9720
ccagtatttg agaccaatgc ctacatactc tagctcaagc tattctcaag aatacctctc   9780
agagtcccat ccgactcaag aaatccacta taacgagtct gagcctcaac cgaatcaacc   9840
gagaacgcca acggaccaaa caacccatga ggataccatc ccacccactc ctccaacagc   9900
tttaactacg aagatgtcta cagaaacatt ccctacatat gacgagtccc gatcggtttc   9960
ccagggtcta aatcttggct taccgataag aggagcagaa cgagttggaa caattcgcga  10020
aagtcctgag cctacatatc ctttatacaa tgagccaatg cgatctcccg cacaatcacg  10080
actaccaatc acgagccaga gatcatcgga tagtatgcgt aggagccata gtcctgaatt  10140
gagaaaacag agcagttatt ctagatatgc acatgatgag cctggattag gaaaatcttt  10200
gggatcttca caagggttca attttggtct ttcaccgacg aaaattccag gttctattgg  10260
aaggtccagc aggatacctg aggtcggaaa tgagtatggt tattcaaaga ctacatatga  10320
ggagccagtg cgttctttag ggacttcgca aggatctaga ttcagtctac agagtacgca  10380
ttcaggtaga gagccttttg aggaaattcc agaaccaggt aatggaaaga ggagtagtaa  10440
tgtgaaaaat ctgttgagtc gattcgaaag tggtgaatcc tcatcttcaa cgcctccgca  10500
acaagagcgt ttcagtatcc cgacatatca agaccgtttc ggcacttctc ttcctcgacc  10560
tgctgataac agatcggtcg ggaaacagcc tcaatacttg caagaaagcc aactcgaagc  10620
tgtgatgccg cttgatcatg gtagatttga tctcatgagt gaggaaagta gtccggtgca  10680
aactcctctt gaagagaggg aacttcagtt tgagagtgaa ggaagtagcg cagtgcaaac  10740
gcctttggaa ggggaatttg atttggatgg gagtacaggt gggaatgtaa atacaggagt  10800
```

accgaagaag aggagaagta agagggggaa gaagaagggt aatggtgggg gaggtattgg 10860
tcaggcttga ggggcaggag aagtaggatc gaaaagtttg agatgtggtt agggtggaaa 10920
tgtgagtcgg atgactgatg gagaatgaag aatgattgat gtttgatggt aatgaaaaag 10980
ttggataaat attgggattc gcatgagttt ttaataattt ttggggtttg tttttataag 11040
tagcgggtat gcaactgggc aggagttttg atataatgct catagagata ctattaatag 11100
tccaatttat attttca 11117

<210> SEQ ID NO 59
<211> LENGTH: 507
<212> TYPE: DNA
<213> ORGANISM: Botrytis cinerea

<400> SEQUENCE: 59
atggacattc ctatgcgtgg ccaaaagccg agcttcagca cacccttacc agaaatccac 60
gtacaagact cacaccaccc cgatcgatat accgatagat actcagatca acacaaatac 120
cattcttcca actcttcaag ggctgcgcct ggaccaatgt ctatacctca cgcgagagag 180
tctcctcctc ctcctctacc accacctaaa tacgttcccg atacagataa cgggggagat 240
cttgggtggc atttcgcaaa tcaaaaccgg gaacccgatt gggcaagaaa tatcccatcg 300
gttcccgccg gctcgagttt gtatgggagc tacagtcgca gtagcatatc agatgagcga 360
ccggacattg gacgtcgagg aagctccaac gccactatca ctgttcatcc gtcgaaagat 420
gcgagcagcc atgcaattgc actgccaaaa gacgaaggct attcgagcct ttctgcttcc 480
aacgcaagca ttgggtcgac acagtga 507

<210> SEQ ID NO 60
<211> LENGTH: 1306
<212> TYPE: DNA
<213> ORGANISM: Botrytis cinerea

<400> SEQUENCE: 60
gctcattgat tctccatctt ctacgctcct acctacccca aaaactcttt caaacccccc 60
cataacgagt tacaatggac ccatatcaga atcaaggtta cggcggtaac cagggctgga 120
ctggtggtgc atggaaccct gcccaacatg ggtacaatcc aaacaacaac tggccaccac 180
aacctccaca gcccccacag caactactcc ctcctcctcc tcagtacaat acgcaagttg 240
cttcttctct tttctgctgc gagaactgcc agcgtgttgc tgctccaact cagccaagcg 300
ttcatgcata taccactcgt ttggcgtttt ttacggcaca catcttgcat cccactgtgg 360
cttcctacac ccaggtacct aaccgcaatc aacacccgaa ttgctttgct agtgatgtac 420
ctcaatctca aacaattgcc cctactgggg gtcatggggg tcatgggggt catggtcaag 480
gtaccaatgc ccagcagatt gcacagcaag tcatccagca gcaaggtggc cagcaacagc 540
atggtttcat gcaacaagct ccaaccggac ctgctgcagg tgctggtact cattacactg 600
ctgttactgg tagcagtcat caatctggct ttaatcagca aggaaactac caagctggtg 660
gtggttatgc tcaaaacaat gctgcacaac aacatcctcg cccaaatggc cctcctagca 720
acacctcgat ggctataatc ggtcctatta tgcatgctgg ctcatcttac agcatcgatc 780
cgaacaccgc catccctctt ccacgatttc ctcgtcctac tttccagcta aatgtcaagt 840
ttcgtcttga acgcttccgt ccagatcctc cacagcagcc ttttcagtat ggaatgccaa 900
attatcaagg cttcaatgcc taccaatacc catcgtacat gaatccctat cctaacactg 960
ccgtctccac ctccactggt ggccctaaat ccagggacaa catggagctt atatggtact 1020
actggccagt tcagctcgag gttcctctct gggctagagg tcagaatact ttgacttccg 1080
caccagatat tggtgctcaa ctcattcgag agggcatgca gatcatcaat ggagagcgtt 1140
ggggcttcat ccagcaccaa gagaatccag agggcttgtg gcacaagcga cgatcttaca 1200
agatcctcga gtgtcctgtt catgggatgt actggaaggt cactgtcttc gttcgtcgtg 1260
gttattaggg tattttagaa ggcattgggt caattttaag ccttga 1306

<210> SEQ ID NO 61
<211> LENGTH: 2519
<212> TYPE: DNA
<213> ORGANISM: Botrytis cinerea

<400> SEQUENCE: 61
gaaagagtca gcttgtgttg gcgcttgttt gggctttgcg caacattgcc agtgttatac 60
ttctcatagc aaatagcgca ggtatcagtt ctgtgaaacc catcattcca taacactacg 120
gactgctttc ttacttctca agatggatat agaggctact aacaagccag cttctctacc 180
cgccgctacg atgccaccaa gtttacaata tatacctgca gaaattcgga gaaagatatt 240
tatatgtctg ttggttagta ctgagctagg agaggcgtct tccattgacc aacttgaggg 300
atatggagcc gatgcgaaat atggcttgag cccacagata ctactcgtct gccgcctttt 360
ccatgaagaa ggtatggaga ttctttatgg cttgaaccaa ttcattatcg aatcactacc 420
gagtatacgc attaaaagaa tggatgtact tcatccgttc accatatgca gtcctttgac 480
tcgctgggac aaccaaccca ccacggatct cccaacccac tccattcaaa agactctatt 540
acacaggaat caagctatta aattcgtcag aaaatggaga ataattttaa gcgccaggct 600
ctatgagccc agaagtcgag atggacttgt tgaattgtgc cgtttactgt gcgagctgca 660
gacactttca ggagggtcat tactgaggga gttagaagta tgcatcattc ccaagggtgt 720
cgaagtcaaa tatggctaca tgaacatgaa cgaaatgcgc gaaagtcttg tgccactgga 780
gctgctacga aatataccta tagtgtcgat tcgaacagcc agcattgatg agataccaga 840
ctttgcatat aggcataagt ggcttgatac accactcgta acaccgtcaa tgctacctac 900
cgcatcctat cgccgcctcc tcatccacct catccgtgga aattcagaag tcgaattgag 960
taccaagatg ttcacttctc ttttggagta cacgcaagcc tttgaaagag atgcccaatt 1020
caagaacgcg atgtccttga gctcccaaga ggtagccgct ttgatgccga agctgcctgc 1080
actaagcgag aatccgttcc tcaacaaaga gtttcactca aaagaattgg ctcacactat 1140
cgagactggt ctacaaagag cacgatatat gaccgagatc gaaagtggag atattaccaa 1200
gaccacccag ttcaaggaag agcgatctgt tatcctgaaa tacttggaac gtcagttctg 1260
caggataagc cacgcatccc acgagctcat cgactttctc aaattacaaa agagaaagtg 1320
gggcgttttt gatcctgctt gtacaaaaaa atacaacggt tttgatatgg cgatttatac 1380
tgaggccatg gttctacttg aggactacgc cgcgtcattt atccgagaat tagacgcatc 1440
aacgaaaaga gcagtgcgcg cgcaatttgg tctttttgag catcgctacg agttaatggc 1500
aagggaagtc aaacttcaaa aatgtaggat agcttacaac agaagagacc ccatcacgtt 1560
tagagcaaac ttccaagaag cggtgagcga tatggagttg cagtatcata ccatactcac 1620
gactagatct aagctatacg attgggacgc tggtagcagt attcccgata tcaatatcgc 1680
accgttgagc tcattcgagg actggcaaat tagatgggag atagaggaac cagcaatcac 1740
cgctataaca gaggtagaag cgcaaaggat tcaacaagat cttcgccgcc agattgccca 1800
gaaatgtttt cttgcacagg aggcagaaaa caaagctccc ggggacaacc aggatttgga 1860
tgcagcgaat tgtgatgagg ctcatgacca gagcgggagc actactgaaa aggaactcga 1920
acttgatatc gccaattggg agtctctacc atatcatgaa gatgacgaag tctctaagct 1980
tatcttacat ctggatgaag aacagcctcc actaccatct actgtcgaag ccctcatgaa 2040
ttctgacaat gattcagaaa atgatttcta cgaagagctt ttcagagatc gcccggaaga 2100
cgatagcttt tgtttggaat ccgaagacga cattgaagtc ggcgatgact gtatcgatag 2160
ggacaggtct acccttcacg acctacctta ccccggggac tctggaggtt ctctatcaca 2220
tgtgttcccg tggatgacac tctctgagct ataattgccc aagtcttatc gaggttgtta 2280
tatttgacca gagttatctc cgataatgct tctgtagtcg tatcatctaa gcccttggtg 2340
gatttatggg attatatccg ttaccactat ggttgtagta gaccttaacg gtcctagttg 2400
tcctaattga tgaactatga ctctgtacac tggattctag aggatttgat gaagctgatg 2460
ggtgcaccag tgggtgcata gactggcggg acacttctca aatttcaaac gttttaaca 2519

<210> SEQ ID NO 62
<211> LENGTH: 1589
<212> TYPE: DNA
<213> ORGANISM: Botrytis cinerea
<400> SEQUENCE: 62
ggtatcgagg gtccaaagtg tggtccgtcc gggtgatgat tatttttttg gctctgcctc 60
atattaacac ttcctgcttc tgttcgagcc caccatttgt ctttctcgaa ttccttgcaa 120
agcatctctc tcatccatcg agcgatgttc tgataacctc ttgtgcctca ttcatcaaga 180
gcgatataaa aacgagggag caagaaaaag agtttgatgt ttgatacttg aattgaatac 240
ctaccaatct acctccctcc tcccaagctt acatctcgac tacgatatca tacccgaagt 300
acatatatac caacggaccc atccaatttc tccctcaaat cttgaaattt tatccttcga 360
gccggtatca cacatatcct tcctaatcaa aagatcgaca atatcaaaaa tgtttacgac 420
gagtatctta acgcttttgg cgataacgac gagtgttttg gtccaggcac atacggtgat 480
tacatacccg ggatggagag gtgataattt gattacgaat gagacttttc cttatggaat 540
gcagtggatg tatccttgcg gcggcatgcc tactaccacc aaccgcactc tctggcccat 600
ccacggcggc gccatctccg ttcaacccgg ctggtttcaa ggtcacgcca ccgccttctt 660
ctactttaat ctcggattcg gcaccgatgg ccccgacaat ggtccccaga acatgtcttt 720
ccccatgacc tccgtcatgc aaatcgtcgg ccctagcaaa aatccttacc cgggaacctt 780
ctgtttgcct caggtgccat tgcccgcaaa tacgacggtt aatgtaggag ataatgcgac 840
gattcaggtc gtggagacgg cgattcatgg ggctgctttg tattcttgcg tagacataac 900
cttcgcactc cccgaagacg tcgccgaagt aaacacctcg aactgcttca actcctccga 960
catctccttt gcaaacgtct acaccatcaa cgatgcctca gcccccggaa cttcctcctc 1020
cgcctcctcc tccgcatctc cttcgcgctc gctctgggct gctagtctcg cgagcgtgct 1080
gggcatcgct atgtggagtt tcttgtagga gatgcgagat ggaaaatgat cggagagaaa 1140
tttgtaattt ctgggagatt acaaacgaaa gatggggagg ggaggggaag agaaaagatg 1200
aaagataatc agaaggaaat tcaaggaagc agaaacaggc agcattgtag atatgataaa 1260
atatgatatg ataccacggg cagatgatag acggacacat caagtgagtg tccctgcctc 1320
tatacccaac aaatcgagat cgaaatctca aaccatggga actgggaacc gggaaccggg 1380
aattgaagca gagcattcaa gtacccaacg aggagctact ttgcatgtat gtatgagcac 1440
tcaggcgttt tatggcgagg attgtgattg gaaggaatga ttttttttatt aatttcattt 1500 taattctcga gtttcgagtt tcgagtttcg atattcaatt tctatctcaa tacaatccaa 1560
ttcaatacaa tcatatcctt tactgcgca 1589

<210> SEQ ID NO 63
<211> LENGTH: 3308
<212> TYPE: DNA
<213> ORGANISM: Botrytis cinerea

<400> SEQUENCE: 63
gatttacacg ggatgtgttg cccttctcca cgacgtcaac agttttctcg acaagtagac 60
agaaaatcat gactgagatc atcccaattc ctgagcccaa gggctggccc attatcaatc 120
atttggtagg ggtcattgat aacgagaatc cgactgagtc tttcaaacat ctagcagagc 180
agttagggag gatttacagg cttcgtctga ttaatatacc catcacattt gtttctagct 240
acaaatatat aaatgagcta tgtaatgaga agaagtttcg gaaagtccct ggagggatat 300
ttaaggaatt gcgagatgca gccaacgatg gattgatcac ggcatatctt gatgaagaga 360
attggggtat cgcccatcga gtgctcatgc ctgcatttgg accctctgct gttcacggca 420
tgttcgatga tatgcatgat attgccgccc agctcaccat gaaatgggcc aggttaggca 480
agtatgaatc atttgtccca gctgaggact tcacacgtct cgcgatggat actctggcat 540
tatgttccat ggattataga ttcaacagct tttacgggcg cgagacacat cctttccttg 600
aggcgatggc tagaacactt ctaaggtcgc gttatcgtgc tcgacgctta aatattccca 660
ttgttaagtt tttctatcaa caagagacga agcagtggta tgaagacatc gcactcctgc 720
gggaagtttc ggatagcatc atacgtcatc gaattaaaca tcccagtcct cgaaaggatt 780
tagtcgctgc tatgttaacg cacaaggacc caatgacagg aaaggtcatg acagaaaaga 840
gcacgactga caacgccttg agttttcttg tcgctggaca cgagacaact gcgggactgc 900
tctcttttac actgtactat ctgctcaaag atcctcgggt ctacaataag gctcgggagg 960
atatcgataa tgtagttgga gaaggccgca ttcgagtaga gcatctttcg aaattaccct 1020
acatcgaagc aatactccgc gaggtcctcc ggctggaacc accactgccg gtattttcgg 1080
tccgtcctta cgaagatacc ttggtcgatg gtcgctttct cgtaaagaag gatgaaggtt 1140
gcgttctcct cctcaagcat gctcatcgcg ataaggaagt gtacggtgag gatgcggatg 1200
agttccgacc cgaacgtatg ctcgacgaac acttcaacaa actcccaccc ggggccttca 1260 aacccttttgg aaatggacaa agagcatgta ttggccgaaa cttcgctctc caagaagcaa 1320
acctgatgct cgtcatgctt ctccagaact ttgacctcgc tttggatgat ccatcatacg 1380
aactgcaaat caaacagacc ttgaccatga agcccaagaa ctttaagatt cgggctaatt 1440
tacgagatgg attgactccg attacactgc agcagcgatt actctatggg acttcgactt 1500
taacagcaac tcaagaagct cgcaaggaat tgcgaaatgt tgctgcaacg gctcaattca 1560
agcccttgac agttctctat ggatcgaatg ccggcacttg tgcacaactg gcacaacttc 1620
taggatcaca tgctcgttcc cacggtttca acgccgtgac tatcgaaact ctcgacgccg 1680
cagtggaaaa agtacccaat gaccatcctg tcattttcat caccacatcc tacgagggtc 1740
aacccacaga caacgccaag cgatttttct cttggctaga gacgtcctcg ggaaaatttc 1800
ttgacggtat cagttatgcc gtttatggtc ttggacatca tgattgggtt tccacgtttc 1860
acaaaattcc taaggccctg gacgctcgat tggagcaagc tggtggagag cgtctgcttc 1920

-continued

```
cactccaact tgatgatgtt ggtgactctg atattttttc cgcctttgat acatgggagg   1980
aagatgtgtt ctggccaaca ttggagaagc agtatggtgt tatcaacgcg aatcatgaga   2040
gtcatgatgt tgatgaactt gatactaagc tagtgagcct tcgaaaaacg accttgagct   2100
actttgtctc cgaagcccaa gttgtcagct ccaaaatctt gactgcccct ggtgagccag   2160
tcaagaaaca cctcgagatt aagttgccag ccaacatgcc atatcaagtc ggggattatc   2220
ttcttacatt accgaaaaat ccccctgaga cagtcgaacg agtgttgaag cattttcaaa   2280
tctctcgcga tactcagaac aatacatttc ctaggattga atcctatact ctcaccaccg   2340
tggaatcaat cgagtcgtat gtagagctga gccatcccgc ctcgaaaaag gccatggcag   2400
tactagttga cgctacaaag aacgagcaag tcaaacaaaa gctacaagag atggctatgg   2460
aactgtactc atctgagatt gagagcaaat acatttctgt tctggatttg ctcgaggcgt   2520
tccctggcat tgaattatca ttaaattcat tcttggcact ccttccacca ctcaaacttc   2580
gtcaatattc catttcgtcc tctccattgt ggaaaccaaa tcacgccacc ttaacttttt   2640
ccctcttgga tgcgccgtca ctggcacacc aaggacgaca tcatggtgta gcaacttcgt   2700
atctcaactc cttgcagaat ggagattccg tccgcgttgc cgtccgaccg tgtcacgatg   2760
ctttccgacc cccacttatc acggaagata ctcctattat catgatcggc gccggttccg   2820
gccttgcacc cttccgcggc tttattcaac aacgatcact tctcactctc aatggcgcca   2880
aactcccaaa agcatatcta tttcaaggct gtcgggaacc tggaaacgat gatatctatg   2940
ctgatgattt atcaacgtgg gaggatgaag ggttgtcaa aattcatcgt gcgtatagtc    3000
gcacacctga gaaagcgggt ggatataagt atgtacagga tgtggttctg ggagagagta   3060
tgaagattgt tgagttgtgg aaggaggggg cgaagttgta tatttgtggg tcacataaaa   3120
tgggggagac tgtcgcagaa gcggtgcaga agattctttc tgaggctgat cttgtggagg   3180
gggagaatgt gaagtggtgg tgggagaaga tgaggaatga caggtatgca gttgatgtat   3240
ttgattagat tatcagtcgg tatatcccaa gataatactg catgtaggct gggaaatttt   3300
gatgaaca                                                            3308
```

<210> SEQ ID NO 64
<211> LENGTH: 3821
<212> TYPE: DNA
<213> ORGANISM: Botrytis cinerea

<400> SEQUENCE: 64

```
gggtaagcag cccacataat gagcatcgta aatagacaaa taaataatgc cgcattcaaa     60
tggctcgcat tgccgtcaac agtaatggag acaaccctcc agatgccaac tctcttccta    120
accccccacg cttcaacgtc gaactaccac ctatatcgtg cttcattgaa gacaaaaatg    180
gtagccccac gagaaagttt ttcacgaccc cagatgaact cacaaatcac ttggagcgca    240
ccacgcatca caaggagagg aaattgtatg ttttggaagg gttgccgatt gaatacgtac    300
aggtgttagg gttacacttc aacatagatg tggatatttt tgattctcat gcgatgagaa    360
agagtgggca attgaataag ctggaatttc caaccaaaat agggaatgag aaaaaagttc    420
gaacttttgc tctggaccat cctgaaatta cgacaaacat taccccgccg cctgaagcca    480
gtggaggagt tgctggtgat ttcatgatac cgtgtaaaac gatagacata tcagatgaaa    540
gctggaatgg aatcagtgta aaattatgtc acgtgacttt ggtgtgcttt cccggggaaa    600
atgggagtga aactttacta ttgcttctcg aaaaccagtc gtgggcgaga agaggcgccc    660
aatttcaaac tgcgggttac cacagtattc ttgcaaatgc cctcaaaagt cttccagagg    720
```

-continued

```
gaaagcagaa atggaaacca tcccgaaaac atgacccggc tttgactcta gcagacgaga    780
tattcaattc tatagaattg ccgggtggca tcctggcttg ggatgacctc acagagatac    840
ttgctgatat cgtactcaga caatggaaat ttgccttggg cgaggtaatc gaacatgcat    900
gtgcatctag atcgattcct tatcacgaaa ttcatcaggt atgtgatctg atagaatcta    960
atatctggac tttggatcgt actgaggctc tctggggccc tcattatgtt gtaagagtgg   1020
aagggtttaa aagactttta aagaaagcaa agcgttatgc acatttattt gtgtggggac   1080
aaattgtgga ggagggtctt gagacaaagg ccaaaaatga gagtgcgact gacaatgagg   1140
atgatgacga taccagctcc agtgcttctt ctaagtcggg agtgcatatt cgtggaggag   1200
agaccttaga tttggaaacc cgccaaagca tcaatagagt gacctacctt ggcggtgtat   1260
tactcccgtt ctccataatc gcggcaatat tttcaatggg tgggaatttt cagcctggtg   1320
gagatcagtt tttcatattt tgggtcatcg ctattccagt atgtatgctt acaacggttt   1380
taatatatgc ggatagtatt cggcgaatga ccttggagca atttgctcaa cagtacgggt   1440
ctgatgcagt gacggcagaa gctgatgata tggttacttc atcaatttct ggcagtgaga   1500
tcatttcata caaagtgggt attaaagaac gtcttaggtc gcgtatccca ggtgtctgga   1560
attcacgcag ggctggttct tcctccagtg ttggctatac agatagcgat gacaattcat   1620
cctctacaga cagtactcag ttacctccag gtctatccat agatggcgat ttgttagttc   1680
gcaggaaaag gaaaaaggtg tcaagatcat ggatttggcg attttggaga cggaaacctc   1740
tgggtcgaaa atcagatccg gagaatgtct tgccatctcc tagacattcg gatcacaatg   1800
tatcttcacc ttctgcacct cctccgactt ctccaccatc cgcgtttcac cctattcgat   1860
cttcaccaca aattacaccg gtgaagccca tacttgttgg aaatgaccgt ccagagtctc   1920
ttacttctga taactctccg acggccgggc cagccccgcc agaaacaccc ccagctagtc   1980
ctccgttacc cgaccctgac ctatccattc ctgaccaaat tatccctgag ccaatagttc   2040
ttgacccagg ctggaatttt gggggaaccc cttcaaagaa atctaaaaaa ggcaaaaaga   2100
caagacaaca caggattgga tacctaaatg atgaattcga tatcccaacc cgtccgaatc   2160
cagccacttc tccaccacat ccgtctacac cagaccccgc ggggatacca ctacctccat   2220
tggattcgga ttctgatgac tggcgagagc gagacagttc tgagggaata catcctgaaa   2280
gatctccatc tccaggtcgt gcagactcgg attatgccac agatcgtgaa cgccgttctt   2340
tggaaagacg aatgagagaa aatgacgacc gagcactgac cagaagagga agtagagaat   2400
atctaggcat tggagatgaa tatgagcgca ttgttgagcg agaaatcatt tatcgacgcc   2460
ggcgccgatc cgagcattct gtgaagtctg agagaaaaca tgtaatagaa aaaacgactg   2520
aaaagcttgt tgaagagcag gaaagaaaac atgcgacaga tgatatcgtg aaagatgatg   2580
atgatgttcc ggaagaccga ggaagacaac gaaaacgatc tacagtacga tgggcacacc   2640
gtggaactta ttatgattat ccaaggcggc caacacccaa cactgatcct actgagatac   2700
cattgccacc atccccagaa gaactatcag aggaagaacg aattagaatg aaactagaga   2760
gagagaaact agaatacctt gagaagttga agcaaaaaga acgacatagg agaatggcgg   2820
agatggaaga ggaacacgca aaaaagcgag cggaagagga atatgcaaga agaatagccg   2880
aagaagaata caagaaaaag gcggcagaaa gtagagctgc caagggaaaa gatcgagcct   2940
actcccctgt ggaatccgat aacaagggat taaaaccagc gataaagttc aaggacgctg   3000
tgggaaggaa attcacgttc ccattccatt tagtgtctac atgggctgga atggaagaat   3060
```

```
tagtgaaaca agccttcctt catgtcgatg tcattgggcc tcacgtcaat gagggtcact   3120

acgatctcct tggccccaca ggcgaaatca tcctccctca agtatgggaa tcagttattg   3180

agcctggttg gttaataact atgcacatgt ggccaatgcc ggagccgcga aggcaagcac   3240

ccgctcctat gcctcctaaa ccagggcatc ccggtaactt tccacctcct cctcctccac   3300

ctggattcac agcaccccag cccggcggcc taattagtgg gcctactccg agaatgaaga   3360

aatctacgca gactggagct tgggactggg tggaaggagc acgtcactcg aaatctcgca   3420

agaaacaaaa gtcggcaccg atacgacttg ggcctcctct accgccttca tttcctaggc   3480

cccctccgcc gccaccggca tctggaagac gagaatctga tacagtcgtc ataatagagg   3540

atctgccgcc aaaagttcac agaagacaaa cgggtatgag cgacagacat agacacggag   3600

caagcggcgg tggcataatt ggaggagcag caaagcctaa tgaggagttg gggtgggtaa   3660

gagccctggg aaccattgtt ggtgtgaagc cggggataca ggtgaaaaaa cgcagtggtg   3720

gaagtagttc atcgtcgagt gtttgatggg tcgttgatga gatgactgac tgctcgtaaa   3780

tttgagaagc taaggtatca atggttgaat gtgtgcctgc a                       3821
```

<210> SEQ ID NO 65
<211> LENGTH: 975
<212> TYPE: DNA
<213> ORGANISM: Botrytis cinerea

<400> SEQUENCE: 65

```
gaagtattaa tctccaactt tcagaccatg tgaggcttca cggaacaaca ccttcgggta     60

caagattaat acaatggcag ccacagcttt atcagcgtta ttctctttgg aggggcaaac    120

cgcactcgtt actggtggta ctcgaggcat tggacaagct gtttgcttag cacttgctga    180

agcaggagca gatttgatct tgatacagcg tagtcgtgag aatctcgaga ctcagaaagc    240

cgtcgaggct ctgggaagga aagctcctat atacaccgcg gacctggcat cgcaggaaga    300

ggtcgccggc atcacatcta ctatcctgaa agatggacac tcgatacaca tcttggtaaa    360

ttgtgctggg attcaaaggc gccatccgag ccacgagttt ccggataaag actggaatga    420

ggtgatccaa gtcaacctca atactgtctt taccctctgt cgcgatgttg gcgcacacat    480

gttgaagctc gaaccatctg ctattactgg ccgaagaggt agcatcatca attttgctag    540

tcttcttacc tttcaaggtg gtcttactgt tccagcatat tccgcatcga aaggcgcggt    600

gggacagctt accaaagctt tatcgaacga atgggcatcg aaaggaatta atgtcaatgc    660

gattgctccg gggtatattg agacggagat gaataccgcc ttgttggcca acccagaacg    720

attgaggagt attagtgaaa gaataccggc gggtcgatgg ggttccccag atgatttcaa    780

ggcgagtgtt gttttcttgg caagcaaggg aagtgcatat atctctggag atattctcac    840

ggtagatggt ggctggatgg gtagataaac acttgtcagg ttaaaataat acatttctaa    900

ttctaattcg acgctctttg actttctgcc gatttcctca attctcacgg tcatccaaat    960

attcagactc tccca                                                     975
```

<210> SEQ ID NO 66
<211> LENGTH: 3867
<212> TYPE: DNA
<213> ORGANISM: Botrytis cinerea

<400> SEQUENCE: 66

```
gtaacaatca acaaatttca tcaaccacca acccaccaca tccattctac aggtttgggg     60

gatttctata tcacgtaccg agacccctgg acgcgtcttg agccatatct gcttttctgc    120
```

-continued

```
ttggtcaagg ccctttgaca acaagtacat ataacaatgg ttctcttcaa gaggaaacca    180
gtgcaatatg cacccaagcc acatgtcgaa aatgaagaca cagaggtctg ggtaattcct    240
gctactggag agtatttctt agagtatgaa caatacttaa gccgaatgga tttctataga    300
cagcataaat tcatttgcca gatttcaggt cattctcagt taacattctt cgacgcactc    360
aagagtgagt tggcaggcgc acaagaagtc gaagaggcat tcccgaatcc attgaagcaa    420
ccagttctaa gacgtgtaca attctcaact atttcccgaa tcgatacctt ggtggacatt    480
attttcgaag agttcagatc cgattatttc cccggcgagg ttgttacagt tcatgtgatt    540
acgggcgatc gacttactgg taccgtaaga gaaaaaacgc acttcggaag caaagttctg    600
ccagatggct cactaagcgc acctttctcg agatatttcg ttagtctgga tggccgacca    660
aatgaagagg cagtggtgga tgaccagcat attactcgtg atcgcaagat attcacaaag    720
caagttctgc gatcttttat taagaaaacc gttacaagag aggcatggac cggcgcgcct    780
tggctggtga agcacgacgt ggccgccatt tacaatatcg ataccaggat tcctccacat    840
cttcgatatg agagtaaagc tgcagaaaga aaacaaaatc aatctcagaa aaaatcggga    900
gggactgatt ttgataatat gattggtagc tttcatggag gaaatggacc acaagctaga    960
ctcccggagt tgaagccagc acccaaaagc cataaaagca agcagcaaca atcccaacta   1020
gcaaagggta agcagcagcc atttttagag caagctcctt taaatttcat ccctgcacat   1080
ttccctcccc atcatttcta cccccaaccc caccccaact acaatccacc acaaattcca   1140
tacaattctc accctcctca tcctcctcaa ccccacccca attacaatcc ccctcctcaa   1200
attccattca atcctcatcc tcaaactcct cccttcatgt ctcacacctt tcaagtcaat   1260
ggacaatcac aacaagcggg accccacttc cagaattttc acaattctag ctttgcgctt   1320
gcgcctcttg catcgcttcc tccggctcct cctccaccgc ctcctatcaa atacccaatt   1380
gaggatttgg aagttcctcc ccgagttgat ggaccgaaac gacccgatat caaatacttt   1440
tcgcaagata atccaatgat ggtgggaaaa ccaaaggccg agggtaatgg cattcacatg   1500
tcatcgattg gacagttact ggagacctgg gacactttga atgtttactg tcaaatcttc   1560
aagttggact cattcacttt tgatgacttt gtcgaagcct tacaatttac atctgaagat   1620
gtagactgcg aactgttcgt cgaaattcat tgcgctgttt tgaaaatctt ggttaattct   1680
gaagccgatg atggagagat gcaaattcgg ttacgagaaa tagaggagtc agatgacgaa   1740
gaagagtccg atgacgaggc tagcgttgca ccatcaccta caccagagcc agagccaaaa   1800
cccaaagggc gcgctaccag aagtagtctc gcaaaagccg aggcagaagc tttacaaaaa   1860
gccgccgaac aacctcccga agagcccgct ggaccagtca acactcatcg cgcagccgag   1920
atggaagata gtcttgagtg ggcccagaag ctaagaaaac gtgatttcaa gaatggtggc   1980
tgggaagcta ttatggtcgg ccttttgtat caactttcga aatacgagag atactttgcc   2040
gcctgtgaat cactccttgt tgaactcgcc cccctcgatt cggagccaac gcaggaaacc   2100
gctcgcctac agtacgctaa acttgacgtt aaccttcgta tcaaggcact gcaaattatt   2160
tgcatgctta cgatggagac taaagcaatt cgtggttaca tggaagagag tagtgaacac   2220
atgacggagc tccgaaagga aaaaataaag taccagcgtg ataagaagga tgctcatgat   2280
gctctcaaaa agctcaatga aacgcgcaaa gcactcgaac caccacccga gccaagtcca   2340
gcgccagcta cagagaagcc tgcagagaaa gaagcttcag ccagcgtcaa cggagatgtg   2400
actatggtcg acgccgagga tgaagttcag gactctcatg gtgatgaaat tatggactca   2460
```

gatggagagg ctcccccaac tcgatcatta cgccgcggat tagatcgagc agcagaacga 2520
aagcgtaagc gtgaggccga gcaggagaag aaagcaaaag cagaagctga gcctaaggcc 2580
cccaaacaat ctaaggccct cacgaaagtt ctcaaagaca tccaaaaatt gcatgatgag 2640
atcaagcatt gcgaggaaga gattgccatt ctcgataatg acctccgaga ggctgattgc 2700
cctcgcactc gtgtacttgg caaggatcga ttctggaatc gctattattg gtttgagcgc 2760
aatggtatgc catatagtgg tcttcctacc agctctactg ctgaggctgg atatgccaac 2820
ggatgtatct ggattcaagg accggatgat cttgagcgcg aaggttatat tgagatgcga 2880
cctgagtggc aagatgagta tcgatataaa ttcaacctga ctgtgccgga aagaaaggtt 2940
atggaggaag gaaatactca tgtattcaat tctcgtgaat ggggatacta tgatgatcct 3000
gagtcagtcg aaggcctgct taattggctt gacgcccgtg gaaacaacga gttgaaactt 3060
cgaaaagaac tccaacttta caaggacaag atcatcactc acatggaaaa gcgcaaggag 3120
tatctcaacc ctagtgatga aaagagtatc gattctagtc acaagcgaat gtccactcgt 3180
ggaaaacaac aacctcatgt tgatcataca gctcatcgat gcctatcctg gcacaacaat 3240
acggcaattg aagaattagg tcacttgcat tccgatccac cacgaaatcg taagcaaact 3300
aagaaggcgg ctcctatttt accaccggca attgaagaag agagacaaac taggagcgaa 3360
gcggctaaga gacagagaaa gcgttaagtt ttcggtgttt tacagctttg agaatgatag 3420
atcacgagcg ctcgcaaaat ttactggtgc gttttgttca tggctatttc atatagaaaa 3480
tcttgaacgc gcatggagtt cattggttct atgtatttga atttggcctt gggaggagtt 3540
tatgggttta tgggcttcaa aaacacattt gaagttggga aataaggaaa tcacaaaagt 3600
catgggagtg cgtgcatata tggtatttta caaaatggat tggtttgtat ttagacggtc 3660
tgtggtgagg gaaagcattg cttgcgttgc atttggatgg tgttggctgg attgtgtttt 3720
gatggttagt tagcactgag agggagcact gaagagagga gagactggag atctgtttgt 3780
atggaatgtt atttgcttca tgagggagcg agcgaagaga gcagtagtat agtgagtgat 3840
gcgaataccc aaaatacata tcaaatt 3867

<210> SEQ ID NO 67
<211> LENGTH: 5770
<212> TYPE: DNA
<213> ORGANISM: Botrytis cinerea

<400> SEQUENCE: 67
ggaactgtgg gcttattcga ggtctgcctc tcttgcaatt ttctctcttc tctttataac 60
tttttgatct aaattttcac atcagctcta ttcaaactac ataattctca ggccacgtgc 120
tactcttcat aactattata tcctattggg gggcgctggt cgtcacacta gtcaaggtat 180
attagtcttc tttctaaaat cttgatacta taagcctgtc gcctcacttt ccacaatgca 240
acaacaacca catagtatca ccagaatcag gatccaataa acttagctcc cttatccttt 300
tcggcttcca gttaccctta tacttcatca cttcatatct acatcactga cgctttcatc 360
tttcaacaat cttctgaaga atttgatgtc gaaaatggag cttgacgata catgggatcc 420
tgatcccttg ccaagtggta gttctaggaa ccaatctcag cctcgattca agagagaaac 480
atctcatcac tctaaggcac aaccggaccc gcagcatcaa tactacgaac aaccaaaaac 540
atctcattca caactcagag gtctgatcgc gcccatgaag ctttatcaag acttttcaga 600
cgatggaagc tcatctgatg aatatcctgt cgtcttgcaa caaccacaga ttaataataa 660
aagggtgaca agtcccgctc aacctgcgaa ggacagacgg aagcgacatc agagtgaaca 720

-continued

```
cccaaatcga attgaacgtg gccgcacaac aaacgtagag gaggttatat atgatcacat    780
ctcagcgatc ccgcggtctc gcaatgaatc cgttgcccgc aatgacgctc gatataagag    840
tgttgcaaat gatgttttcg aagagtatga aagtttcaaa aacacctcag cagttagcag    900
aacatcggtc gcccgtagtc attcgcttgc aagagacttg tatgaggacc aaggttatgt    960
tacaatgaaa gattacaacc ggcagttcga caaagagcca agtgtctttt cacctaacaa   1020
tgctcaaact aagaggcgca tgagggagga gtcaacctac ggatctatgt catctggtac   1080
agatgctcat agaacagctg gccgaagtcg tcaagaaagt tcaaaagcca atcgcgaact   1140
agtcggtgca cccaagaaaa aaaaacgtca tagttattct cgtgcacaaa gtctagcccc   1200
aagaatctca aacgacaata gcgatgttca atatctgggc actgaaaatg gtatgtacag   1260
tgtcagaatt caaaagcagg gaaagaagcc ccaacttcgc tcgccattat ggccaagctt   1320
tgaatctgct gtacccaaac cttactctgc taacagattg aaagggagaa ttgataaatc   1380
tgcctcgatg aagccactcc cacatatgcc aaagaatcaa ccagttagaa tcagatcagt   1440
tgcgtctgat cgcatacaga actattcaag tcaagcccga acggttgatt atggtctcat   1500
tgatgacgac gatgtttatg acacaccatt ggaaaatgat cttcgccgca gatctaagtc   1560
tcaagtgaga gctcataatg ctcccatgaa cttcataaat gctctaccaa agtctagtgt   1620
atttcgaagg aaaaactccg aagtcgcaga acaggttcat cagactccat ccagagactc   1680
aaatagatct aacaatccgg gcgtcactat tgatctcgtt actccagaaa gtactgttta   1740
tgcccgcagt gcaatgcctt ttatacctca gcactggact ccaacaagga gaggcccaat   1800
gaaagtatcg gctccaatgg agatctctga gcaggatggt cttggcacta aaactggaca   1860
acaacctggt caaaatactc atcagcacca agtcattaaa tctagtccta ataatggaca   1920
acaaactgaa gaaaacatac gacaacgaca agcagccgag aagatcatcc gacaagaact   1980
caatgcagat aatgaggctt tgcaagcgga gcttttcgga gaagttattg gtgaaactga   2040
ggaagaaatg agagagcgtg aagaagctaa acgtttggaa gctcaaagag tgcgggaaca   2100
aaaagagaag caagatctca ttgatgctga gaggaagcga aagaagaatg aagcaagagc   2160
caagaaagag aacgagagga aagcggctga gcaggccgag aaggagaaag aagcagcagc   2220
aaaaaaagcc aaacgtgatg ccgaacgcca tcatcaatca ttgaaggagc aacagaatgc   2280
agacgagaga cgtaaggcgg caaacaagtt actacaagag aagaaagaaa gagatttggc   2340
tgcatccaag gtcatcgagg aaaatgtcca agctgcagaa aaagaaagaa aagagaatga   2400
agctaagttt gagcgaatga aacgacaatt ggaaaaactt gaggcgcaag ttaaagcaaa   2460
atcgattgcg gaattgaagc ctgcgagaaa gtctacggct ttggacggta tctcgaacag   2520
agtcaactct cagcctcctc aagtcaggct ttcaacaagc atggaaattg acgatgaaag   2580
ttcattgccc actacacaga cccaaataac acctgtaaac ggtactgata cttcacatac   2640
agcaaatact tcatctactc aagccacacc ttcaataatc accgaagtcg aggatgaaga   2700
ttcactgttc gtttcagaca atcgaaagac agttgtggaa gccactccag aacagcaaat   2760
ttcgaatgat cttcaaaatt tcactgggag ctttagtagt gactcgacaa ttgttcagtc   2820
catagagcat gatcgacctc ctactagtat aactgagatc tttgccaaga caattcacaa   2880
tccaagtggt gacaagactc tcgaagatag ggacgcggag cgagaagcca ttcgaaaaaa   2940
aagagcaaac gagaatgcag ctgccaagca aaaacgagca aattccatac ccgcagagcc   3000
aaaccccgaa atatttgctc aaaaggttgc tccacgggaa gtttctaaag caccatcgaa   3060
```

-continued aagcacgcca aagaaaaaac gtatccagcc gctaacaaag gcattaggag attccatatt 3120
cagtgttaaa ttacagcctc tagccggaca tgagcccgaa ggatacgttc ctcgtgaaca 3180
gtcagaaggt tttcagaatt tcactgagaa ctcttccaca gaccttacag tcttgaaacc 3240
ccgcccactt ccattgactt tacctccccc tcttcctcca ccagtagcat ttactactac 3300
ttcaattaga ccagaaactc gtctgatttc acaagcagag cgagaggaaa ttgaagctaa 3360
tcgccaaaga gtccaggctg cggcacaggc tcggaaggaa aattcgaaca gggcaagatt 3420
ggaggggaga aaagctgcat ctgcgaagaa gagaacagtt gagtatcgca agaggaaaga 3480
gaaagaactc atcgaagagg ctcataaaga gggtaggata ttaggtaatt ctgagctgga 3540
agctagactt gacaagttga tggagaagcg agagcgtgag caaaaacgaa agaaaaatcg 3600
tgcgggagaa aaggcttcat ttaacgaaca tgaacatgaa cctctttcta gaataaatat 3660
acttaaccat tctagcatgc ccgcggcgca aatctcatcc tccgatactg ccagtgattc 3720
taatcaaatt gaagaagatg atgatcctcc ggctctaact ctgaaagagc ataagattaa 3780
aacggccgaa attatgaaag aacgggctca attgcatgca gctcagcgtg cccaaccaca 3840
accgaagaag aaactggaac caatttttga ctcggacgag tctgaggagt ctgtagaaga 3900
tccgatggac gaagagacta cggaaatgta catagagcac gctcgaaaaa acaacaccga 3960
ggctaaagaa gatgtcgaaa agagtgatgt ggttcaatta gaaactcgga ctgaggaaga 4020
cattgctttc gagaaagaga tagaagattt tcttgaagaa gatccaaatt tcgaaggaga 4080
ggctcaagaa gcaaccacta cactcaaccc cgatgaacat agtgctcaga tcgtcctacc 4140
aatgcccaat atgacaagat actttgaggg acaatccgct ccacggtctt ccagtaatct 4200
agagacccaa tcaacgttac ttgcaggacc gattcaaatg gccaaaaaaa tacctcccaa 4260
acctcagcag cccgcatcat atgaaatggt caatttatat atggtcatga cgcaagtgac 4320
acttcacgaa tgtgaagacg aagcaattct caaaaagaag ttccttgata ttgaaaaggc 4380
caacaagtac gcacagatgc ttgtcaacga acacagaaat aaaatgttca gacaacggga 4440
aattctggaa agatgggatt cagaccgtat gtatcatggc caaatcattc acgacaaaca 4500
gaagactacc aagatttttg ttgaatttaa gccaatgaac accgaagata ttgacaaata 4560
tgatccaaca ctggtacgac cgatgtttgc tactcaatac tacatggttc gatttgagaa 4620
agtcgttgaa gaaattgacc ccaaaaccca gaaagtctgt atgaaaaacc atactattgg 4680
atttgcagac tcgggcaagc tatacacggt attagaaatg gcaaatcatg ctgcttccga 4740
atacctcctc aaggaaatca aacccaagga agaagttgag gagcatcata ctacttacga 4800
acaaattctc ctcccggaag tgagagcagg aagagatgat gccaaccaaa cagatcaaat 4860
gttcaattgc gagtttactt gcgaaggagc tccctgggta gatttcaaat cgttcgaagt 4920
tggcgtggaa atgtataaga ctgagggccc ggtcaactga aaaggaaagt gatgaatgtg 4980
cttgcctcgt catcttctat catcaataca aattgtttac tgaaaccatc actgctctgt 5040
ttcttacaac accactctta ttttcatcaa acgacacttc ttggccgcca agtttgcaca 5100
ttttcagata attacaccat atccatttca gcatcacata cattcactat aaataatatc 5160
gacggtttca acaacacctc cacactttgc atcacccccg aaatgccatc atatttcatt 5220
catgcttccc accaaaatca gcatagcatt attattctag tgtatcaaac tcaacatcaa 5280
atcaatcatc atgaaaatcg caatcgctca atcctccaca aattttcatc gccacaaaaa 5340
caaataatac agtcagaaaa gaaagtgcag aagtcagttc agccattaga cgttcaaggg 5400
tagtaatgac acgaacaact cttgggggac tcatcgatga gtttatttct tgctgtttat 5460

```
taataggaag ggcgtgggat ttaggtattt tattttactt tatctgcttt ttattacctt   5520

ttactttact ccggtatttg tggtgacagg ttccgtaagc ttttcagagg aagggggggcg   5580

gtagtgggat cgaataggga gagaaagggg tgaggccata ggcgggtgga gaaaaggggt   5640

gagtttgtgc tgagctaagc tgagcacacg tactgggaaa aagctacgtg acaggaggaa   5700

gattctcgga gagtagggaa caaaacattt tcttttgttg tcgttgtttc aatgaaaatt   5760

attgatacta                                                          5770
```

<210> SEQ ID NO 68
<211> LENGTH: 3944
<212> TYPE: DNA
<213> ORGANISM: Botrytis cinerea

<400> SEQUENCE: 68

```
gacttttctg tctgttctga atgaatgaag gaagaagccc tcgcggatta cgaccctttc     60

tcccattctc ccatccatac acattaaaat taaccatccc atccatccca tccatcccac    120

ccatcccttg tgaactcttt ttccatttgc ttttgctttg gtggaaataa ttaggatcag    180

acaggcagac tggcacacag gcacacaggc acacagccag ccagccagcc agccagagcg    240

cgaccacagg ctgagattaa ggagataatt tactattcat tttgcaaata ttggccaata    300

tcggcgcaac tttatatcgt ttgaaccctt ggatggatgg atgtatctta gtaaagtgtc    360

gaatgattat tgcttgcgaa gtgctctttt ccccgttggt caacagaagc gtgggagctc    420

tgctatattt gcttcttgag ggtttgttca cggcgcaaat cctgcacgaa aaaggaaatc    480

tttggaaagc tgatgtcttg ctctacagtc ccgttaccca tggcttaatg acgatacgat    540

catcttttcg agataccctc tgcgaatgcg accttagaca ttcacgaatc gaagcggccg    600

atttttaaag gacctgtaca catcgatcat ccaacaataa tttacatcaa atacaatggc    660

tgatgatggg ccaccacctc ctcctccccc tcatggcact ccgccaaaat catccggtct    720

gccgccgggg aattatgaca tttttatcat tccaccgcat gcgtcaggtt caggatttct    780

ctatttaccg tcactgcaac caaatgtcaa tagtttcgta gcggggtttg cctcagcgct    840

tgtgcttgtc gcactaactt tcatattaaa accattcatg gataccatga aaggaggtgg    900

agggccagca accttgattc ttatggttgc aattgggttg ggagcttggg cactagggcg    960

gatgcaatcg aacggtgaga ccaggcccgg accaagtcaa ggatcgggtg cacctccgca   1020

tggtggatca tattcaggtg ccaatgataa cacatactcc aatggatcga cttcaagtgg   1080

tgggccacga acttcaggaa ctggattttc acctggatcc acatcagagg gggctggggg   1140

tcctccacct aatccgcagg ccggatctgg cgcaagaaaa agatcaagtg aaggttgtga   1200

agaaactcct cctccttcgc ctgatgccgg tccagagatg ccgggcgcaa cacccaggta   1260

cagtcctggc acaactcctg gcgcaaacga tgacgctcga tcgaaagaaa atgcttcgag   1320

gacggcgtgg gaagaggctc gagaaaggac gagaaggaag gaagaggaga gaaggagggt   1380

agaggccgag aagaagcgaa aggaggattt ggaaaagagg ttgagagagt tgcgagcaaa   1440

ggaagctctt gagcgagctg cccgcgagaa aaaacaaagg gacgaacgcg aagctaggga   1500

acaaaaggaa agagaggaac gagaagccaa ggaacgaaag gaagcagagg aacgagaagc   1560

caaggaacga aaggaagcag aggaacggga agccaaggaa cgaagagata gggaagagct   1620

ggaagctcgg gagaagagag aacgagcagc gcgatggaag gaaagagagg aacgtgaaag   1680

gttggcaaaa ttggagagag aagatcaaca ggctcgagag agaaaggcaa aggaggaccg   1740
```

```
cgaaactcga gaacgaatca aagcagaaac agcgcgaatc agggcagaag caagagcaaa   1800
ctacgatagg agacttaaag aagaattggc taagagggaa gctctaagga aagaagaaga   1860
agccaggagg gaagttttaa ggaaggaaga ggaagccagg agggaagttt taaggaagga   1920
agaggaggcc attaagagag agcaagaaaa gttacgacta gaagctattg ctagagtaga   1980
agccgacaag aaagccagag cagacaaaga aagggcagag gcggaggcaa aagcaaaggc   2040
ggaaaaggca gaggcggagg caaaagcaaa ggcggaaaag gcaagagctg ctgcgaaagc   2100
atgggcagat gctaaagccg cggcagcagc aaaacgtgag gccaaagcca gagaagagcg   2160
cgagaaggaa gtagcggcgc aaatacgtga agtcaaactt aaggaggagc gcgagaaagc   2220
agccgaagta gcagctcaaa tcagggagct caaactccag caagagcgtg aaagggcagc   2280
cgaggtagaa gcgcaaataa gagaagtcaa actccgggaa gaacgtgaaa aggcagccct   2340
agccgcactc gcagcggaac ggagaaaacc gaatacttat tcgaatgctg gagtggggga   2400
gagaataagc ccgtggccaa atggaaaacc gcccacagca acacccgctc cccccactgc   2460
cagctcgata ccccgacctc aagcacaatc caccgcatcc aagaaacccc cggtctcaac   2520
tgcaagaacg tatgcaggta ccgacaagga ttcccagtcc cactcacctt atgcacaatc   2580
gccaaggcca acacgaaaaa agtcactcag ttccttgtat tccgaatcat catacgcggc   2640
ctcacaatcg acaagtagaa ctaccccacc tccttcgaca cgaggagcat atagcaccaa   2700
ggatccggac aagattgtta tcaaaggtgt attcgcattc aataacgcat tccacaaaac   2760
ccccacatct caacttctat ctggtgtcgg ttctgttacc gacggactaa tattaagaat   2820
cacaacagag ggtctcttca ttgatgatga tgtacgaggc gtcgctcaac gagagtggga   2880
tgtcaaagca tggacaatga aactcgtaga ggtatggtgc ccatctttca gacaagcatc   2940
gcgtgttcct cccgctacca cagcgtttaa aaatcccgtt cgacgccttt ggggtctcga   3000
taaagaattg gcagcaagtg aagaagaaaa agatactctt ctagttagta tgctgcaact   3060
ctgtcgggat aattgtcgcg ctcgtgccat ttctagttct tccactgggc attctgctag   3120
tggttctgtc tattctgcca gctcttatgc ttcatctgat actagatcgt ctgtttcatc   3180
tgattatgct gattccattg ggtcgtctaa ttctccttat ggtgagaaat caaagagaac   3240
cactaaccat aatggccaga ctggtgagag tagaacagcc ggtctgcata ttttgagggc   3300
gagcattagg gatcaagaag gcaaaaagta tgtctttgtg gttcaagaag gtgaggcttg   3360
gaaggtagca ctaggattgc agaggttgag gaggggaact caggtgagaa gtttgggtgt   3420
tagtggcatg agtccgaatg atgcaaaggc tacactggat aacttgggat ggttttgaga   3480
gttgggggtg atgggaagat ttcagaatct ctggaatacg ccatggaatg tggagtttgg   3540
aacgcggaat cgtatccctc ggcgaaaagg gatgcgaggc gaatcatgag tcccgaaagt   3600
caaatctagc atttacaaca caacggaagc atcagcgatg gagttttttt tttttttttt   3660
ttttgtcttt ttgtttaagt ttttgtgttt gatactacag tattttcact catctcaagg   3720
agtttatgtg tttgtttgcg cacgggagct gtcgagtttt agttggaact ttcttgtggg   3780
aatttagaat ggaattgggt atcagtacct cttcaatttt ctgaggtgtt tggttagaga   3840
gcgtattgta tgtatcttga atacccggtt ctgtgctaaa gtttgtggtt tgaagtatgt   3900
ttgtgtggaa tgtttggtaa tgaaatggga tggggagagg ggga                    3944
```

<210> SEQ ID NO 69
<211> LENGTH: 2675
<212> TYPE: DNA
<213> ORGANISM: Botrytis cinerea

<400> SEQUENCE: 69
actcgtgcgt ctactgccac tgccactgct gctactttgc tattcaactt cgcctcgcct 60
ttcaattaag aattgtcact tcgtcgcatc tgaggccgga atgctaatat cttctcgtca 120
tctttgaagc caatctcact cgttatcccg tccaattcag tcgatatatt aagagccttt 180
gaagttccga tccaagaaac ctttcgtcta tccatatcgc aagagttcac ttcttcacaa 240
tgaagttcac cccagtttct gttgcgcttc tcagcgtggc cggcgttgcg attgcgcaac 300
cccacaacca tcaacaccgt catccagttc gagcaaacaa ggtcgcacgc gacaatgctg 360
ttgtctctgt gacagaggtt atgccaggtc cagtcgagac agtctacatg cttaacggaa 420
aggatatctc tttggccgaa gtacaagatg gtttgaaatc tggaaaatac gttttggtgg 480
gagacgctgt cgaagacgcc ccttctgcta ctaactggta cactgcaccc gtatctgttg 540
cacccacaac atctgccgct acaacctctt ccgcagctac ctccaccagt tcgatcgtca 600
aggctgctgc agagttcatt gaggtctcct cgtcttccac caaagctgcg tacacttgga 660
aatcaagcgc tgcatcaagc gctgcatcat ccacttcaga atcaagctcg gtcgcctctg 720
tctcctctac cagttctgct gctgcttctt cctcctccgc cagcagctcc acttccgccg 780
cagccagcag ctctacttcc tccagcagcg ccggcaattg ggccgacttc ccaagtggca 840
caatcccttg ttccactttc ccatctgagt atggcccaat cgctgtcgat taccttggtt 900
tagatggctg gatcggtatc caaagcaccc ctggctacac cacttctgct tcctcgatcg 960
ttaccattaa cacactaacc agcggtggat gtgtgaaagg cgctttctgc tcgtatgcat 1020
gcccagcggg ataccagaaa tctcaatggc ctagcgcaca aggaagcact ggtgaatcca 1080
tcggcggtct ttactgtaac tccaagggaa tgctcgagtt gtcccgaact accaccaagc 1140
aactttgcac tgctggatct ggatccgtca aggttgaaaa caagctcagc agcattgttt 1200
ctgtttgccg tactgattac cctggtctcg aggctgaaac ggttccattg tcaacctccc 1260
ctggccaaac ctatgacttg acttgcccag atgccagtaa ctactactca tgggaaggac 1320
ttccaacttc cgcacaatac tacatcaacc cacaaggagc ttctacctct gaagcttgcg 1380
tatggggtga agcaggtaaa aaccttggta actgggctcc tgtcaatgct ggtgtcggca 1440
aagatgcctc tggtaacact tggttgtcaa tcatccctaa caccccaacc aacacatatg 1500
gtaccttgga cttcaccatc actatcgaag gtgatgtctc cggaaaatgc tcgtactcat 1560
ctggaacata ctacaacaat ggtgttgagt cctcaacagg ttgcaccgtc tctgttctcg 1620
caggcggaac cgctacatac gtcttctcat cataggcgct tgagtctcga ttttcccttt 1680
tacaaaattt ccggtgcaca tattgttgtt ttctttccgc gcgcatatcc acaattgcgg 1740
cttatgatcg ttgtagtcac ttttttttt ttcctttaca cgccctcaag ttattctaag 1800
tctcggatgt tcgaactcac gctcgacttg caacgttcaa acaaatttgt caataagata 1860
ccccctccat ccgatctctg aatgtacttc gtgtggtaac ttttcctttg taataaatgt 1920
cgctaatgtt tttacattat tgaagtggaa gatatctgga cgttggaata ctacgttcca 1980
gatggttgtt gtaagcatga atggatttct tgagggggtt ggggctgttg gtagaaaaaa 2040
aggttgtgtt ctcggcagat gaatgttcat atggcgaacg ggaaagctct ctttccttga 2100
agcgatcacc ttggttaact cttctatgta ttcgttactc attttgaagg agacgtgctc 2160
ctggtacaga gtgcccctct atccctacgg cctttttatc aatttgccgc aggcactctt 2220
gcatatgttt tcacactggc tacaaatgtt tggaaggagc gcgcacacga aacaaaaatt 2280

```
accaccatgt ctcttttctg aggagatttg gtagagagct ataacacctg ttgtatgtgg   2340

atgtgaatgg aaaatttgac ggcagaggct gcagaatatg gtgcatgtat caatgtaaag   2400

tagtctagtc ggcacaacac agacagggaa agggagatca gttacactct acttattcta   2460

ccttttcaag aagatgttga gaaatttttg agaacagaaa attccaaaaa aacaaaaaca   2520

aaaaaacaag taaatggagc attcagatga agtgtgtggc ctttttcgtg tatacagatt   2580

aaaatctctt ttcgtatctt ataatttctt catttttctt tcctgacgat gttcacatac   2640

aactaactgt ctttctgaat ctgtgaatat gaata                              2675
```

<210> SEQ ID NO 70
<211> LENGTH: 1630
<212> TYPE: DNA
<213> ORGANISM: Botrytis cinerea

<400> SEQUENCE: 70

```
gtccttttgt ttcttcattc tttcatttca aaatgtattt ttcttctcat tctctcattg     60

cttccgtgct cttggtctct gccgttcaag catacccagg agttcaagca gatcttgttg    120

ttgatatact agctacagcg acatctgcaa ttgttttaga gacccctcca ccttcggaag    180

ggcttcttga caatgtaggg ttgttcaaat tcttcgcaag agccgcgaag aagacaacag    240

caaaaaccac tgctaaaacc actgctaaaa caacagaggc tgcaccgaca acccagaaaa    300

ctacagctcc agcaacaacg caaaaaaacta cagccgtggt gactacaccc acaactacct    360

cggtgaaaac cactgaaaca cctactacca cttcaatcaa gactacttcc atcccgacta    420

cgtcatctat atccacgaaa cctacgtcta cgtctacttc aacgagttcg acttcggttg    480

tagcaccaag tagtacgagt actatctcca aatccttgat ttcaagcacc agctcaattc    540

ctacctcggt ggcttcaatt cagacatctc aagtctcatc ttccactgtg tctccgatct    600

ctagctcgtc aacatctagc tctttggtat ccagtaaaag ttctacttct gtagctacgt    660

cttctcaaat atcaacttct aaaactggtt cattgtccag tgttagtgga gtctccggat    720

ccattgtcag cactggctct ttatcatccc ctactgtctc tacttcggct ggtgggtctg    780

tttcttctgg aatcaattca aagactagtg aatctctcac cagtactgga tcagcatcaa    840

caagaaccgg ttccataacg agcactgctt ccgcttcagc gagtggatcc ctttcatctg    900

gaacaggttc tatcaccagt ggatctctca ccagcactgg gccagtatca tcaggaatca    960

gttcgagctc gatctcaggg agtggaacta taacttcctc ctcccgcatc tcctcctcca   1020

gcggttccat ctcttgttcc gtctccaaca ccgtaacaga cataacctac tttgtttcac   1080

ccgccaccaa cacccttggt tccgtaacaa aactttccac catctcctcc accgccgtca   1140

gaaccatcgg atgttctctc agcgccaaaa ccgccacatc caccgtctcc tcctccgcat   1200

ctatcagtaa aatcgtcatt ccaaccggct atggagatcc catcatgagc gccgaagcca   1260

aaaatgccgc tttctacaaa gccggcgtgg cgggatactc aagccagctg agcgtttaca   1320

gcgcagcctc gacgagaaca agcgggatga ccacaatggc ttctgcgacg gggagtgcgt   1380

cgggcgtgca aagcggttcg ggttcatcta gtgctttgag tgccccgagt agtcttgcaa   1440

gtggcacgac gaaggaaagt gtaagtagtg ttgctaccac ggatgtttcg agtactacta   1500

gtgcgccggc tacttctgag acggcttccg ccacggggtt tgtaggggag atctcttcgc   1560

ttcttaatat cttttaaggg ggaggtgtgg atatatgagg gggctggata ttagcatggg   1620

aatagattca                                                          1630
```

-continued

<210> SEQ ID NO 71
<211> LENGTH: 1918
<212> TYPE: DNA
<213> ORGANISM: Botrytis cinerea

<400> SEQUENCE: 71

```
ggaattgatt catgtatggg tcatcaccct ttccaaatca aaataccctt gcgagcaaca     60
aatatattac cagttaccgc cttgcatact tcttttgttc attcaaaatc atccacaaac    120
agatttgatc caatccgatc caagctttat gacgggcata agcgttggat catgtttcta    180
gccctttggt gaatgctccc ttgactgcct ccaaaagcaa aatctgcttg ttcgattcgt    240
ggatgactgg gatatctagt ttcttgtaca cagattgaat ctccacaact aaccagttca    300
tctaatggca cagtgctagg tcccattccc caacttttgt ataagtatct ttctcttggc    360
cagtttgact tcgaattctt catcgttcaa gcaaacgttt ctttctttac ccatcacatt    420
catttacaca gtcctcggtg actatctaca ttcattactt cattgattga agcttatcaa    480
caacttttca aatccaacgc tcattttttc cacctcacga aaaacttcca aacacttttt    540
ccatcaaaat catcaatctc aagattttat catcaaaaat gtctttctcc aagatcgccg    600
ttgtggctgg tgccgctttt atctctggtg ttgctgctca cggacgtgtc caaggtatca    660
ctgctgatgg tgtttggtac gagggttaca acccagcttt ccaatacgag caagttgcac    720
cagtcgttgc tggatggtcc gacccaactg atcaatcgaa cggtttcatt gcaccagatg    780
cttatggtac atccgacatc atctgccact tggccgctac caatgctcaa ggatacgtta    840
atgtcactgc cggaagtgag gttaacttgc aatggaccac ctggcccgat tcgcatcacg    900
gtccagtcat cgactacctt gctgcctgta ctggaggtga ttgcacaact gttgacaaga    960
ccaccctcgg attcttcaag atcgatggtg taggacttat cgatgattcc accgtcccag   1020
gtacatgggc atctgatcag ctcatcgcca acaacaactc ctggtctgtt accatcccag   1080
agtccttggc accaggtggt tacgttctcc gccacgagat catcgcactc cactccgctg   1140
agcaagccga tggagctcaa aactacccac aatgtattaa cctttgggtt tccggctctg   1200
gatctgctgt tccagctagc gcagatacca ctctcggtac ggctctttac accgagactg   1260
aagccggtgt caacgtcaac atctacgctt ccattgcttc atacgatgtc ccaggtccta   1320
ctcaatgggc ttccgctact gcttccgttg ctcaaggtac ttccggagca gttgccaccg   1380
gagccgccgt cgtttcttca gctgcttctt cagccgccgc cgtagctacc tcaagcgccg   1440
cttcatcggc cgctgttgtc gcctcttcct ccgctcaaac cagcgcacaa gttgccgccg   1500
tcagttccgc tgctccagta gcctcctcct cagctgttgc ctccagctcc gttgctagcg   1560
ttgcttcatc agttgttgcc agttccgctg catcagttgt tacctcagcc ccagctgtca   1620
cctcggcacc ttcaaacgtt gtcactgata tgatcaccga ctacgtcact gttactgacg   1680
tcgtaactgt caccgttacc gctgcataaa ttctgaacct ctttggttta aaatcagcac   1740
ctccttttga ctaaaaatct ttttgatgat attttgatgg tttatttttg gatctgattc   1800
gggctatcgg gcatagcttg gatggaaaat ttatgagccg catgatgagt tggataggct   1860
tcatgtcact ttcttgtata tattatgtcc tgtataaaca gaattgaaca tttttcga     1918
```

<210> SEQ ID NO 72
<211> LENGTH: 3970
<212> TYPE: DNA
<213> ORGANISM: Botrytis cinerea

<400> SEQUENCE: 72

-continued

```
gcttcaaaaa aagtcgcgtc tctgccaaaa agttataagt tataagctta ttgtaagctt     60
taacttcctt tctctccaag agcattaagc attaaattgc gctccttctt gatttgctac    120
tactcatcat cgagagtctt tcttttccct ttcaatttta ttcccctcag gaccttggaa    180
cgaattgaaa ccggtcacaa tgtcgctctt cgggaacacg aatcaaaaca agccgtcgct    240
ctttggtgca ccgcagacca caggagcgtc tacaggtgct agcacgggag gtctttttgg    300
tggattggga acgactgcga ctagccaggc tccatcaacg ggaggaatgt tcggtggaat    360
gggtgctaca agccaacccc aatcgactgg cggtcttttt ggagcaacta caagccaacc    420
tcaatcaacc ggaggccttt ttggaggaac gactacaagc caacctcaat caaccggagg    480
ccttttggc ggaacaacta caagccaacc tcaatcgact ggcggtcttt ttggagcagc    540
caaacctcaa caacaatcag ggacaggatc cggtggttta tttggaggac ttggagcaac    600
tccagcagca acccaaccac aacaaacagg cggtcttttt ggtgcgacta cacaacccca    660
aactacaaac aacacaactg gaggtctctt tggtaattct ttggcacaac cacaacagca    720
gccgcaacaa agtactggtg ggctttttgg aaacacaact acacaaccca acccttcagg    780
atcaatgttc ggtcctactc cacaaatcca gcctctctcg caatctcgac aacaaaatgg    840
aaccagcggt gcctattttg atgctatatt ggagaagagt cgtaagaggg cacacgatga    900
ggattccttg ggcttacaat taggtttggg ggatattcga cagcgcatga agaggctggc    960
tcctagtacc caagatggct ctgtcgatgg aagagctcat tacctattgg cagcttctgg   1020
cgtggaccca ggcgctgcgc tcagagattt gaatctattc accgctgcca caggaagact   1080
tgataggaca gcacctgtag aagcacccat tgatgcggat gtcgaagcat accttacacg   1140
tctggaaacc caaaccacaa tgagcatgat atctgaaggg ttggcacgat ccgttcgaga   1200
tttcgatgat ttcctcgagg agaatgttgc tatggaatgg agtgcacagc gcaagagaat   1260
atatgaacat tttggaatta agcccagaag agaacaaaca acagggccat cagtgagctt   1320
tgcagctaca gctacagaac ctatgggcgg ttttggtcga tcaagacgcg gcaaaggact   1380
cgctcctgga gcatctaaag ggcctggaat cccgcgggct agcgtttttg gaaaatcaag   1440
catgcagaga tctgttatag gagctattac tccaggagga accgcaaacc gcacactttt   1500
tactgatata gagaaagcag atacgaatgg gtcagcacca ggtccaagtg accgattcat   1560
tcgcgagaag caggctcgat atatcgagaa agtccagaac ctaaatggtg ctagactaaa   1620
gaaccttcac tacccaattg cgaacgaatt ctcagctgtt gtagcccaag gtagcgaaca   1680
gcactctgca gatgtttaca gggcatacag atgcttgatg gaaatcgttg gtgaagatcc   1740
tgacccggac agactacaac tccctggcgc ggtcaaacag agacagtttg cagccgcata   1800
cctggatgac aatacaaact cagctcaagc ggccgatttg aaaaagcgga tactcagtgg   1860
atcacttcga tttcttgaaa aggagttttt cgagaatgta gaaactattg ttgccaaaaa   1920
ccccagggaa gcacttgtgg gtggtaagcc tagtcctctc acaaagatcc agggttatgt   1980
tcgtctacgc tcagctcgta aagaccttgc tacagacatc tccgctctac aaattgttaa   2040
tgacgattac gtctgggcag tagtctttta tcttctgaga tctggccacg ttgaggaagc   2100
caatgcttat gtccaagaga acagggaagc attccgggta attgaccgca gcttcatgtt   2160
ttacatcgca gaatatgcca atagcccaga cagaaaatta ggacatgacc ttcaaaatcg   2220
cattcaaagc gaatacagtc agcgaaatcg aatttcccct gagggttcta tagatccttt   2280
cagaatggca tgctacaaga taattggtcg ctgcgaactc cacgttcgcg ctctggatca   2340
aaacattgtc caaaaccagg atgactttgt ctggatacag tttgtccttg cgcgcgaagc   2400
```

```
caaccgagtc gatgaaattg ccagcgatgc atatggactc gcaaatgtac aaaagacatt   2460
caaagatatt ggcgcccgga tgttttccaa gggaaatgaa aatagtggac catttagtgt   2520
gtactttgtg ctgttggtac tttcaggcct attcgaagac gcaatcgacc ttctttatcg   2580
ccatagtatt tctgattgtg ttcatttcgc cacggcactt gacttttacg gcctgcttcg   2640
agtctcagat ccagatgttg cagagggtgg attcttaagt tacacaataa gacaacaacc   2700
tcagatagca tttggattaa tgatgggatt ttacactgca gaatttagag ctgcaaatgt   2760
cagcgctgcc gtggattatc tcaccttgat ctgccttaat agtgacctca aaggcgatgc   2820
tggctcaaaa caagtcgcat tgtgccacga agctctccaa gagctgattt tggaaagcag   2880
agaatttgct ttgttgcttg gagatatcag acaagacgga aagcgcctaa agggagttat   2940
cgaagaacgc ctggaactca tcaatctcag cagcgctgat gatttcatga gaacagtgac   3000
gatacaggca ggaagtgtcg cggatgacaa tgggcgaacc actgatgcag tcctacttta   3060
tcatttagca gaagagtatg acaacgtcgt tactatcctt aacagagccc ttagcgaagc   3120
tattgccgtg cctgtaggcc atagcccgtt gcgattacaa ccactcaagc caaggcctgg   3180
agacaaatcc ggaagagagg cccataccag tctcagtctt acctcaattg atgatccttt   3240
cgaattggct accatcatga cgaagctcta ctcaaataat cgcatgtatc tcaacaagat   3300
caagcaagaa aaccgcgcag cttgtgaggc tttgttaaat atctgccgtg ctaaggaatt   3360
tgttgaaaat agacaatggg ctgaagcatt agatgttgtg cagaatcttg acattcttcc   3420
cttgagcgcc gagggcaacc caagtgcagt acgaagttat gccaccaaat tttcatcact   3480
ctcccaagag gtcgcaaaca ctatccctag tcttttgaca tggacagtct tgtgttgcaa   3540
caaccaaaga acttccctca tgaatgccca atacggaggt aatgagggta ccagacgact   3600
gatgattaat caattgagac aacaaaacat ggacttaacg acttatacca gtcaattaag   3660
atacagattc cctgcgtctc ttcatgaagc tcttgcgagg gctcaatcgg agtaagggat   3720
gaacatatga catgagctta tgagcttgaa tgtatattag aacagcacag tgggaagaga   3780
ttaaaagggc attttgagtt tttatctgga cggaacgaaa tgaaaacatt gggggtctgt   3840
ctactacttt tgtagttgat ttttacagtt tctcatgaac aagtgcatag atgaagaatg   3900
tattgtgttg tctattagaa gattaattat gagtggttaa tgaatacaga atatcgagat   3960
ctcgcttcca                                                          3970
```

<210> SEQ ID NO 73
<211> LENGTH: 1777
<212> TYPE: DNA
<213> ORGANISM: Botrytis cinerea

<400> SEQUENCE: 73

```
gcaatcaatc atctaatcgc gacgacaact ttcaacaatt accatatttc aacaatcatt     60
tggaatcttc tgcgatatac attgaggaat aataacgacc acagtctccg gctcatgatc    120
gcaagtaaat ctcaagatgg ctgatcaacc accagcaatg cagcatgagg actccatcag    180
ttcgcaagat cctcatttac atggcgacaa aggaaagacg aagagtagac ggccagcaaa    240
tacggcattt agacaacaaa gattgaaggc atggcaaccg atcttaacac caaaaaccgt    300
actcccatta ttcttcgcca tcggaatcat tttcgcgcca attggtggag ggttgttata    360
tgctagtagt gtggtccaag aaattgtact cgattattcg aaatgccaca cagatgcgcc    420
aatctgcacg gactacctcg atacaggctc cctgatgccc gatgacaatg ttgaaatgtt    480
```

```
tttcaaaaca cctcacgtat atgatggaac tcctccgcaa tggtgcagac aagatatcaa    540

ccaaacatac tacaacggca gtgttgcgca tgctactgtt cccgctgtac aatgccggct    600

cacattccca atcaaatccg aaatggagcc tcctgtttta ttctattata agctcaccaa    660

cttctaccaa aatcatcgac gatatgctaa gtccttcgat tccgatcagc tttccggcaa    720

agccgttacc gcaagtacca tacattctgg tgattgtacg ccactcacga ctgtaaatga    780

taatggtgtc gacaagccat attatccttg tggtctagca ccaaactctg tgttcaacga    840

tacattttca agtccattcc tacaaaatgt cgcaaacagt acttcaggtg gcgtagtcta    900

tcctatgaag aacaactcgg atgtatcatg gagtagtgat agagagctat atggtcaaac    960

aaagtacaac tggtcggacg tcattgttcc tccaaattgg gttgagagat atccaaacaa   1020

ttatagtgac gattatcatc ccgatctcga gaacgatcaa gcattccaag tttggatgag   1080

actggctggt ttgccaacat ttagtaaact gtttcagaga aatgacgacg atactatgac   1140

gactggacaa tatcaagtca acatcacaca tcttttcaat gttaccgaat atggcggtac   1200

taaatcaatc gttctttcaa cccgtaccgt tatgggtggt aagaatcctt tcctaggtat   1260

cgcctatatc gttgttggag gtttatgtat cctactcggt gcacttttca ccgtcactca   1320

tcttataaaa ccaagaaaat tggcgatca cacatatttg agttggaata acgacaaccc   1380

tacaacggcg actaccagtg gacgtgaaat gggtgcgagc atgggataga cgctggatcg   1440

atatcgaatc aaaaaagggg acgtgtaaaa tagtgatgga tgatgagata tgaggcaggg   1500

ttgttgtatt cgaacatttt cttctacgtt accaatgggc aatatggcgt ctaggtatta   1560

tgagcttttg atctgtgctg cttttgaaaa gcattctgcg atgcgaggaa aagtgggtgg   1620

agggaatctt tggctggact ggggaatcaa tgggtgctat gaatattttg tgctcttatt   1680

tttttgaatt agaaagaaac ttataacttt gaaatatacc acagatgaaa cttgtaaagg   1740

cgaatggact tctggtgttc tcgaatagcc aaacata                            1777
```

<210> SEQ ID NO 74
<211> LENGTH: 3214
<212> TYPE: DNA
<213> ORGANISM: Botrytis cinerea

<400> SEQUENCE: 74

```
ggatgcattt caagattggg attccattcc atcttctagg caactattac gtcgacccac     60

catatttccg gctttttgat gagcaaggtt atgtttcccg gtaagaatat atcattgccg    120

tcatggcacc tccagcgaag agacggaagc gtagtgccat tgaatcctct ccccattcct    180

ctgagaacga ggataatcaa tcaattcagg tgaacaagtt caaaggtcga ttgagcagtt    240

tggcacattc tcctccacca agatcgagct cttctgagcc tgccccaagg tctatgtcgc    300

agtccagtaa ttctacgaga tcctcttctt ttttgaaacc tccagcaaaa gcggccattc    360

atcctcacaa tgctgccccg gtctacttac caaaccaccg taagaagtcc actacaaaga    420

gtcccagcac aagtccagag aaaccaagaa gtaaaggaag agttgaggaa aagcggcaga    480

atgcagatat tcatacgttg tttgcaagac aatcacagag gcagcaagca caaacggaag    540

gcgagacgat acccaaacaa agaatcaagg ttcttaattc gagagatatt cagcaggaga    600

ccgatttaat agacgattta atatcagatg atgacgatgt gggagagggt caagcgcaag    660

caattagcat tgttgggcag gccgccaaac ggggacttgg aaagaacgta ttcataaatt    720

caggtacaaa cacacccagc gccagtcaaa gatttgtaag accgtctcag gcttctacaa    780

tagaacatat ggtcgaggaa gaggatatac gaccttgggc tgaacgcttt gggccaaata    840
```

-continued

```
atctggaaga gcttggggtt cacaagaaga aagtaatgga tgttcgaacc tggcttgata    900
atgttatagg agggcggatg agacaacggt tattgatctt aaagggtgct gccggaaccg    960
gaaagacgac aacagtgcag ctattagcga aagatatggg gtgtgatgtt ctagaatgga   1020
ggaaccctgt tggatcaatc gattcctcag acggctttca gtcaatggct gcacaatttg   1080
aggatttcat ggggcggggt ggaaagtttg gtcaactaga tttattttcc gacgatcatg   1140
gagatattcc agcagaagca gaagtaaaac cgttggatca aaggaagcaa attatactag   1200
tcgaagaatt tccaaacact ttcacgcgtt cttcaagtgc cttgcaatca tttcgatctg   1260
cgatacttca ataccttgca tctaatactc ctcttctttc aatgtcacac aatcctcact   1320
ttaaaagtga tcccatcact cctgtggtaa tgattgtatc agaaacattg ctcacaacga   1380
catcagcgtc tgcagacagc ttcactgctc atcgtcttct tgggccagag attcttcagc   1440
acccgggagt aggagtgata gaattcaatt ctattgcccc gaccatattg gcaaaagctc   1500
tcgagactgt agtacaaaaa gagtcgagaa aatcaggcag gagaaagaca ccaggacccc   1560
aggtattgaa aaagcttggg gaggtgggcg atattagaag tgcaattggc tctttggagt   1620
ttatgtgtct aagaggggat gtcgatgact ggggaggcaa agttgttttc ggcaagggaa   1680
agaaaacaag caaagataca tctttgacaa aaatggaaga ggaatcgctg gagctgatca   1740
ctcgccgcga agctagcttg ggaatcttcc atgccgttgg gaaggttgtt tacaacaagc   1800
gcgaaggaaa ggtatcaggc gatgtggaat ctttgccaca ctttatatct catcaatcac   1860
gtcctaagaa atctgaagta ggcataaacg agcttatcga cgagactggc accgacacac   1920
caaccttcat agctgccctt catgaaaatt acatcctttc atgtgaagca ccaccctctt   1980
ccttcgaatt ctcatctctt gatcacgtca atggctgcat cgatgccctc tctgacagtg   2040
acctcctctg tccctcttgg gacggttcca tccaatcctc cggcttcggt ggtggcataa   2100
caggaaccgg aggcgacatt ctccgccaag acgaaatgtc ctttcaaatt gccgtccgcg   2160
gtatcctttt ctcactccct caccccgtat ctcgtaaagc acctgcagca gcggggttca   2220
gaactggcaa aacaggcgat gcgcataaaa tgttctatcc caccagtctc aaactctggc   2280
gcatgaaaga ggaaatggaa agtacactag atctctgggt tacacgatta ataaaaggag   2340
aaattgatcc cacgagtacg catgcgtcaa gtattaaatc tggcgctgca gtattcgctc   2400
gtcctaaagc tggcacagtc gaaagctgga aagtgaaaat cgccgcacca ttgccctcgc   2460
aatcaaaatc caaatccagc ctcaacactc caaaagaaga agacagccca cccctcctca   2520
ccctcggcgt ctccgctcgt acagaaatgc tcctcgagcg tctcccctac atgatccaaa   2580
tctccaaatc caaatcatcc caccaatcgc gcaacccatt ttcttcctcc tcctcctcct   2640
cctcttccac ttccgccatc acgaacttcc aaaacaaccc ccttctcgcc tccctctcta   2700
aaataacaac cttcactggc atcggtcccg cgcaaacctc cgacgacccc gcctcccttt   2760
ccgatgacga atctcccaat cccaatactg aaaattgggc caccgataaa ccaaacggta   2820
atggtatgga tacacctcgg aagaagaagc aaggcgggaa tatgggggtt tttatgaaga   2880
agggaattgg taatcagaga gcaatgccca tgcagcagtt ggagcagaaa tttgttttga   2940
gcgatgatga tattgaggat gattgattga tgattggaat ctggattggg agtggggcct   3000
caaacgcttg atgaatatgg gggttttggg tgatatgctt gaggtgttcg tggatgaaag   3060
gcatgtgttt tttatgatcc gggatgagat ggtttggtat ttacttcttt gtattgtatt   3120
ttgaaaatca aaattaacat cgagtttcac cgcgtttcaa ttcttttgcg cgttgtcatt   3180
```

ctacaaaata tcaaactact tatttctata caca 3214

<210> SEQ ID NO 75
<211> LENGTH: 3059
<212> TYPE: DNA
<213> ORGANISM: Botrytis cinerea

<400> SEQUENCE: 75
gaagctcaga aattcatctc acaatattaa tatgccctta aatcggtaac aatgaagacg 60
gaatttaagt tctccaatct cttagggact gtttacagcc aaggaaacct tctcttcagt 120
ccagatggat catgtctatt ttctccagta gggaacagag tcacagtttt tgatttagta 180
aataataagt cacatacact tccattcgca catcgaaaga atatagcacg gttgggactt 240
gcgccgcgag gaaacttatt gctttcagtc gatgaagatg gccgcgcgat attgaccaat 300
gtaccgagaa ggattgtcct tcaccacttt tctttcaaat cagctgtatc cgccatatcg 360
ttttcgccat ctgggcgcca tttcgctgtg ggagttggac gaatgatcga agtatggcat 420
acaccctcaa caccggatac aaattcagaa ggggagttag agtttgcgcc atttgttaga 480
cacagagtat ataccggtca ctatgatact gttcaaagca tcgaatggtc gagtgattct 540
cgttttttcc ttagtgcagc aaaagatttg acagcccgga tatggagctt ggatccagaa 600
gaaaccttta tacctactac attggcgggc cacagagaag gtgttatggg cgcatggttt 660
tcgaaagatc aggagactat ttacacttgt agtaaggacg gagcagtatt tcaatgggcg 720
tatatacgga accccaatgc tcctgagcca gaggatgagg atgaggatat ggaaaatccg 780
gacgacgact cgcacatgca atggagaatt acggagcgac attacttcct acagaacaac 840
gctaaggtca attgtgttgc ataccatgcc gaaacgaatc ttttggttgc aggattctcg 900
aatggtgtat ttggactcta cgaaatgcca gaattcaaca tgatccatac cttgagtatc 960
tcacaaaacg atattgactt cgtcacaatt aacaagtctg gagaatggct cgcatttgga 1020
gcctcaaagc tggggcaact cttagtttgg gaatggcaat cagaatcata tatcttgaag 1080
caacaaggcc atttcgattc aatgaattcc ttggtttact ccccagacgg acaaaagatt 1140
atcaccactg ctgacgacgg aaagataaaa gtttgggatg tgaatactgg tttctgtata 1200
gtcactttca cagaacatac cagtggagtc acggcttgtg aatttgccaa gagaggaaat 1260
gttcttttca catcaagtct tgatgggtcg ataagagcat gggatttgat aagatatcga 1320
aatttccgta cttttacagc gcccactaga ctttcattct catccttagc agttgatccc 1380
agtggcgaag tcgtttgcgc gggatcttta gattctttcg atatccatat ttggtcggta 1440
cagactggtc aattactaga tagattatca ggtcacgagg gacctgtatc atcactagct 1500
tttgcgccaa atggaggtgt agtagtaagt ggaagttggg atcatacagt tagaatttgg 1560
tctatttttg accgtacaca aacgagcgaa ccgcttcaac ttcaagcgga tgtattagat 1620
gtcgcattcc gtcccgattc actacagctt gctgtctcaa cactagatgg acagttgaca 1680
ttctggtccg tttcagaagc tgaacaacag tcaggtgttg atggccgaag agacgtttca 1740
ggtggtcgaa aaataaccga ccgaagaacc gccgctaatg ctgcgggcaa caaaagtttc 1800
gggtccctta gatatagcgc agacggatcc tgtgttcttg caggtggtaa cagtaaatac 1860
atatgtttgt attctgtaga ctccctcgtc ttactgaagc gatttaccgt cagtgtcaac 1920
ttatccctat ccggaacgca agagttcctc aacagcaaac ttttgaccga aggtggacca 1980
gccggtctta tcgatgagca aggtgaagcc tctgacctcg aagaccgcat cgatcgatct 2040
ctccccggat caacccgcgg tggagatcct tccgtccgca aaagactccc cgaagtacgc 2100
gttgccggcg tggctttctc tcccacagga agatccttct gcgcagcctc aacagaagga 2160
ctcctcatct acagtctcga cactatgccc ctcttcgacc ccatcgatct cgatctcgcc 2220 gtcacccccct cctccactct ccacgtcctc aacatcgaaa aagattacct caaagctctc 2280
gtcatggcat tccgtctcaa cgaagctccg ctcctccgtc aagtcttcga aggtatccca 2340
caccccaaca tcgcgctcgt agtcgctgaa ttaccagtcg tttacattcc tcgtctgctg 2400
cgttttgtag ccatgcaaac ggaggaatcc cctcatctgg aattttgctt actctgggtc 2460
caagcgatac tcgtttccca tggtcaatgg gttggcgaaa atagaattct agtggactca 2520
gaactaagaa ttgtggggag agcagtgggc aggattagag acgatttgag aaggctggcg 2580
gatgaaaatg tttacatgat tgattatcta cttaatcaac cattagaaaa gggaatcgag 2640
ggtacagatg caggggagaa ggatgtagtg gtcaaagatg tggatattaa tgatgatgat 2700
gatgaggcgg aatggattgg tctagattag gttgtatcat attatatgga aggaaaaaaa 2760
atttaagctg gtttttgtac tcatttttga aaacttggtt gtgtgtatta ttattgttgt 2820
tctcgttgtt gttgtcgcct cccaattttg gaagatcttg tatattcgtt gatcaattat 2880
caggatgcat actctgtctg caaatcaaca tcagtctcgc caaattctct tttgcataaa 2940
tatttacatt cccatcacaa tcttcacccc tatctctatt cgatgcagat ccttctcttc 3000
tagaataaaa ggtcactcac tattaaaata tcatcagccg ctttttctca tcgctcaca 3059

<210> SEQ ID NO 76
<211> LENGTH: 4343
<212> TYPE: DNA
<213> ORGANISM: Botrytis cinerea

<400> SEQUENCE: 76
gaattcgagt gtgatcagtg cgagagtgcc ggcacaatgc aggtgggtgg gtggtacgga 60
agacgaaaaa gacacggccc gaggtgaggc tcatcacgac gccaacaatt ccatactgtt 120
gtgaacctcc aatagatgtc tgggcgttgc ggtatccata cgtccaactt gcatctgcgt 180
acgaaggaat cacatatgca tgaacatgaa catgaacatg aagtggcaag atggttggat 240
cgggtcaatc aatggcgcgc atctattgac tgttgcttga tacaaccgaa agccgacatt 300
ctttagcgta agggctacca aggtctgtgc attgatgggt acctctggcc agtctcgagc 360
cagtcctccg cattgcgaat cctcgctgtg tcaagtcgtt catatgtaga catccgatgt 420
taacgtggac ttgctgtcga ttgacacaaa tatataaaca ccttggatca tgtgtcgttc 480
tatcgccacg catttatatc gaggggatgt tatttccaca tccaagcttt gcggcagaaa 540
agaagtgctc ctggcgcacc gagtcaagcg tcagcagagt aagcagagtc agcaagcaat 600
ggattattca atgggagtct cgtgcgacct tatcggctgc caacttatgc acgtcttttc 660
ttccgagcaa atggttcgac aggagccttc ctttttgcgg aggcgacagc gaatggcatt 720
tgggcgcagt gtctgcctat ctggtaagct gatgaagacg gagagtgcaa ggctggagag 780
tgatggtgat ttaagcatcc catcgccatg gtgatttgac gtaagagatc gttgctttcg 840
tttgattatc gttggtcttt ttttcttgcc ttttcacttt cgcagacaat catcaatcat 900
caaaggtatc atgtcttcta cggcatcttc aagcgattcc gataacagta gaagacgacg 960
ccgacagggt ccaagaccct caccaccacc tcctcctccg ccgtttcaag ggaacaataa 1020
gaaatcaaag aagaggaaca aatacgtagc ccctcaagat acgatcgata aactttggtc 1080
tcgattctcg gtatcaaaat ttagtaaagc tacaaaagtt ttaccaaatg cagcaccttt 1140

-continued

```
tgcgaagggc acatctgcaa agaccgttat tgttcctcca cctggtccgc agaaccagct   1200
cgtttccgaa gactttgaaa gagcggttca agaatgcaga gccaaagtca agaaacttgt   1260
taaagaatgt aggcgcgtta atatgcggtt tcgcgacgcc agctttgata tagactggga   1320
cttgaaatgg gagaaaggaa attgtctaaa tacacttgat gaaataagat ttgaagtttg   1380
caaacaggct cttctcaatc ctacatcctc cgggccgaag gccgtcaaga gagttcacga   1440
aatattcgat aagccaacat tcttaggaga taaaatttct ccttcggatg tcaaacaagg   1500
aagtcttggg gattgttggt tgatggctag tttgacagca ttggcaaata cagacgacgg   1560
aattcaaaga atatgtgttg aatgggacac aaaaattggg atatatggtt ttgtgttcca   1620
tcgtgatggt gaatggatca tttcgatcat cgatgacaag ctctatctaa aatcgccaga   1680
ttgggattca ccctcggtcc acaggcatct actcgagcaa actgaccgag aggatgttga   1740
aaaggattat cgaaaaacgt atcaaaccgg atctcagtca ttattcttcg ctcaatgtaa   1800
agatccaaat caaacatggc ttcctcttct cgaaaaggct tacgctaaag cacacgggga   1860
tttcttttct ttgagtggag gatggatagg ggagggtctt gaagatttga caggaggcgt   1920
aactacggaa cttcttactt cggatattct tgataccgat gaattttggc ataatgaaat   1980
tctcaaggtc aataaagaat tcctttttgg ttgctctact ggtcttctcg attacggtta   2040
tggcaataga gatggaatat ctgaaggcca tgcatacgtt attatggagg ctagagagtt   2100
atctactggc gaacgtctcc taaaattacg gaatccgtgg ggaaagatca aaaaaggtaa   2160
ttgggaaggt ccatggtcag atggaagcaa ggaattcacc cctgaagctc agatagagct   2220
caaccacaaa tttggaaacg atagtgtttt ctggatttca tatcaggatt tactacgcaa   2280
atatcaacat ttcgatcgca ctcggttgtt catggacagt cctgattgga gattgaccca   2340
agactgggtc agtgtagagg tgccatggag atccgagttt gaacagaagt tcaccataac   2400
gcttaagaag gaatcaccca tagttttggt tatgagtcaa ctcgacgaca ggtactttat   2460
tggtctacat ggtcaataca acttcagatt gcagtttcgg gttcatgaga ttaattcacc   2520
cgatgaagaa gattatatcg tccgaagcca tgggaattat cttatgaggc gaagtgtggt   2580
tgctgaattg aaaagtctct ccgccggaac atatacagta tatatgatgg tcatagcaga   2640
aagggataag gatcgacaga gtgttgaaga tgtcgttaaa gatgaattga gtcaaaggga   2700
agataatgaa aaattagcta aagttggtct agcttacgat ctggctcacc agaaaggatt   2760
gtctcatatg gagttaagaa ttaaatccag aaaggctcta gataaagcaa aggcccgaga   2820
atccaggatt gctaaacgta aagtcctttg ggagaaaaga cacattgcgc gggagatact   2880
aaggaagcaa aagaagaaga attatgagaa acgtgaaggt aaagcagcaa aagatactga   2940
gtgggcaaag gaacaagaag aacgtgagct aaaggatcaa ggtgttcaaa cggaagatat   3000
tccagaagtt caagtcgaga aacaagacaa gtcaatgcaa accgaagatc tcaatgagga   3060
gtcaatgaac actacagttg atacacaacc cacaaatgaa agggacaaag cagtacagac   3120
agaaggcttt acaccatctt ctaatgagtc ccagacaact cccgtaactc caaagagtaa   3180
tggttcatct ccacgttcac cgtatacgat gatctcgaga tccggatcta atcgccgcaa   3240
atcactacct ccacctccaa gctttgttaa tcttcgtaga aatccgagtc gtccaccaaa   3300
tcatggtcga gggcctcctc ctccttcttc gaaaccaggt ctatatgtta cttcggaggg   3360
ggagtcaagt gcaagtcctc tttcggatta tgatatgtat agtgacgatg atccgactct   3420
taagccacga aatcagtcaa ccgagccgaa acgcccaaag gaaagggagg ctggtgaaga   3480
tgagccagaa ccatggaatg cggtttgtat cgttggcttc agggtttaca gtaaggatga   3540
```

aggactagtg cttactgttt gcgaggaggg tatggaggaa gtgattgagt tgaaagagga 3600
tagtgaagct ggtactgatg gtgatgtgga agatgctgaa gatgaagatt gccatgagaa 3660
gaaaggagga aatggggaag atttgaaatt aaaagatact gcagcaggaa acgactcaac 3720
actttcagat gtcgcaatca aaattgagcc tgacaaagat ttgaatgtcg ctatctccaa 3780
ttcaccttac gagattactg gaacctcttc gtcagtcaac aatggccttg aagaaattcc 3840
taccgagaag caatcccaag aagccaccaa aattttggaa atagagacaa acggcgacgc 3900
tcagcagaag tcggctcttg ggatctcgga gggtgctaca gatgatatcg tgaaggaatc 3960
agattctcaa tccggcattg caacatcaag cgcttcttcg aactgcactt aaagctcaca 4020
ctgatttttg ttcaggtaac attcagtgta caattcattc ttcagatcag tgcacaatga 4080
aaacaatttc tcgtttttgg aagccccatt ttgatctttc aagcgattca ggcagtctag 4140
gcggtctatg cgagcttctc ggttttatct tcagcaaaat cttcgaaccc gcatgtagtt 4200
ctagtaattc tagtgattac attctcatga ctaatgaaat ttttcgtaat atctgtaggt 4260
agatacaatg atgttagtat tattcccatc aatgaatata ttcagactac tcaatcaaca 4320
caattttcat tggccctttc tca 4343

<210> SEQ ID NO 77
<211> LENGTH: 1715
<212> TYPE: DNA
<213> ORGANISM: Botrytis cinerea

<400> SEQUENCE: 77
gatcaacaat atccatgaac gatatccatg gagaagagaa gaaaagaacc ttgcctccac 60
caccaccacc tccactcttc acattgactc ctcttgagtc ttgagagtcg agacatgcga 120
gacatggtcg gatagacatt aagcgaaaca ccgatggcga aaaatttgat tttcacaagc 180
aaaaaactag taaaagtaga gggaaagccc agacaaaatc cgaattcgat ccgacccttt 240
atcttgaaaa tcctatgcag agtaatagtt attcctatct tactaacaaa ttccatcttc 300
ctataagtta actatctgac tctccctcct tcttgattac taccaacgag acatcacaca 360
tcatcctttt gttttgtttc tgcgatacaa gtacaataga tcaatacatc aacacatccc 420
tacgatatct tcttacccgt tcgaagcttc aaaaaaaggg tccaaatctc caacaagcac 480
acgaccaaag gcacacgatc aaaatgaagg tcttttctag cgactgcaaa ttcgattatt 540
cgtgggaaga ggtttcgact gcaaactgga gaaagtactg tccatggaat cataaatcta 600
ctcacgttat cgccgtcgat acattatccc gacatgtaga tgctgacacc ggaattctac 660
gcaccgaacg tttaattacc tgccaacaat ctgctccaaa atggttacaa tcactcatgg 720
gcggcaaaga tacatcccac gtcttcgaaa cctcatatgt cgatccgatt accaagaaag 780
tcacaatgac atctaccaat ctcacatttt ccaacatcat caatgtgcaa gaaacagttg 840
tctaccaacc cttatcggca aacacaacac aatttgtcca ggcggcacag attactgcat 900
tatgtggtgg atggcaaaaa gtgaagaatg cagttgaaga cgcgacagtt actgcgtttt 960
cggaaaatgc acgcaaagga aaggagggat tcgaagcagt tttggcgatg agcaggaggg 1020
tattcagtga ggagaaaatg agacaacaac aagcggctac cgttactgca taaagttcga 1080
aatttcaaag gcgttttgaa gaggggtttc cgtgaagata ttccggttcg gtccgagata 1140
tacatgatga gattcatatc atttgaatct cctcacatca cgactgaaac gattcctccc 1200
ttgtcctttt tcttcacttc acttcaacca tctcctcact tcatttcggc atttacgagt 1260

```
ttcacatcat tttaggagtt tggggatttt ttattacaag ttccggtata caaaaaagtc   1320

cactttcgga gttctagaag gcgaaattct cggttgcgaa ttctatttta agcgcggcgt   1380

taaaaaagga taaatgggat atttgggtta ggttgggttt tgcttcaaaa agacgattgt   1440

cttttgttgt ctttgaatgg aaaagttatg atattcaaag aaactttcat cctcaacgct   1500

gatgtgggtt attgttacga tacagatacc cctttttttcc ttctttcttt ttttgcggtg   1560

cttttttttt tttcttcttt gaagggggag ataaaaatag atggatagat gggttgattt   1620

tatagatgag gctgaatagg gagatgatgt agatagagtg agcgagtcag tgggtgagag   1680

acttgaagaa aataaatatt agattttact ttata                              1715
```

<210> SEQ ID NO 78
<211> LENGTH: 1333
<212> TYPE: DNA
<213> ORGANISM: Botrytis cinerea

<400> SEQUENCE: 78

```
gattagcctg gatattttgg agttgaatgc ttggagaaac ttggacccaa aatttgaccc     60

ctccttctat cgacttttcc aatcacaaat tcacaaatat aaaccatttc attgccagct    120

atcgattttg tatgtttaga aatacaatca aaatggcaga aacagcagca aaaagactca    180

agacctctcc cgttaccatc ggtactcata atggccattt tcacgcagat gaagccttgg    240

ctgtttacat gcttcgcctt cttcctactt atcaatcttc agagctcatt cgaactcggg    300

atcccaaact tctagagact tgccataccg tggttgatgt gggaggtgaa tacaacgacg    360

aaactaagag atatgatcac catcaacgta ctttcgatac cacattccca aatcgtccta    420

ccaagctctc ttctgcgggg ttagtgtata tgcactacgg caaggcgatt atcgcacaac    480

atctaggtgt cgccgaagat gcggaagaag ttgccgttat ctggagaaag atttacgaaa    540

gctttattga agcacttgat gctcacgata acggtatttc agtctacgac ccaaaggcca    600

tttccgccgc aggcttggag aagaagttca gcgacggagg tttctcatta ggggctatgg    660

tatccagatt gaacccaaac tggaatgacc ccactccatc tgatcctgtc gaggctcaaa    720

aggcagaaga tgagaaattc ttggtagcca gcactagaat gggtgaagaa ttctcaagag    780

atttggatta ctatacaaaa tcgtggttac cagcacgatc aattgtccaa caagcatatg    840

ccaaacgcct acaatacgac tcgaagggaa gaatcttggt gttcgacggt caatctgttc    900

catggaaaga tcatctctac acactggaag atcaagagaa cagcgagaac aaagtactct    960

acgttctcta ccctgaaagc ccacgtccag atgcgaaatg gagaatccaa tgtgtaccag   1020

tcaccaaaga ctctttccaa agcagaaagc cattgcctga ggcatggaga ggtttcagag   1080

atgaggaatt atctcaaatt actggtattc caggaggagt attcgttcat gcagcgggat   1140

tcattggagg aaacaagact ttcgatgggg caagtaagat ggcagcaaca gcggttgatt   1200

tgtgatatcc actaaagtca tgaaaaacat tattatgagg cgttgttcgg tatcaaaagc   1260

caaaaggtta gataggttca agaaatataa aacccaaatc gatgtgttca tacacatcgg   1320

aatctcaaag aca                                                      1333
```

<210> SEQ ID NO 79
<211> LENGTH: 5
<212> TYPE: PRT
<213> ORGANISM: Arabidopsis thaliana
<220> FEATURE:
<221> NAME/KEY: MOD_RES
<222> LOCATION: (4)..(4)
<223> OTHER INFORMATION: Lys or Arg -continued

<400> SEQUENCE: 79

Gly Cys Cys Xaa Pro
1 5

<210> SEQ ID NO 80
<211> LENGTH: 21
<212> TYPE: DNA
<213> ORGANISM: Arabidopsis thaliana

<400> SEQUENCE: 80
tcggaccagg cttcattccc c 21

<210> SEQ ID NO 81
<211> LENGTH: 21
<212> TYPE: DNA
<213> ORGANISM: Arabidopsis thaliana

<400> SEQUENCE: 81
ttgacagaag atagagagca c 21

<210> SEQ ID NO 82
<211> LENGTH: 22
<212> TYPE: DNA
<213> ORGANISM: Arabidopsis thaliana

<400> SEQUENCE: 82
gtcgaactca gtaacgcggg ct 22

<210> SEQ ID NO 83
<211> LENGTH: 21
<212> TYPE: DNA
<213> ORGANISM: Arabidopsis thaliana

<400> SEQUENCE: 83
tttggattga agggagctct t 21

<210> SEQ ID NO 84
<211> LENGTH: 21
<212> TYPE: DNA
<213> ORGANISM: Arabidopsis thaliana

<400> SEQUENCE: 84
tttggattga agggagctct a 21

<210> SEQ ID NO 85
<211> LENGTH: 21
<212> TYPE: DNA
<213> ORGANISM: Arabidopsis thaliana

<400> SEQUENCE: 85
tcgcttggtg caggtcggga a 21

<210> SEQ ID NO 86
<211> LENGTH: 21
<212> TYPE: DNA
<213> ORGANISM: Arabidopsis thaliana

<400> SEQUENCE: 86
ttccacagct ttcttgaact g 21

<210> SEQ ID NO 87
<211> LENGTH: 20

<212> TYPE: DNA
<213> ORGANISM: Arabidopsis thaliana

<400> SEQUENCE: 87
tcccaaatgt agacaaagca 20

<210> SEQ ID NO 88
<211> LENGTH: 22
<212> TYPE: DNA
<213> ORGANISM: Arabidopsis thaliana

<400> SEQUENCE: 88
tccaatgtct tttctagttc gt 22

<210> SEQ ID NO 89
<211> LENGTH: 21
<212> TYPE: DNA
<213> ORGANISM: Arabidopsis thaliana

<400> SEQUENCE: 89
ttctaagttc aacatatcga c 21

<210> SEQ ID NO 90
<211> LENGTH: 21
<212> TYPE: DNA
<213> ORGANISM: Arabidopsis thaliana

<400> SEQUENCE: 90
ggtggaggag gaggcggcgg c 21

<210> SEQ ID NO 91
<211> LENGTH: 21
<212> TYPE: DNA
<213> ORGANISM: Arabidopsis thaliana

<400> SEQUENCE: 91
agttaattga acgttcggcg t 21

<210> SEQ ID NO 92
<211> LENGTH: 21
<212> TYPE: DNA
<213> ORGANISM: Arabidopsis thaliana

<400> SEQUENCE: 92
gttcaataaa gctgtgggaa g 21

<210> SEQ ID NO 93
<211> LENGTH: 21
<212> TYPE: DNA
<213> ORGANISM: Arabidopsis thaliana

<400> SEQUENCE: 93
ttccacagct ttcttgaact t 21

<210> SEQ ID NO 94
<211> LENGTH: 21
<212> TYPE: DNA
<213> ORGANISM: Arabidopsis thaliana

<400> SEQUENCE: 94
cgggtttggc aggacgttac t 21

<210> SEQ ID NO 95

-continued

<211> LENGTH: 22
<212> TYPE: DNA
<213> ORGANISM: Arabidopsis thaliana

<400> SEQUENCE: 95
gaagtcctcg tgttgcattc ct 22

<210> SEQ ID NO 96
<211> LENGTH: 21
<212> TYPE: DNA
<213> ORGANISM: Arabidopsis thaliana

<400> SEQUENCE: 96
cgtaaaaaaa gttgtaactc t 21

<210> SEQ ID NO 97
<211> LENGTH: 22
<212> TYPE: DNA
<213> ORGANISM: Arabidopsis thaliana

<400> SEQUENCE: 97
tccgctgtag cacttcaggc ta 22

<210> SEQ ID NO 98
<211> LENGTH: 21
<212> TYPE: DNA
<213> ORGANISM: Arabidopsis thaliana

<400> SEQUENCE: 98
tcggaccagg cttcatcccc c 21

<210> SEQ ID NO 99
<211> LENGTH: 22
<212> TYPE: DNA
<213> ORGANISM: Arabidopsis thaliana

<400> SEQUENCE: 99
tggtggaaca ctggctcggc cc 22

<210> SEQ ID NO 100
<211> LENGTH: 22
<212> TYPE: DNA
<213> ORGANISM: Arabidopsis thaliana

<400> SEQUENCE: 100
ttagattcac gcacaaactc gt 22

<210> SEQ ID NO 101
<211> LENGTH: 21
<212> TYPE: DNA
<213> ORGANISM: Arabidopsis thaliana

<400> SEQUENCE: 101
ttgaaagtga ctacatcggg g 21

<210> SEQ ID NO 102
<211> LENGTH: 22
<212> TYPE: DNA
<213> ORGANISM: Arabidopsis thaliana

<400> SEQUENCE: 102
gagttaattg aacgttcggc gt 22

<210> SEQ ID NO 103
<211> LENGTH: 24
<212> TYPE: DNA
<213> ORGANISM: Arabidopsis thaliana

<400> SEQUENCE: 103
aaaccgcaac cggatcttaa aggc 24

<210> SEQ ID NO 104
<211> LENGTH: 20
<212> TYPE: DNA
<213> ORGANISM: Arabidopsis thaliana

<400> SEQUENCE: 104
tccgctgtag cacacaggcc 20

<210> SEQ ID NO 105
<211> LENGTH: 21
<212> TYPE: DNA
<213> ORGANISM: Arabidopsis thaliana

<400> SEQUENCE: 105
gggttgatat gagaacacac g 21

<210> SEQ ID NO 106
<211> LENGTH: 21
<212> TYPE: DNA
<213> ORGANISM: Arabidopsis thaliana

<400> SEQUENCE: 106
ttgacagaag agagtgagca c 21

<210> SEQ ID NO 107
<211> LENGTH: 21
<212> TYPE: DNA
<213> ORGANISM: Arabidopsis thaliana

<400> SEQUENCE: 107
agaatagaat ctgtaaaacg a 21

<210> SEQ ID NO 108
<211> LENGTH: 21
<212> TYPE: DNA
<213> ORGANISM: Arabidopsis thaliana

<400> SEQUENCE: 108
aactagaaaa gacattggac a 21

<210> SEQ ID NO 109
<211> LENGTH: 21
<212> TYPE: DNA
<213> ORGANISM: Arabidopsis thaliana

<400> SEQUENCE: 109
gaactagaaa agacattgga c 21

<210> SEQ ID NO 110
<211> LENGTH: 24
<212> TYPE: DNA
<213> ORGANISM: Arabidopsis thaliana

<400> SEQUENCE: 110
aagcacatgt gtagagtcga gcct 24

<210> SEQ ID NO 111
<211> LENGTH: 24
<212> TYPE: DNA
<213> ORGANISM: Arabidopsis thaliana

<400> SEQUENCE: 111
agaacagaga ccgttggaag aaaa 24

<210> SEQ ID NO 112
<211> LENGTH: 21
<212> TYPE: DNA
<213> ORGANISM: Arabidopsis thaliana

<400> SEQUENCE: 112
aagctcagga gggatagcgc c 21

<210> SEQ ID NO 113
<211> LENGTH: 24
<212> TYPE: DNA
<213> ORGANISM: Arabidopsis thaliana

<400> SEQUENCE: 113
cgagaatgat gaaccaatta gatg 24

<210> SEQ ID NO 114
<211> LENGTH: 21
<212> TYPE: DNA
<213> ORGANISM: Arabidopsis thaliana

<400> SEQUENCE: 114
gatcatgttc gcagtttcac c 21

<210> SEQ ID NO 115
<211> LENGTH: 24
<212> TYPE: DNA
<213> ORGANISM: Arabidopsis thaliana

<400> SEQUENCE: 115
aaacaggacc ttaatagaac aacc 24

<210> SEQ ID NO 116
<211> LENGTH: 24
<212> TYPE: DNA
<213> ORGANISM: Arabidopsis thaliana

<400> SEQUENCE: 116
aggatgaaag gtttgactag aact 24

<210> SEQ ID NO 117
<211> LENGTH: 23
<212> TYPE: DNA
<213> ORGANISM: Arabidopsis thaliana

<400> SEQUENCE: 117
ctgcacgggc ttggctcatc cca 23

<210> SEQ ID NO 118
<211> LENGTH: 24
<212> TYPE: DNA
<213> ORGANISM: Arabidopsis thaliana

<400> SEQUENCE: 118
aagctgtggt taactgaaaa agct 24

<210> SEQ ID NO 119
<211> LENGTH: 24
<212> TYPE: DNA
<213> ORGANISM: Arabidopsis thaliana

<400> SEQUENCE: 119
ataagagacg gaacactgga tatg 24

<210> SEQ ID NO 120
<211> LENGTH: 26
<212> TYPE: DNA
<213> ORGANISM: Arabidopsis thaliana

<400> SEQUENCE: 120
taaacaaact gtactttatg agagcc 26

<210> SEQ ID NO 121
<211> LENGTH: 24
<212> TYPE: DNA
<213> ORGANISM: Arabidopsis thaliana

<400> SEQUENCE: 121
atctaaaccc gtcaattcta ggat 24

<210> SEQ ID NO 122
<211> LENGTH: 30
<212> TYPE: DNA
<213> ORGANISM: Arabidopsis thaliana

<400> SEQUENCE: 122
catgggcatc gacaccttgc ggctaggaac 30

<210> SEQ ID NO 123
<211> LENGTH: 24
<212> TYPE: DNA
<213> ORGANISM: Arabidopsis thaliana

<400> SEQUENCE: 123
aagcgaagga cccagcaggg aagc 24

<210> SEQ ID NO 124
<211> LENGTH: 24
<212> TYPE: DNA
<213> ORGANISM: Arabidopsis thaliana

<400> SEQUENCE: 124
ttgaagagga cttggaactt cgat 24

<210> SEQ ID NO 125
<211> LENGTH: 24
<212> TYPE: DNA
<213> ORGANISM: Arabidopsis thaliana

<400> SEQUENCE: 125
ctgcacggtc ttggctcaac ccgc 24

<210> SEQ ID NO 126
<211> LENGTH: 24
<212> TYPE: DNA
<213> ORGANISM: Arabidopsis thaliana

<400> SEQUENCE: 126
atgagagatt cggactatcc agcc 24

<210> SEQ ID NO 127
<211> LENGTH: 24
<212> TYPE: DNA
<213> ORGANISM: Arabidopsis thaliana

<400> SEQUENCE: 127
aacgaaccga ccgtcagaca tgga 24

<210> SEQ ID NO 128
<211> LENGTH: 21
<212> TYPE: DNA
<213> ORGANISM: Arabidopsis thaliana

<400> SEQUENCE: 128
ttgaaagtga ctacatcggg g 21

<210> SEQ ID NO 129
<211> LENGTH: 20
<212> TYPE: DNA
<213> ORGANISM: Arabidopsis thaliana

<400> SEQUENCE: 129
tcccaaatgt agacaaagca 20

<210> SEQ ID NO 130
<211> LENGTH: 21
<212> TYPE: DNA
<213> ORGANISM: Arabidopsis thaliana

<400> SEQUENCE: 130
tttggattga agggagctct a 21

<210> SEQ ID NO 131
<211> LENGTH: 21
<212> TYPE: DNA
<213> ORGANISM: Arabidopsis thaliana

<400> SEQUENCE: 131
ttccacagct ttcttgaact g 21

<210> SEQ ID NO 132
<211> LENGTH: 21
<212> TYPE: DNA
<213> ORGANISM: Arabidopsis thaliana

<400> SEQUENCE: 132
tcggaccagg cttcattccc c 21

<210> SEQ ID NO 133
<211> LENGTH: 21
<212> TYPE: DNA
<213> ORGANISM: Arabidopsis thaliana

<400> SEQUENCE: 133
ttgacagaag atagagagca c 21

<210> SEQ ID NO 134
<211> LENGTH: 22
<212> TYPE: DNA
<213> ORGANISM: Arabidopsis thaliana

<400> SEQUENCE: 134
tccaatgtct tttctagttc gt 22

<210> SEQ ID NO 135
<211> LENGTH: 21
<212> TYPE: DNA
<213> ORGANISM: Arabidopsis thaliana

<400> SEQUENCE: 135
tcgcttggtg caggtcggga a 21

<210> SEQ ID NO 136
<211> LENGTH: 21
<212> TYPE: DNA
<213> ORGANISM: Arabidopsis thaliana

<400> SEQUENCE: 136
ttctaagttc aacatatcga c 21

<210> SEQ ID NO 137
<211> LENGTH: 21
<212> TYPE: DNA
<213> ORGANISM: Arabidopsis thaliana

<400> SEQUENCE: 137
tttggattga agggagctct t 21

<210> SEQ ID NO 138
<211> LENGTH: 24
<212> TYPE: DNA
<213> ORGANISM: Arabidopsis thaliana

<400> SEQUENCE: 138
attatggacc gtccaacttg gccc 24

<210> SEQ ID NO 139
<211> LENGTH: 21
<212> TYPE: DNA
<213> ORGANISM: Arabidopsis thaliana

<400> SEQUENCE: 139
gttcaataaa gctgtgggaa g 21

<210> SEQ ID NO 140
<211> LENGTH: 21
<212> TYPE: DNA
<213> ORGANISM: Arabidopsis thaliana

<400> SEQUENCE: 140
cttagaatac gctatgttgg a 21

<210> SEQ ID NO 141
<211> LENGTH: 22
<212> TYPE: DNA
<213> ORGANISM: Arabidopsis thaliana

<400> SEQUENCE: 141
ttagattcac gcacaaactc gt 22

<210> SEQ ID NO 142
<211> LENGTH: 24
<212> TYPE: DNA
<213> ORGANISM: Arabidopsis thaliana

<400> SEQUENCE: 142
agaatacgct atgttggact taga 24

<210> SEQ ID NO 143
<211> LENGTH: 21
<212> TYPE: DNA
<213> ORGANISM: Arabidopsis thaliana

<400> SEQUENCE: 143
tgaagctgcc agcatgatct a 21

<210> SEQ ID NO 144
<211> LENGTH: 21
<212> TYPE: DNA
<213> ORGANISM: Arabidopsis thaliana

<400> SEQUENCE: 144
gatcatgttc gcagtttcac c 21

<210> SEQ ID NO 145
<211> LENGTH: 21
<212> TYPE: DNA
<213> ORGANISM: Arabidopsis thaliana

<400> SEQUENCE: 145
tcggaccagg cttcatcccc c 21

<210> SEQ ID NO 146
<211> LENGTH: 21
<212> TYPE: DNA
<213> ORGANISM: Arabidopsis thaliana

<400> SEQUENCE: 146
aacggattat gtaagagagg t 21

<210> SEQ ID NO 147
<211> LENGTH: 21
<212> TYPE: DNA
<213> ORGANISM: Arabidopsis thaliana

<400> SEQUENCE: 147
gggttgatat gagaacacac g 21

<210> SEQ ID NO 148
<211> LENGTH: 24
<212> TYPE: DNA
<213> ORGANISM: Arabidopsis thaliana

<400> SEQUENCE: 148
ttgaagagga cttggaactt cgat 24

<210> SEQ ID NO 149
<211> LENGTH: 21
<212> TYPE: DNA
<213> ORGANISM: Arabidopsis thaliana

<400> SEQUENCE: 149
aatggattat gtaagagagg t 21

<210> SEQ ID NO 150
<211> LENGTH: 24
<212> TYPE: DNA
<213> ORGANISM: Arabidopsis thaliana

<400> SEQUENCE: 150
aacatgcgga tttgctttgg cgcc 24

<210> SEQ ID NO 151
<211> LENGTH: 24
<212> TYPE: DNA
<213> ORGANISM: Arabidopsis thaliana

<400> SEQUENCE: 151
tccgctgtag cacacaggcc aatt 24

<210> SEQ ID NO 152
<211> LENGTH: 20
<212> TYPE: DNA
<213> ORGANISM: Arabidopsis thaliana

<400> SEQUENCE: 152
tccgctgtag cacacaggcc 20

<210> SEQ ID NO 153
<211> LENGTH: 24
<212> TYPE: DNA
<213> ORGANISM: Arabidopsis thaliana

<400> SEQUENCE: 153
aggatgaaag gtttgactag aact 24

<210> SEQ ID NO 154
<211> LENGTH: 24
<212> TYPE: DNA
<213> ORGANISM: Arabidopsis thaliana

<400> SEQUENCE: 154
aaacgagaac gtagacagaa caga 24

<210> SEQ ID NO 155
<211> LENGTH: 30
<212> TYPE: DNA
<213> ORGANISM: Arabidopsis thaliana

<400> SEQUENCE: 155
aactgtgacg atagcaagtg ccgtctgagc 30

<210> SEQ ID NO 156
<211> LENGTH: 21
<212> TYPE: DNA
<213> ORGANISM: Arabidopsis thaliana

<400> SEQUENCE: 156
cgatccccgg caacggcgcc a 21

<210> SEQ ID NO 157
<211> LENGTH: 24
<212> TYPE: DNA
<213> ORGANISM: Arabidopsis thaliana

<400> SEQUENCE: 157
aagcgcggaa agaacagtag atgc 24

<210> SEQ ID NO 158
<211> LENGTH: 21
<212> TYPE: DNA

<213> ORGANISM: Arabidopsis thaliana

<400> SEQUENCE: 158
ttgacagaag agagtgagca c 21

<210> SEQ ID NO 159
<211> LENGTH: 23
<212> TYPE: DNA
<213> ORGANISM: Arabidopsis thaliana

<400> SEQUENCE: 159
gagaatgatg aaccaattag atg 23

<210> SEQ ID NO 160
<211> LENGTH: 21
<212> TYPE: DNA
<213> ORGANISM: Arabidopsis thaliana

<400> SEQUENCE: 160
agaatagaat ctgtaaaacg a 21

<210> SEQ ID NO 161
<211> LENGTH: 21
<212> TYPE: DNA
<213> ORGANISM: Arabidopsis thaliana

<400> SEQUENCE: 161
tagcaactgt tctttagacg a 21

<210> SEQ ID NO 162
<211> LENGTH: 21
<212> TYPE: DNA
<213> ORGANISM: Arabidopsis thaliana

<400> SEQUENCE: 162
acacgatgtt caatagattt a 21

<210> SEQ ID NO 163
<211> LENGTH: 24
<212> TYPE: DNA
<213> ORGANISM: Arabidopsis thaliana

<400> SEQUENCE: 163
aacagcatcg tccatcattg aaga 24

<210> SEQ ID NO 164
<211> LENGTH: 24
<212> TYPE: DNA
<213> ORGANISM: Arabidopsis thaliana

<400> SEQUENCE: 164
atagcggaaa ctaattttgg cacc 24

<210> SEQ ID NO 165
<211> LENGTH: 24
<212> TYPE: DNA
<213> ORGANISM: Arabidopsis thaliana

<400> SEQUENCE: 165
aggacattag gtttattgga ttgg 24

<210> SEQ ID NO 166
<211> LENGTH: 21

<212> TYPE: DNA
<213> ORGANISM: Arabidopsis thaliana

<400> SEQUENCE: 166
tttttacggg gataagactg a 21

<210> SEQ ID NO 167
<211> LENGTH: 24
<212> TYPE: DNA
<213> ORGANISM: Arabidopsis thaliana

<400> SEQUENCE: 167
aatgaaaaag ttggaaaagt gcct 24

<210> SEQ ID NO 168
<211> LENGTH: 24
<212> TYPE: DNA
<213> ORGANISM: Arabidopsis thaliana

<400> SEQUENCE: 168
cgagaatgat gaaccaatta gatg 24

<210> SEQ ID NO 169
<211> LENGTH: 21
<212> TYPE: DNA
<213> ORGANISM: Arabidopsis thaliana

<400> SEQUENCE: 169
aactagaaaa gacattggac a 21

<210> SEQ ID NO 170
<211> LENGTH: 24
<212> TYPE: DNA
<213> ORGANISM: Arabidopsis thaliana

<400> SEQUENCE: 170
attatgaacc gtccaacttg gccc 24

<210> SEQ ID NO 171
<211> LENGTH: 23
<212> TYPE: DNA
<213> ORGANISM: Arabidopsis thaliana

<400> SEQUENCE: 171
gagggacgac gatttgtgac acc 23

<210> SEQ ID NO 172
<211> LENGTH: 21
<212> TYPE: DNA
<213> ORGANISM: Arabidopsis thaliana

<400> SEQUENCE: 172
aagctcagga gggatagcgc c 21

<210> SEQ ID NO 173
<211> LENGTH: 24
<212> TYPE: DNA
<213> ORGANISM: Arabidopsis thaliana

<400> SEQUENCE: 173
aaaccgcaac cggatcttaa aggc 24

<210> SEQ ID NO 174

<211> LENGTH: 21
<212> TYPE: DNA
<213> ORGANISM: Arabidopsis thaliana

<400> SEQUENCE: 174
gggacgacga tttgtgacac c 21

<210> SEQ ID NO 175
<211> LENGTH: 21
<212> TYPE: DNA
<213> ORGANISM: Arabidopsis thaliana

<400> SEQUENCE: 175
ggatggtgag ggacgacgat t 21

<210> SEQ ID NO 176
<211> LENGTH: 22
<212> TYPE: DNA
<213> ORGANISM: Arabidopsis thaliana

<400> SEQUENCE: 176
tgacgagaga acttattggc ct 22

<210> SEQ ID NO 177
<211> LENGTH: 24
<212> TYPE: DNA
<213> ORGANISM: Arabidopsis thaliana

<400> SEQUENCE: 177
atttaatttg atgggttgag ttgt 24

<210> SEQ ID NO 178
<211> LENGTH: 24
<212> TYPE: DNA
<213> ORGANISM: Arabidopsis thaliana

<400> SEQUENCE: 178
aatccggtag aacactgaaa tggt 24

<210> SEQ ID NO 179
<211> LENGTH: 24
<212> TYPE: DNA
<213> ORGANISM: Arabidopsis thaliana

<400> SEQUENCE: 179
aagcagtggc ggatctaggg agga 24

<210> SEQ ID NO 180
<211> LENGTH: 24
<212> TYPE: DNA
<213> ORGANISM: Arabidopsis thaliana

<400> SEQUENCE: 180
atcggacagt acaactctac gtac 24

<210> SEQ ID NO 181
<211> LENGTH: 24
<212> TYPE: DNA
<213> ORGANISM: Arabidopsis thaliana

<400> SEQUENCE: 181
aaagaggatt taagtagata gtac 24

<210> SEQ ID NO 182
<211> LENGTH: 26
<212> TYPE: DNA
<213> ORGANISM: Arabidopsis thaliana

<400> SEQUENCE: 182
ggtgagggac gacgatttgt gacacc 26

<210> SEQ ID NO 183
<211> LENGTH: 21
<212> TYPE: DNA
<213> ORGANISM: Arabidopsis thaliana

<400> SEQUENCE: 183
tgcaaggttc aagaacggat c 21

<210> SEQ ID NO 184
<211> LENGTH: 24
<212> TYPE: DNA
<213> ORGANISM: Arabidopsis thaliana

<400> SEQUENCE: 184
aaacaggacc ttaatagaac aacc 24

<210> SEQ ID NO 185
<211> LENGTH: 21
<212> TYPE: DNA
<213> ORGANISM: Arabidopsis thaliana

<400> SEQUENCE: 185
aacgtttaga aagagatggg g 21

<210> SEQ ID NO 186
<211> LENGTH: 22
<212> TYPE: DNA
<213> ORGANISM: Arabidopsis thaliana

<400> SEQUENCE: 186
aatgggatgg agaacaaact gg 22

<210> SEQ ID NO 187
<211> LENGTH: 21
<212> TYPE: DNA
<213> ORGANISM: Arabidopsis thaliana

<400> SEQUENCE: 187
ataagactga aacatatatg t 21

<210> SEQ ID NO 188
<211> LENGTH: 24
<212> TYPE: DNA
<213> ORGANISM: Arabidopsis thaliana

<400> SEQUENCE: 188
actcgagact gttttggaaa caaa 24

<210> SEQ ID NO 189
<211> LENGTH: 24
<212> TYPE: DNA
<213> ORGANISM: Arabidopsis thaliana

<400> SEQUENCE: 189
atttcaggag tagaattttt cgcc 24

<210> SEQ ID NO 190
<211> LENGTH: 24
<212> TYPE: DNA
<213> ORGANISM: Arabidopsis thaliana

<400> SEQUENCE: 190
atcctatcgg ctgattcggt taga 24

<210> SEQ ID NO 191
<211> LENGTH: 20
<212> TYPE: DNA
<213> ORGANISM: Arabidopsis thaliana

<400> SEQUENCE: 191
gatggtgagg gacgacgatt 20

<210> SEQ ID NO 192
<211> LENGTH: 24
<212> TYPE: DNA
<213> ORGANISM: Arabidopsis thaliana

<400> SEQUENCE: 192
atactctaat ggatggattg ttgt 24

<210> SEQ ID NO 193
<211> LENGTH: 22
<212> TYPE: DNA
<213> ORGANISM: Arabidopsis thaliana

<400> SEQUENCE: 193
tccgctgtag cacttcaggc ta 22

<210> SEQ ID NO 194
<211> LENGTH: 22
<212> TYPE: DNA
<213> ORGANISM: Arabidopsis thaliana

<400> SEQUENCE: 194
tccgctgtag cacttcaggc ta 22

<210> SEQ ID NO 195
<211> LENGTH: 24
<212> TYPE: DNA
<213> ORGANISM: Arabidopsis thaliana

<400> SEQUENCE: 195
taaacatctg atcgtttgac ttga 24

<210> SEQ ID NO 196
<211> LENGTH: 21
<212> TYPE: DNA
<213> ORGANISM: Arabidopsis thaliana

<400> SEQUENCE: 196
acggtatctc tcctacgtag c 21

<210> SEQ ID NO 197
<211> LENGTH: 24
<212> TYPE: DNA
<213> ORGANISM: Arabidopsis thaliana

<400> SEQUENCE: 197
ggtttagaat tggattgtaa caga 24

<210> SEQ ID NO 198
<211> LENGTH: 24
<212> TYPE: DNA
<213> ORGANISM: Arabidopsis thaliana

<400> SEQUENCE: 198
gaaccgaccg tcagacatgg atga 24

<210> SEQ ID NO 199
<211> LENGTH: 24
<212> TYPE: DNA
<213> ORGANISM: Arabidopsis thaliana

<400> SEQUENCE: 199
accggaactg cttgaaataa tgga 24

<210> SEQ ID NO 200
<211> LENGTH: 24
<212> TYPE: DNA
<213> ORGANISM: Arabidopsis thaliana

<400> SEQUENCE: 200
attgagtaac aggaggacta tgcc 24

<210> SEQ ID NO 201
<211> LENGTH: 24
<212> TYPE: DNA
<213> ORGANISM: Arabidopsis thaliana

<400> SEQUENCE: 201
gagaaactaa agtcggcgga cgac 24

<210> SEQ ID NO 202
<211> LENGTH: 24
<212> TYPE: DNA
<213> ORGANISM: Arabidopsis thaliana

<400> SEQUENCE: 202
agatgatggg cttagatgat gggc 24

<210> SEQ ID NO 203
<211> LENGTH: 20
<212> TYPE: DNA
<213> ORGANISM: Arabidopsis thaliana

<400> SEQUENCE: 203
gttttggaca ggtatcgaca 20

<210> SEQ ID NO 204
<211> LENGTH: 23
<212> TYPE: DNA
<213> ORGANISM: Arabidopsis thaliana

<400> SEQUENCE: 204
aaacatctga tcgtttgact tga 23

<210> SEQ ID NO 205
<211> LENGTH: 23
<212> TYPE: DNA
<213> ORGANISM: Arabidopsis thaliana

<400> SEQUENCE: 205
ttgaggataa tgttgcataa ata 23

<210> SEQ ID NO 206
<211> LENGTH: 23
<212> TYPE: DNA
<213> ORGANISM: Arabidopsis thaliana

<400> SEQUENCE: 206
accgtgaggc caaacttggc ata 23

<210> SEQ ID NO 207
<211> LENGTH: 20
<212> TYPE: DNA
<213> ORGANISM: Arabidopsis thaliana

<400> SEQUENCE: 207
ggatggtgag ggacgacgat 20

<210> SEQ ID NO 208
<211> LENGTH: 21
<212> TYPE: DNA
<213> ORGANISM: Arabidopsis thaliana

<400> SEQUENCE: 208
atcatgcgat ctctttggat t 21

<210> SEQ ID NO 209
<211> LENGTH: 20
<212> TYPE: DNA
<213> ORGANISM: Arabidopsis thaliana

<400> SEQUENCE: 209
tccgctgtag cacttcaggc 20

<210> SEQ ID NO 210
<211> LENGTH: 20
<212> TYPE: DNA
<213> ORGANISM: Arabidopsis thaliana

<400> SEQUENCE: 210
tcaatgcatt gaaagtgact 20

<210> SEQ ID NO 211
<211> LENGTH: 24
<212> TYPE: DNA
<213> ORGANISM: Arabidopsis thaliana

<400> SEQUENCE: 211
agcatatcat gatgtggttg gtgt 24

<210> SEQ ID NO 212
<211> LENGTH: 24
<212> TYPE: DNA
<213> ORGANISM: Arabidopsis thaliana

<400> SEQUENCE: 212
tggaaggatt acgggccatt gcct 24

<210> SEQ ID NO 213
<211> LENGTH: 24
<212> TYPE: DNA
<213> ORGANISM: Arabidopsis thaliana

<400> SEQUENCE: 213
aaccggatgt atgcagagat gatc 24

<210> SEQ ID NO 214
<211> LENGTH: 24
<212> TYPE: DNA
<213> ORGANISM: Arabidopsis thaliana

<400> SEQUENCE: 214
aggaaatact atgctgtaaa aagg 24

<210> SEQ ID NO 215
<211> LENGTH: 24
<212> TYPE: DNA
<213> ORGANISM: Arabidopsis thaliana

<400> SEQUENCE: 215
actaactaag gtactatgga ttgg 24

<210> SEQ ID NO 216
<211> LENGTH: 24
<212> TYPE: DNA
<213> ORGANISM: Arabidopsis thaliana

<400> SEQUENCE: 216
agaacagaga ccgttggaag aaaa 24

<210> SEQ ID NO 217
<211> LENGTH: 21
<212> TYPE: DNA
<213> ORGANISM: Arabidopsis thaliana

<400> SEQUENCE: 217
actttctgga gaccaaaccc t 21

<210> SEQ ID NO 218
<211> LENGTH: 21
<212> TYPE: DNA
<213> ORGANISM: Arabidopsis thaliana

<400> SEQUENCE: 218
tgcgggaagc atttgcacat g 21

<210> SEQ ID NO 219
<211> LENGTH: 21
<212> TYPE: DNA
<213> ORGANISM: Arabidopsis thaliana

<400> SEQUENCE: 219
tggattatgt aagagaggtg a 21

<210> SEQ ID NO 220
<211> LENGTH: 21
<212> TYPE: DNA
<213> ORGANISM: Arabidopsis thaliana

<400> SEQUENCE: 220
tgattgagcc gtgtcaatat c 21

<210> SEQ ID NO 221
<211> LENGTH: 22
<212> TYPE: DNA
<213> ORGANISM: Arabidopsis thaliana

<400> SEQUENCE: 221
tggtggaaca ctggctcggc cc 22

<210> SEQ ID NO 222
<211> LENGTH: 21
<212> TYPE: DNA
<213> ORGANISM: Arabidopsis thaliana

<400> SEQUENCE: 222
actcataaga tcgtgacacg t 21

<210> SEQ ID NO 223
<211> LENGTH: 24
<212> TYPE: DNA
<213> ORGANISM: Arabidopsis thaliana

<400> SEQUENCE: 223
taaacatctg atcgtttgat ttga 24

<210> SEQ ID NO 224
<211> LENGTH: 24
<212> TYPE: DNA
<213> ORGANISM: Arabidopsis thaliana

<400> SEQUENCE: 224
agagataaga aacgatagtc ggtt 24

<210> SEQ ID NO 225
<211> LENGTH: 26
<212> TYPE: DNA
<213> ORGANISM: Arabidopsis thaliana

<400> SEQUENCE: 225
ggcccacggg tcggatctgt tgtggc 26

<210> SEQ ID NO 226
<211> LENGTH: 24
<212> TYPE: DNA
<213> ORGANISM: Arabidopsis thaliana

<400> SEQUENCE: 226
aatatgtatg tgttggaagg gtgt 24

<210> SEQ ID NO 227
<211> LENGTH: 23
<212> TYPE: DNA
<213> ORGANISM: Arabidopsis thaliana

<400> SEQUENCE: 227
cgcggataat atgggcttga cca 23

<210> SEQ ID NO 228
<211> LENGTH: 22
<212> TYPE: DNA
<213> ORGANISM: Arabidopsis thaliana

<400> SEQUENCE: 228
gtcgaactca gtaacgcggg ct 22

<210> SEQ ID NO 229
<211> LENGTH: 21
<212> TYPE: DNA
<213> ORGANISM: Arabidopsis thaliana

<400> SEQUENCE: 229
ggtggaggag gaggcggcgg c 21

<210> SEQ ID NO 230
<211> LENGTH: 22
<212> TYPE: DNA
<213> ORGANISM: Arabidopsis thaliana

<400> SEQUENCE: 230
gagttaattg aacgttcggc gt 22

<210> SEQ ID NO 231
<211> LENGTH: 21
<212> TYPE: DNA
<213> ORGANISM: Arabidopsis thaliana

<400> SEQUENCE: 231
agttaattga acgttcggcg t 21

<210> SEQ ID NO 232
<211> LENGTH: 24
<212> TYPE: DNA
<213> ORGANISM: Arabidopsis thaliana

<400> SEQUENCE: 232
aagcacatgt gtagagtcga gcct 24

<210> SEQ ID NO 233
<211> LENGTH: 21
<212> TYPE: DNA
<213> ORGANISM: Arabidopsis thaliana

<400> SEQUENCE: 233
ttccacagct ttcttgaact t 21

<210> SEQ ID NO 234
<211> LENGTH: 23
<212> TYPE: DNA
<213> ORGANISM: Arabidopsis thaliana

<400> SEQUENCE: 234
ctgcacgggc ttggctcatc cca 23

<210> SEQ ID NO 235
<211> LENGTH: 24
<212> TYPE: DNA
<213> ORGANISM: Arabidopsis thaliana

<400> SEQUENCE: 235
aagctgtggt taactgaaaa agct 24

<210> SEQ ID NO 236
<211> LENGTH: 24
<212> TYPE: DNA
<213> ORGANISM: Arabidopsis thaliana

<400> SEQUENCE: 236
ataagagacg gaacactgga tatg 24

<210> SEQ ID NO 237
<211> LENGTH: 26
<212> TYPE: DNA

<213> ORGANISM: Arabidopsis thaliana

<400> SEQUENCE: 237
taaacaaact gtactttatg agagcc 26

<210> SEQ ID NO 238
<211> LENGTH: 21
<212> TYPE: DNA
<213> ORGANISM: Arabidopsis thaliana

<400> SEQUENCE: 238
cgggtttggc aggacgttac t 21

<210> SEQ ID NO 239
<211> LENGTH: 24
<212> TYPE: DNA
<213> ORGANISM: Arabidopsis thaliana

<400> SEQUENCE: 239
atctaaaccc gtcaattcta ggat 24

<210> SEQ ID NO 240
<211> LENGTH: 30
<212> TYPE: DNA
<213> ORGANISM: Arabidopsis thaliana

<400> SEQUENCE: 240
catgggcatc gacaccttgc ggctaggaac 30

<210> SEQ ID NO 241
<211> LENGTH: 22
<212> TYPE: DNA
<213> ORGANISM: Arabidopsis thaliana

<400> SEQUENCE: 241
gaagtcctcg tgttgcattc ct 22

<210> SEQ ID NO 242
<211> LENGTH: 24
<212> TYPE: DNA
<213> ORGANISM: Arabidopsis thaliana

<400> SEQUENCE: 242
aagcgaagga cccagcaggg aagc 24

<210> SEQ ID NO 243
<211> LENGTH: 21
<212> TYPE: DNA
<213> ORGANISM: Arabidopsis thaliana

<400> SEQUENCE: 243
cgtaaaaaaa gttgtaactc t 21

<210> SEQ ID NO 244
<211> LENGTH: 24
<212> TYPE: DNA
<213> ORGANISM: Arabidopsis thaliana

<400> SEQUENCE: 244
ctgcacggtc ttggctcaac ccgc 24

<210> SEQ ID NO 245
<211> LENGTH: 24

<212> TYPE: DNA
<213> ORGANISM: Arabidopsis thaliana

<400> SEQUENCE: 245
atgagagatt cggactatcc agcc 24

<210> SEQ ID NO 246
<211> LENGTH: 24
<212> TYPE: DNA
<213> ORGANISM: Arabidopsis thaliana

<400> SEQUENCE: 246
aacgaaccga ccgtcagaca tgga 24

<210> SEQ ID NO 247
<211> LENGTH: 21
<212> TYPE: DNA
<213> ORGANISM: Arabidopsis thaliana

<400> SEQUENCE: 247
tcggaccagg cttcattccc c 21

<210> SEQ ID NO 248
<211> LENGTH: 22
<212> TYPE: DNA
<213> ORGANISM: Arabidopsis thaliana

<400> SEQUENCE: 248
tccaatgtct tttctagttc gt 22

<210> SEQ ID NO 249
<211> LENGTH: 24
<212> TYPE: DNA
<213> ORGANISM: Arabidopsis thaliana

<400> SEQUENCE: 249
tccgctgtag cacacaggcc aatt 24

<210> SEQ ID NO 250
<211> LENGTH: 21
<212> TYPE: DNA
<213> ORGANISM: Arabidopsis thaliana

<400> SEQUENCE: 250
tcggaccagg cttcatcccc c 21

<210> SEQ ID NO 251
<211> LENGTH: 21
<212> TYPE: DNA
<213> ORGANISM: Arabidopsis thaliana

<400> SEQUENCE: 251
tttggattga agggagctct a 21

<210> SEQ ID NO 252
<211> LENGTH: 21
<212> TYPE: DNA
<213> ORGANISM: Arabidopsis thaliana

<400> SEQUENCE: 252
tttggattga agggagctct t 21

<210> SEQ ID NO 253

<211> LENGTH: 21
<212> TYPE: DNA
<213> ORGANISM: Arabidopsis thaliana

<400> SEQUENCE: 253
ttgacagaag atagagagca c 21

<210> SEQ ID NO 254
<211> LENGTH: 21
<212> TYPE: DNA
<213> ORGANISM: Arabidopsis thaliana

<400> SEQUENCE: 254
ttgaaagtga ctacatcggg g 21

<210> SEQ ID NO 255
<211> LENGTH: 21
<212> TYPE: DNA
<213> ORGANISM: Arabidopsis thaliana

<400> SEQUENCE: 255
tcgcttggtg caggtcggga a 21

<210> SEQ ID NO 256
<211> LENGTH: 21
<212> TYPE: DNA
<213> ORGANISM: Arabidopsis thaliana

<400> SEQUENCE: 256
tgaagctgcc agcatgatct a 21

<210> SEQ ID NO 257
<211> LENGTH: 29
<212> TYPE: DNA
<213> ORGANISM: Arabidopsis thaliana

<400> SEQUENCE: 257
tccgctgtag cacacaggcc aatttcact 29

<210> SEQ ID NO 258
<211> LENGTH: 22
<212> TYPE: DNA
<213> ORGANISM: Arabidopsis thaliana

<400> SEQUENCE: 258
tccgctgtag cacttcaggc ta 22

<210> SEQ ID NO 259
<211> LENGTH: 24
<212> TYPE: DNA
<213> ORGANISM: Arabidopsis thaliana

<400> SEQUENCE: 259
ttgaagagga cttggaactt cgat 24

<210> SEQ ID NO 260
<211> LENGTH: 21
<212> TYPE: DNA
<213> ORGANISM: Arabidopsis thaliana

<400> SEQUENCE: 260
ttctaagttc aacatatcga c 21

-continued

<210> SEQ ID NO 261
<211> LENGTH: 22
<212> TYPE: DNA
<213> ORGANISM: Arabidopsis thaliana

<400> SEQUENCE: 261
ttagattcac gcacaaactc gt 22

<210> SEQ ID NO 262
<211> LENGTH: 27
<212> TYPE: DNA
<213> ORGANISM: Arabidopsis thaliana

<400> SEQUENCE: 262
ctactgcacg gtcttggctc aacccgc 27

<210> SEQ ID NO 263
<211> LENGTH: 21
<212> TYPE: DNA
<213> ORGANISM: Arabidopsis thaliana

<400> SEQUENCE: 263
atcatgcgat ctctttggat t 21

<210> SEQ ID NO 264
<211> LENGTH: 20
<212> TYPE: DNA
<213> ORGANISM: Arabidopsis thaliana

<400> SEQUENCE: 264
tcccaaatgt agacaaagca 20

<210> SEQ ID NO 265
<211> LENGTH: 21
<212> TYPE: DNA
<213> ORGANISM: Arabidopsis thaliana

<400> SEQUENCE: 265
ttccacagct ttcttgaact g 21

<210> SEQ ID NO 266
<211> LENGTH: 21
<212> TYPE: DNA
<213> ORGANISM: Arabidopsis thaliana

<400> SEQUENCE: 266
cttagaatac gctatgttgg a 21

<210> SEQ ID NO 267
<211> LENGTH: 21
<212> TYPE: DNA
<213> ORGANISM: Arabidopsis thaliana

<400> SEQUENCE: 267
aactagaaaa gacattggac a 21

<210> SEQ ID NO 268
<211> LENGTH: 21
<212> TYPE: DNA
<213> ORGANISM: Arabidopsis thaliana

<400> SEQUENCE: 268
gaactagaaa agacattgga c 21

<210> SEQ ID NO 269
<211> LENGTH: 24
<212> TYPE: DNA
<213> ORGANISM: Arabidopsis thaliana

<400> SEQUENCE: 269
ctgcacggtc ttggctcaac ccgc 24

<210> SEQ ID NO 270
<211> LENGTH: 20
<212> TYPE: DNA
<213> ORGANISM: Arabidopsis thaliana

<400> SEQUENCE: 270
tccgctgtag cacacaggcc 20

<210> SEQ ID NO 271
<211> LENGTH: 24
<212> TYPE: DNA
<213> ORGANISM: Arabidopsis thaliana

<400> SEQUENCE: 271
attatggacc gtccaacttg gccc 24

<210> SEQ ID NO 272
<211> LENGTH: 25
<212> TYPE: DNA
<213> ORGANISM: Arabidopsis thaliana

<400> SEQUENCE: 272
ctactgcacg ggccggctca acccg 25

<210> SEQ ID NO 273
<211> LENGTH: 24
<212> TYPE: DNA
<213> ORGANISM: Arabidopsis thaliana

<400> SEQUENCE: 273
agaatacgct atgttggact taga 24

<210> SEQ ID NO 274
<211> LENGTH: 24
<212> TYPE: DNA
<213> ORGANISM: Arabidopsis thaliana

<400> SEQUENCE: 274
aaaccgcaac cggatcttaa aggc 24

<210> SEQ ID NO 275
<211> LENGTH: 21
<212> TYPE: DNA
<213> ORGANISM: Arabidopsis thaliana

<400> SEQUENCE: 275
cgatccccgg caacggcgcc a 21

<210> SEQ ID NO 276
<211> LENGTH: 21
<212> TYPE: DNA
<213> ORGANISM: Arabidopsis thaliana

<400> SEQUENCE: 276
ttgacagaag agagtgagca c 21

<210> SEQ ID NO 277
<211> LENGTH: 24
<212> TYPE: DNA
<213> ORGANISM: Arabidopsis thaliana

<400> SEQUENCE: 277
aacagcatcg tccatcattg aaga 24

<210> SEQ ID NO 278
<211> LENGTH: 21
<212> TYPE: DNA
<213> ORGANISM: Arabidopsis thaliana

<400> SEQUENCE: 278
ttccacagct ttcttgaact t 21

<210> SEQ ID NO 279
<211> LENGTH: 21
<212> TYPE: DNA
<213> ORGANISM: Arabidopsis thaliana

<400> SEQUENCE: 279
gttcaataaa gctgtgggaa g 21

<210> SEQ ID NO 280
<211> LENGTH: 24
<212> TYPE: DNA
<213> ORGANISM: Arabidopsis thaliana

<400> SEQUENCE: 280
aggatgaaag gtttgactag aact 24

<210> SEQ ID NO 281
<211> LENGTH: 21
<212> TYPE: DNA
<213> ORGANISM: Arabidopsis thaliana

<400> SEQUENCE: 281
agaatagaat ctgtaaaacg a 21

<210> SEQ ID NO 282
<211> LENGTH: 21
<212> TYPE: DNA
<213> ORGANISM: Arabidopsis thaliana

<400> SEQUENCE: 282
tttctagtgg gtcgtattca c 21

<210> SEQ ID NO 283
<211> LENGTH: 23
<212> TYPE: DNA
<213> ORGANISM: Arabidopsis thaliana

<400> SEQUENCE: 283
ctgcacggtc ttggctcaac ccg 23

<210> SEQ ID NO 284
<211> LENGTH: 24
<212> TYPE: DNA
<213> ORGANISM: Arabidopsis thaliana

<400> SEQUENCE: 284
aacgaaccga ccgtcagaca tgga 24

<210> SEQ ID NO 285
<211> LENGTH: 23
<212> TYPE: DNA
<213> ORGANISM: Arabidopsis thaliana

<400> SEQUENCE: 285
ctgcacgggc ttggctcatc cca 23

<210> SEQ ID NO 286
<211> LENGTH: 24
<212> TYPE: DNA
<213> ORGANISM: Arabidopsis thaliana

<400> SEQUENCE: 286
tgcacggtct tggctcaacc cgcc 24

<210> SEQ ID NO 287
<211> LENGTH: 26
<212> TYPE: DNA
<213> ORGANISM: Arabidopsis thaliana

<400> SEQUENCE: 287
tactgcacgg tcttggctca acccgc 26

<210> SEQ ID NO 288
<211> LENGTH: 26
<212> TYPE: DNA
<213> ORGANISM: Arabidopsis thaliana

<400> SEQUENCE: 288
ctactgcacg ggcttggctc atccca 26

<210> SEQ ID NO 289
<211> LENGTH: 21
<212> TYPE: DNA
<213> ORGANISM: Arabidopsis thaliana

<400> SEQUENCE: 289
gatcatgttc gcagtttcac c 21

<210> SEQ ID NO 290
<211> LENGTH: 24
<212> TYPE: DNA
<213> ORGANISM: Arabidopsis thaliana

<400> SEQUENCE: 290
aagcacatgt gtagagtcga gcct 24

<210> SEQ ID NO 291
<211> LENGTH: 21
<212> TYPE: DNA
<213> ORGANISM: Arabidopsis thaliana

<400> SEQUENCE: 291
tagcaactgt tctttagacg a 21

<210> SEQ ID NO 292
<211> LENGTH: 21
<212> TYPE: DNA
<213> ORGANISM: Arabidopsis thaliana

<400> SEQUENCE: 292
tttgcatata ctcgaatacc t 21

<210> SEQ ID NO 293
<211> LENGTH: 21
<212> TYPE: DNA
<213> ORGANISM: Arabidopsis thaliana

<400> SEQUENCE: 293
aagctcagga gggatagcgc c 21

<210> SEQ ID NO 294
<211> LENGTH: 22
<212> TYPE: DNA
<213> ORGANISM: Arabidopsis thaliana

<400> SEQUENCE: 294
aagatccgga ctacaacaaa gc 22

<210> SEQ ID NO 295
<211> LENGTH: 25
<212> TYPE: DNA
<213> ORGANISM: Arabidopsis thaliana

<400> SEQUENCE: 295
actgcacggt cttggctcaa cccgc 25

<210> SEQ ID NO 296
<211> LENGTH: 21
<212> TYPE: DNA
<213> ORGANISM: Arabidopsis thaliana

<400> SEQUENCE: 296
aacgtttaga aagagatggg g 21

<210> SEQ ID NO 297
<211> LENGTH: 20
<212> TYPE: DNA
<213> ORGANISM: Arabidopsis thaliana

<400> SEQUENCE: 297
tagccaagga tgacttgcct 20

<210> SEQ ID NO 298
<211> LENGTH: 26
<212> TYPE: DNA
<213> ORGANISM: Arabidopsis thaliana

<400> SEQUENCE: 298
ctactgcacg ggccggctca acccgc 26

<210> SEQ ID NO 299
<211> LENGTH: 21
<212> TYPE: DNA
<213> ORGANISM: Arabidopsis thaliana

<400> SEQUENCE: 299
agaatacgct atgttggact t 21

<210> SEQ ID NO 300
<211> LENGTH: 27
<212> TYPE: DNA
<213> ORGANISM: Arabidopsis thaliana

<400> SEQUENCE: 300
agtaacgcgg gcttgtgatc caagtgg 27

<210> SEQ ID NO 301
<211> LENGTH: 24
<212> TYPE: DNA
<213> ORGANISM: Arabidopsis thaliana

<400> SEQUENCE: 301
aagcgcggaa agaacagtag atgc 24

<210> SEQ ID NO 302
<211> LENGTH: 21
<212> TYPE: DNA
<213> ORGANISM: Arabidopsis thaliana

<400> SEQUENCE: 302
acggtatctc tcctacgtag c 21

<210> SEQ ID NO 303
<211> LENGTH: 21
<212> TYPE: DNA
<213> ORGANISM: Arabidopsis thaliana

<400> SEQUENCE: 303
aatgggagat gtccggaatg a 21

<210> SEQ ID NO 304
<211> LENGTH: 24
<212> TYPE: DNA
<213> ORGANISM: Arabidopsis thaliana

<400> SEQUENCE: 304
agaacagaga ccgttggaag aaaa 24

<210> SEQ ID NO 305
<211> LENGTH: 23
<212> TYPE: DNA
<213> ORGANISM: Arabidopsis thaliana

<400> SEQUENCE: 305
agagataaga aacgatagtc ggt 23

<210> SEQ ID NO 306
<211> LENGTH: 21
<212> TYPE: DNA
<213> ORGANISM: Arabidopsis thaliana

<400> SEQUENCE: 306
ataagactga aacatatatg t 21

<210> SEQ ID NO 307
<211> LENGTH: 24
<212> TYPE: DNA
<213> ORGANISM: Arabidopsis thaliana

<400> SEQUENCE: 307
gttcgatccc cggcaacggc gcca 24

<210> SEQ ID NO 308
<211> LENGTH: 23
<212> TYPE: DNA
<213> ORGANISM: Arabidopsis thaliana

<400> SEQUENCE: 308
aactaaaccg gaacagtgta cct 23

<210> SEQ ID NO 309
<211> LENGTH: 22
<212> TYPE: DNA
<213> ORGANISM: Arabidopsis thaliana

<400> SEQUENCE: 309
tggtggaaca ctggctcggc cc 22

<210> SEQ ID NO 310
<211> LENGTH: 21
<212> TYPE: DNA
<213> ORGANISM: Arabidopsis thaliana

<400> SEQUENCE: 310
tcgataaacc tctgcatcca g 21

<210> SEQ ID NO 311
<211> LENGTH: 23
<212> TYPE: DNA
<213> ORGANISM: Arabidopsis thaliana

<400> SEQUENCE: 311
aaacatctga tcgtttgact tga 23

<210> SEQ ID NO 312
<211> LENGTH: 23
<212> TYPE: DNA
<213> ORGANISM: Arabidopsis thaliana

<400> SEQUENCE: 312
ctggaatact tgaactacca tct 23

<210> SEQ ID NO 313
<211> LENGTH: 21
<212> TYPE: DNA
<213> ORGANISM: Arabidopsis thaliana

<400> SEQUENCE: 313
cgggtttggc aggacgttac t 21

<210> SEQ ID NO 314
<211> LENGTH: 23
<212> TYPE: DNA
<213> ORGANISM: Arabidopsis thaliana

<400> SEQUENCE: 314
aagacaatca gcacggacat tgt 23

<210> SEQ ID NO 315
<211> LENGTH: 25
<212> TYPE: DNA
<213> ORGANISM: Arabidopsis thaliana

<400> SEQUENCE: 315
ggggacatta agatggtgga acact 25

<210> SEQ ID NO 316
<211> LENGTH: 24
<212> TYPE: DNA

<213> ORGANISM: Arabidopsis thaliana

<400> SEQUENCE: 316
atgagagatt cggactatcc agcc 24

<210> SEQ ID NO 317
<211> LENGTH: 23
<212> TYPE: DNA
<213> ORGANISM: Arabidopsis thaliana

<400> SEQUENCE: 317
ctagttcgtc gatatgttga act 23

<210> SEQ ID NO 318
<211> LENGTH: 25
<212> TYPE: DNA
<213> ORGANISM: Arabidopsis thaliana

<400> SEQUENCE: 318
tactgcacgg gccggctcaa cccgc 25

<210> SEQ ID NO 319
<211> LENGTH: 21
<212> TYPE: DNA
<213> ORGANISM: Arabidopsis thaliana

<400> SEQUENCE: 319
gggttgatat gagaacacac g 21

<210> SEQ ID NO 320
<211> LENGTH: 22
<212> TYPE: DNA
<213> ORGANISM: Arabidopsis thaliana

<400> SEQUENCE: 320
acttagaata cgctatgttg ga 22

<210> SEQ ID NO 321
<211> LENGTH: 24
<212> TYPE: DNA
<213> ORGANISM: Arabidopsis thaliana

<400> SEQUENCE: 321
tgttcgatcc acgctcaccg cacc 24

<210> SEQ ID NO 322
<211> LENGTH: 27
<212> TYPE: DNA
<213> ORGANISM: Arabidopsis thaliana

<400> SEQUENCE: 322
aacgaaggac ctatgggtga aacgctt 27

<210> SEQ ID NO 323
<211> LENGTH: 21
<212> TYPE: DNA
<213> ORGANISM: Arabidopsis thaliana

<400> SEQUENCE: 323
aaacgtttag aaagagatgg g 21

<210> SEQ ID NO 324
<211> LENGTH: 25

<212> TYPE: DNA
<213> ORGANISM: Arabidopsis thaliana

<400> SEQUENCE: 324
ggggacatta agatggtggg acact 25

<210> SEQ ID NO 325
<211> LENGTH: 23
<212> TYPE: DNA
<213> ORGANISM: Arabidopsis thaliana

<400> SEQUENCE: 325
gaatgacaca tgtaaacatc tga 23

<210> SEQ ID NO 326
<211> LENGTH: 26
<212> TYPE: DNA
<213> ORGANISM: Arabidopsis thaliana

<400> SEQUENCE: 326
gtgctttggc gagagtagta ctagga 26

<210> SEQ ID NO 327
<211> LENGTH: 22
<212> TYPE: DNA
<213> ORGANISM: Arabidopsis thaliana

<400> SEQUENCE: 327
gagggacgac gatttgtgac ac 22

<210> SEQ ID NO 328
<211> LENGTH: 22
<212> TYPE: DNA
<213> ORGANISM: Arabidopsis thaliana

<400> SEQUENCE: 328
gtcgaactca gtaacgcggg ct 22

<210> SEQ ID NO 329
<211> LENGTH: 21
<212> TYPE: DNA
<213> ORGANISM: Arabidopsis thaliana

<400> SEQUENCE: 329
tatcaagatc catcttactc t 21

<210> SEQ ID NO 330
<211> LENGTH: 23
<212> TYPE: DNA
<213> ORGANISM: Arabidopsis thaliana

<400> SEQUENCE: 330
gttcgatcca cgctcaccgc acc 23

<210> SEQ ID NO 331
<211> LENGTH: 23
<212> TYPE: DNA
<213> ORGANISM: Arabidopsis thaliana

<400> SEQUENCE: 331
aatgtctgtt ggtgccaaga ggg 23

<210> SEQ ID NO 332

<211> LENGTH: 23
<212> TYPE: DNA
<213> ORGANISM: Arabidopsis thaliana

<400> SEQUENCE: 332
gttcgatccc cggcaacggc gcc 23

<210> SEQ ID NO 333
<211> LENGTH: 20
<212> TYPE: DNA
<213> ORGANISM: Arabidopsis thaliana

<400> SEQUENCE: 333
cgatccccgg caacggcgcc 20

<210> SEQ ID NO 334
<211> LENGTH: 26
<212> TYPE: DNA
<213> ORGANISM: Arabidopsis thaliana

<400> SEQUENCE: 334
aacgaaggac ctatgggtga aacgct 26

<210> SEQ ID NO 335
<211> LENGTH: 29
<212> TYPE: DNA
<213> ORGANISM: Arabidopsis thaliana

<400> SEQUENCE: 335
gatgggacgt tgggtcgatc tcattgggc 29

<210> SEQ ID NO 336
<211> LENGTH: 23
<212> TYPE: DNA
<213> ORGANISM: Arabidopsis thaliana

<400> SEQUENCE: 336
agagaggaca gaagaaacta ccc 23

<210> SEQ ID NO 337
<211> LENGTH: 23
<212> TYPE: DNA
<213> ORGANISM: Arabidopsis thaliana

<400> SEQUENCE: 337
aaaccggaac agtgtaccta act 23

<210> SEQ ID NO 338
<211> LENGTH: 23
<212> TYPE: DNA
<213> ORGANISM: Arabidopsis thaliana

<400> SEQUENCE: 338
ctgcacgggc cggctcaacc cgc 23

<210> SEQ ID NO 339
<211> LENGTH: 25
<212> TYPE: DNA
<213> ORGANISM: Arabidopsis thaliana

<400> SEQUENCE: 339
gcccacgggt cggatctgtt gtggc 25

<210> SEQ ID NO 340
<211> LENGTH: 21
<212> TYPE: DNA
<213> ORGANISM: Arabidopsis thaliana

<400> SEQUENCE: 340
ggagggtcga atcttagcga c 21

<210> SEQ ID NO 341
<211> LENGTH: 23
<212> TYPE: DNA
<213> ORGANISM: Arabidopsis thaliana

<400> SEQUENCE: 341
aagtaacgtc ctgccaaacc cgt 23

<210> SEQ ID NO 342
<211> LENGTH: 23
<212> TYPE: DNA
<213> ORGANISM: Arabidopsis thaliana

<400> SEQUENCE: 342
gtatcgttcc aattttatcg gat 23

<210> SEQ ID NO 343
<211> LENGTH: 23
<212> TYPE: DNA
<213> ORGANISM: Arabidopsis thaliana

<400> SEQUENCE: 343
tagcaactgt tctttagacg act 23

<210> SEQ ID NO 344
<211> LENGTH: 23
<212> TYPE: DNA
<213> ORGANISM: Arabidopsis thaliana

<400> SEQUENCE: 344
aaggaggtgg aaatgatgat att 23

<210> SEQ ID NO 345
<211> LENGTH: 20
<212> TYPE: DNA
<213> ORGANISM: Arabidopsis thaliana

<400> SEQUENCE: 345
gggttgatat gagaacacac 20

<210> SEQ ID NO 346
<211> LENGTH: 23
<212> TYPE: DNA
<213> ORGANISM: Arabidopsis thaliana

<400> SEQUENCE: 346
aaccatatct tttgtcggaa gat 23

<210> SEQ ID NO 347
<211> LENGTH: 22
<212> TYPE: DNA
<213> ORGANISM: Arabidopsis thaliana

<400> SEQUENCE: 347
gctcgttccc agctggacca cc 22

<210> SEQ ID NO 348
<211> LENGTH: 24
<212> TYPE: DNA
<213> ORGANISM: Arabidopsis thaliana

<400> SEQUENCE: 348
gatatgatcg atgttcctaa atta 24

<210> SEQ ID NO 349
<211> LENGTH: 23
<212> TYPE: DNA
<213> ORGANISM: Arabidopsis thaliana

<400> SEQUENCE: 349
agcggttgtt agcgattggc acc 23

<210> SEQ ID NO 350
<211> LENGTH: 22
<212> TYPE: DNA
<213> ORGANISM: Arabidopsis thaliana

<400> SEQUENCE: 350
gcacggtctt ggctcaaccc gc 22

<210> SEQ ID NO 351
<211> LENGTH: 23
<212> TYPE: DNA
<213> ORGANISM: Arabidopsis thaliana

<400> SEQUENCE: 351
gggagggtgc tatgcttaag gtc 23

<210> SEQ ID NO 352
<211> LENGTH: 23
<212> TYPE: DNA
<213> ORGANISM: Arabidopsis thaliana

<400> SEQUENCE: 352
ggtcaagtct gttgagatgc acc 23

<210> SEQ ID NO 353
<211> LENGTH: 20
<212> TYPE: DNA
<213> ORGANISM: Arabidopsis thaliana

<400> SEQUENCE: 353
gctcgggtct catgtcttct 20

<210> SEQ ID NO 354
<211> LENGTH: 26
<212> TYPE: DNA
<213> ORGANISM: Arabidopsis thaliana

<400> SEQUENCE: 354
gtgcttgggc gatagtagta ctagga 26

<210> SEQ ID NO 355
<211> LENGTH: 22
<212> TYPE: DNA
<213> ORGANISM: Arabidopsis thaliana

<400> SEQUENCE: 355
tgtccgtgct gattgtcttg ct 22

<210> SEQ ID NO 356
<211> LENGTH: 23
<212> TYPE: DNA
<213> ORGANISM: Arabidopsis thaliana

<400> SEQUENCE: 356
agtgcattcg ggtcatatgg tac 23

<210> SEQ ID NO 357
<211> LENGTH: 20
<212> TYPE: DNA
<213> ORGANISM: Arabidopsis thaliana

<400> SEQUENCE: 357
gggacgggtt tggcaggacg 20

<210> SEQ ID NO 358
<211> LENGTH: 23
<212> TYPE: DNA
<213> ORGANISM: Arabidopsis thaliana

<400> SEQUENCE: 358
acttatttac aatggctgcc act 23

<210> SEQ ID NO 359
<211> LENGTH: 28
<212> TYPE: DNA
<213> ORGANISM: Arabidopsis thaliana

<400> SEQUENCE: 359
gaggcaagtt ctttgacccg ttaggact 28

<210> SEQ ID NO 360
<211> LENGTH: 21
<212> TYPE: DNA
<213> ORGANISM: Arabidopsis thaliana

<400> SEQUENCE: 360
ggtgccaaga gggaaaaggg c 21

<210> SEQ ID NO 361
<211> LENGTH: 21
<212> TYPE: DNA
<213> ORGANISM: Arabidopsis thaliana

<400> SEQUENCE: 361
gaggactacg atgttggtga t 21

<210> SEQ ID NO 362
<211> LENGTH: 23
<212> TYPE: DNA
<213> ORGANISM: Arabidopsis thaliana

<400> SEQUENCE: 362
aaccggatct taaaggcgta aga 23

<210> SEQ ID NO 363
<211> LENGTH: 23
<212> TYPE: DNA
<213> ORGANISM: Arabidopsis thaliana

<400> SEQUENCE: 363

-continued atgcacgtga aaaaacgcgg act 23

<210> SEQ ID NO 364
<211> LENGTH: 22
<212> TYPE: DNA
<213> ORGANISM: Arabidopsis thaliana

<400> SEQUENCE: 364
tgcacgggcc ggctcaaccc gc 22

<210> SEQ ID NO 365
<211> LENGTH: 23
<212> TYPE: DNA
<213> ORGANISM: Arabidopsis thaliana

<400> SEQUENCE: 365
aaccgtgact gatttgtttc ata 23

<210> SEQ ID NO 366
<211> LENGTH: 23
<212> TYPE: DNA
<213> ORGANISM: Arabidopsis thaliana

<400> SEQUENCE: 366
ttcgatcccc ggcaacggcg cca 23

<210> SEQ ID NO 367
<211> LENGTH: 21
<212> TYPE: DNA
<213> ORGANISM: Arabidopsis thaliana

<400> SEQUENCE: 367
tgacatggga ctgcctaagc t 21

<210> SEQ ID NO 368
<211> LENGTH: 25
<212> TYPE: DNA
<213> ORGANISM: Arabidopsis thaliana

<400> SEQUENCE: 368
ggggacattt agatggtgga acact 25

<210> SEQ ID NO 369
<211> LENGTH: 22
<212> TYPE: DNA
<213> ORGANISM: Arabidopsis thaliana

<400> SEQUENCE: 369
gtttggcagg acgttactta at 22

<210> SEQ ID NO 370
<211> LENGTH: 24
<212> TYPE: DNA
<213> ORGANISM: Arabidopsis thaliana

<400> SEQUENCE: 370
tgcacgggct tggctcatcc catc 24

<210> SEQ ID NO 371
<211> LENGTH: 23
<212> TYPE: DNA
<213> ORGANISM: Arabidopsis thaliana

<400> SEQUENCE: 371
gtttggcagg acgttactta ata 23

<210> SEQ ID NO 372
<211> LENGTH: 22
<212> TYPE: DNA
<213> ORGANISM: Arabidopsis thaliana

<400> SEQUENCE: 372
ctgcacgggc cggctcaacc cg 22

<210> SEQ ID NO 373
<211> LENGTH: 23
<212> TYPE: DNA
<213> ORGANISM: Arabidopsis thaliana

<400> SEQUENCE: 373
aacagcatcg tccatcattg aag 23

<210> SEQ ID NO 374
<211> LENGTH: 22
<212> TYPE: DNA
<213> ORGANISM: Arabidopsis thaliana

<400> SEQUENCE: 374
gagggaaaag ggctattaag ct 22

<210> SEQ ID NO 375
<211> LENGTH: 22
<212> TYPE: DNA
<213> ORGANISM: Arabidopsis thaliana

<400> SEQUENCE: 375
gtaaacatct gatcgtttga ct 22

<210> SEQ ID NO 376
<211> LENGTH: 20
<212> TYPE: DNA
<213> ORGANISM: Arabidopsis thaliana

<400> SEQUENCE: 376
gaatacttga actaccatct 20

<210> SEQ ID NO 377
<211> LENGTH: 21
<212> TYPE: DNA
<213> ORGANISM: Arabidopsis thaliana

<400> SEQUENCE: 377
ttagatgacc atcaacaaac t 21

<210> SEQ ID NO 378
<211> LENGTH: 23
<212> TYPE: DNA
<213> ORGANISM: Arabidopsis thaliana

<400> SEQUENCE: 378
ggtttcgatc ccgacaatga cct 23

<210> SEQ ID NO 379
<211> LENGTH: 22
<212> TYPE: DNA
<213> ORGANISM: Arabidopsis thaliana

<400> SEQUENCE: 379
gagtgacgct tgggacgaaa ct 22

<210> SEQ ID NO 380
<211> LENGTH: 23
<212> TYPE: DNA
<213> ORGANISM: Arabidopsis thaliana

<400> SEQUENCE: 380
aggctgtgaa cggtaaccaa aac 23

<210> SEQ ID NO 381
<211> LENGTH: 22
<212> TYPE: DNA
<213> ORGANISM: Arabidopsis thaliana

<400> SEQUENCE: 381
cacggtctaa aagttatgga gt 22

<210> SEQ ID NO 382
<211> LENGTH: 23
<212> TYPE: DNA
<213> ORGANISM: Arabidopsis thaliana

<400> SEQUENCE: 382
tctagttcgt cgatatgttg aac 23

<210> SEQ ID NO 383
<211> LENGTH: 21
<212> TYPE: DNA
<213> ORGANISM: Arabidopsis thaliana

<400> SEQUENCE: 383
actcataaga tcgtgacacg t 21

<210> SEQ ID NO 384
<211> LENGTH: 20
<212> TYPE: DNA
<213> ORGANISM: Arabidopsis thaliana

<400> SEQUENCE: 384
gttttggaca ggtatcgaca 20

<210> SEQ ID NO 385
<211> LENGTH: 23
<212> TYPE: DNA
<213> ORGANISM: Arabidopsis thaliana

<400> SEQUENCE: 385
gaagaggata gttgttacgc act 23

<210> SEQ ID NO 386
<211> LENGTH: 23
<212> TYPE: DNA
<213> ORGANISM: Arabidopsis thaliana

<400> SEQUENCE: 386
atcaccgttg agagaagtac tgg 23

<210> SEQ ID NO 387
<211> LENGTH: 23
<212> TYPE: DNA
<213> ORGANISM: Arabidopsis thaliana

<400> SEQUENCE: 387
aggaggttct ggccgaagcc cgt 23

<210> SEQ ID NO 388
<211> LENGTH: 23
<212> TYPE: DNA
<213> ORGANISM: Arabidopsis thaliana

<400> SEQUENCE: 388
ctcacggtct aaaagttatg gag 23

<210> SEQ ID NO 389
<211> LENGTH: 21
<212> TYPE: DNA
<213> ORGANISM: Arabidopsis thaliana

<400> SEQUENCE: 389
tatatgtttc agtcttatcc c 21

<210> SEQ ID NO 390
<211> LENGTH: 22
<212> TYPE: DNA
<213> ORGANISM: Arabidopsis thaliana

<400> SEQUENCE: 390
gtctaatgat tgtgaagtgc ct 22

<210> SEQ ID NO 391
<211> LENGTH: 23
<212> TYPE: DNA
<213> ORGANISM: Arabidopsis thaliana

<400> SEQUENCE: 391
tgacgagaga acttattggc ctt 23

<210> SEQ ID NO 392
<211> LENGTH: 22
<212> TYPE: DNA
<213> ORGANISM: Arabidopsis thaliana

<400> SEQUENCE: 392
ccggccaact gtacatatac at 22

<210> SEQ ID NO 393
<211> LENGTH: 23
<212> TYPE: DNA
<213> ORGANISM: Arabidopsis thaliana

<400> SEQUENCE: 393
gatccatgta agtcttaggc tgt 23

<210> SEQ ID NO 394
<211> LENGTH: 23
<212> TYPE: DNA
<213> ORGANISM: Arabidopsis thaliana

<400> SEQUENCE: 394
ggaagggtgc ttagcctaag gtc 23

<210> SEQ ID NO 395
<211> LENGTH: 23
<212> TYPE: DNA

<213> ORGANISM: Arabidopsis thaliana

<400> SEQUENCE: 395
gtatgatcgc atccgttagt ata 23

<210> SEQ ID NO 396
<211> LENGTH: 23
<212> TYPE: DNA
<213> ORGANISM: Arabidopsis thaliana

<400> SEQUENCE: 396
aaccttgaag caaactggac agg 23

<210> SEQ ID NO 397
<211> LENGTH: 21
<212> TYPE: DNA
<213> ORGANISM: Arabidopsis thaliana

<400> SEQUENCE: 397
cgtaaaaaaa gttgtaactc t 21

<210> SEQ ID NO 398
<211> LENGTH: 23
<212> TYPE: DNA
<213> ORGANISM: Arabidopsis thaliana

<400> SEQUENCE: 398
aacgaaccga ccgtcagaca tgg 23

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 399
gcggcggtcc aatgtctttt c 21

<210> SEQ ID NO 400
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 400
gtcgtatcca gtgcagggtc cgaggtattc gcactggata cgacacgaac 50

<210> SEQ ID NO 401
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 401
gcggcggaga atacgctatg ttgg 24

<210> SEQ ID NO 402
<211> LENGTH: 50
<212> TYPE: DNA

<213> ORGANISM: Artificial Sequence
<220> FEATURE:
<223> OTHER INFORMATION: Description of Artificial Sequence: Synthetic
primer

<400> SEQUENCE: 402
gtcgtatcca gtgcagggtc cgaggtattc gcactggata cgactctaag 50

<210> SEQ ID NO 403
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 403
gcggcggcgt aaaaaaagtt g 21

<210> SEQ ID NO 404
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 404
gtcgtatcca gtgcagggtc cgaggtattc gcactggata cgacagagtt 50

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 405
gcggcggaca cgatgttcaa t 21

<210> SEQ ID NO 406
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 406
gtcgtatcca gtgcagggtc cgaggtattc gcactggata cgactaaatc 50

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 407
gcggcgggtc gaactcagta a 21

<210> SEQ ID NO 408
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
gtcgtatcca gtgcagggtc cgaggtattc gcactggata cgacgcccgc 50

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
ggcggtcgga ccaggcttc 19

<210> SEQ ID NO 410
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
gtcgtatcca gtgcagggtc cgaggtattc gcactggata cgacggggaa 50

<210> SEQ ID NO 411
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
ctcgtattgc gggaagcatt t 21

<210> SEQ ID NO 412
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
gtcgtatcca gtgcagggtc cgaggtattc gcactggata cgaccatgtg 50

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
acaatcctat ctttcggaag c 21

<210> SEQ ID NO 414
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 414
agactcttct tcttgaagac ag 22

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
gattgtgcaa agtctcaaca 20

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
attgggtttg actatatgtc tta 23

<210> SEQ ID NO 417
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
gtgcagggtc cgaggt 16

<210> SEQ ID NO 418
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
gccttggcac ccgagaattc ca 22

<210> SEQ ID NO 419
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
tcgaatcttt gaacgcacat tgcgc 25

<210> SEQ ID NO 420
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 420
tggcagaagc acaccgagaa cctg 24

<210> SEQ ID NO 421
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 421
cttatcggat ttctctatgt ttggc 25

<210> SEQ ID NO 422
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 422
gagctcctgt ttatttaact tgtacatacc 30

<210> SEQ ID NO 423
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 423
tgctccagaa gctttgttcc aa 22

<210> SEQ ID NO 424
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 424
tcggagatac ctgggtacat ag 22

<210> SEQ ID NO 425
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 425
cagtggtcgt acaaccggta tt 22

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 426
gtctcttaca atttcccgct ct 22

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 427
ggaagaagaa gacttacacc 20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 428
agtccacact taccacagta 20

<210> SEQ ID NO 429
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 429
ttggactctc acttgtctca tca 23

<210> SEQ ID NO 430
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 430
atcagccata gcagtcgata aac 23

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 431
gacgttgtca tggagggact 20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 432
actttccttt cctggggcag 20

<210> SEQ ID NO 433
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 433
gcggcattgt aaatgactac ttc 23

<210> SEQ ID NO 434
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 434
catcctccaa taaattcttc acg 23

<210> SEQ ID NO 435
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 435
gatttggctc agatcaagaa aga 23

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 436
accttaccct tctccaactc aac 23

<210> SEQ ID NO 437
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 437
cacaacggga acacacact 19

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 438
tcctgaaagc acagcaacca 20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 439
ggttgctgca agccctctaa 20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 440
cttttccatg cggccttgag 20

<210> SEQ ID NO 441
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 441
atctgaggta ccggtagtgt tgatcctgtg agctaaa 37

<210> SEQ ID NO 442
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 442
atctgactcg agtatcagat tttccttcag tgactcc 37

<210> SEQ ID NO 443
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 443
atctgactgc agacgatcaa atctagtcct tttgagg 37

<210> SEQ ID NO 444
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 444
atctgatcta gaggaatttg tatgagagcg agttttc 37

<210> SEQ ID NO 445
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 445
atctgaggta ccgatcttac agaacaagga atgagga 37

<210> SEQ ID NO 446
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 446
atctgactcg agcaggtgtg tatggcggca tgtt 34

<210> SEQ ID NO 447
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 447
atctgagaat tctctccaag acaataagag cacagtt 37

<210> SEQ ID NO 448
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 448
atcccatcta gaataaaatg ctgcatttgg atca 34

<210> SEQ ID NO 449
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 449
atctgaggta ccaccaaact ctgtaattcc ctctctt 37

<210> SEQ ID NO 450
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 450
atctgagtcg acgtctataa ctccctccga ccagt 35

```
<210> SEQ ID NO 451
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451

atctgactgc agcgaattct acgagatatc agagcag                              37


<210> SEQ ID NO 452
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452

atctgatcta gaactaaaca gcagcagaaa agatgag                              37


<210> SEQ ID NO 453
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453

caccatggct cgttgtagca acaatc                                          26


<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454

aggcttatat ccgtaggtac                                                 20


<210> SEQ ID NO 455
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455

caccatggta cgttttagta acagtc                                          26


<210> SEQ ID NO 456
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456

agaattgttg aaaccattgg aac                                             23
```

<210> SEQ ID NO 457
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 457
gatccaatgt cttttctagt tcgttctctc ttttgtattc c 41

<210> SEQ ID NO 458
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 458
gaacgaacta gaaaagacat tggatcaaag agaatcaatg a 41

<210> SEQ ID NO 459
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 459
gaacaaacta gaaaacacat tggatcacag gtcgtgatat g 41

<210> SEQ ID NO 460
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 460
gatccaatgt gttttctagt ttgttctaca tatatattcc t 41

<210> SEQ ID NO 461
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 461
gacgtaaaaa aagttgtaac tcttctctct tttgtattcc 40

<210> SEQ ID NO 462
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 462
gaagagttac aacttttttt acgtcaaaga gaatcaatga 40

<210> SEQ ID NO 463
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 463
gaagcgttac aacttatttt acgtcacagg tcgtgatatg 40

<210> SEQ ID NO 464
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 464
gacgtaaaat aagttgtaac gcttctacat atatattcct 40

<210> SEQ ID NO 465
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 465
gatctgttac taaaacgtac cactctctct tttgtattcc 40

<210> SEQ ID NO 466
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 466
gagtggtacg ttttagtaac agatcaaaga gaatcaatga 40

<210> SEQ ID NO 467
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 467
gagtagtacg ttttactaac agttcacagg tcgtgatatg 40

<210> SEQ ID NO 468
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 468
gaactgttag taaaacgtac tactctacat atatattcct 40

CONTROLLING FUNGAL PATHOGENS USING RNAI-BASED STRATEGY

CROSS-REFERENCE TO RELATED PATENT APPLICATIONS

This application is a U.S. National Stage Application of PCT/US2018/054412, International Filing Date Oct. 4, 2018 and which claims benefit of priority to U.S. Provisional Patent Application No. 62/573,546, filed Oct. 17, 2017, which is incorporated by reference for all purposes.

STATEMENT AS TO RIGHTS TO INVENTIONS MADE UNDER FEDERALLY SPONSORED RESEARCH AND DEVELOPMENT

This invention was made with Government support under National Institutes of Health Grant No. R01 GM093008-07 and National Science Foundation award number 1557812. The government has certain rights in this invention.

SEQUENCE LISTING

The instant application contains a Sequence Listing which has been submitted electronically in ASCII format and is hereby incorporated by reference in its entirety. Said ASCII copy, created on Mar. 25, 2020, is named 081906-1180048_SL.txt and is 373,832 bytes in size.

BACKGROUND OF THE INVENTION

Pathogens and pests cause diseases on humans, animals and plants, posing serious threats to global health and crop production. Animal and plant hosts have also evolved various immune mechanisms to fight against infection. It has been long known that proteins and metabolites, such as effectors from the pathogens and pests (Cui, H. T. et al., *Annual Review of Plant Biology, Vol* 66 66, 487-511, doi: 10.1146/annurev-arplant-050213-040012 (2015); Stuart, J., *Curr Opin Insect Sci* 9, 56-61, doi: 10.1016/j.cois.2015.02.010 (2015)), or antimicrobial molecules from the hosts (Lehrer, R. I. and Ganz, T., *Current opinion in immunology* 11, 23-27 (1999); Hegedus, N. and Marx, F., *Fungal Biol Rev* 26, 132-145, doi:10.1016/j.fbr.2012.07.002 (2013)), move from pathogens/pests to hosts and vice versa to manipulate cellular processes and protein functions in the interacting organism. Recently, it has been established that mobile small RNAs (s R N A s) can induce gene silencing in interacting organisms, a phenomenon called cross-kingdom RNAi or cross-organism RNAi (Weiberg, A. et al., *Current opinion in biotechnology* 32, 207-215, doi:10.1016/j.copbio.2014.12.025 (2015); Wang, M. et al., *Curr Opin Plant Biol* 38, 133-141, doi:10.1016/j.pbi.2017.05.003 (2017); Buck, A. H. et al., *Nature communications* 5, 5488, doi:10.1038/ncomms6488 (2014)). But how do these mobile sRNAs travel across the boundaries between organisms? Within the bodies of animal organisms, sRNAs are transported between cells and systemically by a variety of mechanisms, including extracellular vesicles (EVs), specific transmembrane proteins, high-density lipoprotein complexes, gap junctions, and other transport mechanisms (Mittelbrunn, M. and Sanchez-Madrid, F., *Nature reviews. Molecular cell biology* 13, 328-335, doi:10.1038/nrm3335 (2012)). In most animal circulation systems and body fluids, a class of extracellular vesicles called exosomes play an important role in sRNA trafficking and host immunity. For example, mammalian cells, such as B-cells, T-cells, or dendritic cells secrete sRNA-containing exosomes and transport sRNAs into recipient cells to modulate immunity (Robbins, P. D. and Morelli, A. E., *Nature reviews. Immunology* 14, 195-208, doi:10.1038/nri3622 (2014)). Within a plant, sRNAs travel systemically through vasculature or move from cell to cell likely through cytoplasmic channels called plasmodesmata (Molnar, A. et al., *Science* 328, 872-875, doi:10.1126/science.1187959 (2010)). Much less is known about the sRNA trafficking pathways between interacting organisms. A case in point is the gastrointestinal nematode *Heligmosomoides polygyrus* that secretes exosomes to transport miRNAs into mammalian cells to suppress host immunity (Buck, A. H. et al., *Nature communications* 5, 5488, doi:10.1038/ncomms6488 (2014)). In contrast, the mechanism by which sRNAs are transported from hosts to interacting pathogens and pests is unclear.

In the case of plants interacting with their pathogens and pests, it has been observed in many pathosystems that sRNAs derived from transgenes can successfully move from plant cells and silence virulence genes of their invaders to inhibit infection. This so-called host-induced gene silencing has become an effective method for crop protection (Wang, M. et al., *Curr Opin Plant Biol* 38, 133-141, doi:10.1016/j.pbi.2017.05.003 (2017); Nunes, C. C. and Dean, R. A., *Molecular Plant Pathology* 13, 519-529, doi:10.1111/j.1364-3703.2011.00766.x (2012)). However, studies of cross-kingdom trafficking of plant endogenous sRNAs are still limited, and have mostly concerned abundant microRNAs (miRNAs) (Zhang, T. et al., *Nature plants* 2, 16153, doi:10.1038/nplants.2016.153 (2016); Zhu, K. et al., *PLoS Genet* 13, e1006946, doi:10.1371/journal.pgen.1006946 (2017)). This is likely attributable to the challenges associated with separating and purifying pathogen cells from infected tissues.

BRIEF SUMMARY OF THE INVENTION

The present application provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide that inhibits fungal expression of one or more target genes as listed in Table 1 or Table 2, wherein the plant has increased resistance to a fungal pathogen compared to a control plant lacking the expression cassette.

In some embodiments, the plant comprises two, three, four or more heterologous expression cassettes, wherein each expression cassette comprises a polynucleotide inhibits fungal expression of a distinct fungal target gene. In some embodiments, the plant comprises one or more heterologous expression cassettes for expressing two, three, four or more polynucleotides that inhibit fungal expression of distinct fungal target gene (e.g., two or more fungal target genes from a species of fungal pathogen).

In some embodiments, the polynucleotide comprises an antisense nucleic acid or inhibitory RNA (RNAi) that targets one or more target genes of Table 1 or Table 2 (including any sequences set forth herein) or a fragment thereof (e.g., a sequence of at least 15, 20, 30, 40, 50, 60, 70, 80, 90, 100, 150, 200, 250, 300, 350, 400, 450, 500 or more contiguous nucleotides of a target gene of Table 1 or Table 2). In some embodiments, the polynucleotide comprises a nucleic acid having a sequence that is identical or complementary to at least 15, 20, 25, 30, 35, 40 or more contiguous nucleotides of a target gene of Table 1 or Table 2. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to any of a target gene of Table 1 or Table 2 or a fragment thereof (e.g., at least 15, 16, 17, 18, 19, 20, 21, 22, 23, 24, 25, 26, 27, 28, 29, 30, 31, 32, 33, 34, 35, 36, 37, 38, 39, 40, at least 50, at least 60, at least 70, at least 80, at least 90, at least 100, at least 150, at least 200, at least 250, at least 300, at least 350, at least 400, at least 450, or at least 500 contiguous nucleotides thereof). In some embodiments, the polynucleotide comprises an inverted repeat of a fragment (e.g., at least 15, 20, 25, 30, 35, 40 or more contiguous nucleotides) of any of a target gene of Table 1 or Table 2, and further comprises a spacer region separating the inverted repeat nucleotide sequences. In some embodiments, the polynucleotide comprises a sequence that is identical or substantially identical (e.g., at least 60%, 65%, 70%, 75%, 80%, 85%, 90%, 91%, 92%, 93%, 94%, 95%, 96%, 97%, 98%, or 99% identical) to one or more target genes of Table 1 or Table 2, or a fragment thereof, or a complement thereof.

The present application also provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide that inhibits fungal expression of one or more target genes of Table 1 or Table 2, wherein the plant has increased resistance to a fungal pathogen compared to a control plant lacking the expression cassette.

In some embodiments, the pathogen is *Botrytis*. In some embodiments, the pathogen is *Botrytis* spp. In some embodiments, the pathogen is *B. cinerea*. In some embodiments, the pathogen is *Verticillium* spp. In some embodiments, the pathogen is *V. dahilae*. In some embodiments, the pathogen is *Sclerotinia* spp. In some embodiments, the pathogen is *S. sclerotiorum*. In some embodiments, the pathogen is *Phytophthora* spp.

In some embodiments, the promoter is an inducible promoter. In some embodiments, the promoter is pathogen inducible. In some embodiments, the promoter is stress-inducible. In some embodiments, the promoter is a constitutive promoter.

In another aspect, the present invention provides for expression cassettes comprising: a promoter operably linked to a polynucleotide that inhibits expression of one or more target genes of Table 1 or Table 2. In some embodiments, the promoter is heterologous to the polynucleotide. Isolated nucleic acids comprising said expression cassettes are also provided.

In still another aspect, the present invention provides for expression vectors comprising an expression cassette as described herein.

In another aspect, methods of making a pathogen-resistant plant are provided. In some embodiments, the method comprises:

introducing the nucleic acid comprising an expression cassette as described herein into a plurality of plants; and selecting a plant comprising the expression cassette.

In some embodiments, the method of making a pathogen-resistant plant comprises: contacting a plant or a plant part with a dsRNA or sRNA duplexes that inhibits fungal expression of one or more target genes of Table 1 or Table 2, wherein the plant has increased resistance to a fungal pathogen compared to a control plant or a plant part that has not been contacted with the RNAs. In some embodiments, the RNAs further comprise a second dsRNA or sRNA duplexes that inhibits fungal expression of a second target gene of Table 1 or Table 2. In some embodiments, the method further comprises contacting the plant with a second or more dsRNAs or sRNA duplexes that inhibits expression of orthologous genes of the targets of Table 1 or Table 2 from another pathogen or multiple other pathogens. In some embodiments, the dsRNA or sRNA are contained within liposomes.

In some embodiments, the method of making a pathogen-resistant plant comprises: contacting a plant or a plant part with a construct comprising a promoter operably linked to a polynucleotide that inhibits fungal expression of a target gene of Table 1 or Table 2, wherein the plant has increased resistance to a fungal pathogen compared to a control plant that has not been contacted with the construct. In some embodiments, the construct further comprises a second polypeptide that inhibits fungal expression of a second target gene of Table 1 or Table 2. In some embodiments, the method further comprises contacting the plant with a second construct comprising a second promoter operably linked to a second polynucleotide that inhibits a second target gene which is a second target gene of Table 1 or Table 2 or an ortholog thereof from another pathogen or multiple other pathogens. In some embodiments, the dsRNA or sRNA are contained within liposomes.

In yet another aspect, methods of cultivating a plurality of pathogen-resistant plants are provided.

In another aspect, synthetic liposome comprising dsRNA or sRNA duplexes that target one or more target genes of Table 1 or 2 from one or more pathogens is provided.

BRIEF DESCRIPTION OF THE DRAWINGS

FIG. 1A, Microscopic images of purified fungal protoplasts isolated from *B. cinerea*-infected *Arabidopsis* using the sequential protoplast purification method. Scale bars, 20 μm. FIG. 1B, TAS1c-siR483, TAS2-siR453, IGN-siR1 and miRNA166 were detected by sRNA RT-PCR in *B. cinerea* protoplast ($Bc^{Col}$) purified from *B. cinerea*-infected *Arabidopsis*. For the control of $Bc^{Col}$ (Ctrl), cultured *B. cinerea* mixed with uninfected leaves was subjected to the same procedure. FIG. 1C, TAS1c-siR483, TAS2-siR453, IGN-siR1 and miRNA166 were detected in EVs isolated from mock-treated and *B. cinerea*-infected *Arabidopsis*. FIG. 1D, sRNAs were detected in the EVs following micrococcal nuclease treatment in the presence or absence of 1% Triton-X-100. In FIGS. 1B and 1C, TAS1c-siR585 and TAS2-siR710 were used as controls for TAS1c-siR483 and TAS2-siR453, respectively; IGN-siR107 was used as a control for IGN-siR1; miRNA822 was used as a control for miRNA166. In b-d, Actin genes of *B. cinerea* and *Arabidopsis* were used as controls. The 'total' lane indicates total RNA extracts from whole leaves.

FIG. 2A, Expression levels of TET8 and TET9 were induced by *B. cinerea* infection. TET7 and PDF1.2 were used as controls. The *Arabidopsis* ubiquitin 5 (UBQ5) was used as an internal control. The asterisks indicate the significant difference (two-tail t-test, P<0.01). Error bars indicate the SD of three technical repeats. Similar results were obtained from at least three biological replicates. FIG. 2B, *B. cinerea* induces accumulation of TET8-associated vesicles at the sites of infection. *Arabidopsis* leaves expressing TET8-GFP under its native promoter, were stained for 30 minutes with FM4-64 to show extracellular membrane structures, and the plasma membrane of plant and fungal cells. Scale bars, 10 μm. FIG. 2C, Numerous TET8-GFP-associated ELVs that isolated from the apoplastic fluid of TET8-GFP transgenic plants were observed by confocal microscope. Scale bars, 10 μm. FIG. 2D, GFP-labeled TET8 protein was accumulated in the EV fraction. The 'total' lanes indicate whole leaf protein extracts. RuBisCo blot was used as a control. FIG. 2E, TET8-GFP-labelled ELVs were taken up by *B. cinerea* cells. 1% Triton-X-100 treatment eliminated TET8-GFP signals outside of the fungal cells, but did not eliminate the signals inside the fungal cells. Scale bars, 10 μm. FIG. 2F, Plant endogenous sRNAs were detected in *B. cinerea* cells 2 hours post incubation with ELVs followed by 1% Triton-X-100 treatment. Actin of *B. cinerea* and *Arabidopsis* were used as controls.

FIG. 3A, TET8-CFP with TET9-YFP were co-localized in vesicles that accumulated at the site of fungal infection. Scale bars, 10 μm. FIGS. 3B and 3C, TET8 was co-immunoprecipitated (Co-IP) with TET9. Total proteins (input) were immunoprecipitated with Anti-FLAG M2 affinity gel. FLAG- or GFP-tagged proteins were detected by Western blot using anti-FLAG and anti-GFP antibodies, respectively. FIG. 3D, The tet8 mutant and the amiRNA-TET9/tet8 lines (tet8/9) were more susceptible to *B. cinerea* than the wild type plants. Relative lesion sizes were measured at 2 dpi using imageJ. Error bars indicate the SD of more than 10 leaves. The asterisks indicate significant difference (two-tail t-test, P<0.01). FIG. 3E, Expression of TAS1c-siR483, TAS2-siR453, IGN-siR1 and miRNA166 was decreased in the purified *B. cinerea* protoplast ($Bc^{Col}$) isolated from *B. cinerea*-infected tet8 and tet8 amiRNA-TET9 lines (tet8/9) as compared with that from the wild-type plants. For the control of $Bc^{Col}$ (Ctrl), cultured *B. cinerea* mixed with uninfected leaves was subjected to the same procedure. The *B. cinerea*-derived sRNA Bc-siR3 0.1, *Arabidopsis* Actin gene, and *B. cinerea* Actin gene were used as controls.

FIG. 4A, The dcl2/3/4 triple mutant exhibited enhanced disease susceptibility to *B. cinerea* as compared with the wild type plants. Relative lesion sizes were measured at 2 dpi using imageJ. FIG. 4B, Relative expression of *B. cinerea* target genes of TAS1c-siR483 and TAS2-siR453 was de-repressed in *B. cinerea* collected from the dcl2/3/4 triple mutant compared with those from wild-type plants. The Actin gene of *B. cinerea* was used as the internal control. FIG. 4C, Mutant strains of *B. cinerea* with deletions in TAS1c-siR483 and TAS2-siR453 targets displayed significantly reduced virulence on *Arabidopsis* leaves. Relative lesion sizes were measured at 3 dpi using imageJ. Fungal biomass was measured by quantitative PCR. In FIGS. 4B and 4C, error bars indicate the SD of three technical repeats of quantitative PCR. Similar results were obtained from at least three biological replicates. In pathogen assays a and c, error bars indicate the SD of over 10 leaves. The asterisks indicate significant difference (two-tail t-test, P<0.01).

(FIG. 6A) Fungal pathogens *Sclerotinia sclerotiorum* is capable of taking up external RNAs from the environment. (FIG. 6B) SIGS of DCL1/2 or fungal vesicle trafficking genes of *S. sclerotiorum* inhibit fungal virulence on plants.

FIG. 11A, The expression of *B. cinerea* target genes of TAS1c-siR483, TAS2-siR453 and IGN-siR1 was reduced in *B. cinerea* isolated from infected *Arabidopsis* leaves as compared with that from grown on the medium. FIG. 11B, Relative expression of the *B. cinerea* target gene of IGN-siR1 was de-repressed in *B. cinerea* collected from the dcl2/3/4 triple mutant compared to it from wild-type plants. In FIGS. 11A and 11B, the Actin gene of *B. cinerea* was used as the internal control. Error bars indicate the SD of three technical replicates. Similar results were obtained from at least three biological replicates. The asterisks indicate significant difference (two-tail t-test, P<0.01).

FIG. 12A, Expression levels of each gene in corresponding mutant lines were measured by RT-PCR. The Actin gene of *B. cinerea* was used as the internal control. FIG. 12B, Bc-vps51Δ and Bc-dcnt1Δ0 mutants showed significantly reduced growth rate after 4 days on medium; however, the Bc-sac1Δ mutant did not show any growth defects when compared with wild-type strains.

FIG. 13A, Expression of TAS1c-siR483 and TAS2-siR453 in transgenic overexpression *Arabidopsis* lines was examined by Northern blot analysis. U6 used as a loading control. Lines with high tasiRNA expression were selected for further experiments. FIG. 13B, Pathogen assays of TAS1c-siR483ox and TAS2-siR453 ox plants. Relative lesion sizes were measured at 3 dpi using imageJ. Error bars indicate the SD of over 10 leaves. FIG. 13C, Bc-VPS51 and Bc-DCTN1 were suppressed in infected TAS1c-siR483ox plants compared to the wild type; Bc-SAC1 was suppressed in infected TAS2-siR453ox plants compared to the wild type, as measured by quantitative RT-PCR. The Actin gene of *B. cinerea* was used as the internal control. Error bars indicate the SD of three technical replicates. Similar results were obtained from at least three biological replicates. In FIGS. 13B and 13C, the asterisks indicate significant difference (two-tail t-test, P<0.01).

FIG. 14A, Transgene-derived Bc-DCL1-sRNAs and Bc-DCL2-sRNAs were detected by sRNA RT-PCR in purified *B. cinerea* protoplasts (BcCol) from *B. cinerea*-infected Bc-DCL1/2-RNAi plants but not in the mock-treated plants mixed with *B. cinerea* mycelium before protoplast formation. FIG. 14B, Transgene-derived Bc-DCL1-sRNAs and Bc-DCL2-sRNAs were detected in EVs from *B. cinerea*-infected *Arabidopsis* Bc-DCL1/2-RNAi plants. At-siR1003 and Actin genes of *B. cinerea* and *Arabidopsis* were used as controls. The 'total' lane indicates total RNA extracts from whole leaves.

DEFINITIONS

Figure 1A:
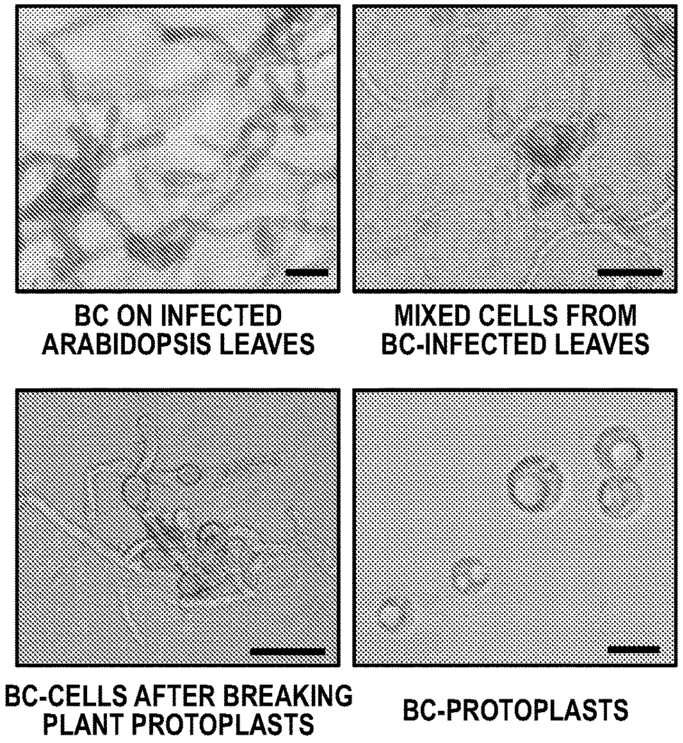
FIGS. 1A-1D: Plant endogenous sRNAs are exported into fungal cells via extracellular vesicles (EVs).

The term "pathogen-resistant" or "pathogen resistance" refers to an increase in the ability of a plant to prevent or resist pathogen infection or pathogen-induced symptoms. Pathogen resistance can be increased resistance relative to a particular pathogen species or genus (e.g., *Botrytis*), increased resistance to multiple pathogens, or increased resistance to all pathogens (e.g., systemic acquired resistance). In some embodiments, resistance of a plant to a pathogen is "increased" when one or more symptoms of pathogen infection are reduced relative to a control (e.g., a plant in which a polynucleotide that inhibits expression of a fungal pathogen target gene is not expressed).

"Pathogens" include, but are not limited to, viruses, bacteria, nematodes, fungi, oomycetes or insects (see, e.g., Agrios, *Plant Pathology* (Academic Press, San Diego, Calif. (1988)). In some embodiments, the pathogen is a fungal pathogen. In some embodiments, the pathogen is *Botrytis*. In some embodiments, the pathogen is *Verticillium*. In some embodiments, the pathogen is *Sclerotinia*. In some embodiments, the pathogen is an oomycete pathogen.

The term "nucleic acid" or "polynucleotide" refers to a single or double-stranded polymer of deoxyribonucleotide or ribonucleotide bases read from the 5' to the 3' end. Nucleic acids may also include modified nucleotides that permit correct read through by a polymerase and do not significantly alter expression of a polypeptide encoded by that nucleic acid.

The phrase "nucleic acid encoding" or "polynucleotide encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

Two nucleic acid sequences or polypeptides are said to be "identical" if the sequence of nucleotides or amino acid residues, respectively, in the two sequences is the same when aligned for maximum correspondence as described below. "Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity" or "substantially identical," as used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

The term "complementary to" is used herein to mean that a polynucleotide sequence is complementary to all or a portion of a reference polynucleotide sequence. In some embodiments, a polynucleotide sequence is complementary to at least 15, at least 20, at least 25, at least 30, at least 40, at least 50, at least 75, at least 100, at least 125, at least 150, at least 175, at least 200, or more contiguous nucleotides of a reference polynucleotide sequence. In some embodiments, a polynucleotide sequence is "substantially complementary" to a reference polynucleotide sequence if at least 70%, at least 75%, at least 80%, at least 85%, at least 90%, or at least 95% of the polynucleotide sequence is complementary to the reference polynucleotide sequence.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

Detailed Description of the Invention

I. Introduction

A number of fungal virulence genes have been discovered. Moreover, it has been found that targeting (reducing) expression of these target genes in fungi will reduce their virulence and thus allow for control of them on plants. In some cases, dsRNAs, sRNA duplexes, sRNAs, antisense molecules or other polynucleotides targeting one or more of these target genes can be contacted to fungal pathogens, thereby reducing the fungal virulence.

Thus, one aspect of the present invention relates to controlling the diseases caused by aggressive fungal and oomycete pathogens by silencing one or more of the target genes of Table 1 or Table 2. In some embodiments, silencing is achieved by generating transgenic plants that express antisense constructs, double stranded RNA, RNA hairpin structures, or RNA duplexes (e.g., RNAi) that target one or more of the target genes of Table 1 or Table 2. In some embodiments, silencing is achieved by contacting (e.g., spraying) plants with sRNA duplexes or double stranded RNAs that target one or more of the target genes of Table 1 or Table 2. In some embodiments, silencing is achieved by contacting (e.g., spraying) plants with sRNA duplexes or double stranded RNAs that target one or more of the target genes from different pathogens.

II. Target Genes of Table 1 or Table 2

In one aspect, methods of inhibiting or silencing expression of one or more of the target genes of Table 1 or Table 2 in fungi are provided. In some embodiments, the method comprises expressing in a plant an expression cassette comprising a promoter operably linked to a polynucleotide that inhibits expression one or more of the target genes of Table 1 or Table 2. In some embodiments, the method comprises contacting the plant with sRNA duplexes or double stranded RNAs that inhibit one or more of the target genes of Table 1 or Table 2. In some embodiments, the polynucleotide comprises an antisense nucleic acid that is complementary to one or more of the target genes of Table 1 or Table 2 or a fragment thereof. In some embodiments, the polynucleotide comprises sRNA duplexes or dsRNAs that target one or more of the target genes of Table 1 or Table 2 or a fragment thereof (optionally from different pathogens). In some embodiments, the polynucleotide sequence comprises an inverted repeat of a sequence targeting one or more of the target genes of Table 1 or Table 2, optionally with a spacer present between the inverted repeat sequences. In some embodiments, the promoter is an inducible promoter. In some embodiments, the promoter is a constitutively active promoter.

In yet another aspect, expression cassettes comprising a promoter operably linked to a polynucleotide that inhibits expression in a pathogen of one or more of the target genes of Table 1 or Table 2, or isolated nucleic acids comprising said expression cassettes, are provided. In some embodiments, the expression cassette comprises a promoter operably linked to a polynucleotide comprising an antisense nucleic acid that is complementary to one or more of the target genes of Table 1 or Table 2 or a fragment thereof. In some embodiments, the expression cassette comprises a promoter operably linked to a polynucleotide comprising a double stranded nucleic acid that targets one or more of the target genes of Table 1 or Table 2 or a fragment thereof. In some embodiments, a plant in which the expression cassette is introduced has increased resistance to the pathogen compared to a control plant lacking the expression cassette.

TABLE 1

*Botrytis cinerea* target genes that are involved in vesicle trafficking

| Gene name | Target gene ID | Gene description | Targeted by At_siRNA | Aligned score | Homolog in Sclerotinia |
|---|---|---|---|---|---|
| DTCN | BC1G_10508 | Dynactin protein | TAS1c-siR483 (tasiRNA) | 4.25 | SS1G_04144 |
| VPS51 | BC1G_10728 | VPS51 family protein | TAS1c-srR483 (tasiRNA) | 3.5 | SS1G_09028 |
| SAC1 | BC1G_08464 | Polyphosphoinositide phosphatase | TAS2-siR453 (tasiRNA) | 3.5 | SS1G_10257 |
| VPS52 | BC1G_09781 | Vps52/Sac2 family protein | MIR159A (MicroRNA) | 4.5 | SS1G_01875 |
| Rgd1p | BC1G_15133 | GTPase activating protein | MIR396A (MicroRNA) | 4 | SS1G_03990 |

TABLE 1-continued

*Botrytis cinerea* target genes that are involved in vesicle trafficking

| Gene name | Target gene ID | Gene description | Targeted by At_siRNA | Aligned score | Homolog in Sclerotinia |
|---|---|---|---|---|---|
| UFD1 | BC1G_10526 | Endoplasmic reticulum-associated Ubiquitin fusion degradation protein UFD1 | S10018 (IGN) | 4.5 | SS1G_04151 |
| Integral | BC1G_03606 | Hypothetical protein similar to integral membrane protein | S10140 (IGN) | 4.5 | None |
| Sec31p | BC1G_03372 | WH2 motif protein | S1353733 (ORF) | 3 | SS1G_06679 |
| Gyp5p | BC1G_04258 | GTPase-activating protein | S1353733 (ORF) | 4 | SS1G_10712 |
| Pan1p | BC1G_09414 | Cytoskeleton regulatory protein | S1353733 (ORF) | 3 | SS1G_05987 |
| Srv2p | BC1G_14507 | Adenylyl cyclase-associated protein | S1353733 (ORF) | 3 | SS1G_13327 |

TABLE 2

*Botrytis cinerea* genes targeted by host sRNAs

<table>
<tr><th>Target gene ID</th><th>Putative function of target gene</th><th>GO_biological process</th><th>Targeted by sRNA</th><th>sRNA type</th><th>Aligned score</th><th>Target gene alignment sRNA 3'-5'</th></tr>
<tr><td>BC1G_10728</td><td>Conserved hypothetical VPS51 protein</td><td>vesicle transport</td><td>TAS1c-siR483</td><td>tasiRNA</td><td>3.5</td><td>:||x|x|x||||||||||x</td></tr>
<tr><td>BC1G_10508</td><td>Predicted dynactin protein</td><td>vesicle transport</td><td>TAS1c-siR483</td><td>tasiRNA</td><td>4.25</td><td>|||||x:|||||||:|||xx</td></tr>
<tr><td>BC1G_08464</td><td>Polyphosphoinositide phosphatase</td><td>vesicle transport</td><td>TAS2-siR453</td><td>tasiRNA</td><td>3.5</td><td>:||||||x|||||x|||||</td></tr>
<tr><td>BC1G_15133</td><td>Hypothetical protein similar to GTPase activating protein</td><td>vesicle transport</td><td>MIR396A</td><td>miRNA</td><td>4</td><td>|:|||:||x||||||||x||</td></tr>
<tr><td>BC1G_09781</td><td>Hypothetical protein similar to Vps52/Sac2 family protein</td><td>vesicle transport</td><td>MIR159A</td><td>miRNA</td><td>4.5</td><td>||||x||||:|||||x||||:</td></tr>
<tr><td>BC1G_05327</td><td>Pyruvate carboxylase</td><td>metabolic process</td><td>IGN-siR1</td><td>IGN</td><td>4.5</td><td>x|x|x|||||||||x|||:</td></tr>
<tr><td>BC1G_15423</td><td>Predicted FAD binding protein</td><td>metabolic process</td><td>TAS1c-siR602</td><td>tasiRNA</td><td>3.75</td><td>|||x:|||||||||||:||:</td></tr>
<tr><td>BC1G_09454</td><td>Retinol dehydrogenase 12</td><td>metabolic process</td><td>MIR157A</td><td>miRNA</td><td>2.5</td><td>x||||||x|||||||||||:</td></tr>
<tr><td>BC1G_15945</td><td>Hypothetical protein similar to GAL4-like transcription factor</td><td>regulation of transcription</td><td>MIR396A</td><td>miRNA</td><td>4</td><td>|:|x|:|||||||||||x||</td></tr>
<tr><td>BC1G_14887</td><td>Histone-lysine N-methyltransferase</td><td>regulation of transcription</td><td>MIR396A</td><td>miRNA</td><td>3</td><td>:|x||:|||||:||||||||</td></tr>
<tr><td>BC1G_07589</td><td>Histone-lysine N-methyltransferase</td><td>regulation of transcription</td><td>MIR396A</td><td>miRNA</td><td>4.5</td><td>x||||||:|||x|||||:|</td></tr>
<tr><td>BC1G_05475</td><td>Hypothetical protein similar to microcystin synthetase</td><td>biosynthetic process</td><td>MIR159B</td><td>miRNA</td><td>4.5</td><td>||x||||:|||||x||||:|</td></tr>
<tr><td>BC1G_07401</td><td>Botrytis cinerea (B05.10) glutaminyl-tRNA synthetase</td><td>biosynthetic process</td><td>S10044</td><td>TE</td><td>4.5</td><td>||x|:|||||||:||||||x|</td></tr>
<tr><td>BC1G_09015</td><td>Dual specificity protein kinase POM1</td><td>signal transduction</td><td>MIR158A</td><td>miRNA</td><td>3.5</td><td>|x||||x|:||||||||||:</td></tr>
<tr><td>BC1G_03832</td><td>R3H domain of encore-like and DIP1-like protein</td><td>cell cycle</td><td>MIR159A</td><td>miRNA</td><td>4</td><td>||||xx|x||||||||||||</td></tr>
<tr><td>BC1G_09907</td><td>Predicted membrane protein involved in the export of O-antigen and teichoic acid</td><td>cell wall biogenesis</td><td>MIR168</td><td>miRNA</td><td>4.5</td><td>x||x|x||:||||||||||x</td></tr>
</table>

TABLE 2-continued

<table>
<tr><th colspan="7">Botrytis cinerea genes targeted by host sRNAs</th></tr>
<tr><th>Target gene ID</th><th>Putative function of target gene</th><th>GO_biological process</th><th>Targeted by sRNA</th><th>sRNA type</th><th>Aligned score</th><th>Target gene alignment sRNA 3'-5'</th></tr>
<tr><td>BC1G_02544</td><td>Hypothetical protein similar to B230380D07Rik protein</td><td>unknown</td><td>MIR166A</td><td>miRNA</td><td>4.5</td><td>|||x||x||||||||||x|:</td></tr>
<tr><td>BC1G_11528</td><td>Predicted protein</td><td>unknown</td><td>MIR159B</td><td>miRNA</td><td>3.5</td><td>||x||||::|||||||:||||</td></tr>
<tr><td>BC1G_11528</td><td>Predicted protein</td><td>unknown</td><td>MIR159A</td><td>miRNA</td><td>4.5</td><td>x|x||||::|||||||:||||</td></tr>
<tr><td>BC1G_04218</td><td>Predicted protein</td><td>unknown</td><td>MIR396A</td><td>miRNA</td><td>4.25</td><td>||||x:||||||||x|||||</td></tr>
<tr><td>BC1G_00860</td><td>Domain of unknown function (DUF4211) protein</td><td>unknown</td><td>MIR158A</td><td>miRNA</td><td>4.5</td><td>|||x|||x||||||||x|:</td></tr>
<tr><td>BC1G_04811</td><td>redicted protein</td><td>unknown</td><td>S10086</td><td>IGN</td><td>3</td><td>||||x|||||||||:|:|||</td></tr>
<tr><td>BC1G_05162</td><td>Predicted protein</td><td>unknown</td><td>S10131</td><td>ORF</td><td>4.5</td><td>x|x|||x|:||||||:|||||</td></tr>
<tr><td>BC1G_06835</td><td>Predicted protein</td><td>unknown</td><td>S10131</td><td>ORF</td><td>3</td><td>|:|x|||x|||||||||||:</td></tr>
<tr><td>BC1G_10526</td><td>Endoplasmic reticulum-associatedUbiquitin fusion degradation protein UFD1</td><td>vesicle transport</td><td>S10018</td><td>IGN</td><td>4.5</td><td>x|:||||x|||||x|||||</td></tr>
<tr><td>BC1G_03606</td><td>Hypothetical protein similar to integral membrane protein</td><td>vesicle transport</td><td>S10140</td><td>IGN</td><td>4.5</td><td>|x|:|||||||||:|:|||x</td></tr>
<tr><td>BC1G_04443</td><td>Ketol-acid reductoisomerase</td><td>metabolic process</td><td>S10052</td><td>IGN</td><td>4</td><td>x|x||x|||:||||||||</td></tr>
<tr><td>BC1G_12479</td><td>Isopenicillin N synthase and related dioxygenases</td><td>metabolic process</td><td>S10117</td><td>IGN</td><td>4</td><td>|||xx||x||||||||||</td></tr>
<tr><td>BC1G_06676</td><td>Fatty-acid amide hydrolase 1</td><td>metabolic process</td><td>MIR8167</td><td>miRNA</td><td>4.5</td><td>|:|||:|:|||:|x|||||||</td></tr>
<tr><td>BC1G_12472</td><td>Serine threonine-protein phosphatase dullard protein</td><td>regulation of transcription</td><td>S10131</td><td>ORF</td><td>4.5</td><td>||||:|x||||||x|:|||||</td></tr>
<tr><td>BC1G_02471</td><td>RNA polymerase III</td><td>regulation of transcription</td><td>S10071</td><td>IGN</td><td>4</td><td>x|||||||||||||||x||x</td></tr>
<tr><td>BC1G_03511</td><td>Hypothetical protein similar to peptide synthetase</td><td>biosynthetic process</td><td>S10083</td><td>Anti-ORF</td><td>3.5</td><td>x|:||x||x|||||||||||</td></tr>
<tr><td>BC1G_03981</td><td>Hypothetical protein similar to sulfate/anion exchanger</td><td>regulation of transport</td><td>MIR8167</td><td>miRNA</td><td>4.5</td><td>|||:||x||||||||x||:|</td></tr>
<tr><td>BC1G_14507</td><td>70-kDa adenylyl cyclase-associated protein</td><td>vesicle transport</td><td>S1353733</td><td>ORF</td><td>3</td><td>x||x||x|||||||||||||</td></tr>
<tr><td>BC1G_09414</td><td>Protein similar to actin cytoskeleton-regulatory complex protein PAN1</td><td>vesicle transport</td><td>S1353733</td><td>ORF</td><td>3</td><td>x||x||x|||||||||||||</td></tr>
<tr><td>BC1G_04258</td><td>GTPase-activating protein GYPS</td><td>vesicle transport</td><td>S1353733</td><td>ORF</td><td>4</td><td>x|||||x||||||||||x||</td></tr>
<tr><td>BC1G_03372</td><td>Hypothetical WH2 motif protein</td><td>vesicle transport</td><td>S1353733</td><td>ORF</td><td>3</td><td>x||x||||||||||||||:|</td></tr>
<tr><td>BC1G_14667</td><td>Predicted protein</td><td>unknown</td><td>MIR396B</td><td>miRNA</td><td>4.5</td><td>::|x|||x|||||||||||x</td></tr>
<tr><td>BC1G_14204</td><td>Predicted protein</td><td>unknown</td><td>S1353733</td><td>ORF</td><td>3.5</td><td>|:|xx||x||||||||||:|||</td></tr>
<tr><td>BC1G_10316</td><td>Predicted protein</td><td>unknown</td><td>S1353733</td><td>ORF</td><td>4.5</td><td>x|:||||:||||x|||||||:</td></tr>
<tr><td>BC1G_05030</td><td>Predicted protein</td><td>unknown</td><td>S1353733</td><td>ORF</td><td>4.25</td><td>x:|||||||||||x||||||</td></tr>
<tr><td>BC1G_00624</td><td>Predicted protein</td><td>unknown</td><td>S1353733</td><td>ORF</td><td>4</td><td>x||x||||||||||||||:|x</td></tr>
<tr><td>BC1G_15490</td><td>Bifunctional P-450/NADPH-P450 reductase</td><td>metabolic process</td><td>MIR396A *</td><td>miRNA</td><td>4.5</td><td>|x|:||:|:||||||||x|||</td></tr>
<tr><td>BC1G_14979</td><td>Hypothetical protein similar to mitochondrial ATP synthase B</td><td>metabolic process</td><td>S1353733</td><td>ORF</td><td>3</td><td>x||x||x|||||||||||||</td></tr>
<tr><td>BC1G_14979</td><td>Hypothetical protein similar to mitochondrial ATP synthase B</td><td>metabolic process</td><td>MIR396B</td><td>miRNA</td><td>4</td><td>|||||||||:||||||||:|</td></tr>
<tr><td>BC1G_12936</td><td>2-deoxy-D-gluconate 3-dehydrogenase</td><td>metabolic process</td><td>MIR396A *</td><td>miRNA</td><td>4</td><td>|||x|||x|||||||x||||</td></tr>
<tr><td>BC1G_04424</td><td>Hypothetical protein similar to ITC1</td><td>regulation of transcription</td><td>S1353733</td><td>ORF</td><td>3</td><td>x||x|||x||||||||||||</td></tr>
</table>

TABLE 2-continued

<table>
<tr><th colspan="7">Botrytis cinerea genes targeted by host sRNAs</th></tr>
<tr><th>Target gene ID</th><th>Putative function of target gene</th><th>GO_biological process</th><th>Targeted by sRNA</th><th>sRNA type</th><th>Aligned score</th><th>Target gene alignment sRNA 3'-5'</th></tr>
<tr><td>BC1G_14463</td><td>Hypothetical protein similar to Usolp</td><td>mitotic cell cycle</td><td>S1353733</td><td>ORF</td><td>4</td><td>x||x||x||||:|||||||||</td></tr>
<tr><td>BC1G_10235</td><td>Hypothetical protein similar to Smc4p</td><td>mitotic cell cycle</td><td>S1353733</td><td>ORF</td><td>4</td><td>||||x||x||||||||||x||</td></tr>
<tr><td>BC1G_12627</td><td>Hypothetical protein similar to cell wall synthesis protein</td><td>cell wall biogenesis</td><td>S1353733</td><td>ORF</td><td>4.25</td><td>||:||:x|:|||||||||:||</td></tr>
<tr><td>BC1G_09656</td><td>Hypothetical protein similar to HKR1</td><td>cell wall biogenesis</td><td>S1353733</td><td>ORF</td><td>4.5</td><td>x||x|||:||||||||||:|x</td></tr>
<tr><td>BC1G_07658</td><td>Hypothetical protein similar to endoglucanase IV</td><td>RNA catabolic process</td><td>S1353733</td><td>ORF</td><td>4.5</td><td>|::|:||||||:||||||:|:</td></tr>
<tr><td>BC1G_02429</td><td>Ribonuclease HI large subunit</td><td>RNA catabolic process</td><td>S1353733</td><td>ORF</td><td>4</td><td>x|||:|||:||:|||||:|||</td></tr>
<tr><td>BC1G_09103</td><td>Botrytis cinerea (B05.10) hypothetical protein similar to cell division cycle mutant</td><td>cell cycle</td><td>S1092315</td><td>TE</td><td>4.5</td><td>||x||||||:||:|||||||x|</td></tr>
<tr><td>BC1G_02638</td><td>Cell cycle checkpoint protein RAD17</td><td>cell cycle</td><td>S1353733</td><td>ORF</td><td>4.5</td><td>x||x||x||||||:|||||:</td></tr>
<tr><td>BC1G_02869</td><td>Guanine nucleotide-binding protein G(I)/G(S)/G(T) subunit beta-1</td><td>cell proliferation</td><td>S1353733</td><td>ORF</td><td>4</td><td>|||||:|x||x||||||||||:</td></tr>
<tr><td>BC1G_09169</td><td>Hypothetical protein similar to calpain 2 catalytic subunit</td><td>cell proliferation</td><td>S1353733</td><td>ORF</td><td>4</td><td>x||x||x|||||||||||:||</td></tr>
<tr><td>BC1G_07037</td><td>Hypothetical protein similar to Msf1p</td><td>tRNA processing</td><td>S519888</td><td>ORF</td><td>4.5</td><td>:|x||||||||:|||||x||</td></tr>
<tr><td>BC1G_10614</td><td>Hypothetical protein similar to GAMM1 protein</td><td>cell surface receptor signaling pathway</td><td>MIR396A *</td><td>miRNA</td><td>4.5</td><td>:||x|x|x|||||||||||x</td></tr>
</table>

In some embodiments, the pathogen gene to be targeted or silenced is from a viral, bacterial, fungal, nematode, oomycete, or insect pathogen. In some embodiments, the target gene is from a fungal pathogen. Examples of plant fungal pathogens include, but are not limited to, *Botyritis, Verticillium, Magnaporthe, Sclerotinia, Puccinia, Fusarium, Mycosphaerella, Blumeria*, and *Melampsora*. See, e.g., Dean et al., *Mol Plant Pathol* 13:804 (2012). In some embodiments, the pathogen is *Botyritis*. In some embodiments, the pathogen is *Botyritis cinera*. In some embodiments, the pathogen is *Verticillium*. In some embodiments, the pathogen is *V. dahilae*. In some embodiments, the pathogen is *Sclerotinia.*

In some embodiments, one or more of the target genes of Table 1 or Table 2 is targeted, silenced, or inhibited in order to increase resistance to the pathogen in a plant by expressing in the plant, or contacting to the plant, a polynucleotide that inhibits expression of the pathogen target gene(s) or that is complementary to the target gene(s) or a fragment thereof. In some embodiments, the polynucleotide comprises an antisense nucleic acid that is complementary to one or more of the target genes of Table 1 or Table 2 or a fragment thereof. In some embodiments, the polynucleotide comprises a double stranded nucleic acid (e.g., RNA) that targets one or more of the target genes of Table 1 or Table 2, or its promoter, or a fragment thereof. In some embodiments, the polynucleotide comprises a double-stranded nucleic acid having a sequence that is identical or substantially similar (at least 60%, 65%, 70%, 75%, 80%, 85%, 90%, 91%, 92%, 93%, 94%, 95%, 96%, 97%, 98%, or 99% identical) to one or more of the target genes of Table 1 or Table 2 or a fragment thereof. In some embodiments, a "fragment" of a target gene of Table 1 or Table 2 or promoter thereof comprises a sequence of at least 15, 16, 17, 18, 19, 20, 21, 22, 23, 24, 25, 26, 27, 28, 29, 30, 20, 30, 40, 50, 60, 70, 80, 90, 100, 150, 200, 250, 300, 350, 400, 450, 500 or more contiguous nucleotides of the target gene of Table 1 or Table 2 or promoter (e.g., comprises at least (e.g., at least 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500 or more contiguous nucleotides of one of the sequences provided herein). In some embodiments, the double stranded nucleic acid is a sRNA duplex or a double stranded RNA.

Host-Induced Gene Silencing

In some embodiments, the methods of inhibiting or silencing expression in a fungal pathogen of one or more of the target genes of Table 1 or Table 2 (e.g., RNAs comprising any of SEQ ID NOS: 1-78) utilizes a host-induced gene silencing (HIGS) mechanism for producing in a host plant inhibitory RNA that subsequently moves into the pathogen to inhibit expression of a pathogen gene or region. In some embodiments, HIGS is used to produce in a plant inhibitory RNAs (e.g., sRNAs or double stranded RNA) that target one or more of the target genes of Table 1 or Table 2. In some embodiments, wherein a pathogen has more than one target gene as shown in Table 1 or 2, RIGS is used to produce inhibitory RNAs (e.g., sRNAs) that target two or more of the target genes of the pathogen. In some embodiments, HIGS is used to produce inhibitory RNAs (e.g., sRNAs) against gene targets of multiple pathogens.

The use of HIGS for silencing expression of pathogen genes in plants is described, e.g., in Nowara et al. (*Plant Cell* (2010) 22:3130-3141); Nunes et al. (*Mol Plant Pathol* (2012) 13:519-529); and Govindarajulu et al. (*Plant Biotechnology Journal* (2014) 1-9). Pathogen sRNAs are described, for example, in US 2015/0203865, incorporated by reference herein.

Gene expression may also be suppressed by means of RNA interference (RNAi) (and indeed co-suppression can be considered a type of RNAi), which uses a dsRNA having a sequence identical or similar to the sequence of the target gene. RNAi is the phenomenon in which when a dsRNA having a sequence identical or similar to that of the target gene is introduced into a cell, the expressions of both the inserted exogenous gene and target endogenous gene are suppressed. The dsRNA may be formed from two separate complementary RNAs or may be a single RNA with internally complementary sequences that form a dsRNA or hairpin RNA. Although complete details of the mechanism of RNAi are still unknown, it is considered that the introduced dsRNA is initially cleaved into small fragments, which then serve as indexes of the target gene in some manner, thereby degrading the target gene. RNAi is also known to be effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct. Genom.* 5: 240-244 (2004); Lu, et al., *Nucleic Acids Research* 32(21):e171 (2004)). For example, to achieve suppression of expression of one or more of the target genes of Table 1 or Table 2 using RNAi, a gene fragment (e.g., from a target gene) in an inverted repeat orientation with a spacer could be expressed in plants to generate dsRNA having the sequence of an mRNA encoded by one or more of the target genes of Table 1 or Table 2 (e.g., RNAs comprising any of SEQ ID NOS: 1-78), or a substantially similar sequence thereof (including those engineered not to translate the protein) or fragment thereof, is introduced into a plant or other organism of interest. The resulting plants/organisms can then be screened for a phenotype associated with the target protein and/or by monitoring steady-state RNA levels for transcripts encoding the protein from the pathogens. Although the genes used for RNAi need not be completely identical to the target gene, they may be at least 70%, 80%, 90%, 95% or more identical to the target gene sequence. See, e.g., U.S., Patent Publication No. 2004/0029283 for an example of a non-identical siRNA sequence used to suppress gene expression. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211. Gene silencing in plants by the expression of sRNA duplexes is also described, e.g., in Lu et al., *Nucleic Acids Res.* 32(21): e171 (2004).

The RNAi polynucleotides can encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 10, 15, 20, 50, 100, 150, 200, or more nucleotides in length. In some cases, fragments for use in RNAi will be at least substantially similar to coding sequences for regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected cells have been engineered to express hairpin RNAs or double stranded RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by dsRNA is discussed in further detail by Hammond et al., *Nature Rev Gen* 2: 110-119 (2001), Hamilton et al., Science, 286:950-2. 1999, Fire et al., *Nature* 391: 806-811 (1998) and Timmons and Fire, *Nature* 395: 854 (1998).

Yet another way to suppress expression of a gene in a plant is by recombinant expression of a microRNA that suppresses the target gene. Artificial microRNAs are single-stranded RNAs (e.g., between 18-25 mers, generally 21 mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

Spray-Induced Gene Silencing

To avoid generating transgenic plants, another way to suppress expression of a gene in a plant is by application of pathogen gene—targeting dsRNAs, sRNA duplexes or sRNAs to a surface of a plant or part of a plant (e.g., onto a leaf, flower, fruit, or vegetable). For example the dsRNA or sRNA duplexes can be sprayed or otherwise contacted (e.g., by brushing, dipping, etc.) onto the plant surface. Methods of applying dsRNA and sRNA duplex onto external plant parts are described, for example, in Wang et al, *Nature Plants,* 19; 2:16151 (2016). WO 2013/02560 and in Gan et al., *Plant Cell Reports* 29:1261-1268 (2010).

In some embodiments, double stranded RNAs, sRNA duplexes or sRNAs can be applied as naked RNAs in an aqueous (e.g., water) solution. In some embodiments, such treatments can be effective up to 8 days or more (see, e.g., Wang et al, *Nature Plants,* 19; 2:16151 (2016); Koch A, et al., *PLoS Pathog.* 2016 Oct. 13; 12(10)).

In some embodiments, pathogen gene—targeting dsRNAs or sRNA duplexes can be applied in cationic liposomes, or other artificial lipid nanoparticles that can protect RNA molecules and enhance the pathogen uptake efficiency. For example, some eukaryotic pathogens, such as *Botrytis cinerea*, can efficiently take up lipid membrane vesicles within 1-2 hours (See, e.g., FIG. 2E).

An exemplary method of forming cationic liposomes comprising dsRNA or sRNA duplexes follows: In some embodiments, the first step is the formation of complexes of a lipid film. This can be achieved for example, by mixing DOTAP, cholesterol, and DSPE-PEG2000 (2:1:0.1). Then, the lipid film can be hydrated using a solution of RNA (e.g., in dextrose or sucrose (w/v)) prepared using RNase-free $dH_2O$, and finally by sonication or extrusion (pass them through membranes that contain pores of a defined size) for size reduction that lead to the formation of PEG-lipid vesicles with embedded dsRNAs or sRNA duplexes. Once loaded on lipid vesicles, the RNAs will not leak out, and can be contacted to plants for long term protection.

In some embodiments, pathogen gene—targeting dsRNAs or sRNAs can be synthesized in planta and extracted from the plant for subsequent use on a target plant. As a non-limiting example, constructs for producing one or more dsRNA or sRNA sequences of interest can be transiently introduced into a plant (e.g., *N. benthamiana*), for example by infiltration with *Agrobacterium*. The dsRNA or sRNA sequences are produced by the plant and then RNA is extracted from one or more tissues of the plant in order to extract the dsRNA or sRNA sequences of interest.

Antisense and Sense Technology

In some embodiments, antisense technology is used to silence or inactive one or more of the target genes of Table 1 or Table 2 in a fungal pathogen. The antisense nucleic acid sequence transformed into plants will be substantially identical to at least a fragment of the gene to be silenced. In some embodiments, the antisense nucleic acid sequence that is transformed into plants is identical or substantially identical to one or more of the target genes of Table 1 or Table 2 in the pathogen to be blocked. In some embodiments, the antisense polynucleotide sequence is complementary to the one or more of the target genes of Table 1 or Table 2 (e.g., RNAs comprising any of SEQ ID NOS: 1-78) of the pathogen to be blocked. However, the sequence does not have to be perfectly identical to inhibit expression. Thus, in some embodiments, an antisense polynucleotide sequence that is substantially complementary (e.g., at least 70%, at least 75%, at least 80%, at least 85%, at least 90%, or at least 95% complementary) to one or more of the target genes of Table 1 or Table 2 to be blocked can be used (e.g., in an expression cassette under the control of a heterologous promoter, which is then transformed into plants such that the antisense nucleic acid is produced).

In some embodiments, an antisense or sense nucleic acid molecule comprising or complementary to only a fragment of one or more of the target genes of Table 1 or Table 2 (e.g., RNAs comprising any of SEQ ID NOS: 1-78) can be useful for producing a plant in which pathogen gene expression is silenced. For example, a sequence of about 15, 20, 30, 40, 50, 100, 150, 200, 250, 300, 350, 400, 450, or 500 nucleotides can be used.

Catalytic RNA molecules or ribozymes can also be used to inhibit expression of a one or more of the target genes of Table 1 or Table 2 (e.g., RNAs comprising any of SEQ ID NOS: 1-78) of a pathogen. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the sequence intended to be repressed. This minimal identity will typically be greater than about 65% to the target gene sequence (e.g., one or more of the target genes of Table 1 or Table 2), but a higher identity can exert a more effective repression of expression of the endogenous sequences. In some embodiments, sequences with substantially greater identity are used, e.g., at least about 80%, at least about 95%, or 100% identity are used. As with antisense regulation, the effect can be designed and tested so as to not significantly affect expression of other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. In some embodiments, a sequence of the size ranges noted above for antisense regulation is used, e.g., at least about 15, 20, 30, 40, 50, 60, 70, 80, 90, 100, 150, 200, 250, 300, 350, 400, 450, 500 or more nucleotides.

III. Methods of Making Plants Having Increased Pathogen Resistance

In another aspect, methods of making plants having increased pathogen resistance are provided. In some embodiments, the method comprises:

- introducing into a plant a heterologous expression cassette comprising a promoter operably linked to a polynucleotide that inhibits fungal expression of one or more of the target genes of Table 1 or Table 2; and
- selecting a plant comprising the expression cassette.

In some embodiments, the method further comprises introducing into the plant a second heterologous expression cassette comprising a second promoter operably linked to a second polynucleotide that inhibits fungal expression of a second target gene of Table 1 or Table 2; and selecting a plant comprising the second expression cassette.

In some embodiments, a plant into which the expression cassette(s) has been introduced has increased pathogen resistance relative to a control plant lacking the expression cassette(s). In some embodiments, a plant into which the expression cassette has been introduced has enhanced resistance to a fungal pathogen (e.g., *Botyritis* or *Verticillium* or *Sclerotinia*) relative to a control plant lacking the expression cassette.

In some embodiments, the promoter is heterologous to the polynucleotide. In some embodiments, the polynucleotide encoding the sRNA-resistant target is operably linked to an inducible promoter. In some embodiments, the promoter is pathogen inducible (e.g., a *Botrytis* or *Verticillium* or *Sclerotinia* inducible promoter). In some embodiments, the promoter is stress inducible (e.g., an abiotic stress inducible promoter).

In some embodiments, the method comprises:

contacting a plurality of plants with a construct comprising a promoter operably linked to a polynucleotide that inhibits fungal expression of a target gene of Table 1 or Table 2, wherein the plant has increased resistance to a pathogen compared to a control plant that has not been contacted with the construct.

In some embodiments, the method further comprises selecting a plant having increased pathogen resistance.

In some embodiments, the method comprises:

contacting a plant or a part of a plant with a dsRNA, sRNA duplexes, or sRNAs that targets a target gene of Table 1 or Table 2, wherein the plant or part of the plant has increased resistance to the pathogen compared to a control plant that has not been contacted with the dsRNAs, sRNAs or sRNA duplexes.

In some embodiments, the method comprises contacting the plant or the part of the plant with two, three, four, five, or more dsRNAs or sRNA duplexes (e.g., siRNAs) or sRNAs for targeting two, three, four, five, or more target gene of Table 1 or Table 2 from one, two, three or more different pathogens.

In some embodiments, the dsRNA or sRNA duplex (e.g., siRNA) or sRNA is sprayed or brushed onto the plant or part of the plant (e.g., onto a leaf, a fruit, or a vegetable).

Liposomes and Cationic Liposome Delivery Systems

Liposomes can be used to deliver dsRNAs or sRNA duplexes (e.g., siRNAs) or sRNAs that target one or more target gene of Table 1 or Table 2, or alternatively, one or more (e.g., two or more) fungal pathogen dicer-like (DCL) transcripts. The dsRNAs or sRNA duplexes or sRNAs can be packaged into liposomes and subsequently sprayed or otherwise contacted to plants in an amount sufficient to inhibit infection or pathogenesis by a fungal pathogen. Exemplary fungal DCL genes are described for example in U.S. patent application Ser. No. 14/809,063, which is incorporated by reference. Exemplary DCLs include those from *Botrytis* or *Verticillium*, as described for example in U.S. patent application Ser. No. 14/809,063.

Liposomes are vesicles comprised of concentrically ordered lipid bilayers that typically encapsulate an aqueous phase. Liposomes form when lipids, molecules having a polar head group attached to one or more long chain aliphatic tails, such as phospholipids, are exposed to water. Upon encountering such media, the lipids aggregate to form a structure in which only the polar head groups are exposed to the external media to form an external shell inside which the aliphatic tails are sequestered. A variety of liposome structures can be formed using one or more lipids. Examples of liposome structures include, e.g., small unilamellar vesicles (SUVs), large unilamellar vesicles (LUVs), and multilamellar vesicles (MLVs).

Figure 22:
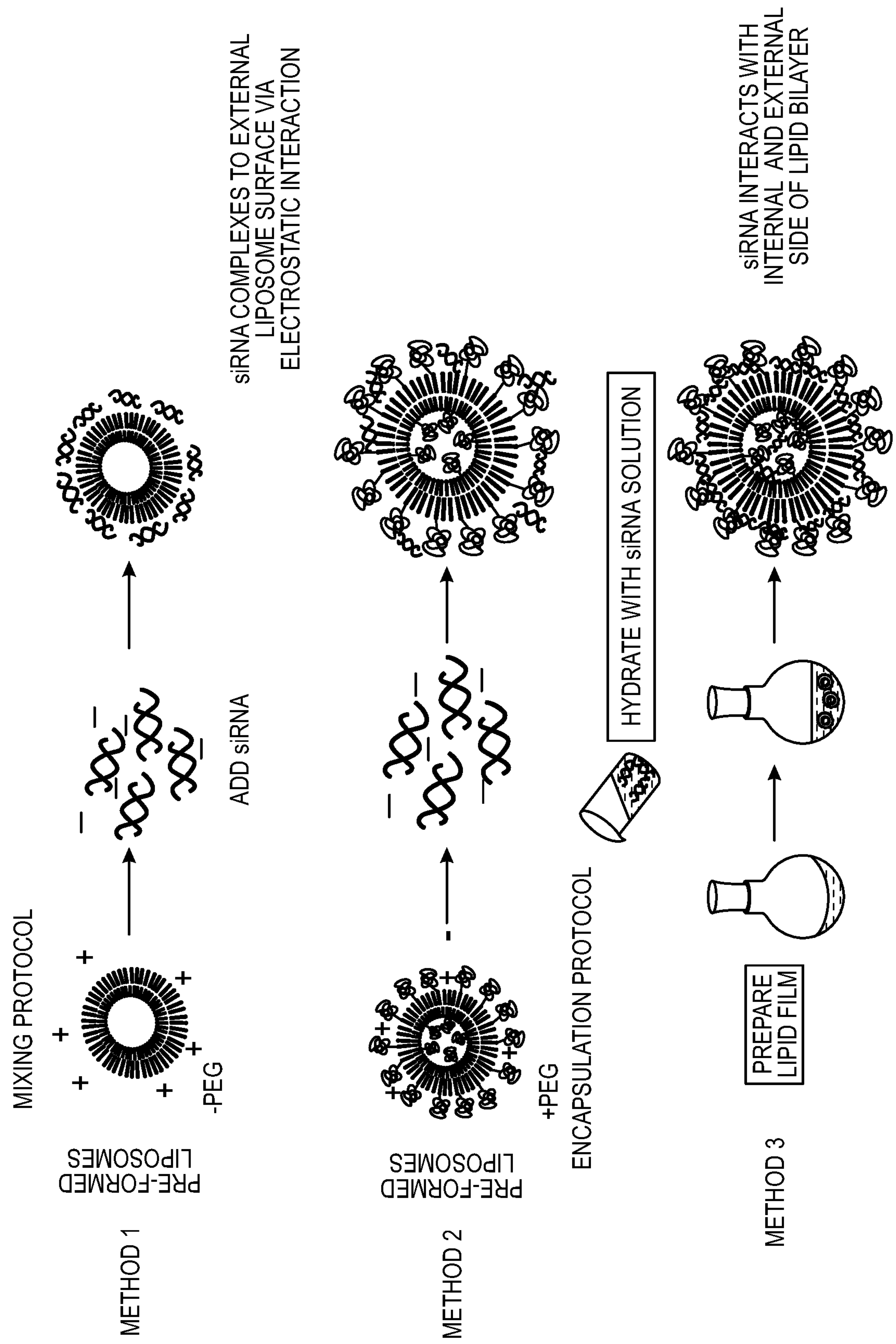
FIG. 22: A schematic drawing shows cationic liposome delivery systems for siRNA delivery (thin-film hydration) (Podesta and Kostarelos, *Methods Enzymol.* 464:343-54, 2009).

Cationic liposomes have a liposomal structure with one or more cationic groups that give a net positive charge. Three methods of siRNA delivery using cationic liposome delivery systems are shown in FIG. 22. Method 1 includes the following steps (see, e.g., Pandi et al., *Int J Pharm.* 550(1-2):240-250, 2018; Muralidharan et al., *J Nanobiotechnology.* 14(1):47, 2016; Taruttis et al., *Nanoscale.* 6(22):13451-6, 2014; and Zou et al., *Cancer Gene Ther.* 7(5):683-96, 2000): (1) DOTAP and cholesterol (2:1) are dissolved in chloroform:methanol (4:1 v/v) and the organic solvent is evaporated under pressure for 30 min at 40° C. using a rotoevaporator. The resulting thin lipid film is flushed with a stream of $N_2$ to remove any trace of the organic solvent. (2) The lipid film is hydrated in $H_2O$ by rapid pipetting to produce large, multilamellar liposomes (MLVs). The MLVs are reduced to small, by extrusion through a 0.4 μm Anotop 10 filter (Whatman, UK). The liposome solution is then incubated at room temperature for a minimum 30 min to allow stabilization. (3) Liposomes and siRNA are diluted separately into 50% final volume. The siRNA is added to the liposome by rapid pipetting to prevent localized high siRNA:liposome concentrations. This is mixed thoroughly by pipetting and brief vortexing. The mixture is then incubated at room temperature for 20 min to allow complexation to occur.

Method 2 includes the following steps (see, e.g., Khatri et al., *J Control Release.* 182:45-57, 2014; and Amadio et al., *Pharmacol Res.* 111:713-720, 2016): (1) PEGylated liposomes are prepared using the same protocol in Method 1. Briefly, DSPE-PEG2000 (5 mol %) is dissolved in the organic solvent with DOTAP and cholesterol. The PEGylated liposome is hydrated, reduced in size, and measured in the same way in Method 1. (2) Liposomes and siRNA are diluted separately into 50% final volume. The siRNA is added to the liposome by rapid pipetting to prevent localized high siRNA:liposome concentrations. This is mixed thoroughly by pipetting and brief vortexing. The mixture is then incubated at room temperature for 20 min to allow complexation to occur.

Method 3 includes the following steps (see, e.g., Kedmi et al., *Biomaterials.* 31(26):6867-75, 2010; Mendez et al., *Biomaterials.* 35(35):9554-61, 2014; and Tagami et al., *J Control Release.* 151(2):149-54, 2011): (1) DOTAP, cholesterol, and DSPE-PEG2000 (2:1:0.1) are dissolved in chloroform:methanol (4:1, v/v). The organic solvent is evaporated under pressure at 40° C. for 30 min and the lipid film is flushed with $N_2$ to remove residual solvent. (2) The lipid film is hydrated using a solution of siRNA in RNase-free $dH_2O$. The amount of siRNA used to hydrate the film is calculated from the charge ratio. (3) Size reduction is performed by extrusion through a 0.4 μm Anotop 10 filter (Whatman, UK). The PEGylated liposome/siRNA solution is then incubated at room temperature for a minimum of 30 min to allow stabilization. The complex should be maintained in a sterile environment for subsequent gene silencing experiments.

IV. Polynucleotides and Recombinant Expression Vectors

The isolation of polynucleotides of the invention may be accomplished by a number of techniques. For instance, oligonucleotide probes based on the sequences disclosed here can be used to identify the desired polynucleotide in a cDNA or genomic DNA library from a desired plant species.

To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon a sequence disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Polynucleotides can also be synthesized by well-known techniques as described in the technical literature. See, e.g., Carruthers et al., Cold Spring Harbor Symp. *Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Once a polynucleotide sequence that inhibits expression of target gene of Table 1 or Table 2 or a fragment thereof, is obtained, it can be used to prepare an expression cassette for expression in a plant. In some embodiments, expression of the polynucleotide is directed by a heterologous promoter.

Any of a number of means well known in the art can be used to drive expression of the polynucleotide sequence of interest in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, expression can be conditioned to only occur under certain conditions (e.g., using an inducible promoter).

For example, a plant promoter fragment may be employed to direct expression of the polynucleotide sequence of interest in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide sequence of interest in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO/2005/085449; U.S. Pat. No. 6,653,535; Li et al., *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include the presence of a pathogen, anaerobic conditions, elevated temperature, or the presence of light.

In some embodiments, the promoter is a constitutive promoter. In some embodiments, the promoter is an inducible promoter. In some embodiments, the promoter is stress inducible (e.g., inducible by abiotic stress). In some embodiments, the promoter is pathogen inducible. In some embodiments, the promoter is induced upon infection by *Botyrtis*. Non-limiting examples of pathogen inducible promoters include *Botyritis*-Induced Kinase 1 (BIK1) and the plant defensing gene PDF1.2. See, e.g., Penninckx et al., *Plant Cell* 10:2103-2113 (1998); see also Veronese et al., *Plant Cell* 18:257-273 (2006).

In some embodiments, a polyadenylation region at the 3'-end of the coding region can be included. The polyadenylation region can be derived from a NH3 gene, from a variety of other plant genes, or from T-DNA.

The vector comprising the sequences will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

V. Production of Transgenic Plants

As detailed herein, embodiments of the present invention provide for transgenic plants comprising recombinant expression cassettes for expressing a polynucleotide sequence as described herein. In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

In some embodiments, the transgenic plants comprising recombinant expression cassettes for expressing a polynucleotide sequence as described herein have increased or enhanced pathogen resistance compared to a plant lacking the recombinant expression cassette, wherein the transgenic plants comprising recombinant expression cassettes for expressing the polynucleotide sequence have about the same growth as a plant lacking the recombinant expression cassette. Methods for determining increased pathogen resistance are described, e.g., in Section VI below.

A recombinant expression vector as described herein may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional

*Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the polynucleotide sequence of interest is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced pathogen resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

After the expression cassette is stably incorporated in transgenic plants and confirmed to be operable, it can be introduced into other plants by sexual crossing. Any of a number of standard breeding techniques can be used, depending upon the species to be crossed.

The expression cassettes and constructs (e.g., antisense and siRNAs) as described herein can be used to confer increased or enhanced pathogen resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and *Zea*. In some embodiments, the plant is a tomato plant. In some embodiments, the plant is a vining plant, e.g., a species from the genus *Vitis*. In some embodiments, the plant is an ornamental plant. In some embodiments, the plant is a vegetable- or fruit-producing plant. In some embodiments, the plant is a monocot. In some embodiments, the plant is a dicot.

VI. Selecting for Plants with Increased Pathogen Resistance

Plants (or parts of plants) with increased pathogen resistance can be selected in many ways. One of ordinary skill in the art will recognize that the following methods are but a few of the possibilities. One method of selecting plants or parts of plants (e.g., fruits and vegetables) with increased pathogen resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen, compound, or plant is used. Generally, increased resistance is measured by the reduction or elimination of disease symptoms (e.g., reduction in the number or size of lesions or reduction in the amount of fungal biomass on the plant or a part of the plant) when compared to a control plant. In some embodiments, resistance is increased when the number or sizes of lesions or amount of fungal biomass on the plant or on a part of the plant is decreased by at least about 10%, 20%, 30%, 40%, 50%, 60%, 70%, 80%, 90% or more relative to a control (e.g., relative to a plant in which a heterologous polynucleotide has not been expressed).

Increased pathogen resistance can also be determined by measuring the increased expression of a gene operably linked a defense related promoter. Measurement of such expression can be measured by quantifying the accumulation of RNA or subsequent protein product (e.g., using northern or western blot techniques, respectively (see, e.g., Sambrook et al. and Ausubel et al.).

VII. Examples

Example 1

Figure 1B:
Figure 7A:
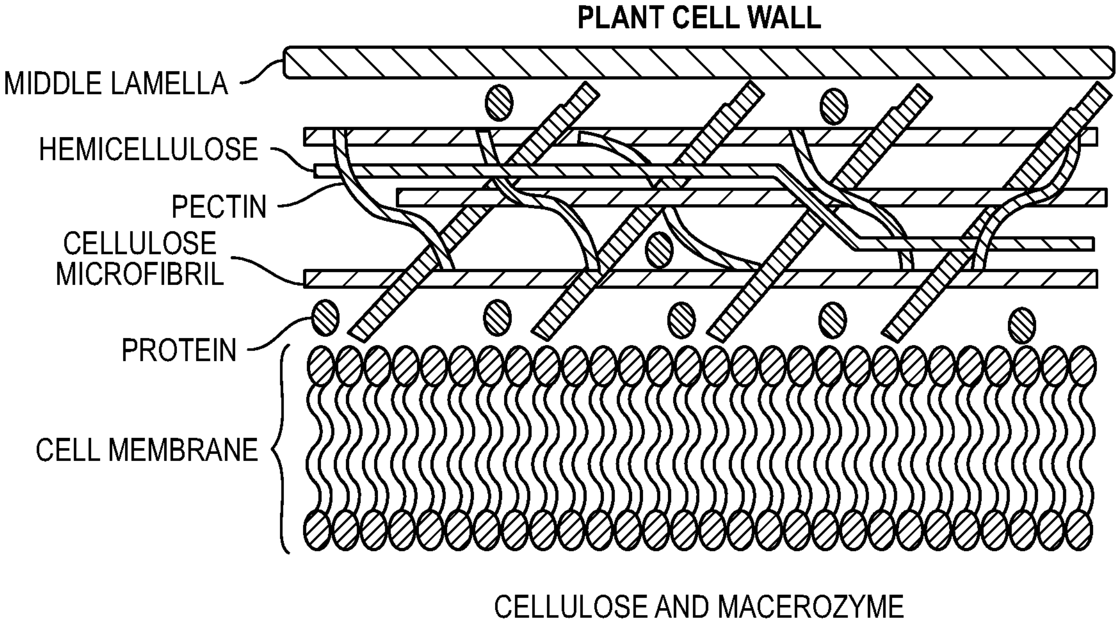
FIGS. 7A and 7B: Representations of the plant and fungal cell walls. Plant cell walls (FIG. 7A), mainly composed of cellulose, hemicellulose, pectin, and proteins, can be digested by cellulose and macerozyme. Fungal cell walls (FIG. 7B), mainly compose of chitin, glucans, and proteins, can be digested by lysing enzyme from *Trichoderma harzianum.*
Figure 7B:
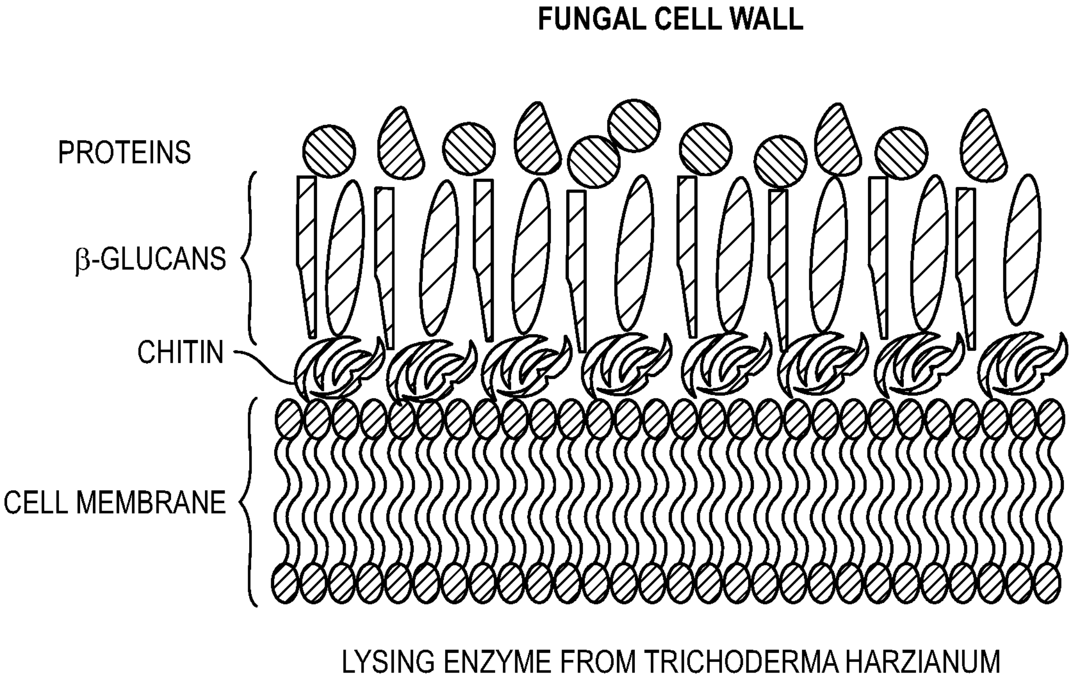

To identify plant host endogenous mobile sRNAs and to investigate how host sRNAs get into interacting fungal cells, we used an *Arabidopsis*—*B. cinerea* interaction system that displays bidirectional sRNA trafficking and RNAi (Weiberg, A. et al. Fungal sRNAs suppress plant immunity by hijacking host RNA interference pathways. (*Science* 342, 118-123, doi:10.1126/science.1239705 (2013); Wang, M. et al., *Nature plants* 2, 16151, doi:10.1038/nplants.2016.151 (2016)). Because the cell wall compositions of plants and fungi are different (Cosgrove, D. J., *Nature Reviews. Molecular cell biology* 6, 850-861, doi:10.1038/nrm1746 (2005); Bowman, S. M. and Free, S. J., *Bioessays* 28, 799-808, doi:10.1002/bies.20441 (2006)) (FIGS. 7A and 7B), we developed an efficient sequential protoplast purification method to isolate pure fungal cells from infected tissues (FIG. 1A). Weprofiled sRNAs isolated from the purified *B. cinerea* protoplasts, and identified nearly 80 *Arabidopsis* host sRNAs in both biological replicates by using 10 normalized reads per million of total reads (RPM) as a cutoff (Supplementary Table 1). To validate the deep sequencing results and to test whether host sRNAs are transported into fungal cells by a selective or concentration-dependent process (more abundant sRNAs are more likely to be transported into fungal cells), we performed sRNA profiling on total RNAs for comparative analysis. We found that although the more abundant sRNAs were more likely to be transported (Supplementary Table 2), there is clear selection in transferred sRNAs. Among the transferred *Arabidopsis* sRNAs, five were lowly abundant (<10 RPM) in the total sRNA libraries (Supplementary Table 3). Only 29 were present in the hundred most abundant sRNAs in the total sRNA libraries, 16 of which were miRNAs (Supplementary Table 2). miR166, miR159, and miR157 were among the most abundant sRNAs in both *B. cinerea* protoplast sRNA libraries and total sRNA libraries. Most strikingly, of the two trans-acting small interfering RNAs (tasiRNAs) generated from the same TAS2 mRNA precursor, only TAS2-siR453 was present in the *B. cinerea* protoplast libraries, although TAS2-siR710 had 30 times higher reads than TAS2-siR453 in the total sRNA libraries. Similarly, TAS1c-siR483, but not TAS1c-siR585, was highly enriched in the *B. cinerea* protoplast sRNA libraries, although both of them are generated from the same TAS1c mRNA precursor and belong to the top 20 most abundant sRNAs in the total sRNA libraries (Supplementary Table 2 and 3). Furthermore, *Arabidopsis* sRNAs that derived from an intergenic region, such as IGN-siR1 but not IGN-siR107, were highly enriched in the *B. cinerea* cells, although IGN-siR107 occurred at higher level in the total sRNA libraries (Supplementary Table 2 and 3). These deep sequencing results were validated by sRNA RT-PCR analysis of two additional biological replicates (FIG. 1B). These results suggest that host endogenous sRNAs are selectively delivered into fungal cells and that it is not simply the most abundant sRNAs that diffuse into the fungal cell.

Figure 1C:
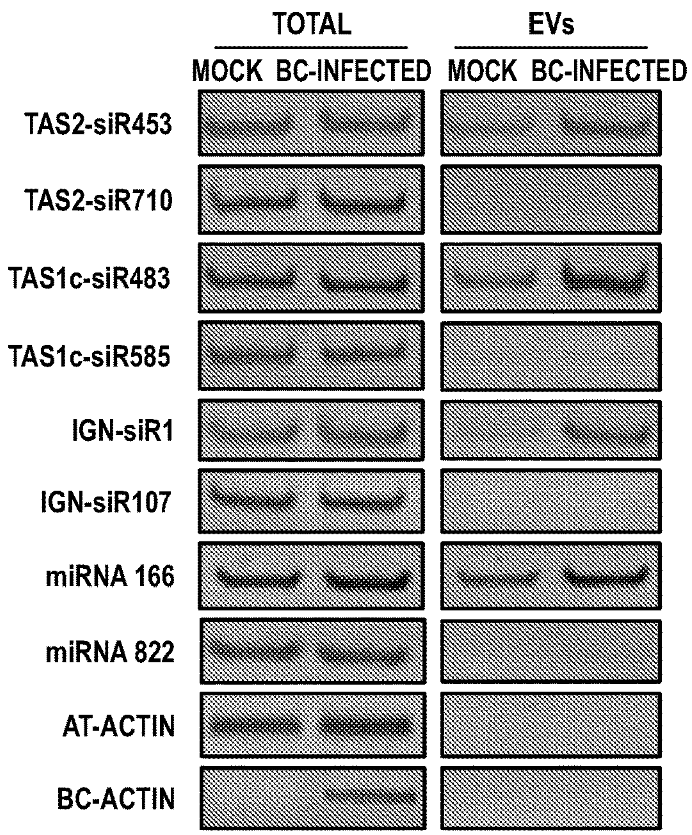
Figure 1D:
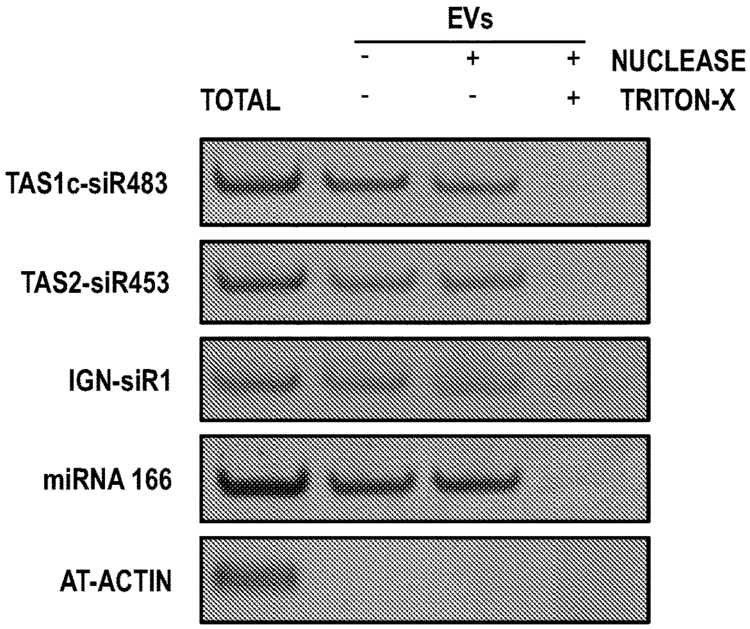

Extracellular vesicles (EVs) are implicated in sRNA communications between cells and systemic transport in animal systems (Colombo, M. et al., *Annu Rev Cell Dev Biol* 30, 255-289, doi:10.1146/annurev-cellbio-101512-122326 (2014)). To test whether EV secretion is the mechanism by which plant hosts transfer sRNAs into *B. cinerea* cells, we profiled sRNAs of EVs isolated from the apoplastic fluids of *Arabidopsis* leaves using filtration and differential ultra-centrifugation methods. In both of the biological replicates analyzed, TAS2-siR453 and TAS1c-siR483 were accumulated to much higher levels in EVs than either TAS2-siR710 or TAS1c-siR585 (Supplementary Table 2 and 4), consistent with the results obtained from the *B. cinerea* protoplast samples. miRNAs, such as miR166, that were abundant in both total and *B. cinerea* protoplast samples were also abundant in the EVs. In contrast, sRNAs, such as miR822, that were abundant in total sRNA populations but below detection levels in the *B. cinerea* protoplast samples were accumulated to a very low level in EVs (Supplementary Table 2). Furthermore, the sRNAs that derived from intergenic region, such as IGN-siR1, accumulated at a much higher level in EVs than IGN-siR107 (Supplementary Table 2 and 4) indicating a correlation between EVs and *B. cinerea* protoplast samples. These deep sequencing results were validated by sRNA RT-PCR analysis of two additional biological replicates (FIG. 1C). Among the *Arabidopsis* sRNAs that transferred into *B. cinerea* protoplasts, 36 were present in the EV libraries, but 12 sRNAs were not (Supplementary Table 4). These latter sRNAs may utilize an EV-independent pathway to move into fungal cells, or they are still EV-dependent, but just under the level of detection in the EV fraction. To confirm that these sRNAs are indeed inside the EVs instead of simply bound to the surface, we performed nuclease protection assays. TAS1c-siR483 and TAS2-siR453, IGN-siR1 as well as miRNA166 were protected from nuclease digestion unless Triton-X-100 was added to rupture the EV membrane (FIG. 1D). These findings support that plant cells utilize secreted EVs to transfer sRNAs into fungal cells and that secretion is likely mediated by the selective inclusion of sRNAs into EVs.

Figure 2A:
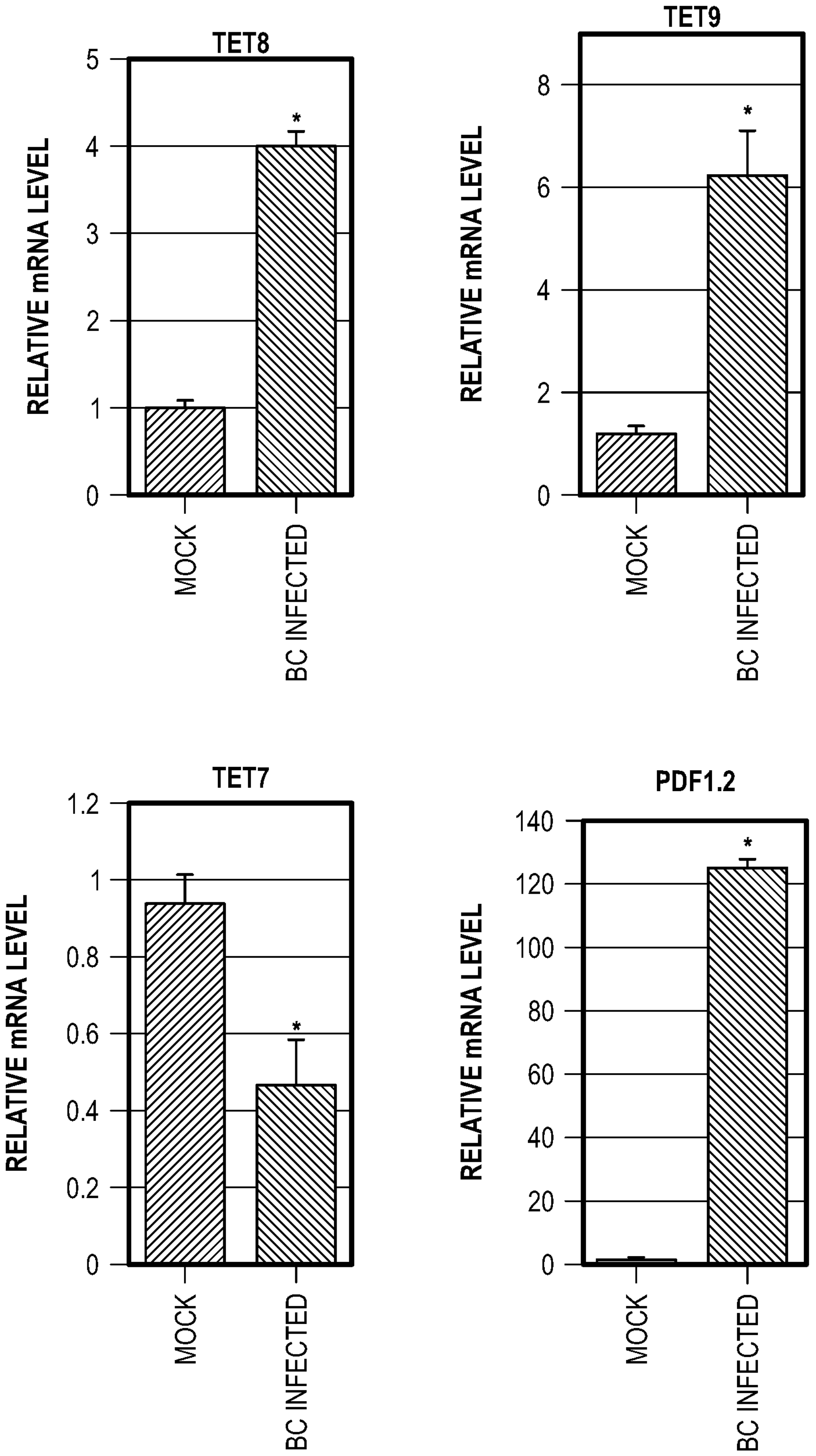
FIGS. 2A-2F: Tetraspanin-associated exosome-like vesicles (ELVs) were involved in plant endogenous sRNA transport.
Figure 8A:
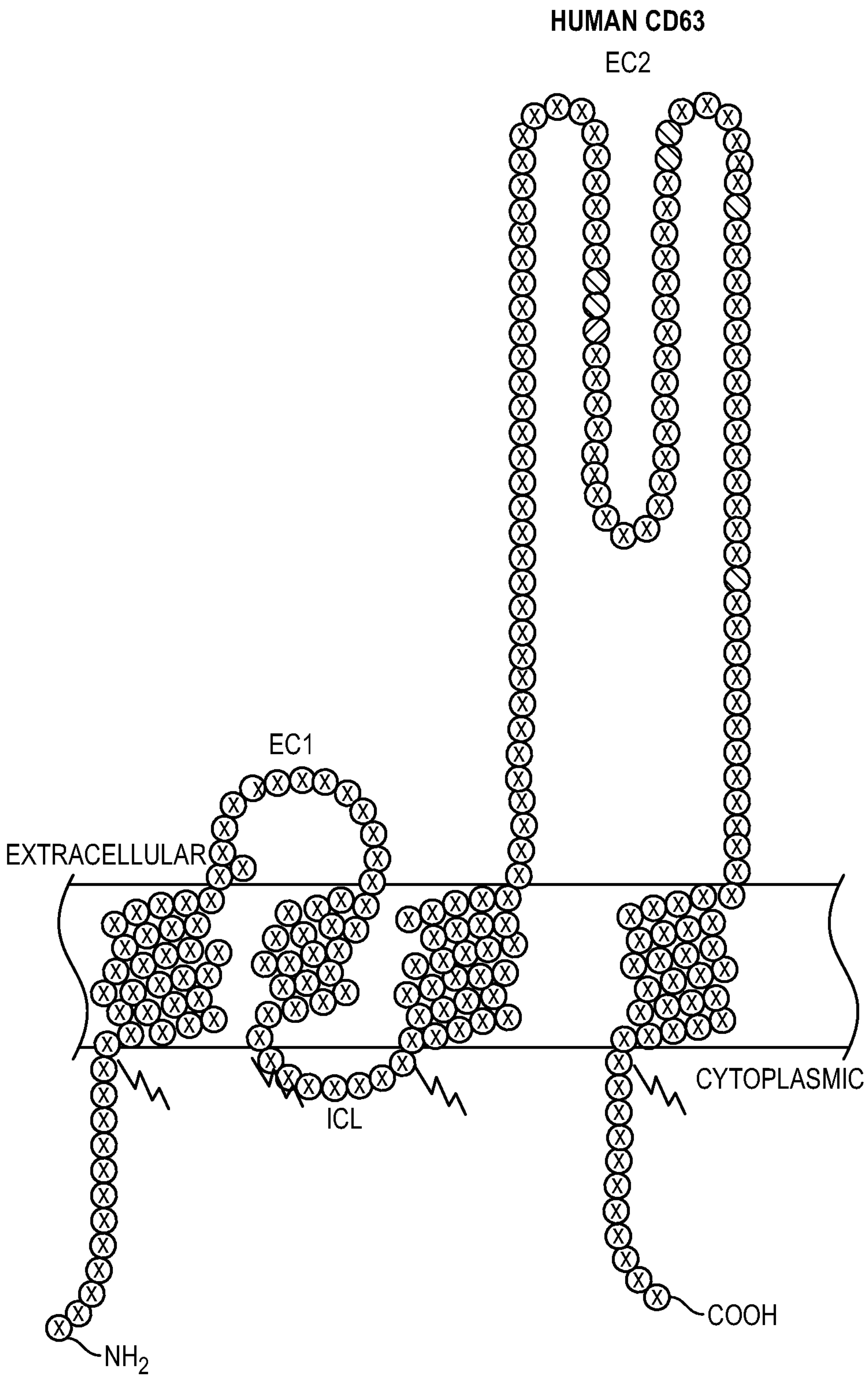
FIGS. 8A-8C: The structures and the topology of plant tetraspanins TET8 and TET9 are similar to that of human CD63. Images were made by online tool Protter (http://molbiol-tools.ca/Protein_secondary_structure.htm). Conserved cysteines, the plant GCCK/RP motif (SEQ ID NO: 79) and animal CCG motif in EC2 (large extracellular domain) were marked. In plant, a conserved cysteine in EC1 (small extracellular domain) also marked. Potential palmitoylation sites in the transmembrane domains are indicated with red zigzag lines.
Figure 8B:
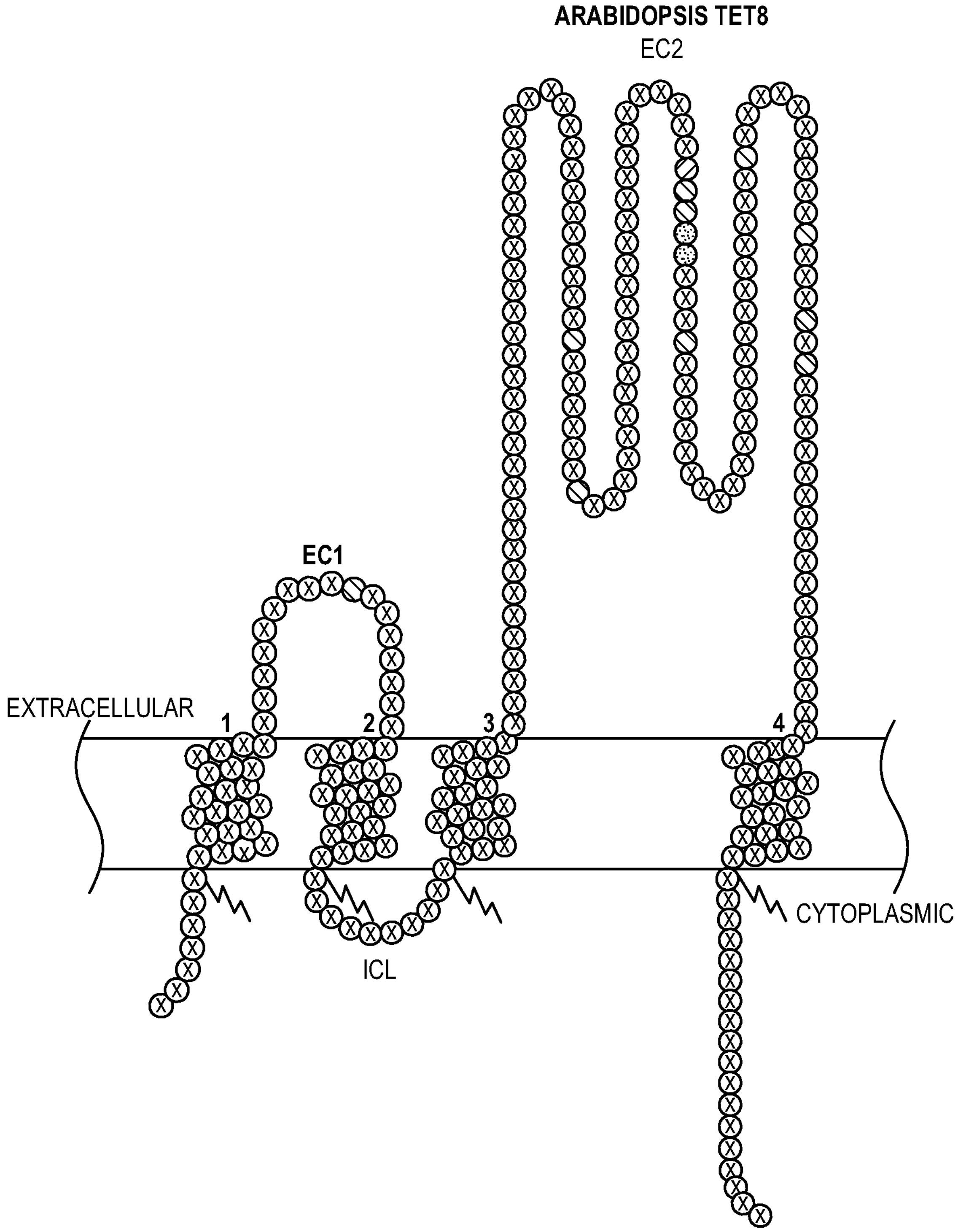
Figure 8C:
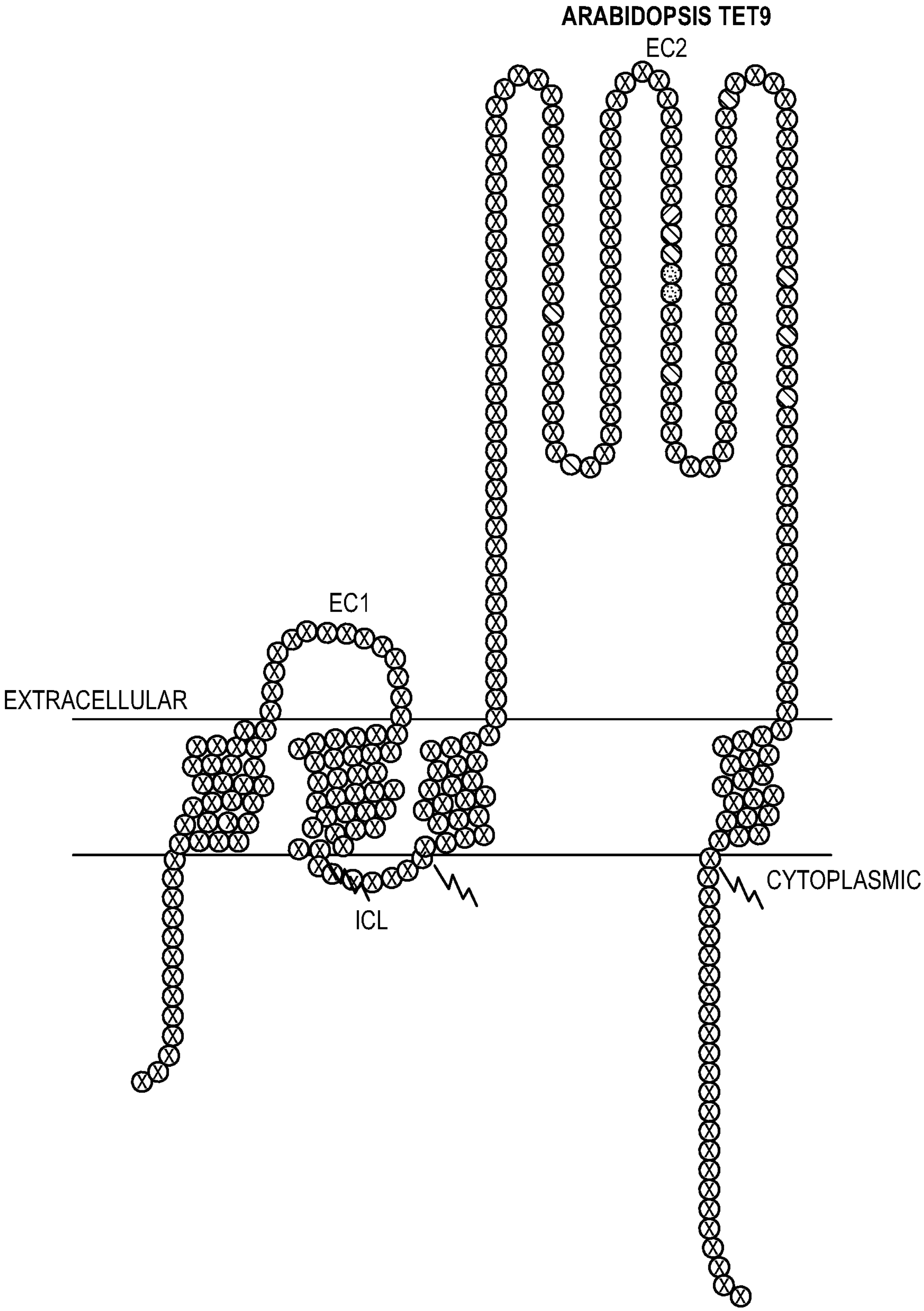

Animal EVs are classified into different categories, such as exosomes, shedding microvesicles and apoptotic bodies based on their specific protein markers and origins (Mathivanan, S. et al., *J Proteomics* 73, 1907-1920, doi:10.1016/j.jprot.2010.06.006 (2010)), whereas plant EVs have not been well defined. Because exosomes have been shown to play an important role in transferring miRNAs between animal cells within an organism (Colombo, M. et al., *Annu Rev Cell Dev Biol* 30, 255-289, doi:10.1146/annurev-cell-bio-101512-122326 (2014)) or even between interacting organisms from nematode parasites to mammalian host cells (Buck, A. H. et al., *Nature communications* 5, 5488, doi:10.1038/ncomms6488 (2014)), we hypothesize that plants may also employ exosome-like vesicles (ELVs) to transfer sRNAs. Tetraspanins, such as CD63, CD81 and CD9, are small membrane proteins that serve as specific exosome markers in mammalian cells (Mathivanan, S. et al., *J Proteomics* 73, 1907-1920, doi:10.1016/j.jprot.2010.06.006 (2010)). *Arabidopsis* has 17 TETRASPANIN (TET)-like genes (Boavida, L. C. et al., *Plant Physiol* 163, 696-712, doi:10.1104/pp.113.216598 (2013)), but expression analysis reveals that only two closely related tetraspanin genes, TET8 and TET9 (Boavida, L. C. et al., *Plant Physiol* 163, 696-712,doi:10.1104/pp.113.216598 (2013); Wang, F. et al., *Plant Physiol* 169, 2200-2214, doi:10.1104/pp.15.01310 (2015)) are highly induced by *B. cinerea* infection (Ferrari, S. et al., *Plant Physiol* 144, 367-379, doi:10.1104/pp.107.095596 (2007)) (FIG. 2A), suggesting their potential function in defense responses. The structure and topology of TET8 and TET9 are most similar to the exosome marker CD63 in animals (Boavida, L. C. et al., *Plant Physiol* 163, 696-712, doi:10.1104/pp.113.216598 (2013)) (FIGS. 8A-8C).

Figure 2B:
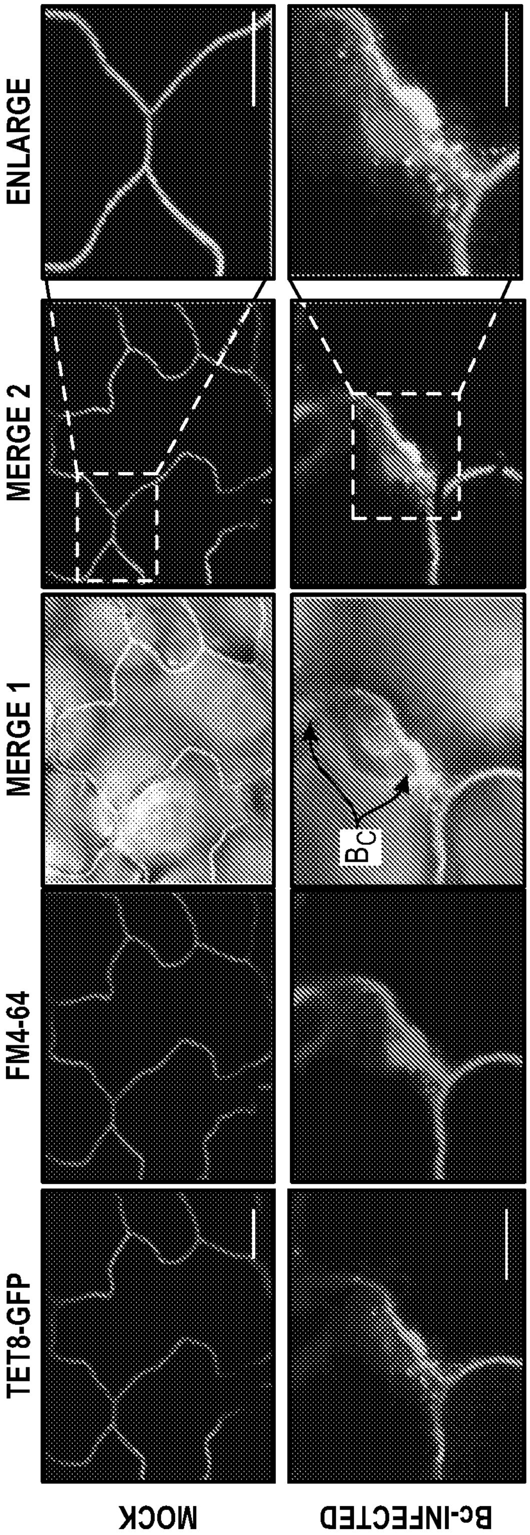

Because TET8 is expressed at a much higher level than TET9 in the leaves and at fungal infection sites (Ferrari, S. et al., *Plant Physiol* 144, 367-379, doi:10.1104/pp.107.095596 (2007)), we mainly focused on TET8 for subsequent analysis. Short staining by lipophilic dye FM4-64 allows visualization of membrane structures, such as fungal cell membranes and EVs that occur outside of plant cell (Nielsen, M. E. et al., *Proc Natl Acad Sci USA* 109, 11443-11448, doi:10.1073/pnas.1117596109 (2012)). In transgenic plants expressing TET8-GFP under its native promoter, there was an accumulation of TET8-GFP at the fungal infection sites that were coincident with FM4-64 staining patterns (FIG. 2B). These observations suggest that TET8 is involved in host responses to fungal infection, and that TET8-associated membrane structures/vesicles are likely to be secreted.

Figure 2C:
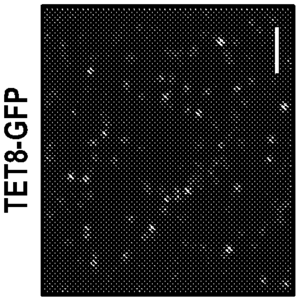
Figure 2D:
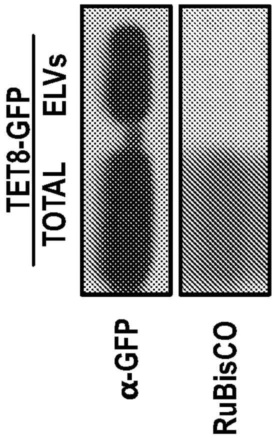

To confirm that TET8-associated vesicles are secreted, we isolated the extracellular apoplastic vesicles from transgenic plants expressing TET8-GFP. Numerous TET8-GFP-labeled fluorescent EVs were observed (FIG. 2C). Consistent with this result, an immunoblot for GFP revealed the presence of TET8-GFP exclusively in the ELVs derived from TET8-GFP plants (FIG. 2D). Thus, TET8 serves as a good marker for plant ELVs.

Figure 2E:
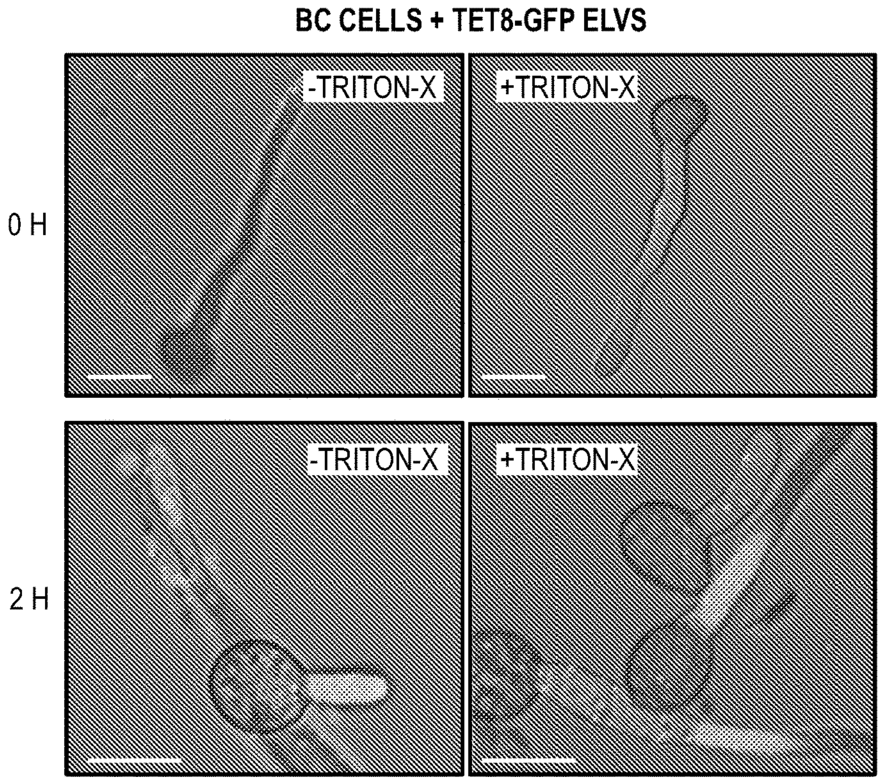
Figure 2F:
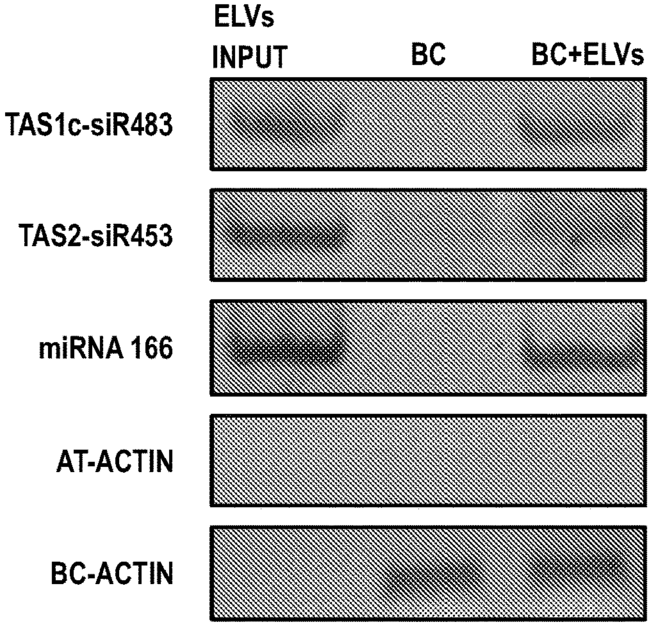

To test whether plant ELVs can be taken up by fungal cells, we isolated EVs from apoplast fluids containing TET8-GFP labeled ELVs and incubated them with *B. cinerea* cells in vitro. GFP signals were clearly observed in the fungal cells within 2 hours (FIG. 2E). After treatment with 1% Triton-X-100, a procedural step that ruptures all EVs but not fungal cells, the GFP signal still maintained in the fungal cells (FIG. 2E), indicating that *B. cinerea* cells are capable of taking up plant secreted ELVs. Consistent with the occurrence of ELV uptake by the fungal pathogen, TAS1c-siR483, TAS2-siR453, and miRNA166 were detected inside fungal cells (FIG. 2F). These results support the conclusion that TET8-associated host ELVs are important for host sRNA transfer to fungal cells.

Figure 3A:
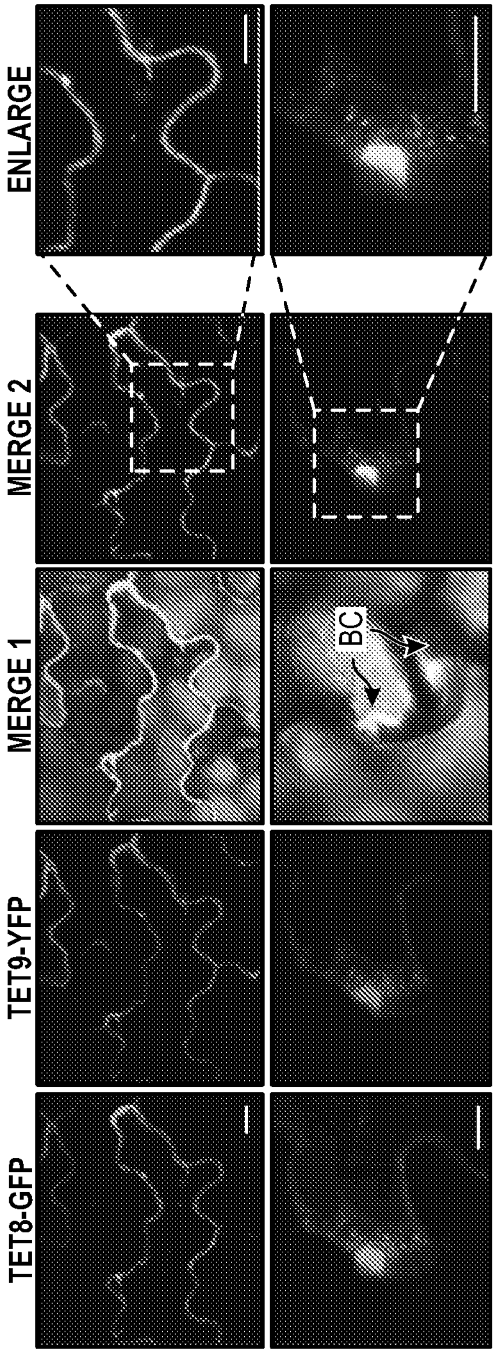
FIGS. 3A-3E: TET8 and TET9 interact with each other and regulate sRNA secretion and host immunity.
Figure 3B:
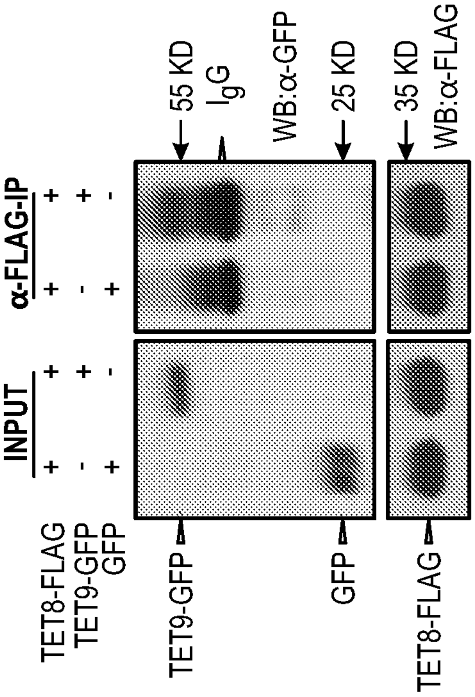
Figure 3C:
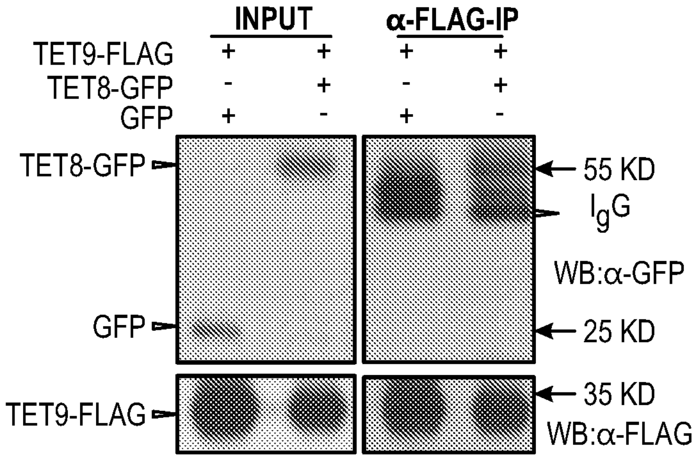
Figure 3D:
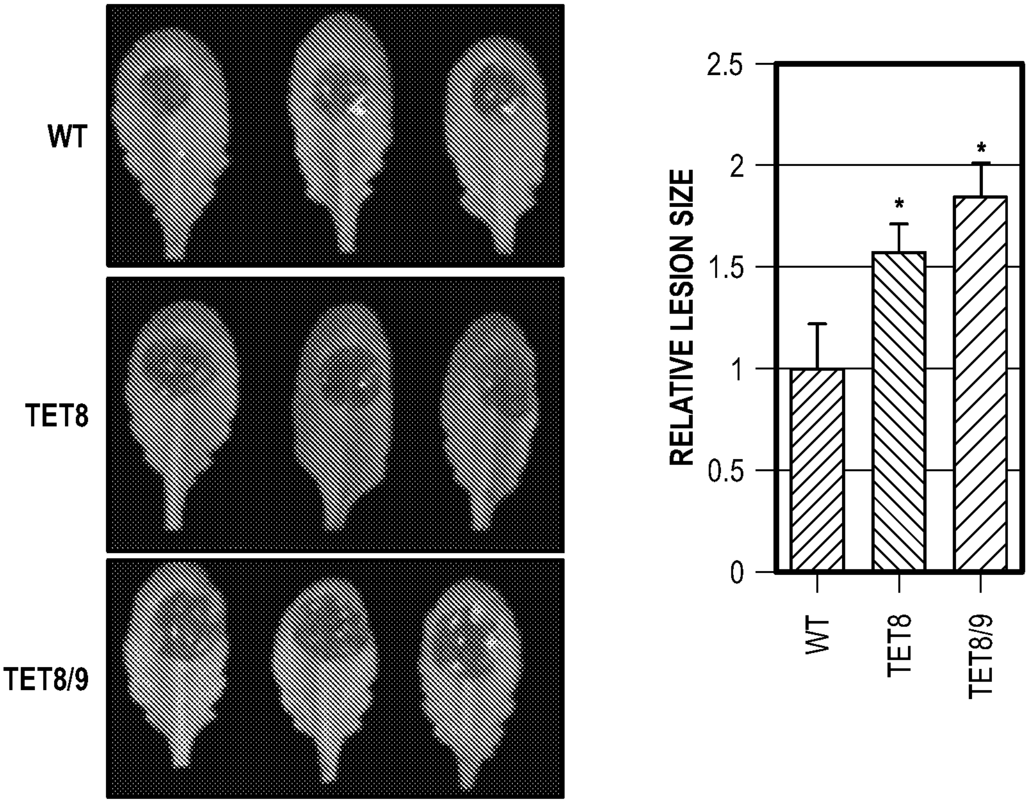
Figure 3E:
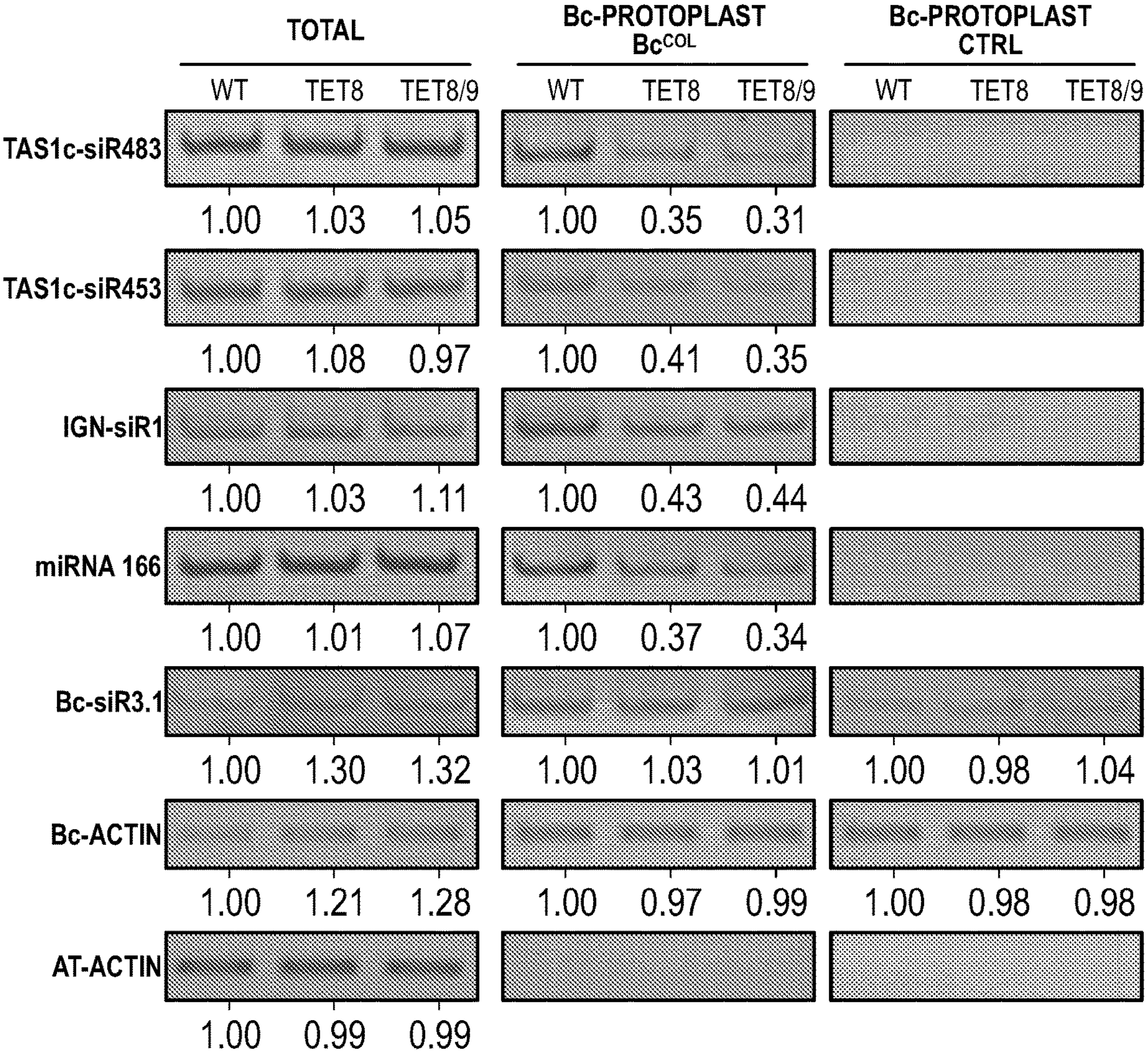
Figure 9:
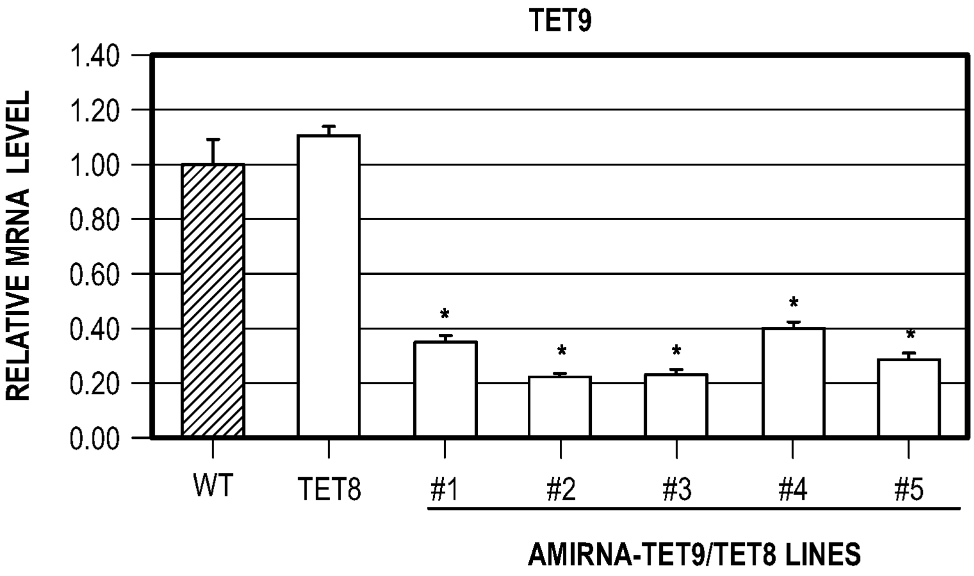
FIG. 9: Characterization of the tet8 tet9 knock-down lines. TET9 transcript levels were measured in the 4-week-old tet8 mutant expressing a TET9 artificial miRNA construct and control plants (wild-type [WT], and the tet8 mutant). Quantitative RT-PCR measurements were normalized to *Arabidopsis* Actin mRNA levels. The asterisks indicate significant difference (two-tail t-test, P<0.01). Lines with strong suppression of TET9 expression were selected for the experiments presented in this study.

Tetraspanin proteins often interact with each other and form specific membrane microdomains that are essential for their cellular functions (Andreu, Z. and Yanez-Mo, M., *Frontiers in immunology* 5, 442, doi:10.3389/fimmu.2014.00442 (2014)). As TET9 is the only other *Arabidopsis* tetraspanin gene that is induced by *B. cinerea* infection (Ferrari, S. et al., *Plant Physiol* 144, 367-379, doi:10.1104/pp.107.095596 (2007)) (FIG. 2A), we examined whether TET8 and TET9 interact with each other and function together in response to fungal attack. Indeed, TET8-CFP protein was co-localized with TET9-YFP at the fungal infection sites (FIG. 3A). Interaction of TET8 with TET9 was further confirmed by reciprocal co-immunoprecipitation (Co-IP) in vivo (FIGS. 3B and 3C). To obtain insight into the physiological role of TET8 and TET9, we challenged the loss-of-function mutants with *B. cinerea*. The tet8 single mutant displayed enhanced susceptibility to fungal infection as compared with the wild type (FIG. 3D). Enhanced susceptible phenotype was potentiated in the double mutant when TET9 was knocked down in the tet8 mutant background (FIG. 3D and FIG. 9). Furthermore, levels of transferred host sRNAs to fungal cells were reduced in tet8, and the tet8tet9 double mutant, even though the total cellular level of these sRNAs was unchanged (FIG. 3E). These results suggest that TET8 and TET9-associated ELVs are important for host sRNA transfer into fungal cells, and contribute to plant immune responses against fungal infection.

Figure 4A:
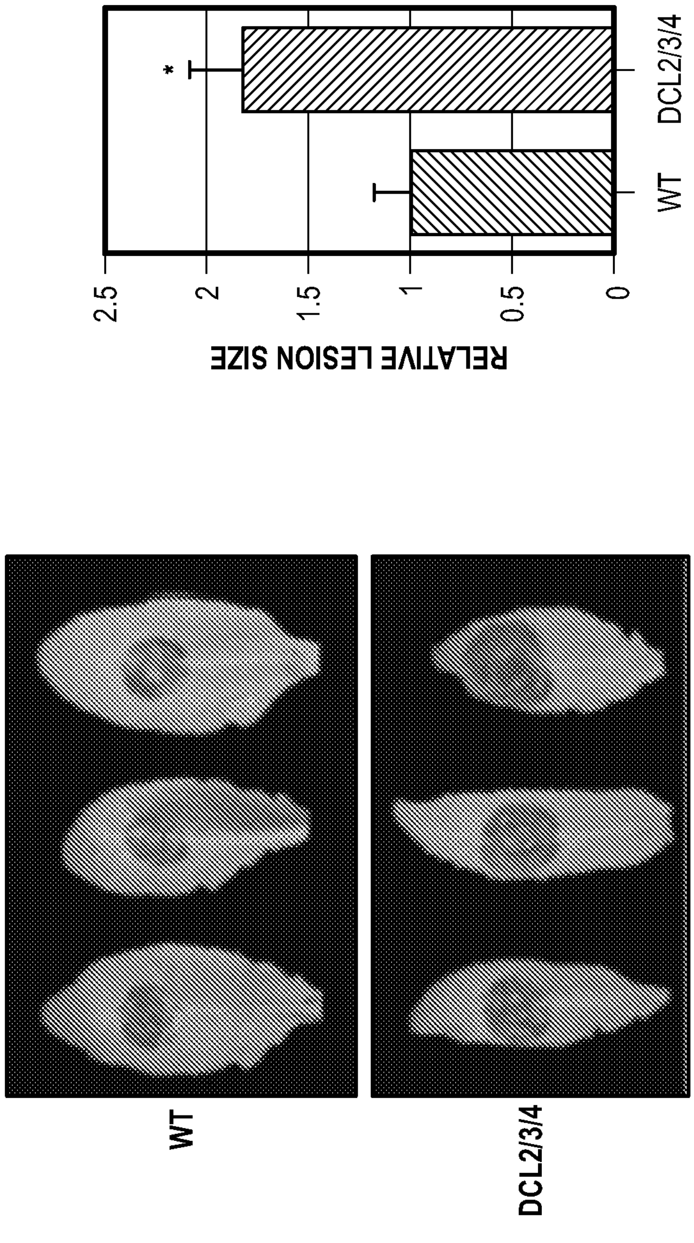
FIGS. 4A-4C: Transferred plant endogenous sRNAs suppress *B. cinerea* virulence genes and reduce fungal pathogenicity.
Figure 4B:
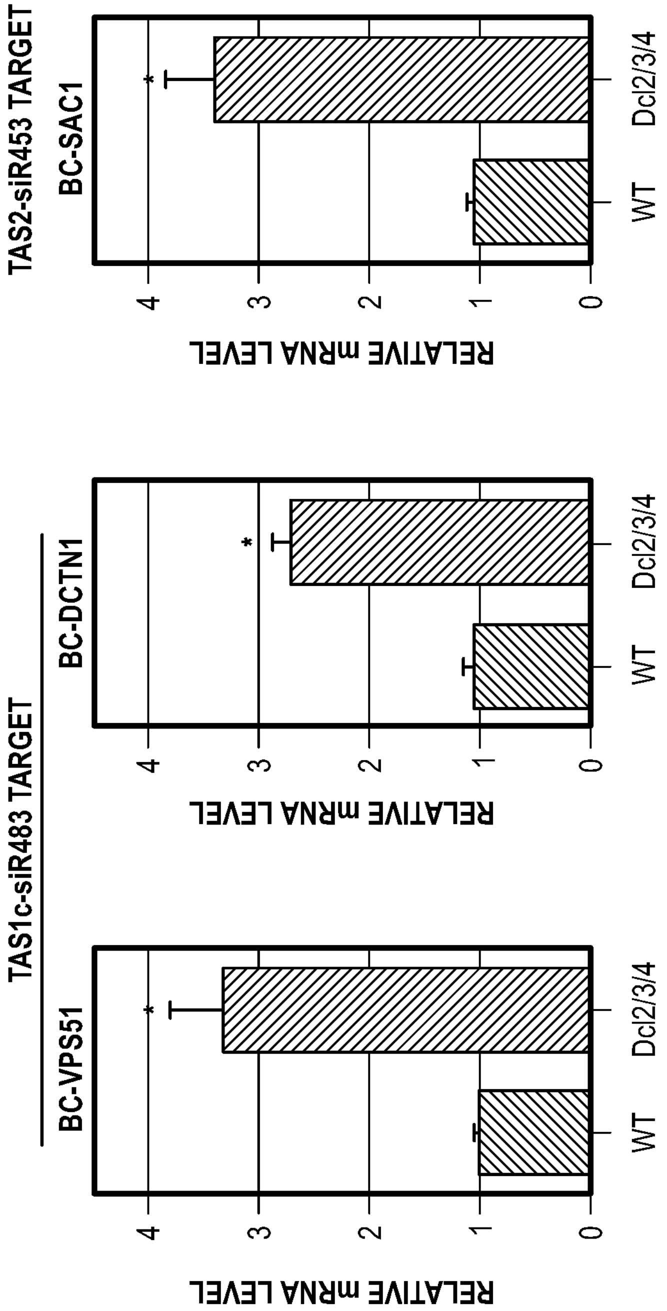
Figure 10:
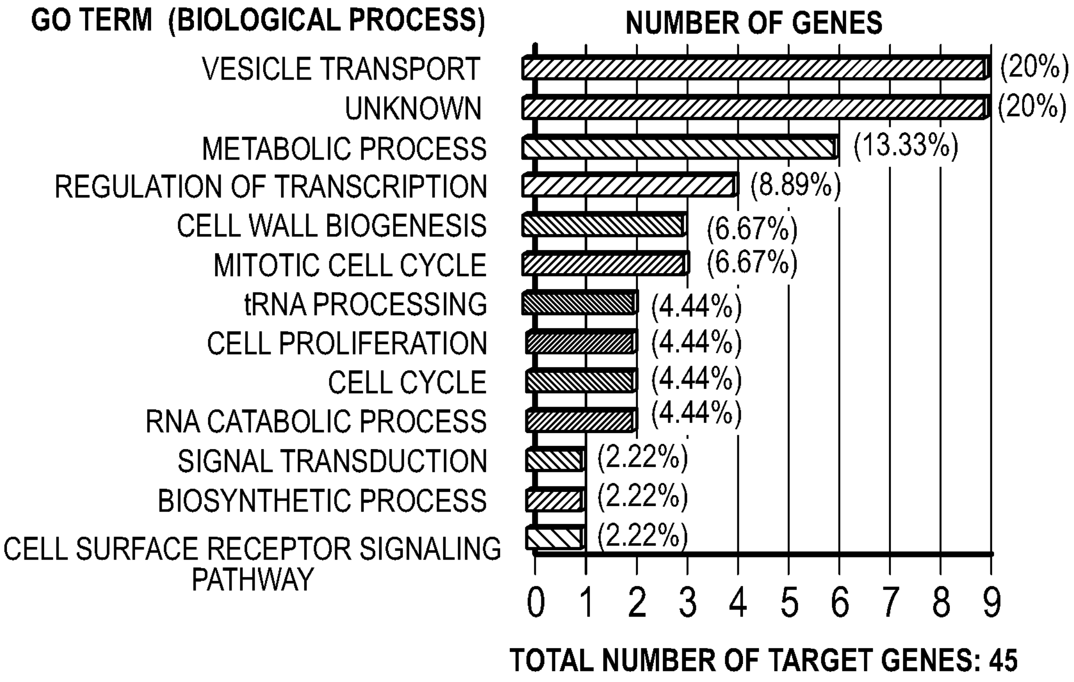
FIG. 10: Gene Ontology (GO) enrichment analysis of *B. cinerea* target genes.
Figure 11A:
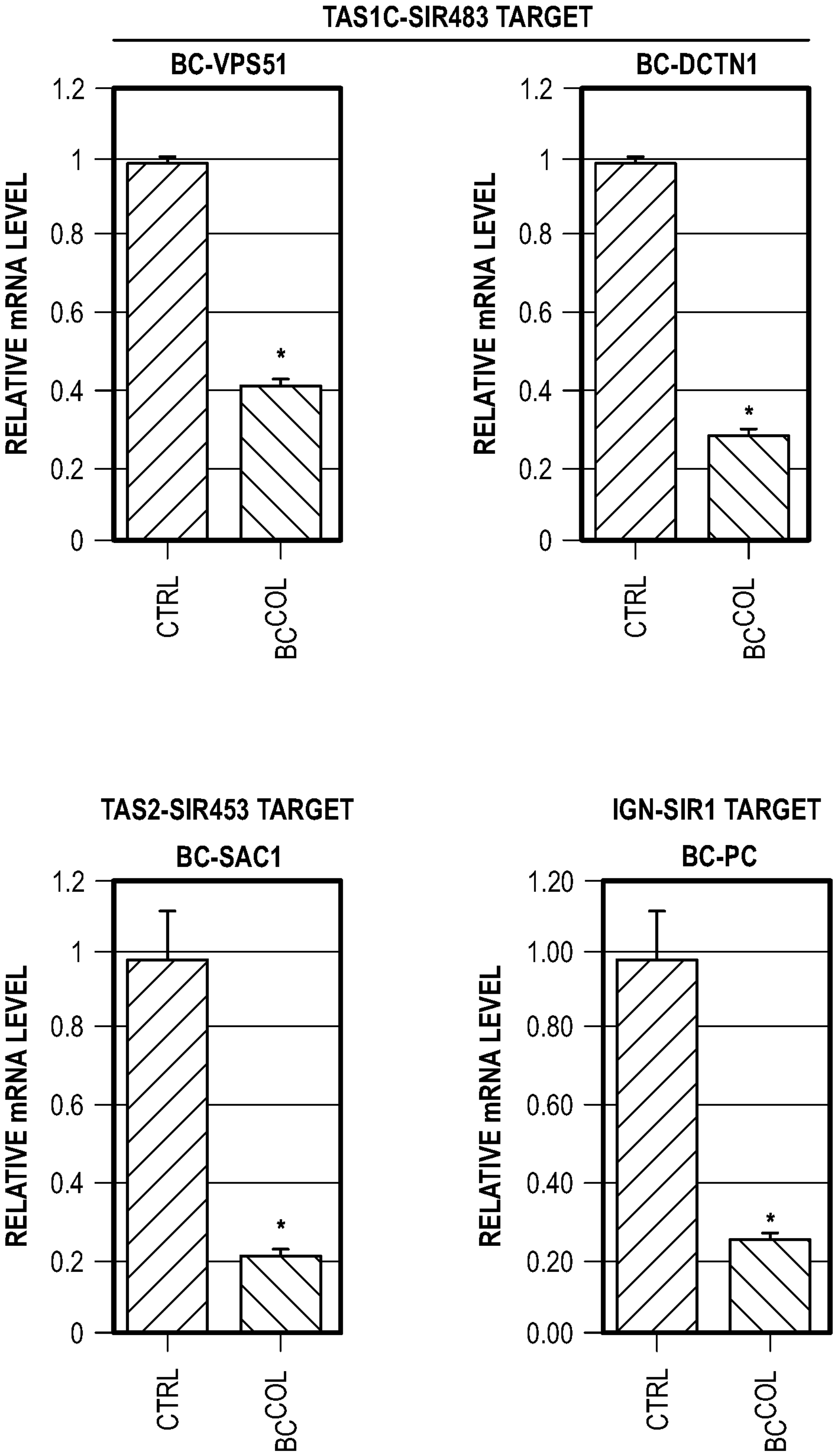
FIGS. 11A and 11B: The expression of *B. cinerea* target genes of TAS1c-siR483, TAS2-siR453 and IGN-siR1 was analyzed by quantitative RT-PCR.
Figure 11B:
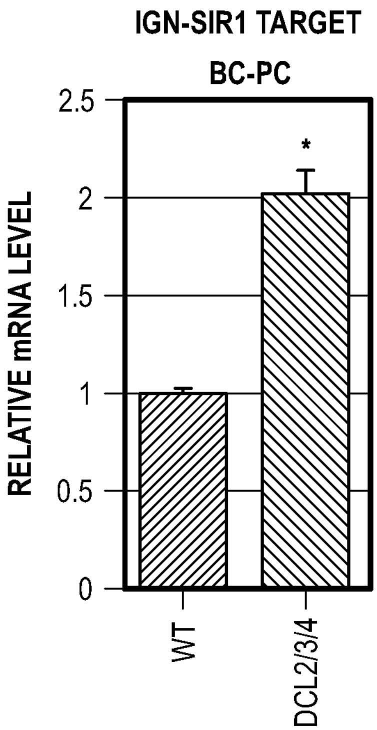

To determine whether transferred host sRNAs contribute to host immunity and are functional in the fungal cells, we first performed infection assay on the *Arabidopsis* siRNA biogenesis triple mutant dcl2/3/4 that showed markedly reduced tasiRNA and heterochromatic siRNA production (Henderson, I. R. et al., *Nat Genet* 38, 721-725, doi:10.1038/ng1804 (2006); Gasciolli, V. et al., *Curr Biol* 15, 1494-1500, doi:10.1016/j.cub.2005.07.024 (2005)). Enhanced susceptibility to *B. cinerea* was observed in the triple mutant as compared with the wild type (FIG. 4A), suggesting that these transferred host tasiRNAs and heterochromatic siRNAs are likely to suppress fungal virulence by target fungal essential genes. We found that at least seventeen of the transferred *Arabidopsis* sRNAs have predicted target genes in *B. cinerea* (Supplementary Table 1 and 5). Gene ontology enrichment analysis of these fungal targets revealed a strong bias towards vesicle transport pathways (9 out of 45 genes) (FIG. 10), suggesting that vesicle trafficking is important for fungal virulence. We performed functional analysis on TAS1c-siR483 and TAS2-siR453 and the most abundant siRNA from intergenic region IGN-siR1 in the *B. cinerea* protoplast sRNA libraries, because they showed clear selective transport into fungal cells (FIGS. 1B and 1C). TAS1c-siR483 and TAS2-siR453 target two *B. cinerea* genes (BC1G_10728 and BC1G_10508) and one gene (BC1T 08464) respectively, all of which are involved in vesicle transport pathways. BC1G_10728 encodes a vacuolar protein sorting 51 (Bc-Vps51), which is the homolog of the Golgi-associated retrograde protein (GARP)/Vps51 in yeast and the Vps51 subunit in mammals (Bonifacino, J. S. and Hierro, A., *Trends Cell Biol* 21, 159-167, doi:10.1016/itcb.2010.11.003 (2011); Luo, L. et al., *Mol Biol Cell* 22, 2564-2578, doi:10.1091/mbc.E10-06-0493 (2011); Liu, Y. et al., *PLoS Pathog* 7, e1002305, doi:10.1371/journal.ppat.1002305 (2011)). VPS 51 plays a key role in the virulence of *Candida albicans*, a human fungal pathogen (Liu, Y. et al., *PLoS Pathog* 7, e1002305, doi:10.1371/journal.ppat.1002305 (2011)). BC1G_10508 encodes the large subunit of the dynactin (DCTN) complex Bc-DCTN1, which is the homolog of Nip 100p in yeast and p150$^{glued}$ in mammals (Steinmetz, M. O. and Akhmanova, A., *Trends Biochem Sci* 33, 535-545, doi:10.1016/j.tibs.2008.08.006 (2008)). DCTN binds to kinesin II and dynein and coordinates vesicle trafficking (Dell, K. R., *The Journal of cell biology* 160, 291-293, doi:10.1083/jcb.200301040 (2003); Schroer, T. A., *Annu Rev Cell Dev Biol* 20, 759-779, doi:10.1146/annurev.cellbio.20.012103.094623 (2004)). BC1T 08464 encodes a suppressor of actin (SAC1)-like phosphoinositide phosphatase that plays an important role in secretory membrane trafficking (Foti, M. et al., *Mol Biol Cell* 12, 2396-2411 (2001); Guo, S. et al., *J Biol Chem* 274, 12990-12995 (1999)). IGN-siR1 targets BC1G_05327, which encodes pyruvate carboxylase (Bc-PC) that catalyzes the formation of oxaloacetate (OAA), an important intermediate in the tricarboxylic acid cycle (Plassard, C. and Fransson, P., *Fungal Biol Rev* 23, 30-39, doi:10.1016/j.fbr.2009.08.002 (2009)). OAA is an important precursor of organic acids in fungi, such as oxalate (Plassard, C. and Fransson, P., *Fungal Biol Rev* 23, 30-39, doi:10.1016/j.fbr.2009.08.002 (2009)), and causes wilting symptoms in infected plants (vanKan, J. A. L., *Trends in Plant Science* 11, 247-253, doi:10.1016/j.tplants.2006.03.005 (2006)). Indeed, these predicted target genes were indeed down-regulated after infection (FIG. 11A). Relative expression of these predicted *B. cinerea* target genes was clearly elevated in *B. cinerea* collected from the infection sites of the dcl2/3/4 triple mutant that has largely reduced levels of tasiRNAs and siRNAs (FIG. 4B and FIG. 11B), supporting specific silencing of fungal genes by transferred plant sRNAs.

Figure 4C:
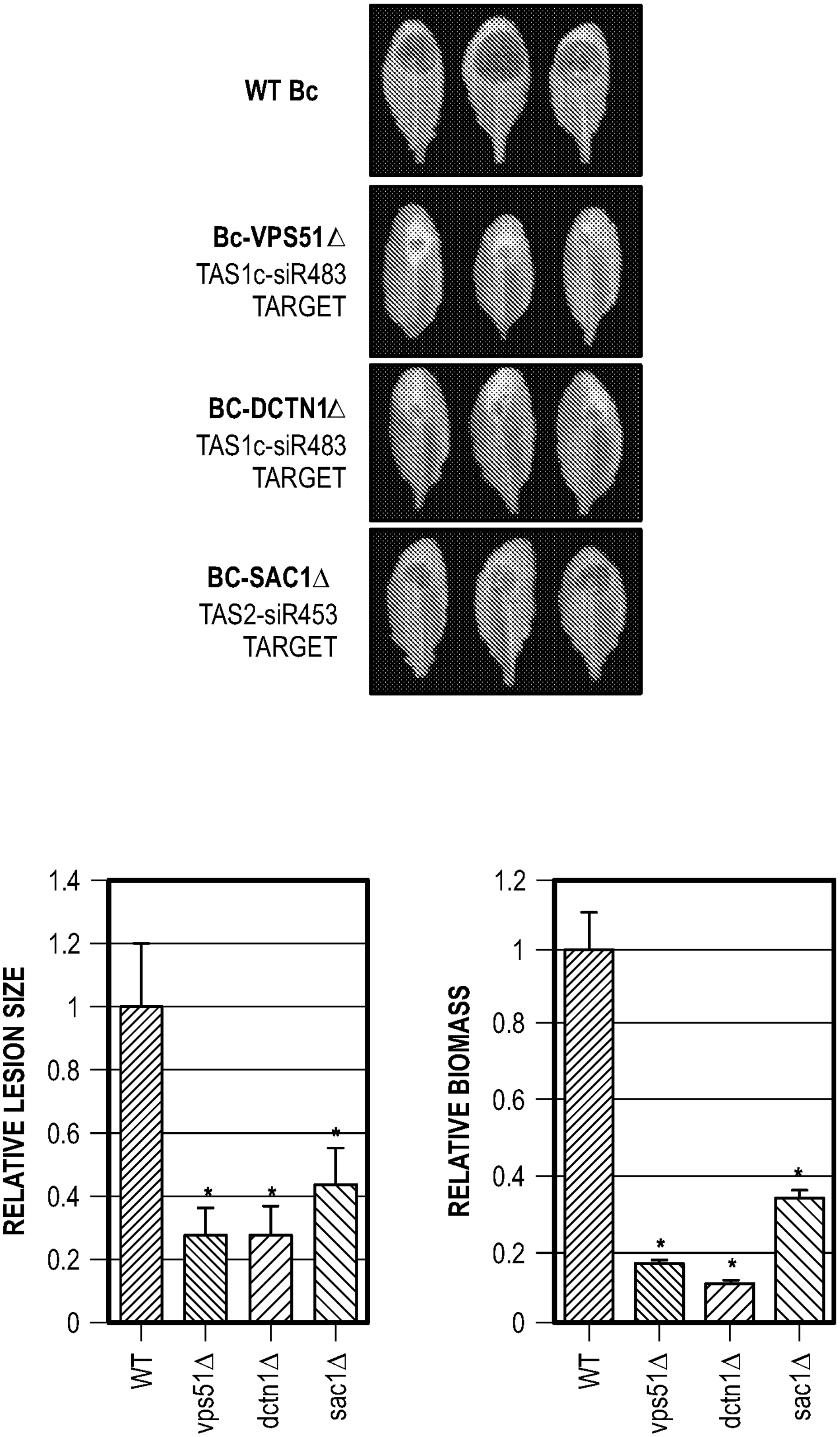
Figure 5A:
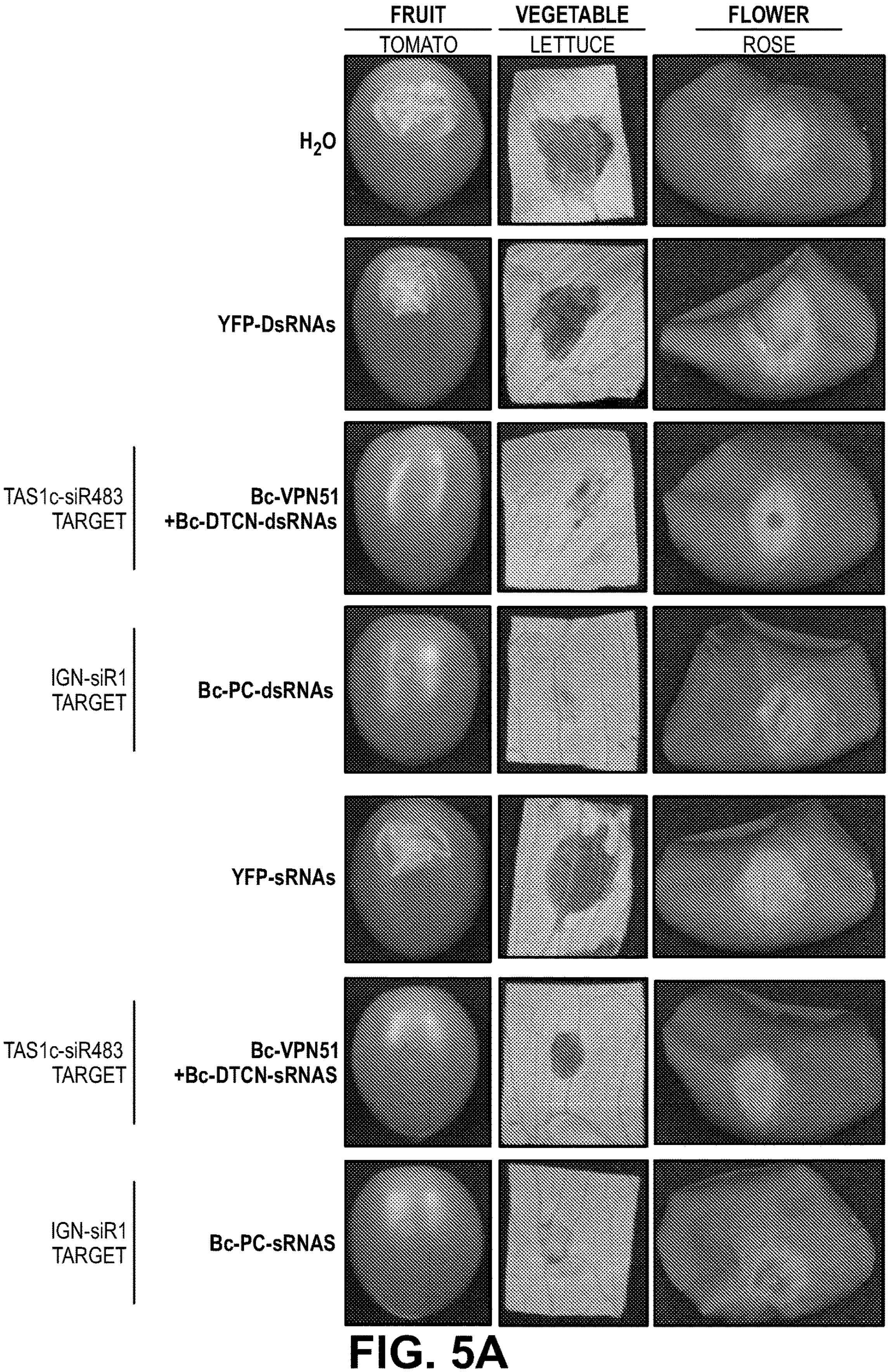
FIGS. 5A and 5B: Spraying dsRNAs or sRNA duplexes that targeting fungal genes of the vesicle trafficking pathways on plants efficiently inhibits fungal virulence and growth of *B. cinerea* (FIG. 5A). Quantification is shown in FIG. 5B.
Figure 5B:
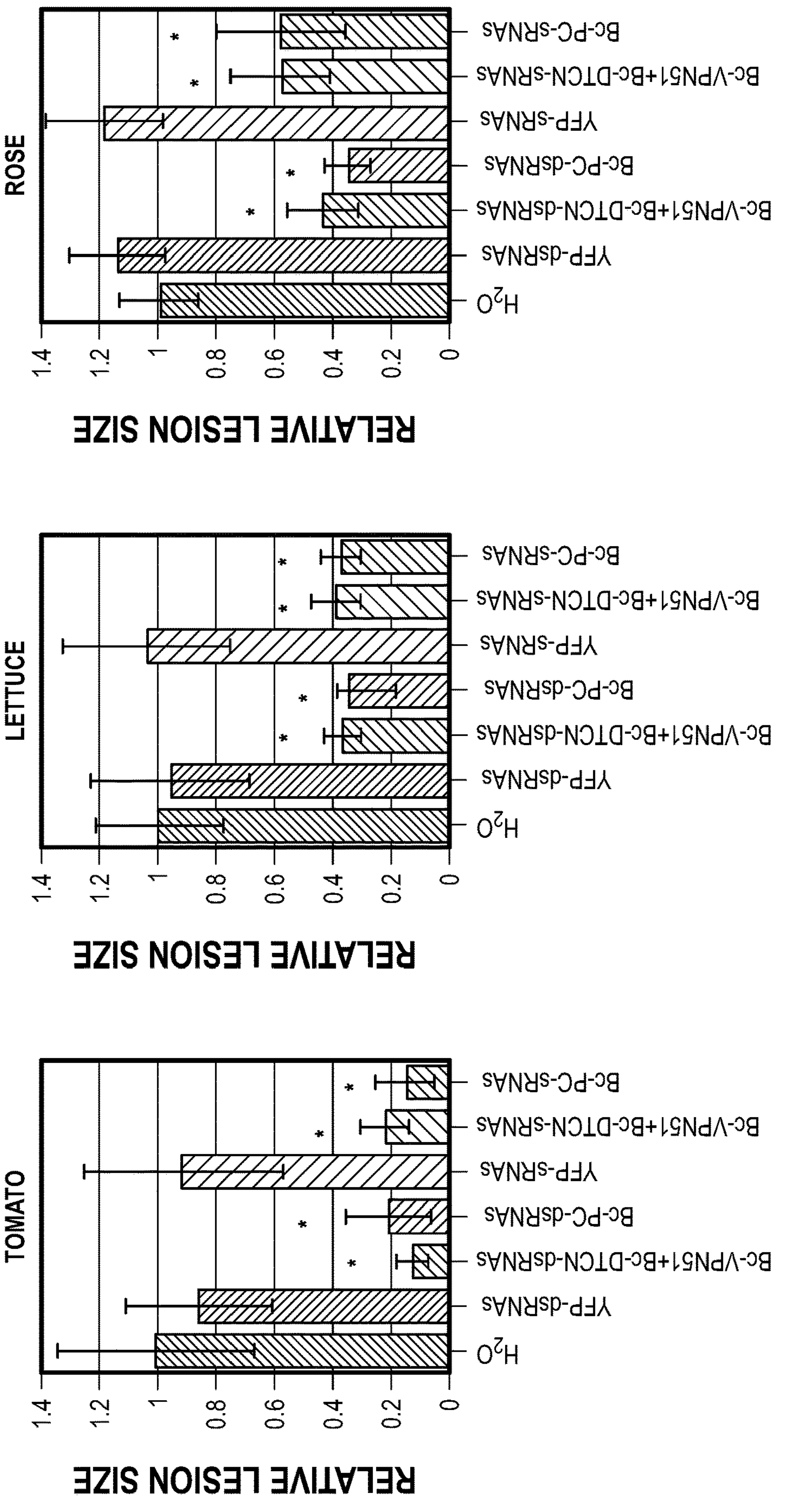
Figure 5B:
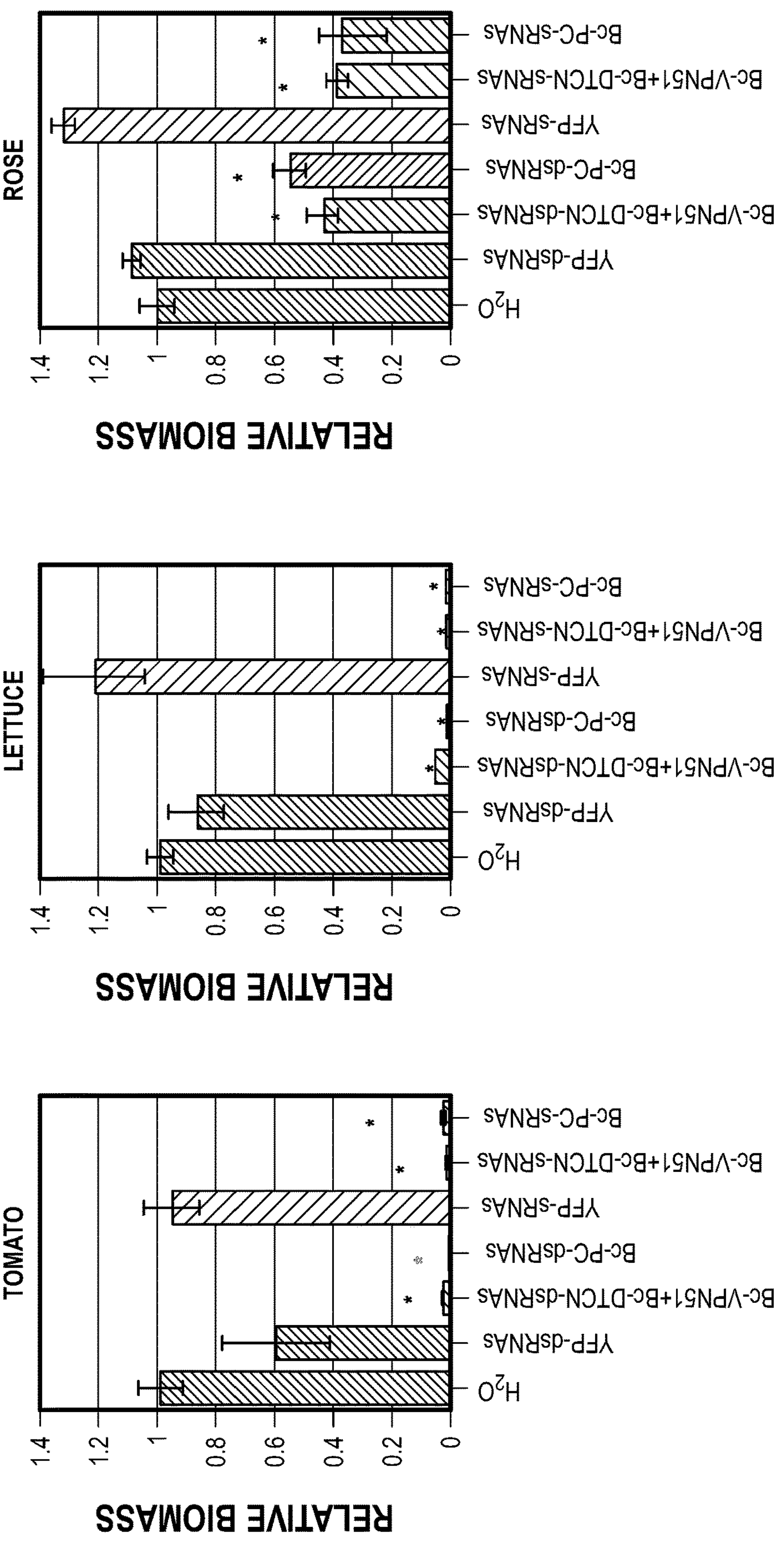
Figure 6A:
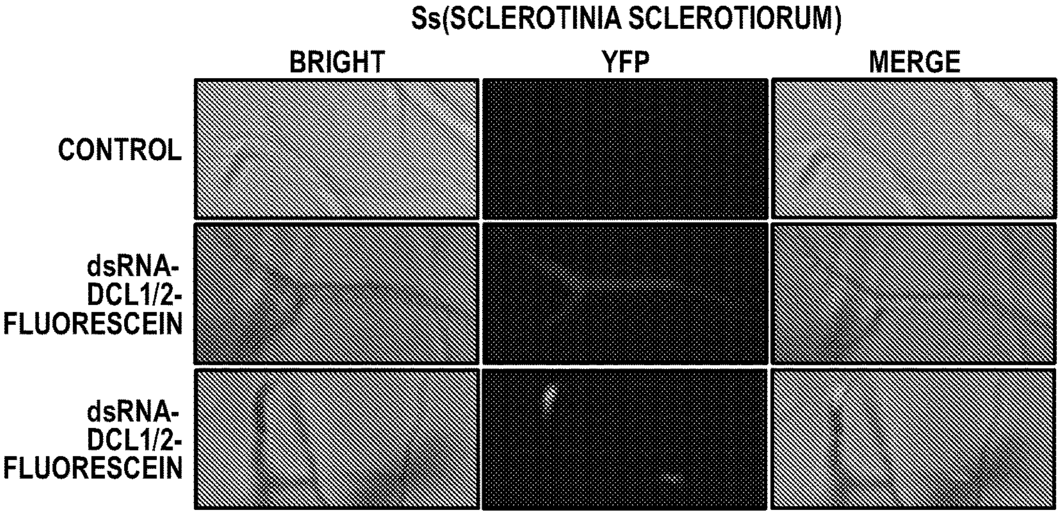
FIGS. 6A and 6B.
Figure 6B:
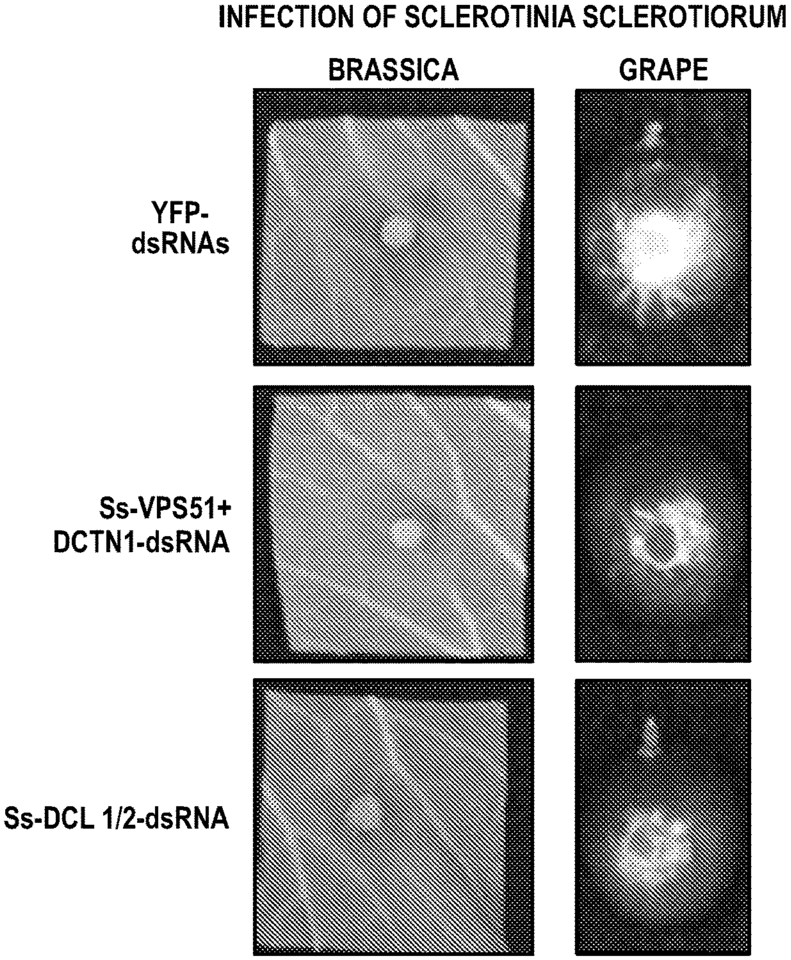
Figure 12A:
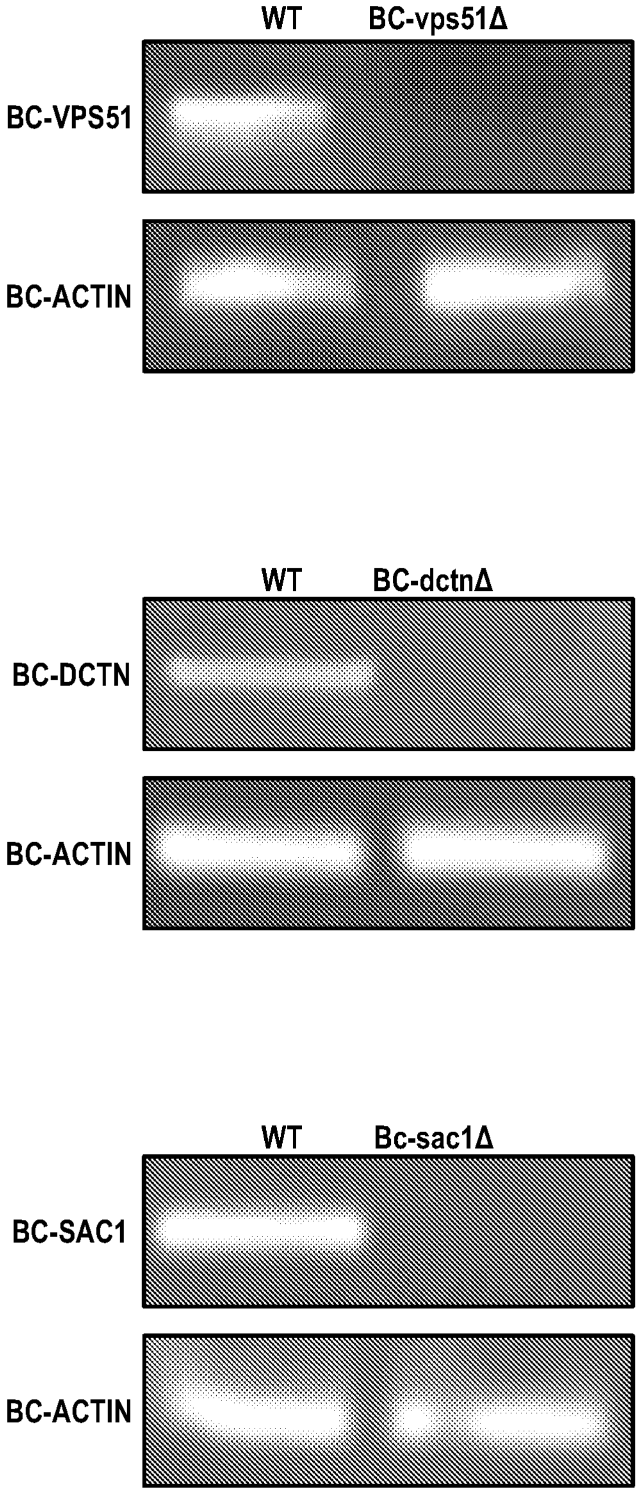
FIGS. 12A and 12B: The deletion mutant strains of *B. cinerea* vps51Δ, dcnt1Δ and sac1Δ were generated by homologous recombination.
Figure 12B:
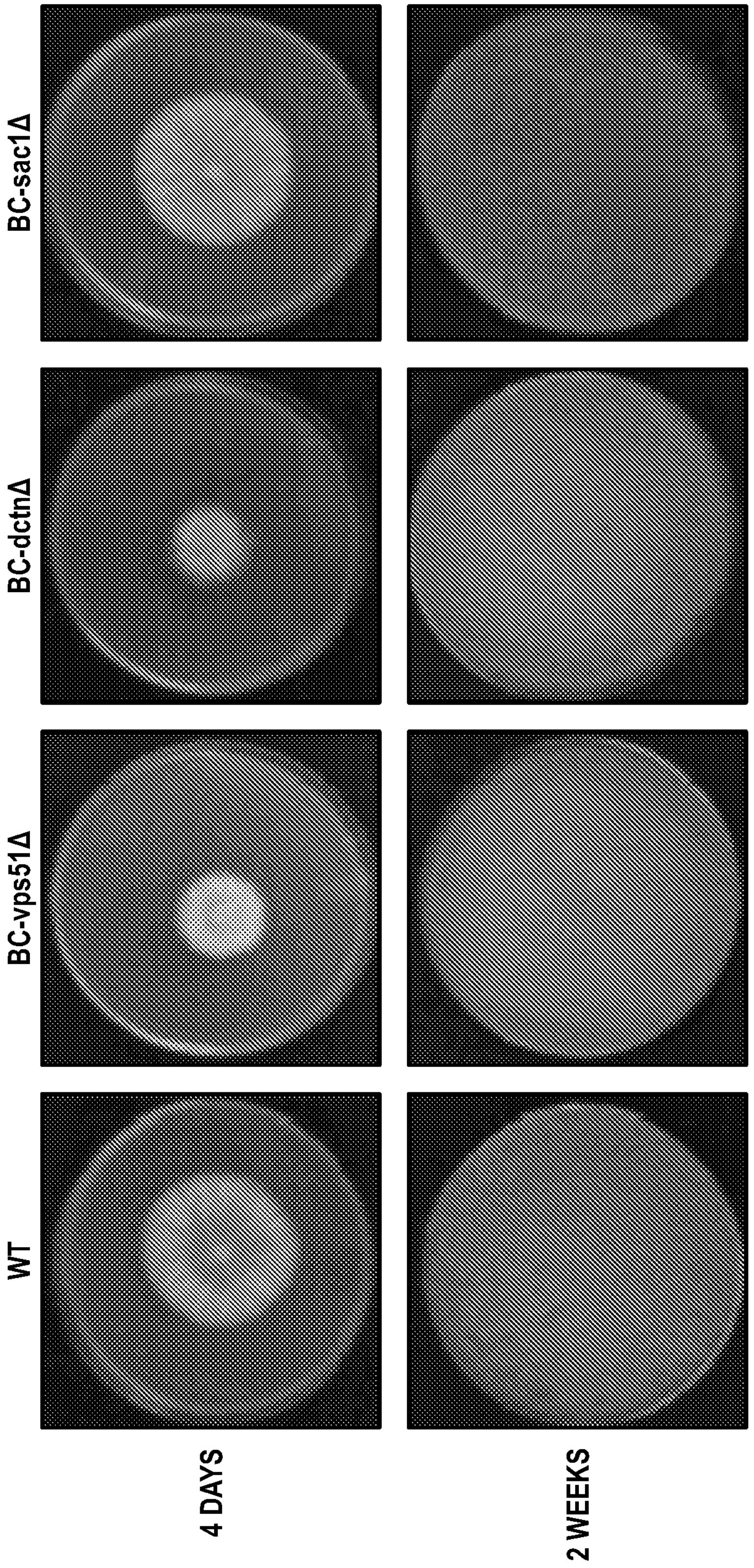

To determine the role of these target genes in vesicle trafficking pathways is important for *B. cinerea* pathogenicity, we attempted to generate mutant strains that deleted these target genes using homologous recombination. We generated vps51Δ,dctn1Δ and sac1Δ mutant strains (FIG. 12A). The vps51Δ and dctn1Δ mutant strains showed reduced virulence on *Arabidopsis* (FIG. 4C) and reduced growth on media (FIG. 12B). The sac1.4 mutant strain showed reduced virulence on *Arabidopsis* (FIG. 4C) but no obvious reduced in growth on media (FIG. 12B). Thus, functional study of transferred host sRNAs led to the identification of an important virulence pathway that is essential for fungal infection—the fungal trafficking pathway.

Figure 13A:
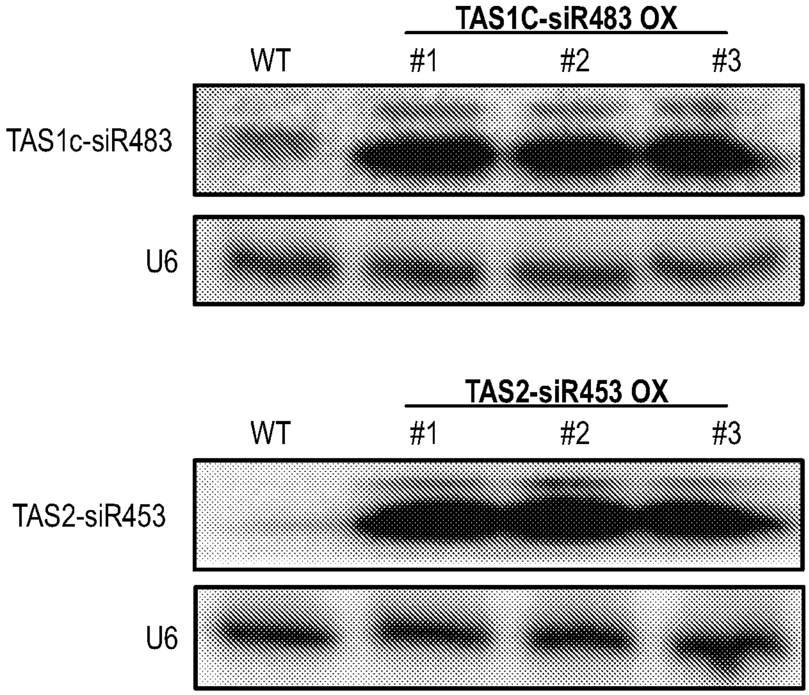
FIGS. 13A-13C: At-sRNA overexpression plants exhibited decreased disease susceptibility to *B. cinerea* as compared with wild type.
Figure 13B:
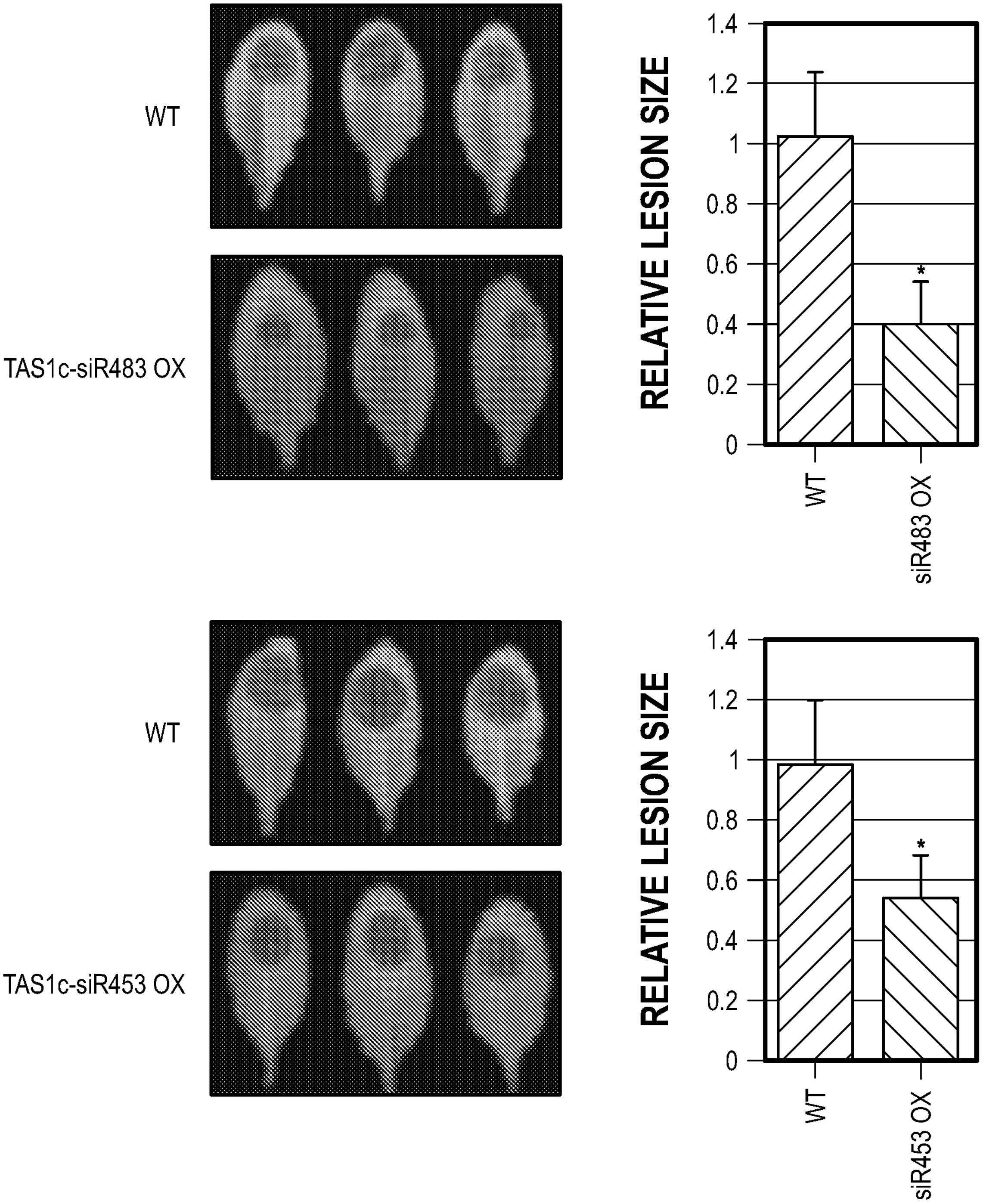
Figure 13C:
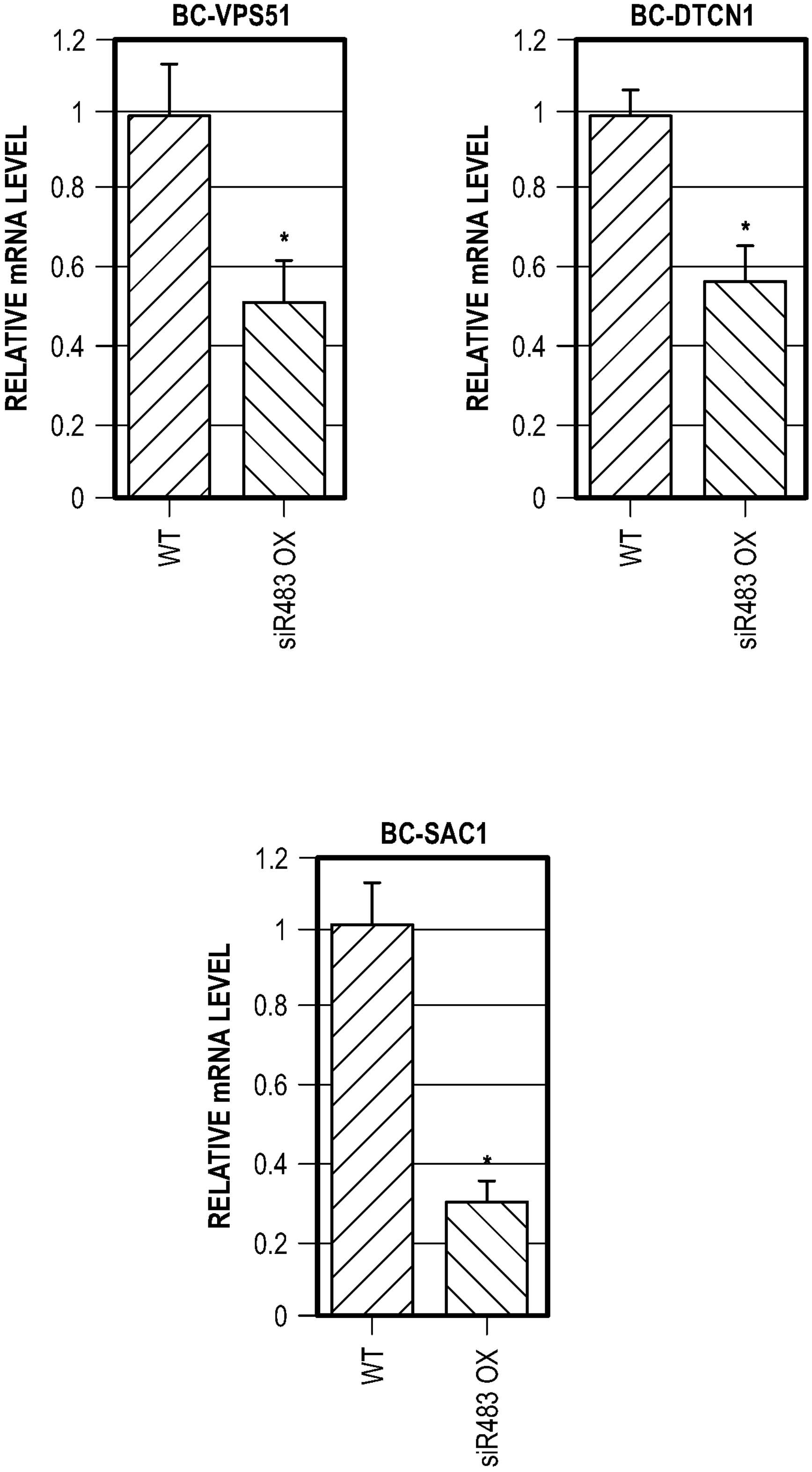

To further confirm the positive effect of the transferred host sRNAs on host plant immunity, we generated transgenic *Arabidopsis* lines that overexpress TAS1c-siR483 or TAS2-siR453 (FIG. 13A). Both overexpression lines displayed reduced susceptibility to *B. cinerea* (FIG. 13B). Consistent with the pathogen assay results, reduced expression of fungal target genes was observed in *B. cinerea*-infected overexpression lines (FIG. 13C). These findings strongly support that these transferred host sRNAs contribute to host immunity.

Figure 14A:
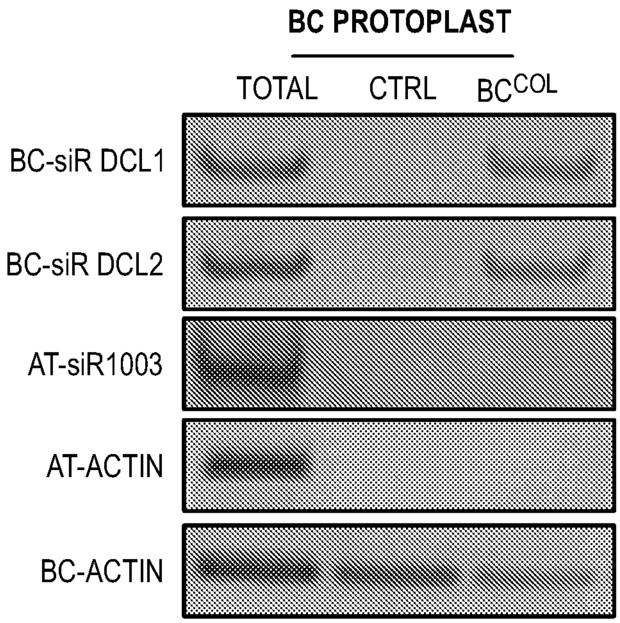
FIGS. 14A and 14B: Plants transfer transgene-derived sRNAs into fungal cells by EVs as well.
Figure 14B:
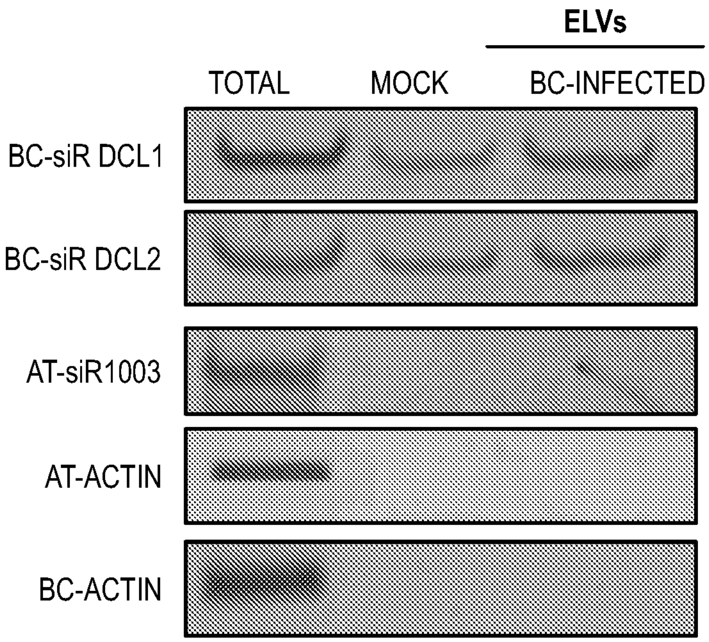

In this study, we report that plant ELVs play an essential role in cross-kingdom sRNA trafficking between plant host *Arabidopsis* and interacting fungal pathogen *B. cinerea*. *Arabidopsis* has evolved an ELV-mediated sRNA export pathway to deliver its endogenous sRNAs into *B. cinerea* cells to silence fungal genes involved in vesicle trafficking and reduce fungal virulence. Although such cross-kingdom sRNA trafficking mechanism has not enabled *Arabidopsis* to fully overcome *B. cinerea* infection, it has made *Arabidopsis* one of *B. cinerea*'s least favorite hosts, as many other plants are more susceptible to *B. cinerea* than *Arabidopsis*. Functional studies of host mobile sRNAs will help identify novel virulence pathways and genes in the interacting pathogens and pests. Furthermore, since transgene-derived Bc-DCL-targeting sRNAs were detected in EV fractions isolated from transgenic *Arabidopsis* expressing the Bc-DCL RNAi construct (Wang, M. et al., *Nature plants* 2, 16151, doi:10.1038/nplants.2016.151 (2016)) (FIGS. 14A and 14B), it appears that transgene-derived sRNAs are delivered by ELV-mediated trafficking pathways as well. The discovery of exosome-mediated cross-kingdom sRNA trafficking mechanisms involved in plant immunity may be useful in developing effective strategies for the delivery of membrane protected RNA with the goal of enhancing the control of pre- and post-harvest diseases in crop species.

Methods and Materials

Plant materials used in this study include the *Arabidopsis thaliana* ecotype Col-0 and *Nicotiana benthamiana. Arabidopsis* mutants tet8 (Salk_136039), dcl2-ldcl3-ldcl4-2 (dcl2/3/4) and $TET8_{pro}$::TET8-GFP lines were described previously (Boavida, L. C. et al., *Plant Physiol* 163, 696-712, doi:10.1104/pp.113.216598 (2013); Henderson, I. R. et al., *Nat Genet* 38, 721-725, doi:10.1038/ng1804 (2006)). For a detailed description of transgenic lines, see Methods online.

Isolate Pure Fungal Cells from Infected Plant Leaves.

*B. cinerea* protoplasts were purified from infected *Arabidopsis* leaves using a method that takes advantage of the differences between plant and fungi cell wall components (Cosgrove, D. J., *Nature reviews. Molecular cell biology* 6, 850-861, doi:10.1038/nrm1746 (2005); Bowman, S. M. and Free, S. J., *Bioessays* 28, 799-808, doi:10.1002/bies.20441 (2006)). A detailed protocol was included in the Methods online.

Extracellular Vesicles Isolation.

Plant extracellular vesicles were isolated from apoplastic fluids and purified by differential ultracentrifugation (Rutter, B. and Innes, R. W., *Plant Physiol*, doi:10.1104/pp.16.01253 (2016)). For a detailed description, see Methods.

Illumina HiSeq Data Analysis of sRNA Libraries.

The sequences were mapped to *Arabidopsis* (TAIR10) or *B. cinerea* B05.10 genomes and only the reads that matched perfectly to each genome will be used for further analysis. Details of sRNA cloning and illumina HiSeq data analysis are provided in Methods.

Materials. Plant materials used in this study include the *Arabidopsis thaliana* ecotype Col-0 and *Nicotiana benthamiana. Arabidopsis* mutants tet8 (Salk_136039), dcl2-ldcl3-ldcl4-2 (dcl2/3/4) and $TET8_{pro}$::TET8-GFP lines were described previously (Boavida, L. C. et al., *Plant Physiol,* 163, 696-712, doi:10.1104/pp.113.216598 (2013); Henderson, I. R. et al., *Nat Genet,* 38, 721-725, doi:10.1038/ng1804 (2006)). CFP or YFP-tagged TET8 and TET9 constructs were generated in pEarleyGate binary vectors. To generate the construct for the sRNA overexpression lines, the sRNA precursor was cloned using a miR319 backbone (Schwab, R. et al., *Plant Cell,* 18, 1121-1133, doi:10.1105/tpc.105.039834 (2006)) into a pEarleyGate destination vector using LR clonase II (Invitrogen). *Arabidopsis* plants were transformed using floral dip method with *Agrobacterium tumefaciens* strain GV3101 carrying the cloned vectors. *B. cinerea* used was strain B05.10. For generating *B. cinerea* target gene knockout mutants, we used a homologous recombination-based method to knock out *B. cinerea* genes described previously (Levis, C., Fortini, D. & Brygoo, Y., *Current genetics,* 32, 157-162 (1997)). All primers are listed in Supplementary Table 6.

Fungal Pathogen Assays.

The *B. cinerea* spores were diluted in 1% sabouraud maltose broth buffer to a final concentration of $10^5$ spores/ml for drop inoculation of four-week-old *Arabidopsis* (Wang, M. et al., *Nature plants* 2, 16151, doi: 10.1038/nplants.2016.151 (2016)). The lesion sizes of *B. cinerea*-infected plant materials were calculated using ImageJ software. The relative fungal DNA content (fungal biomass) was quantified as described previously (Wang, M. et al., *Nature plants* 2, 16151, doi:10.1038/nplants.2016.151 (2016)).

Isolate Pure Fungal Cells from Infected Plant Leaves.

*B. cinerea* protoplasts were purified from infected *Arabidopsis* leaves using a method that takes the advantage of the differences between plant and fungi cell wall components (Cosgrove, D. J., *Nature reviews. Molecular cell biology,* 6, 850-861, doi:10.1038/nrm1746 (2005); Bowman, S. M. & Free, S. J., *Bioessays,* 28, 799-808, doi:10.1002/bies.20441 (2006)). After rinsing with sterilized water to remove ungerminated spores, the leaves were homogenized for 1 minute in isolation buffer (0.02 M MOPS buffer pH 7.2, 0.2 M sucrose) using a blender. The homogenate was centrifuged (1,500 g, 10 minutes) and the pellets were resuspended in 1% Triton X-100 then washed 3 times with isolation buffer to remove plant contents. The pellets were then processed for plant cell wall digestion as described previously (Yoo, S. D., Cho, Y. H. & Sheen, J., *Nature protocols,* 2, 1565-1572, doi:10.1038/nprot.2007.199 (2007)), followed by resuspension in 1% Triton X-100 and washing in isolation buffer 5 times to remove plant contents. The fungal protoplasts were isolated by incubation for 2-3 hours in lysing enzyme solution (2% lysing enzyme from *Trichoderma harzianum* (Sigma) in 0.6 M KCl, 50 mM $CaCl_2$). The fungal protoplasts were filtered through a 40 μm nylon mesh, and gently overlaid with a 30% sucrose solution to form a distinct interface with the fungal tissue suspension and centrifuged at 4° C. for 10 minutes at 5,000 rpm. The fungal protoplasts were collected from the interface of the sucrose layer and the tissue suspension layer. The sucrose was removed from the purified protoplast solution by diluting five- to ten-fold with SM buffer (1.2 M-sorbitol and 0.02 M-MES, pH 6.0) and centrifuging (5,000 rpm for 5 minutes) in an angle head rotor. The pellet was resuspended in Trizol Reagent (Invitrogen) for RNA extraction.

Extracellular Vesicle Isolation.

Plant extracellular vesicles were isolated from apoplastic fluids and purified by differential ultracentrifugation (Rutter, B. & Innes, R. W., *Plant Physiol, doi:*10.1104/pp.16.01253 (2016)). The apoplastic fluids were extracted from *Arabidopsis* leaves by vacuum infiltration with infiltration buffer (20 mM MES, 2 mM $CaCl_2$), 0.1 M NaCl, pH 6.0), then with low spinning at 900 g to collect the infiltrate. Before purification of vesicles, cellular debris was removed by spinning at 2,000 g for 30 minutes and filtering the apoplastic fluids through a 0.45 μm filter and then spun at 10,000 g for 30 minutes. After the large cell debris and large vesicles were removed by successive centrifugations at increasing speeds, the pellet from 100,000 g has been known as the exosomes (Thery, C. et al., *Current protocols in cell biology*/editorial board, Juan S. Bonifacino . . . [et al.] Chapter 3, Unit 3 22, doi:10.1002/0471143030.cb0322s30 (2006)). Thus, the final supernatant was spun at 100,000 g for 1 hour and the pelleted material is washed with filtered infiltration buffer at 100,000 g for 1 hour to collect extracellular vesicles.

sRNA Cloning and Illumina HiSeq Data Analysis.

The sRNA libraries were made using Illumina TruSeq® Small RNA Sample Prep Kits and sequenced on an Illumina HiSeq system. The sequence datasets of sRNA libraries (PRJNA407577) were deposited in the NCBI database. The sRNA sequencing reads were preprocessed with the procedure of quality control and adapter trimming by using fastxtoolkit (http://hannonlab.cshl.edu/fastx_toolkit/index-.html). The sequences were mapped to *Arabidopsis* (TAIR10) or *B. cinerea* B05.10 genomes and only the reads that matched perfectly to each genome were used for further analysis. After removal of tRNA-, rRNA-, snoRNA-, and snRNA-mapped reads, the read numbers of sRNA in each library were normalized by the total number of sRNA reads, resulting in reads per million (RPM). The sRNAs selected for analysis were detected in both biological repeats. For purified *B. cinerea* cell libraries, using 10 normalized reads per million (RPM) sRNA reads as a cutoff, and the sRNAs selected for analysis had 10 times higher read numbers than the control libraries. For total *Arabidopsis* sRNA libraries, using 10 normalized RPM sRNA reads as a cutoff. For *Arabidopsis* extracellular vesicles libraries, using 40 normalized RPM sRNA reads as a cutoff. The *B. cinerea* target gene prediction for *Arabidopsis* sRNAs was performed as previously described (Weiberg, A. et al., *Science,* 342, 118-123, doi:10.1126/science.1239705 (2013)). The sRNAs list is given in Supplementary Table 1-5.

sRNA and Gene Expression Analyses.

RNA was extracted using the Trizol method. Purified RNA was treated with DNase I and first strand cDNA was synthesized from the Superscript III kit (Invitrogen, Carlsbad, Calif.). sRNA RT-PCR was performed as previously described (Weiberg, A. et al., *Science,* 342, 118-123, doi: 10.1126/science.1239705 (2013)). Quantitative PCR was performed with the CFX384 real-time PCR detection system (Bio-Rad) using the SYBR Green mix (Bio-Rad) (Primers are described in Supplementary Table 6). When determining if the sRNAs were protected inside the vesicles, EVs received 10 U micrococcal nuclease (Thermo Fisher) treatments with or without Triton-X-100. For Triton-X-100 treatment, vesicles were incubated with 1% Triton-X-100 on ice for 30 minutes before the nuclease treatments. Nuclease treatment was carried out at 37° C. for 15 minutes followed by RNA isolation. Expression of sRNAs uptake by *B. cinerea* cells were determined by ligation-based sRNA RT-PCR, which was described previously (Wang, M. et al., *RNA biology,* 1-8, doi:10.1080/15476286.2017.1291112 (2017)). All primer sequences are listed in Supplementary Table 6.

Confocal Microscopy Analyses.

Following the protocol of visualization of membranes and extracellular vesicles in plants (Nielsen, M. E. et al., *Proc Natl Acad Sci USA,* 109, 11443-11448, doi:10.1073/pnas.1117596109 (2012)), leaves with or without *B. cinerea* infection were syringe infiltrated with 10 μM FM4-64 30 minutes before examination. Samples were examined using a 40× water immersion or dip-in lens mounted on a Leica TCS SP5 confocal microscope (Leica Microsystems). For visualization of ELV-associated GFP-fluorescence in ultracentrifuge fractions, suspended pellets were examined using a 40× water immersion or dip-in lens mounted on a Leica TCS SP5 confocal microscope. For visualization of ELV uptake, purified ELVs were mixed with germinated *B. cinerea* at 37° C. for 2 hours following confocal analyses. For Triton-X-100 treatment, the incubated fungal cells were washed with 1% Triton-X-100 for 15 minutes to remove nonspecific associations. Samples were examined on a 40× water immersion or dip-in lens mounted on a Leica TCS SP5 confocal microscope.

Supplementary Table 1

This file contains a list of *Arabidopsis* endogenous sRNAs that present in the sRNA libraries of purified *B. cinerea* protoplasts from the infected tissue. The normalized reads of these sRNAs in the EVs and total sRNA libraries are compared.

Supplementary Table 2

This table contains the list of top 100 *Arabidopsis* sRNAs that present in the total sRNA libraries. The normalized reads of these sRNAs in the *B. cinerea* protoplast and EVs sRNA libraries are compared.

Supplementary Table 3

This table contains the list of sRNA in purified *B. cinerea* protoplast sRNA libraries that not present in top 100 total sRNA libraries. The normalized reads of these sRNAs in the *B. cinerea* protoplast and EVs sRNA libraries are compared.

Supplementary Table 4

This file contains a list of *Arabidopsis* sRNAs that present in EVs. The normalized reads of these sRNAs in the *B. cinerea* protoplast and total sRNA libraries are compared.

Supplementary Table 5

This table contains the list of *B. cinerea* genes targeted by *Arabidopsis* endogenous sRNAs that are present in the sRNA libraries of purified *B. cinerea* protoplasts.

Supplementary Table 6

This table contains the list of primers used in this study.

SUPPLEMENTARY TABLE 1

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| | | | | | | Normalized read counts of BC | | | | Normalized read counts of EVs | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | Control_RPT1 | Control_RPT2 | B05_RP T1 | B05_RP T2 | MOCK_RP T1 | MOCK_RP T2 | B05_RP T1 | B05_RP T2 | MOCK_RP T1 | MOCK_RP T2 |
| MIR 166A | miRNA | 80 | TCGGACCAGGCTTCATTCCCC | 21 | 1 | 2415.44 | 35891.69 | 59.59 | 169.58 | 71636.21 | 20786.48 | 16380.72 | 9618.88 | 16129.57 | 16838.16 | 36093.26 | 30198.15 |
| MIR 157A | miRNA | 81 | TTGACAGAAGATAGAGAGCAC | 21 | 1 | 782.00 | 157.24 | BCF | BCF | 6941.03 | 1249.49 | 939.99 | 321.31 | 13949.47 | 11099.11 | 18196.99 | 19707.76 |
| IGN-siR1 | IGN | 82 | GTCGAACTCAGTAACGCGGGCT | 22 | 1 | 433.46 | 355.19 | BCF | BCF | 105.33 | 74.19 | 40.49 | 56.52 | 136.68 | 133.25 | 84.62 | 81.67 |
| MIR 159B | miRNA | 83 | TTTGGATTGAAGGGAGCTCTT | 21 | 2 | 305.19 | 151.75 | BCF | BCF | 7688.04 | 130.81 | 871.93 | 21.03 | 8098.22 | 6334.70 | 9457.97 | 13016.50 |
| MIR 159A | miRNA | 84 | TTTGGATTGAAGGGAGCTCTA | 21 | 3 | 302.10 | 613.36 | BCF | BCF | 8165.26 | 123.00 | 942.56 | 24.44 | 19855.85 | 13861.61 | 31216.26 | 23555.57 |
| MIR 168A | miRNA | 85 | TCGCTTGGTGCAGGTCGGGAA | 21 | 1 | 290.60 | 197.77 | 10.85 | 17.75 | 5522.36 | 15253.57 | 944.21 | 318.94 | 9532.05 | 14836.25 | 7841.71 | 7457.34 |
| MIR 396A | miRNA | 86 | TTCCACAGCTTTCTTGAACTG | 21 | 5 | 255.21 | 176.77 | BCF | BCF | 1976.09 | 2100.71 | 308.56 | 450.90 | 17322.33 | 16887.83 | 9892.52 | 14254.15 |

SUPPLEMENTARY TABLE 1-continued

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| | | | | | | Normalized read counts of BC | | | | Normalized read counts of EVs | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | Control_RPT1 | Control_RPT2 | B05_RP T1 | B05_RP T2 | MOCK_RP T1 | MOCK_RP T2 | B05_RP T1 | B05_RP T2 | MOCK_RP T1 | MOCK_RP T2 |
| MIR 158A | miRNA | 87 | TCCCAAATGTAGACAAAGCA | 20 | 2 | 236.63 | 528.20 | BCF | BCF | 2044.96 | 7085.01 | 381.76 | 1184.60 | 20391.65 | 14562.15 | 18382.09 | 17208.83 |
| TAS1c-siR483 | tasiRNA | 88 | TCCAATGTCTTTTCTAGTTCGT | 22 | 1 | 232.21 | 498.31 | BCF | BCF | 27673.80 | 1940.62 | 5574.65 | 890.84 | 13779.67 | 9137.97 | 11358.65 | 14444.95 |
| TAS1c-siR602 | tasiRNA | 89 | TTCTAAGTTCAACATATCGAC | 21 | 1 | 156.13 | 131.88 | BCF | BCF | 3060.15 | 1905.48 | 479.98 | 558.42 | 8724.58 | 6840.09 | 9787.78 | 11121.49 |
| S1353533 | ORF | 90 | GGTGGAGGAGGGCGGC | 21 | 19 | 128.27 | 65.63 | BCF | BCF | BCF | BCF | BCF | BCF | BCF | BCF | BCF | BCF |
| S519888 | ORF | 91 | AGTTAATTGAACGTTCGGCGT | 21 | 1 | 113.67 | 33.82 | BCF | BCF | BCF | BCF | BCF | BCF | 54.71 | 67.83 | 33.05 | 35.76 |
| MIR 396 A* | miRNA | 92 | GTTCAATAAAGCTGTGGGAAG | 21 | 3 | 76.96 | 13.07 | BCF | BCF | 506.38 | 1036.69 | 167.20 | 152.77 | 3850.59 | 3879.47 | 2787.25 | 3357.24 |
| MIR 396B | miRNA | 93 | TTCCACAGCTTTCTTGAACTT | 21 | 4 | 26.10 | 16.91 | BCF | BCF | 650.60 | 105.43 | 143.83 | 40.21 | 250.71 | 153.27 | 249.45 | 272.07 |

SUPPLEMENTARY TABLE 1-continued

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of BC B05_RP T1 | B05_RP T2 | Control_RPT1 | Control_RPT2 | Normalized read counts of EVs B05_RP T1 | B05_RP T2 | MOCK_RP T1 | MOCK_RP T2 | Normalized read counts of TOTAL B05_RP T1 | B05_RP T2 | MOCK_RP T1 | MOCK_RP T2 |
|---|---|---|---|---|---|---|---|---|---|---|---|---|---|---|---|---|---|
| S272 4436 | TE | 94 | CGGGTT TGGCAG GACGTT ACT | 21 | 1 | 19.02 | 16.74 | BCF | BCF | 139.36 | 283.09 | 124.35 | 128.92 | 24.32 | 28.73 | 30.41 | 23.75 |
| S109 2315 | TE | 95 | GAAGTC CTCGTG TTGCAT TCCT | 22 | 1 | 14.15 | 13.25 | BCF | BCF | BCF | BCF | BCF | BCF | 83.64 | 196.45 | 259.14 | 203.99 |
| TAS 2-si R453 | tasi RNA | 96 | CGTAAA AAAAGT TGTAAC TCT | 21 | 1 | 13.27 | 23.01 | BCF | BCF | 40.51 | 113.24 | BCF | BCF | 48.21 | 44.29 | 67.28 | 46.71 |
| S466 8053 | IGN | 97 | TCCGCT GTAGCA CTTCAG GCTA | 22 | 0 | 297.68 | 347.00 | BCF | BCF | 4164.86 | 1173.35 | 528.16 | 258.73 | 484.86 | 747.43 | 623.62 | 418.41 |
| MIR 165A | miRNA | 98 | TCGGAC CAGGCT TCATCC CCC | 21 | 0 | 243.27 | 6209.88 | BCF | BCF | 8720.25 | 866.84 | 2016.08 | 441.94 | 2152.01 | 1879.23 | 4357.68 | 4284.16 |
| S180 4551 | IGN | 99 | TGGTGG AACACT GGCTCG GCCC | 22 | 0 | 191.08 | 107.47 | BCF | BCF | 165.28 | 191.33 | BCF | BCF | 306.89 | 325.99 | 309.09 | 266.80 |
| MIR 403 | miRNA | 100 | TTAGAT TCACGC ACAAAC TCGT | 22 | 0 | 159.67 | 108.78 | BCF | BCF | 2766.45 | 1882.05 | 409.87 | 299.09 | 3045.43 | 2092.35 | 2905.66 | 2255.49 |

SUPPLEMENTARY TABLE 1-continued

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of BC: B05_RP T1 | B05_RP T2 | Control_RPT1 | Control_RPT2 | Normalized read counts of EVs: B05_RP T1 | B05_RP T2 | MOCK_RP T1 | MOCK_RP T2 | Normalized read counts of TOTAL: B05_RP T1 | B05_RP T2 | MOCK_RP T1 | MOCK_RP T2 |
|---|---|---|---|---|---|---|---|---|---|---|---|---|---|---|---|---|---|
| MIR 161 | miRNA | 101 | TTGAAA GTGACT ACATCG GGG | 21 | 0 | 126.50 | 259.13 | BCF | BCF | 6187.95 | 1761.00 | 975.20 | 571.82 | 26180.86 | 26166.46 | 38715.83 | 32807.12 |
| S117 8334 | ORF | 102 | GAGTTA ATTGAA CGTTCG GCGT | 22 | 0 | 113.67 | 33.82 | BCF | BCF | BCF | BCF | BCF | BCF | 59.95 | 77.84 | 37.17 | 37.47 |
| S373 61 | ORF | 103 | AAACCG CAACCG GATCTT AAAGGC | 24 | 0 | 108.81 | 30.25 | BCF | BCF | 760.38 | 175.71 | 260.02 | 134.48 | 768.90 | 964.45 | 1220.20 | 1000.81 |
| S466 7987 | IGN | 104 | TCCGCT GTAGCA CACAGG CC | 20 | 0 | 83.60 | 47.94 | BCF | BCF | 908.24 | 1993.33 | 138.48 | 349.08 | 1508.04 | 1548.23 | 1255.46 | 1086.45 |
| MIR 398B | miRNA | 105 | GGGTTG ATATGA GAACAC ACG | 21 | 0 | 64.58 | 28.50 | BCF | BCF | 123.96 | 2493.13 | 52.61 | 252.37 | 1904.86 | 2112.37 | 2282.19 | 2880.78 |
| MIR 156D | miRNA | 106 | TTGACA GAAGAG AGTGAG CAC | 21 | 0 | 60.60 | 243.88 | BCF | BCF | 747.01 | 679.41 | 160.10 | 70.20 | 1280.18 | 889.76 | 1473.62 | 1477.01 |
| TAS 3-si R392 | tasi RNA | 107 | AGAATA GAATCT GTAAAA CGA | 21 | 0 | 52.63 | 21.09 | BCF | BCF | 454.53 | 103.47 | BCF | BCF | 1239.51 | 794.13 | 903.03 | 1012.56 |

SUPPLEMENTARY TABLE 1-continued

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of BC B05_RP T1 | B05_RP T2 | Control_RPT1 | Control_RPT2 | Normalized read counts of EVs B05_RP T1 | B05_RP T2 | MOCK_RP T1 | MOCK_RP T2 | Normalized read counts of TOTAL B05_RP T1 | B05_RP T2 | MOCK_RP T1 | MOCK_RP T2 |
|---|---|---|---|---|---|---|---|---|---|---|---|---|---|---|---|---|---|
| TAS1C-siR539 | tasiRNA | 108 | AACTAGAAAAGACATTGGACA | 21 | 0 | 50.42 | 52.73 | BCF | BCF | 1332.38 | 1509.15 | 661.39 | 946.23 | 860.72 | 655.13 | 1030.40 | 1181.58 |
| TAS1c-siR541 | tasiRNA | 109 | GAACTAGAAAAGACATTGGAC | 21 | 0 | 50.42 | 52.73 | BCF | BCF | 1313.75 | 1507.20 | 660.36 | 946.23 | 854.43 | 652.91 | 1025.11 | 1178.15 |
| S158710 | IGN | 110 | AAGCACATGTGTAGAGTCGAGCCT | 24 | 0 | 32.73 | 14.73 | BCF | BCF | 326.92 | 134.71 | BCF | BCF | 260.14 | 266.32 | 309.24 | 357.97 |
| S373543 | IGN | 111 | AGAACAGAGACCGTTGGAAGAAAA | 24 | 0 | 30.96 | 26.76 | BCF | BCF | 193.23 | 60.52 | BCF | BCF | 341.90 | 312.83 | 345.67 | 379.08 |
| MIR390A | miRNA | 112 | AAGCTCAGGAGGGATAGCGCC | 21 | 0 | 29.63 | 95.09 | BCF | BCF | 299.78 | 66.38 | BCF | BCF | 770.58 | 654.95 | 1014.09 | 1003.72 |
| S2622267 | IGN | 113 | CGAGAATGATGAACCAATTAGATG | 24 | 0 | 28.75 | 21.62 | BCF | BCF | BCF | BCF | BCF | BCF | 875.81 | 3484.17 | 1130.00 | 921.25 |
| MIR167A* | miRNA | 114 | GATCATGTTCGCAGTTTCACC | 21 | 0 | 27.42 | 29.81 | BCF | BCF | 342.72 | 6319.70 | 114.49 | 412.02 | 2224.96 | 2093.65 | 4748.01 | 2986.47 |

SUPPLEMENTARY TABLE 1-continued

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of BC B05_RP T1 | B05_RP T2 | Control_RPT1 | Control_RPT2 | Normalized read counts of EVs B05_RP T1 | B05_RP T2 | MOCK_RP T1 | MOCK_RP T2 | Normalized read counts of TOTAL B05_RP T1 | B05_RP T2 | MOCK_RP T1 | MOCK_RP T2 |
|---|---|---|---|---|---|---|---|---|---|---|---|---|---|---|---|---|---|
| S34270 | IGN | 115 | AAACAGGACCTAACAACC | 24 | 0 | 25.65 | 21.88 | BCF | BCF | BCF | BCF | BCF | BCF | 582.34 | 421.99 | 525.48 | 434.89 |
| S470808 | IGN | 116 | AGGATGAAAGGTTTGACTAGAACT | 24 | 0 | 24.77 | 23.45 | BCF | BCF | 466.27 | 70.28 | BCF | BCF | 1492.32 | 1099.55 | 953.57 | 1083.81 |
| S2898187 | ORF | 117 | CTGCACGGGCTTGGCTCATCCCA | 23 | 0 | 24.33 | 14.99 | BCF | BCF | 375.53 | 93.71 | BCF | BCF | BCF | BCF | BCF | BCF |
| S164118 | IGN | 118 | AAGCTGTGGTTAACTGAAAAAGCT | 24 | 0 | 23.88 | 13.68 | BCF | BCF | BCF | BCF | BCF | BCF | BCF | BCF | BCF | BCF |
| S539660 | IGN | 119 | ATAAGAGACGGAACACTGGATATG | 24 | 0 | 21.67 | 18.74 | BCF | BCF | BCF | BCF | BCF | BCF | 63.31 | 46.15 | 80.95 | 73.49 |
| S1490475 | Anti_ORF | 120 | TAAACAAACTGTACTTTATGAGAGCC | 26 | 0 | 20.79 | 10.02 | BCF | BCF | BCF | BCF | BCF | BCF | 18.66 | 19.83 | 21.74 | 32.59 |
| S619170 | TE | 121 | ATCTAAACCCGTCAATTCTAGGAT | 24 | 0 | 15.04 | 26.41 | BCF | BCF | BCF | BCF | BCF | BCF | 28.09 | 31.32 | 70.37 | 61.62 |

SUPPLEMENTARY TABLE 1-continued

The list of Arabidopsis endogenous sRNAs that are present in the sRNA libraries of purified *B. Cinerea* protoplasts from the infected tissue
The normalized reads of these small RNAs in the EV and total sRNA libraries are compared. Normalized read counts are given in reads per million (RPM) in purified *B. Cinerea* protoplast sRNA libraries (BC), EVs sRNA libraries (EVs), and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of BC B05_RP T1 | B05_RP T2 | Control_RPT1 | Control_RPT2 | Normalized read counts of EVs B05_RP T1 | B05_RP T2 | MOCK_RP T1 | MOCK_RP T2 | Normalized read counts of TOTAL B05_RP T1 | B05_RP T2 | MOCK_RP T1 | MOCK_RP T2 |
|---|---|---|---|---|---|---|---|---|---|---|---|---|---|---|---|---|---|
| S842617 | ORF | 122 | CATGGGCATCGACACCTTGCGGCTAGGAAC | 30 | 0 | 14.60 | 80.89 | BCF | BCF | BCF | BCF | BCF | BCF | BCF | BCF | BCF | BCF |
| S161025 | IGN | 123 | AAGCGAAGGACCCAGCAGGGAAGC | 24 | 0 | 13.71 | 20.05 | BCF | BCF | BCF | BCF | BCF | BCF | BCF | BCF | BCF | BCF |
| MIR163 | miRNA | 124 | TTGAAGAGGACTTGGAACTTCGAT | 24 | 0 | 13.27 | 67.55 | BCF | BCF | 4095.45 | 416.19 | 465.90 | 70.27 | 1843.99 | 1476.88 | 742.27 | 657.09 |
| S1007073 | ORF | 125 | CTGCACGGTCTTGGCTCAACCCGC | 24 | 0 | 12.83 | 17.87 | BCF | BCF | 1176.01 | 183.52 | BCF | BCF | 25.36 | 38.55 | 23.65 | 26.13 |
| S640613 | Anti_ORF | 126 | ATGAGAGATTCGGACTATCCAGCC | 24 | 0 | 11.50 | 12.81 | BCF | BCF | 130.04 | 54.67 | BCF | BCF | 151.14 | 152.15 | 211.84 | 197.26 |
| S111989 | IGN | 127 | AACGAACCGACCGTCAGACATGGA | 24 | 0 | 11.06 | 13.34 | BCF | BCF | 389.30 | 44.90 | BCF | BCF | 175.88 | 149.93 | 445.27 | 419.59 |

SUPPLEMENTARY TABLE 2

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| MIR 161 | miRNA | 128 | TTGAAAGTGACTACATCGGGG | 21 | 0 | 26180.86 | 26166.46 | 38715.83 | 32807.12 | 126.50 | 259.13 | BCF | BCF | 6187.95 | 1761.00 | 975.20 | 571.82 |
| MIR 158A | miRNA | 129 | TCCCAAATGTAGACAAAGCA | 20 | 2 | 20391.65 | 14562.15 | 18383.09 | 17208.83 | 236.63 | 528.20 | BCF | BCF | 2044.96 | 7085.01 | 381.76 | 1184.60 |
| MIR 159A | miRNA | 130 | TTTGGATTGAAGGGAGCTCTA | 21 | 3 | 19855.85 | 13861.61 | 31216.26 | 23555.57 | 302.10 | 613.36 | BCF | BCF | 8165.26 | 123.00 | BCF | BCF |
| MIR 396A | miRNA | 131 | TTCCACAGCTTTCTTGAACTG | 21 | 5 | 17322.33 | 16887.83 | 9892.52 | 14254.15 | 255.21 | 176.77 | BCF | BCF | 1976.09 | 2100.71 | 308.56 | 450.90 |
| MIR 166A | miRNA | 132 | TCGGACCAGGCTTCATTCCCC | 21 | 1 | 16129.57 | 16833.16 | 36093.26 | 30198.15 | 2415.44 | 35891.69 | 59.59 | 169.58 | 71636.21 | 20786.48 | 16380.72 | 9618.88 |
| MIR 157A | miRNA | 133 | TTGACAGAAGATAGAGAGCAC | 21 | 1 | 13949.47 | 11099.11 | 18196.99 | 19707.76 | 782.00 | 157.24 | BCF | BCF | 6941.03 | 1249.49 | 939.99 | 321.31 |
| TAS1c-siR483 | tasiRNA | 134 | TCCAATGTCTTTTCTAGTTCGT | 22 | 1 | 13779.67 | 9137.97 | 11358.65 | 14444.95 | 232.21 | 498.31 | BCF | BCF | 27673.80 | 1940.62 | 5574.65 | 890.84 |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| MIR 168A | miRNA | 135 | TCGCTT GGTGCA GGTCGG GAA | 21 | 1 | 9532.05 | 14836.25 | 7841.71 | 7457.34 | 290.60 | 197.77 | 10.85 | 17.75 | 5522.36 | 15253.57 | 944.21 | 318.94 |
| TAS1 c-si R602 | tasi RNA | 136 | TTCTAA GTTCAA CATATC GAC | 21 | 1 | 8724.58 | 6840.09 | 9787.78 | 11121.49 | 156.13 | 131.88 | BCF | BCF | 3060.15 | 1905.48 | 479.98 | 558.42 |
| MIR 159B | miRNA | 137 | TTTGGA TTGAAG GGAGCT CTT | 21 | 2 | 8098.22 | 6334.70 | 9457.97 | 13016.50 | 305.19 | 151.75 | BCF | BCF | 7688.04 | 130.81 | BCF | BCF |
| S702 284 | TE | 138 | ATTATG GACCGT CCAACT TGGCCC | 24 | 0 | 6026.92 | 5603.58 | 4017.89 | 4953.26 | BCF | BCF | BCF | BCF | 821.55 | 44.90 | BCF | BCF |
| MIR 396 A* | miRNA | 139 | GTTCAA TAAAGC TGTGGG AAG | 21 | 3 | 3850.59 | 3879.47 | 2787.25 | 3357.24 | 76.96 | 13.07 | BCF | BCF | 506.38 | 1036.69 | 167.20 | 152.77 |
| TAS1 c-si R581 | tasi RNA | 140 | CTTAGA ATACGC TATGTT GGA | 21 | 0 | 3328.00 | 3481.02 | 4680.58 | 4292.48 | BCF | BCF | BCF | BCF | 1368.44 | 507.61 | 370.54 | 243.78 |
| MIR 403 | miRNA | 141 | TTAGAT TCACGC ACAAAC TCGT | 22 | 0 | 3045.43 | 2092.35 | 2905.66 | 2255.49 | 159.67 | 108.78 | BCF | BCF | 2766.45 | 1882.05 | 409.87 | 299.09 |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| TAS1c-siR585 | tasiRNA | 142 | AGAATACGCTATGTTGGACTGAGA | 24 | 0 | 2930.55 | 3161.70 | 4144.23 | 3788.31 | BCF | BCF | BCF | BCF | 781.04 | 144.47 | 191.70 | 54.95 |
| MIR167A | miRNA | 143 | TGAAGCTGCCAGCATGATCTA | 21 | 2 | 2600.39 | 1982.82 | 2671.64 | 3152.59 | BCF | BCF | BCF | BCF | 5139.95 | 123777.84 | 1392.37 | 10493.13 |
| MIR167A* | miRNA | 144 | GATCATGTTCGCAGTTTCACC | 21 | 0 | 2224.96 | 2093.65 | 4748.01 | 2986.47 | 27.42 | 29.81 | BCF | BCF | 342.72 | 6319.70 | 114.49 | 412.02 |
| MIR165A | miRNA | 145 | TCGGACCAGGCTTCATCCCCC | 21 | 0 | 2152.01 | 1879.23 | 4357.68 | 4284.16 | 243.27 | 6209.88 | BCF | BCF | 8720.25 | 866.84 | 2016.08 | 441.94 |
| S300747 | ORF | 146 | AACGGATTATGTAAGAGAGGT | 21 | 0 | 1973.41 | 2863.87 | 2596.27 | 3497.37 | BCF | BCF | BCF | BCF | BCF | BCF | BCF | BCF |
| MIR398B | miRNA | 147 | GGGTTGATATGAGAACACACG | 21 | 0 | 1904.86 | 2112.37 | 2282.19 | 2880.78 | 64.58 | 28.50 | BCF | BCF | 123.96 | 2493.13 | 52.61 | 252.37 |
| MIR163 | miRNA | 148 | TTGAAGAGGACTTGGAACTTCGAT | 24 | 0 | 1843.99 | 1476.88 | 742.27 | 657.09 | 13.27 | 67.55 | BCF | BCF | 4095.45 | 416.19 | 465.90 | 70.27 |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| sRNA ID | sRNA type | SEQ ID NO: | sRNA sequence 5'-3' | sRNA length | Number of target gene in BC | Normalized read counts of TOTAL B05_RP T1 | B05_RP T2 | MOCK_RP T1 | MOCK_RP T2 | Normalized read counts of BC B05_RP T1 | B05_RP T2 | Control_RP T1 | Control_RP T2 | Normalized read counts of EVs B05_RP T1 | B05_RP T2 | MOCK_RP T1 | MOCK_RP T2 |
|---|---|---|---|---|---|---|---|---|---|---|---|---|---|---|---|---|---|
| S625977 | ORF | 149 | AATGGATTATGTAAGAGAGGT | 21 | 1 | 1700.06 | 2023.60 | 2450.54 | 3388.91 | BCF | BCF | BCF | BCF | BCF | BCF | BCF | BCF |
| S251821 | IGN | 150 | AACATGCGGATTTGCTTTGGCGCC | 24 | 0 | 1654.15 | 2689.29 | 978.98 | 1384.91 | BCF | BCF | BCF | BCF | BCF | BCF | BCF | BCF |
| S4667991 | IGN | 151 | TCCGCTGTAGCACACAGGCCAATT | 24 | 0 | 1623.75 | 1686.48 | 1394.73 | 1193.19 | BCF | BCF | BCF | BCF | 10318.78 | 3359.96 | 850.64 | 565.68 |
| S4667987 | IGN | 152 | TCCGCTGTAGCACACAGGCC | 20 | 0 | 1508.04 | 1548.23 | 1255.46 | 1086.45 | 83.60 | 47.94 | BCF | BCF | 908.24 | 1993.33 | 138.48 | 349.08 |
| S470808 | IGN | 153 | AGGATGAAAGGTTTGACTAGAACT | 24 | 0 | 1492.32 | 1099.55 | 953.57 | 1083.81 | 24.77 | 23.45 | BCF | BCF | 466.27 | 70.28 | BCF | BCF |
| S91611 | IGN | 154 | AAACGAGAACGTAGACAGAACAGA | 24 | 0 | 1441.59 | 1346.78 | 1536.49 | 1382.27 | BCF | BCF | BCF | BCF | BCF | BCF | BCF | BCF |
| S331775 | IGN | 155 | AACTGTGACGATAGCAAGTGCCGTCTGAGC | 30 | 0 | 1430.90 | 1768.40 | 1567.64 | 1469.49 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| miRNA8175 | miRNA | 156 | CGATCCCCGGCAACGGCGCCA | 21 | 0 | 1350.82 | 932.76 | 1766.55 | 1263.78 | BCF | BCF | BCF | BCF | 757.14 | 933.21 | 101.93 | 57.69 |
| S161570 | IGN | 157 | AAGCGCGGAAAGAACAGTAGATGC | 24 | 0 | 1342.02 | 1631.07 | 1241.65 | 1047.13 | BCF | BCF | BCF | BCF | 229.29 | 138.62 | BCF | BCF |
| MIR156D | miRNA | 158 | TTGACAGAAGAGAGTGAGCAC | 21 | 0 | 1280.18 | 889.76 | 1473.62 | 1477.01 | 60.60 | 2 43.88 | BCF | BCF | 747.01 | 679.41 | 160.10 | 70.20 |
| S3260548 | IGN | 159 | GAGAATGATGAACCAATTAGATG | 23 | 1 | 1249.36 | 4768.49 | 2127.64 | 1384.12 | 26.10 | 77.40 | BCF | BCF | BCF | BCF | BCF | BCF |
| TAS3-siR392 | tasiRNA | 160 | AGAATAGAATCTGTAAAACGA | 21 | 0 | 1239.51 | 794.13 | 903.03 | 1012.56 | 52.63 | 21.09 | BCF | BCF | 454.53 | 103.47 | BCF | BCF |
| TAS1C-siR196 | tasiRNA | 161 | TAGCAACTGTTCTTTAGACGA | 21 | 1 | 1129.46 | 923.86 | 825.61 | 1359.84 | BCF | BCF | BCF | BCF | 310.71 | 302.61 | 91.63 | 53.61 |
| TAS2-siR710 | tasiRNA | 162 | ACACGATGTTCAATAGATTTA | 21 | 0 | 1093.61 | 1062.86 | 462.31 | 949.75 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| S98162 | IGN | 163 | AACAGCATCGTCCATCATTGAAGA | 24 | 0 | 981.88 | 1123.46 | 1141.17 | 958.85 | BCF | BCF | BCF | BCF | 665.58 | 82.00 | BCF | BCF |
| S1643241 | IGN | 164 | ATAGCGGAAACTAATTTTGGCACC | 24 | 0 | 981.67 | 1011.89 | 607.31 | 727.42 | BCF | BCF | BCF | BCF | BCF | BCF | BCF | BCF |
| S1323429 | ORF | 165 | AGGACATTAGGTTTATTGGATTGG | 24 | 0 | 955.26 | 818.78 | 710.88 | 863.32 | BCF | BCF | BCF | BCF | BCF | BCF | BCF | BCF |
| TAS2-siR441 | tasiRNA | 166 | TTTTTACGGGGATAAGACTGA | 21 | 0 | 930.52 | 1024.31 | 563.83 | 975.08 | BCF | BCF | BCF | BCF | BCF | BCF | BCF | BCF |
| S598359 | Anti_ORF | 167 | AATGAAAAAGTTGGAAAAGTGCCT | 24 | 0 | 886.29 | 680.52 | 565.44 | 742.33 | BCF | BCF | BCF | BCF | BCF | BCF | BCF | BCF |
| A2622267 | IGN | 168 | CGAGAATGATGAACCAATTAGATG | 24 | 0 | 875.81 | 3484.17 | 1130.00 | 921.25 | 28.75 | 21.62 | BCF | BCF | BCF | BCF | BCF | BCF |
| TAS1 | tasiRNA | 169 | AACTAGAAAAGACATTGGACA | 21 | 0 | 860.72 | 655.13 | 1030.40 | 1181.58 | 50.42 | 52.73 | BCF | BCF | 1332.38 | 1509.15 | 661.39 | 946.23 |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| S2030573 | TE | 170 | ATTATGAACCGTCCAACTTGGCCC | 24 | 0 | 806.64 | 1293.03 | 723.95 | 898.16 | BCF | BCF | BCF | BCF | BCF | BCF | BCF | BCF |
| S3371252 | IGN | 171 | GAGGGACGACGATTTGTGACACC | 23 | 0 | 784.63 | 1156.08 | 1094.89 | 790.49 | BCF | BCF | BCF | BCF | 1722.90 | 1048.40 | 321.53 | 99.38 |
| MIR390A | miRNA | 172 | AAGCTCAGGAGGGATAGCGCC | 21 | 0 | 770.58 | 654.95 | 1014.09 | 1003.72 | 29.63 | 95.09 | BCF | BCF | 299.78 | 66.38 | BCF | BCF |
| S37361 | ORF | 173 | AAACCGCAACCGGATCTTAAAGGC | 24 | 0 | 768.90 | 964.45 | 1220.20 | 1000.81 | 108.81 | 30.25 | BCF | BCF | 760.38 | 175.71 | 260.02 | 134.48 |
| S3820025 | IGN | 174 | GGGACGACGATTTGTGACACC | 21 | 0 | 729.07 | 984.65 | 857.64 | 701.69 | BCF | BCF | BCF | BCF | 1142.80 | 942.98 | 153.51 | 98.49 |
| S3767705 | IGN | 175 | GGATGGTGAGGGACGACGATT | 21 | 0 | 715.66 | 957.96 | 1008.22 | 838.12 | BCF | BCF | BCF | BCF | 2069.27 | 739.93 | 258.93 | 57.83 |
| S4884863 | ORF | 176 | TGACGAGAGAACTTATTGGCCT | 22 | 0 | 687.15 | 467.77 | 597.32 | 753.55 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| sRNA ID | sRNA type | SEQ ID NO: | sRNA sequence 5'-3' | sRNA length | Number of target gene in BC | Normalized read counts of TOTAL B05_RP T1 | B05_RP T2 | MOCK_RP T1 | MOCK_RP T2 | Normalized read counts of BC B05_RP T1 | B05_RP T2 | Control_RP T1 | Control_RP T2 | Normalized read counts of EVs B05_RP T1 | B05_RP T2 | MOCK_RP T1 | MOCK_RP T2 |
|---|---|---|---|---|---|---|---|---|---|---|---|---|---|---|---|---|---|
| S2135042 | TE | 177 | ATTTAATTTGATGGGTTGAGTTGT | 24 | 0 | 683.59 | 722.04 | 298.95 | 500.87 | BCF | BCF | BCF | BCF | BCF | BCF | BCF | BCF |
| S578997 | TE | 178 | AATCCGGTAGAACACTGAAATGGT | 24 | 0 | 659.06 | 509.10 | 651.53 | 668.31 | BCF | BCF | BCF | BCF | BCF | BCF | BCF | BCF |
| S414602 | IGN | 179 | AAGCAGTGGCGGATCTAGGGAGGA | 24 | 0 | 614.41 | 1228.91 | 862.93 | 902.51 | BCF | BCF | BCF | BCF | BCF | BCF | BCF | BCF |
| S1791055 | IGN | 180 | ATCGGACAGTACAACTCTACGTAC | 24 | 0 | 594.08 | 272.25 | 251.94 | 455.87 | BCF | BCF | BCF | BCF | BCF | BCF | BCF | BCF |
| S125711 | IGN | 181 | AAAGAGGATTTAAGTAGATAGTAC | 24 | 1 | 593.66 | 515.21 | 349.93 | 430.28 | BCF | BCF | BCF | BCF | BCF | BCF | BCF | BCF |
| S3905459 | IGN | 182 | GGTGAGGGACGACGATTTGTGACACC | 26 | 0 | 589.46 | 713.88 | 833.55 | 687.97 | BCF | BCF | BCF | BCF | BCF | BCF | BCF | BCF |
| S4961031 | IGN | 183 | TGCAAGGTTCAAGAACGGATC | 21 | 0 | 588.00 | 462.95 | 428.53 | 587.29 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| S34270 | IGN | 184 | AAACAGGACCTTAATAGAACAACC | 24 | 0 | 582.34 | 421.99 | 525.48 | 434.89 | 25.65 | 21.88 | BCF | BCF | BCF | BCF | BCF | BCF |
| TAS3-siR342 | tasiRNA | 185 | AACGTTTAGAAAGAGATGGGG | 21 | 0 | 569.97 | 516.51 | 668.57 | 760.67 | BCF | BCF | BCF | BCF | 252.78 | 95.66 | BCF | BCF |
| S629539 | IGN | 186 | AATGGGATGGAGAAGAAACTGG | 22 | 0 | 568.50 | 432.37 | 392.24 | 405.21 | BCF | BCF | BCF | BCF | BCF | BCF | BCF | BCF |
| TAS2-siR461 | tasiRNA | 187 | ATAAGACTGAAACATATATGT | 21 | 0 | 542.51 | 399.94 | 367.41 | 377.50 | BCF | BCF | BCF | BCF | 177.44 | 164.00 | BCF | BCF |
| S976189 | IGN | 188 | ACTCGAGACTGTTTTGGAAACAAA | 24 | 0 | 497.44 | 464.80 | 461.73 | 423.15 | BCF | BCF | BCF | BCF | BCF | BCF | BCF | BCF |
| S2148545 | Anti_ORF | 189 | ATTTCAGGAGTAGAATTTTTCGCC | 24 | 0 | 498.70 | 437.56 | 298.51 | 382.51 | BCF | BCF | BCF | BCF | BCF | BCF | BCF | BCF |
| S1770669 | IGN | 190 | ATCCTATCGGCTGATTCGGTTAGA | 24 | 0 | 497.44 | 464.80 | 461.73 | 423.15 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| S3487804 | IGN | 191 | GATGGTGAGGGACGACGATT | 20 | 1 | 495.55 | 704.25 | 453.79 | 295.82 | BCF | BCF | BCF | BCF | 586.18 | 821.93 | BCF | BCF |
| S1622646 | IGN | 192 | ATACTCTAATGGATGGATTGTTGT | 24 | 0 | 493.46 | 891.43 | 307.62 | 404.68 | BCF | BCF | BCF | BCF | BCF | BCF | BCF | BCF |
| S4668053 | IGN | 193 | TCCGCTGTAGCACTTCAGGCTA | 22 | 0 | 488.86 | 744.43 | 623.62 | 418.41 | 297.68 | 347.00 | BCF | BCF | 4164.86 | 1173.35 | 528.16 | 258.73 |
| S4668053 | IGN | 194 | TCCGCTGTAGCACTTCAGGCTA | 22 | 0 | 488.86 | 747.43 | 623.62 | 418.41 | 297.68 | 347.00 | BCF | BCF | 4164.86 | 1173.35 | 528.16 | 258.73 |
| S4287096 | TE | 195 | TAAACATCTGATCGTTTGACTTGA | 24 | 0 | 479.41 | 424.77 | 423.09 | 361.53 | BCF | BCF | BCF | BCF | BCF | BCF | BCF | BCF |
| MIR391 | miRNA | 196 | ACGGTATCTCTCCTACGTAGC | 21 | 1 | 478.36 | 603.43 | 533.86 | 224.04 | BCF | BCF | BCF | BCF | 222.81 | 179.61 | BCF | BCF |
| IGN-siR107 | IGN | 197 | GGTTTAGAATTGGATTGTAACAGA | 24 | 0 | 462.85 | 430.15 | 453.94 | 406.92 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| sRNA ID | sRNA type | SEQ ID NO: | sRNA sequence 5'-3' | sRNA length | Number of target gene in BC | Normalized read counts of TOTAL B05_RP T1 | B05_RP T2 | MOCK_RP T1 | MOCK_RP T2 | Normalized read counts of BC B05_RP T1 | B05_RP T2 | Control_RP T1 | Control_RP T2 | Normalized read counts of EVs B05_RP T1 | B05_RP T2 | MOCK_RP T1 | MOCK_RP T2 |
|---|---|---|---|---|---|---|---|---|---|---|---|---|---|---|---|---|---|
| S3083589 | TE | 198 | GAACCGACCGTCAGACATGGATGA | 24 | 0 | 453.21 | 503.91 | 1065.66 | 1032.22 | BCF | BCF | BCF | BCF | BCF | BCF | BCF | BCF |
| S846357 | Anti_ORF | 199 | ACCGGAACTGCTTGAAATAATGGA | 24 | 0 | 448.60 | 414.58 | 371.23 | 333.30 | BCF | BCF | BCF | BCF | BCF | BCF | BCF | BCF |
| S2093887 | IGN | 200 | ATTGAGTAACAGGAGGACTATGCC | 24 | 0 | 440.00 | 390.30 | 183.34 | 262.05 | BCF | BCF | BCF | BCF | BCF | BCF | BCF | BCF |
| S3238006 | IGN | 201 | GAGAAACTAAAGTCGGCGGACGAC | 24 | 0 | 429.10 | 399.38 | 315.26 | 374.20 | BCF | BCF | BCF | BCF | BCF | BCF | BCF | BCF |
| S1218093 | Anti_ORF | 202 | AGATGATGGGCTTAGATGATGGGC | 24 | 0 | 423.44 | 468.88 | 413.69 | 365.62 | BCF | BCF | BCF | BCF | BCF | BCF | BCF | BCF |
| S1484048 | IGN | 203 | GTTTTGGACAGGTATCGACA | 20 | 1 | 421.35 | 568.77 | 294.69 | 258.48 | BCF | BCF | BCF | BCF | 45.37 | 439.27 | BCF | BCF |
| S35060 | TE | 204 | AAACATCTGATCGTTTGACTTGA | 23 | 0 | 421.35 | 407.72 | 361.98 | 263.36 | BCF | BCF | BCF | BCF | 153.13 | 117.14 | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| sRNA ID | sRNA type | SEQ ID NO: | sRNA sequence 5'-3' | sRNA length | Number of target gene in BC | Normalized read counts of TOTAL B05_RP T1 | B05_RP T2 | MOCK_RP T1 | MOCK_RP T2 | Normalized read counts of BC B05_RP T1 | B05_RP T2 | Control_RP T1 | Control_RP T2 | Normalized read counts of EVs B05_RP T1 | B05_RP T2 | MOCK_RP T1 | MOCK_RP T2 |
|---|---|---|---|---|---|---|---|---|---|---|---|---|---|---|---|---|---|
| S5421719 | TE | 205 | TTGAGGATAATGTTGCATAAATA | 23 | 0 | 402.27 | 315.06 | 161.60 | 221.93 | BCF | BCF | BCF | BCF | BCF | BCF | BCF | BCF |
| S855381 | IGN | 206 | ACCGTGAGGCCAAACTTGGCATA | 23 | 0 | 398.92 | 277.44 | 231.52 | 229.85 | BCF | BCF | BCF | BCF | BCF | BCF | BCF | BCF |
| S3767704 | IGN | 207 | GGATGGTGAGGGACGACGAT | 20 | 1 | 384.66 | 533.19 | 750.69 | 603.26 | BCF | BCF | BCF | BCF | 275.47 | 259.66 | BCF | BCF |
| MIR292B | miRNA | 208 | ATCATGCGATCTCTTTGGATT | 21 | 2 | 375.02 | 243.89 | 406.20 | 400.59 | BCF | BCF | BCF | BCF | 2126.79 | 1710.01 | 409.99 | 150.67 |
| S4668051 | IGN | 209 | TCCGCTGTAGCACTTCAGGC | 20 | 1 | 368.73 | 513.73 | 341.56 | 269.96 | BCF | BCF | BCF | BCF | BCF | BCF | BCF | BCF |
| MIR161* | miRNA | 210 | TCAATGCATTGAAAGTGACT | 20 | 3 | 355.31 | 207.57 | 324.08 | 322.21 | BCF | BCF | BCF | BCF | BCF | BCF | BCF | BCF |
| S1252933 | TE | 211 | AGCATATCATGATGTGGTTGGTGT | 24 | 0 | 345.88 | 447.01 | 214.04 | 287.25 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| sRNA ID | sRNA type | SEQ ID NO: | sRNA sequence 5'-3' | sRNA length | Number of target gene in BC | Normalized read counts of TOTAL B05_RP T1 | B05_RP T2 | MOCK_RP T1 | MOCK_RP T2 | Normalized read counts of BC B05_RP T1 | B05_RP T2 | Control_RP T1 | Control_RP T2 | Normalized read counts of EVs B05_RP T1 | B05_RP T2 | MOCK_RP T1 | MOCK_RP T2 |
|---|---|---|---|---|---|---|---|---|---|---|---|---|---|---|---|---|---|
| S5012356 | IGN | 212 | TGGAAGGATTACGGGCCATTGCCT | 24 | 0 | 345.04 | 382.15 | 254.88 | 277.35 | BCF | BCF | BCF | BCF | BCF | BCF | BCF | BCF |
| S274111 | IGN | 213 | AACCGGATGTATGCAGAGATGATC | 24 | 0 | 342.95 | 387.89 | 247.83 | 266.00 | BCF | BCF | BCF | BCF | BCF | BCF | BCF | BCF |
| S1305579 | TE | 214 | AGGAAATACTATGCTGTAAAAAGG | 24 | 0 | 342.74 | 288.56 | 257.82 | 250.70 | BCF | BCF | BCF | BCF | BCF | BCF | BCF | BCF |
| S949704 | ORF | 215 | ACTAACTAAGGTACTATGGATTGG | 24 | 0 | 342.32 | 352.68 | 232.99 | 308.09 | BCF | BCF | BCF | BCF | BCF | BCF | BCF | BCF |
| S373543 | IGN | 216 | AGAACAGAGACCGTTGGAAGAAAA | 24 | 0 | 341.90 | 312.83 | 345.67 | 379.08 | 30.96 | 26.76 | BCF | BCF | 193.23 | 60.52 | BCF | BCF |
| S1029881 | IGN | 217 | ACTTTCTGGAGACCAAACCCT | 21 | 0 | 338.54 | 442.38 | 614.36 | 372.09 | BCF | BCF | BCF | BCF | BCF | BCF | BCF | BCF |
| MIR822A | miRNA | 218 | TGCGGGAAGCATTTGCACATG | 21 | 3 | 335.19 | 297.45 | 498.89 | 578.19 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| S5051044 | ORF | 219 | TGGATTATGTAAGAGAGGTGA | 21 | 0 | 312.34 | 497.61 | 541.06 | 651.68 | BCF | BCF | BCF | BCF | BCF | BCF | BCF | BCF |
| MiR170 | miRNA | 220 | TGATTGAGCCGTGTCAATATC | 21 | 1 | 312.13 | 261.13 | 181.28 | 272.73 | BCF | BCF | BCF | BCF | BCF | BCF | BCF | BCF |
| S1804551 | IGN | 221 | TGGTGGAACACTGGCTCGGCCC | 22 | 0 | 306.89 | 325.99 | 309.09 | 266.80 | 191.08 | 107.47 | BCF | BCF | 165.28 | 191.33 | BCF | BCF |
| MIR5026 | miRNA | 222 | ACTCATAAGATCGTGACACGT | 21 | 1 | 306.89 | 289.85 | 295.87 | 292.79 | BCF | BCF | BCF | BCF | 45.37 | 48.81 | BCF | BCF |
| S4287100 | IGN | 223 | TAAACATCTGATCGTTTGATTTGA | 24 | 0 | 299.76 | 288.56 | 230.35 | 232.09 | BCF | BCF | BCF | BCF | BCF | BCF | BCF | BCF |
| S1153819 | IGN | 224 | AGAGATAAGAAACGATAGTCGGTT | 24 | 0 | 299.34 | 179.58 | 269.87 | 296.48 | BCF | BCF | BCF | BCF | BCF | BCF | BCF | BCF |
| S3785664 | IGN | 225 | GGCCCACGGGTCGGATCTGTTGTGGC | 26 | 0 | 298.72 | 336.00 | 151.02 | 144.35 | BCF | BCF | BCF | BCF | BCF | BCF | BCF | BCF |

SUPPLEMENTARY TABLE 2-continued

The list of top 100 Arabidopsis sRNAs that present in the total sRNA libraries
The normalized reads of these small RNAs in the Bc protoplast and EV sRNA libraries are compared here. Normalized read counts are given in reads per million (RPM) in total sRNA libraries (TOTAL), Purified B. Cinerea sRNA libraries (BC) and EVs sRNA libraries (EVs) respectively.

| sRNA ID | sRNA type | SEQ ID NO: | sRNA sequence 5'-3' | sRNA length | Number of target gene in BC | Normalized read counts of TOTAL | | | | Normalized read counts of BC | | | | Normalized read counts of EVs | | | |
|---|---|---|---|---|---|---|---|---|---|---|---|---|---|---|---|---|---|
| | | | | | | B05_RP T1 | B05_RP T2 | MOCK_RP T1 | MOCK_RP T2 | B05_RP T1 | B05_RP T2 | Control_RP T1 | Control_RP T2 | B05_RP T1 | B05_RP T2 | MOCK_RP T1 | MOCK_RP T2 |
| S559726 | IGN | 226 | AATATGTATGTGTTGGAAGGGTGT | 24 | 0 | 294.10 | 457.76 | 146.76 | 222.99 | BCF | BCF | BCF | BCF | BCF | BCF | BCF | BCF |
| S2669656 | IGN | 227 | CGCGGATAATATGGGCTTGACCA | 23 | 0 | 279.85 | 441.64 | 293.52 | 288.83 | BCF | BCF | BCF | BCF | BCF | BCF | BCF | BCF |

SUPPLEMENTARY TABLE 3

The list of sRNA in Purified *B. Cinerea* sRNA libraries (BC) that are not present in top 100 TOTAL libraries
The normalized reads of these small RNAs in the Bc protoplast and EV sRNA libraries are compared here. Normalized read counts are given in reads per million (RPM) in total sRNA libraries (TOTAL), Purified *B. Cinerea* sRNA libraries (BC) and EVs sRNA libraries (EVs) respectively.
RPT, Repeat; BCF, below the cut off.

| | | | | | Number of target | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| IGN-siR1 | IGN | 228 | GTCGAACTCAGT AACGCGGGCT | 22 | 1 | 136.68 | 133.25 | 84.62 | 81.67 | 433.46 | 355.19 | BCF | BCF | 105.33 | 74.19 | 40.49 | 56.52 |
| S1353733 | ORF | 229 | GGTGGAGGAGGA GGCGGCGGC | 21 | 19 | BCF | BCF | BCF | BCF | 128.27 | 65.63 | BCF | BCF | BCF | BCF | BCF | BCF |
| S1178334 | ORF | 230 | GAGTTAATTGAA CGTTCGGCGT | 22 | 0 | 59.95 | 77.84 | 37.17 | 37.47 | 113.67 | 33.82 | BCF | BCF | BCF | BCF | BCF | BCF |
| S519888 | ORF | 231 | AGTTAATTGAAC GTTCGGCGT | 21 | 1 | 54.71 | 67.83 | 33.05 | 35.76 | 113.67 | 33.82 | BCF | BCF | BCF | BCF | BCF | BCF |
| S158710 | IGN | 232 | AAGCACATGTGT AGAGTCGAGCCT | 24 | 0 | 260.14 | 266.32 | 309.24 | 357.97 | 32.73 | 14.73 | BCF | BCF | 326.92 | 134.71 | BCF | BCF |
| MIR396B | miRNA | 233 | TTCCACAGCTTT CTTGAACTT | 21 | 4 | 250.71 | 153.27 | 249.45 | 272.07 | 26.10 | 16.91 | BCF | BCF | 650.60 | 105.43 | 143.83 | 40.21 |
| S2898187 | ORF | 234 | CTGCACGGGCTT GGCTCATCCCA | 23 | 0 | BCF | BCF | BCF | BCF | 24.33 | 14.99 | BCF | BCF | 375.53 | 93.71 | BCF | BCF |
| S164118 | IGN | 235 | AAGCTGTGGTTA ACTGAAAAAGCT | 24 | 0 | BCF | BCF | BCF | BCF | 23.88 | 13.68 | BCF | BCF | BCF | BCF | BCF | BCF |
| S539660 | IGN | 236 | ATAAGAGACGGA ACACTGGATATG | 24 | 0 | 63.31 | 46.15 | 80.95 | 73.49 | 21.67 | 18.74 | BCF | BCF | BCF | BCF | BCF | BCF |
| S1490475 | Anti_ ORF | 237 | TAAACAAACTGT ACTTTATGAGAG CC | 26 | 0 | 18.66 | 19.83 | 21.74 | 32.59 | 20.79 | 10.02 | BCF | BCF | BCF | BCF | BCF | BCF |
| S2724436 | TE | 238 | CGGGTTTGGCAG GACGTTACT | 21 | 1 | 24.32 | 28.73 | 30.41 | 23.75 | 19.02 | 16.74 | BCF | BCF | 139.36 | 283.09 | 124.35 | 128.92 |
| S619170 | TE | 239 | ATCTAAACCCGT CAATTCTAGGAT | 24 | 0 | 28.09 | 31.32 | 70.37 | 61.62 | 15.04 | 26.41 | BCF | BCF | BCF | BCF | BCF | BCF |

SUPPLEMENTARY TABLE 3-continued

The list of sRNA in Purified *B. Cinerea* sRNA libraries (BC) that are not present in top 100 TOTAL libraries
The normalized reads of these small RNAs in the Bc protoplast and EV sRNA libraries are compared here. Normalized read counts are given in reads per million (RPM) in total sRNA libraries (TOTAL), Purified *B. Cinerea* sRNA libraries (BC) and EVs sRNA libraries (EVs) respectively.
RPT, Repeat; BCF, below the cut off.

| | | | | | | Normalized read counts of TOTAL | | | | Normalized read counts of BC | | | | Normalized read counts of EVs | | | |
|---|---|---|---|---|---|---|---|---|---|---|---|---|---|---|---|---|---|
| sRNA ID | sRNA type | SEQ ID NO: | sRNA sequence 5'-3' | sRNA length | Number of target gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S842617 | ORF | 240 | CATGGGCATCGA CACCTTGCGGCT AGGAAC | 30 | 0 | BCF | BCF | BCF | BCF | 14.60 | 80.89 | BCF | BCF | BCF | BCF | BCF | BCF |
| S1092315 | TE | 241 | GAAGTCCTCGTG TTGCATTCCT | 22 | 1 | 83.64 | 196.45 | 259.14 | 203.99 | 14.15 | 13.25 | BCF | BCF | BCF | BCF | BCF | BCF |
| S161025 | IGN | 242 | AAGCGAAGGACC CAGCAGGGAAGC | 24 | 0 | BCF | BCF | BCF | BCF | 13.71 | 20.05 | BCF | BCF | BCF | BCF | BCF | BCF |
| TAS2-siR453 | tasiRNA | 243 | CGTAAAAAAAGT TGTAACTCT | 21 | 1 | 48.21 | 44.29 | 67.28 | 46.71 | 13.27 | 23.01 | BCF | BCF | 40.51 | 113.24 | BCF | BCF |
| S1007073 | ORF | 244 | CTGCACGGTCTT GGCTCAACCCGC | 24 | 0 | 25.36 | 38.55 | 23.65 | 26.13 | 12.83 | 17.87 | BCF | BCF | 1176.01 | 183.52 | BCF | BCF |
| S640613 | Anti_ ORF | 245 | ATGAGAGATTCG GACTATCCAGCC | 24 | 0 | 151.14 | 152.15 | 211.84 | 197.26 | 11.50 | 12.81 | BCF | BCF | 130.04 | 54.67 | BCF | BCF |
| S111989 | IGN | 246 | AACGAACCGACC GTCAGACATGGA | 24 | 0 | 175.88 | 149.93 | 445.27 | 419.59 | 11.06 | 13.34 | BCF | BCF | 389.30 | 44.90 | BCF | BCF |

SUPPLEMENTARY TABLE 4

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| MIR166A | miRNA | 247 | TCGGAC CAGGCT TCATTC CCC | 21 | 1 | 71636.21 | 20786.48 | 16380.72 | 9618.88 | 2415.44 | 35891.69 | 59.59 | 169.58 | 16129.57 | 16838.16 | 36093.26 | 30198.15 |
| TAS1c-siR483 | tasiRNA | 248 | TCCAAT GTCTTT TCTAGT TCGT | 22 | 2 | 27673.80 | 1940.62 | 5574.65 | 890.84 | 232.21 | 498.31 | BCF | BCF | 13779.67 | 9137.97 | 11358.65 | 14444.95 |
| S4667991 | IGN | 249 | TCCGCT GTAGCA CACAGG CCAATT | 24 | 0 | 10318.78 | 3359.96 | 850.64 | 565.68 | BCF | BCF | BCF | BCF | 1623.75 | 1686.48 | 1394.73 | 1193.19 |
| MIR165A | miRNA | 250 | TCGGAC CAGGCT TCATCC CCC | 21 | 0 | 8720.25 | 866.84 | 2016.08 | 441.94 | 243.27 | 6209.88 | BCF | BCF | 2152.01 | 1879.23 | 4357.68 | 4284.16 |
| MIR159A | miRNA | 251 | TTTGGA TTGAAG GGAGCT CTA | 21 | 3 | 8165.26 | 123.00 | 942.56 | 24.44 | 302.10 | 613.36 | BCF | BCF | 19855.85 | 13861.61 | 31216.26 | 23555.57 |
| MIR159B | miRNA | 252 | TTTGGA TTGAAG GGAGCT CTT | 21 | 2 | 7688.04 | 130.81 | 871.93 | 21.03 | 305.19 | 151.75 | BCF | BCF | 8098.22 | 6334.70 | 9457.97 | 13016.50 |
| MIR157A | miRNA | 253 | TTGACA GAAGAT AGAGAG CAC | 21 | 1 | 6941.03 | 1249.49 | 939.99 | 321.31 | 782.00 | 157.24 | BCF | BCF | 13949.47 | 11099.11 | 18196.99 | 19707.76 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| MIR161 | miRNA | 254 | TTGAAA GTGACT ACATCG GGG | 21 | 0 | 6187.95 | 1761.00 | 975.20 | 571.82 | 126.50 | 259.13 | BCF | BCF | 26180.86 | 26166.46 | 38715.83 | 32807.12 |
| MIR168A | miRNA | 255 | TCGCTT GGTGCA GGTCGG GAA | 21 | 1 | 5522.36 | 15253.57 | 944.21 | 318.94 | 290.60 | 197.77 | 10.85 | 17.75 | 9532.05 | 14836.25 | 7841.71 | 7457.34 |
| MIR167A | miRNA | 256 | TGAAGC TGCCAG CATGAT CTA | 21 | 2 | 5139.95 | 123777.84 | 1392.37 | 10493.13 | BCF | BCF | BCF | BCF | 2600.39 | 1982.82 | 2671.64 | 3152.59 |
| S4667996 | IGN | 257 | TCCGCT GTAGCA CACAGG CCAATT TCACT | 29 | 0 | 4867.31 | 204.99 | 455.06 | 54.80 | BCF | BCF | BCF | BCF | 29.35 | 36.69 | BCF | BCF |
| S4668053 | IGN | 258 | TCCGCT GTAGCA CTTCAG GCTA | 22 | 0 | 4164.86 | 1173.35 | 528.16 | 258.73 | 297.68 | 347.00 | BCF | BCF | 484.86 | 747.43 | 623.62 | 418.41 |
| MIR163 | miRNA | 259 | TTGAAG AGGACT TGGAAC TTCGAT | 24 | 0 | 4095.45 | 416.19 | 465.90 | 70.27 | 13.27 | 67.55 | BCF | BCF | 1843.99 | 1476.88 | 742.27 | 657.09 |
| TAS1c-siR602 | tasiRNA | 260 | TTCTAA GTTCAA CATATC GAC | 21 | 1 | 3060.15 | 1905.48 | 479.98 | 558.42 | 156.13 | 131.88 | BCF | BCF | 8724.58 | 6840.09 | 9787.78 | 11121.49 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| MIR403 | miRNA | 261 | TTAGAT TCACGC ACAAAC TCGT | 22 | 0 | 2766.45 | 1882.05 | 409.87 | 299.09 | 159.67 | 108.78 | BCF | BCF | 3045.43 | 2092.35 | 2905.66 | 2255.49 |
| S2794789 | IGN | 262 | CTACTG CACGGT CTTGGC TCAACC CGC | 27 | 0 | 2256.83 | 464.66 | 559.74 | 63.98 | BCF | BCF | BCF | BCF | 37.73 | 76.36 | 45.98 | 13.59 |
| MIR393B | miRNA | 263 | ATCATG CGATCT CTTTGG ATT | 21 | 2 | 2126.79 | 1710.01 | 409.99 | 150.67 | BCF | BCF | BCF | BCF | 375.02 | 243.89 | 406.20 | 400.59 |
| MIR158A | miRNA | 264 | TCCCAA ATGTAG ACAAAG CA | 20 | 2 | 2044.96 | 7085.01 | 381.76 | 1184.60 | 236.63 | 528.20 | BCF | BCF | 20391.65 | 14562.15 | 18382.09 | 17208.83 |
| MIR396A | miRNA | 265 | TTCCAC AGCTTT CTTGAA CTG | 21 | 5 | 1976.09 | 2100.71 | 308.56 | 450.90 | 255.21 | 176.77 | BCF | BCF | 17322.33 | 16887.83 | 9892.52 | 14254.15 |
| TAS1c-siR581 | tasiRNA | 266 | CTTAGA ATACGC TATGTT GGA | 21 | 0 | 1368.44 | 507.61 | 370.54 | 243.78 | BCF | BCF | BCF | BCF | 3328.00 | 3481.02 | 4680.58 | 4292.48 |
| TAS1c-siR539 | tasiRNA | 267 | AACTAG AAAAGA CATTGG ACA | 21 | 0 | 1332.38 | 1509.15 | 661.39 | 946.23 | 50.42 | 52.73 | BCF | BCF | 860.72 | 655.13 | 1030.40 | 1181.58 |

SUPPLEMENTARY TABLE 4-continued

The list of At-sRNAs that present in EVs.
The normalized reads of these small RNAs in the
*B. cinerea* protoplast and total sRNA libraries are compared.
Normalized read counts are given in reads per million (RPM)
in EVs sRNA libraries (EVs), Purified *B. Cinerea* sRNA
libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| TAS1c-siR541 | tasiRNA | 268 | GAACTAGAAAAGACATTGGAC | 21 | 0 | 1313.75 | 1507.20 | 660.36 | 946.23 | 50.42 | 52.73 | BCF | BCF | 854.43 | 652.91 | 1025.11 | 1178.15 |
| S1007073 | ORF | 269 | CTGCACGGTCTTGGCTCAACCCGC | 24 | 0 | 1176.01 | 183.52 | BCF | BCF | 12.83 | 17.87 | BCF | BCF | 25.36 | 38.55 | 23.65 | 26.13 |
| S4667987 | IGN | 270 | TCCGCTGTAGCACACAGGCC | 20 | 0 | 908.24 | 1993.33 | 138.48 | 349.08 | 83.60 | 47.94 | BCF | BCF | 1508.04 | 1548.23 | 1255.46 | 1086.45 |
| S702284 | TE | 271 | ATTATGGACCGTCCAACTTGGCCC | 24 | 0 | 821.55 | 44.90 | BCF | BCF | BCF | BCF | BCF | BCF | 6026.92 | 5603.58 | 4017.89 | 4953.26 |
| S2794744 | Anti_ORF | 272 | CTACTGCACGGGCCGGCTCAACCCG | 25 | 0 | 805.75 | 111.28 | BCF | BCF | BCF | BCF | BCF | BCF | 10.27 | 12.42 | BCF | BCF |
| TAS1c-siR585 | tasiRNA | 273 | AGAATACGCTATGTTGGACTTAGA | 24 | 0 | 781.04 | 144.47 | 191.70 | 54.95 | BCF | BCF | BCF | BCF | 2930.55 | 3161.70 | 4144.23 | 3788.31 |
| S37361 | ORF | 274 | AAACCGCAACCGGATCTTAAAGGC | 24 | 0 | 760.38 | 175.71 | 260.02 | 134.48 | 108.81 | 30.25 | BCF | BCF | 768.90 | 964.45 | 1220.20 | 1000.81 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_RPT1 | B05_RPT2 | MOCK_RPT1 | MOCK_RPT2 | B05_RPT1 | B05_RPT2 | Control_RPT1 | Control_RPT2 | B05_RPT1 | B05_RPT2 | MOCK_RPT1 | MOCK_RPT2 |
| miRNA8175 | miRNA | 275 | CGATCC CCGGCA ACGGCG CCA | 21 | 0 | 757.14 | 933.21 | 101.93 | 57.69 | BCF | BCF | BCF | BCF | 1350.82 | 932.76 | 1766.55 | 1263.78 |
| MIR156D | miRNA | 276 | TTGACA GAAGAG AGTGAG CAC | 21 | 0 | 747.01 | 679.41 | 160.10 | 70.20 | 60.60 | 243.88 | BCF | BCF | 1280.18 | 889.76 | 1473.62 | 1477.01 |
| S98162 | IGN | 277 | AACAGC ATCGTC CATCAT TGAAGA | 24 | 0 | 665.58 | 82.00 | BCF | BCF | BCF | BCF | BCF | BCF | 981.88 | 1123.46 | 1141.17 | 958.85 |
| MIR396B | miRNA | 278 | TTCCAC AGCTTT CTTGAA CTT | 21 | 4 | 650.60 | 105.43 | 143.83 | 40.21 | 26.10 | 16.91 | BCF | BCF | 250.71 | 153.27 | 249.45 | 272.07 |
| MIR396A* | miRNA | 279 | GTTCAA TAAAGC TGTGGG AAG | 21 | 3 | 506.38 | 1036.69 | 167.20 | 152.77 | 76.96 | 13.07 | BCF | BCF | 3850.59 | 3879.47 | 2787.25 | 3357.24 |
| S470808 | IGN | 280 | AGGATG AAAGGT TTGACT AGAACT | 24 | 0 | 466.27 | 70.28 | BCF | BCF | 24.77 | 23.45 | BCF | BCF | 1492.32 | 1099.55 | 953.57 | 1083.81 |
| TAS3-siR392 | tasiRNA | 281 | AGAATA GAATCT GTAAAA CGA | 21 | 0 | 454.53 | 103.47 | BCF | BCF | 52.63 | 21.09 | BCF | BCF | 1239.51 | 794.13 | 903.03 | 1012.56 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| sRNA ID | sRNA type | SEQ ID NO: | sRNA sequence 5'-3' | sRNA length | Number of target gene in BC | Normalized read counts of EVs B05_RPT1 | B05_RPT2 | MOCK_RPT1 | MOCK_RPT2 | Normalized read counts of BC B05_RPT1 | B05_RPT2 | Control_RPT1 | Control_RPT2 | Normalized read counts of TOTAL B05_RPT1 | B05_RPT2 | MOCK_RPT1 | MOCK_RPT2 |
|---|---|---|---|---|---|---|---|---|---|---|---|---|---|---|---|---|---|
| MIR841A | miRNA | 282 | TTTCTAGTGGGTCGTATTCAC | 21 | 1 | 418.47 | 119.09 | BCF | BCF | BCF | BCF | BCF | BCF | 212.56 | 168.65 | 326.87 | 331.58 |
| S2898195 | IGN | 283 | CTGCACGGTCTTGGCTCAACCCG | 23 | 0 | 392.54 | 93.71 | BCF | BCF | BCF | BCF | BCF | BCF | 11.74 | 18.90 | BCF | BCF |
| S111989 | IGN | 284 | AACGAACCGACCGTCAGACATGGA | 24 | 0 | 389.30 | 44.90 | BCF | BCF | 11.06 | 13.34 | BCF | BCF | 175.88 | 149.93 | 445.27 | 419.59 |
| S2898187 | ORF | 285 | CTGCACGGGCTTGGCTCATCCCA | 23 | 0 | 375.53 | 93.71 | BCF | BCF | 24.33 | 14.99 | BCF | BCF | BCF | BCF | BCF | BCF |
| S4964170 | IGN | 286 | TGCACGGTCTTGGCTCAACCCGCC | 24 | 0 | 371.48 | 898.07 | 260.94 | 148.69 | BCF | BCF | BCF | BCF | BCF | BCF | BCF | BCF |
| S4403479 | IGN | 287 | TACTGCACGGTCTTGGCTCAACCCGC | 26 | 0 | 366.21 | 50.76 | BCF | BCF | BCF | BCF | BCF | BCF | 22.01 | 17.24 | 29.53 | 24.15 |
| S2794780 | ORF | 288 | CTACTGCACGGGCTTGGCTCATCCCA | 26 | 0 | 342.72 | 111.28 | BCF | BCF | BCF | BCF | BCF | BCF | BCF | BCF | BCF | BCF |

SUPPLEMENTARY TABLE 4-continued

The list of At-sRNAs that present in EVs. The normalized reads of these small RNAs in the *B. cinerea* protoplast and total sRNA libraries are compared. Normalized read counts are given in reads per million (RPM) in EVs sRNA libraries (EVs), Purified *B. Cinerea* sRNA libraries (BC) and total sRNA libraries (TOTAL) respectively. RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| MIR167A* | miRNA | 289 | GATCAT GTTCGC AGTTTC ACC | 21 | 0 | 342.72 | 6319.70 | 114.49 | 412.02 | 27.42 | 29.81 | BCF | BCF | 2224.96 | 2093.65 | 4748.01 | 2986.47 |
| S158710 | IGN | 290 | AAGCAC ATGTGT AGAGTC GAGCCT | 24 | 0 | 326.92 | 134.71 | BCF | BCF | 32.73 | 14.73 | BCF | BCF | 260.14 | 266.32 | 309.24 | 357.97 |
| TAS1C-siR196 | tasiRNA | 291 | TAGCAA CTGTTC TTTAGA CGA | 21 | 1 | 310.71 | 302.61 | 91.63 | 53.61 | BCF | BCF | BCF | BCF | 1129.46 | 923.86 | 825.61 | 1359.84 |
| TAS2-siR165 | tasiRNA | 292 | TTTGCA TATACT CGAATA CCT | 21 | 0 | 305.45 | 327.99 | 45.30 | 76.87 | BCF | BCF | BCF | BCF | 171.26 | 104.71 | 154.25 | 175.36 |
| MIR390A | miRNA | 293 | AAGCTC AGGAGG GATAGC GCC | 21 | 0 | 299.78 | 66.38 | BCF | BCF | 29.63 | 95.09 | BCF | BCF | 770.58 | 654.95 | 1014.09 | 1003.72 |
| MIR850A | miRNA | 294 | AAGATC CGGACT ACAACA AAGC | 22 | 0 | 271.82 | 158.14 | BCF | BCF | BCF | BCF | BCF | BCF | 50.73 | 164.39 | 86.67 | 78.51 |
| S995284 | IGN | 295 | ACTGCA CGGTCT TGGCTC AACCCG C | 25 | 0 | 261.70 | 46.86 | BCF | BCF | BCF | BCF | BCF | BCF | BCF | BCF | 14.25 | 10.69 |

SUPPLEMENTARY TABLE 4-continued

The list of At-sRNAs that present in EVs. The normalized reads of these small RNAs in the *B. cinerea* protoplast and total sRNA libraries are compared. Normalized read counts are given in reads per million (RPM) in EVs sRNA libraries (EVs), Purified *B. Cinerea* sRNA libraries (BC) and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of EVs B05_RPT1 | B05_RPT2 | MOCK_RPT1 | MOCK_RPT2 | Normalized read counts of BC B05_RPT1 | B05_RPT2 | Control_RPT1 | Control_RPT2 | Normalized read counts of TOTAL B05_RPT1 | B05_RPT2 | MOCK_RPT1 | MOCK_RPT2 |
|---|---|---|---|---|---|---|---|---|---|---|---|---|---|---|---|---|---|
| TAS3-siR342 | tasiRNA | 296 | AACGTTTAGAAAGAGATGGGG | 21 | 0 | 252.78 | 95.66 | BCF | BCF | BCF | BCF | BCF | BCF | 569.97 | 516.51 | 668.57 | 760.67 |
| S4435833 | miRNA | 297 | TAGCCAAGGATGACTTGCCT | 20 | 1 | 252.50 | 1182.35 | 58.76 | 58.72 | BCF | BCF | BCF | BCF | 233.21 | 82.29 | 275.89 | 236.84 |
| S2794745 | IGN | 298 | CTACTGCACGGGCCGGCTCAACCCGC | 26 | 0 | 250.76 | 91.76 | BCF | BCF | BCF | BCF | BCF | BCF | BCF | BCF | BCF | BCF |
| TAS1c-siR586 | tasiRNA | 299 | AGAATACGCTATGTTGGACTT | 21 | 1 | 245.09 | 64.43 | 46.84 | 27.18 | BCF | BCF | BCF | BCF | 100.20 | 64.68 | 104.01 | 117.96 |
| S1452355 | IGN | 300 | AGTAACGCGGGCTTGTGATCCAAGTGG | 27 | 0 | 232.53 | 199.14 | 90.83 | 52.21 | BCF | BCF | BCF | BCF | BCF | BCF | BCF | BCF |
| S161570 | IGN | 301 | AAGCGCGGAAAGAACAGTAGATGC | 24 | 0 | 229.29 | 138.62 | BCF | BCF | BCF | BCF | BCF | BCF | 1342.02 | 1631.07 | 1241.65 | 1047.13 |
| MIR391 | miRNA | 302 | ACGGTATCTCTCCTACGTAGC | 21 | 1 | 222.81 | 179.61 | BCF | BCF | BCF | BCF | BCF | BCF | 478.36 | 603.43 | 533.86 | 224.04 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| TAS1b-siR89 | tasiRNA | 303 | AATGGG AGATGT CCGGAA TGA | 21 | 1 | 221.59 | 101.52 | BCF | BCF | BCF | BCF | BCF | BCF | 131.85 | 141.96 | 161.30 | 125.22 |
| S373543 | IGN | 304 | AGAACA GAGACC GTTGGA AGAAAA | 24 | 0 | 193.23 | 60.52 | BCF | BCF | 30.96 | 26.76 | BCF | BCF | 341.90 | 312.83 | 345.67 | 379.08 |
| S1153818 | TE | 305 | AGAGAT AAGAAA CGATAG TCGGT | 23 | 0 | 185.94 | 91.76 | 124.23 | 45.69 | BCF | BCF | BCF | BCF | BCF | BCF | 10.28 | 11.35 |
| TAS2-siR461 | tasiRNA | 306 | ATAAGA CTGAAA CATATA TGT | 21 | 0 | 177.44 | 164.00 | BCF | BCF | BCF | BCF | BCF | BCF | 542.51 | 399.94 | 367.41 | 377.50 |
| S4195153 | TE | 307 | GTTCGA TCCCCG GCAACG GCGCCA | 24 | 0 | 176.62 | 60.52 | BCF | BCF | BCF | BCF | BCF | BCF | 252.39 | 223.32 | 436.61 | 308.23 |
| S311972 | TE | 308 | AACTAA ACCGGA ACAGTG TACCT | 23 | 0 | 167.31 | 60.52 | BCF | BCF | BCF | BCF | BCF | BCF | BCF | BCF | 14.84 | 13.19 |
| S1804551 | IGN | 309 | TGGTGG AACACT GGCTCG GCCC | 22 | 0 | 165.28 | 191.33 | BCF | BCF | 191.08 | 107.47 | BCF | BCF | 306.89 | 325.99 | 309.09 | 266.80 |

SUPPLEMENTARY TABLE 4-continued

The list of At-sRNAs that present in EVs.
The normalized reads of these small RNAs in the
*B. cinerea* protoplast and total sRNA libraries are compared.
Normalized read counts are given in reads per million (RPM)
in EVs sRNA libraries (EVs), Purified *B. Cinerea* sRNA
libraries (BC) and total sRNA libraries (TOTAL) respectively.
RPT, Repeat; BCF, below the cut off.

| sRNA ID | sRNA type | SEQ ID NO: | sRNA sequence 5'-3' | sRNA length | Number of target gene in BC | Normalized read counts of EVs B05_RPT1 | B05_RPT2 | MOCK_RPT1 | MOCK_RPT2 | Normalized read counts of BC B05_RPT1 | B05_RPT2 | Control_RPT1 | Control_RPT2 | Normalized read counts of TOTAL B05_RPT1 | B05_RPT2 | MOCK_RPT1 | MOCK_RPT2 |
|---|---|---|---|---|---|---|---|---|---|---|---|---|---|---|---|---|---|
| MIR162B | miRNA | 310 | TCGATAAACCTCTGCATCCAG | 21 | 1 | 161.64 | 228.42 | BCF | BCF | BCF | BCF | BCF | BCF | 160.15 | 143.26 | 184.22 | 159.79 |
| S35060 | TE | 311 | AAACATCTGATCGTTTGACTTGA | 23 | 0 | 153.13 | 117.14 | BCF | BCF | BCF | BCF | BCF | BCF | 421.35 | 407.72 | 361.98 | 263.36 |
| S2907277 | IGN | 312 | CTGGAATACTTGAACTACCATCT | 23 | 0 | 139.76 | 165.95 | 115.08 | 60.13 | BCF | BCF | BCF | BCF | BCF | BCF | 41.13 | 24.81 |
| S2724436 | TE | 313 | CGGGTTTGGCAGGACGTTACT | 21 | 1 | 139.36 | 283.09 | 124.35 | 128.92 | 19.02 | 16.74 | BCF | BCF | 24.32 | 28.73 | 30.41 | 23.75 |
| S366682 | IGN | 314 | AAGACAATCAGCACGGACATTGT | 23 | 0 | 132.47 | 181.57 | BCF | BCF | BCF | BCF | BCF | BCF | BCF | BCF | BCF | BCF |
| S3849690 | IGN | 315 | GGGGACATTAAGATGGTGGAACACT | 25 | 0 | 130.04 | 183.52 | 49.88 | 101.82 | BCF | BCF | BCF | BCF | BCF | BCF | BCF | BCF |
| S640613 | Anti_ORF | 316 | ATGAGAGATTCGGACTATCCAGCC | 24 | 0 | 130.04 | 54.67 | BCF | BCF | 11.50 | 12.81 | BCF | BCF | 151.14 | 152.15 | 211.84 | 197.26 |

SUPPLEMENTARY TABLE 4-continued

The list of At-sRNAs that present in EVs.
The normalized reads of these small RNAs in the *B. cinerea* protoplast and total sRNA libraries are compared. Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| sRNA ID | sRNA type | SEQ ID NO: | sRNA sequence 5'-3' | sRNA length | Number of target gene in BC | Normalized read counts of EVs | | | | Normalized read counts of BC | | | | Normalized read counts of TOTAL | | | |
|---|---|---|---|---|---|---|---|---|---|---|---|---|---|---|---|---|---|
| | | | | | | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S2806230 | IGN | 317 | CTAGTT CGTCGA TATGTT GAACT | 23 | 0 | 128.82 | 306.52 | 172.05 | 129.29 | BCF | BCF | BCF | BCF | BCF | BCF | BCF | BCF |
| S4403442 | Anti_ ORF | 318 | TACTGC ACGGGC CGGCTC AACCCG C | 25 | 0 | 124.77 | 44.90 | BCF | BCF | BCF | BCF | BCF | BCF | BCF | BCF | BCF | BCF |
| MIR398B | miRNA | 319 | GGGTTG ATATGA GAACAC ACG | 21 | 0 | 123.96 | 2493.13 | 52.61 | 252.37 | 64.58 | 28.50 | BCF | BCF | 1904.86 | 2112.37 | 2282.19 | 2880.78 |
| S1010856 | IGN | 320 | ACTTAG AATACG CTATGT TGGA | 22 | 0 | 121.13 | 54.67 | BCF | BCF | BCF | BCF | BCF | BCF | 43.39 | 43.18 | 51.71 | 52.12 |
| S5185716 | IGN | 321 | TGTTCG ATCCAC GCTCAC CGCACC | 24 | 0 | 120.32 | 115.19 | BCF | BCF | BCF | BCF | BCF | BCF | BCF | BCF | BCF | BCF |
| S284031 | IGN | 322 | AACGAA GGACCT ATGGGT GAAACG CTT | 27 | 0 | 118.70 | 62.47 | BCF | BCF | BCF | BCF | BCF | BCF | BCF | BCF | BCF | BCF |
| S99841 | IGN | 323 | AAACGT TTAGAA AGAGAT GGG | 21 | 0 | 118.29 | 74.19 | BCF | BCF | BCF | BCF | BCF | BCF | 306.47 | 213.68 | 401.94 | 411.94 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| sRNA ID | sRNA type | SEQ ID NO: | sRNA sequence 5'-3' | sRNA length | Number of target gene in BC | Normalized read counts of EVs B05_RPT1 | B05_RPT2 | MOCK_RPT1 | MOCK_RPT2 | Normalized read counts of BC B05_RPT1 | B05_RPT2 | Control_RPT1 | Control_RPT2 | Normalized read counts of TOTAL B05_RPT1 | B05_RPT2 | MOCK_RPT1 | MOCK_RPT2 |
|---|---|---|---|---|---|---|---|---|---|---|---|---|---|---|---|---|---|
| S3849698 | Anti_ORF | 324 | GGGGACATTAAGATGGTGGGACACT | 25 | 0 | 114.64 | 171.81 | 45.41 | 89.60 | BCF | BCF | BCF | BCF | BCF | BCF | BCF | BCF |
| S3155730 | Anti_ORF | 325 | GAATGACACATGTAAACATCTGA | 23 | 0 | 114.24 | 224.52 | BCF | BCF | BCF | BCF | BCF | BCF | 16.35 | 10.01 | 10.58 | 12.14 |
| S4099527 | TE | 326 | GTGCTTTGGCGAGAGTAGTACTAGGA | 26 | 0 | 113.02 | 113.24 | BCF | BCF | BCF | BCF | BCF | BCF | BCF | BCF | BCF | BCF |
| S3371251 | IGN | 327 | GAGGGACGACGATTTGTGACAC | 22 | 0 | 108.57 | 64.43 | BCF | BCF | BCF | BCF | BCF | BCF | 26.41 | 41.33 | 31.73 | 29.03 |
| IGN-siR1 | IGN | 328 | GTCGAACTCAGTAACGCGGGCT | 22 | 1 | 105.33 | 74.19 | 40.49 | 56.52 | 433.46 | 355.19 | BCF | BCF | 136.68 | 133.25 | 84.62 | 81.67 |
| S4493439 | IGN | 329 | TATCAAGATCCATCTTACTCT | 21 | 3 | 103.30 | 48.81 | BCF | BCF | BCF | BCF | BCF | BCF | 39.83 | 26.69 | 40.84 | 41.17 |
| S4195144 | IGN | 330 | GTTCGATCCACGCTCACCGCACC | 23 | 0 | 97.63 | 185.47 | BCF | BCF | BCF | BCF | BCF | BCF | BCF | BCF | BCF | BCF |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S639704 | Anti_ ORF | 331 | AATGTC TGTTGG TGCCAA GAGGG | 23 | 0 | 96.41 | 78.09 | BCF | BCF | BCF | BCF | BCF | BCF | BCF | BCF | BCF | BCF |
| S4195152 | TE | 332 | GTTCGA TCCCCG GCAACG GCGCC | 23 | 0 | 94.79 | 42.95 | BCF | BCF | BCF | BCF | BCF | BCF | BCF | BCF | BCF | BCF |
| S2646760 | TE | 333 | CGATCC CCGGCA ACGGCG CC | 20 | 1 | 93.17 | 285.04 | BCF | BCF | BCF | BCF | BCF | BCF | BCF | BCF | BCF | BCF |
| S284030 | IGN | 334 | AACGAA GGACCT ATGGGT GAAACG CT | 26 | 0 | 91.96 | 91.76 | BCF | BCF | BCF | BCF | BCF | BCF | BCF | BCF | BCF | BCF |
| S3484554 | IGN | 335 | GATGGG ACGTTG GGTCGA TCTCAT TGGGC | 29 | 0 | 90.34 | 82.00 | BCF | BCF | BCF | BCF | BCF | BCF | BCF | BCF | BCF | BCF |
| S1149208 | TE | 336 | AGAGAG GACAGA AGAAAC TACCC | 23 | 0 | 87.10 | 72.24 | 71.61 | 54.43 | BCF | BCF | BCF | BCF | 13.63 | 12.79 | BCF | BCF |
| S87743 | TE | 337 | AAACCG GAACAG TGTACC TAACT | 23 | 0 | 87.10 | 44.90 | BCF | BCF | BCF | BCF | BCF | BCF | 15.51 | 31.88 | 12.78 | 14.25 |

SUPPLEMENTARY TABLE 4-continued

The list of At-sRNAs that present in EVs. The normalized reads of these small RNAs in the *B. cinerea* protoplast and total sRNA libraries are compared. Normalized read counts are given in reads per million (RPM) in EVs sRNA libraries (EVs), Purified *B. Cinerea* sRNA libraries (BC) and total sRNA libraries (TOTAL) respectively. RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S2898159 | IGN | 338 | CTGCACGGGCCGGCTCAACCCGC | 23 | 0 | 86.29 | 91.76 | BCF | BCF | BCF | BCF | BCF | BCF | BCF | BCF | BCF | BCF |
| S3582663 | IGN | 339 | GCCCACGGGTCGGATCTGTTGTGGC | 25 | 0 | 84.26 | 201.09 | BCF | BCF | BCF | BCF | BCF | BCF | 24.32 | 17.61 | 12.78 | 13.85 |
| S3745708 | IGN | 340 | GGAGGGTCGAATCTTAGCGAC | 21 | 0 | 83.45 | 56.62 | BCF | BCF | BCF | BCF | BCF | BCF | 34.38 | 38.92 | 44.95 | 27.05 |
| S484509 | Anti_ORF | 341 | AAGTAACGTCCTGCCAAACCCGT | 23 | 0 | 83.05 | 146.42 | BCF | BCF | BCF | BCF | BCF | BCF | BCF | BCF | BCF | BCF |
| S4002660 | Anti_ORF | 342 | GTATCGTTCCAATTTTATCGGAT | 23 | 0 | 82.24 | 150.33 | BCF | BCF | BCF | BCF | BCF | BCF | 48.84 | 52.26 | 73.01 | 49.61 |
| S4433586 | IGN | 343 | TAGCAACTGTTCTTTAGACGACT | 23 | 0 | 80.62 | 101.52 | BCF | BCF | BCF | BCF | BCF | BCF | BCF | BCF | BCF | BCF |
| S447310 | ORF | 344 | AAGGAGGTGGAAATGATGATATT | 23 | 0 | 80.21 | 44.90 | BCF | BCF | BCF | BCF | BCF | BCF | BCF | BCF | BCF | BCF |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S3875595 | Anti_ ORF | 345 | GGGTTGATATGAGAACACAC | 20 | 0 | 80.21 | 2288.13 | 40.84 | 163.65 | BCF | BCF | BCF | BCF | 10.69 | 16.86 | BCF | BCF |
| S263266 | IGN | 346 | AACCATATCTTTTGTCGGAAGAT | 23 | 0 | 78.18 | 48.81 | BCF | BCF | BCF | BCF | BCF | BCF | 17.82 | 13.16 | 16.01 | 15.83 |
| S3649197 | IGN | 347 | GCTCGTTCCCAGCTGGACCACC | 22 | 0 | 76.56 | 165.95 | BCF | BCF | BCF | BCF | BCF | BCF | BCF | BCF | BCF | BCF |
| S3438612 | IGN | 348 | GATATGATCGATGTTCCTAAATTA | 24 | 0 | 74.54 | 58.57 | BCF | BCF | BCF | BCF | BCF | BCF | BCF | BCF | BCF | BCF |
| S1280309 | ORF | 349 | AGCGGTTGTTAGCGATTGGCACC | 23 | 0 | 74.13 | 117.14 | BCF | BCF | BCF | BCF | BCF | BCF | 136.26 | 160.12 | 119.73 | 146.86 |
| S3548872 | IGN | 350 | GCACGGTCTTGGCTCAACCCGC | 22 | 0 | 73.73 | 862.93 | 45.07 | 134.70 | BCF | BCF | BCF | BCF | BCF | BCF | BCF | BCF |
| S3829653 | IGN | 351 | GGGAGGGTGCTATGCTTAAGGTC | 23 | 1 | 72.51 | 89.81 | BCF | BCF | BCF | BCF | BCF | BCF | BCF | BCF | BCF | BCF |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S3894000 | ORF | 352 | GGTCAAGTCTGTTGAGATGCACC | 23 | 0 | 72.11 | 134.71 | BCF | BCF | BCF | BCF | BCF | BCF | BCF | BCF | BCF | BCF |
| S3648408 | IGN | 353 | GCTCGGGTCTCATGTCTTCT | 20 | 1 | 66.44 | 273.33 | BCF | BCF | BCF | BCF | BCF | BCF | BCF | BCF | BCF | BCF |
| S4099310 | TE | 354 | GTGCTTGGGCGATAGTAGTACTAGGA | 26 | 0 | 66.44 | 74.19 | BCF | BCF | BCF | BCF | BCF | BCF | BCF | BCF | BCF | BCF |
| S5147946 | IGN | 355 | TGTCCGTGCTGATTGTCTTGCT | 22 | 1 | 64.01 | 76.14 | BCF | BCF | BCF | BCF | BCF | BCF | BCF | BCF | BCF | BCF |
| S1499603 | TE | 356 | AGTGCATTCGGGTCATATGGTAC | 23 | 0 | 63.20 | 46.86 | BCF | BCF | BCF | BCF | BCF | BCF | BCF | BCF | BCF | BCF |
| S3821314 | ORF | 357 | GGGACGGGTTTGGCAGGACG | 20 | 0 | 61.58 | 138.62 | BCF | BCF | BCF | BCF | BCF | BCF | 21.17 | 28.17 | 14.98 | 17.68 |
| S1013425 | ORF | 358 | ACTTATTTACAATGGCTGCCACT | 23 | 0 | 61.58 | 50.76 | BCF | BCF | BCF | BCF | BCF | BCF | 16.14 | 16.31 | 17.78 | 15.04 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S3365114 | ORF | 359 | GAGGCA AGTTCT TTGACC CGTTAG GACT | 28 | 0 | 59.55 | 56.62 | 150.89 | 64.13 | BCF | BCF | BCF | BCF | BCF | BCF | BCF | BCF |
| S3908870 | Anti_ ORF | 360 | GGTGCC AAGAGG GAAAAG GGC | 21 | 1 | 59.55 | 269.42 | BCF | BCF | BCF | BCF | BCF | BCF | 50.31 | 56.53 | 55.09 | 46.18 |
| S3347795 | ORF | 361 | GAGGAC TACGAT GTTGGT GAT | 21 | 0 | 58.74 | 370.94 | BCF | BCF | BCF | BCF | BCF | BCF | BCF | BCF | BCF | BCF |
| S274029 | ORF | 362 | AACCGG ATCTTA AAGGCG TAAGA | 23 | 0 | 58.74 | 142.52 | BCF | BCF | BCF | BCF | BCF | BCF | BCF | BCF | BCF | BCF |
| S1894035 | TE | 363 | ATGCAC GTGAAA AAACGC GGACT | 23 | 0 | 58.33 | 41.00 | BCF | BCF | BCF | BCF | BCF | BCF | BCF | BCF | BCF | BCF |
| S4964105 | IGN | 364 | TGCACG GGCCGG CTCAAC CCGC | 22 | 0 | 58.33 | 244.04 | 43.13 | 59.76 | BCF | BCF | BCF | BCF | BCF | BCF | BCF | BCF |
| S276315 | TE | 365 | AACCGT GACTGA TTTGTT TCATA | 23 | 0 | 57.93 | 68.33 | BCF | BCF | BCF | BCF | BCF | BCF | 16.14 | 11.12 | BCF | BCF |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S1896074 | IGN | 366 | TTCGATCCCCGGCAACGGCGCCA | 23 | 0 | 57.12 | 50.76 | BCF | BCF | BCF | BCF | BCF | BCF | 304.17 | 193.11 | 460.26 | 293.58 |
| MIR848A | miRNA | 367 | TGACATGGGACTGCCTAAGCT | 21 | 0 | 54.28 | 460.75 | BCF | BCF | BCF | BCF | BCF | BCF | BCF | BCF | BCF | BCF |
| S3849740 | IGN | 368 | GGGGACATTTAGATGGTGGAACACT | 25 | 0 | 53.47 | 105.43 | BCF | BCF | BCF | BCF | BCF | BCF | BCF | BCF | BCF | BCF |
| S4261718 | Anti_ ORF | 369 | GTTTGGCAGGACGTTACTTAAT | 22 | 0 | 52.66 | 76.14 | BCF | BCF | BCF | BCF | BCF | BCF | BCF | BCF | BCF | BCF |
| S4964134 | ORF | 370 | TGCACGGGCTTGGCTCATCCCATC | 24 | 0 | 52.26 | 83.95 | BCF | BCF | BCF | BCF | BCF | BCF | BCF | BCF | BCF | BCF |
| S4261719 | Anti_ ORF | 371 | GTTTGGCAGGACGTTACTTAATA | 23 | 0 | 51.85 | 48.81 | BCF | BCF | BCF | BCF | BCF | BCF | BCF | BCF | BCF | BCF |
| S2898158 | IGN | 372 | CTGCACGGGCCGGCTCAACCCG | 22 | 0 | 51.85 | 142.52 | BCF | BCF | BCF | BCF | BCF | BCF | BCF | BCF | BCF | BCF |

SUPPLEMENTARY TABLE 4-continued

The list of At-sRNAs that present in EVs.
The normalized reads of these small RNAs in the
*B. cinerea* protoplast and total sRNA libraries are compared.
Normalized read counts are given in reads per million (RPM)
in EVs sRNA libraries (EVs), Purified *B. Cinerea* sRNA
libraries (BC) and total sRNA libraries (TOTAL) respectively.
RPT, Repeat; BCF, below the cut off.

| | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S242686 | IGN | 373 | AACAGC ATCGTC CATCAT TGAAG | 23 | 0 | 51.85 | 70.28 | BCF | BCF | BCF | BCF | BCF | BCF | BCF | BCF | BCF | BCF |
| S3369834 | Anti_ ORF | 374 | GAGGGA AAAGGG CTATTA AGCT | 22 | 0 | 50.64 | 76.14 | BCF | BCF | BCF | BCF | BCF | BCF | BCF | BCF | BCF | BCF |
| S3948143 | ORF | 375 | GTAAAC ATCTGA TCGTTT GACT | 22 | 0 | 50.64 | 156.19 | 57.66 | 76.94 | BCF | BCF | BCF | BCF | 24.74 | 24.46 | 14.98 | 14.12 |
| S3144730 | IGN | 376 | GAATAC TTGAAC TACCAT CT | 20 | 0 | 49.83 | 450.99 | 45.19 | 263.92 | BCF | BCF | BCF | BCF | BCF | BCF | BCF | BCF |
| MIR827A | miRNA | 377 | TTAGAT GACCAT CAACAA ACT | 21 | 0 | 49.83 | 89.81 | BCF | BCF | BCF | BCF | BCF | BCF | 62.47 | 105.45 | 49.07 | 35.63 |
| S3940632 | ORF | 378 | GGTTTC GATCCC GACAAT GACCT | 23 | 0 | 49.02 | 66.38 | BCF | BCF | BCF | BCF | BCF | BCF | BCF | BCF | BCF | BCF |
| S3398825 | ORF | 379 | GAGTGA CGCTTG GGACGA AACT | 22 | 0 | 49.02 | 113.24 | 59.71 | 48.43 | BCF | BCF | BCF | BCF | BCF | BCF | 10.58 | 10.69 |

SUPPLEMENTARY TABLE 4-continued

The list of At-sRNAs that present in EVs.
The normalized reads of these small RNAs in the
*B. cinerea* protoplast and total sRNA libraries are compared.
Normalized read counts are given in reads per million (RPM)
in EVs sRNA libraries (EVs), Purified *B. Cinerea* sRNA
libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S1382018 | IGN | 380 | AGGCTG TGAACG GTAACC AAAAC | 23 | 0 | 47.80 | 64.43 | BCF | BCF | BCF | BCF | BCF | BCF | BCF | BCF | BCF | BCF |
| S2312814 | IGN | 381 | CACGGT CTAAAA GTTATG GAGT | 22 | 0 | 46.99 | 52.71 | BCF | BCF | BCF | BCF | BCF | BCF | BCF | BCF | BCF | BCF |
| S4766414 | IGN | 382 | TCTAGT TCGTCG ATATGT TGAAC | 23 | 0 | 46.99 | 64.43 | BCF | BCF | BCF | BCF | BCF | BCF | BCF | BCF | BCF | BCF |
| S346019 | TE | 383 | ACTCAT AAGATC GTGACA CGT | 21 | 1 | 45.37 | 48.81 | BCF | BCF | BCF | BCF | BCF | BCF | 306.89 | 289.85 | 295.87 | 292.79 |
| S1484048 | IGN | 384 | GTTTTG GACAGG TATCGA CA | 20 | 1 | 45.37 | 439.27 | BCF | BCF | BCF | BCF | BCF | BCF | 421.35 | 568.77 | 294.69 | 258.48 |
| S3110547 | IGN | 385 | GAAGAG GATAGT TGTTAC GCACT | 23 | 0 | 44.56 | 46.86 | BCF | BCF | BCF | BCF | BCF | BCF | BCF | BCF | BCF | BCF |
| S1726881 | IGN | 386 | ATCACC GTTGAG AGAAGT ACTGG | 23 | 1 | 44.16 | 42.95 | BCF | BCF | BCF | BCF | BCF | BCF | BCF | BCF | 11.61 | 13.59 |

SUPPLEMENTARY TABLE 4-continued

The list of At-sRNAs that present in EVs.
The normalized reads of these small RNAs in the *B. cinerea* protoplast and total sRNA libraries are compared.
Normalized read counts are given in reads per million (RPM) in EVs sRNA libraries (EVs), Purified *B. Cinerea* sRNA libraries (BC) and total sRNA libraries (TOTAL) respectively.
RPT, Repeat; BCF, below the cut off.

| | | | | | Number of target | Normalized read counts of EVs | | | | Normalized read counts of BC | | | | Normalized read counts of TOTAL | | | |
|---|---|---|---|---|---|---|---|---|---|---|---|---|---|---|---|---|---|
| sRNA ID | sRNA type | SEQ ID NO: | sRNA sequence 5'-3' | sRNA length | gene in BC | B05_ RPT1 | B05_ RPT2 | MOCK_ RPT1 | MOCK_ RPT2 | B05_ RPT1 | B05_ RPT2 | Control_ RPT1 | Control_ RPT2 | B05_ RPT1 | B05_ RPT2 | MOCK_ RPT1 | MOCK_ RPT2 |
| S1346557 | TE | 387 | AGGAGG TTCTGG CCGAAG CCCGT | 23 | 0 | 43.75 | 58.57 | BCF | BCF | BCF | BCF | BCF | BCF | BCF | BCF | 24.09 | 17.29 |
| S2826446 | IGN | 388 | CTCACG GTCTAA AAGTTA TGGAG | 23 | 0 | 43.35 | 50.76 | BCF | BCF | BCF | BCF | BCF | BCF | BCF | BCF | BCF | BCF |
| S4491090 | IGN | 389 | TATATG TTTCAG TCTTAT CCC | 21 | 0 | 43.35 | 50.76 | BCF | BCF | BCF | BCF | BCF | BCF | 108.38 | 103.60 | 112.09 | 135.38 |
| S4046464 | TE | 390 | GTCTAA TGATTG TGAAGT GCCT | 22 | 0 | 43.35 | 64.43 | BCF | BCF | BCF | BCF | BCF | BCF | 55.34 | 89.33 | 40.40 | 30.88 |
| S4884864 | ORF | 391 | TGACGA GAGAAC TTATTG GCCTT | 23 | 0 | 43.35 | 52.71 | BCF | BCF | BCF | BCF | BCF | BCF | BCF | BCF | 10.58 | 12.67 |
| S2542718 | TE | 392 | CCGGCC AACTGT ACATAT ACAT | 22 | 0 | 42.13 | 50.76 | BCF | BCF | BCF | BCF | BCF | BCF | BCF | BCF | 12.05 | 12.27 |
| S3448137 | IGN | 393 | GATCCA TGTAAG TCTTAG GCTGT | 23 | 0 | 41.73 | 44.90 | BCF | BCF | BCF | BCF | BCF | BCF | BCF | BCF | 12.34 | 15.31 |

SUPPLEMENTARY TABLE 4-continued

The list of At-sRNAs that present in EVs. The normalized reads of these small RNAs in the *B. cinerea* protoplast and total sRNA libraries are compared. Normalized read counts are given in reads per million (RPM) in EVs sRNA libraries (EVs), Purified *B. Cinerea* sRNA libraries (BC) and total sRNA libraries (TOTAL) respectively. RPT, Repeat; BCF, below the cut off.

| sRNA ID | sRNA type | SEQ ID NO: | sRNA sequence 5'-3' | sRNA length | Number of target gene in BC | Normalized read counts of EVs B05_RPT1 | B05_RPT2 | MOCK_RPT1 | MOCK_RPT2 | Normalized read counts of BC B05_RPT1 | B05_RPT2 | Control_RPT1 | Control_RPT2 | Normalized read counts of TOTAL B05_RPT1 | B05_RPT2 | MOCK_RPT1 | MOCK_RPT2 |
|---|---|---|---|---|---|---|---|---|---|---|---|---|---|---|---|---|---|
| S3696733 | IGN | 394 | GGAAGGGTGCTTAGCCTAAGGTC | 23 | 0 | 41.32 | 89.81 | BCF | BCF | BCF | BCF | BCF | BCF | BCF | BCF | BCF | BCF |
| S4004827 | TE | 395 | GTATGATCGCATCCGTTAGTATA | 23 | 0 | 40.92 | 54.67 | BCF | BCF | BCF | BCF | BCF | BCF | BCF | BCF | BCF | BCF |
| S281438 | TE | 396 | AACCTTGAAGCAAACTGGACAGG | 23 | 0 | 40.51 | 42.95 | BCF | BCF | BCF | BCF | BCF | BCF | BCF | BCF | BCF | BCF |
| TAS2-siR453 | tasiRNA | 397 | CGTAAAAAAAGTTGTAACTCT | 21 | 1 | 40.51 | 113.24 | BCF | BCF | 13.27 | 23.01 | BCF | BCF | 48.21 | 44.29 | 67.28 | 46.71 |
| S283245 | TE | 398 | AACGAACCGACCGTCAGACATGG | 23 | 0 | 40.11 | 41.00 | BCF | BCF | BCF | BCF | BCF | BCF | BCF | BCF | BCF | BCF |

Supplementary Table 5 The list of *B.Cinerea* genes targeted by *Arabidopsis* endogenous sRNAs that are present in the sRNA libraries of purified *B.Cinerea* protoplasts

<table>
<tr><th>Target gene ID</th><th>Putative function of target gene</th><th>GO_biological process</th><th>Targeted by sRNA</th><th>sRNA type</th><th>Aligned score</th><th>Target gene alignment sRNA 3'-5'</th></tr>
<tr><td>BC1G_10728</td><td>Conserved hypothetical VPS51 protein</td><td>vesicle transport</td><td>TAS1c-siR483</td><td>tasiRNA</td><td>3.5</td><td>:||x|x|x||||||||||||x</td></tr>
<tr><td>BC1G_10508</td><td>Predicted dynactin protein</td><td>vesicle transport</td><td>TAS1c-siR483</td><td>tasiRNA</td><td>4.25</td><td>||||||x:||||||||:|||xx</td></tr>
<tr><td>BC1G_08464</td><td>Polyphosphoinositide phosphatase</td><td>vesicle transport</td><td>TAS2-siR453</td><td>tasiRNA</td><td>3.5</td><td>:||||||x||||||x|||||</td></tr>
<tr><td>BC1G_15133</td><td>Hypothetical protein similar to GTPase activating protein</td><td>vesicle transport</td><td>MIR396A</td><td>miRNA</td><td>4</td><td>|:|||:||x||||||||x||</td></tr>
<tr><td>BC1G_14507</td><td>70-kDa adenylyl cyclase-associated protein</td><td>vesicle transport</td><td>S1353733</td><td>ORF</td><td>3</td><td>x||x||x||||||||||||||</td></tr>
<tr><td>BC1G_09781</td><td>Hypothetical protein similar to Vps52/Sac2 family protein</td><td>vesicle transport</td><td>MIR159A</td><td>miRNA</td><td>4.5</td><td>||||x||||:|||||x||||:</td></tr>
<tr><td>BC1G_09414</td><td>Hypothetical protein similar to actin cytoskeleton-regulatory complex protein PAN1</td><td>vesicle transport</td><td>S1353733</td><td>ORF</td><td>3</td><td>x||x||x||||||||||||||</td></tr>
<tr><td>BC1G_04258</td><td>GTPase-activating protein GYPS</td><td>vesicle transport</td><td>S1353733</td><td>ORF</td><td>4</td><td>x|||||x||||||||||x||</td></tr>
<tr><td>BC1G_03372</td><td>Hypothetical WH2 motif protein</td><td>vesicle transport</td><td>S1353733</td><td>ORF</td><td>3</td><td>x||x|||||||||||||||:|</td></tr>
<tr><td>BC1G_02544</td><td>Hypothetical protein similar to B230380D07Rik protein</td><td>unknown</td><td>MIR166A</td><td>miRNA</td><td>4.5</td><td>|||x||x||||||||||x|:</td></tr>
<tr><td>BC1G_14667</td><td>Predicted protein</td><td>unknown</td><td>MIR396B</td><td>miRNA</td><td>4.5</td><td>::|x|||x||||||||||||x</td></tr>
<tr><td>BC1G_14204</td><td>Predicted protein</td><td>unknown</td><td>S1353733</td><td>ORF</td><td>3.5</td><td>|:|x||x||||||||||:|||</td></tr>
<tr><td>BC1G_11528</td><td>Predicted protein</td><td>unknown</td><td>MIR159B</td><td>miRNA</td><td>3.5</td><td>||x||||::|||||||:||||</td></tr>
<tr><td>BC1G_11528</td><td>Predicted protein</td><td>unknown</td><td>MIR159A</td><td>miRNA</td><td>4.5</td><td>x|x||||::|||||||:||||</td></tr>
<tr><td>BC1G_10316</td><td>Predicted protein</td><td>unknown</td><td>S1353733</td><td>ORF</td><td>4.5</td><td>x|:||||:||||x|||||||:</td></tr>
<tr><td>BC1G_05030</td><td>Predicted protein</td><td>unknown</td><td>S1353733</td><td>ORF</td><td>4.25</td><td>x:||||||||||||x||||||</td></tr>
<tr><td>BC1G_04218</td><td>Predicted protein</td><td>unknown</td><td>MIR396A</td><td>miRNA</td><td>4.25</td><td>||||x:||||||||x|||||</td></tr>
<tr><td>BC1G_00860</td><td>Domain of unknown function (DUF4211) protein</td><td>unknown</td><td>MIR158A</td><td>miRNA</td><td>4.5</td><td>|||x|||x|||||||||x|:</td></tr>
<tr><td>BC1G_00624</td><td>Predicted protein</td><td>unknown</td><td>S1353733</td><td>ORF</td><td>4</td><td>x||x||||||||||||||:|x</td></tr>
<tr><td>BC1G_05327</td><td>Pyruvate carboxylase</td><td>metabolic process</td><td>IGN-siR1</td><td>IGN</td><td>4.5</td><td>x|x|x|||||||||||||x|||:</td></tr>
<tr><td>BC1G_15490</td><td>Bifunctional P-450/NADPH-P450 reductase</td><td>metabolic process</td><td>MIR396A*</td><td>miRNA</td><td>4.5</td><td>|x|:||:|:||||||||x|||</td></tr>
<tr><td>BC1G_15423</td><td>Predicted FAD binding protein</td><td>metabolic process</td><td>TAS1c-siR602</td><td>tasiRNA</td><td>3.75</td><td>|||x:||||||||||||:||:</td></tr>
<tr><td>BC1G_14979</td><td>Hypothetical protein similar to mitochondrial ATP synthase B</td><td>metabolic process</td><td>S1353733</td><td>ORF</td><td>3</td><td>x||x||x|||||||||||||</td></tr>
<tr><td>BC1G_14979</td><td>Hypothetical protein similar to mitochondrial ATP synthase B</td><td>metabolic process</td><td>MIR396B</td><td>miRNA</td><td>4</td><td>|||||||||:|x|||||||:|</td></tr>
<tr><td>BC1G_12936</td><td>2-deoxy-D-gluconate 3-dehydrogenase</td><td>metabolic process</td><td>MIR396A*</td><td>miRNA</td><td>4</td><td>|||x|||x||||||||x||||</td></tr>
<tr><td>BC1G_09454</td><td>Retinol dehydrogenase 12</td><td>metabolic process</td><td>MIR157A</td><td>miRNA</td><td>2.5</td><td>x|||||||x|||||||||||:</td></tr>
<tr><td>BC1G_15945</td><td>Hypothetical protein similar to GAL4-like transcription factor</td><td>regulation of transcription</td><td>MIR396A</td><td>miRNA</td><td>4</td><td>|:|x|:||||||||||||x||</td></tr>
<tr><td>BC1G_14887</td><td>Histone-lysine N-methyltransferase</td><td>regulation of transcription</td><td>MIR396A</td><td>miRNA</td><td>3</td><td>:|x||:|||||:|||||||||</td></tr>
<tr><td>BC1G_14887</td><td>Histone-lysine N-methyltransferase</td><td>regulation of transcription</td><td>MIR396B</td><td>miRNA</td><td>3.5</td><td>x|x||:|||||:|||||||||</td></tr>
<tr><td>BC1G_07589</td><td>Histone-lysine N-methyltransferase</td><td>regulation of transcription</td><td>MIR396A</td><td>miRNA</td><td>4.5</td><td>x||||||:|||x|||||||:|</td></tr>
<tr><td>BC1G_07589</td><td>Histone-lysine N-methyltransferase</td><td>regulation of transcription</td><td>MIR396B</td><td>miRNA</td><td>4</td><td>:||||||:|||x||||||:|</td></tr>
<tr><td>BC1G_04424</td><td>Hypothetical protein similar to ITC1</td><td>regulation of transcription</td><td>S1353733</td><td>ORF</td><td>3</td><td>x||x|||x||||||||||||</td></tr>
<tr><td>BC1G_14463</td><td>Hypothetical protein similar to Uso1p</td><td>mitotic cell cycle</td><td>S1353733</td><td>ORF</td><td>4</td><td>x||x||x||||:|||||||||</td></tr>
<tr><td>BC1G_10235</td><td>Hypothetical protein similar to Smc4p</td><td>mitotic cell cycle</td><td>S1353733</td><td>ORF</td><td>4</td><td>|||x||x|||||||||||x||</td></tr>
<tr><td>BC1G_03832</td><td>R3H domain of encore-like and DIP1-like protein</td><td>mitotic cell cycle</td><td>MIR159A</td><td>miRNA</td><td>4</td><td>||||xx|x||||||||||||</td></tr>
<tr><td>BC1G_12627</td><td>Hypothetical protein similar to cell wall synthesis protein</td><td>cell wall biogenesis</td><td>S1353733</td><td>ORF</td><td>4.25</td><td>||:||:x|:|||||||||:||</td></tr>
<tr><td>BC1G_09907</td><td>Predicted membrane protein involved in the export of O-antigen and teichoic acid [Cell wall/membrane/envelope biogenesis</td><td>cell wall biogenesis</td><td>MIR168A</td><td>miRNA</td><td>4.5</td><td>x||x|x||:|||||||||||x</td></tr>
<tr><td>BC1G_09656</td><td>Hypothetical protein similar to HKR1</td><td>cell wall biogenesis</td><td>S1353733</td><td>ORF</td><td>4.5</td><td>x||x|||:||||||||||:|x</td></tr>
</table>

-continued

<table>
<tr><th colspan="7">Supplementary Table 5 The list of B.Cinerea genes targeted by Arabidopsis endogenous sRNAs that are present in the sRNA libraries of purified B.Cinerea protoplasts</th></tr>
<tr><th>Target gene ID</th><th>Putative function of target gene</th><th>GO_biological process</th><th>Targeted by sRNA</th><th>sRNA type</th><th>Aligned score</th><th>Target gene alignment sRNA 3'-5'</th></tr>
<tr><td>BC1G_07658</td><td>Hypothetical protein similar to endoglucanase IV</td><td>RNA catabolic process</td><td>S1353733</td><td>ORF</td><td>4.5</td><td>|::|:||||||:||||||:|:</td></tr>
<tr><td>BC1G_02429</td><td>Ribonuclease HI large subunit</td><td>RNA catabolic process</td><td>S1353733</td><td>ORF</td><td>4</td><td>x|||:|||:||:|||||:|||</td></tr>
<tr><td>BC1T_09103</td><td>Botrytis cinerea (B05.10) hypothetical protein similar to cell division cycle mutant (1320 nt)</td><td>cell cycle</td><td>S1092315</td><td>TE</td><td>4.5</td><td>||x||||||:||:|||||||x|</td></tr>
<tr><td>BC1G_02638</td><td>Cell cycle checkpoint protein RAD17</td><td>cell cycle</td><td>S1353733</td><td>ORF</td><td>4.5</td><td>x||x||x||||||:|||||:</td></tr>
<tr><td>BC1G_02869</td><td>Guanine nucleotide-binding protein G(I)/G(S)/G(T) subunit beta-1</td><td>cell proliferation</td><td>S1353733</td><td>ORF</td><td>4</td><td>||||:|x||x|||||||||:</td></tr>
<tr><td>BC1G_09169</td><td>Hypothetical protein similar to calpain 2 catalytic subunit</td><td>cell proliferation</td><td>S1353733</td><td>ORF</td><td>4</td><td>x||x||x||||||||||:||</td></tr>
<tr><td>BC1T_07401</td><td>Botrytis cinerea (B05.10) glutaminyl-tRNA synthetase</td><td>tRNA processing</td><td>S2724436</td><td>TE</td><td>4.5</td><td>||x|:|||||||:||||||x|</td></tr>
<tr><td>BC1G_07037</td><td>Hypothetical protein similar to Msf1p</td><td>tRNA processing</td><td>S519888</td><td>ORF</td><td>4.5</td><td>:|x||||||||:|||||x||</td></tr>
<tr><td>BC1G_10614</td><td>Hypothetical protein similar to GAMM1 protein</td><td>cell surface receptor signaling pathway</td><td>MIR396A*</td><td>miRNA</td><td>4.5</td><td>:||x|x|x|||||||||||x</td></tr>
<tr><td>BC1G_05475</td><td>Hypothetical protein similar to microcystin synthetase</td><td>biosynthetic process</td><td>MIR159B</td><td>miRNA</td><td>4.5</td><td>||x||||:||||||x||||:|</td></tr>
<tr><td>BC1G_09015</td><td>Dual specificity protein kinase POM1</td><td>signal transduction</td><td>MIR158A</td><td>miRNA</td><td>3.5</td><td>|x||||x|:|||||||||:</td></tr>
</table>

SUPPLEMENTARY TABLE 6

Primers used in this study

| Primer | SEQ ID NO: | sequence(5'-3') | description |
|---|---|---|---|
| TAS1c-siR483-F | 399 | GCGGCGGTCCAATGTCTTTTC | sRNA Rev. transcription PCR |
| TAS1c-siR483-RT | 400 | GTCGTATCCAGTGCAGGGTCCGAGGTATTCGCACTGGATACGACACGAAC | |
| TAS1c-siR585-F | 401 | GCGGCGGAGAATACGCTATGTTGG | |
| TAS1c-siR585-RT | 402 | GTCGTATCCAGTGCAGGGTCCGAGGTATTCGCACTGGATACGACTCTAAG | |
| TAS2-siR453-F | 403 | GCGGCGGCGTAAAAAAAGTTG | |
| TAS2-siR453-RT | 404 | GTCGTATCCAGTGCAGGGTCCGAGGTATTCGCACTGGATACGACAGAGTT | |
| TAS2-siR710-F | 405 | GCGGCGGACACGATGTTCAAT | |
| TAS2-siR710-RT | 406 | GTCGTATCCAGTGCAGGGTCCGAGGTATTCGCACTGGATACGACTAAATC | |
| IGN-siR1-F | 407 | GCGGCGGGTCGAACTCAGTAA | |
| IGN-siR1-F-RT | 408 | GTCGTATCCAGTGCAGGGTCCGAGGTATTCGCACTGGATACGACGCCCGC | |
| miRNA166-F | 409 | GGCGGTCGGACCAGGCTTC | |
| miRNA166-RT | 410 | GTCGTATCCAGTGCAGGGTCCGAGGTATTCGCACTGGATACGACGGGGAA | |
| miRNA822-F | 411 | CTCGTATTGCGGGAAGCATTT | |
| miRNA822-RT | 412 | GTCGTATCCAGTGCAGGGTCCGAGGTATTCGCACTGGATACGACCATGTG | |
| Bc-DCL1-F | 413 | ACAATCCTATCTTTCGGAAGC | |
| Bc-DCL1-RT | 414 | AGACTCTTCTTCTTGAAGACAG | |
| Bc-DCL2-F | 415 | GATTGTGCAAAGTCTCAACA | |
| Bc-DCL2-RT | 416 | ATTGGGTTTGACTATATGTCTTA | |
| sRNA PCR universal R | 417 | GTGCAGGGTCCGAGGT | |
| lib-RT reverse primer | 418 | GCCTTGGCACCCGAGAATTCCA | |
| Bc-ITS F | 419 | TCGAATCTTTGAACGCACATTGCGC | Biomass |
| Bc-ITS R | 420 | TGGCAGAAGCACACCGAGAACCTG | |

SUPPLEMENTARY TABLE 6-continued

Primers used in this study

| Primer | SEQ ID NO: | sequence(5'-3') | description |
|---|---|---|---|
| At-iASK1 | 421 | CTTATCGGATTTCTCTATGTTTGGC | |
| At-iASK2 | 422 | GAGCTCCTGTTTATTTAACTTGTACATACC | |
| Bc-actin F | 423 | TGCTCCAGAAGCTTTGTTCCAA | qRT-PCR Gene Expression |
| Bc-actin R | 424 | TCGGAGATACCTGGGTACATAG | |
| At-actin F | 425 | CAGTGGTCGTACAACCGGTATT | |
| At-actin R | 426 | GTCTCTTACAATTTCCCGCTCT | |
| UBQ5 F | 427 | GGAAGAAGAAGACTTACACC | |
| UBQ5 R | 428 | AGTCCACACTTACCACAGTA | |
| Bc-Vps51-F | 429 | TTGGACTCTCACTTGTCTCATCA | |
| Bc-Vps51-R | 430 | ATCAGCCATAGCAGTCGATAAAC | |
| Bc-DCTN1-F | 431 | GACGTTGTCATGGAGGGACT | |
| Bc-DCTN1-R | 432 | ACTTTCCTTTCCTGGGGCAG | |
| Bc-SAC1-F | 433 | GCGGCATTGTAAATGACTACTTC | |
| Bc-SAC1-R | 434 | CATCCTCCAATAAATTCTTCACG | |
| Bc-PC-F | 435 | GATTTGGCTCAGATCAAGAAAGA | |
| Bc-PC-R | 436 | ACCTTACCCTTCTCCAACTCAAC | |
| TET8-F | 437 | CACAACGGGAACACACACT | |
| TET8-R | 438 | TCCTGAAAGCACAGCAACCA | |
| TET9-F | 439 | GGTTGCTGCAAGCCCTCTAA | |
| TET9-R | 440 | CTTTTCCATGCGGCCTTGAG | |
| Bc-SAC1-5'F-KpnI | 441 | ATCTGAGGTACCGGTAGTGTTGATCCTGTGAGCTAAA | *B. cinerea* target gene knock out constructs |
| Bc-SAC1-5'R-XhoI | 442 | ATCTGACTCGAGTATCAGATTTTCCTTCAGTGACTCC | |
| Bc-SAC1-3'F-PstI | 443 | ATCTGACTGCAGACGATCAAATCTAGTCCTTTTGAGG | |
| Bc-SAC1-3'R-XbaI | 444 | ATCTGATCTAGAGGAATTTGTATGAGAGCGAGTTTTC | |
| Bc-DCTN1-5'F-KpnI | 445 | ATCTGAGGTACCGATCTTACAGAACAAGGAATGAGGA | |
| Bc-DCTN1-5'R-XhoI | 446 | ATCTGACTCGAGCAGGTGTGTATGGCGGCATGTT | |
| Bc-DCTN1-3'F-EcoRI | 447 | ATCTGAGAATTCTCTCCAAGACAATAAGAGCACAGTT | |
| Bc-DCTN1-3'R-XbaI | 448 | ATCCCATCTAGAATAAAATGCTGCATTTGGATCA | |
| Bc-VPS51-5'F-KpnI | 449 | ATCTGAGGTACCACCAAACTCTGTAATTCCCTCTCTT | |
| Bc-VPS51-5'R-SalI | 450 | ATCTGAGTCGACGTCTATAACTCCCTCCGACCAGT | |
| Bc-VPS51-3'F-PstI | 451 | ATCTGACTGCAGCGAATTCTACGAGATATCAGAGCAG | |
| Bc-VPS51-3'R-XbaI | 452 | ATCTGATCTAGAACTAAACAGCAGCAGAAAAGATGAG | |
| TET8 F | 453 | CACCATGGCTCGTTGTAGCAACAATC | Subcellular Localization |
| TET8 R | 454 | AGGCTTATATCCGTAGGTAC | |
| TET9 F | 455 | CACCATGGTACGTTTTAGTAACAGTC | |
| TET9 R | 456 | AGAATTGTTGAAACCATTGGAAC | |
| TAS1c-siR483 I miR-s | 457 | gaTCCAATGTCTTTTCTAGTTCGTtctctcttttgtattcc | sRNA over expression |
| TAS1c-siR483 II miR-a | 458 | gaACGAACTAGAAAAGACATTGGAtcaaagagaatcaatga | |
| TAS1c-siR483 III miR*s | 459 | gaACAAACTAGAAAACACATTGGAtcacaggtcgtgatatg | |
| TAS1c-siR483 IV miR*a | 460 | gaTCCAATGTGTTTTCTAGTTTGTtctacatatatattcct | |
| TAS2-siR453 I miR-s | 461 | gaCGTAAAAAAAGTTGTAACTCTTctctcttttgtattcc | |
| TAS2-siR453 II miR-a | 462 | gaAGAGTTACAACTTTTTTTACGtcaaagagaatcaatga | |
| TAS2-siR453 III miR*s | 463 | gaAGCGTTACAACTTATTTTACGtcacaggtcgtgatatg | |
| TAS2-siR453 IV miR*a | 464 | gaCGTAAAATAAGTTGTAACGCTTctacatatatattcct | |
| miRNA-TET9 I miR-s | 465 | gaTCTGTTACTAAAACGTACCACtctctcttttgtattcc | |
| miRNA-TET9 II miR-a | 466 | gaGTGGTACGTTTTAGTAACAGAtcaaagagaatcaatga | |
| miRNA-TET9 III miR*s | 467 | gaGTAGTACGTTTTACTAACAGTtcacaggtcgtgatatg | |
| miRNA-TET9 IV miR*a | 468 | gaACTGTTAGTAAAACGTACTACtctacatatatattcct | |

Example 2—Naked RNA Uptake and Vesicle-Mediated RNA Uptake

Figure 15:
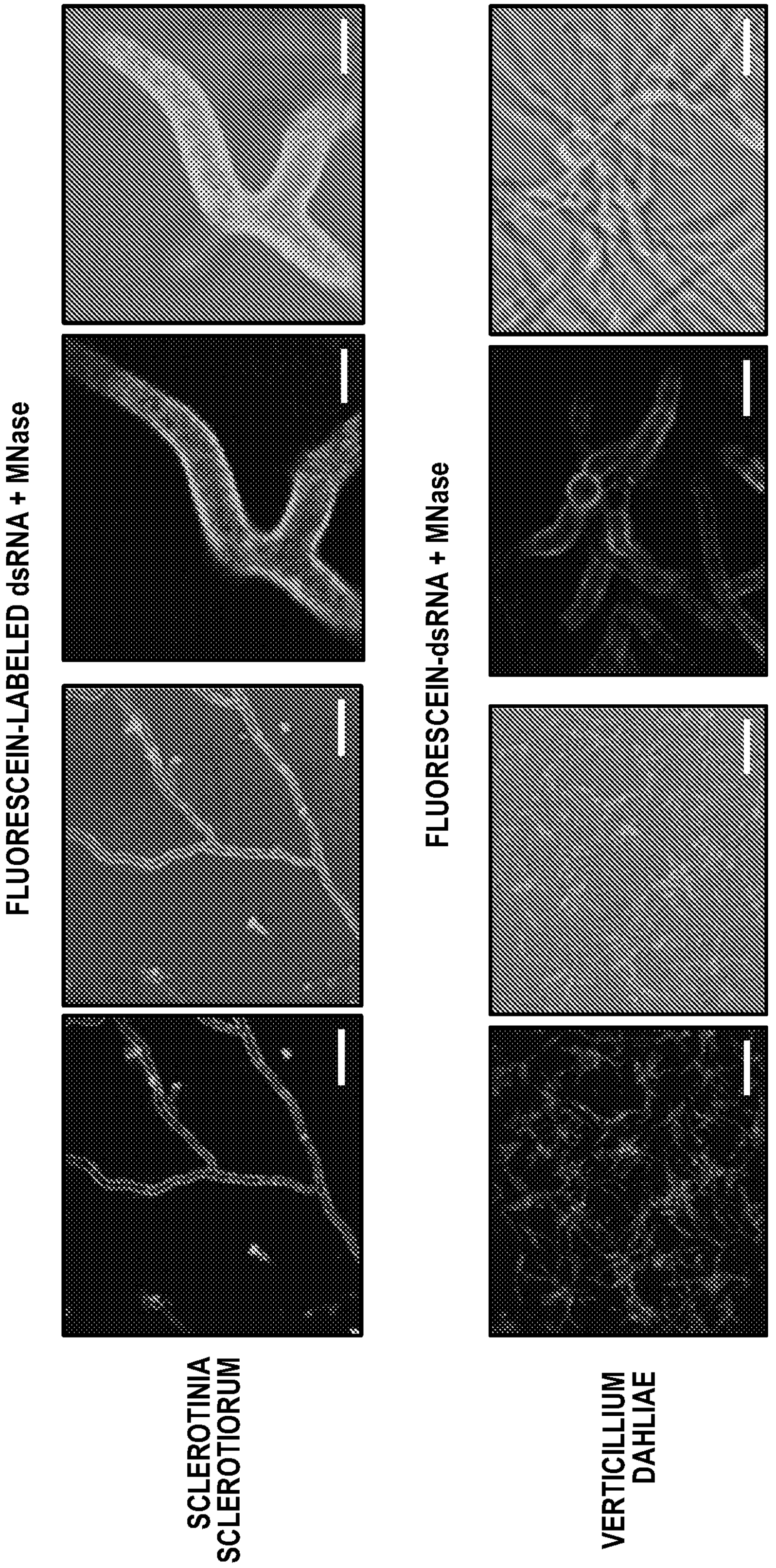
FIG. 15: Images show that many fungi can take up naked RNAs from the environment, which makes for example spray-induced gene silencing possible to control these fungal pathogens.
Figure 16A:
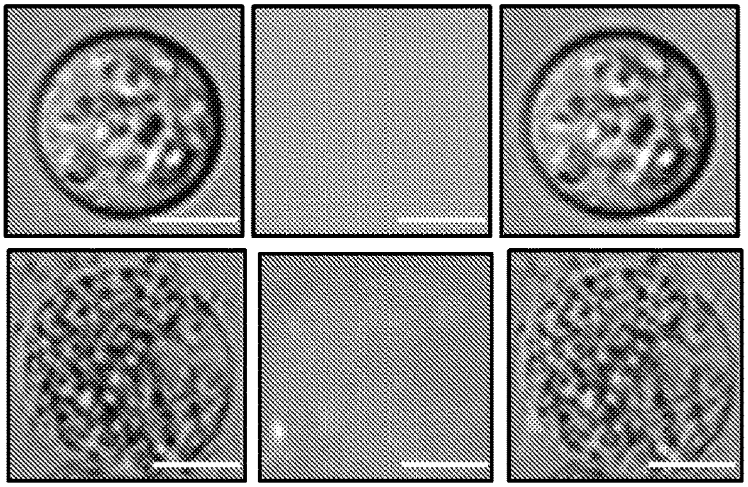
FIGS. 16A-16C: Images show the potato late blight oomycete pathogen, which caused Irish famine in 1800—*P. infestans*—can also take up naked RNAs from the environment. Different cell types have different uptake efficiency.
Figure 16B:
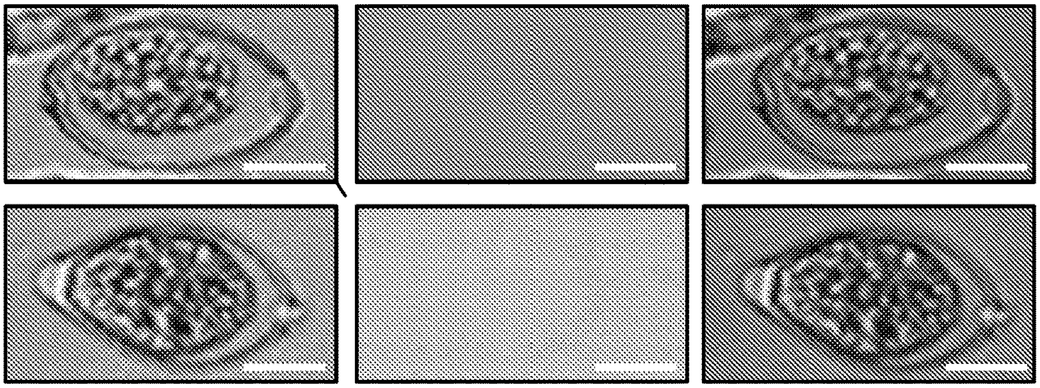
Figure 16C:
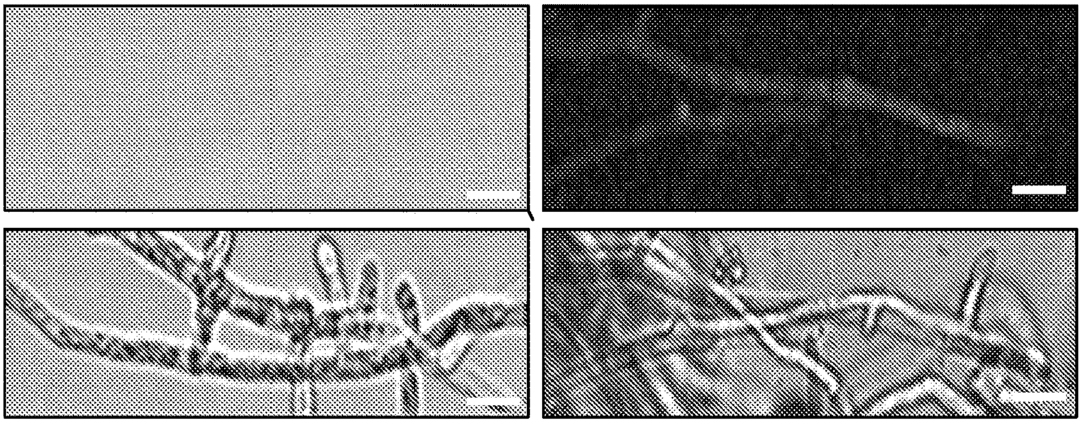

Many fungi can take up naked RNAs from the environment, which makes the spray induced gene silencing possible to control these fungal pathogens (FIG. 15). Moreover, *Phytophthora infestans*, the potato late blight oomycete pathogen, which caused Irish famine in the 1800s, can also take up naked RNAs from the environment. As shown in FIGS. 16A and 16B, different cell types have different uptake efficiency.

Figure 17A:
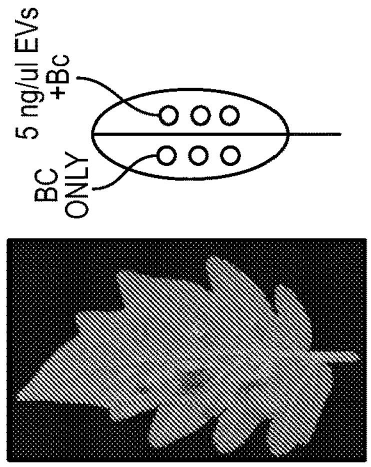
FIGS. 17A-17E: Treatment with extracellular vesicles isolated from *Arabidopsis* efficiently suppressed grey mould disease symptoms caused by *B. cinerea.*
Figure 17B:
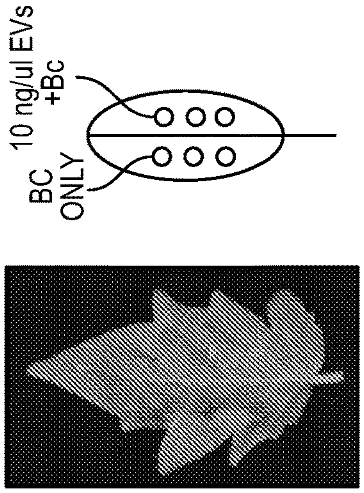
Figure 17C:
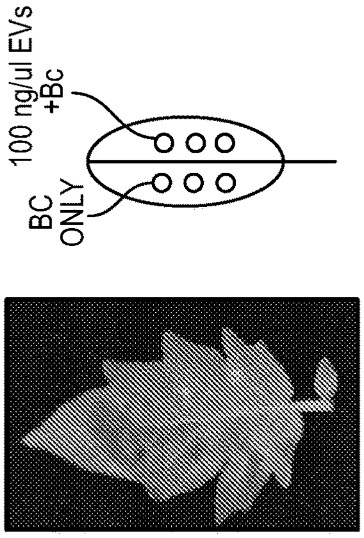

Furthermore, treatment with extracellular vesicles isolated from *Arabidopsis* efficiently suppressed grey mould disease symptoms caused by *B. cinerea*. As shown in FIGS. 17A-17C, extracellular vesicles (EVs) extracted from the *B.*

*cinerea*-infected *Arabidopsis* leaves were mixed with *B. cinerea* spores and dropped onto the tomato leaves (right side of the leaf). Non-treated spores used as control (left side of the leaf). EVs were quantified by the protein concentration of EVs. EVs of 5 ng/μl, 10 ng/μl, and 100 ng/μ1 had strong inhibition on grey mold disease symptoms, and the high concentration of EV treatment (100 ng/μl) can even suppress the disease lesion size (infected without EVs) on the other side of the leaves, suggesting that EVs can move long distance within the plant tissue.

Figure 17D:
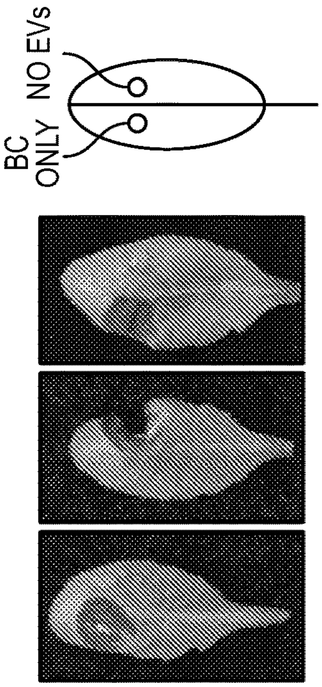
Figure 17E:
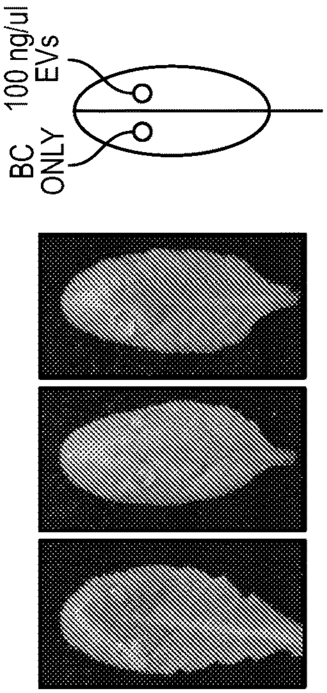

To confirm that external EVs can traffick in the leaves, we dropped only the *B. cinerea* spores on the left side of *Arabidopsis* leaves, and only the 100 ng/μ1 EVs on the right side. We found that EVs (100 ng/μl) can clearly reduce the lesion size on the other side of the leaves (FIGS. 17D and 17E). These results support that EVs can travel within the plant tissue, which increase the capability of plant protection.

Example 3—Liposome-Mediated RNA Uptake

Figure 18:
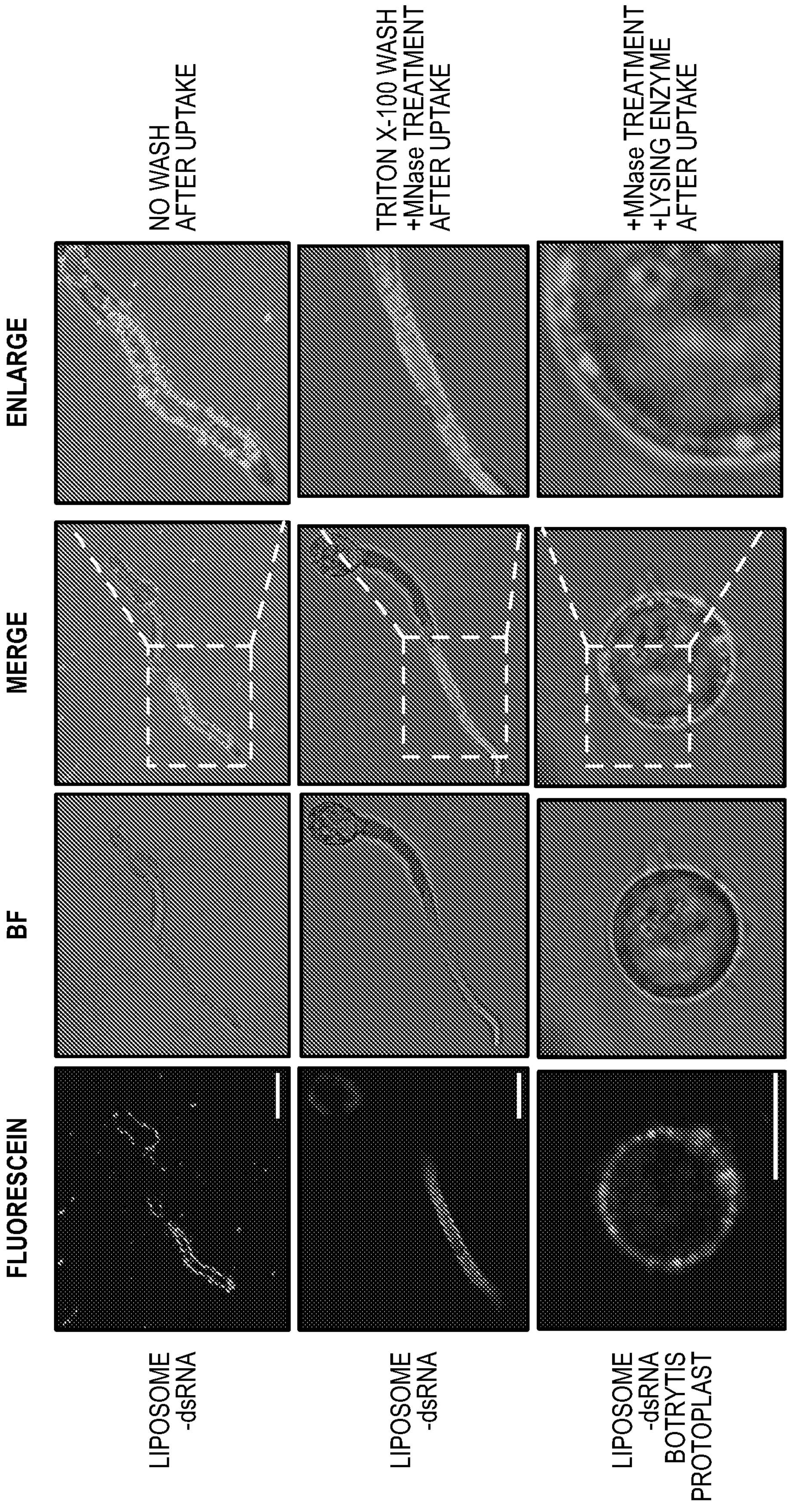
FIG. 18: Images show that liposomes containing fluorescein-labelled Bc-DCL1/2-dsRNAs were taken up efficiently by *B. cinerea* cells.

To investigate whether fungi can take up RNA-containing liposomes from the environment, we synthesized fluorescein—labelled Bc-DCL1/2-dsRNAs targeting Bc-DCL1/2 genes and encapsulated the RNAs into liposomes. The liposomes were mixed with *B. cinerea* cells and fluorescent RNAs were accumulated inside the *B. cinerea* cells within 3 h, suggesting that liposomes can efficiently deliver dsRNA into fungal cells. Fluorescence signals remained visible in the *B. cinerea* cells after triton X-100 wash and MNase treatment, confirming that the labeled RNAs were inside the fungal cells. Fluorescence signals was observed in *B. cinerea* protoplasts after MNase treatment. Liposome-fluorescein-labelled-dsRNAs was applied onto germinated *B. cinerea* spores and protoplasts were isolated after culturing for 3 h. The fluorescent signals were detected within fungal protoplasts after MNase enzyme treatment. As shown in FIG. 18, liposomes containing fluorescein-labelled Bc-DCL1/2-dsRNAs were taken up efficiently by *B. cinerea* cells.

Figure 19:
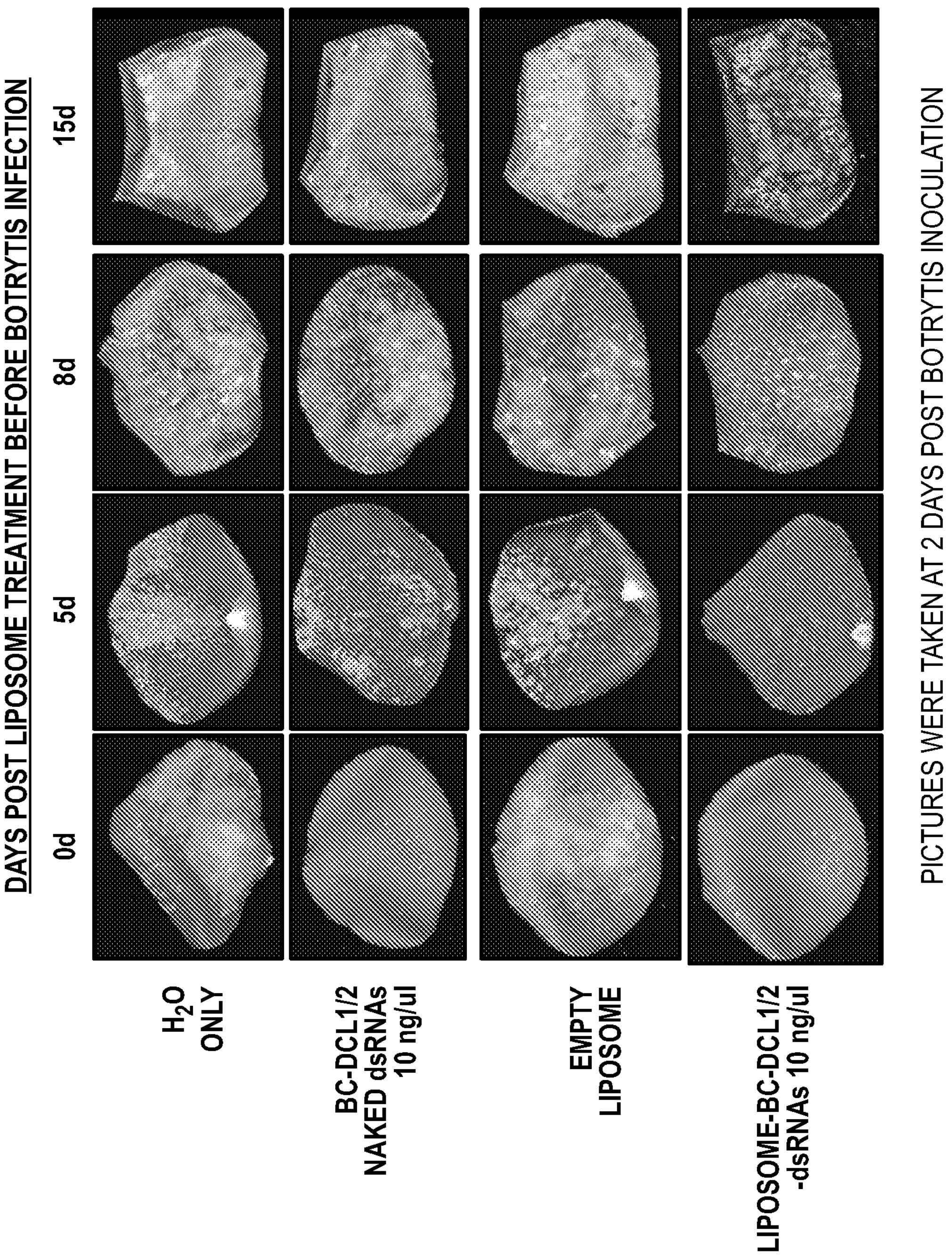
FIG. 19: Images show that externally applied liposomes carrying Bc-DCL1/2-dsRNAs remain effective on plants for two weeks to inhibit pathogen virulence on flower petals.
Figure 20:
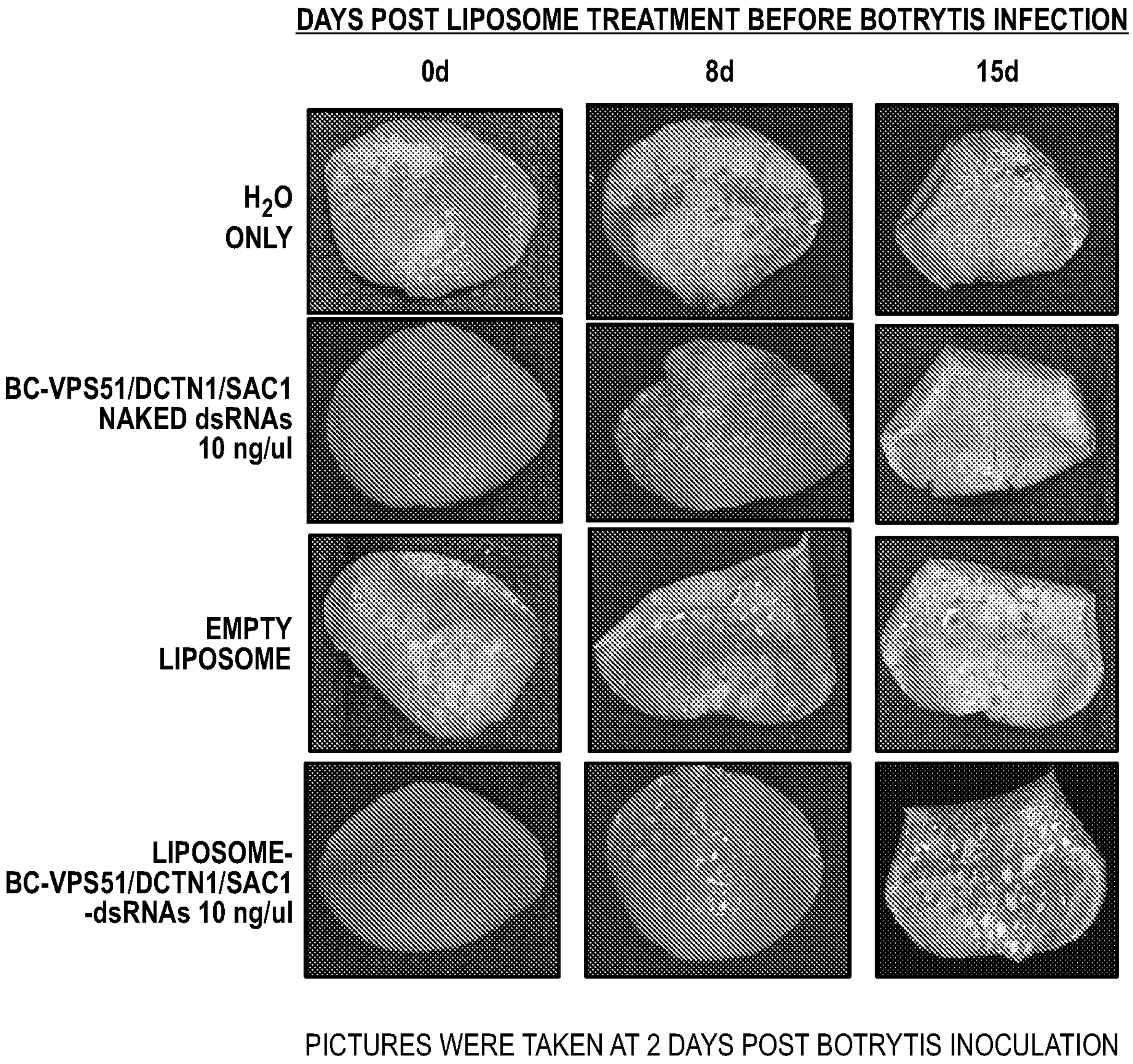
FIG. 20: Images show liposome-protected dsRNAs that target trafficking pathway genes VPS51, DCTN1, and SAC1 were effective for up to 15 days.

Example 4—Liposome Stabilization of RNAs dsRNA-containing liposomes were sprayed on the rose petals first and then challenged with *B. cinerea* at 0, 5, 8, and 15 days post liposome spray treatment. $H_2O$, naked dsRNAs, and empty liposomes were used as controls. Pictures were taken 2 days after the fungal inoculation (dpi). We found that the liposome-dsRNAs remained effective for up to 15 days after RNA treatment whereas naked RNAs were effective up to 5 days. Thus, liposomes provide a longer protection than naked dsRNA against *B. cinerea* infection. Encapsulation of RNAs with liposomes protects and stabilizes RNAs and extends their effective period on plants than naked RNAs. FIG. 19 shows that liposomes containing double stranded RNAs and/or small RNAs were taken up efficiently by fungal cells. Externally applied liposomes carrying Bc-DCL1/2-dsRNAs remained effective on plants for two weeks to inhibit pathogen virulence on flower petals. FIG. 20 further shows liposome-protected dsRNAs that target trafficking pathway genes VPS51, DCTN1, and SAC1 were effective for up to 15 days.

Example 5—Liposome Stabilization of RNAs

Figure 21A:
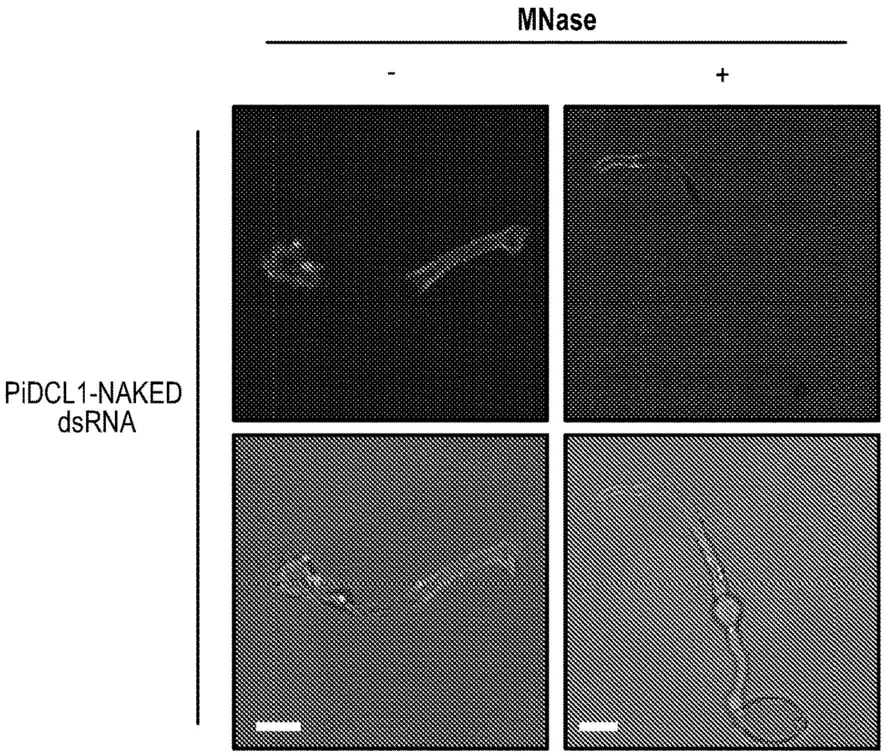
FIGS. 21A and 21B: Images show that *Phytophthora infestans* cysts take up both naked dsRNAs and liposome-protected dsRNAs. Scale bars, 10 μm.
Figure 21B:
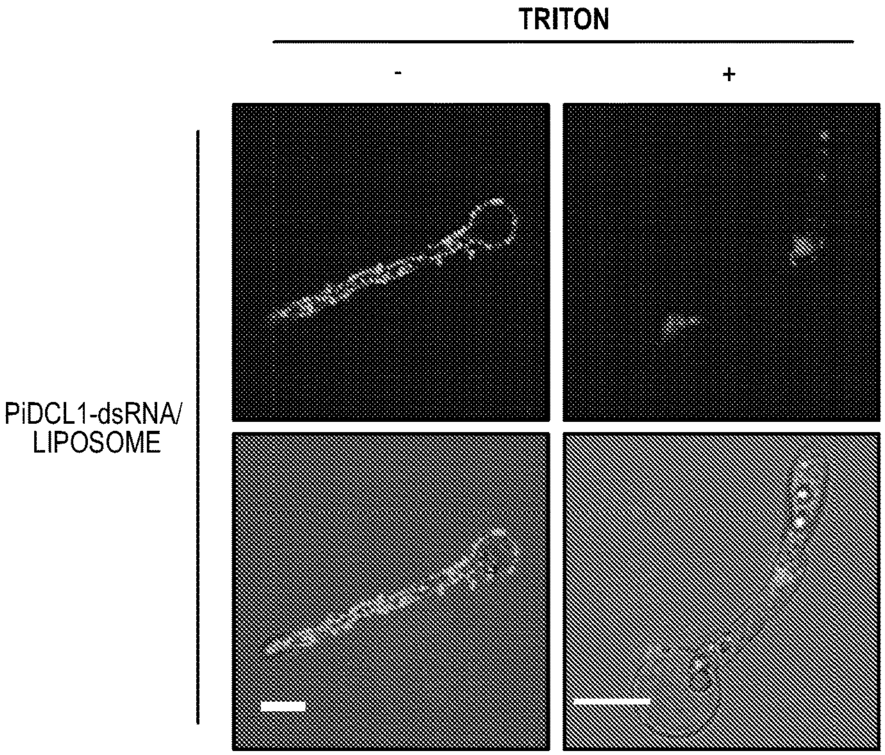

Fluorescein-labeled PiDCL1 dsRNA were applied onto *P. infestans* cysts and fluorescent signals were detected in the *P. infestans* cells at 12 h post culturing in water. As shown in FIG. 21A, fluorescence signals remained visible in the *P. infestans* cells after MNase treatment. Further, fluorescein-labeled PiDCL1 dsRNA were packed into liposome and applied onto *P. infestans* cysts. The fluorescent signals were detected in the *P. infestans* cells at 12 h post culturing in water. As shown in FIG. 21B, fluorescence signals remained visible in the *P. infestans* cells after Triton treatment. This experiment shows that *Phytophthora infestans* cysts take up both naked dsRNAs and liposome-protected dsRNAs.

Example 6—Cationic Liposome Delivery Systems

Method 3 of the cationic liposome delivery system for siRNA delivery is used on HeLa cells. HeLa cells are transfected with siPlk1 using: DOTAP:Chol liposomes mixed with siRNA; DOTAP:Chol:DSPE-PEG2000 (5 mol %) liposomes mixed with siRNA; or DOTAP:Chol:DSPE-PEG2000 (5 mol %) liposomes hydrated with siRNA using the encapsulation protocol. Liposome/siRNA complexes are prepared at N/P 2:1, 4:1, and 6:1 with a final siRNA concentration of 50 nM. Cell viability is assessed by the MTT assay 48 h posttransfeccion (Zou et al., *Cancer Gene Ther.* 7(5):683-96, 2000).

Example 7—Extrusion Method to Prepare sRNA Liposomes

Figure 23A:
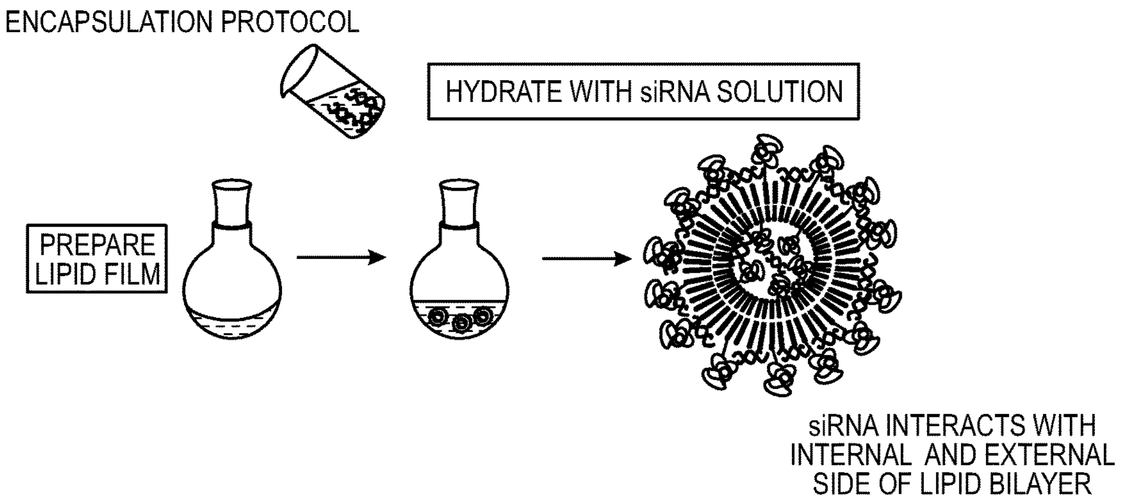
FIGS. 23A and 23B: Schematic drawings and images show sRNA liposome preparation by extrusion method.
Figure 23B:
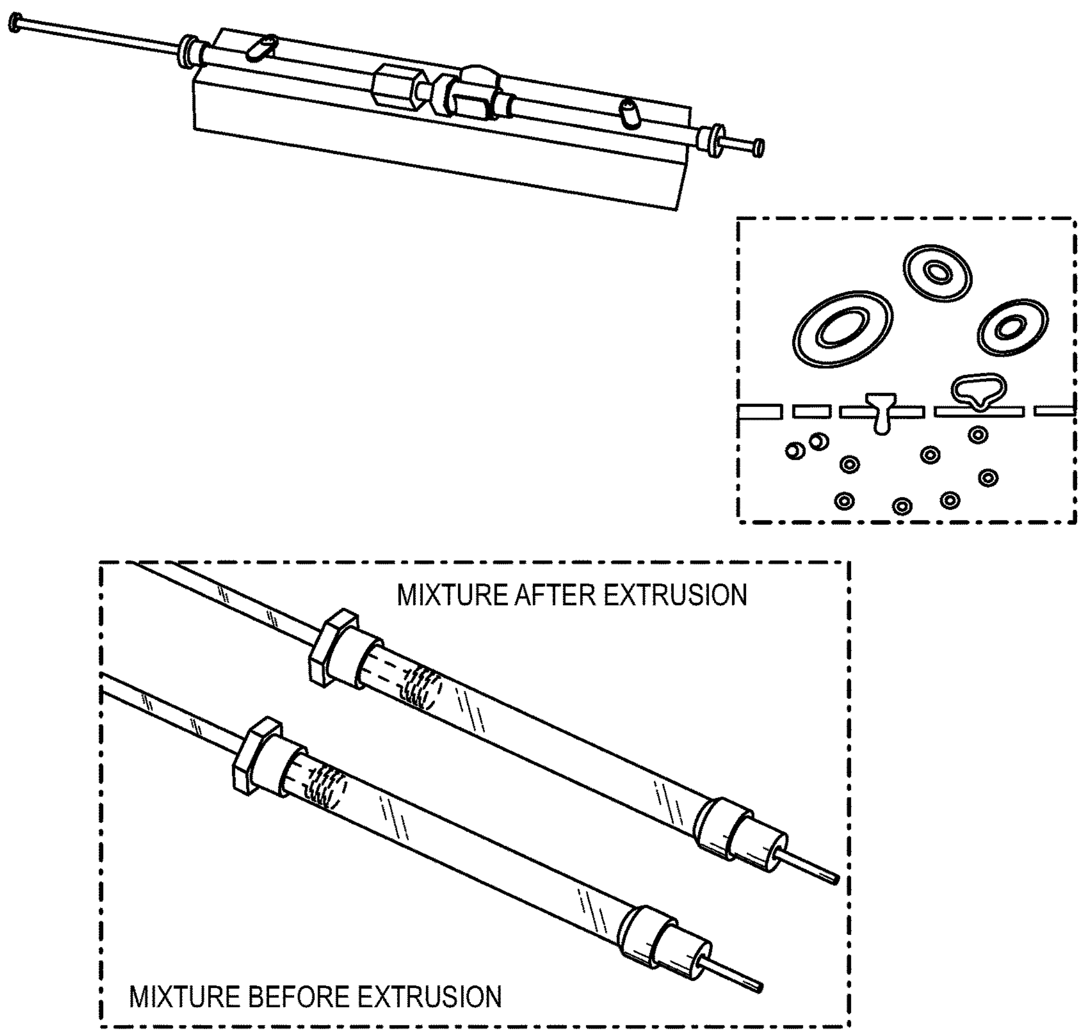

We made sRNA liposomes for encapsulation of siRNA using the lipid film hydration method (Podesta and Kostarelos, *Methods Enzymol.* 464:343-54, 2009). DOTAP, cholesterol, and DSPE-PEG2000 (2:1:0.1) were dissolved in chloroform: methanol (4:1, v/v). After mixing the lipids, the organic solvent was evaporated under hood for 120 min. The lipid film was hydrated using a solution of siRNA in RNase-free $dH_2O$. The amount of siRNA used to hydrate the film was calculated from the charge ratio (N:P) (FIG. 23A). After hydration at 4° C. overnight, the crude liposome was extruded by Mini-Extruder (FIG. 23B). Extrusion of liposomes was performed using a Mini-Extruder (Avanti Polar Lipids, Alabaster, USA). Liposomes were extruded 11 times through a 0.4 μm polycarbonate membrane.

Informal Sequence Listing

*Botrytis cinerea*, Bc_DTCN, BC1G_10508

SEQ ID NO: 1

*GCAGGGGTCGGATCAACATGTCTATAAACAAACATATGTACCGGCGTTGATCTCTCCTGCAGACTGCATTTGCACTTG*

*CTTCCCTCTTCCTCCTCCCGTTTCCTGGTCTTCTTCTACAAGCTGCAGGCGAGAGAGATAACTTCTACGCACCTTCCAT*

*ATCCCTCACCTCTTCTCTCCCCACAAGTTCGTTCATAATCCTTTCGTCCTGTTGTTTTGTCTAGCATTACCTTGCAATTCT*

*TAACAACGGCCGATCGTGGACATCAATCAATAAAAAGGACGACAAATCATCTTATAATTATTATCCCAAACTTTCATTGC*

-continued

ACAAATTTGAATTGGATACTCATTTGGCTTTATTCGGAGCGATAAACGTAGAAATTAATCGTATAGGGGCTTTTATCAGA

CAATCAAGAACGGTGATTGGCTCACAGCGGTGAATTGTGAGGGGTGGTAATACAGAAAACAAATAGTATAGGGAGTAT

TTTTGGGTGGATTGTTACCAATGTCTACCACAAGAATCTCAACACCGAAAAGGTCCCCCAAAAAATCGACTTTTGTCAA

AACTGGAATCTTGACCACCAAATCAACGCCCAATCTCAACGCCTCCTATAATTTGGCATTACTACAAGCTTCAGGAGCT

ACACCCGTTCCTGCATATCCTTCCAATAACGGTCAAAGTTTTGCCCTAAATAATCCTAGGTCGCAACCGTCTCGACAAG

TCTCACTCGCTTCCCTTACCTCGAATTCACTTGCGACAATCCCGGATGCAAGCAAGAGATACCCTCTTTCTACAGTCTT

TGATGAGGATATGCCAACAGTAGGCAACATGCCGCCATACACACCTGCTCGAGTTGGCGGTGGACCGGAAGAACTAG

AGGTTGGTGATATAGTCGATGTGCCAGGTAACATGTATGGTATCGTCAAATTTGTTGGCAGTGTGCAAGGCAAAAAGG

GTGTATTTGCTGGGGTAGAATTAAGTGAAACGTTTGCTTCGAAAGGGAAAAACAATGGCGATGTCGAAGGAATTCAATA

CTTTGACACAACCATCGATGGTGCTGGGATTTTTCTTCCAGTCAACAGGGCGAAGAGACGTAGCACCCCTTCGTCGCA

TGATGAGTCATTTCCCCTTTCACCGGCGTCTCCATCGATGGGCAATAGGGCTGGGAGATTAGGATCTGAATTAAATGG

TCAGCCAACACCTTTGTTACCAAAATTCGGTCAATCTGTTGGTCCAGGCAGAGCGGCAAACCCATATGTCCAAAAAACA

CGTCCATCCATGGCTACACCTACCACCTCAAGACCGGAATCACCAGTTCGAAGAGCAGCCAATGCCAACCCATCATTA

AATACACCTGCACAAAGAGTCCCATCTCGATATGCAAGCCCTGCGCAGGCAAACTTTGGACAGAGCGTTAGAGGAACA

CAAGATTCTAGAGATCCAAGTAAGAAAGTTGGCTACACCCCCCGAAATGGCATGAAAACACCAATACCTCCACGAAGT

GTTTCTGCACTTGGAACGGGGAATAGACCTGCACCAATGAACTCGATGAATTTCAGTGATGAAGAGACACCTCCTGCA

GAGATTGCACGTACGGCAACAAACGGAAGCGTAGGCTCAGTCTCTTCTTTCAACGCGAAATTACGTCCAGCATCAAGA

TCCGCATCGCGTACAACTTCCAGGGCTACCGACGACGAATTTGAGCGATTGAGAAGTTTGTTAGAAGATCGCGATAGG

GAAATAAAAGAACAGGCTTCTATTATAGAAGACATGGAGAAAACTCTCAGTGAAGCACAATCGTTGATGGAGAACAATA

ACGAGAACGCAAGTGGTAGACATAGTCAGGGAAGTGTGGATGACAAGGACGCAACACAGTTGAGAGCAATAATACGT

GAAAAGAACGACAAAATCGCCATGCTGACTGCCGAGTTTGATCAGCATCGAGCTGATTTCAGAAGCACGATAGACACG

CTCGAAATGGCCGGTGCGGAAACCGAGCGAGTGTACGACGAGCGCATGCGTGTTCTCGTAATGGAGCTCGATACAAT

GCACGAGAATAGTCATGATGTAAAGCACGTTGCTGTACAACTGAAACAGCTAGAAGAGCTCGTTCAGGAGCTCGAGGA

AGGTCTTGAAGATGCACGACGTGGTGAAGCCGAAGCTCGGGGAGAAGTTGAGTTCTTGCGTGGAGAGGTTGAAAGAA

CTCGATCTGAACTCCGCCGCGAGCGAGAGAAGACTGCCGAAGCTCTTAGCAACGCAAATTCTCCTACGAGCGCAAGT

GCGGAAACACATTCCAAAGAGATTGCTCAGAGAGATGACGAGATTCGTGGATTGAAAGCCATCATCCACTCGCTCAGC

AGAGATGCCATACCTGATGGGAATTTCTCGGATCATGAGGCAACACCAAATATTCTACGACCTGGACTAAACCGAAGT

CGAACAGAAAGTGCTTCGGTTTCTGAGGAGGAGCGCCGTACTCGGGAAAAGCTAGAGCGAGAAGTGAGTGAGCTTC

GTGCTCTCGTCGAAAGCAAAGACAATAAAGAAGAACAAATGGAGCGCGAGTTGGAGGGATTGCGAAGAGGAAGTGTT

AGCAATCCTACTACGCATCGTACTAGTGCCATGAGCAGCGGAACTGTGACTCAGGATAGGAATTCTCTCCAAGACAAT

AAGAGCACAGTTGTAAGCTGGCGAGAACGTGGTGCCTCAGATGCTCGCCGCTACAATCTGGATTCAATGCCAGAGAA

TGACAGCTACTCCTCTGCAGCTGAGGATTTCTGTGAATTATGCGAAACCTCAGGTCATGATGTTCTACATTGCCCGATG

TTTGGCCCCAATGGTAACAGCAGCAATTCTAAGGATGAGTCACCTAAACAGCAACGAACAGGAAAAGACGTTGTCATG

GAGGGACTTAAATTATCACCCAAACCTTCTCAAGAAGAATACAAACCGGCGCCGTTAGCGCCAGCTAAGAAGTCGCCT

GATGCGTCGCCTATCAAGACTGTTCCCAACCTTATGGAACCAGGACCTGCCCCAGGAAAGGAAAGTGGAGTAATCAA

CATGGATAAATGGTGCGGTGTATGTGAAAGAGATGGACATGACAGTATTGATTGTCCTTTTGAAGATGCTTTTTAGGAG

ACTACTGCTTTCGATGTTTCAGGATAAGCAGTCACAACGACGACTTTTTTCATAGATTTTCTTTGTTAATCATAGGCAAG

GCCGCATTGCATTGCAGGAGCGTAATCCGTCTGCGATATACCCTTTCGGTTCTCTGTTTGAAGTATGCTTTTCAAGCGA

TAAGTTTAGAGGGGAAGATGATGTTTTTACGAGGATTGAATGAGATGGATGAATGCAGGCTAAATCGGGGAAGGGGG

AGGGAAGACAAACATGAGTTGAACGGACGTAATGATCATGTAGTATACTTTGTCAAATTAATGATCCAAATGCA

-continued

*Sclerotinia sclerotiorum*, Ss_DTCN, SS1G_04144

SEQ ID NO: 2

*ATGTCGACTACAAGAATCTCAACTCCAAAAAGGTCTCCAAAAAAATCGACATTCACTAAAACAGGAATTCAAGTCACAAA*

*ATCAACTCCCAATCTCGGTGCCTCCTACAATTTGGCTTTATTACAAGCTTCAGGAGCTTCACCGGTTCTTGCACATTTTT*

*CCAATAACGGTCAGGGTTTTGGTCTAAACAATCCTAGGTCGAAGCCATCTCGACAAGTCTCACTCGCATCCCTTACCTC*

*AAATTCACTGGCGGCAATACCGGATGCTAGTAAAAGATACCCTCTTTCAACCGTTTTTGATGAGGATATGCCACCAGCA*

*GGCAACATGTATACACCTTCTCGAGTTGGTGGTGGGCCCGATGAGTTGGAGGTGGGTGACATAGTTGATGTTCCTGG*

*TAACATGTATGGTACTGTCAGATTTGTCGGCAGTGTGCAAGGCAAGAAGGGGGTCTTTGCCGGAGTGGAATTGGATG*

*AGATGTTTGCTTCCAAAGGGAAGAACAATGGTGATGTTGAAGGTCAATCAGTTGGCCCAGGTAGAATTCAAAAAACCC*

*GACCATCGATAGCCACACCAACCACATCACGACCAGAGTCTCCAGTACGAAGAGCAGCCGCTGCTAGGACATCAATA*

*AATGCACCCGGGCAGAGAGTCCCATCTCGATATGGAAGTCCTGCAGCGGCGAACTTTGGGCAGAACATTAGAGGAGT*

*GCAAGATGCTAGAGACCCAAGCAAGAAAGTCGGTTACGCCCCAACAAATGGCATGAAGACACCAGTCCCTCCACGAA*

*GTGTTTCGGCACTTGGCACAGGGAGTAGACCTGCAGCAATGAACCTCAGTGATGAAGATACACCTTCTGCTGGAATTA*

*CACGGACGGCAACAAACGGGAGTGTGAGCTCAATCTCTTCCTTCAACGCAAAGTTACGACCTGCATCAAGATCCGCCT*

*CGCGTGCGTCCCGAGCTACTGACGACGAGGTCGAGCGATTGAGAGGTCTACTGGAGGAGCGCGATCGGGAAATAAA*

*AGCACAAGCTTCAATCATAGAAGACATGGAAAAGACTCTTAGTGAAGCTCAGTCACTGATGGAGGACAACAATGAGAA*

*CGCGGGCGGTCATAGAGATAGCCGGGGAAGCATGGAGGACAAAGACGCAGCACAATTGAGAGCAATAATTCGTGAA*

*AAGAATGAAAAAATCGCCATGCTGACTGCTGAGTTTGATCAGCATCGAGCTGATTTCAGAAGTACAATAGACACACTTG*

*AGATGGCTGGTGCTGAAACCGAAAGAGTCTACGATGAGCGCATGAGTAATCTTGTAATGGAGCTCAGGACGATGCAT*

*GAGAACAGTCATGATGTGAAGCATGTTGCTGTACAACTGAAACAGCTAGAAGAGCTTGTTCAGGAGCTTGAGGAAGGT*

*CTTGAAGATGCGCGGCGTGGTGAAGCCGAGGCTCGCGGTGAGGTCGAGTTCTTGCGTGGAGAGGTTGAAAGAACTC*

*GATCTGAGCTTCGTCGTGAGCGGGAGAAAACTGCTGAAGCTCTCAGTAACGCAAATCCTGCTACGGGTGTGGGTGCA*

*GCAACACTTTCTAAAGAGATTGCACAAAGAGATGACGAGATCCGCGGTTTGAAAGCTATCATTCACTCGCTTAGCCGA*

*GATGCCATACCTGATGGGAATTTCTCGGATCATGAAAAGACACCAAGTGTTACACGACCAGGGCTACATCGAAGCCGT*

*ACGGAAAGCGCTTCAGCTTCAGAGGAGGAGCGTCTTAGCCGGGAGAAGTTGGAACGAGAAGTGAGCGAACTTCGTG*

*CCGTCGTAGAAAGTAAAGACAGCAAGGAAGAAGAAATGGAGCGTGAGCTAGAGGGGCTACGAAGGGGAAGTGTCAG*

*CAATTCTACTACGCAGCGTACTAGTGCCATTAGCAGTGGAACTGCAACCCAGGATAGAAACTCTGTCCGAGATTCCAA*

*AGGCACAGTTGGAAGCTGGCGGGACCGCGAAGGAACATCGGATGTTCACCACCACAACTTGGAGTCAATGCCAGAG*

*ATTGACGGTTACTCTTCAGCAGCGGAGGATTTCTGTGAATTGTGCGAGGCATCAGGTCATGATGTTCTACATTGCCCC*

*ATGTTCGGTCCTAATGGTAATAGTGGCAACTCTAGAGAGGAGTCTCCTAAAGAGCAACGAACAGGAAAAGACGTTGTC*

*ATGGAAGGACTCAAACTATCACCCAAACTAGCGCAAGAAGAATACGAACCAGCACCTTTAGCACCAGCCAAGAAGTCG*

*TCTGATGACTCGCCTATTAAAACCATCCCTAACCTCATGGACCCAGGTGCTGCTCCAGGAAAAGCAAGTGGAGTCATC*

*AATATGGACAAATGGTGCGGTGTATGTGAACGAGATGGACATGACAGCATTGACTGTCCGTTTGAAGATGCATTTTAG*

*Botrytis cinerea*, Bc_VPS51, BC1G_10728

SEQ ID NO: 3

*GACACATGCGATATGCAAAGTCTAGAACCTCGAATACTGATTCGAAAAAGACTGGCAATTCCATAAATCTACAGTATATT*

*TTAATCCGCAACTCATGAATGACTACATTTAATACGAATTACAAACATTCCCTAACGCCAAAATGGCAGCTACGATTCCC*

*CTCTCCACTACAACATGCTTGACCTCCTCAGAAGCTTTCAAATATCCTCTTCCACAGATTCGTCAATTCCACCGCGATCT*

*CACTACAGAGCTTGACGAGAAAAATGCACGTCTGCGGACACTGGTCGGAGGGAGTTATAGACAATTACTTGGAACCG*

*CCGAGCAAATCTTACAGATGCGACAGGATATTAGTGGAGTAGAGGAAAAGTTAGGCAAAGTAGGAGAAGGATGTGGG*

*AGAAATGTGTTGGTTGGAATGGTTGGCGGATTGGGAAAATTACAGGGAGAAATGAAGAATGGAAAGAAGGGCGAGGA*

*AATGCGGGTTGTGGCTAAGATGAAGGTATTGGGTATGTGTGGGATTGTGGTTGGGAAGCTCTTGAGGAGACCAGGGC*

-continued

*GAATGGATGGGGATGGTGGGAGAGGGAAGGAATTAGTAGTTGCTGCGAAAGTCTTAGTTTTGAGCCGATTGTTGGCG*

*AAGAGCTTGGAGAATACTGGAGATAAGGAATTCGTTGAAGAAGCGAAGAAGAAGAGGTCGGCTTTGACGAAGCGATT*

*GTTACGCGCAGTTGAAAAGACATTGGTTTCCGTCAAGGATGCTGAAGATAGAGACGATTTGGTACAGACACTTTGTGC*

*ATACAGTCTAGCTACTAGTTCTGGCACCAAAGACGTCTTGCGACATTTCTTAAATGTTCGTGGTGAAGCAATGGCTTTA*

*GCGTTTGACGATGAAGAGGAGTCGAACAAGCAGACCTCAGGTGTCCTACGCGCTTTGGAAATATATACGAGAACTTTA*

*CTAGATGTACAGGCTCTAGTGCCAAGGAGGCTGAGCGAAGCGTTGGCTGTGCTGAAGACGAAACCTTTACTGAAAGA*

*TGACAGCATTCGGGAAATGGAGGGATTGAGGTTGGATGTATGTGAGCGGTGGTTTGGCGATGAGATTATTTACTTCAC*

*ACCTTATGTCCGGCATGATGATTTGGAAGGGTCATTGGCGGTTGAAACACTACGAGGTTGGGCGAAGAAAGCGTCAG*

*AAGTGTTACTGGAAGGTTTTACGAAGACTCTTCAAGGGGGATTAGACTTTAAAGTAGTTGTTGAACTACGAACAAAGAT*

*TCTGGAGGTGTGGGTTAGAGATGGAGGCAAAGCAAGGGGATTCGATCCCTCTATACTTCTAAATGGCTTACGAGACGT*

*TATAAACAAACGACTCGTAGAGTTATTAGAAACTAGAGTTGGCAAACTTCATCTAGTGGGGACAGAGATAGAGTCCACA*

*TTAGCAACATGGCAAGAAGGAATCACCGACATACATGCAAGTCTTTGGGACGAAGATATGATGGCAACCGAGCTCAGC*

*AATGGTGGTAACATTTTCAAGCAAGACATACTTGCTCGCACGTTCGGACGGAACGATGCTGTTTCAAGAGTTGTTAACA*

*GTTTTCACACTTGGAGACATCTCATCGAGGAAATTGGTACTTATATTGATGAACTGAAGAAACAAAGATGGGATGATGA*

*TTTGGAAGATATGGAAGATGATGAAAGTCTCGAATCACGACAAAACCTTCTTAGCAAGGAAGATCCACAAATGCTACAA*

GATCATCTCGATTCAAGCTTAGAAAATTCGTTCCAGGAGTTACACGCAAAGATCACTTCACTGGTGGACCAGCAAAAAG

*ATAGTAAACATATCGGGAAAAATATCGATATATATTCTCCGAATTCTACGAGATATCAGAGCAGAATTACCTAGTAACCCT*

*GCACTACAAAAGTTTGGACTCTCACTTGTCTCATCACTGCACGAAAATCTCGCAGGTATGGTCTCAGAAAACGCCATCT*

*TAGCCCTTGCAAAATCTCTCAAGAAGAAGAAGGTTGCGGGCAGAGCATTATGGGAGGGTACACCGGAACTTCCTGTTC*

*AGCCCTCCCCAGCAACATTCAAATTTTTGAGAGGTTTATCGACTGCTATGGCTGATGCTGGAGCCGATCTATGGAGCC*

*CTGTTGCCGTCAAAGTGTTGAAAGCGCGTCTGGACACCCAAGTTGAAGACCAATGGAGTAAGGCTCTAAAAGATG*

*AGGAAGAGCCTAGCAATGGAATCTCTGGTTCTCCCACCAATGCTCCCGAAGCAGATGCCGAGGAAAAAGAAGGGGAC*

*GCTTCTGCTCCTAATCCTGCTGCTGCTGTAGAAGTAGATGAAGAAAAACAAAAGGATTTACTAAAGCAATCACTGTTCG*

*ATATATCTGTCTTGCAGCAAGCTTTAGAATCACAGTCAGACAATAAGGAGAACAAACTTAAGAACTTAGCGGATGAGGT*

*GGGAGGAAAACTAGATCTCGAGGCGAGGGAAAGGAAACGTATGGTTAATGGCGCGGCGGAGTATTGGAAGAGGTGC*

*AGTCTTTTGTTTGGACTTTTAGCGTAGATTCCAGATGGATGAATTAGTGAGAGGCTTATAATGAATTATATTACGAATAC*

*TTTACTTTTGAGTATTCA*

*Sclerotinia sclerotiorum*, Ss_VPS51, SS1G_09028

SEQ ID NO: 4

*ATGGCATCTACAACCCTCTCCACAACAACATGCTTCACTTCCTCGGAAGCATTTAAACATCCTCTCCCTCAAATCCGGC*

*AATTCCACCGCGATCTCACCACCGAACTTGATGAGAAAAACGCACGTCTACGTACACTTGTCGGAGGTAGTTATAGAC*

*AATTACTGGGAACCGCTGAACAAATCCTACAAATGCGCAAGGATATCCGTGAAGTGGAGGAAAAGTTGGGGGAAGTA*

*GGGGAAGGATGTGGAAGAAATGTATTAGTTGGGATGGCTTCTGGATTAGGTAAATTACAGGGAGAAATGAAGAATGGG*

*AAGAAAGGGGAGGAAATAAGGGGATTGGCTAGAATGAAGGGTTTGGGTATGTGTGGGATTGTGGTTGGGAAACTTTT*

*GAGGAGGCAGGGAAGAGTGGATGGGGAGGGGAGAGGGAAAAGTTTAGTGATTGCTGCGAAAGTTTTGGTTTTGAGT*

*CGGTTGTTGGCGAAGAGTTTGGAGGGTTGTGTGAATAGTGCGGATAGAGAATTTGTTGAGGAGGCAAAGAAGAAGAG*

*GGTGGTTTTGACGAAACGATTGTTACGGGCGGTTGAGAAGACATTAGTCTCGACCAAGGATGGTGAAGATAGAGAAG*

*ACCTGGTACAGGCTCTTTGCGCGTATAGTCTTGCTACTAGCTCTGGTGCGAAAGACGTTTTACGACATTTTCTAAATGT*

*CCGAGGGGAAGCAATGGCATTAGCATTCGAAGACGAAGAGGAATCGAACCAGGAGACATCAGGTGTTTTGCGGGCAT*

*TGGAAATATATACGAGGACTTTACTTGATGTACAAGCATTGGTACCGAGTAGACTTAGCCAAGCATTGGCTGCGCTGAA*

*GACGAAACCTTTATTGAAAGATGAAAGTATTCGAGATTTGGAGGGATTGAGATTAGATGTATGTGAGCGGTGGTTTGGT*

*GATGAAATTCTTTACTTTACACCTTATGTTCGACACGATGATTTGGAAGGATCATTAGCCGTTGAGACATTAAGAGGTTG*

-continued

*GGCGAAGAAAGCATCAGAGGTACTACTGGAAGGATTCACAAAGACTCTTCAAGGTGGCTTGGACTTCAAGGTAGTAGT*

*CGAATTACGGACAAAGATATTGGAGGTATGGATACGGGATGGAGGAAAGGCAAGAGGGTTTGATCCGTCTATACTTCG*

*AGATGGACTGCGAGGTGTTGTTAACGAACGACTTGTAGAGTTATTGGAAACTCGAGTTGGCAAACTTCATCTAGTGGG*

*AACAGAAATAGAATCCACATTGGCTACATGGGAGAAATGGATTACTGATCATCATGCTAGTCTATGGGATGAAGATATG*

*ATGGCAACGGAACTCAGCAATGGAGGTAATATGTTCAAACAAGACATTCTTGCTCGTACCTTTGGACGTAATGATGCTG*

*TTTCAAGAGTAGTCAACAGTTTTCAGACTTGGAGACATCTCATCAAGGAAATAGGTACTGTTATTGATGAATTGAAGAAA*

*CAAAGATGGGATGATGATTTAGAAGATATCGAAGATGAAGAAAGTCTTGAGTCGCGACAAAATCTTCTTAGTAAGAAAG*

*ATCCACAAATGTTGCAAGATCATCTTGATTCAAGCTTAGAAAAAGCTTTTCAGGAGTTACATACGAAAATCACGACACTT*

*GTGGAGCAATACAAAGATAGCGAGCATATCGGAAAGATATCAATGTATATTTTACGAATTTTACGAGATATCCGAGCAG*

*AGCTACCGACAAATCCATCACTACAACAATTCGGTCTTTCACTGATCCCATTACTACACGAGAGCCTTGCCAGCACAGT*

*TTCTGAAAACCCTATCTCTTCTCTAGCAAAATCGCTCAAGAAAAAAAAAGTTGCAGGAAGAGCATTATGGGAAGGAACA*

*CCGGAACTTCCAATTCAACCTTCACCTGCTACATTTAAATTTCTTCGTGCTTTATCAAATGCTATGGCTGATGCTGGAGC*

*AGATCTTTGGAGTCCTATTGCTATTAAGACTTTGAAAGTACATCTCGATTCCCAAATTAATGAGAAATGGAGCATAGCCT*

*TGTCAGAGAAGATGGCTAGTAATAAAACAACTACTTCTTCCAGCAATCCACCCGATACTGAAAAATCCGCGGAAACAGA*

*AGAACCAAAAAATGAAGTTCAATCCCCGTTGGATAAAGAAGTAGAAGAAGAAAAAGAAAAAAATCTACTAAAACAATATT*

*TATTCGATATCTTCGTCTTACAACAAGCTTTAGCGCTACAATCTATACAATTTGGGGATAAGGAAAAGGAAAAGGAAAAA*

*GGGATTATGGGGATGAAAATCAAGAATTTGAGTGATGAGATTGAATTGGAATTGAAGCTTGAGATGCAGGAGAGGAAG*

*AGGGTGGGGAATGGTGCGAGGGAGTATTGGAAGAGGACGGGGCTTTTGTTTGGGTTTTTGGTGTAG*

Botrytis cinerea, Bc_SAC1 BC1G_08464

SEQ ID NO: 5

*GATCCACCCACATCCTTCCTCATATGACTTCGATGATAATTACATAGACACTGCCAGTATGCCTGGCCTCGTTCGCAAA*

*CTCCTTATCTTTGCCGCCATCGATGGGTTGATTTTGCAACCAGCAGCGCCAAAAGGCCAACGCCCCGCCCCCGCAAC*

*GAAGATCGCATACAAAGATAAGCATATCGGGCCAGTATTGAGTGATTTGCAGGATCTGGAGGGGTCGTCTGCGAAAA*

*GTTTCGAGGCATTTGGTATTGTCGGTCTCTTGACGGTTTCCAAAAGCTCCTTCCTGATATCGATTACGAAAAGAGAGCA*

*AGTCGCACAAATACAAGGGAAACCTATATATGTTATTACTGAAGTGGCTTTGACCCCATTAAGTTCCAAGAACGAAGCA*

*GAGATCTCGATTGATAGTACGAAAGCGGGGTTATTGAAGAGTAATATCGAGGGGCAGCATGGCTTGGACGAGAGTGA*

*TAGCGAGGATGATGTCGTTAGCGATGAAGTGGAGGACGATACAGCAGTAGAAGCACACAAAAGAACGAGTAGCGTAG*

*CTGAAGATGTGATCTCGAAGAAGGGGGGATATGGAAGATTTGCTCAAAAATGGTTCTCGAAGAAAGGATGGGCCGTG*

*GACCAGAAGAAGAACCTGGGGATGAGCGCTGAGCCGTATTCCACAGTGGAGCAAGCTTCCAAGGCCACCGATGTAC*

*CAGCTACGATTTCAGGAGTCACTGAAGGAAAATCTGATATCTCAATTCCCGATAAGGGCAAGGAAATTGAGGACATTG*

*AAACTCCTGAAAATATTAGCGACATTGCAGAGAGCATGCTGCCAAAATTACTACGAACATCGCAGATATTGTTTGGGGC*

*CTCTCGGAGTTACTACTTTTCTTACGACCATGATATCACAAGAAGTTTGGCAAATAAGAGGAATACAAATTCTGAATTGC*

*CATTGCACAAGGAAGTTGATCCACTCTTCTTCTGGAATCGGCATCTTACTTTACCATTTATTGATGCTGGCCAGTCTTCT*

*CTTGCCTTGCCTCTTATGCAGGGCTTTGTAGGACAGCGTGCATTTTCAATGGATAGTAATCCACCAAACCCTGCTATAG*

*GTTCAGACACTGGAAAGACTTCCGTGCAGATGAAGGATATTACAACAAGTAGTTCGGATGAGCAAATTTACACAGCAC*

*GTGCTGGTACAGACAAGTCGTATCTATTGACGTTAATATCTAGAAGGTCAGTCAAACGTGCCGGGCTTAGATATTTACG*

*CCGGGGTGTGGATGAGGACGGCAATACAGCCAATGGCGTGGAAACAGAGCAAATCTTATCGGATTCTGCTTGGGGCC*

*CTTCGAGTAAGACATATTCGTTCGTTCAGATACGTGGCAGCATTCCCATATTCTTCTCCCAGTCACCTTACTCTTTTAAA*

*CCTGTACCTCAAGTTCACCACTCTACCGAAACAAATTATGAAGCTTTCAAGAAGCATTTTGATAATATAAGTGATCGCTA*

*CGGGGCCATTCAAGTGGCTTCCTTGGTGGAGAAGCATGGAAACGAGGCAATAGTCGGTGGAGAGTACGAGAAATTGA*

*TGACTCTCCTTAATGTCTCCCGAGCTAGCGAGCTTAGGAAATCCATTGGGTTTGAATGGTTTGATTTCCATGCTATTTG*

-continued

CAAAGGTATGAAATTTGAGAATGTCAGCCTGCTCATGGAAATACTGGACAAGAAGCTTGACTCGTTTTCGCACACTGTT

GAAACCGATGGGAAACTTGTATCGAAACAGAATGGCGTTTTAAGGACTAACTGTATGGATTGTCTGGATCGAACAAAC

GTTGTTCAAAGTGCAGTGGCAAAGCGAGCACTTGAAATGCAGTTAAAGAATGAGGGACTAGATGTCACTCTACAAATT

GATCAAACTCAACAATGGTTCAATACTTTGTGGGCCGACAATGGTGACGCCATTTCTAAGCAATACGCTTCTACAGCAG

CATTGAAGGGAGACTTTACTCGTACTAGGAAGCGGGATTATAAGGGGGCCATCACAGATATGGGGCTTTCTATCTCCA

GATTTTATAGCGGCATTGTAAATGACTACTTCAGTCAAGCTGCCATTGATTTCCTGCTTGGAAATGTGAGCTATCTTGTT

TTTGAAGACTTCGAGGCAAACATGATGAGCGGTGATCCTGGCGTTTCGATGCAAAAAATGAGGCAACAAGCCATTGAT

GTTTCTCAGAAACTCGTTGTTGCTGACGACCGTGAAGAATTTATTGGAGGATGGACATTTCTCACTCCGCAGGTACCCA

ATACGATCAAATCTAGTCCTTTTGAGGAATCCGTCCTCCTATTGACAGATGCTGCATTGTATATGTGCAATTTTGATTGG

AATATCGAGAAAGTATCATCTTTCGTGAGAGTGGACTTGAACCAGGTGAACGGCATCAAGTTTGGAACATACATCACGA

GTACTTTGTCACAAGCCCAGGCAGATGAGAAGAGGAATGTGGGCTTTGTAATAACTTATAAGGCTGGTTCAAACGACA

TTATTCGCGTGAACACGAGATCTATGGCTACGGAATTTCCTTCTTCGAAACTCTCTCTCGAAGACAAAACATCCACGCC

CGCTTCTACATCTACCACCAACTCTGTCGTCGCCCCAATTGCCGCCGGGTTTGCAAACCTAATCTCAGGTTTACAAAAT

CAAAGTATAGCGGAACCTAAAGATCTCGTGAAGGTTCTCGCATTCAAGGCTCTACCCTCCAGATCTGCGGTATCAGAT

GAAGGAGTTAGTGAGGCCGAGCAAGTGAAGAGTGTCTGTGGAGAGATTAGAAGAATGGTTGAGATTGGAAGTATAAG

AGAGGCTGGAGAGGAGAGAAAGGATATTGTAGAGGAGGGTACTATCATTAGTTTGGCCGAGGCCAAGAAAAGCACGG

GACTATTCGATGTGCTGGGACATCAGGTGAAGAAACTGGTTTGGGCTTAATGAAAGTGTATCGATACTCGTGCTAGTA

ATGCTTAGAGCAAAAGAAGCACTTCTTGAAGGATTTACGAATGGAATTGTGGAAGTTGGCAGGGAGGTTAGCGATCGT

CAAGAACGGGTATGTGGAATTCAATTCCATATTGAAGCTGCGAAACTCATTAACTTCAATAGAAGTGGATGTGTAGATA

GACCCGAGTATATGGTATTGGCCAGATAAGTAATTTTAATGGGGA

*Sclerotinia sclerotiorum*, Ss_SAC1, SS1G_10257

SEQ ID NO: 6

ATGCCTGGCCTCGTTCGAAAGCTTCTTATCTTTGCCGCCATTGATGGCTTGATTCTGCAACCAACGGCGCAAAAAGGC

CAGCGCCCCGCCCCCGCAACGAAGATCACGTATAAAGATAAGCATGTCGGACCAGCATCTTATGATTCTCACGATTAC

GAGGGGCCGTCTGCCAAAGGCTTTGAAGCATTCGGGATTGTCGGTCTCTTGACGGTTTCTAAAAGCTCCTTCTTAATA

TCGATTACGAAAAGGGAACAAGTCGCACAAATACAAGGAAAACCTATATATGTTATTACTGAAGTAGCTTTGACCCCTC

TAGCTTCCAGGATAGAAGCAGAGAACTCGATCAACAAAACAAGAGCGGGATTGTTAAAGAGTAGTATTGAAGATCATG

GATTGGACGACAGTGATAGTGAGGATGACGAAGTCAATGTTAGTGACGAAGTGGAGGACGATACAGCAATAGAAACA

CATACAAGAACGAGCAGTGTGGCCGAAGATGTAATTTCGAAGAAGGGAGGGTATGGGAGATTCGCTCAAAAATGGTT

CTCGAAGAAAGGATGGGCTGTGGACCAGAAGAGGAACCTGGGAATGAGCACTGAACCGTATGCTGCACGAGAGCAA

GATGCCAGGTCTGCCGACGTAGCAGCTACCACTTCAAAGGATGCTGAAGTGGAACCTGAGGTTTTGATTTCCGATGAG

GTCAGGGACATTGAAAATGTTGGAAAGTCTGACAAGGTTAAGAACGTTCAGGATATTGCTGAGAGCATGCTGCCAAAG

TTACTGCGTACGACACAAATATTGTTTGGGACCTCCCGGAGTTACTATTTTTCTTACGATCATGATATCACAAGAAGTTT

GGCCAATAAAAGGAACACAAACTCTGAATTGCCATTGCATAAGGAGTCGATCCACTCTTCTTCTGGAACCGACACCTTC

TGTTACCATTTATTGATGCTGGGCAAGCTTCACTTGCCTTGCCTATTATGCAGGGCTTCGTAGGACAACGAGCATTTGT

AATGGATAGCAATCCGCCAAAGCCTGTTGTAGGTTCGGACACTGAGAAGACCTCCATGGAACTGAATGAGATCACAAC

AGATAGTTCGGATGAACAAATCTCCACAGCACGTGTTAGTGCAGATAAGCCATATCTATTGACATTAGTGTCTAGAAGA

TCGGTTAAGCGTGCCGGGCTTAGATATCTTCGTCGAGGTGTGGATGAGGACGGCAATACCGCCAATGGTGTGGAGAC

GGAGCAAATTTTAATCAGATTCTACTTGGGCTCCTTCAAGTAA

*Botrytis cinerea*, Bc_VPS52, BC1G_09781

SEQ ID NO: 7

GATACAAAAGCTTTCGAAAGCCGCTTGAGTAAGTAAGAAGGCAATAAGAGAGGTCCTCGTCCGTGTCGAGATGTGATG

CTTGAGTCATTTTCCTGGTATAGCTTCTGCAATCGAGTTCACACTCTACTACTTGATTCAGATTACACCAGGAGTAACAC

-continued

CTCAAGTATTCCATATTAAATACAAACCTTTCCCATCTTAATCTATTGTTGGCGCATGGGGAGAGGAATTAATTGCTTTG

CTTTTTGGCCATCAGGATGTGGTCATTAGATCGATTATCCGGACACACAACACCTTCTGCCTCTCCACCTCCCCCGTTA

AATAGGATCCCAAATCTCCCTCGTCGTCCGAGTCATCTTGTGCCATCCCCAGTTGGTGGTAGACCTCCTTTCAACCCA

AGATCGTCTTCCCTGTCGTTAATCTCCAATGACTCTAATTCATCGTTGCTATCATCACGGAGACCCAATGGTTCGAATCT

CAAACAAGCAGTCACATCTCCGAATGTGCCAGATCCTTTGGAGGTTTTGGGAACACTACTGAATAATGGGGAAGAGAC

AAAATTGCCATCAGCGAAAAGCCCGGGGGCGACAAATGGGACAGTTGCTCCCATTGAAGAGGAAGACGATGAAGGC

GAATGGGATTTCGGAGGTTTAAGTCTGCAAGACATTGTAGCAGGAGAACCTCTCGATGTTGAGGATGAGCATGTGTAT

AAATCTCAAACGCTGGAAGAATATGAGCGCGAGAAAGAGAAGTTTGAAGACCTCCATCGATCAATTCGCGCCTGCGAT

GACGTTCTTAATTCAGTCGAGATAAACCTCACAAGCTTTCAAAACGACCTTGCTATGGTATCTGCGGAGATTGAAACTC

TGCAAGCACGATCGACGGCTTTGAGTGTAAGGTTGGAAAATCGCAAAGTAGTAGAGAACGGACTTGGGCCTATAGTG

GAGGAGATCAGTGTCTCTCCAGCTGTCGTTAAAAAAATTGTGGATGGAGCTATAGATGAAGCTTGGGTTCGAGCATTG

GCGGAAGTTGAGAAACGATCAAAAGCAATGGATGCTAAATCGAAGGAGCAACGTACTATAAAGGGCGTGAACGATCTT

AAGCCTTTACTGGAGAATCTAGTTTCCAAGGCATTGGAAAGAATCAGAGATTTCCTCGTTGCTCAAGTGAAAGCATTGC

GATCGCCCAATATAAATGCACAGATCATTCAGCAACAGCACTTTCTTCGCTATAAGGATTTATATGCATTCTTGCATAGA

CATCACCCAAAGTTGGCTGAGGAGCTTGGTCAAGCATATATGAATACAATGCGATGGTACTTCCTTAATCAGTTCACGA

GGTATTTGAAGGCGTTGGAAAAGATCAAGCTTCATGTGTTGGACAGATACGATGTGCTCGGATCAGATGACGGGTCTC

GTAAGGCCACTCTTCTTTCAGGATCCAAACAGACAGGTCCACCACACGACGCATTCAATCTAGGTCGACGAATCGACC

TTCTCAAGACGCCAAACCAAACTGCACTTCCCTCTTTCTTAGCCGAAGAAGACAAACAAACCCACTATATGGAATTTCC

TTTCCGTAACTTCAACCTCGCACTGATTGATAACGCTTCCGCCGAATACTCCTTTCTTACCTCTTTCTTCTCTCCCTCTC

TAAGCTACGCTACCATTTCCCGACACTTCAACTACATCTTCGAACCCACTTTTTCCCTCGGCCAATCTCTCACCAAATCC

CTCATCCACGAGTCCCATGATTGTCTCGGCCTCCTCCTATGTGTGCGCTTGAATCAACACTTTGCATTTTCCCTTCAAC

GCCGCAAGATCCCCGCTGTAGATTCCTACATAAATGCAACATCCATGCTCCTCTGGCCACGCTTCCAACTCACAATGG

ATATCCACTGCGAATCCGTCCGCACCCTAACATCCGCTCTCCCTACCCGCAAACCCTCAGCTTCGGAACAAGCTAAAC

AATCTGCAGCTCCACACTTCATGACCCAACGTTTCGGTCAATTCCTACAGGGTATCTTAGAATTGAGTACGGAAGCGG

GAGATGATGAACCTGTAGCGAGTAGTTTGGCAAGATTGAGAGGCGAGATGGAAGCATTTTTGACAAAGTGCGCGGGG

GTTATGCCGGATAAGAGGAAGAAGGAACGATTTTTGTTTAATAATTATTCGTTGATTTTGACAATTGTAGGGGACGTAG

AGGGTAAATTAGCCGGGGAACAAAGGGCGCATTTTGAGGAGCTGAAGAAAGCTTTTGGAGATGGTGTCTGATCCTTCA

CTTCATTTTGATACTTAATTGGAAGTTTTTGAGCGTGTACACTTATCAAAGCGTATTATTTGATCATGTATTTTGTATTTGT

GAAGAGAAACAAAGAACTTTTATTATGGTAGAAATAGAGCCGGAAATAATCTATGCTGTGGAAGAAACCA

*Sclerotinia sclerotiorum*, Ss_VPS52, SS1G_01875

SEQ ID NO: 8

ATGTGGTCATTAGACCGATTATCTGGACATACAACACCTTCTGCTTCTCCACCTCCACCATTAAATAGGAACCCCAGTC

TACCTCGTCGTCCGACTCATCTTGCGCCATTACCAGTCGGCGGTAGACCTCCATTTAATCCGAGATCCTCTTCCCTATC

ATTAGTCTCCAATGACTCCAGTACATCCTTGCTACCATCGCGGAGACCCAACGGGTCGAACCCCAAACAAGCAGCTAC

ACCACCCAATGTGCCAGATCCTTTAGAGGTTTTAGGAAGAATATTAAACAATGGAGAAGAGGCAAAATCACCACCTGC

GAAGGGCTTGGGAGCCATAAATGGAACAGCCGCTCCCATAAGAGAGAAAGATGATGAAGGCGAATGGGACTTCGAAG

GTTTAAGTCTACAAGATATCGTGGCAGAGGAACCTTCTGTCACTGAGGATGAGCATGTATATAAATCACAAACACTTGA

AGAATATGAGCGTGATATGGATAAGTTTGAAGATCTCCACAGATCGATTCGCGCTTGCGATGATGTCCTAAATTCCGTC

GAAATAAACCTCACCAGCTTTCAGAACGATCTTGCTATGGTTTCTGCGGAGATCGAAACTCTACAAGCACGATCAACG

GCGTTGAGTGTACGGTTGGAAAATCGAAAGGTGGTAGAGAATGGACTTGGACCTATAGTGGAGGAGATCAGCGTCTC

CCCAGCCGTCGTTAAGAAGATTGTGGATGGAGCTATAGATGAAGCTTGGGTTCGAGCATTGGCGGAAATCGAGAAGC

-continued

*GATCAAAGGCTATCGATGCAAAATCAAAGGAACAACAGAATATAAAGGGGGTTAATGATCTCAAGCCTCTATTGGAGAA*

*TCTAGTGTCTAAGGCACTGGAAAGAATCCGAGATTTCCTCGTTGCTCAAGTGAAAGCTTTGCGATCCCCCAATATAAAT*

*GCCCAGATTATTCAACAGCAGCACTTCCTACGTTACAAAGATCTCTATGCTTTCTTGCATAGACATCACCCAAAATTGG*

*CCGAGGAACTTGGTCAAGCATATATGAATACGATGCGATGGTACTTTCTCAATCAATTTACACGGTACGCAAAAGCATT*

*GGAAAAGATCAAGCTCCATGTGTTGGACAGACACGATGTTCTCGGGTCAGATGATGGATCTCGCAAGACCACGCTCCT*

*CTCCGCGTCTAAACAAACAGGTCCACCACATGATGCATTCAATTTAAGTCGACGAATCGATCTTCTCAAAACCTCCAAC*

*GAAATTGCACTGCCGTCCTTTCTAGCAGAAGAAGACAAACAAACTCATTACATGGAATTCCCCTTCCGGAATTTCAACC*

*TCGCCCTAATCGACAACGCTTCCGCCGAATACTCCTTCCTAACCTCATTCTTCTCCCCGTCACTAACCTACGCAACCAT*

*CTCTCGCTACTTCACCTATATCTTCGAACCCACCTTCTCCCTCGGCCAATCGATCACCAAATCCCTCGTCCATGAGTCA*

*CACGATTGTCTTGGTCTCCTCCTGTGCGTGCGTCTTAACCAACATTTTGCATTTTCTCTCCAGCGCCGGAAAATCCCTG*

*TCGTAGATTCATATATCAACGCAACATCCATGCTCCTCTGGCCGCGCTTCCAACTCACAATGGACACACACTGCGACT*

*CGGTCCGCACCCTGACCTCGGCCCTCCCCACCCGAAAACCATCGGCTTCAGAACAAGCGAAACAATCCGCCGCCCC*

*CCATTTCATGACTCAACGTTTCGGCCAATTTCTTCAGGGCATTTTGGAACTAAGCACGGAAGCTGGAGATGATGAACC*

*CGTGGCGAGTAGTCTAGCGAGACTGAGAAGCGAGATGGAAGCGTTTTTGTCAAAGTGTGCGGCGATTATGCCGGATA*

*AGAGAAAGAAGGAACGATTTTTGTATAATAATTATTCGTTGATATTGACCATTGTGGGGGATGTGGAGGGGAAATTGGC*

*TGGGGAACAGAGGGCGCATTTTGAGGGATTAAAGAACGCTTTTGGGGAGGGCATTTAA*

*Botrytis cinerea*, Bc_Rgd1p, BC1G_15133

SEQ ID NO: 9

*GAGTATTCTCGATTAGACAATTAGAATTCTCGAACAATAGAAGCCGGAGCTCGAGTTCCTCGATCTTTACCTACCTGAA*

*GTCTCTCGATCAGAAGAGTGTCAAATTCCTATGATATCAATGATTATTGAGGATATATTTACAAAATCAAATCTCTTCAAT*

*GAATCTCTATCTACCTAAGCAAGTCAATTATGATTGATTACAATTATCGTTGTTGCACGGAATCCAGTCGCATTTGGTCC*

*CGGTCACTCGTAACAGCAACCACATCGGTATTTCGTAGATTCCCGAGTATTGCCTTTACATACCTAAGGAACTTTAAAT*

*CCCCCCAACAACAGAATTGACGACAGAATTACTACCATTACAAGTGAAAACACTCCATGGTACCCAAATACAACAGTCT*

*CATATAGCCATTTGATCGCAACTCGCATCTTTCATCTACAAAATGTCGTTTGGAGGGGACATCGGACTCGATACAACAT*

*CGTCGTCCAATGCTGCTGGTAATGGCGGCAACCAGGGCGAGACAACTGGAAGACCTGCCACCCCTCAAGATGCAAC*

*CGCAAAAGCAGTTCAAGATGTCACAAGCTCGGAGATTGGAATATCAACCTTGTTAACCCGACTGAAACAAAGTATTGCT*

*TCCGCAAAGGAATTCGCACTTTTCCTCAAGAAACGGTCCATCATGGAAGAGGAACATTCGAACGGTTTAAAAAAGCTGT*

*GTAAGGCAACCGGGGATAATATTCGCAGACCAGAGCATCGACACGGATCGTTTCTACAGTCATACGAAGAGGTCCTCA*

*TTATACACGAGCGAATGGCCGAGAATGGGGCTCAATTTGGCGTGTCTCTACATCAGATGCATGAGGATCTTATCGAAA*

*TGGCTTCGAACATAGAGAAGGGCAGAAAGCATTGGAAGAATACTGGGTTGGCAGCAGAACAACGTGCTGCTGATACC*

GAAGCTGCCATGAAGAAGTCGAAGGCGAAGTACGACTCTCTGGCAGACGAGTATGATAGAGCTCGCACTGGGGACA

*GGCAACCAGGAAAGATTTTTGGCCTCAAGGGCCCCAAATCGGCAGCGCAACATGAAGAGGACCTTCTTCGCAAAGTC*

*CAGGCTGCCGATGCAGATTATGCGTCCAAGGTACAAGCTGCGCAAAGCCAACGAACCGAGCTCTGGTCAAAATCAAG*

*ACCTGAGGCTGTGAAAGCTCTAGAAGATCTCATTCAAGAATGCGACTCTGCATTGACATTGCAGATGCAGAAGTTTGC*

*ATCCTTTAACGAAAAGCTACTTTTGAGCAATGGCTTGAATATAAGCCCTATCAAAGGAAAAGAGCAAGGGACATTAAAT*

*CGCAGTCTCCGTGAAGTTGTTCACGCAATTGATAATGTTAAAGACCTGAGCAACTACATCAGTAGCTTCTCTGGTAACA*

*TGCAGTCCCGGATCACGGAAATCAAATATGAGCGTAATCCGGTTTTGCAACCCGCACAAAATACCGCTCAGCGACAAT*

*CGGATCCCAACGCTCTCCAAGCTCGACAAGGACCCGTAATACCACCACAGCCATCTCACCAAGTTCATATGAGCCAAC*

*CTTTTAATCAAAGCAGTCCCCCAACTCACCAGCGCGAAAGAAGCTTTAGCCATGGCCCATCTCTTTCGCAACACATCGT*

*TGCACCTGTTGTATCGCCCACTAACCCAATATCCACCTCTCCCGACTTCAATACCTGGTCACCTCGTGCAGATGGCCC*

*CCCCCAGATATCAACCTTGCCATTTCAGCCACAACCTCAAAACGAGACACCAATACAACAGACACCACAAAACCCTACA*

*ACGCATGCACCAGTGTCCCATGGCCCATCCTCGGCACCACTATTCGGAGCGGGATCGGCTCCAGCTCCAGGCAACA*

-continued

*GCACTCATCTAGCACCTTTGAAACCAGTGTTTGGACTCAGCCTCGAGGAACTCTTTGACAGAGATGGCTCTGCTGTTC*

*CAATGATTGTCTACCAGTGTATTCAAGCAGTTGACCTCTTTGGGCTCGAGGTCGAAGGAATATACCGGCTATCTGGTA*

*CCGCATCTCATATAATGAAGATCAAGGCAATGTTCGATAACGACGCATCTAAGGTGGACTTCCGTAACCCGGAAAGCT*

*TCTTTCACGATGTCAATAGTGTGGCTGGTCTTCTCAAACAGTTCTTCCGCGAACTCCCAGACCCTTTATTGACTATCGA*

*GCAATATCCTGCATTTATCGAGGCTGCAAAGCATGATGATGAAATAGTCCGTCGCGACTCTCTACATGCGATCATCAAT*

*GGCCTTCCTGATCCCAATTACGCTACTCTTCGAGCCTTGACTTTACATTTAAATAGAGTACAGGAGAGTTCGGCATCTA*

*ACAGGATGACTGCAAGCAACTTGGCCATAGTATTTGGCCCTACACTCATGGGTGCTAATTCAGGACCGAACATGTCAG*

*ATGCTGGGTGGCAGGTTCGTGTCGTTGACACTATTTTGAAAAACACTTATCAGATATTTGACGACGACTGAGGCGAAG*

*AAGATTGTCGATTGACTTGAAGAGTTCTTAACGAGATACCATAGCTGCTCATATTATGAACCTGCCTTTGGAACAGAAA*

*CAAGGGCAGGGAATTCCTAGCATCAGACCTCTATTTGCCGACAAGACATTCTAAAGAAAGTACATGCCACTGTATTTCG*

*AATACTATTATTGTAAGGCACGGGCCTGTTGACAAATATTTACGGTCTATCAAGCGAGTGTACGTCAGGGGGTGGTCT*

*ACACCACGATCGATTTTGTAGGGTCATGTGCTCAGCTCTGATGCCAGTATTGGTGCAACTATTGAATCAAAAGGGTACC*

*AAGGTTTCAATACTCGTTAATTTTGGATCACGAAAAGATCA*

*Sclerotinia sclerotiorum*, Ss_Rgd1p, SS1G_03990

SEQ ID NO: 10

*ATGTCATTTGGAGGGGACACCGGACTTGATTCATCATCGTCGCCCAATATCGTCGGCAATGGCAACAATGGCGAGACA*

*ATCGGAAGGCCTGCAACTCCTCAAGATGCAGCCACGAAAGCGGTTCACGATGTTACAAGCTCCGAGGTGATTGAGTC*

*AACCAATTGGAATATCAACCTTGTTGAACCGGTTGAAACAGAGCATTGCTTCCGCAAAGGCAGTCCCCCCCGAACTTT*

*CAACGTCTGCATAGATATGGAGCTGACTTCTTCGAAACAGGAGTTCGCACTTTTCCTCAAAAAAAGGTCCATAATGGAA*

*GAGGAACATTCGAATGGATTAAAAAAGCTGTGTAAAGCAACTGGAGATAATATTCGCAAACCAGAGCATCGCCATGGT*

*TCATTCCTGCAGTCATATGAAGAGATTCTTATTATACACGAGCGAATGGCCGAAAACGGGGCTCAATTTGGCGTGTCTC*

*TACATCAGATGCATGAAGACCTTATTGAAATGGCTTCGAATATAGAGAAGGGTAGGAAGCACTGGAAAAATACTGGCTT*

*GGCAGCAGAGCAGCGTGCTGCTGACACGGAAGCCGCCATGAGAAAGTCAAAGGCGAAATATGATAGCTTGGCGGAT*

*GAGTACGACAGAGCTCGCACCGGAGATAGGCAACCGGGCAAGATATTTGGCCTCAAGGGACCTAAATCGGCAGCGC*

*AACATGAAGAGGACCTTCTCCGTAAGGTTCAGGCTGCAGATGCAGATTATGCAGCGAAGGTACAAGCTGCACAAAGC*

*CAGCGCTCTGAGCTCTGGTCAAAGTCAAGACCCGAGGCGGTGAAAGCGCTAGAAGATCTCATTCAGGAGTGTGACTC*

*TGCATTGACATTACAAATGCAGAAATTTGCGTCCTTCAACGAAAAGTTACTTCTTAGCAATGGTTTGAACATAAGCCCTA*

*TCAAAGCCAAAGAACAAGGCACCTCGAATCGTAGTCTGCGTGAAGCTGTTCATGCCATCGATAACGTTAAAGACCTGA*

*GCAACTACATCAGTAGCTTTGCCGGTAAGGTACCATCACGGGTCACGGAAATAAGATACGAGCGTAACACGGTCTTGC*

*AACCTGCAGCAAATATTGCCCAACGACAATCAGACCCCAACGCTCTCAACTCTCGACAAGGACCAGGAATATCATCTC*

*AGCAACCTCATCAGGTGCATGTAAGCCAAACCTTTAACCAAGGCACTCCGCAAACACACCAGCACGAAAGAAGTTTTA*

*GTCACGGCCCCTCTCTTTCGCAACACATCGTTCCAACTGTTGCATCGCCCACGGCGCCAACATCCACCTCCCCTGACT*

*TCACCACCTGGTCACCTCGTACAGATGGGCCTCCTCAAATCTCAACATTGCCGTTTCAGCCACTGCCTCAGAACGAGA*

CAGTTTTGCAACAAACACCACCAAATCCTACGACTCATGCTCCAGCATCCCATGGACCACCTTCGGCACTATTATCTGG

*ACCAGGACCTCCGGCTTCAGGCAATAATACACATCTAGCGCCTTTGAAACCAGTATTTGGGCTTAGCCTCGAGGAGCT*

*CTTTGAGAGAGATGGCTCTGCTGTTCCTATGATTGTCTATCAATGTATTCAAGCAGTTGACCTCTTTGGGCTCGAGGTT*

*GAAGGGATATACCGACTATCTGACGCATCTAAGGTGGACTTTCGTAACCCTGAAAGCTTCTTCCACGACGTTAATAGTG*

*TCGCTGGCCTTTTGAAGCAGTTTTTCGAGAGCTCCCAGACCCTCTACTGACTAGTGAACAATACCCCGCATTCATCGA*

*GGCCGCAAAGCATGATGATGAAACAGTCCGTCGCGACTCTCTTCATGCCATCATTAATGGCCTCCCCGATCCTAACTA*

-continued

*TGCTACTTTGCGCGCCTTAACCTTACATTTAAATCGAGTGCAGGAAAGTTCGGCGTCTAACAGGATGACTGCAAGCAA*

*CCTGGCTATTGTATTTGGACCTACTCTCATGGGAGCTAATTCTGGACCAAACATACAAGATGCTGGGTGGCAGGTTCG*

*CGTCATTGACACCATTTTGAACAACACCTATCAGATATTTGATGACGACTGA*

*Botrytis cinerea*, Bc_Ufd1, BC1G_10526

SEQ ID NO: 11

*GTTTCCAAGTACAGTACAGTACCACTTCAAGTACATAAACTCAGCGCTCTTCTTGAGATAAAAGGTTAAAGGGTTGCAA*

*GATTTCTTTGATACATATCATTGGAAATAAAGTATTCCGGATTACATTAGAGGAAGCTCACTGTAACAGGTTTCTGCTTT*

*GTTGTTCATGGACATGATGGCAGCAACTCCAGACATTTCTTTGACCTGGTCATCAGTCTATAAAGTCGCCCCAAAAGAC*

*AACGTCTCGCTGCCCGGGGACAAGATACTACTACCTCAATCAGCGCTGGAACAACTACTATCGGCATCTACAGTTACG*

*GTGAATTCTAACACTCGCCCCAGCAATGTTGCATTTGATCCATTCAATCCATATTCATTGGCAGCCGCTCGCATAGAAC*

*AGTCGCAATGGAGAGATACCCAACAACAACTGCCCCATCCTCTCACCTTTAGGCTGGTCAACTCGAAGAACGGAAATG*

*TAGTATATGCAGGAATTCGAGAGTTCTCGGCAGATGAAGGAGAAGTTGTCTTAAGCCCATTTTTGCTAGAGGCATTAG*

*GGATCACTGCGCCCTTACGAAATCCAACACCACCAAGTTCAAAGGTTGAAAGCAGGAGAGGGTCGCCGGATACGCCT*

*ATAGATCTTACAGATAACCCTGCAATCGATCTTACGGGTGACGAGATGATAGACCTTACAGACGAAACCGAAGAACCG*

*GCGCAGATCACTGTACATGCGAAACAATTACCTAAAGGCACATACGTGAGGCTAAGGCCATTGGAGGCTGGTTATAAT*

*CCCGAGGATTGGAAATCATTGCTCGAAAAACACATGCGAGAAAATTTCACAACTTTAACGAAAGGAGAAATATTGACGG*

*TTCGAGGTTCAAAGTCGGAGGAATTCCGATTTCTGATTGATAAGTTTGCACCGGAAGGAGATGCAGTTTGCGTTGTTG*

*ATACAGATCTAGAGGTCGATATTGAGGCTTTGAATGAAGAGCAGGCTCGGGAAACCTTGAAGCAAATCATGTCAAAGG*

*CACAAAAAGCTCCAGGAACGGCTCAAGGGAGTTCAATTGGCGGAGAATTAGATCTTTGGAATGCTTTGCAGGGACAG*

*GTCGCAGAAGGTGATTATGTCGACTATACTTTACCTTCATGGGATCGATCAAATGGTCTTGATATTGAGCTTTCACTTGA*

*GGACGATGGTGATGGTGATGTGGAGATATTCATTAGTCCTCAATCAGCCCATCAAAGAGCAAAACCACGGGAGGATGA*

*ACATGTTCTCGGAGATTTCTCAAGTGACAAAATCAAGAGAATAACCATACAACAATCAAATGTGGAATTAGACGGAGCT*

*GATGCTATATTAATTTCTTTATACTGTCGAGGAACTGGAGCAGGCTCTGAGCCACCACATGGACCACGGAAGTATTCCA*

*TTAGAGTAAAATCGCTTGAAAAGGGGGCAAGCAATGGGGCCCCAAGCAACCCAATCTCGCTCGAAGAAGATGCCGAA*

*ATGCATGGATCTGATGAGGAGCAATGTAAAAATTGTCATCAATGGGTGCCAAAGCGGACAATGATGCTTCATGAGAAC*

*TTTTGTCTCCGCAATAATATCTCATGCCCTCATTGCAATGGCGTCTTTCAGAAGAAATCTTCAGAATGGCTGAATCATTG*

*GCATTGTCCTCATGATTCAGCCCATGGAAATTCCTCAGAAAGCAAAACTAAACACGACTCTATTTTTCACGAAGCTCGA*

*CAATGTCCCAATTGCCCTTACGAAGCAACAAATATGAGGGATCTTGCCACTCACCGTACGTCTATTTGTCCTGGCAAGA*

*TCATTCTATGTCAATTTTGCCATCTTGAAGTTCCTCAAGAGGGCGACCCCTTCGATCCGTCTCCAGAAAGTCTTATTTCC*

*GGACTTACAGCACACGAGCTTGCAGATGGGGCTCGAACTACGGAATGTCACCTGTGCAGCAAAATTGTTCGACTTCG*

*GGATATGACCACCCATCTTAAACATCACGAACTCGAAAAGAATAGCCGATTTAAACCAGCCATCTGTAGAAATGCAATC*

*TGCGGTAGAACTCTGGAGGGCGTTGGTAAGAATGGGGAAGTGGGCGCTGGATCGAGAATGGGCCAAGGACCTGGTA*

*ATGATTTGGGTCTTTGCAGTATCTGCTTCGGTCCACTATACGCTAGTATGCACGACCCATTAGGAAAAGCAATGAAACG*

*CCGCGTGGAACGAAGGTATCTGAGCCAGATGATCACGGGATGCGGCAAGAAATGGTGTACAAACATCTATTGCAAGA*

*CTGCAAGGGCGAAAGAAGCGAATGGGCCTCAGGCAATACTAGCGATGAAAGATGCCCTTCCTCTTATTCAGCCATTAG*

*TAGCCCAAGTAGAGGATAAGACCGAACCGATGCATTTCTGTGTCGATGAAGGAAACCAGAAGAGAAGAAATCTGGCTG*

*AAATGTTAGCTATGGAGCCTGGAGGTTGGGAATTGGAGTGGTGTGTTGCGGCTTGTGAAGCAGAAGGTGCAAATCTT*

*GATAAGGCCAGGACATGGTTATCTAATTGGGCTCCCAAGAAAGCTTGATGTGGTTCAGATCTGGAAGATATTTTGGTAT*

*GGATGAAAGGGATGGAGCATGGCGTGGTACCGATTGCATAAGTAAGGGAGTTCTGGTGGCTGATGACGATATGATAT*

GATATGATACCAATTTATAGACCCGATTTTGTTGTGCGTACATAAATATACATGGTTGGCGTCGCATTAGCTAGAGATAG

*ATCGAACAGATTAAGAATTTACTGCTAATACATAAACATATATACATTCTTCA*

-continued

*Sclerotinia sclerotiorum*, Ss_Ufd1, SS1G_04151

SEQ ID NO: 12

*ATGGCGGCGACTCCAGATATCTCTTTGAAATGGTCATCAGTCTATAAAGTTGCCTCAAAAGACAGCATATCTCTGCCTG*

*GTGATAAGATACTGTTACCGCAGTCTGCTCTGGAACAGCTATTAGCAGCATCTACGGTTACGGTCAATTCTAACAGCC*

*GCCTAATGTCGCATTCGATCCATTTAATCCATATTCTTTAGCAGCAGCTCGCATAGAACAGTCGCAATGGAGAGA*

*TACTCAACAGCAACTACCTCATCCTCTCACATTTAGGCTCGTCAATTCAAAGAATGGGAATGTGGTACATGCAGGAATC*

*CGAGAGTTCTCTGCAGATGAGGGAGAAGTTGTCCTGAGCCCATTCTTGCTTGAGGCATTGGGAATCTCTGCGCCCAC*

*ACGAAAATCTACGCCAAGTCCCAAAGTTGAGAGCGAGAGAGGATCCCCTAGTGCGCCTATAGACCTTACAGATAACCC*

*TTCGATTGACCTTACACGCGATGAGACGATAGATCTTACAGATGAAATTGAAGAATCTGCGCAAATCACCGTACATGCG*

*AAACAGCTATCTAAAGGTACATATGTGAGGTTAAGGCCGTTGGAAGCTGGGTATAATCCTGAGGACTGGAAATCGTTA*

*CTAGAAAGACATTTGCGGGAAAATTTTACAACTTTAACAAATGGAGAAATATTAACGGTTCGAGGGTCAAAGTCAGAGG*

*AATTTCGATTTTTGATTGACAAACTCGCGCCTGAAGGAGATGGGATTTGTGTTGTTGACACCGATTTAGAGGTCGATAT*

*AGAAGCTTTGAATGAGGAACAAGCCCGAGAAACCTTGAAGCAAATCATGGCAAAGGCACAAAAAGCTCCAGGAACGG*

*CCCAAGGAAGTTCTATCGGTGGAGAATTAGACCTATGGAAAGCTTCGCAAGGACAGATTGCTGAAGGAGATTACGTGG*

*ATTATACTTTACCTTCATGGGATCGATCAAATGACCTTGAGATTGAGCTGTCGCTCGAGGATGATGGCGATGTGGAGAT*

*TTTTATTAGCCCTCAATCAGCTCATCAAAGAGCAAAACCGCGAGAAGATGAGCATGTTTTTGGAGATTTCTCAGAAAAT*

*AAAACCAAGAGGCTCGTCATACAACAATCAGACGTGGAATTAATAGGAGCTGATGCAATACTAATTTCCATATACTTCC*

*GAGGGTCTGGAAGTGAGTCATCACAGGGGTTACGGAAATACTCTCTTAGAGTGAAATCGCTTGAGAAAGGGGCAAGC*

*AATGGATCTTCAAGTAATCCAGTTTCGCCCGAAGAAGATACTGAAATGCATGGATCTGATGAGGAGCAATGTAAAAATT*

*GCCATCAATGGGTACCGAAGCGGACAATGATGCTTCATGAAAACTTCTGTCTTCGTAATAATGTCTCATGTCCTCATTG*

*TAACAACGTGTTTCAGAATCCCAAGAATGGCAGGATCATTGGCATTGTCCTTATGATTCTTCCTACGGAAATACA*

*CCAGCAAGCAAAACCAAACACGATTCTGTATTTCACGAATCCCGCCAATGTCCCAATTGTCCCTATGAAGCAACAAATC*

*TCAGAGATCTTGCTACCCATCGTACGTCTGTATGTCCCGGCAAGGTTATTCTTTGTCAATTCTGCCATCTCGAAGTCCC*

*CCAAGAAGGCGACCCCTTCGATCCGTCCCCTGAAAGTCTCATATCTGGGCTCACAGCCCACGAGCTCGCTGATGGAG*

*CTCGAACTACGGAATGTCACCTTTGCAGCAGGATCGTTCGACTTCGCGATATGTCCACGCATCTCAAGCACCACGAAC*

*TTGAGAAGAACAATCGATTCAAACCAGACATCTGTAGGAATGTCAACTGTGGTAGAACTTTGGACGGTGTTGGTAAGAA*

*CGGGGAAGTAGGAGCAGGTTCGAGGATGGGTCAAGGACCAGGTAATGATTTGGGTCTTTGTAGTATTTGCTTCGGCC*

*CACTATACGCTAGTATGCACGACCCGTTAGGAAAGGCGATGAAGCGTCGTGTGGAACGAAGATACTTGAGCCAAATAA*

*TTACGGGATGTGGCAAGAAATGGTGTACAAATCTCTATTGTAAGACTGCAAAGACTAAAGACGCCAATGGGCCCCAGG*

*TGGCATTATCGGTAAAAGATGCACTTCCCCTCATTCAACCATTACTAGCCCAATTAGAGGATAAGACCGAACCAATGTA*

*TTTCTGTGTGGATGAAGCAAATCAGAAGAGGAGAAATCTGGCGGAAATGTTGGCCATGGAACCAGGAGGTTGGGATC*

*TAGAGTGGTGTGTTGCGGCTTGCGAAGCAGAAGGTCCAAATCTTGATAAAGTCAGGACATGGTTAAGTAATTGGGCTC*

*CAAGAAAAGCATGA*

*Botrytis cinerea*, Bc_Integral, BC1G_03606

SEQ ID NO: 13

*GGATCGCAACTAACTCTTCTGGAAGGTTCTTGTGGCAATATCAACCACATGGATCTTCAGTACCACCGCCGTCAAATTG*

*GCTGTGCTTGGGTTATATATGCGAATCTTCACCACGCCCGTTTTCAAGCGATGGGCCGTCTCTTTGATGACCATAGAC*

*GTTTGTTTCGGTATCACCTTCTTCGTCGTGTTTTTAACTCATTGCAACCCAGTCTCTCAAGAATGGAACCCTGTTCCACG*

*GGGTTCATGCAGATCTCTAACATTGTCCGAGTTTTCCTCCATCGCTCTCAATCTGGCTCTCGACACGGCAATCATCATT*

*CTCCCTATGCCATGGCTATACAAGCTTCAAATCGCATTAAATCACAAGCTTTTTGTGATGGTCATGTTCAGTTTCGGCTT*

*TGCAACTATTGCCATCATGTGCTATCGTCTTGAATTGACAGCCCGAAGCCCTTCTGATCCCATGATTGCCATTGCAAGA*

*GTCGGAGTGCTGAGCAATCTCGAGCTTTGGATTGGTATTATTGTTGCCTGCTTACCTACTATGAAACCTTTTGTTAGAG*

*TATATCTCAGACCCAGCCTATCAAAGCTCTCCCAAAAACTTTATGGCAGCCCCACAGTGTCAACAAAAGACGAAAATCC*

-continued

*ACAACTTCAGCTAAGGAACTTCGGGGGTTCCGGACCTTCACGCCCCCAAAAAAAACAGTAACTACACTGAACTTTCTG*

*AAGCTCCATCTGTGCAGACAGATACTGACGAGTTGCATCTCGTTCCAAATGAATCATCCAATTTTGATGCAAATTGTGA*

*ATCTAGCAACA*

*Botrytis cinerea*, Bc_Sec31p, BC1G_03372

SEQ ID NO: 14

*GAAGCTTTAAAACATACGATTATTTGATCCTGTTTGAACACGTTTTCTTGAAATTTCAAGCTTGAATGAAACACAACACCA*

*AGTCTATCGGCCAAAGGACCCCTTTGAGATTGCATTGAGCGTTGTCCCATCTCAAGATTTAACAACTGTTATTCACGAA*

*ATCATGCCTCCACCACCACCACCTCCTCCTCCGCCGCCTCCTCCGCCTGGAGGAGCTCCAGGAGGTATGCCATCCAG*

*ACCACCTGCGAAAGTTGCTGCAAATAGAGGCGCACTTTTGTCGGATATCACGAAGGGAAGAGCACTCAAGAAAGCTGT*

*AACTAACGATCGATCGGCACCGGTAGTAGGCAAAGTATCTAATGGTTCTGGACCTGCGCCAATAGGAGGTGCTCCTC*

*CAGTACCGGGAATGGCAAAACCTCCCGGTGGATTTGGCGCACCGCCAGTACCAGGAGGAAATAGAGCTCGAAGTGAT*

*AGTAACCAAGGGAGCAATAATGCGGTTTCGGGGATGGAACAAGCTCCACAGTTAGGAGGAATATTCGCAGGCGGCAT*

*GCCCAAGTTGAAGAAACGAGGTGGAGGAGTAGATACTGGCGCAAACCGCGACTCATCGACTGCATCGGAACCAGAAT*

*TCTCTGCTCCCAGACCGCCAGGTATGGCTGCTCCCAGACCTCCAACAAATGCAGCTCCGCCTTTGCCATCAGTCCGG*

*CCTCCTCCTCAACCTAGCGCTAGTACTCCCGCATTTGCGCCCTCGGTTGCAAATCTGAGAAAGACCGGCGGGCCATC*

*TATTTCTCGTCCTGCATCCTCAACCTCTCTCAAGGGGCCACCACCCCCTATTGGCAAAAAACCTCCTCCACCCCCTGG*

*AACTCGAAAGCCATCATCAGCGCTATCAACCCCACCACCACCACCGCCTCCAGCATTCGCCCCTCCACCTCCTTCTTC*

*AGCACCTCCGCCACCTGTTGCACCTCCACCACCACCTTCCCCAGCTCCACGCCCTCCGAGTAACCCACCTCGATCAC*

*ATGCACCACCGCCACCACCACCACCACCACCACCAACATCTCCACCTTCGACTAACGGAGGTAACCCAAGTCTTGCTA*

*TACAAGCAACAATTCGTGCTGCTGGCCAAGCATCACCAATGGGTGCACCACCACCACCACCACCGCCTCCTCCTCCAT*

*CTAATGGGCCTCCCTCTCTCTCGTCGCACAGAACGCCATCTCCGCCCGCGGCACCCCCAGCGGCACCCCCAGCGGC*

*ACCAATATCAAGAAGTCAAAGTCAACAAGGAAGAACTCACACAATGGATTCCAGTTCTTATACCCTTTCATCAAACGGC*

*AGTTTACCGCAAGCCTCTAGTTCTAGCAGAAGAATCATGATCAATGATCCTCGATGGAAATTTACAGATGAATCGGTAT*

*TCCCAAAACCTCGAGATTTTATTGGTGGGCCCAAAAAATACCGGGCTGGTCGTGGAAGTAGTGTTCCGTTGGATCTGA*

*GTGCTTACCATTAAGAATTTCGCTTACCAAAAAGAATATAACTCTTCGGATCGTATTCATGTGTTACCATTATGATTTAAG*

*GCGTTATAGCGGGATATCATTTAGAATCCGGTAAGGCGGCATCAAGCTATCTGAATTGGGAGTTATACATCAGGACAC*

*TAAAGATCGTCAAAAAATTTCCCCTGAATCGCGAGATGGAGATTGACGAGAGACATCAGCTCACTACCCAGGGTACCG*

*AGGAGGAAATCGCAGCTATAAATATCACGGGTGATGGGCAAATTCCACAGTGGAACCTTAAAAGAATGAGTACGGAGA*

*ATATTAAACTTTTGAGATTTATCTTTCTCTTCCTGTGATTTTAACCA*

*Sclerotinia sclerotiorum*, Bc_Sec31p, SS1G_06679

SEQ ID NO: 15

*ATGCCTCCTCCACCTCCTCCACCACCTCCTCCTCCACCGGGATTTGGTGGTCCTCCTCCCCCTCCACCTCCTGGAGG*

*AGCCCCAGGATCGATGCCATCAAGGCCACCTGCGAAGGTCGCTGCCAATAGAGGCGCACTTTTGTCAGATATCACAA*

*AAGGAAGAACACTCAAAAAGGCTGTAACCAACGACAGATCGGCACCAATAGTAGGCAAAGTATCCGGTGGCTCTGGG*

*CAAATGCCAATAGGAGGTGCTCCACCAGTACCTGGAATGGCAAAACCTCCTGGGGGTTTCGGCGCACCACCCGTACC*

*TGGGGGAAACAGAGCTCGAAGTGACAGTGAACATGGGAACGGCGTGTCTGCAGGAATGGAACAACCTCCACAGTTAG*

*GAGGAATTTTCGCAGGTGGCATGCCCAAGTTAAAGAAACGAGGCGGAGGAGTAGACACTGGCGCAAATCGAGATTCA*

*TCATTCACATCAGAACCCGAATTTTCTGCGCCTAAACCACCAGGTATGGCAGCTCCTAGACCTCCAATAAATGCAGCTC*

*CTCCGTTACCATCAGCCCGGCCTCCTCCTCAGCCCAGTCCTTCGGCACCTACATTCGCGCCATCGATTGCCAATTTGC*

*GAAAAACTGCTGGGCCATCAATTTCTCGACCTGCTTCTTCAACTTCTCTCAAGGGACCACCACCTCCTATTGGCAAGAA*

*ACCTCCTCCACCTCCTGGGACTCGAAAGCCATCAGCTTTATCAGCCCCACCACCGCCATCATCATTCGCACCTCCACC*

*TCCTTCTTCGGCCCCTCCACCGCCTGCTGCACCGCCGCCACCACCTTCTCCAGCTCCGCGCCCTCCCAGTAACCCAC*

-continued

*CTCGAGCACATGCGCCCCCTCCTCCACCAACGTCTCCACCTTCGGCTAATGGAGGTGGTCAGAGTCTTGCTATGCAA*

*GCAGCAATTCGTGCTGCCGGTCAAGCATCACCAATGGGTGCACCCCCTCCACCGCCGCCACCCCCATCTAGTGGACC*

*ACCCTCTATATCGTCACACAGAGCGCCATCTCCGCCTGCACCGCCAGCTGCACCAATATCAAGAAGTCAAAGTCAACA*

*ACAAGGAAGAACTCACCCAATGGATTCTAGCTCATATACTCTATCGTCGAACGGTACCTTACCGAAAACCGCCAGCTCT*

*GATAGGAGAGTTACAATCAACGATTCTAGATGGAAATTCACCGACGAATCAGTATTTCCCAAACCTCGGGAGTTTATTG*

*GTGGACCCAAGAAATATCGGGCTGGCCGTGGGAGCAGTGTTCCGTTGGATCTTAGTGCTTTCCATTGA*

*Botrytis cinerea*, Bc_Gyp5p, BC1G_04258

SEQ ID NO: 16

*GATATTGTACACGAGCCTCTTCCTGCATTGATTGATTGATTGCTCTTACACATATCCAGTTCATCTCCCACAAAATACCA*

*AGCGGCCGCATTTGGATGCAACATACATACTCACTACCTTCCACTTCACCTACCTACCTACTGACTTAATATACCTTCTT*

*GTCATCTTTGATGGCACTGAATAAAGTACCTTCCTATTAAAACTACCTCAACCAGTCCAGTCATTACTACCCACCTTACA*

*TCTCGAGAAGCCTCCTTCCTCGATATACATTCTTCTCTTATATTAATGCAAAGATGTCGGAGCACGAACATCAAAAACAT*

*CTTTCCGATTCTGAAGAAGATTCCATAATGGAAGAGAGAGAGGAGAAAAAGGGAAAAGACGAGATAGAGGAGAAAGA*

*CAAAAAAGACGAGAAAGACGAGATAGAGGAGAAAGAGGAGAAAGAGGAGAAGGAGAAAGACAAAAAAGACGAGGAA*

*GAGAGAGAGGAGAGAGAGGAGAGAGAAGAGAGAGAAGAGAGAGAGGATACAGTTGATCAGAGTTCTGATCATGAGA*

*GTGACACCTTCGAGGATGCCAATGATGTTGAAGACATTGCAGACACTCTTACCTCCCCAGTTGAAAGGACAAGATCTTT*

*AACGAAACGAAGATCATCATCCATTAAGAGCAATACACAAGACCTCAGTACCGATATCCCATCGGTCCCAACAGTACCA*

*CTTCCAGAAACGAATGGCGAAACGAATGACGAACAAATAGAATCCGATAATCCACTACCTAAATCTCCCCTTTTAACAT*

*CTCATCGCATGTCCACTACATCCCTACATAATGTGAATCTCGAAGACGGTGATGATTTTGGATCACCTCCACCACCTCC*

*TCCCGTTTCGAAAGTAGCACCAGAAGATCAACCACCCGAATTACCTCCAAAGCCCAATACAATAATTCCAATGCAGGG*

*CCTTTCTGGAGCCCTTCCAGATGTGCCATTCTCACCGCCCCCTCCTCCTCCTCCCGCTCCTCCCGCTCCTGCAAACCT*

*CGCTGCGCCAGCACCTGTCACCAGAAAATTAACCAGCCCATTCTCATGGCTGTCGAGAAATACCTCGGCTCCAAAAGA*

*GAACGTCAAGTCACCGCCATTACCTTCATCTCACGCAACCGAGCGTAGACATACCGCTTCTTCGATAGCGACCATTAG*

*CAGCAATCCTGAAATGATGGTAAACAAATTGGAGGAGGGTAATGATACAGATGCCGCGAATGGAGTTAGACGACCTG*

*GGAGGAATAGTTTACGGGACAGGTTTAAGCTCGTGAGAATGCGAGAAGAGGCTGGAATAACAGAATTGCCTGAAGAA*

*AAGGATGAAGCAGGCAACACAGCATTTGGGGGTCTCATTAGGCAGAGTACAAGTCTTGGTTTGGGATTTACCGCCTCA*

*AATGATGACAAAGACCCTTCTCCCGTATCTCCTGGTCCGCCTACGAGTCCCAACCCAATTAGTGTCAACCCTGCATTA*

*GCCCCCGGTACGGCATCTGGAGTTTCTGCAGGCCCTTCTGCATTGGGTGAATCAGAAGCACCAGTCGATTGGGATTT*

*GTGGCAAAATGTCGTCTGGGAAGGACCAGCTGCGGTAGCAAGAACAAGTGCAGAAGAGCTGAATCACGCTATTGCAA*

*CTGGTATACCACATGCTATCAGAGGCGTGGTATGGCAAGTATTGGCGGAGAGTAAGAATGAAGAGCTCGAGGTTGTC*

*TATCGGAATTTGGTCAATCGGGGCACAGACAAGGACAAGGACAGGATGAGTACATCTAGTGGGACACAAAGCAATGG*

*ATCAATCAAGGAGATTGTGGTTTCATCAGCATCATCAATACATTCAGAGAAATCTACACCCGCTACGACAATCACCAAT*

*GGAATGAGATCTCCTTCTCCCCCTAGTGAAAAGGATGTAGCCCAGTCTTTGGCTGAAAAGAAAAAGAAAGCTAAGGAG*

*GATGCGGCGGCATTGACAAAACTCGAGAGAGCCATAAAGCGGGACTTGGGTGCTCGAACAAGTTATTCAAAATTCGCT*

*GCAAGTGCTGGACTACAAGATGGATTATTCGGTTTATGCAAAGCATATGCTCTTTATGATGAAGGTGTTGGTTATGCAC*

*AAGGCATGAATTTCTTAGTTATGCCTTTGCTTTTCAACATGCCCGAAGAAGAAGCATTCTGTCTATTAGTACGACTTATG*

*AATCAGTATCACCTTCGAGATCTTTTTATTCAGGATATGCCAGGTCTACATAAACATCTTTATCAGTTTGAGAGATTATTA*

*GAAGATTTTGAACCAGCATTGTATTGTCATCTCCATCGACGTCAGGTCACACCTCACTTATATGCTACGCAATGGTTCC*

*TAACTCTTTTCGCCTATCGATTTCCATTACAGCTTGTGCTTCGAATTTACGATCTCATTTTAAGCGAGGGTCTCGAGGCT*

*ATTCTCAAATTTGGAATTGTACTCATGCAAAAGAATGCAGCTCATCTACTCACCCTCCATGATATGGCTGCATTGACTAC*

*GTTCCTGAAAGATCGACTTTTCGATGTTTACATTGATGCTTCACCTTCAGCAGGATCAATTCTAGAATCTGGTTTCTTTG*

*GAAATTCAGGAGCGACTATCGATAAGGAAGTTTATCGAGCAGATCATATGATTCAAGATGCTTGTGCCGTCAAAATTAC*

-continued

*ACCCAAAATGCTGGAAACTTACGCATTAGAATGGGAGGAAAAGACCAAGATAGAAAAGGATCGTGAAGCAGAATTAGA*

*ACACTTGAAATCAACAAATGTCGCCCTTACACACAAAGTTCGACGTCTGGAAGAAAGAGTCGAATCTCACGATACGGA*

*GCACGCAGCTTTGGCAACTGAACTTGTTCGGACTAAGGTCGAAAATCAAGAGATTCATGAAGAAACAGAAGTTCTTAAA*

*GAACAAGTTAAAGAACTGAAAAAAGTAATTGATAAGCTACCGGAAGAAATTGAAGCGAAATTACAGAGTGAGATGGATA*

*GATTGATGAAGAGAAATCAAGAAGTTCATGAAGAAAATCAAAAATTGGAGGATGAAATGAATGAAATGGAACAAAACTT*

*GGTGGAAACAAAAATGAAATATGCTGAGATGAATGCGGCCCATGAAGCTCTAACTCGTAAATGGACGGATTTGAGAAA*

*AGCTTTGGGTGATTAATATCGTTACTTTGAGATATCCTAAATTATTAAATACGACTTGTACAGTTCTTCTCAATTGATACC*

*GATGCCTTTGAAGTTTTTGGGGGGTAGGGGAGAGAGGCGTAAATGCCTATATTGGGGAACGAAGGAACAATGCTCTC*

*GTTTGGAAGCTTGCTGGATTTCTTGCTAGGTGGAGGGGATGATTGGGAATCAATCAGATTATACAGGTACTGCTGCAT*

TGGTACGCAAATGGTATAGGAATTGGCGTGGGTTGTAAAAGTACCGGAGAAATACTTTGGGTGCTTGCTTGTCTTGTTT

*CTCTCTCTTTTTTTTAGTCGTTTTAGCGAGTTGTGATGTTGGTAGGAAAGAAATTAAGAAATTATGGACGGGTAGGGGG*

*AGTGGAGAGAGGAAGGGAGGGGGTGAAAGAGGGTGGGGGGAGGGGAAGAAATAAAAATTAAGAATAAATGATCA*

*Sclerotinia sclerotiorum*, Ss_Gyp5p, SS1G_10712

SEQ ID NO: 17

*ATGTCTGATCACGAGCATCAACAGCATCATTCCGATGCAGAAAAAGATTCAATAATGGAAGAAACAGAGAAGAGGGTT*

*GAGCAGAGTTCGGATCATGAGAGTGACATGTTCGAAGATGCCAACGATGTTGAAGACCTCACAGATACTCCTACTTCC*

*CCAATTGAGAGAACTAGGTCTTTGACGAAACGAAGATCATCATCTATTAAGAGCAGTACACAAGATATCAGTAGCGATA*

*TTCCATCGGTCCCAACAGTACCACTTCCAGAATCAAATGGCGAAACGAATGACGAACAATTAGAATCCGATATTCCACC*

*ACCTAAATCCCCCCTTTTGACATCCCATCGCATGTCCGCTTCTTCCCTCCATAATGTAAATCTCGAAGACGGTGATGAT*

*TTTGGTTCACCTCCACCACCTCCTCCACTTTCGAAAGTAGCACCAGAGGAAATGACACCTGATCAACCACCCGAATTAC*

*CACCAAAACCCAGCATAATTACTCCAATGCAAGGTCTTTCTGGAATCCTTCCAGATGTGCCATTCTCACCGCCACCACC*

*CCCTCCTCCTGCTCCCGCGCCTGCGAATCTTCCTGCGCCCGCACCCGTTACAAGAAAATTAACTAGTCCATTTTCATG*

*GCTTTCAAGAAATACCTCGGCTCCAAAAGAGAACGTAAAATCGTCACCATTGCCCTCACCTCATGCGAATGAGCGAAG*

*ACATACCGCTTCCTCGATAGCAACCGTCGGCAGCAGTTCAGAAATGATGCTAAATAAATTGGAGGAGGGCAATGAAAC*

*AGATACCACGAATGGGGTCAGACGGCCTGGGAGGAATAGTCTGCGGGACAGATTTAAGCTCGTGAGAATGCGTGAG*

*GAGGCCGGTATTACAGAGTTGCCTGAAGAACAGGACGAGGCAGGCAATATAGCATTTGGAGGACTCATTAGACAGAG*

*TACAACTCTTGGTATGGGCTTTACAGGCTCTCACGACGACAAAGACCACTCACCCAACGGAGGTGTTCCACCTGCGAC*

*TCATAACCCAGTCAGTGTCAATCCAGCATTGGCCCCAGGTACGGCGTCTGGGGTTTCTGCGGGCCCTTCTGCGATGG*

*GTGATCCAGAAGCACCGGTCGACTGGGATTTGTGGCAGAATGTTGTGTACGAAGGGCCAGCCGCGGTAGCAAGGAC*

*AAGTGCAGAAGAACTCAATCAAGCTATCGCAACTGGTATACCGCATGCTATCAGAGGTGTGGTATGGCAAGTTTTGGC*

*AGAAAGTAAGAACGAAGAGCTCGAGGTTCTCTATAGAAGCTTGGTAAATCGAGGTACAGACAAGGACAAGGACAGGAT*

*GAGTACATCTAGCGGAGTACAAAGCAATGGATCAATAAAGGAGACTGTGGTTTCATCGGCATCGTCGATACATTCCGA*

*GAAATCTACCCCGGCAACTACTGTCACCAATGGAATGAGATCTCCCTCTCCGCCGAGCGAGAAAGATGTAGCATTGTC*

*GTTAGCTGAGAAGAAAAAGAAAGCGAAGGAAGATGCAGCGGCTCTGACAAAACTCGAGAGAGCCATCAAGCGAGACT*

*TGGGTGCTCGAACGAGTTATTCAAAATTTGCTGCAAGTGCTGGACTTCAAGATGGATTATTCGGTTTATGCAAGGCATA*

*TGCTCTTTATGATGAAGGTGTTGGCTACGCGCAAGGCATGAACTTTTTAGTTATGCCTCTGCTGTTTAACATGCCTGAA*

*GAAGAAGCATTCTGTCTATTAGTACGACTTATGAATCAGTATCACCTTAGAGATCTTTTTATTCAGGATATGCCAGGTCT*

*TCATAAGCATCTTTATCAATTCGAGAGATTATTAGAAGATTTCGAACCGGCGTTGTATTGCCACCTCCATCGACGTCAA*

*GTTACACCTCATTTATACGCAACACAATGGTTCCTTACTCTTTTCGCCTATCGTTTCCCATTACAACTTGTGCTTCGAATT*

*TATGATCTCATTCTTAGCGAAGGTCTTGAGGCAATTCTTAAATTTGGCATCGTACTCATGCAAAAGAATGCGGCCCACC*

*TTCTTACACTCACTGATATGGCTGCATTAACCACATTCCTTAAGGATCGACTTTTCGATGTTTATATTGATGCTTCTCCTT*

-continued

*CAGCAGGATCAATACTGGAAAATGGTTTCTTCGGAAATTCTGGTGCGAGTATTGATAAAGAAGTTTATCGAGCGGATCA*

*TATGATTCAAGATGCTTGTGCTGTCAAGATAACTCCAAAGATGTTAGAAACGTACGCATTAGAATGGGAAGAAAAAACC*

*AAATTGGAGAAAGAACGAGAAGCAGAGTTAGAAAACTTAAATTGACGAATATCTCTCTCACACACAAAGTTCGACGTCT*

*AGAAGAAAGAGTCGAATCTCATGATACCGAGCACGCGGCCTTGGCTACTGAGCTTGTTCGTACTAAAGTCGAAAATCA*

*GGAAATTCATGAAGAGATCGAGACTTTGAGGGAACAAGTTAAGGAGTTAAAAAATGTGATTGAAAAGCAACCTGACGA*

*AATCGAAGCAAAATTACAGAGTGAGATGGATCGATTAATGAAGAGAAATCAAGAAGTACATGAAGAAAATCAAAAACTC*

*GAGGATGAAATGAATGAAATGGAACAAAATTTGGTGGAAACAAAGATGAAATACGCCGAGATTAATGCAGCTCATGAA*

*GCTTTGAATCGGAAATGGACGGATTTGAGGAAAGCATTGGGCGATTAA*

*Botrytis cinerea*, Bc_Pan1p, BC1G_09414

SEQ ID NO: 18

*GGCTTCAATTGACGTTGAAACATGAATGCTGAATGATGATACGATACACTTTACTTCAGCCCCTTTAACATTTTGTCGCA*

*AAATCGGTGAAACTTGGGTTGTATGTATTTGTATATTAAAGATCGCTAAGCCCAGCCTCTATGGTAACAGATTACCTGA*

*GCTTCGTCATTTCGACCCCCGGACCGTGATCTTCTACCAACCTCGAACCCATTCCTTCAAATAAATGTCACAAATCTAT*

*CTTTCTTCATACCTATTTCTTTTTTGTTCATACTCATAATGTTTTCGGGTTCGAACTCGTACCTTGGTGGTAACACCGGC*

CGCCAACCACCACAGCAACCGCAACAACAATATGGTGGTTTCCAGCCAAACCAAGGTTTCCAACCACAGCAGACTGGT

*TTCCAGCCACAACAGACTGGTTTTCAACCTCAACCCCACAGGATATGGTAATGCGGCTCCTTTACAACCCAATTTCACCG*

*GTTATCCACTTCAACCACAGCCTACGGGATATTCTCAGCCCTCTCAAGCAGGCTTCCCTGGAGGCCAGCAGCAACAG*

*CAGCAGTTCAACAATGCTCCTCAACAGCAGAACTTCCAAACGGGAGCTCCCCCAATCCCGCAGATTCCGCAGCAATTC*

*CAGCAGCCTCAACAAACGCAACAGGCTCAACCACCTCCTGCACCTCCTGTGCAGCAACCGCAAGCGACCGGATTTGC*

*TGCAATGGCAGATTCATTTAAACCTGCTGCTGCAGAGCCATCGAAGCCAAGAGGACGCAGAGCCTCCAAGGGGGGAG*

*CAAAGATACCTAGTATACGACTTTCCTTCATTACAGCCCAAGATCAAGCAAAGTTCGAAACTCTTTTCAAATCCGCTGTT*

*GGGGATGGGCAAACACTTTCTGGGGAGAAATCGAGGGATCTTTTACTACGCTCAAAACTAGACGGGAACTCACTGTC*

*GCAAATATGGACGCTCGCAGACACTACAAGATCTGGACAGCTACATTTTCCCGAATTCGCATTGGCTATGTACCTCTGT*

*AATCTCAAGCTAGTCGGCAAGCAGTTACCATCCGTGCTTCCCGATGTTATCAAAAATGAAGTTTCTAGCATGGTGGATA*

*TCATAAACTTCGCTATAGATGATGATGCACCAGCGGCAACGAATGCGCCCAGTTTTGATGGTCGACAAAACACCGCGA*

*CACCTCCGACTATCCAACAACCACAGCCAATGGCGTCTAATTCCGCCCTTCTCACTGCGCAAATGACAGGTTACCCTG*

*GACAGCAGAATAACTTTTCGGGTGGATTTCAACCACAACAAACAGGCTTCCAGGGCCAAATGCAAACTGGCTTTTCTG*

*GACAGCAAGGCGGATTGCAACCTCAGCCAACTGGATATAATCAGATGTCAAACCCTCAAGCAACGGGCTATAATGGAC*

*CGCGCCCTCCAATGCCTCCTATGCCATCTAACTTCAGTTCTCATTTATCTCCGGCTCAGACGGGTATGCAAGGTGGAA*

*TGATCGCGCCATTGAATAGCCAGCCTACAGGAGTCGATGGCCAATGGGGCTTGGTAAATGCGCCAGCCCCCAATATC*

*GATCTATTACATTCCCGGATGATGCCGCAACAGGGTCGAGAACAAGGCAACTTCACCACGGCTGGTATAACAGGCAAT*

*GCTGAAATTCCATGGGGAATTACGAAAGACGAGAAGACCAGATATGATTCCGTTTTCAAAGCTTGGGATGGGTTTGGT*

*AAAGGATATATTAGCGGTGATGTCGCTATTGAAGTTTTTGGGCAGAGTGGTCTCCCGAAGCCTGACCTGGAGCGCGTA*

*TGGACCTTAGCAGATCACGGCAACAAGGGAAAGCTCAACATGGATGAATTCGCGGTTGCCATGCATTTGATTTATCGA*

*AAGCTTAATGGATATCCTCTACCAGCCCAACTACCTCCGGCGCTCATACCCCCTTCCACTCGTAACTTCAATGATTCGA*

*TTGGGGCTGTCAAATCTTTACTTCATCAAGAATCTAATTTCCGCAAGAACTCTGGTGCTACCCTTTTGCCACAAAAGACT*

*GGAGTGAGCTACCTCAAAAATCATTCTTTCCGTGGTGATGCTACCCCAGGTCGCACAGGCCGTAAAGACGCTACAGTA*

*TACAAAAATAACGACGATGATGTTGGGTATAAATCTAGTGCTCGTCGCAGACTCGGGGCCTCTTCTCCACGACCTTCG*

*TCTCCGGGATCAACAACTTCCAACGATGACCTTTCACTAGACCAGCTTAGAAAGAAAATCGCGGAGAGACAAGTGATA*

*CTGGATGCAATTGATTTCAAGGCCGAAAATGCTGCAGATGAAGATGATGCTCTTGATCGTAAAGATCGTCGTGAAGCA*

*GAGGATCTTTATCACCGCATTCGTCGTATTCAAGAGGATATCGATGCGCATCCAGACGCATCGTTGCGTAATGTTGATT*

*CCGGCGCCGAGCGTCGTGCTTTGAAAAGACAGTTGCAGACATTGACAGATAAACTTCCAGATATTGCTTCGCGTGTCC*

-continued

*GAAGAACGGAAAGAAGCATTGCTGATGCCAAGCTTGAACTATTCCGTCTAAAGGATGCCAAAGCTCACCCTGGAAGTG*

*CCTCTAGCATTGTTGGAACTGGTCCTGGCGGCGCTATCACCGAATCAGATAGACTCAAAGCAAGAGCCAAGGCTATGA*

*TGCAACAACGTTCTGCTGCTCTCACTGGTAAGAAGATTGAGGCGAGTAATGATGACTTGGATGCGCCAAAACGCCTCG*

*AAGAAGAAAATCTCAAGATTCGAACTGAGAAGGAAAACAACGAGCGCATGGTTCAAGATGTTGAAGAGAGTGTCCGTG*

*ACTTTTCACGAGGACTGGAGGATAGTCTCAAAGATGGTGGTGAGAGCTCGTCCAGTGAGCATGAGAAGAGACGTTGG*

*GAGGATGGGCTAGGTGTTGAGGATGAAGTGAAGGACTTCATCTTCGATTTGCAAAGGAGCAGCAGGAGTGCCAGAGT*

*TCGAACTGATGATCGCAGCAGAGAGACTCCTCGTACTGAAGCGTCTCATGCTAGCCCTGCTCCAGCAGCTCGTAGCG*

*AAACTCCATCGTCACAGCCATCATCTACACCAACCCCTGCTGGAGGTTCATACTCACAATACAAGACTCCTGAAGATAG*

*AGCAGCTTATATCAAGCAACAGGCCGAGAAGCGCATGGCTGAACGTCTAGCTGCTCTTGGTATCAAGGCACCATCTAA*

*ATCTGGAGAAACAACACAACAGAGACTGGAACGTGAAAAGAATGAGCGTGCAGCCAAACTCAGACAAGCAGAAGAGG*

*AAGATGCTAAACGTGAAGCTGAGAGGCAAGCTAGGATCGCTGAAGAGCAGGGTGCACCACCACCTGCCCCCGAGCA*

*ACCAAAGGAAACCGCGAAAAAGCCACCTCCACCCCCTTCAAGGAAGGCCGCAAGAAGTGACGCTAGTGAGCGCAAG*

*GCCGAAGAGGAGAGAATCATTAACGAGCAAAAGGCACAAATTATTGCCACAAATGAGCTAGAGGACGATGCTCAACGA*

*CAAGAGGCCGAGCTTGCAAAGGAACGCGAGGCGGCTCAGGCTCGTGTCAAGGCCTTGGAAGACCAAATGAAGGCCG*

*GGAAATTGAAGAAAGAAGAGGAGAAAAAGAAGAGAAAGGCTCTCCAAGCTGAGACCAAACAACAAGAAGCTCGTCTC*

GCAGCTCAACGCGCAGAGATTGAAGCCGCACAAGCACGTGAGCGAGAATTGCAACGTCAACTTGAAGCTATTGACGA

*TTCAGATTCATCTGATGATGACGAAGGTCCTGAGCAAGTTACCCCTCAAGCATCAACGCCCACTCAAGGAAGTCAAGA*

*GCTTGAGCGCAAAGAACCTTCTCCACCACCTCCTCCACCTTCAATTCCAGTTGTTGTATCACCAGTCCCTGCTATTGCA*

*ACAACAACTAGTCTTCCATCACCAACCCCACAAGTTACTAGCCCTGTTGTCAGCCCTCCAGTCGATACAGAGACCCGC*

*AATCCTTTCTTGAAGAAAATGGCCCAATCCGGTGACGCATCTACCGCATCTACTGCATCTAACAATCCATTCCATCGTC*

*TTCCTGCTCAAGAGCTTTCTACACCTGCACCAATTCAAGTTCAACCAACAGGTAACAGGCCATCTCGTGTTCGTCCAGA*

*AGAAGATGATTGGGATGTCGTCGGATCTGACAAAGAGGATGATTCCTCTGACGATGAAGGACCAGGTGCAGGTGGTG*

*CGCGTCATTTGGCATCGATCCTTTTCGGAACCATGGCACCTCCTCGCCCATTGTCATCCATGGGTAACGAAGCTACAT*

*CTGCGCCTGAATCTCCTGCTGTAGCATCTCCACCAGCGGCAACCCCCCCACCTCCACCAGTACCTAACTTCAATGCAC*

*CGCCACCTCCTCCAATGCCATCAGCCGGTGCGCCAGGTGGTCCTCCACCACCACCTCCTCCTCCACCAGGGATGGG*

*TGCTCCACCTCCACCACCAATGCCACCAATGGGAGGCGCTCCTGCTCCACCAGCAGGTGTACGACCAGCTGGTCTCT*

*TGGGTGAAATCCAGATGGGGCGATCGTTGAAAAAGACACAAACTAAAGACAAGAGTTCAGCTGCTGTTGCTGGAAGG*

*GTTTTGGATTAAATACCTTTCAAATCATTGAGAAGAGACAAGATGAAATGGAGGTTTGTGGTTAGCGAGCCTAAGAACA*

*TGGATTGTATTATAAATTACTTTTGGTTCATAGTATTGGGCAAGGGGGCTTAGGTGTGGAAGGTGCGAAACAGGAAAG*

*ATAAGAGACGAGCATAATTTGTAGTCGAAGTAGCAATTTGAAAATATTCGTTCGTTTTGATAGTCATTTGATGCACTTAT*

*CACCA*

*Sclerotinia sclerotiorum*, Ss_Pan1p, SS1G_05987

SEQ ID NO: 19

*ATGTTTTCGGGTTCGAACTCGTATCTAGGTGGTAATAGTGGCCGGCAACCGCCACAACAACAACCACAGCAACAGCAA*

*CAGTATGGCGGTTTTCAGCCAAATCAAGGTTTCCAACCACAACAGACTGGCTTCCAGCCACAACAGACTGGTTTCCAA*

*CCTCAACCCACTGGGTACGGAAACGTCGCTCCTTTGCAACCCAATTTCACAGGTTATCCTCTTCAAGCACAACCTACA*

*GGATATTCTCAGCCGCCTCAATCAGGGTTTCCCGGAGGCCAGCAGCAGTTCAACAATGCTCCTCAACAGCAGAGCTT*

*CCAGACGGGAGCTCCGCCAATGCCGCAGATTCCACAACAATTCCAGCAGCAGCCTCAACAAATACAGCAAGCCCAGC*

*CATCTCCAGCAGCTCCCGTGCAGCAACCGCAAGCCACGGGATTTGCAGCGATGGCAGATTCATTCAAATCTGCTTCA*

*GAACCATCGAAGCCAAGAGGACGCAGAGCCTCTAAGGGTGGAGCAAAGATACCCAGTATAAGACTTTCGTTCATTACA*

*GCCCAAGATCAAGCGAAGTTTGAAACCCTTTTCAAGTCCGCAGTCGGAGACGGCCAAACATTGTCTGGCGAGAAATC*

-continued

GAGGGATCTCTTACTGCGCTCAAAGTTAGATGGGAACTCATTGTCGCAAATATGGACGCTCGCAGACACTACAAGATC

TGGACAATTACATTTCCCCGAGTTCGCATTGGCAATGTACCTTTGCAATCTTAAGCTCGTCGGCAAGTCACTACCCTCG

GTACTTCCCGATCAGATCAAGAATGAAGTTTCTAGCATGGTAGATATCATAAATTTTGCTATAGAAGATGATGGGCCAG

CAGGAACGAATGCGCCGAGTTTTGATAGTCGACAGAGTACTGCAACGCCTCCGACTATCCAGCAGCCACAGCCAATG

CCGTCAAATTCTGCTTTACTCACTGCGCAAATGACTGGTTTCCCTGGACAGCAAAATAACTTCTCCGGTGGGTTTCAAT

CGCAACCGACAGGTTTCCAGAGCTCAATGCAAACTGGCTTTCCTGGGCAGCAAGGAGGATTGCAGCCTCAGCCAACT

GGATTCAGTCAGAATATGTCAAACCCTCAAGCAACGGGATATACTGGACCGCGCCCTCCAATGCCCCCTATGCCATCA

AACTTCAGTTCCAATCTGTCTCCTGCTCAGACGGGTATGCAAGGCGGCATGATTGCTCCGCTGAATAGCCAACCTACA

GGAGTCCCAGGTCAATGGGGATTGGTCAATGCGCCTGCAACTGGTTTGCCTAACATCGATCTACTACAATCTCGGATG

ATGCCGCAGCAAGGCCGAGAACAAGGCAATTTTACTACAGCTGGCATAACAGGCAATGCCGTCATTCCATGGGCAGT

TACAAAGGAAGAGAAGACTAGGTACGATTCCGTCTTCAAAGCTTGGGATGGATTTGGAAAAGGATTCATTGGTGGTGA

TGTCGCTATCGAGGTCTTCGGGCAGAGTGGCCTTGAAAAGCCCGACTTGGAACGCATCTGGACCTTATCGGATCACG

GCAACAAGGGAAAGCTTAACATGGATGAATTTGCGGTTGCCATGCATTTGATCTATCGAAAGCTTAATGGATATCCTCT

ACCAGCTCAATTACCTCCCGAGCTTGTACCCCCCTCCACTCGTAACTTCAATGATTCAATTGGAGCCGTCAAATCGTTG

CTTCATCAAGAATCAGATTTCCGAAAGAATTCTGGCGCGACACTTTTGCCCCAAAAGACTGGACTGAAGAAGAAAGTCA

GAGAGAAGCAAGTGTTATTGGACGCGATTGATTTCAAGGACGAAAATGCTGCGGATGAAGACGATGCCCTTGATCGTA

AGGATCGTCGTGAAGCAGAAGATTTGTATCGTCGCATTCGTCGTATCCAAGAGGACATTGATGCGCACCCAGACGCTT

CATTGCGTAACGTTGACTCCGGCGCCGAGCGTCGTGCCATGAAGAGACAGTTGCAGACATTGACAGATAAACTTCCG

GATATTGCGTCGCGTGTTCGACGAACAGAAAGAAGCATTGCCGATGCAAAGCTTGAACTCTTTCGTCTAAAGGATGCA

AAAGCTCACCCTGGAAGTGCTTCCAGCATTGTTGGAACTGGTCCAGGTGGCGCGGTTACCGAATCAGATAGACTCAAA

GCAAGAGCTAAGGCCATGATGCAACAACGCTCTGCTGCTCTCACTGGCAAGAAGATTGAGATAAGTAATGATGATTTG

GATGCACCAAAACGCCTCGAGGAAGAAAACCTTAAGATCAGAACCGAGAAGGAAAATAATGAGCGAATGGTTCAAGAT

GTCGAAGAAAGTGTCCGCGATTTTTCACGGGGTCTGGAGGATAGTCTCAAAGATGGTGGCGAGAGTTCATCTAGCGA

GCATGAAAAAAAGACGCTGGGAGGATGGGCTCGGTGTTGAAGATGAAGTCAAGGACTTCATCTTTGATTTGCAAAGGAG

CAGTAGAAGTGCAAAAGTTAGGACTGACGATCGCAGTAGGGAGGCTCCCACTGAGACGTCTCGTGTTAGCTCCGCTC

CAGCAGCTCGTAGTGAAACTCCATCGTCGCAGCCTTCATCTACACCAACCCCTTCTGCAGGTACATATTCACAATATAA

GACAGCAGAAGATAGAGCAGCGTACATCAAGCAACAGGCAGAGCAGCGCATGGCTGAGCGTCTAGCTGCTCTTGGC

ATTAGGGCACCTTCTAAACCTGGAGAGACAACACAACAGAGATTGGAGCGTGAGAAGAATGAGCGTGCTGCTAAACTC

AAGCAAGCGGAAGAGGAAGATGCTAGACGTGAGGCCGAAAGGCAAGCTAGAATTGCTGAAGAGCAGGGAGTGGCCC

CACATACACCGGATCAACCAAAAGAAATTACGAAAAAGCCACCTCCGCCGCCTTCGAGGAAGGCTGCAAGAAGCGAC

GCTAGTGAACGTAAATTCGAAGAGGATAGAATCCTCAAGGAGCAAAAGTCACAAATTATTGCCACAAATGAGCTAGAG

GACGATGCTCAACGACAAGAAAATGAGCTTGCAAAAGAGCGCGAGGCAGCTCAAGCTCGTGTGAAGGCATTGGAAGA

GCAAATGAAGGCTGGGAAATTGAAGAAAGAAGAGGAAAAGAAGAAGAGAAAGGCTCTACAAGCCGAGACGAAGCAAC

AAGAAGCTCGTCTTGCAGCTCAACGTGCGGAGATCGAAGCCGCCCAAGCACGTGAGCGGGAATTGCAACGTCAACTG

GAAGCTATTGATGATTCAGACTCATCAGATGATGATGAAGGTCCAGAGCAAGTTACTCCTCAAGCGTCAACACCAACTC

AGGGGAGCCAAGAATTTGAGCGCAAAGAAGCCTCTCCACCCCCCTCCTCCTCCCTCAGTCCCAGTCATTGTATCACCC

GTCCCTGCGGCAGCAACAACAACCAGCCTTCCCCCACCAACCCCACAAGTTACTAGCCCTGTTGTCAGCCCTCCAGC

TGAAACAGAAACCCGCAATCCTTTCCTGAAGAAAATGGCTCAATCTGGTGATGCTTCTGCCGCATCTACTGCATCTAAC

AACCCATTCCATCGTCTTCCTTCTCAAGAACTTCCCGCTCCTGCGCCAATTCAGGTTCAGCCAACAGGTAACAGACCAT

CTCGTGTCCGTCCAGAAGAGGATGATTGGGACGTTGTTGGATCTGACAAGGAGGATGATTCCTCTGATGATGAAGGA

CCTGGTGCAGGCGGCGCGCGTCACTTGGCATCGATTCTTTTTGGAACCATGGGACCTCCTCGTCCTTTGTCGGCTAT

-continued

*GGGCAACGAAGCTACATCCGCACCTCATTCGCCTGCTGCGGCATCTCCACCAGTGGCATCTCCACCACCTCCACCAC*

*CCATGCCATCAGCCGGTGCACCAGGCGGTCCACCTCCACCACCTCCTCCTCCGCCACCAGGAATGGGTGCTCCACC*

*TCCACCACCAATGCCTCCCATGGGAGGGGCTCCTGCGGCCCCACCTGCGGGTGGACGACCAGCTGGATTCTTGGGT*

*GAAATCCAGATGGGGAAAGCTTTGAAGAAGACACAAACTAAGGACAAGAGTGCAGCTGCTACGGCTGGGCGAGTTTT*

*GGATTAA*

*Botrytis cinerea*, Bc_Srv2p, BC1G_14507

SEQ ID NO: 20

*GGGTGTGGGTGTAGATGAATTAAATGAAGAACATCAGCGTTCCAAGGTAATCCGTATCCATCATATCACATCACATCTC*

*TTCACATCACTCCAATATTCTCTCTTCTATCCTCTCTCTCTCTCTCTCCCTCTCCCTCTCTGTCTTCCTCCCCCTCGC*

*CGTCGTCGCTTCATTGTAGGAGACCTCTTTCTCGTCGCTCCATACCAGTCCCGCAAATCGATAGCTTCTTCCATTTGCC*

*TGCTAATTACCATTCCATATTACATTATTTATATGCGTAATTAGCAACCTTTTGCCTCCTTCCCCTTGCATTAGCACCACG*

*AAACATCGAGAACCAGACAGCTCCATTCCCTCAAACAACCTCCTATTCGATCGATCATTCCTTCTTCAACAAGACTTTG*

*GAACAACTACTGCACTTCAATATGTCTCAACAACCTGAAGCTGTAAATAATATGCATAATTTGACTACGCTCATAAAACG*

*ACTCGAAGCCGCAACCTCTCGTCTTGAAGATATAGCTTCCTCTACCATTCCACCACCTGCTTCATCATCCATCCCTCTA*

*ATTTCTCCTCCGGCCGAAGCTGCGAAAACAAATGGCACAACTCCGCCGCCGCCAACGATCCAAACACCAGATATCAAA*

*AAGATCATCGAGGATCCAATCCCAGGAGTAGTCTCAGAGTTCGATAATTTTATTCAGGGGGCGGTTAAGAAATATGTTA*

*ACTTGAGTGATGAGATTGGAGGGGTTGTTGCGCAGCAGGCATCTAGTGTATTGAAGGCATATGTCGGACAACGAAGAT*

*ATATTTTGATCACTACAAAGTCAAAGAAACCTGGCATGCAAGATGAACCATTCCAAAAGCTCATCAAACCTCTTCAGGAT*

*TCATTTACTGCCGTTGATGATATCCGAAAGTCCAATCGTGCATCTCCATTCTTCAATCATCTCAGTGCTGTTTCTGAAAG*

*TATTGGTGTACTTGCCTGGGTTACAATGGACAACAAACCATTTAAACATGTCGATGAATCATTGGGATCTGCTCAATATT*

*ACGGAAACAGAGTATTGAAGGAATTTAAGGAGAAAGACCCAAAACAAGTCGAATGGATTCAAGCATTCTATCAAATCTT*

*TAAAGATCTCAGCGAATATGCTAAGGATAACTTCCCAAACGGTATTCCATGGAATCCAAAGGGTGAAGATTTGGAAGTT*

*GCGATTAAGGATGTAGATGAAAAGGCTCCAGCCCCTCCTGCTCCTCATCCAAAGGCTGCAACTGCTGGAGGTGCCGC*

ACCACCACCACCCCCTCCACCTCCTCCTCCACCAGTCTTCGATGACATTCCATCAAAGCCAGCACCAAACCAAGCAGA

*TTCAGGTGCTGGACTAGGAGCCGTTTTCTCTGAACTGAATAAAGGAGCAGACGTTACAAAAGGATTGCGCAAAGTGAA*

*TGCTGATCAAATGACACATAAAAATCCTTCTTTGAGAGCAGGTGCTACAGTTCCCACCAGAAGTGATAGTCAATCCAGT*

*ATTAATTCGAACCGAGGAAAGAGTCCTGCTCCTGGTAAAAAGCCCAAGCCAGAGAGTATGAGAACTAAGAAACCCCCT*

*GTTAAAAAATTGGAGGGTAACAAGTGGTTTATTGAAAACTACGAAAACGAGTCTGAGCCAATCACAATTGAAGCATCTA*

*TTTCACACTCGATCCTCATTTCCCGCTGCTCAAAAACCACTATTATCATTAAAGGAAAAGCAAACGCTATTTCTATTGAC*

*AACTCCCCTCGTCTTGCCTTGGTAATTGATAGTCTCGTCTCATCGATTGATGTTATCAAAGCACCAAACTTCGCACTTCA*

*AGTACTGGGCACATTGCCAACGATTATGATGGATCAAGTTGATGGTGCTCAAATTTACTTGGGGAAGGAGAGTTTGAA*

*CACGGAAGTCTTCACGAGTAAATGTAGTAGTGTCAATGTGCTACTTCCAGATTTGGAGAGTGCAGACGGGGAAGGAGA*

*TTACAAGGAGGTGCCGTTGCCCGAACAGTTGAGGACTTGGGTGGAGAATGGAAAGGTCAAGAGTGAGATTGTTGAAC*

*ATGCTGGATAGATTGGTTGAGATGGATTGTGGAGTTTGGGGAGAGGCTCTGGCGAAAACTTGTTGGGGGTGAGGGGT*

*AATGAGATGTGATGGAGAATCTGGGTAGATTTGATATTATAGAGATAGTTGAGTGAAGTTTTATATCATCGCATGTTAGT*

*TGAAGTTTTCAGGCAGAGTAGAAGTCAAAGTTGAATTGTACATATCTATGTATATGTATATCCGAGGCTTGTCTCGCTTT*

*GTTGTTTAGTAGATTTCAAACCGAAGATTTTCTACTCATCATATCGTGCCGTGTGTTTTATATTGGGCGATGTGTCGTTG*

*TGCTTTTTCTCTCTCTATCTCTTTTACTTTCAGGGAAATAAATATA*

*Sclerotinia sclerotiorum*, Ss_Srv2p, SS1G_13327

SEQ ID NO: 21

*ATGGCTACAAATAATATGCATAATTTGACGACGCTCATAAAACGACTCGAAGCCGCGACCTCACGCTTAGAAGATATAG*

*CCTCATCAACTATTCCCCCTCCCAGTACTCCCAAAACAAATGGTACAACAAGCGTCGCATCTCCTACCGTACAAGCCG*

-continued

CTACTCCTACAGTTGTAGCCCCGACTATTCAAACCATTATCGAAGATCCAGTTCCTGAATCAATCAGCGAATTCGATGC

TCTAATTCAGGGGCCTGTGAAGAAATATGTTAATCTTAGTGATGAGATTGGTGGGGTCGTTGCGGAACAGGCATCCGG

TGTATTGAAAGCATTTGTCGGGCAGCGAAGATACATTTTAATTACCACGAAGTCGAAGAAACCCGCTATGCAAGATGAA

CCATTCAAAAAACTCATCAAACCTACTCAAGATTCATTCTCTGCTGTTGACAAAATTCGAAAGTCTAATCGTGATTCACC

GTATTTCATTAATCTCAGTGTTGTTTCGGAAAGTATTGGTGTACTTGCTTGGGTTACAATGGATAATAAACCATATAAAC

ATGTTGATGAATCATTGGCATCGGCTCAATACTTTGGAAATAGATTATTGAAGGAATTCAAGGAGAAAGATCCCAAACA

AGTTGAATGGCTTCAAGCATTTTATCAAATCTTCAAAGAACTTAGCGAATATGCTAAGAATAACTACCCAAATGGTATTC

CGTGGAATCCGAAGGGAGCAGATTTAGAAGATGCTATCAACGAAGTAGATTCGAACGCTCCAGCCCCTCCTGCTCCTC

ACCCAACAGCGACTAGTGGAGGAGCCGCGGCACCACCACCACCTCCTCCTCCTCCTCCTCCACCAGTTTTCGACGAC

ATTCCAACAAAATCTGCACCAAAGCCAGGAGATGCAAGTGCTGGACTAGGAGCTGTTTTCTCTGAGTTGAATAAGGGA

GCAGATGTTACGAAGGGATTGCGCAAAGTCAATGCTGAACAAATGACACATAAGAATCCATCTTTAAGAGCAGGTGCT

ACTGTTCCTACTAGAAGTGATAGTCAATCTAGTATTAGTTCGAACCGTGGAAAGAGTCCTGCTCCTGGTAAGAAACCTA

AGCCAGAGAGTATGAGAACTAAGAAACCTCCTGTTAAGAAGTTGGAGGGTAACAAGTGGTTTATTGAGAACTACGAAA

ATGAATCATCGCCAATTGAAATCGAAGCTTCAATTTCGCATTCGATCCTCATTTCCCGTTGCTCAAAAACTACAATCATG

ATTAAAGGAAAAGCAAACGCCATTTCCATTGATAATTCCCCTCGTCTTTCCCTAATTATCGAGAGTCTCGTTTCATCAAT

TGATGTTATTAAAGCACAAAGTTTTGCGCTTCAGGTATTGGGGACATTGCCAACAATTATGATGGATCAGGTTGATGGT

GCACAAATTTACCTTGGGAAGGAAAGTTTGAACACGGAAGTTTTCACGAGTAAATGTAGTAGTGTTAATGTACTATTAC

CGGATCTGGAAAGTGAAGAGGGTGAGGGTGATTACAAGGAGGTGCCATTGCCGGAGCAATTGAGGACTTGGATTGAA

GATGGGAAGGTTAGAAGTGAGATTGTGGAACATGCCGGTTAG

BC1G_10728

SEQ ID NO: 22

GACACATGCGATATGCAAAGTCTAGAACCTCGAATACTGATTCGAAAAAGACTGGCAATTCCATAAATCTACAGTATATT

TTAATCCGCAACTCATGAATGACTACATTTAATACGAATTACAAACATTCCCTAACGCCAAAATGGCAGCTACGATTCCC

CTCTCCACTACAACATGCTTGACCTCCTCAGAAGCTTTCAAATATCCTCTTCCACAGATTCGTCAATTCCACCGCGATCT

CACTACAGAGCTTGACGAGAAAAATGCACGTCTGCGGACACTGGTCGGAGGGAGTTATAGACAATTACTTGGAACCG

CCGAGCAAATCTTACAGATGCGACAGGATATTAGTGGAGTAGAGGAAAAGTTAGGCAAAGTAGGAGAAGGATGTGGG

AGAAATGTGTTGGTTGGAATGGTTGGCGGATTGGGAAAATTACAGGGAGAAATGAAGAATGGAAAGAAGGGCGAGGA

AATGCGGGTTGTGGCTAAGATGAAGGTATTGGGTATGTGTGGGATTGTGGTTGGGAAGCTCTTGAGGAGACCAGGGC

GAATGGATGGGGATGGTGGGAGAGGGAAGGAATTAGTAGTTGCTGCGAAAGTCTTAGTTTTGAGCCGATTGTTGGCG

AAGAGCTTGGAGAATACTGGAGATAAGGAATTCGTTGAAGAAGCGAAGAAGAAGAGGTCGGCTTTGACGAAGCGATT

GTTACGCGCAGTTGAAAAGACATTGGTTTCCGTCAAGGATGCTGAAGATAGAGACGATTTGGTACAGACACTTTGTGC

ATACAGTCTAGCTACTAGTTCTGGCACCAAAGACGTCTTGCGACATTTCTTAAATGTTCGTGGTGAAGCAATGGCTTTA

GCGTTTGACGATGAAGAGGAGTCGAACAAGCAGACCTCAGGTGTCCTACGCGCTTTGGAAATATATACGAGAACTTTA

CTAGATGTACAGGCTCTAGTGCCAAGGAGGCTGAGCGAAGCGTTGGCTGTGCTGAAGACGAAACCTTTACTGAAAGA

TGACAGCATTCGGGAAATGGAGGGATTGAGGTTGGATGTATGTGAGCGGTGGTTTGGCGATGAGATTATTTACTTCAC

ACCTTATGTCCGGCATGATGATTTGGAAGGGTCATTGGCGGTTGAAACACTACGAGGTTGGGCGAAGAAAGCGTCAG

AAGTGTTACTGGAAGGTTTTACGAAGACTCTTCAAGGGGGGATTAGACTTTAAAGTAGTTGTTGAACTACGAACAAAGAT

TCTGGAGGTGTGGGTTAGAGATGGAGGCAAAGCAAGGGGATTCGATCCCTCTATACTTCTAAATGGCTTACGAGACGT

TATAAACAAACGACTCGTAGAGTTATTAGAAACTAGAGTTGGCAAACTTCATCTAGTGGGGACAGAGATAGAGTCCACA

TTAGCAACATGGCAAGAAGGAATCACCGACATACATGCAAGTCTTTGGGACGAAGATATGATGGCAACCGAGCTCAGC

AATGGTGGTAACATTTTCAAGCAAGACATACTTGCTCGCACGTTCGGACGGAACGATGCTGTTTCAAGAGTTGTTAACA

GTTTTCACACTTGGAGACATCTCATCGAGGAAATTGGTACTTATATTGATGAACTGAAGAAACAAAGATGGGATGATGA

-continued

*TTTGGAAGATATGGAAGATGATGAAAGTCTCGAATCACGACAAAACCTTCTTAGCAAGGAAGATCCACAAATGCTACAA*

*GATCATCTCGATTCAAGCTTAGAAAATTCGTTCCAGGAGTTACACGCAAAGATCACTTCACTGGTGGACCAGCAAAAAG*

*ATAGTAAACATATCGGGAAAAATATCGATATATATTCTCCGAATTCTACGAGATATCAGAGCAGAATTACCTAGTAACCCT*

*GCACTACAAAAGTTTGGACTCTCACTTGTCTCATCACTGCACGAAAATCTCGCAGGTATGGTCTCAGAAAACGCCATCT*

*TAGCCCTTGCAAAATCTCTCAAGAAGAAGAAGGTTGCGGGCAGAGCATTATGGGAGGGTACACCGGAACTTCCTGTTC*

*AGCCCTCCCCAGCAACATTCAAATTTTTGAGAGGTTTATCGACTGCTATGGCTGATGCTGGAGCCGATCTATGGAGCC*

*CTGTTGCCGTCAAAGTGTTGAAAGCGCGTCTGGACACCCAAGTTGAAGACCAATGGAGTAAGGCTCTAAAAGAAAAAG*

*AGGAAGAGCCTAGCAATGGAATCTCTGGTTCTCCCACCAATGCTCCCGAAGCAGATGCCGAGGAAAAAGAAGGGGAC*

*GCTTCTGCTCCTAATCCTGCTGCTGCTGTAGAAGTAGATGAAGAAAAACAAAAGGATTTACTAAAGCAATCACTGTTCG*

*ATATATCTGTCTTGCAGCAAGCTTTAGAATCACAGTCAGACAATAAGGAGAACAAACTTAAGAACTTAGCGGATGAGGT*

*GGGAGGAAAACTAGATCTCGAGGCGAGGGAAAGGAAACGTATGGTTAATGGCGCGGCGGAGTATTGGAAGAGGTGC*

*AGTCTTTTGTTTGGACTTTTAGCGTAGATTCCAGATGGATGAATTAGTGAGAGGCTTATAATGAATTATATTACGAATAC*

*TTTACTTTTGAGTATTCA*

BC1G_10508

SEQ ID NO: 23

*GCAGGGGTCGGATCAACATGTCTATAAACAAACATATGTACCGGCGTTGATCTCTCCTGCAGACTGCATTTGCACTTG*

*CTTCCCTCTTCCTCCTCCCGTTTCCTGGTCTTCTTCTACAAGCTGCAGGCGAGAGAGATAACTTCTACGCACCTTCCAT*

*ATCCCTCACCTCTTCTCTCCCCACAAGTTCGTTCATAATCCTTTCGTCCTGTTGTTTTGTCTAGCATTACCTTGCAATTCT*

*TAACAACGGCCGATCGTGGACATCAATCAATAAAAAGGACGACAAATCATCTTATAATTATTATCCCAAACTTTCATTGC*

*ACAAATTTGAATTGGATACTCATTTGGCTTTATTCGGAGCGATAAACGTAGAAATTAATCGTATAGGGGCTTTTATCAGA*

*CAATCAAGAACGGTGATTGGCTCACAGCGGTGAATTGTGAGGGGTGGTAATACAGAAAACAAATAGTATAGGGAGTAT*

*TTTTGGGTGGATTGTTACCAATGTCTACCACAAGAATCTCAACACCGAAAAGGTCCCCCAAAAAATCGACTTTTGTCAA*

*AACTGGAATCTTGACCACCAAATCAACGCCCAATCTCAACGCCTCCTATAATTTGGCATTACTACAAGCTTCAGGAGCT*

*ACACCCGTTCCTGCATATCCTTCCAATAACGGTCAAAGTTTTGCCCTAAATAATCCTAGGTCGCAACCGTCTCGACAAG*

*TCTCACTCGCTTCCCTTACCTCGAATTCACTTGCGACAATCCCGGATGCAAGCAAGAGATACCCTCTTTCTACAGTCTT*

*TGATGAGGATATGCCAACAGTAGGCAACATGCCGCCATACACACCTGCTCGAGTTGGCGGTGGACCGGAAGAACTAG*

*AGGTTGGTGATATAGTCGATGTGCCAGGTAACATGTATGGTATCGTCAAATTTGTTGGCAGTGTGCAAGGCAAAAAGG*

*GTGTATTTGCTGGGGTAGAATTAAGTGAAACGTTTGCTTCGAAAGGGAAAAACAATGGCGATGTCGAAGGAATTCAATA*

*CTTTGACACAACCATCGATGGTGCTGGGATTTTTCTTCCAGTCAACAGGGCGAAGAGACGTAGCACCCCTTCGTCGCA*

*TGATGAGTCATTTCCCCTTTCACCGGCGTCTCCATCGATGGGCAATAGGGCTGGGAGATTAGGATCTGAATTAAATGG*

*TCAGCCAACACCTTTGTTACCAAAATTCGGTCAATCTGTTGGTCCAGGCAGAGCGGCAAACCCATATGTCCAAAAAACA*

*CGTCCATCCATGGCTACACCTACCACCTCAAGACCGGAATCACCAGTTCGAAGAGCAGCCAATGCCAACCCATCATTA*

*AATACACCTGCACAAAGAGTCCCATCTCGATATGCAAGCCCTGCGCAGGCAAACTTTGGACAGAGCGTTAGAGGAACA*

*CAAGATTCTAGAGATCCAAGTAAGAAAGTTGGCTACACCCCCCGAAATGGCATGAAAACACCAATACCTCCACGAAGT*

*GTTTCTGCACTTGGAACGGGGAATAGACCTGCACCAATGAACTCGATGAATTTCAGTGATGAAGAGACACCTCCTGCA*

*GAGATTGCACGTACGGCAACAAACGGAAGCGTAGGCTCAGTCTCTTCTTTCAACGCGAAATTACGTCCAGCATCAAGA*

*TCCGCATCGCGTACAACTTCCAGGGCTACCGACGACGAATTTGAGCGATTGAGAAGTTTGTTAGAAGATCGCGATAGG*

*GAAATAAAAGAACAGGCTTCTATTATAGAAGACATGGAGAAAACTCTCAGTGAAGCACAATCGTTGATGGAGAACAATA*

*ACGAGAACGCAAGTGGTAGACATAGTCAGGGAAGTGTGGATGACAAGGACGCAACACAGTTGAGAGCAATAATACGT*

*GAAAAGAACGACAAAATCGCCATGCTGACTGCCGAGTTTGATCAGCATCGAGCTGATTTCAGAAGCACGATAGACACG*

*CTCGAAATGGCCGGTGCGGAAACCGAGCGAGTGTACGACGAGCGCATGCGTGTTCTCGTAATGGAGCTCGATACAAT*

-continued

GCACGAGAATAGTCATGATGTAAAGCACGTTGCTGTACAACTGAAACAGCTAGAAGAGCTCGTTCAGGAGCTCGAGGA

AGGTCTTGAAGATGCACGACGTGGTGAAGCCGAAGCTCGGGGAGAAGTTGAGTTCTTGCGTGGAGAGGTTGAAAGAA

CTCGATCTGAACTCCGCCGCGAGCGAGAGAAGACTGCCGAAGCTCTTAGCAACGCAAATTCTCCTACGAGCGCAAGT

GCGGAAACACATTCCAAAGAGATTGCTCAGAGAGATGACGAGATTCGTGGATTGAAAGCCATCATCCACTCGCTCAGC

AGAGATGCCATACCTGATGGGAATTTCTCGGATCATGAGGCAACACCAAATATTCTACGACCTGGACTAAACCGAAGT

CGAACAGAAAGTGCTTCGGTTTCTGAGGAGGAGCGCCGTACTCGGGAAAAGCTAGAGCGAGAAGTGAGTGAGCTTC

GTGCTCTCGTCGAAAGCAAAGACAATAAAGAAGAACAAATGGAGCGCGAGTTGGAGGGATTGCGAAGAGGAAGTGTT

AGCAATCCTACTACGCATCGTACTAGTGCCATGAGCAGCGGAACTGTGACTCAGGATAGGAATTCTCTCCAAGACAAT

AAGAGCACAGTTGTAAGCTGGCGAGAACGTGGTGCCTCAGATGCTCGCCGCTACAATCTGGATTCAATGCCAGAGAA

TGACAGCTACTCCTCTGCAGCTGAGGATTTCTGTGAATTATGCGAAACCTCAGGTCATGATGTTCTACATTGCCCGATG

TTTGGCCCCAATGGTAACAGCAGCAATTCTAAGGATGAGTCACCTAAACAGCAACGAACAGGAAAAGACGTTGTCATG

GAGGGACTTAAATTATCACCCAAACCTTCTCAAGAAGAATACAAACCGGCGCCGTTAGCGCCAGCTAAGAAGTCGCCT

GATGCGTCGCCTATCAAGACTGTTCCCAACCTTATGGAACCAGGACCTGCCCCAGGAAAGGAAAGTGGAGTAATCAA

CATGGATAAATGGTGCGGTGTATGTGAAAGAGATGGACATGACAGTATTGATTGTCCTTTTGAAGATGCTTTTTAGGAG

ACTACTGCTTTCGATGTTTCAGGATAAGCAGTCACAACGACGACTTTTTTCATAGATTTTCTTTGTTAATCATAGGCAAG

GCCGCATTGCATTGCAGGAGCGTAATCCGTCTGCGATATACCCTTTCGGTTCTCTGTTTGAAGTATGCTTTTCAAGCGA

TAAGTTTAGAGGGGAAGATGATGTTTTTACGAGGATTGAATGAGATGGATGAATGCAGGCTAAATCGGGGAAGGGGG

AGGGAAGACAAACATGAGTTGAACGGACGTAATGATCATGTAGTATACTTTGTCAAATTAATGATCCAAATGCA

BC1G_08464

SEQ ID NO: 24

GATCCACCCACATCCTTCCTCATATGACTTCGATGATAATTACATAGACACTGCCAGTATGCCTGGCCTCGTTCGCAAA

CTCCTTATCTTTGCCGCCATCGATGGGTTGATTTTGCAACCAGCAGCGCCAAAAGGCCAACGCCCCGCCCCCGCAAC

GAAGATCGCATACAAAGATAAGCATATCGGGCCAGTATTGAGTGATTTGCAGGATCTGGAGGGGTCGTCTGCGAAAA

GTTTCGAGGCATTTGGTATTGTCGGTCTCTTGACGGTTTCCAAAAGCTCCTTCCTGATATCGATTACGAAAAGAGAGCA

AGTCGCACAAATACAAGGGAAACCTATATATGTTATTACTGAAGTGGCTTTGACCCCATTAAGTTCCAAGAACGAAGCA

GAGATCTCGATTGATAGTACGAAAGCGGGGTTATTGAAGAGTAATATCGAGGGGCAGCATGGCTTGGACGAGAGTGA

TAGCGAGGATGATGTCGTTAGCGATGAAGTGGAGGACGATACAGCAGTAGAAGCACACAAAAGAACGAGTAGCGTAG

CTGAAGATGTGATCTCGAAGAAGGGGGGATATGGAAGATTTGCTCAAAAATGGTTCTCGAAGAAAGGATGGGCCGTG

GACCAGAAGAAGAACCTGGGGATGAGCGCTGAGCCGTATTCCACAGTGGAGCAAGCTTCCAAGGCCACCGATGTAC

CAGCTACGATTTCAGGAGTCACTGAAGGAAAATCTGATATCTCAATTCCCGATAAGGGCAAGGAAATTGAGGACATTG

AAACTCCTGAAAATATTAGCGACATTGCAGAGAGCATGCTGCCAAAATTACTACGAACATCGCAGATATTGTTTGGGGC

CTCTCGGAGTTACTACTTTTCTTACGACCATGATATCACAAGAAGTTTGGCAAATAAGAGGAATACAAATTCTGAATTGC

CATTGCACAAGGAAGTTGATCCACTCTTCTTCTGGAATCGGCATCTTACTTTACCATTTATTGATGCTGGCCAGTCTTCT

CTTGCCTTGCCTCTTATGCAGGGCTTTGTAGGACAGCGTGCATTTTCAATGGATAGTAATCCACCAAACCCTGCTATAG

GTTCAGACACTGGAAAGACTTCCGTGCAGATGAAGGATATTACAACAAGTAGTTCGGATGAGCAAATTTACACAGCAC

GTGCTGGTACAGACAAGTCGTATCTATTGACGTTAATATCTAGAAGGTCAGTCAAACGTGCCGGGCTTAGATATTTACG

CCGGGGTGTGGATGAGGACGGCAATACAGCCAATGGCGTGGAAACAGAGCAAATCTTATCGGATTCTGCTTGGGGCC

CTTCGAGTAAGACATATTCGTTCGTTCAGATACGTGGCAGCATTCCCATATTCTTCTCCCAGTCACCTTACTCTTTTAAA

CCTGTACCTCAAGTTCACCACTCTACCGAAACAAATTATGAAGCTTTCAAGAAGCATTTTGATAATATAAGTGATCGCTA

CGGGGCCATTCAAGTGGCTTCCTTGGTGGAGAAGCATGGAAACGAGGCAATAGTCGGTGGAGAGTACGAGAAATTGA

TGACTCTCCTTAATGTCTCCCGAGCTAGCGAGCTTAGGAAATCCATTGGGTTTGAATGGTTTGATTTCCATGCTATTTG

CAAAGGTATGAAATTTGAGAATGTCAGCCTGCTCATGGAAATACTGGACAAGAAGCTTGACTCGTTTTCGCACACTGTT

-continued

*GAAACCGATGGGAAACTTGTATCGAAACAGAATGGCGTTTTAAGGACTAACTGTATGGATTGTCTGGATCGAACAAAC*

*GTTGTTCAAAGTGCAGTGGCAAAGCGAGCACTTGAAATGCAGTTAAAGAATGAGGGACTAGATGTCACTCTACAAATT*

*GATCAAACTCAACAATGGTTCAATACTTTGTGGGCCGACAATGGTGACGCCATTTCTAAGCAATACGCTTCTACAGCAG*

*CATTGAAGGGAGACTTTACTCGTACTAGGAAGCGGGATTATAAGGGGGCCATCACAGATATGGGGCTTTCTATCTCCA*

*GATTTTATAGCGGCATTGTAAATGACTACTTCAGTCAAGCTGCCATTGATTTCCTGCTTGGAAATGTGAGCTATCTTGTT*

*TTTGAAGACTTCGAGGCAAACATGATGAGCGGTGATCCTGGCGTTTCGATGCAAAAAATGAGGCAACAAGCCATTGAT*

*GTTTCTCAGAAACTCGTTGTTGCTGACGACCGTGAAGAATTTATTGGAGGATGGACATTTCTCACTCCGCAGGTACCCA*

*ATACGATCAAATCTAGTCCTTTTGAGGAATCCGTCCTCCTATTGACAGATGCTGCATTGTATATGTGCAATTTTGATTGG*

*AATATCGAGAAAGTATCATCTTTCGTGAGAGTGGACTTGAACCAGGTGAACGGCATCAAGTTTGGAACATACATCACGA*

*GTACTTTGTCACAAGCCCAGGCAGATGAGAAGAGGAATGTGGGCTTTGTAATAACTTATAAGGCTGGTTCAAACGACA*

*TTATTCGCGTGAACACGAGATCTATGGCTACGGAATTTCCTTCTTCGAAACTCTCTCTCGAAGACAAAACATCCACGCC*

*CGCTTCTACATCTACCACCAACTCTGTCGTCGCCCCAATTGCCGCCGGGTTTGCAAACCTAATCTCAGGTTTACAAAAT*

*CAAAGTATAGCGGAACCTAAAGATCTCGTGAAGGTTCTCGCATTCAAGGCTCTACCCTCCAGATCTGCGGTATCAGAT*

*GAAGGAGTTAGTGAGGCCGAGCAAGTGAAGAGTGTCTGTGGAGAGATTAGAAGAATGGTTGAGATTGGAAGTATAAG*

*AGAGGCTGGAGAGGAGAGAAAGGATATTGTAGAGGAGGGTACTATCATTAGTTTGGCCGAGGCCAAGAAAAGCACGG*

*GACTATTCGATGTGCTGGGACATCAGGTGAAGAAACTGGTTTGGGCTTAATGAAAGTGTATCGATACTCGTGCTAGTA*

*ATGCTTAGAGCAAAAGAAGCACTTCTTGAAGGATTTACGAATGGAATTGTGGAAGTTGGCAGGGAGGTTAGCGATCGT*

*CAAGAACGGGTATGTGGAATTCAATTCCATATTGAAGCTGCGAAACTCATTAACTTCAATAGAAGTGGATGTGTAGATA*

*GACCCGAGTATATGGTATTGGCCAGATAAGTAATTTTAATGGGGA*

BC1G_15133

SEQ ID NO: 25

*GAGTATTCTCGATTAGACAATTAGAATTCTCGAACAATAGAAGCCGGAGCTCGAGTTCCTCGATCTTTACCTACCTGAA*

*GTCTCTCGATCAGAAGAGTGTCAAATTCCTATGATATCAATGATTATTGAGGATATATTTACAAAATCAAATCTCTTCAAT*

*GAATCTCTATCTACCTAAGCAAGTCAATTATGATTGATTACAATTATCGTTGTTGCACGGAATCCAGTCGCATTTGGTCC*

*CGGTCACTCGTAACAGCAACCACATCGGTATTTCGTAGATTCCCGAGTATTGCCTTTACATACCTAAGGAACTTTAAAT*

*CCCCCCAACAACAGAATTGACGACAGAATTACTACCATTACAAGTGAAAACACTCCATGGTACCCAAATACAACAGTCT*

*CATATAGCCATTTGATCGCAACTCGCATCTTTCATCTACAAAATGTCGTTTGGAGGGGACATCGGACTCGATACAACAT*

*CGTCGTCCAATGCTGCTGGTAATGGCGGCAACCAGGGCGAGACAACTGGAAGACCTGCCACCCCTCAAGATGCAAC*

*CGCAAAAGCAGTTCAAGATGTCACAAGCTCGGAGATTGGAATATCAACCTTGTTAACCCGACTGAAACAAAGTATTGCT*

*TCCGCAAAGGAATTCGCACTTTTCCTCAAGAAACGGTCCATCATGGAAGAGGAACATTCGAACGGTTTAAAAAAGCTGT*

*GTAAGGCAACCGGGGATAATATTCGCAGACCAGAGCATCGACACGGATCGTTTCTACAGTCATACGAAGAGGTCCTCA*

*TTATACACGAGCGAATGGCCGAGAATGGGGCTCAATTTGGCGTGTCTCTACATCAGATGCATGAGGATCTTATCGAAA*

*TGGCTTCGAACATAGAGAAGGGCAGAAAGCATTGGAAGAATACTGGGTTGGCAGCAGAACAACGTGCTGCTGATACC*

*GAAGCTGCCATGAAGAAGTCGAAGGCGAAGTACGACTCTCTGGCAGACGAGTATGATAGAGCTCGCACTGGGGACA*

*GGCAACCAGGAAAGATTTTTGGCCTCAAGGGCCCCAAATCGGCAGCGCAACATGAAGAGGACCTTCTTCGCAAAGTC*

*CAGGCTGCCGATGCAGATTATGCGTCCAAGGTACAAGCTGCGCAAAGCCAACGAACCGAGCTCTGGTCAAAATCAAG*

*ACCTGAGGCTGTGAAAGCTCTAGAAGATCTCATTCAAGAATGCGACTCTGCATTGACATTGCAGATGCAGAAGTTTGC*

ATCCTTTAACGAAAAGCTACTTTTGAGCAATGGCTTGAATATAAGCCCTATCAAAGGAAAAGAGCAAGGGACATTAAAT

*CGCAGTCTCCGTGAAGTTGTTCACGCAATTGATAATGTTAAAGACCTGAGCAACTACATCAGTAGCTTCTCTGGTAACA*

*TGCAGTCCCGGATCACGGAAATCAAATATGAGCGTAATCCGGTTTTGCAACCCGCACAAAATACCGCTCAGCGACAAT*

*CGGATCCCAACGCTCTCCAAGCTCGACAAGGACCCGTAATACCACCACAGCCATCTCACCAAGTTCATATGAGCCAAC*

-continued

*CTTTTAATCAAAGCAGTCCCCCAACTCACCAGCGCGAAAGAAGCTTTAGCCATGGCCCATCTCTTTCGCAACACATCGT*

*TGCACCTGTTGTATCGCCCACTAACCCAATATCCACCTCTCCCGACTTCAATACCTGGTCACCTCGTGCAGATGGCCC*

*CCCCCAGATATCAACCTTGCCATTTCAGCCACAACCTCAAAACGAGACACCAATACAACAGACACCACAAAACCCTACA*

*ACGCATGCACCAGTGTCCCATGGCCCATCCTCGGCACCACTATTCGGAGCGGGATCGGCTCCAGCTCCAGGCAACA*

*GCACTCATCTAGCACCTTTGAAACCAGTGTTTGGACTCAGCCTCGAGGAACTCTTTGACAGAGATGGCTCTGCTGTTC*

*CAATGATTGTCTACCAGTGTATTCAAGCAGTTGACCTCTTTGGGCTCGAGGTCGAAGGAATATACCGGCTATCTGGTA*

*CCGCATCTCATATAATGAAGATCAAGGCAATGTTCGATAACGACGCATCTAAGGTGGACTTCCGTAACCCGGAAAGCT*

*TCTTTCACGATGTCAATAGTGTGGCTGGTCTTCTCAAACAGTTCTTCCGCGAACTCCCAGACCCTTTATTGACTATCGA*

*GCAATATCCTGCATTTATCGAGGCTGCAAAGCATGATGATGAAATAGTCCGTCGCGACTCTCTACATGCGATCATCAAT*

*GGCCTTCCTGATCCCAATTACGCTACTCTTCGAGCCTTGACTTTACATTTAAATAGAGTACAGGAGAGTTCGGCATCTA*

*ACAGGATGACTGCAAGCAACTTGGCCATAGTATTTGGCCCTACACTCATGGGTGCTAATTCAGGACCGAACATGTCAG*

*ATGCTGGGTGGCAGGTTCGTGTCGTTGACACTATTTTGAAAAACACTTATCAGATATTTGACGACGACTGAGGCGAAG*

*AAGATTGTCGATTGACTTGAAGAGTTCTTAACGAGATACCATAGCTGCTCATATTATGAACCTGCCTTTGGAACAGAAA*

*CAAGGGCAGGGAATTCCTAGCATCAGACCTCTATTTGCCGACAAGACATTCTAAAGAAAGTACATGCCACTGTATTTCG*

*AATACTATTATTGTAAGGCACGGGCCTGTTGACAAATATTTACGGTCTATCAAGCGAGTGTACGTCAGGGGGTGGTCT*

*ACACCACGATCGATTTTGTAGGGTCATGTGCTCAGCTCTGATGCCAGTATTGGTGCAACTATTGAATCAAAAGGGTACC*

*AAGGTTTCAATACTCGTTAATTTTGGATCACGAAAAGATCA*

BC1G_09781

SEQ ID NO: 26

*GATACAAAAGCTTTCGAAAGCCGCTTGAGTAAGTAAGAAGGCAATAAGAGAGGTCCTCGTCCGTGTCGAGATGTGATG*

*CTTGAGTCATTTTCCTGGTATAGCTTCTGCAATCGAGTTCACACTCTACTACTTGATTCAGATTACACCAGGAGTAACAC*

*CTCAAGTATTCCATATTAAATACAAACCTTTCCCATCTTAATCTATTGTTGGCGCATGGGGAGAGGAATTAATTGCTTTG*

*CTTTTTGGCCATCAGGATGTGGTCATTAGATCGATTATCCGGACACACAACACCTTCTGCCTCTCCACCTCCCCCGTTA*

*AATAGGATCCCAAATCTCCCTCGTCGTCCGAGTCATCTTGTGCCATCCCCAGTTGGTGGTAGACCTCCTTTCAACCCA*

*AGATCGTCTTCCCTGTCGTTAATCTCCAATGACTCTAATTCATCGTTGCTATCATCACGGAGACCCAATGGTTCGAATCT*

*CAAACAAGCAGTCACATCTCCGAATGTGCCAGATCCTTTGGAGGTTTTGGGAACACTACTGAATAATGGGGAAGAGAC*

*AAAATTGCCATCAGCGAAAAGCCCGGGGGCGACAAATGGGACAGTTGCTCCCATTGAAGAGGAAGACGATGAAGGC*

*GAATGGGATTTCGGAGGTTTAAGTCTGCAAGACATTGTAGCAGGAGAACCTCTCGATGTTGAGGATGAGCATGTGTAT*

*AAATCTCAAACGCTGGAAGAATATGAGCGCGAGAAAGAGAAGTTTGAAGACCTCCATCGATCAATTCGCGCCTGCGAT*

*GACGTTCTTAATTCAGTCGAGATAAACCTCACAAGCTTTCAAAACGACCTTGCTATGGTATCTGCGGAGATTGAAACTC*

*TGCAAGCACGATCGACGGCTTTGAGTGTAAGGTTGGAAAATCGCAAAGTAGTAGAGAACGGACTTGGGCCTATAGTG*

*GAGGAGATCAGTGTCTCTCCAGCTGTCGTTAAAAAAATTGTGGATGGAGCTATAGATGAAGCTTGGGTTCGAGCATTG*

*GCGGAAGTTGAGAAACGATCAAAAGCAATGGATGCTAAATCGAAGGAGCAACGTACTATAAAGGGCGTGAACGATCTT*

*AAGCCTTTACTGGAGAATCTAGTTTCCAAGGCATTGGAAAGAATCAGAGATTTCCTCGTTGCTCAAGTGAAAGCATTGC*

*GATCGCCCAATATAAATGCACAGATCATTCAGCAACAGCACTTTCTTCGCTATAAGGATTTATATGCATTCTTGCATAGA*

*CATCACCCGTTGGCTGAGGAGCTTGGTCAAGCATATATGAATACAATGCGATGGTACTTCCTTAATCAGTTCACGA*

*GGTATTTGAAGGCGTTGGAAAAGATCAAGCTTCATGTGTTGGACAGATACGATGTGCTCGGATCAGATGACGGGTCTC*

*GTAAGGCCACTCTTCTTTCAGGATCCAAACAGACAGGTCCACCACACGACGCATTCAATCTAGGTCGACGAATCGACC*

*TTCTCAAGACGCCAAACCAAACTGCACTTCCCTCTTTCTTAGCCGAAGAAGACAAACAAACCCACTATATGGAATTTCC*

*TTTCCGTAACTTCAACCTCGCACTGATTGATAACGCTTCCGCCGAATACTCCTTTCTTACCTCTTTCTTCTCTCCCTCTC*

*TAAGCTACGCTACCATTTCCCGACACTTCAACTACATCTTCGAACCCACTTTTTCCCTCGGCCAATCTCTCACCAAATCC*

CTCATCCACGAGTCCCATGATTGTCTCGGCCTCCTCCTATGTGTGCGCTTGAATCAACACTTTGCATTTTCCCTTCAAC

-continued

GCCGCAAGATCCCCGCTGTAGATTCCTACATATGCAACATCCATGCTCCTCTGGCCACGCTTCCAACTCACAATGG

ATATCCACTGCGAATCCGTCCGCACCCTAACATCCGCTCTCCCTACCCGCAAACCCTCAGCTTCGGAACAAGCTAAAC

AATCTGCAGCTCCACACTTCATGACCCAACGTTTCGGTCAATTCCTACAGGGTATCTTAGAATTGAGTACGGAAGCGG

GAGATGATGAACCTGTAGCGAGTAGTTTGGCAAGATTGAGAGGCGAGATGGAAGCATTTTTGACAAAGTGCGCGGGG

GTTATGCCGGATAAGAGGAAGAAGGAACGATTTTTGTTTAATAATTATTCGTTGATTTTGACAATTGTAGGGGACGTAG

AGGGTAAATTAGCCGGGGAACAAAGGGCGCATTTTGAGGAGCTGAAGAAAGCTTTTGGAGATGGTGTCTGATCCTTCA

CTTCATTTTGATACTTAATTGGAAGTTTTTGAGCGTGTACACTTATCAAAGCGTATTATTTGATCATGTATTTTGTATTTGT

GAAGAGAAACAAAGAACTTTTATTATGGTAGAAATAGAGCCGGAAATAATCTATGCTGTGGAAGAAACCA

BC1G_05327

SEQ ID NO: 27

GGGTCTATTCACACCTCTCCCTCGATCAATACGACGTCTGCGGCTTCTGCAACCCATTGAGAAAGGTAGAAAAGAGGT

TCAAAAAGTCGAGATTCCCCGTGCCTATTCTTCCTTCTTCTTCCTGTTCTCCTCCCACTTTCCTCCGTGTGATACTTCGT

CTATATCTACCTCACCCCCTCCCCCTCGAACGCAGATTGTACCGATACCCCAAGTGATTCCGCCGTACCGTGTACGCG

TTTTCATTAATTTACCATATCGTATTACCTACCTATTACCTACTACCTATTACCCATTACCTACTCCCTCCCACCACTACT

CGACTCTACCTGGGTGCGTTGCGATTATATTCTTCTTCTTAGTAGCTCGTTTTACTAGAAAGCTTTCCCACCCACCCAG

CTTGAACCCCTCCATTACCAAGAACTTTAAACGCTACCCATCCATCCTTGGGCCGAACCTAGACCGAAAACCCCTCCG

TCCGTTGTGATAAATCCAACGAGCACAGAAGCTCAACAAATACCATCACCGTCCAAATCCCAATCTTCTCAAACGTTCA

GTCATGGCTCACCACGATGAGAAAGGTCCTCATGGAGATGGAGCTTACAGTGAGGTTTTTGAGGAGGGTTCCGACAT

CAAACACCCACATACCGTCCATCGTATCAGAGCCAACTCCTCTATTATGCAACTGAAGAAGATTCTTGTTGCCAATCGT

GGAGAAATTCCTATTCGTATCTTCCGTACAGCCCACGAGCTTTCTCTCCAAACAGTCGCAGTCTTTAGTTATGAGGACC

GTCTTAGTATGCACAGGCAGAAGGCCGATGAAGCATATGTTATTGGAAAGCGGGGTCAATACACACCAGTCGGTGCTT

ACTTGGCTGGAGATGAAATCATCAAGATTGCTCTCGAACATGGCGTTCAAATGATTCATCCTGGTTATGGTTTCCTTTCT

GAAAATGCCGAGTTTGCAAGAAACGTTGAGAAGGCTGGACTTATCTTCGTTGGTCCTTCGCCAACCGTTATCGATGCC

CTTGGAGACAAGGTATCTGCCAGAGAAATCGCCATCAAGGCCGGTGTACCAGTCGTTCCAGGTACCGAAGGAGCTGT

CGAAAAATTCGAGGATGTAAAGAAATTCACCGATGAATATGGTTTCCCAATTATCATCAAGGCAGCATATGGAGGTGGT

GGACGTGGTATGCGTGTTGTCCGACAACAAGCAGAACTCGAAGATTCTTTCAACCGTGCCACATCCGAAGCCAAGTC

GGCTTTTGGTAATGGAACTGTTTTCGTCGAAAGATTTCTCGACAAACCAAAGCACATTGAGGTACAACTTTTGGGAGAT

AACCACGGAAACATTGTTCACTTGTACGAACGTGATTGTTCCGTACAACGTAGACATCAAAAGGTGGTAGAAATCGCAC

CAGCTAAGGATCTTCCCCAATCAGTTAGAGATAACCTCTTGGCCGATGCTGTCAGACTTGCCAAGTCGGTCAACTACC

GCAACGCAGGAACGGCTGAATTCTTGGTTGATCAACAAAACCGTTACTACTTTATCGAAATCAACCCACGTATTCAAGT

CGAACATACTATCACCGAAGAGATCACTGGAATTGATCTTATTGCAGCACAAATTCAAATCGCTGCAGGTGCAACCCTT

GCTCAATTGGGTCTTACACAAGATCGCATTTCCACCAGAGGTTTTGCTATTCAATGTCGTATCACCACAGAAGATCCAT

CCCAGGGATTCTCACCAGATACTGGAAAGATTGAAGTCTATCGTTCAGCTGGTGGTAACGGAGTTCGTCTTGATGGTG

GTAATGGATTCGCTGGCGCAGTTATTACTCCTCATTATGATAGTATGTTGGTCAAATGTACTTGCCAAGGATCTACTTAT

GAAATTGCTCGAAGAAAGGTCCTTCGTGCTTTGATCGAATTCCGTATTCGTGGTGTCAAGACCAACATTCCTTTCTTGG

CTACTTTACTCACTCATCCTACCTTTATTGACGGTAACTGCTGGACCACATTCATCGACGATACCCCTGAACTGTTCGAT

TTGGTCGGTAGTCAAAACCGTGCTCAAAAATTGTTGGCATACCTTGGAGATGTTGCCGTAAACGGAAGTAGCATCAAA

GGTCAAATGGGAGAACCAAAATTCAAGGGTGAAATCATCATGCCAGAACTCTTTGATGAGAGTGGAGCCAAGATTGAT

ACCTCTGTACCATGCAAAAAGGGATGGAGAAACATTCTTCTTGAGGAAGGTCCTGAGGGATTCGCCAAGGCTGTCAGA

GCAAACAAAGGATGTCTTCTCATGGACACAACATGGCGTGATGCTCATCAATCGCTTCTTGCTACACGTGTTCGAACA

GTTGATCTTTTGAACATTGCAAAGGAGACAAGTCACGCTTACAGCAACTTGTACAGTTTGGAATGTTGGGGTGGAGCTA

-continued

*CTTTCGATGTTGCCATGCGTTTCCTTTATGAAGATCCATGGGACAGACTCAGAAAGATGAGAAAGCTTGTTCCAAACAT*

*TCCGTTCCAAATGTTGTTGCGTGGAGCTAACGGTGTTGCTTACTCTTCATTGCCTGATAATGCTATCTATCACTTCTGTG*

*AGCAAGCAAAGAAACATGGTGTTGATATTTTCAGAGTTTTTGATGCTTTGAACGATATTGATCAACTTGAGGTTGGTATC*

*AAGGCTGTACACAAGGCTGGTGGTGTTGTTGAGGGTACAATTTGCTACTCAGGTGACATGTTGAACCCAGCCAAGAAA*

*TACAACTTGGAGTACTACTTGTCTTTGGCTGAGAAGCTTGTTGCTCTTAAAATTCACATCTTGGGTGTTAAGGATATGGC*

*TGGTGTTCTTAGACCAAGAGCTGCTACATTGTTGATTGGAGCTCTTCGCAAGAAGTATCCCGATCTTCCAATCCACGTT*

*CATACTCACGACTCTGCCGGAACTGGTGTCGCATCTATGGTTGCTTGCGCTCAAGCAGGTGCTGATGCTGTCGACACT*

*GCTACTGATAGTTTGTCTGGTATGACATCTCAACCAAGTGTTGGAGCTGTCCTTGCTTCATTGGAAGGATCAGAGCTTG*

*ACCCAGGCTTGAACGTTCACCATGTTCGAGCTATCGATACCTACTGGTCTCAACTTCGTCTCATGTACTCACCGTTTGA*

*GGCTGGTTTACACGGACCAGACCCAGACGTGTACGAGCATGAGATACCCGGTGGTCAATTGACCAACATGATGTTCC*

*AAGCATCTCAACTTGGTCTCGGTGCTCAATGGGCCGAGACAAAGAAAGCTTATGAGCAGGCCAATGACTTACTGGGTG*

*ATATCGTCAAGGTCACTCCAACATCTAAGGTTGTTGGTGACTTGGCACAATTCATGGTTTCCAACAAACTTGACTTCGA*

*TTCCGTTCAAGCTAGAGCCAGTGAATTGGATTTCCCAGGTTCCGTTTTGGAATTCTTTGAAGGTTTGATGGGTCAACCA*

*TACGGTGGTTTCCCTGAACCATTGAGAACCAATGCTCTCCGTGGCCGACCCAAGCTCGACAAGCGCCCTGGTCTCAC*

*TCTTGCGCCACTTGATTTGGCTCAGATCAAGAAAGACATCCATGCTAAATGGGGCAGCGTTACTGAGTGCGATGTTTC*

*AAGTTATGCCATGTACCCTAAGGTCTTTGATGAGTACCGAAAGTTCGTTCAGAAGTACGGTGATTTGAGTGTTCTTCCA*

*ACTAGATATTTCCTCTCGAGACCAGAAATTGGAGAGGAATTCCATGTTGAGTTGGAGAAGGGTAAGGTTTTGATCTTGA*

*AGCTTCTTGCTGTTGGTCCATTGTCAGATACCACCGGACAAAGAGAGGTCTTCTACGAGATGAACGGAGAAGTTCGAC*

*AAGTCACAATTGATGACAACAAGGCAGCTGTTGAGAACACAAGCAGACCAAAGGCCGATCCAGGAGATTCCAGCCAA*

*GTTGGAGCTCCTATGTCAGGTGTTGTCGTTGAGTTGAGAGTCAAGGATGGTGGTGAGGTTAAGAAGGGTGATCCACTT*

*GCTGTCTTGAGTGCCATGAAGATGGAAATGGTTATCTCTGCACCACATGCTGGTAAGGTCAGCAGTATGCAAATCAAG*

*GAGGGAGATTCAGTTGGAGGTTCTGATCTCATCTGTAAAATTGTCAAGGCAGGAGAGTAAATAGCAAATTTCAGTGTGA*

*ATGCAAGTTTTGGAGCGGTTATTATGATATCAGATGTTGCAAGTATTGATGGGATGAATGGATTATGATTGACAGGTTTA*

*AAGGTTATTGCTTGACCTACTTTTTATAGAATTATGAATAAGCTTTTATCAATTTCTGGTGTTTTTAGTGTCCTCATGAATT*

*GTATGTAACCTAACATGATGTGAAAATTGAGAGCCAATGATGTAATACTGCCTCTCGTATACA*

BC1G_15423

SEQ ID NO: 28

*GGAGAGGCGAGGGAGGGATTACTTGAAGATTATTTATACGAAATGATTTTCCCTATGTTTTGTTCCCGAGATTGTTTTC*

*CTCCATTGCTTTCTTCATTCTTGTAAAACCAAGTTTTTTTTCTTGTTCTACTTTGAGAAACTTTCTTCAGATATACCTGGC*

*GCTTAAATCTGCAATCCAACAACTACCCCACCGGCTCTTCACATTTGCCAACCTCGCATATCTCGCATCTACCCCCTGC*

*ATATCATACCAAGTATATAGAAGGTCGAGGTCACACTGACTCTCACCATAACGAGTCACAATGATCTCCCATCATTTTG*

*AAAGTCTCCCTGTTCCTCCCCTAGAGAATCTCAGCACAGAATATATACTCCAAGAAATTATCGACCACATTGGAAAACT*

*CGCCGATGATCTCCCACACACCAAGCTCAATTTGTTTCGCAAACAACTCTGGGACATTAGAAATCGGAATGTGGATCC*

*AAAAACACATTTGCGAGGTTTATTGAGAGTGTTTGAAAATACACATACATTCAAACATGCATTTGAGGAACTAGAACCCG*

*GTTTGCAAGCGCAGATTCGTGCGTTTATGGATGATGAAAAGGATGTGAAGGAGGAGGAGATTATGGGCATGGGGAAA*

*GTCAAAGGGGAATTTTTCATTCCGCCATCGCCGGCAGTGAAACATCATTTCAAGGAGATGGTCAAGGAGACGGTGAG*

*GGAAAAGGCTCACGAGAAGAAGATGAAGTTGGTGCAGAGTAAAGTGATGAAGAAGATTCAAGAAGCGAAAGAGGAGA*

*TTGAAAGAGAGATTGTGGAGGAGGTGGGAGGCCATATCGAGATGATTCAGAAGGTTGAGGACCATGTGGGGGAGTTT*

*TGGGGGAGACATGGTCACTTGGGAGCGTTGCTGAAGAGCAATGATGTTGTCTCTTTGACTTCAAAACTAGATGCTTCG*

*ATGCTTGGAAGTGGGAAATCTCCAAAGATCTGGGAAGATGAGAGAGGAGAGAGGATCATGGAAGTCCACAAAAAATGC*

*CCCGTTTCATAATTGGGGGAACAGCGTGAAGAATACTCCTCTTTATACCTTTGTTCCTACCACAGTTCTGGGCCTGTCG*

*AATCTGGTCAAGTGGGCTAAAGTCGAGGGTTATAGAGTGAGATGTAGTGGGTACAGACACTCGTGGAGTAATACTTTC*

-continued

*TCGCAAGACAAACAGATTTTGGTCAGTATGTTGAACTTGGAGAGTGTGGAAAAAAATCCCGGATGTCATGAGCATTACG*

*AAGGAGAAAGGAGATGTGGATTTGAATGGAGATGGAGTGATAGATGTCAATGAATTAAAGACGATTGAGTTGGCGCCG*

*AAAATTGAGGGATTGAGTTTGGCGGGGGATGAAAAAGGGAAAATGCTCTGTAGAGTTGGAGCGGCGGTTACGAATGA*

*ACAGTTTAGGAGGTGGGCCGTGGGTCATGGCAAATGGGCCTTGCCGGTGGATGTTATTCTTGTTGAGGTCACAGCAG*

*GTGGCGTCAACGGTCCCATTTGTCACGGCGCCGGTCGTCGTCATCAAACAGTATCAGATTATGTTCGTGCCATCGAAT*

ACATCGATGCAAATGGTGTGCACCGCACCGTGACAAAACCAGCCCATCTCCGCGCCGCAGCTGGTTGTTTCGGACTC

*CTCGGTATCGTAACCCACATAACACTCCTCCTCTCCCCCATGACATACGCCGTTCTCCGCCCCACCAAACCCGACATT*

*GCACTTGCCATCCCCCCTCTCTCCCCTACCGATATCCCCATCGCGCTCCGCAAATCGTGGACCCCAGCCCAATACGC*

*CGATGCGCTGAAAGAGTTTGAAGATAAAGCCAATAATGACTATTACAGCGAATGGTTTTGGTTTACGCGCAGTCAGCA*

*GGCGTGGGTCAATACGTGGAATGATACGGCGGATGCTGAGGGCGCAGTCGAGTATCCGAGCCCGTTTGATACGTTTG*

*TGCAGTGGGTTCAGGGGTGGGTGGGGAGTGTGTTGACGGGGAGTGAGGTTTTTGGTTTGTTGCCGGGGAGGTGGCA*

*GGCTTGTATCTTGAGTTCTTTTGGGATGGTCGCACTCCCCCCCTTTGAATTCAACGAATTCGAACAAAAGAAAACGGTC*

*GAATACAAAACCGCTCTTCCCAACGGTCTCCATTTCCGTCGCGGCATCCAAAACATGCGAGTCCGCGACCTCGAATTC*

*CAAATCCCCATCCCCTGTCTCCCCAACGCAACGCCCGATTACACCATCGTCCGACGCGCCTGGTGGGATATCATCAA*

*CCTCTGCTATCGCGATTCGGAAACGCCGATGCGGCTCACGCTCGAGTTACGGATCATGGGGGATTCGAATCTGATTAT*

*GGCGCCTCAGAGAGGGAATCGCTGGGGCACGGCGAGTATTGAGATTCTGAGTGTGCCCGATGCGGTGAGGGATGAG*

*GAGTGGTTGCCGTTTTGTCAGGAGGTGGTGGATTTGTGGGCGGGGTATAAAGGGAGGATGAGTGTTGATGGGGAAG*

*AGCGGTTGTTGAATGTGAGGCCCCATTGGGCGAAGGAGTGGGAGGGGGTGAAGATTAGAGGGAGGAAGGCGAGGG*

*AGTATGTGAGAGAGGTGGGGTATAGAGAGGAAGTGGGCGAGTTTCGAGCGGTGCTGGGTGAGATTGGGAGGGAGCA*

*GGGGTGGGGGTTGGAGGATTTGAAGGGGAGGTTTAGTAATGAGTTGTGGGATTATGTGGTTTTTGATGGGATGGAGG*

*GGGGGAAGGTAAAGGGGGGAGAGGGGGTGCAGAATGTTAAGATGGGGAAGGGAAACCCTGTTGTGATGGATGTCG*

*GTGTGGATGTTAAAGAGAACAAAGAGACTAAACCTCTTGGAGGGGTGGATGGTACAAAAACCACTAGTCCGGAGAATT*

*TAACAGATAACTTGATGTTGGAGAGGAAGGGGAAGGGGAAGGAACAGGAACAGGAACGGAAACGGGAAATCAAGATC*

*AACGAGGTGGAAAGTGTCGAGTCGAAGGGAGTAGCTAATAACGTAAGCGAGGTGAAGAGTTTGAGTAGTTCTGCTGT*

*GCAGGTGCAGGGGAAGGTGGTTGGGATTCAGGGAGGGAGTCACGCGTGTGGGGTTTTGCCTGTTAGGTTGGGGCG*

*GTAGATGATTGGATTTTTTGGGGGGGGGGGGTTCTTGTTTTTCTTTTCTTGGAGGAGAAGGGAAGGGTGGGATGGA*

*TTCTTTGGTTTGGGGGTTTGGGGACTTGGGACTTGGGGTTGGGGTAGGGAGGGAAGGAAGGAAAGGGAATGAGAAA*

*GGGAATTGGAAGGGGTGTTTATTA*

BC1G_09454

SEQ ID NO: 29

*GAAACGTGATGATGAAATTAATTCGAATTTCACCAAATGCTATGGAGCTTTCCAAAAATCCGATTTCATCATGTCTTTCTT*

*CGTTCTCCTCACCTCTATTCTTATCCTTCTTTTGTCTATACCTCTCTTCTACCGTACAAAATGGTGGAGGGATGGGCTCG*

*AGCAAGTGTGTTTCAGACGGATTCCAATCAATGCGCTATCAATATCAAGTCTCCCCTCGAACTTCTCCATGCTATTAACT*

*CCAGTGCTCAGAATATCTCTTTCAAGACCTATTTCCACAATGTCATTCTTCTTAAATCATTTGAAATCACACACCCTAGTT*

*ACCTTACCCATTCCTGAAAAGAAGTTTACGGGGAAAACAATCATTGTCACAGGGAGTAATAGTGGATTGGGACTAGAG*

*GCCGCGAGGTGGTTTGTCCGTCTCGATGCCCAAAAAGTCATCCTTGCCGTCCGCTCCCTCTCAAAAGGTGAAGCTGC*

*ACGTCAATCCATCATAAGCAGTACCTCCTGCTCTCCAGACACCCTCGAAGTATGGAATCTCGATCTTTGCTCTCAATCT*

*TCTGTCAGAGAATTCGCGCATCGAGCAAATGCGCTCCCGAGACTTGATGTTTTGGTATCGAATGCTGGAATCTATGTTT*

*TTGATTTCGAAGTAGCAGAGGAAAATGAAGAGACGATTTGTGTAAATGTAATTAATACGTTTTTGTTGGCTTTGCTTTTG*

*TTGCCTCTGAGGGAAACTAGTATAGAATATGATACGAGGGGGGTAATGACATTCACGGGAAGTTTCGTGCATCAT*

*CTTACTACGTTCCCGGAACGGCGAGCCGGGAACGTATTTGAAGAATTGCGAGTGGAGGAAAGAGCAGATATGAAAGA*

-continued

TCGATATAATGTGAGTAAACTCATCTCTCTGCTATTTTCCCGAGAACTCGCGTTTGCTCTTCGCGAATCTGAGAGGCGC

GGGAGGGAGGGACATGTTGTTGCGAATATTGTAATCCCGGGTTGGTGGATACGGAGATTATGAGACATGCGACGGG

AGCTACGAAACATTTGGTGAGGGGAGCGATGAAATTGATGGCGAGAAGTGTTGAGGAGGGGAGTAGGACTTTAGTGC

ATGCTGCTGGAGGAGAGGAGGAAACGAATGGAATGTATTTGGATGATTGTAAGATTGGGAAAGTATCACCATGGACAA

CATCACTCGATGGGATAGCAACCCAAAAAGACATTTGGATGGAATTATCGCAGGAATTGGAGAAGGTAGAACCAGGTA

TCATGGGGAATGTATGAGAGATTTAGATCGAAATTTATACTGCCTTTTGTAATCAATTCCCATGCCATTGTGTTAAAATTT

TGGGCATAAGTAACA

BC1G_15945

SEQ ID NO: 30

GAACTTTAAGGCGGAACCCGTATCTCAATCGGCACTAGCCCCAGCAAGAACGAACACACTCCAATCCAATTGGCTTTC

GCTGCTCACAATGATATTTCATGGTGGTCTCGGTGTATTGTCGCAATTCAATTCACCTCATACTCAAACTAATCACCAAG

AGCGACTCAATCGACAATTCGATTTGGTCAATCCTTACACCAATGCTTTATGGCAATTTCACGGATCGCTCATAGGAGA

ATCCAACAGTGACAAAGTATCGGCGGACAATATAATTGAGAACCGACAGAAGCGACGGATTGGGTGTCCAACGGCTT

CTTCCACCTCACTACATGATACGGCGTTTTCCGGCGCATTAGTTGCGACGATGCCTCCAAAACGAAATGCTTCTGGTG

AGCCAAACGGTTCGAATGCGCCCGTTGCTAAGCACATTAAATCGGAACAACATCCAGAAGAATTCTCAAATACCGTGA

AGAAGAAACTGCTGGCATCCACGAGAACTGGCCAAGCTTGCGACCGTTGTAAGGTTCGCAAGATACGATGCGATGGA

TTGGCTGGCGGTTGTTCGCCATGTATCCAAAACCACAACGAGTGTAAAACGACAGATAGAATAACAGGTCGTGCGACA

TCGCGGGGTTATGTGGAGGGAATCGAACAACAAAATCGAGATCTGCATCTTCGCATTCAGGAATTGGAGCATCGATTG

ATGCAAGGCGGTGCGGATATCAAACCGGCGAATGGTTATCAGGATTCGGGATCGGGCCAATATGGTTATGCTCAATC

CTCAAATGGCATGCAATCAACATGGAGCTCGACAGGTCCAGCATATACTTCACCCACTTCAACTACGTCGAACAATGG

CCAGCAGCAAGAAACTAATATGTTTCGCGCATTGCCTGCCTATCGCGCTGGATGTATGGGCGATAATTATCTCGGAGT

ATCGCCTGGCAGTTCTCACTTGAGCGCAATCAAAGGGACGGCTTTGTCGATTTTGGGTATGGAAATTGATATTGCGGA

CTTCCGTTCAACGGATATGGATGAACCAGATCCTTCGATTTTCCATCCCCAGCTATACAATAAATCATATCAGTCTTTTA

TGCAATCGGCTTGGAATGTAAATCCAAGGATTGAAAAGGTTGAATTGCCCGCACGCTCAGAGGCTCTCATTTATGCGG

AGTGGTATTTTCGTGTTATTAACCCATACTGTCCTCTACTTCACAGAGGCACTTTCATGAGATTGTTAACTCGCATGTAC

GACGATCCCAACTTTCGCCCCACGACTGCTGAGAATGTTATTGTTCATATGCTGTTCGCCATCATGTTCTTTCAATACG

CGACCAGAAATTGGGAAGATGCCGAACAACAAGCCAGTTTGAATTCTCAATCAAATACACATTATCATTACTGTCTTGG

AATGTTCTATCAACTGGCATGTAGTCACACAGCACAAGATGTTCAAGCATTGGCCTTGATCTGCTTGCACCTTCGAAAC

TTTCCTAAGCCGGGAGCCAGTTGGGTGCTTGCAAGAATGGCAATGACTCTTGCTATTGAGCTTGGCCTTCACCGATCA

ATGAAGAGATGGGCACCTGAATCGAACACGCTTAGTGAGCTCGACATTGAAATGCGCCGACGAACATTTTGGGTCATC

CTTGCTGTCAATGTCACTCTTAGCGGCAAGCTTGGCCGTCCAATGCCCCTTCGAAATGAAGATTACGACGTCGAATGT

CCATCACAAATTGATGACGATTACATTCCCGGAGAGGGTATAGATCCACCCAATCCAATAAAATGTAACCATGAGATTG

GAATTCAAGGTTTCAAATTGATACCATGCTATTTGGAGCTTTATTCGACTATCTATTCGATTTCTCGTCAACCAAGTACCT

ATATTGCAACTGTTAACCGATTGGAGGCAAAGATTCGTGCTTGGAAAGATGACTTGCCCCCAGAGCTTGTGAACGGAG

AGTTGGGACACAATGAACAAGAAGGACGGGTATTTGCTCTTTATGCTCAATCTTGGTCTCAAGAATTCCGTCTTCTTCT

TCGCCATCCTTCAGTTTCTATGACCACAGATCCAGATTTCAACGCGGAGAGTATGAGAATTTGTGTAGAGTCTTCCCGC

CAAATGTTAGGAGTTGTTCGTCAACTGCAGAAGTATAAGAGCCTTGATACGACTTGGTACAATACCTCAGTTTTTGTTAT

GGCACTTACTACTACACTTTTTGCCCAATGGGAAAAGCGTGGAGGGACTTCATCAGCTGATTTGGCTGCATTGAGAGA

AGAGATGGATATTTGGTTGGATATTATGGGTGATATAGGTTCACTTCTTGGTTCGGGAACACGGCTTAAGAAAGCTGTG

CAAGTTGTCACCGATGGGACACTCGGATTACTAAGTCGAAATTTACCTGCTAAGAATGACAAGAGCTACGCTTCCAATA

ATAATGCCCAGGAAGAAGTCAGACCTTCGGAGCAAACATCGAATACCAATGGAAATAATGGTTATCCGGTCAATGCTC

AAAACTTTAATTATAATGAACCAACTTCTGCTACGGGGACTGCGCCTACACCTAACTATTCACCCTCCGAAGGTCAAAT

-continued

*GTCTCATCAACAAACACCCTATCCAGCAGCAACCCAATATTCACCATATCTTGAATCGGCTTCTGGTACTTCGGATTTG*

*ACATATGCGCAACCAGAGAATCAAGGTTATGGAGGATATTCGGCCCCAACTAGTGATTCTGTAGAAGCACCATTAATTG*

*CTGCGTTAGCTGCTCAGGCAACGCAGGTCGCCCCTAATACATGGCACAGAAACCCGATCCAGGTCAACACAGCGCCA*

*ACACAAGCCTGGCAACATTGGACATCTACCGTCACAGGTAACCTTGAGCCACAAGAATGTTACTCGGCAAGTGCTCTA*

*ATGCAATTAGGAGGAAGAGATATGAGTAATGGCGACACAACACAATTGAATACATCGATGGGCGATGTTCAAAGCGGA*

*GGAGTTAGTGAGCCAGGACATTTGGGTGGTCAAGTTTCGGGAGCCATCGCGGGTACTTGGCCGCTTAATCTTTTTGAT*

*ATTGGTGTGAATGGTTCGACGGGTTGATCCTTTTGGCTTTTCTGCTTGTGATTAATTTTCTTGTGCATATTATGATGGTG*

*GATGGAGATAACCGGCGTCTTAAGGATGGATGGGGAAAGATAGAAAGGCATGGTGCAATGGACGGGCCGGTCGGCT*

*TACTTGGAGTTATCAGGCGGTGGAAGGGGACTACA*

BC1G_14887

SEQ ID NO: 31

*GAGCAATTATTAGCAATTATCAACTACTTTGGGGGCTGAAAGCCATTTCAATTCATGAGTAGTGATATGTGAGCATTGG*

*GGCAGAGGAATTTAAGAGTTTGGTCTTTGCAATATGTTGCAGAGGTGAAATTGGAGGTTCAGCCGTCGCATTTCCATTA*

*CTTCGCTCCCATCTCAATCCATCCTCCCGTCCAACTTTTCCACGTCCCACATTCATTCACCGTGGCAAACAAGATCTTT*

*ATGCTCTTGCCAGCAGAAACTCGACCATATTTACGTCTGCGAAGCAATATCGACCTCGCCAGCTAATATTTCGCGACCT*

*TGCATGCAAGCTATTCGCGTTTTGCCATCCAGGCGCAACCACTTTCTTGACTTTCAGGTGTGCGCGCAACAAACAAGA*

*ATTAATTGCTTGCAAAGTCAAGGGGGCTTTATAACTACCAACATCATTAATACGGCGTTGTGTTCTACCGCCGTTGGGT*

*ACTTCACGTCTGCCACCACTAGTAAGGGAACAAAAGGCCGCTTCGAACACATTAATAAATAGTTCGGCTTCCCCTTCG*

*CCTCAACACACAAAAACAAAGTAATCGCACCACAACCTTACAAAGTCTCCTGCTCACGATGGAGGATGACATTCGGGA*

*GCTCCAGCCAGAAGCTGTAGATGCTGCGATTGGTGAAATGAAGATTGAGGAGGGGATTGAGGTCCAGGATTTTGCCA*

*ATGGCTTAAATGGATATATTTCTACTCCTACAGAAATCAAGAGATCTCACTCCAGCACACCGGGTCTTGTAAATTCTCG*

*CTCTCAGACACCGCCCAGAAAGCAAAGCACCAGCCAAACACCAAAATCCGGAGATGAAGAGGAAGAAGAGGTTATTG*

*GCGGTGATATCACCGTCACCGTCGAACCTGGCAAGGCACCGAAGCTATCGAGAAAATCGTCACAAAAAGTAATCCCTC*

*GACCACCCCCTCTCTTCAACGATCTTCCAGATTCTACAGAGGAGGCAGCTTCGGTATTTCAGGTAATCAAGGATTGTAT*

*TTATGGAGCTAAGCACATGGGAGCTTCAGATCACGATGCGTTGGATTGTGATTGTCCCGAGGAATTCAGCGATGGAAA*

*AAATTATGCCTGCGGAGAGGATTCTGATTGCATTAATCGACTGACCAAAATGGAATGTGGTGGAGGTCATAAAGATTG*

*CAATTGTGGTTTGGATTGTCAGAATCAACGCTTTCAACGCAAACAGTATGCCAAAGTTTCAGTGATCAAGACAGATAAA*

*AAGGGTTACGGTTTACGCGCAAATACTGATCTACAGCCTGATGATTTCATTTTCGAGTATATCGGAGAAGTTATTAACG*

*AACCAACGTTTCGACGACGTACTGTCCAATATGATCAGGAGGGGATCAAGCATTTCTATTTCATGTCTCTCACGAAGCA*

*TGAATTCGTGGATGCAACGAAAAAAGGGAATCTAGGTCGATTTTGCAATCATTCTTGTAATCCAAATTGCTATGTCGATA*

*AGTGGGTGGTCGGAGAAAAGTTGCGCATGGGCATTTTTGCCGAGCGTGCAATCAAAGCCGGAGAAGAGTTGGTCTTC*

*AATTATAATGTTGATCGATACGGTGCCGACCCTCAACCTTGCTATTGCGGCGAACCGAATTGTACCGGATTCATTGGA*

*GGCAAGACTCAAACTGAGCGTGCTACTAAACTTCCTCATGCTACCATTGAAGCTCTTGGTATCGATGATGGTGATGGTT*

*GGGACACAGCTGTTGCCAAGAAACCTCGGAAAAAGAAGACAGGTGAGGATGATGAAGAATATGTCAACAACGTTCAAC*

*CCAAGGGGCTCGATGAAAATGGAGTGCGGAAGGTTATGGCAACTCTTATGCAATGCAAAGAAAAATGGATTGCTGTCA*

*AGTTGCTTGGTCGAATCCAACGTTGCGATGATGATAAAGTTCGAAACAGAGTTATACAAATGCACGGTTATCAAATTCT*

*TCGTACGACCTTGACTACTTGGAAGGAAGACAACAACGTGATCCTCCAAGTTCTCGACGTCCTTTACAAATTTCCACGA*

*CTTACTCGAAACAAAATTGTTGATTCCAAAATCGAAACAGTTCTAGAAGAATTCACAACTTCCGAGCATGAAGATGTTGC*

*TTTCGAGTCAAAGAGGCTATTGGAAGCATGGAGCAAATTGGAGCATGCGTATCGAATCCCAAGAAGAGCCCCAACTCT*

*TGTTGCACAAGTATTTGAGCGGCGTCCAGACCAAGTAGAAAAGGTCACTCCATCGCCATCCCCTGTTATTGTCGCCCC*

*TACTGGCCCCCGAAGTGGTGTTCCTCAACGCAACGCCAATTTCGTTGCCAATCGCTCAATTTCTCGGCGCCCGTTCGT*

-continued

*CCCCATGGTATTACCACCTGGCTGGTTTACTGCGATGGACCAAAACGGAAATGCTTATTATTACAGTAAGACGGGACA*

*AACAACATGGGAGAGGCCATTTATGCCAGCAGGGGTATCGCCACCACCTCCACCACCCAAGGCAGCTCCAAAGAGTG*

*TGCAAACACAAAAAGCTCTTCAAGATATTATCGACAGTATTACAAAGGAGCCCTCGACGACTCCGGCACTTTCCTCCCA*

*TTCCGCCGAGGGTACACCCAAGGAGAAGAAGAAGAAGCCTGTGGAAAAGTGGCGCTCATTGCCTATCGAGAAGCAGA*

*TGAAACTGTACGAAAATACTTTATTTCCTCACATCAAACACGTAATGCAAAAATATTCTGGCAAACTTCCCAAGGATGAT*

*CTTAAAAAATTCGCCAAGGAATGTGGAAAGAAGCTCGTGGCTTCTGATTTCAAAAACAATCGCATTGAAGATCCCACAA*

*AGATATCTGACAGAAATCAAAGGAAAGTAAAGCAATATGTGTTTGAATATTTTAAGAAGGCTGTGGAAAAGAAAAGGGA*

*GATGGACGCCAAGCGAGCAGAGAGGAAAAGACGCGAAGCGCAGGCTAAAATCAATGGAAACGGCACGAGTGAAAAG*

*GGGATAAAGCGAGAGAATGTAAATTTGATCAGTAGTCCGGATGTGATTGATAATGAGGACGTAGAAGTTAACATACCAA*

*GTCCAACCGCATCGCCTAGTGGACAACTCGAGATGGAGTTGTTGAAGAGGAAGAGGGAAGATGACGAGGAAAGTCCA*

*TCGGAGAACAAGAGGGTAAAAGAGGATGATACTGAGAGTGCAACACCAACGGATTCATCTACGCCTCCTCCGCCTCC*

*TCCGCCGCCGCCCGCGGAAGGGATGCCTATGGCAGAGTCGGAAGATCCGGAGATGGCTAATGGCGAGGGAGAGGT*

*GAAAGAAGAAACGGAAGAGGAAAGAGAGTTAAGGATGCAGGAAGAAGATTTAATGAGGGAGAATGAAGAGGCTATGA*

*AGATGGAAATGGAAGTAGATACTGATGGAAGGTTAAAGGGGAATAATGGTTGTAGTGAGCATATCAATGGTGGAAATA*

*GTTGTGGGGAAGTCTCAACGGAGGGATGATATTTATTGCCAATGGAGGGACACAAAATTGGGAACCGCCTGTATCAAC*

*ATCATCATTATCTTCATTCAAAAAAAATCATCGGCATCGCATCGCATCGCATCGCATCAGGGGTCGGTTATATCATATTT*

ATTATATGGATAGGGGAGCGAACTAAGTGAGTTTGGCGTTTACAATTTCTTCATCTCGTATTGGAGATCGAGAGATGAA

*CATCATCTTAGATCAAAAGGATAGTTGGAAGGGATAGTCACAGAACAAATACACCCTGCTATTCCTCATGCATTAAAGG*

*AAAGTAGGCTATTTAGATACTAGGCAGTAAATGGAAATCAAGTGAAGTGTAATGATAATTATTAATCAAATGGCATTTGT*

*GAAAACTCCA*

BC1G_07589

SEQ ID NO: 32

*GAGTCGTGCCTGTCTGCAAGACTTTATTATTAGTCTTCATTAAATTTAACTCTTTCAAGATATACACTACATACACTACAT*

*ACTTCAATTTTCACTTCGCCCAGCCGTTTATACCCATCTTGAAGTTACAGCGAAAACATATTTTAATCTATCATTTTATTG*

*CATCTTACAAATAGTCCAATATTTGTTTATACTTTTGTTCTTGTTCTCAAAATCTGCAGGAATGAGCTTGAATTTTGGACT*

*GACCAATATTAAACCTGTGGCGCCAAAATTTAAATCCGAAAAGGTTCCAAAACAGAGGCCGACTCTATCTAGTAGGACA*

*TCCAGTAATGGCCTTCGAATTGGAACACCTGTATCCAAAGTCACTGATGCTCGTGGCAGACTAGCCGTCCCAAGCCCT*

*CCCCCCGAGGCAGGAAAGAAGAGGAAAGAAAGAGAAATCAGCGGAAGCCGCAACACTAAAAGAAACACAACTCTAAC*

*CCTTCGAAAAAGCCCCAGTCAACAGCCGTTGACGAGTGATAGCGAGGAAGATGAAGAGATCGCCGTGTCTTCCAAAC*

*GGGCCAAGCCGGAAAACATCGAGCCTGATTTGAAGAGGAATTTGAAGGACAAAAAAGCCTTTTCGACTGAACCCGATA*

*ATACGCAAGGCTCTACATGCAGAATGATCCATGCGGCGGATGTCATGATGACGAAACGCACGGCTAAGAGCGGCGAG*

*AAAGTTTGCGATAGGAAGAAGGAAGACGGCGACGCGGTCCTTCTAAGATATCCCAGTGTCAGTCGCAGAGAAAGATA*

*CCAACTTATCTCCGAAGGCGAAGTTATTGATCCCGCAGGAGAAGATTTGATCAACCCTTATGACGAGATACCGAAGATT*

*GTGGAAATTGTCAAGGATGAATATTTGACCGATGAACAAGCAGCGGAGTTCGCACATCCGGAAACGGGTATAATTCGA*

*AAAATCAACAAAGCGACGAACAATATTACCTGGACTCTTTCCAGCGCAAAAAAGCCCCACGACAAAGAGAAAATGAAG*

*GGGCTGTTGCTTGAGTTCAGGAATGCTGTGGGAGCTTACAATGACGCGCTCAGCACTCTCACTAAAAATGGATCGCTG*

*GCGAAAAATCTAGAAAACAAGCATTCACTGTCGTCTAAGCTTCTCAAAATGGTTCTCCAGCAAGTTTACGACCGAGCAG*

*TGTCTCCCCAAGTTGACTTGACTAATAAATACCAAAATGGCACGGATTATGTTTACGGCGAGCTCACATTCCCGTTCAT*

*ATCCCGAATCCTCAGGGAGGATACTCGCATGAAATCCGATCAAGTTTTCATAGATCTTGGTTCGGGAGTAGGAAATGT*

*CGTCGTGCATGCCGCGCTACAAGTTGGTTGCGAAAGTTGGGGTTGCGAAATAATGCCTAACTGCTGTAAGCTGGCTTC*

*CTTACAACAGACAGAATTTTCCGCACGCTGTAGGGCGTGGGGCCTCAGCGCCGGGTCAGTCAACCTCGAGGAAGGG*

*AATTTCTTGAATAACGAAAACATTCTCAAAGTTATGAAGAGGGCTGATGTTATCTTGGTTAACAATCAAGTTTTCGCACC*

-continued

TGCTTTGAACCAAAGTCTTGTGAACCTATTCTTGGATTTAAAAGAGGGTTGCAAGATTGTAAGTTTAAAAACTTTCGTAC

CGGATGGTCACGTTATAAATTCTTACAATGAACACAATCCCATCAATTTATTGCGGGTGGAAAAAAAGACGTACGCGGA

AGGCGACGTTAGTTGGCATTCTAATGGAGGGGATTACTACGTTACTACGAAGGACAGCACTATCGTAGCTAAGTATCA

CCAGACCCCAAAGGATAGAAAGACACGGGGGAGTCGGGTTAGATGATTTTTGAATTTGAATATACGGTTTCCTTGCAC

AGTTGATACCATTGGGAAGGTTATTATTGGGTACTTGAGCACGAAGCGATATCACAGCGAGGCAGCATAGAGTAGATG

TATGGATAAATGTATGTATTTGTAACA

BC1G_05475

SEQ ID NO: 33

GATGCTGTGAAGCTAGCTCGACATATCTTGATCTCTTTCAAAAGAATTATCCTCCACCTGCATTGACTCCACCCTGAGT

ACCACAGCATTAGCACGAAATGGCCCCAGCTAACATAATAAGCATTCTGAGGCTCTGCGCTAGCAGAGACGACGGGC

GCGGTATTGTCACTTATCCACTGGGAAGCAGAAACAGTGTGAAGACGTTATACAAAGATTTAGAGTTCCAAGTGATCCA

CAACGCAAGATTCCTGTCACGTATCTCCAACTTCAGACCAAGATCAATCGTTTTACTTCATTTCACGGATCACCTTGATA

ACATCGTATGGTTTTGGTCCGTAATTGCTGCTGGAGGCATTCCTGCACTATCAACACCATTCAGTAATGTTGAAACCCA

GCGCCTGAAACATATTGCACATTTACACAATCTCTTGAAGGCTCCCCTCTGCATAACGAGACGTTCCTTGTTAGATCAG

TTCTCGGATCAGGATATACTGAGACCATACGTTATCGAAGACATCTTCTCCGCTCAAGTCGCCTTAGAAAATGATAATA

TAGACGAACTTGGTCAAGTTGCAAGAGAAGAGCATCCGGAAGACTTAGCTATATTAATGCTTACCTCTGGCAGCACGG

GAAACGCAAAAGCCGTCTGCTTGACTCATGGCCAAATTTTTGCCTCAATGGCTGGAAAGTCTTCAGTTCGGAAGGATA

TCCCCAAGGATTTCTCTGCCCTGAACTGGATAGGCTTTGACCATGTCGCCAACTTGACAGAGATACACCTTGAAGCCA

TGTACCTTAATATAGACCAAGTTCACGTACAGGCTCCAGATGTCATTTCTAACCCTCTGTTTTTACTGGAACTCATACAC

AAGCATCGTGTGGGATGGACATTTGCACCAAACTTTTTCTTGGGAAAATTGAGGAAACAGCTAGACACAGTTATTGTGG

ACACAAGTCTCTACCTAGACTTAAGCTGTCTCCGTCTTTTGGTTTCCGGTGGCGAGGCAAATGTCGTGGAGACATGTG

ATGTTCTTTCCCGCCATCTAGAAAAATACGGAGCACCATCAAATGTGATCTCTGCAGCCTTTGGTATGACAGAAACCTG

CGCTGGGTCTATCTATAATCTCGATTGCCCTAGATACGATGTTCATAATATGCAGCAGTTCTGTTCTCTTGGGCGTTGC

GTACCGGGAATAGAGATGCGAGTTACAATCCCTCAGGCTGGCGATGAAATTGTCCGGGCTTCAGCCAACGAACTTGG

CCTTCTTGAACTTCGTGGACCTATCGTGTTCAAGTCCTATTTCAATAATAAGTCCGCCACAACAGCTTCCTTCACTCCAG

ATGGCTGGTTTAGAACAGGAGATCACGCCACGATCGATCGAGCTGGAATGCTCCATCTGGCAGGGAGGACAAACGAT

ACCATGAACATCAATGGCGTTAAGTATCTCCCGAACGAGCTAGAGGCTGCTATCGAAGAGGTTGGAATTGAGGGTGTG

ACACCGAGTTACACAGTATGTTTTTCCTTTCGTCCACTTGGTGCGGAATCAGAGCAAATCGAAGTTGTTTACTTGCCCT

CCTTTGGACCCCAAAATGTCGATGCTCGAATTGCAGCTCGAGACGCCATTATTCAAGTCACAATGTTGCAAACTGGCT

CTCGACCTTCAGTTCTGCCATTGAACGATGCTTTGCTGCAGAAAACGACACTCGGAAAACTCTCTCGCGCCAAAATCA

GAGCTGCATTTGAACGTGGTGACTATAAGAAATGCCTGGAATTTGATAAGATGCAGATCGAAATATATAATTCATCCCA

TATGCAACAACCTTGTACTGAGAGTGAACGCATCATTCAAGAAGTATTTTGCGAGGATCTAGATCTCCATCCGCAAGAG

TTTGGCGTCAATACACATGTGTTTGAGATTGGCATTACCTCCATCCATTTAATCCGATTGAAGCAGAAACTTCAAAGCC

GCTTCTCTATCCCAGAGATTCCCATTCGCATGATGATGCAAAATTCGACCGTTCGAGAGTTAGCCACGGCTTTGGAGA

ACCTCGGTAAACCACGAAACTATGAACCCATCATATCACTTCAGAATATCGGACAAAAGGCTCCTCTATGGCTCTTTCA

CCCAGGAGTTGGCGAAGTTCTCGTATTTCTCAATCTCGCAAAGTATCTTCCTGATCGCCCAGTATTTGCTCTTCGTGCT

CGAGGCTTCGAAAAGGGGGAAACATTTTTCACAGATATTAAAGAAGCAGTAAACACATATTTCGAAGCCATAAAGAGCA

AGCAACCGAAAGGTCCATATCTTCTCGCAGGTTATTCGTATGGTACAATGCTCGCATTTGAAACCGCGAAACTGCTAGA

AGCGAGCGGTGATGAGATTTCCTTCCTTGGATCCTTCAACCTGCCCCCACATATCAAATTCAGAATGAGACAACTTGAT

TGGACCGAATGCTTGCTGCATCTGGCCTACTTCCTTAGTCTCATCGATGTCGAGCATTGCGAGATAATGGCACCACAG

CTCCGACAATATTCCAAAAAGCAAGCCATCCAATGCATCAGCAAAGTCGCAAACCCAAACCGTCTTCTTGAGCTTTCAC

-continued

*TCAATGAAGAGATGCTTGGAAATTGGGTCGACCTTTCATATAGGCTGCAGAGCATGGCAAATAACTATGACCCCTCGG*

*GAACAGTTGCGATGATAGATATATTTGTTGCAGATCCCTTGCAAGCTGTGGCAGCGAATAGAGAGGATTGGAGGAAAA*

*ATTGCTTAAGCAAATGGGCGGATTTTAGCAGATCGAAACCAAGATTTCACGATGTAATGGGCGAGCATTACACAATGAT*

*TGGGGCGGACCATGTTTTCAGTTTCCAGCAGACTTTCCGTAAGGCATTAGAAGCAAGGGGATGTTGAAATTTTCGCAA*

*GATATAATAATATTATGCGAACCATACCTACTGCAGGTAGCAGTGTTTGGAGCAATGAAGGCAATATACTATGAACTGT*

*CCGAACATTATGCTAATATTTATAATTGTTAGATAGCACGTGTATTTTCA*

BC1G_07401

SEQ ID NO: 34

*GTTTAACCATCAAGATAATAACTGAAAAATCCTATCCACATCTGAAGCTCCTGAGCCTCGAGATATTTTCAAAAGCTCGA*

*GAGCATTAAACTACACCACAATCTAATCGGTTTGACCTTATCGTTCAATATGGCGGACGCAATTACCGAAGGAACGGC*

*CAAGCTCCAGCTTGATGAGGAGACAGGTGAGATGGTCTCGAAGGCCGAACTGAAGAAGAGATTGGCAAAACGTGCGA*

*AGAAAGCAGCACAAGCAAAAGCAAAATCAGCAGCACCACCTAAAGAAGCTGCTGCAACTAAACCTAAGAAGCCAGAAG*

*AGACCAAAGCAGCAGAGCCATCAAATGTATTCGCCCAAGGATTTCTCTCAGAAGTGTACAAGGAGCGTCCTGTCAAAC*

*CAGTCTTTACCCGATTTCCACCTGAACCCAATGGATACTTGCATATCGGTCATGCAAAAGCTATTGCTGTCAATTTCGG*

*ATTTGCTAAGTATCATGGCGGTCAGTGTTATCTGAGATTTGATGACACCAATCCCGAAGCAGAGGAAGAGAAATATTTT*

*ACAGCGAATAAAGAAATGGTTTCGTGGTTGGGCTTCACACCTTACAAGATTACACATTCCAGCGATAATTTCGATAAAC*

*TTTATGAGAAGGCAGAGGAGCTTATCAACTTAGGGGGGGCTTATGTTTGCCACTGTGGTGATGCTGAAATCAAAGCTC*

*AGAGAGGAGGTGAAGCACGGGGTCCGAGATTTAGATGCGAGCATGCGAACCAATCGATCGAAGAAAATTTGAGAAAG*

*TTTAGAGCCATGCGAGATGGCGAATACAAACCTAGGGAGGCATTCTTGCGCATGAAGCAGAACATTGAAGATGGAAAC*

*CCTCAAATGTGGGATTTGGCAGCATATCGAGTCTTGGATGCTAAACATCATCTAACGGGAGATAAATGGAAGATTTATC*

*CAACATACGACTTCACTCATTGTCTTTGCGATAGTTTTGAGAACATCACACACTCGCTTTGCACGACCGAGTTCATTCTA*

*TCAAGAGTATCGTACGAATGGTTGAATAGTACACTGAAAGTATACGAGCCCATGCAGAGAGAATATGGTCGCCTAAGC*

*ATTACGGGTACTGTCCTTTCTAAGCGAAAGCTCAAGAAACTTGTGGACGACAACTATGTTAGAGGATGGGATGATCCA*

*AGACTATATACATTGATTGGAATCAAAAGACGTGGTGTACCTCCTGGAGCAATCCTTGAGTTCATCAACGAACTAGGAG*

*TGACGACTGCTCCTACCAACATTCAACTTTCTCGTTTTGATCAAACTGTTCGTAAGTACTTGGAGCTCACAGTTCCCAG*

*ACTTATGTTAGTTCTGGATCCTGTACCTGTCGTCATCGAGGATGCCGAAGAGCTTGAACTTGACATTCCATTCTCACCT*

*AAAGTACCGGCAATGGGCAGCCACAAGGTCAAGTTGACTAGAACTGTTTACATTGAGAGAAGTGATTTCAGAGAAGTT*

*GATAGCAAAGATTACTTCCGTCTCGCCCCTGGAAAATCTGTCGGTCTACTACACGTTCCATACCCAGTCAAGGCAGTC*

*TCATTCTCTAAGGATGGAGATAAGGTCACAGAGATTCGTGCCGTCTACGATAAGGAGAGCAAGAAGCCCAAAACTTAC*

*ATTCATTGGGTTGCAGATGGTTCAAAAAATGTCGAAGTTAGAATTTTCAACAGTCTCTTCAAGAGTGAAAAGCCAGACG*

*ATGCTGAAGGTGGTTTCTTAAATGACATCAACCCTGATAGCGAAGAAGTTTGGCCCAATGCTGTTATCGAGTCTGGATT*

*TGACGAGGTACGAAAACGAGCTCCATGGCCAGAAGCTGCTGGAGAATCGGAGCTCGGCAAGGGAGGTCCTGAATCT*

*GTCAGATTCCAGGCCATGCGTGTAGCATACATGGCAATGGATTCGGACTCAACGGATGATAAGATTATATTGAATCGC*

*ATTGTTAGTTTGAAGGAGGATGCTGGAAAGTAGGGAATTAGGGGCCATTATGCAAGGGTCCAAAGAACTCATCAATTG*

*AGAAGTGCATGGGATATCATGAATGAATGATTTGTTGCAAAGAAGTTTACGTCTAGTCAAGAATATACTGGCCTTGAAA*

*AGCAGATTCATGCGCAAACAATTGAAGGGAATACTGAGTGAACAGCGTATCA*

BC1G_09015

SEQ ID NO: 35

*GAGCAAAAAGAAAAGACACTGCCCTTCCTGCGGACAGACTGTGCATACCGTACACACTACGTCCTACACGCTACTTGC*

*TACTTGCTACTCACTACTCGTACATAAACACAACGGTGCTAAAGGCAGAGGACCCCAGTCTTCTATTCTTCCAGTCCAG*

*TCGTCCAGTCGTCCAGTCGCCCAGTCGCCCAGTCGCCCAGCCCAGTCAGTCTCCCAGCCCATTCTCCCACTCGTCCC*

*AGTGCTCCCTCGCACCCTCGCACCCTCACACCCTCACACCCTCAGTCACTCACACGCAGTCACTCTCATCAGTCAGTA*

*CAGAATCTAGATCCACTTTTTGTTTCTATAGGCAACGGAAAAGACCTTGGTCATAAACCCCCAACCCTGACCACCCTGA*

-continued

CTTTCCTGAGCCACCTCGAATCTCGAAAAGGTACGGGAAACATCAAGCTTTTATCCCATTCGCAGCACCAGCAACCAG

TAACGGGAACGTACAGGTACAGGCTTGCAATCCATTCCCCCAAATATTGTTCAACTCCTCTTAGTCTATCTGCAGCCGC

AAAGAGACTGACTCTCCATACAATAAAAAAAATACAACATCCACCGCTATCTTCATTTCACCACTAAACACAATCCACGA

GCCATTCCTCGAGATATCTTCCAAACTTCGAATGCAAAAAGAGGAGACCGTCAATTGACGCGCTTGATTTCTGTGGAG

AAGAGAAAAAAAAAAAGATATTGACTCTCGAGAGACGCAGATACAGATAGCTTTCCGCTGCATTTTACTGGGTTCCTATT

TACAACGACTTCCCTGTTTACTAGTTATACCCTACGACGGCCATTTGAAATGAGATAGTCTATCGACAAACTCGGCCCT

TAAACGGACTGAGCTCAAGGAAAAGCAAAATCCTTTACTCGAGATTAATTTCTGTCGCTGGCTTTCCCCAGTGACTTTG

GTTCCTTATTCATGATTCGGGAACAGAGGGCTCCATCAGGTCCACGGCCTGACCTTTCACCCACAAGACAAAGGATTG

CTGAGAATTATCCTCCCAGTGTAGGCACCGGAGGATCGCGTCTGATAGCCGGGACAGAGCCTACACTGCATGCTCCG

CAACGAAACAATCATACTTTATTTACATTTGGGGCTCACAACGACGATAGTTCGACGTCTTACGACTTCTTGCCTTCTCC

CAGTTTTGACGACCTGCAAACCAGCATCTCCAATGAACTACAGCTTGCAGCTCAATATCCGGCAACAGGTGGGGGAGA

TTCAATGCCGAGAGAGAAGCCTTCAATGGGGGAAATCAAAGCATCTATGAACAATGGGCGGGGAATAGGTTCTGCGC

GTGGAGTGTCTGGACCACGACCGGCGAGAACCTCCTCTTTTCAACGTAGGCAGAGTGTGAGCAATCGTCAAGGTAGC

ATATCTTCAACAACTTCTTCAACTGCATCGGGGAATATGGACCCACCATCTGCTCCTCTAGCTGTTCGAACCCGACGAA

ATCAATATCCTCCGATATCTGGAAGTGCTGCCTCCAATGCGCCTGCTGCTAGAATACCGCGCAGATCTGTCGGAGGC

GCTGAGTCGGATAGCTCGAGCAAGGCGGGGACCACACAAAGACGACGTCCGAGTCTTGCTCCAAGTACATCATTACA

ATCTTTGTCGGATGCTGCCAATGCATCTGCAAGAATGAATAATACAGGGGTTCCAAGTTATATGGACGGAGCAAGAGG

TACAACGGCCTCGAGAGCAGCGAAAACTAAATCATTGCAACCTCCGAGTAAAGGGCAACCCCAAGTTTCTATTCAGCC

TGGCACACCAGATCACAGCAGATCATCATCCCTTGCTGCAAAGTCACCAGGGAGGCCCAGTGCAACAGGAATACCTG

CAACCACACCATCATCAACCTCGAAGCGGATGTCAGTTTTGCCAGGTACTTCCCATGCAAGTGGGCTTGGGGCTAGAA

CCATCAGCCCTACGGATACTCGAAGAGCCAAACGTTTATCGACTCATCAAGGAAACCCAACCGTTTCGCCGGGTACAC

CGCCAACTCCACAACCTGACTCTTATCCCGCATTTACTCCTCGAGGGTCTTCAAGATCTCCTTCCATGTTACCTAGAAA

GGTGCCTACACCTTCATCATCTCGAACTACCCCGGATAGTAACCGTAAGTACAATTCTGCTATTTCAGCTGCGTCGAGT

TCAAGCTGTAACACATCTCGAAATACTGCAGGTTCCTTACAGCCTCGAGTATCGTCACTTGCCCCCACAGCATCAAGG

TTACCAACACCTAAGTCACGAAATGTTCATAGCTCCGCTGGCAATAATGAGGAGGAGGATGTTCCGCCAGTTCCCGCG

ATTCCCAAAGCGTATGAATCCCCCAAAGATTCACCTATCGAAACTCCATTTTTCACCAAGAGGAAATCAAGTATGCCTTT

TGATGCTAGTAGTATTAACAGTACTTCAACAAATAGCATTTCTGGTAGGAATTCTGCACGTGAGCCAACTAAGGTTGAA

CGAGAGCCAAAGAGGTCAAGGCATGCACCACCCAGCTCGAATTCGGATCTTGAACAGCAAAAACAGAATACCACGAC

TCCCAAGAAAAAGAACCTTCAACCACTTCGTCTGCCACCCTTGAATTTGTTACCATTGAGTGCCCCCACGGCTGCAAA

GGCTGCGGCCATATCCAATCCTGAGCCCTTACCAAATGGTGCCATTACTCCTCCGCCTAAGCGGACAAATACAAAAAC

TCCAAGTTCACCCATGACAGCTTCCAAGACCTCATTCTTTTCCCGTCGCAACGAAGACAAATCAGAGCATCATATGCCC

AAAATGCGGAGCAATAGCTCTATTCATCATAGACCAACGGAGTCTTCGCAAGTATTTGGAAGTAACGGTGGGACAAAG

CCTATACCTATAGCTAATAACCGTCCACCGCCGCCTAGGGAAACCTCCCCATATTTGTCCTCATCTCTCCCTAAGAATA

ACGCTGGCCAACATCTTATGCCTCGATCCAAAACTAGTGGTGATTTCACTACGATGGACACCTCGACGACTGAAAACA

AGCCGGCAAGGTTGACTGGACCACGTGCCTTAAAGGTGAATAGATTAGCTAAAACGGATACTCCTGCGGAAGTCTCAA

GTCCAGAAGAACCCCCAACACCATCTTCAACAACTTCATTGCGAAGAAAGTTGAGTCTAGGCTGGAAGCGATCTGGAT

CGAAGAACACCGCCAGTGCTGCTCAAGCAACAGGCGGAAGAGAAGCCAATCAGCCTCCTCCTCCCCCAAAACATGAC

AATATGCCACCACCTAGATTGCCTGCTTCTTCTACCATGAATAATATGAGTAGCAATAATAAGGAAATACCTAGTCCTAG

TCCCTCGGTCAAGTCAACCACTACTACTTATCTCAATTCCAGTCGAAGAAAGAGCTCAGTTTCAAGCCTCAATATGATC

ACAGGTCACGACAGAACAAAGAGTGATAGCTGGGGTTTGAATCGAAACAGTCCGAAGAAAGAGACATCAACCGACTCT

-continued

*ATGGCTTCTGAAAGGAATATCCCAACCGCGACTTCTCGAACTACATCTTCGGTTATGCATAGAATGCTGAATCCAAAGG*

*CTTCCAGTACCAGTATTAGACATCAGGATCACTGGACAGCGGAATTGGACAAGGATGATCTTCTGGCAGAAGATGAGA*

*TGAAGAAGCTCGGGAATAAACGAAAGGAAACAGAGACGGCAGCTCGTCAATTGGATGCTCTAAGAAAACGTGCTACTC*

*CTAAGGATCGAGCGAACCCTCAACAGGCCCTCAAACTTGTCTCGCATCTCAACATTTATGAGAAGGGGGAAATTGTCG*

*ATTACAAGGACATTTACTTCTGTGGAACATCTAGTGCAGCTAAACACGTTGGTCAGCTTCAATCTGATGCTGCCAATTT*

*CGGGTATGATGATGAAAGAGGAGATTATCAAATCGCCACTGGAGATCATCTCTCATATCGTTATGAAATCATCGATGTT*

*CTTGGCAAGGGAAGTTTTGGTCAAGTCGTAAGATGTATTGATCACAAGACTGGAGGATTAGTAGCTATAAAGATCATTC*

*GGAACAAGAAGAGATTCCATCAGCAAGCTTTGGTAGAGGTTAACATCCTCCAAAAGTTACGCGAATGGGATCCCAAAA*

*ACAAGCACAGCATGGTCAACTTTGTTCAAAGCTTTTACTTCCGTGGTCATCTTTGTATCTCTACTGAACTTTTAGATATG*

*AATCTTTATGAGCTCATCAAAGCTCATTCTTTCAGAGGTTTCTCACTGAAGATCGTTCGGCGATTTACAAAGCAAATGCT*

*TAGCAGTTTGTTGCTTTTGAAATCAAAGAAGGTCATTCATTGTGATTTGAAGCCCGAAAATATTCTCCTCGCACATCCTC*

*TTCATTCGGAGATTAAGGTTATTGACTTTGGATCAAGTTGTTTCGAGAATGAGAAGGTATATACATACATTCAATCCCGA*

*TTCTACCGATCGCCTGAAGTCATTCTCGGTATGACATATGGTATGCCAATAGATATGTGGAGTCTTGGATGTATCTTGG*

*CGGAACTTTTTACTGGAGTACCGATCTTTCCTGGTGAAAACGAACAGGAACAACTCGCCTGCATCATGGAAGTGTTTG*

*GTCCACCGGAAAAGCATTTGATTGAGAAGAGTACTCGCAAAAAGCTCTTCTTTGATTCTCTCGGAAAACCACGTCTTAC*

*GGTATCTTCAAAGGGACGTAGACGTCGACCATCCTCAAGATCGCTTCAACAAACCATCAAATGCGATGACGAAGTTTT*

*CCTTGACTTTTTGGCGCGTTGTCTCAGGTGGGATCCTGAAAAGCGTCTGAAACCTGATGAAGCTGTTAGACATGAATT*

*CATCACTGGCCAAAAACCTACTGCTCCACCTCGTATCAATACTCGAATCGACTCGCCAATAAAGCGACACAATACCACC*

*GCTGCACCTGCCTCCAATAGGCCTCTTCCAGAACCACCTGCTACTAGTTACAAGAGTGGTTCATCTGTTCGGCCACCC*

*GCAGCTGGGACAAGCCCAAGTAAAGCTCTTCCACCTCGAAGACAATCCAATGCCACAACATTAACTGGACCTCCTGGG*

*CCGAAACGTACAAGTACTGGAACCGTGGCAATTTCTGGTGGTAGCAGCTTACCCCGAGTTACACGAAGCGTCAGCTC*

*GAAACAGGATTTAGCATCAGCGGGGGCATCGGCAGCTATGAGTAGTCGGCGAGCATTATAGAATATGTAATGTATGAA*

*ACGAAAAGTGTTGAGAGTGAATAAATCATTCATATCACTCATTGGGTACATAAGGAGCGGATTATACGAATAGACGAGT*

*TTTTATTACTTCACTGCCATTTTCTTCCTTTCCTTCGTTTGAAGTTGTCCTTTATTGCATAGCAGCGAGGTCAACCGGAG*

*CATTTTTCTTTTCACATTTTTTTTCTTGTCCATGATGCATACCCACTGCGCAACAACTATACATACCTCATTCGTTTAAAAA*

*CACAATGCGAATCGTATAAATCTAGCCGAAGTCTTTCATTTGATACACTGAAAGTTAATCAGGCGTTCTTGTGGCAGCA*

*GGGCTGTGAGCTGGAACAGTCTGGAGTATCCTTTTTGCGGACCGACCGCGCATTCATTGATACGCATATAAACACTAC*

*TATAATTTAATTTGACGTCTTTCATTCACGAACTTATTTACTGGGAGTTTGGGAGTTTTTTTAATTAAGAAAAGATGGGT*

*TGGAGGGGAAGATGAAGGAGGGGAAAAACATTTGTGGGGATGAGGAGGCTCGTTCGAAATAGCTTGTTCGAGGAAG*

*CTTGTTTGCATGTAGGGAGCTTGTTTGTATGGAGACTTTGGTCGCAGTAAATGCAATGCATAGCAAAAGGAAGGAAGC*

GGGTACGGATTGGAATTGAATGATAGGGAATTGACGAATAGCATTGAGATGAATAAGATGAATAAATTA

BC1G_03832

SEQ ID NO: 36

*GGCCAGCACAATCAATCAATCTCTTGATTTGATTTCCTAATAATCTGATGATGCACTTTGGAGATTCTTGAGATCTCCTG*

*TATGTGAACATCGACTTTTTATCCCGACCATACCAACCCAGTTATCACATATTCAAGCAAACTTTTACCGGTGTATTGAT*

*ACCCAAGACTTATCTGGGAAGGGAAAATAGTTTGTCGGTAATAGGAGTATCGGCGTATCAATTATCTTTGAAGGAAGTG*

*GGTTGTACCAAAAACCACATCAGGTATTCCACCAGACAATTCGGTACCGCAAAACGAATCTTCTAAAAGGACGGAAAC*

*CTTCAATTCACATTACTATTTTACAAAAGCTTGTCGGCCCAACGACAATGACCAGATGTCTATTCTTTCCATTGAACGCT*

*TTTGTTAATCTACTTCCTTAATCTACACCACTTCCAAAAGTATCCATTCTTCGACGACCCCTCTGCCAACCTGGGATTTC*

*GACATTGTCCAATCTGGACATATACGCTCATTTCCGCGATTTGATTTACAATTAACGCATACCTTTCATGGCTACTGCGC*

*CAATGACGACAGATCCATCGAGGCTGTCATTCGCAAAGGTTGCCGCTTCAGCTGGGAAGGATAATGTAGCTCTCGCTT*

*CGTTCGCAAAAATTGCTGCTTCTTCAACTTCTGTACGAGATACGAGATCTGAAAACATAGCTCCAACTGTACATAAAAAC*

-continued

AAAGACACAAATATGCCTAGTGCTACACGCAATGATACTGGCAGTATGGCCACTCTCAAAGAGACGGGCACATCGACA

AACGATCAATCCTCAAAGAAGAGGACAATTACCGAGAGCAAACCTACGGCTGCTAAGAAGGAATCGGATTTGGCAGAT

GCGGTTAAAGCGATGCACATTCGTGATATCACACCAAGCCTTGTTGTAAATGGTTCAGGGATTGCACCTCCAACCCAC

AAAAGAGATTTGGGAGAAGGATTCCCAGAAGATCCATTTCAGAGAACAGAATCTGGGTCCGACCTAGGAACGAAGCCT

CCAAGTTTGGATGGAAAGAGCATTACCTCAGGCACAACGTTCGCTTTGGACGAGAAGGAGTCTTTACGTCCCGATGAC

AGCGCGAGCGTAAAAGCAGCCGAAGATGATGATACATTTTCTGGTCGCGGTTCCATTGTTGCTGGTTCTAGAATTGGA

TCTGAAGCAGCTGCAAGAGCTTATCGTGCACAGTTCTATGAGGCTCCTGATCGACGTAGTATACAACTCATGCAGGAG

CGTCAAACTCAGGGCATTGTTACTCCTCAAAGTGGTTCCTCTGGGCAGCAAACCACGGATGATAAATCCAAGCCGCTT

GTAGGCCCATCAGGATCAACTGAAGCAGCATTTACACTCTTCTATCGCCAGACTCCCGACGAAAAGCTTTTGGAGGCA

TTAGAGTCGCCAAAAGACCGCATCTTTCTCCTTCGTCTCGAGAAGGATGTTATCGAGTTTGTGAAGGACTCCAAGGAA

CCTTTCATTGATCTCCCACCGTGTAACTCCTTTTGCAGAATGCTGACTCACAAGTTGGCGGATTACTACCACATGACAC

ATCAAGTCGATGCTGTAGTTGGAGCAGTCCGTATTTTCCGAACACCATTTTGCAGGATTCCGCCATCACTAACAAGCAT

TTCCAATCCTCCTACTACTGGAAATACCCCACCTCCCAATCTACCTGCAATGAAGATCATGCGTAGAGGTGGTGATGGT

GACACTGGACCGAGCCCCTCAAAAGCTACTTCCGAGACTGGAAGCGATGGCAAGGAAAAGGCACAGTCCGCTAAAGA

GAAACTTTCGCGAGAGGAGCGAGAAGCCGTTTATCTTGCGGCTCGAGAAAGAATTTTCGGCAAAGAAGACAAATCTGG

CGAGGCTACACCAGAAACCGACGAGGGTAACGAGATGTCACGTTCCAGCTCTGTTTCTACAAAGGATAAAGGCAAGA

GGGGTAAAGTTGGAAAACAGCGTCGTGATGACTCTGAAAGCTTCGACGTTCGATCTCAATACACTCCCTACTTTCCAC

AACAACAAAATCAGCCGGCCTGGATCCCCACCCAGAATTTCGGCGCAATGGGAGTTCAGCAATACAATGGCGTCATG

CCAAACAATTATCAAAACCAGATGCAACCTCAATATGCTCCACCTCCGCAACCATTTAATCCTGCTATGATGAGCAATG

GAAACATGCAACCATACAATAATATGACACCACCGCAATTTCCTCAGCAAAGTCAGCCACGTTACCAACCACATAGCGC

TCCAATTACGACTTACGGCACACCTGCACAGTCCCCTCAACCTCCCCAACAATGGATTCCACAGAATCAATACCCAGG

AGGCCAGTATCAGTCACGAGGACCTGTTGCAGGAGGACCACCTAACACTATCCCTTACGCTTTTGGACAACTACCCAG

CACGGTAAACCCAGCCGATCCCAAAAGTCAACACCCGATTCCGGGAAGTTTCATTAATAGACATGCCTTCAATCCAAA

GACGCAGTCGTTTGTTCCTGGCAGTCAAGGTCTTCCTATCCCGCAGCCCATGTCTCATCATGGATCTCCTCACCATGG

TTCCCCACACCATGGATCTCCTCATCTCTCTTACAGCAACTTCTCTCCACCTCAGCAACAATACGGGGCTGGAATGGG

TTATAGCATGGCGAGACAAGGGTCTAATAGCTCTTTACCCTCGTATCATGCATCTCCACACATGGCACATAGACCAATG

ATGCATCAGAATATGCCGCAAGGTCTTCCTCAAGGCCTTTCCCAAGGTCACCTTCAAGGCTTACCACAAGGTTTGCCA

CAAGCTATGCCACATGGTATGCCACCAGGAATGCCACAGGGCATGGTTCCAAATGGTCAAGTTGGAAGCCACCTTCCT

AACTTTGGCAACCCGGCAACTTTACCTCCAAAGCCTCCAACTGGTGTTTAGGTGTCTTTTGAGGAATTGCGGATACATT

CTGTGATGAATAAACGGTGGCGTATGGTAGCATTGGTGGAGTTAGTGGGAAATGTGGGCATTAAAACGAAAGTCATTT

TAAGTACCTGGTTTATATTGGCTGATAGACCTATGATTACAAATACAATACATTTGATTACACCA

BC1G_09907

SEQ ID NO: 37

GACAGTCATTCTTCCCTTCCTGAGAATTTCTCCATATCAATCTTCTCATCATCACATGCGCACATGGACTCGCAAATGC

GAATGACAGGGCTGAGTGAATTCTGAGTAGTGCATGACTCGATTCGAAGTTCTATAATAGTTGAATCAGGATTCAGGAC

TTGATAGTACATCCCGCCCAATCAACCTCTTTGGTAAAAAGAGGGGGAGATATTCTCGCTGAGTATCACATCACCGCAA

AAGTTGACACATTCTTCTCAGCCCCTTTTCCACTGATCGAAATTCTGCATACTAAATTCTATCTTTCCCTAGTTCACTTAC

ACACGAGTGCACCACTGGGATATCTTATGTGTTTCGGATTGAGCAGGAAGTGAATAATATTAGTGTGTAATTTCCTAGT

TCGAGGCAATGCGGAATTTTAGATGACTTCGTGTAGAATCCAAACTCCAATTCATAAAGCTTTATAATCCTGCACAGCT

GTCTCTTTTCTCACACAACTAACTATATTTCATCCCCACGAACCAGTCTCGGAGAGTCAAATAAATATACCTGTTCGCAT

CATGGTTGATAAAGCCCAAGATGAGGCGGAAAAGGCCGCTTTGAACCCATCTCCAGAAGAAGGCGCCGTTCCCAAGG

-continued

*AGAAAGTTGTTGAGCGAAGAGGTATGCCAGGGATTTGGAAGTCAGGAAGAAACTGCGTTTCGTACTTCGCTAGTCTCA*

*GCATCTTCACGATCACCACTCTCCTGATGATTCCGGGCCTCGCTCTTGCGTGCTATCATCAGAGAGCACTTCAACTCC*

*TTACGCTTACTACCATATCTACTGCTCCTGGTAAGACTATTGGAGGTTTGAATGCACAAATGGAAGTGGAGACAATCT*

*CACCTACAAGATTTATCTATGGTATTATTGTATCTTGGGCGTTGCTGCTGGAACTGGCAATTTTGTGACCATAACGGAT*

*GTTTGTCATCAATCAAGACAAGCATTGACCTATCACATTCTCCCTTCCCTCAATTCAACTTTCATACCCCCTCTTCCTGG*

*ATACGATGCCTCTGGTCCTATCATGACAATAAATGGTCTCTTTCAGAACTACGCATACCCGGCTTTCGCTTCATATGTC*

*GCCGCCATTTTTCTCTTGATAATTTTTGCAAGTTTCTTCAACTTGTGGTTCGGTGCTACCGCCACGCCACATAAGAAGAT*

*ACTTATGCTCGTACTTTCCATCTTTACAGGTTGTTTCGCTACCCTTGCAGCACTCCAAACCTATCTCTGCTACCAAACCG*

*TCTACGTGCTCAACCAAATCATGAAATATTCCAAATCCACTCTAAAAATATCCGTCACACCCGGTTTTCTCTACCTCATC*

*ATCATTCATCTCTTCTGGATCATCCTTCTTCTCAACGTCCTCATCATTCCCATCACAACTTGCACCAAGCGTCGCCGCG*

*CTAAGCGACAACTTCAAGCCCTAGAAGCCGATGCACAAGAGCTCAAAGAAAAAGAGACTCTAGGCGGCGACACGAAT*

*GTACGTAGTAGTCCAGCGAAGTCTGCTGATTCAGATTCTAGTGACGATGATCACGATATGTCTCCTCGTGGTGTGCCT*

*CAGTATGGTATGCCTCCTTATGGTATGTCCGCATATCCTCATCCCGGTATGCAAAATGAAGGATACTATGGTCATGGCT*

*ATGATATGCCGATGCCTATGCAACCACAGTCTGGAGAGCGCAAGAACAAGGGGAAGCGAGAGCAAGGAAGAGACAG*

*CGAACGACGACAACTCAGAGAATCTGATGTTTGAAAATTGCATATCTGCAATATCATGATTTTTTATACCATTTTAGTTGA*

*ATTCCTAGATTTAGGATGACTTGGAGGAGTTGGGCGGGCCAAATAAATTTCACAACTTTCA*

BC1G_02544

SEQ ID NO: 38

*GACGCGCAAGCAATTCCTTTTGATCAATAAGTTGAATGAAAACTCACTGTCCCCAATACCTCCTTCTGTGTCAAACATCT*

*TTACTCCATCTCTTGTGAGGAAGAAACATCAAAGTTGTCGCAATTGCTTTAACACGATTGATTCCCCAGCCGCATACATT*

*CCACAGCGAGAGCGCAGATACGGATACGATACCCACACATCTTACTTATCGATACCATCCATAGTCTTTCGAGCTTTG*

*GAAGTTCTATTTAGACAGTTGCTAGTAGTTTCCACGATCAAACCCCTTTGGAAGGCCTTGGGGAGGAGCTCGATTGCGT*

*CCTTCTACAAAACTGAAAGCTGTATAAGACAATTTGAAAAGCAGAGCTGTGGTTGGATGCTGTTATCGACTTGTTTTGA*

*ATTGCTTATGACCTCATGGTTCTCTGATACCGATATTTGAGGAATCCAAGATATCAATCTTACCCCGGATATTCATTCGA*

*CAGGAACAAAGCTTCGTCCCGCTCCAAATAATACCTCTTGCCATACAAAAATCGTCATTCACGATGGTCACTCGAAAGC*

*CCGTTCCCCAATCTAGCATCCCTTCCAACAACACCTCATTGCCGCCATACCCCATATCCCCAGTTTCTTCCGATCCACA*

*TCATATTTCACACCCCGAAAGGAACCACAATGCGATTTATGATAGCTCTACAAATGACCTAGAGCCTAATGTTTGGAAT*

*GAAGAGGAGCATTCTCATCCTGATCCCAAAAGCCTACCTAACGCTTTAAGAGTTGGCCCATCGACAATCCCTCCCAGG*

*CCTTCTCAGGATATGTTAAAACCCAGTCCCTCAACCACGAACCCATTTTTAAGGAGGCAGCAATCGCAGAGTTCGCAA*

*AGTGCAGCATCCGATGGGAAGGAAAGTAGCGCAGATATCTGGAATGAGCTCACAGAGAAACCCACACAGCCGGCTTA*

*TCCACCCCCTCCTCCTCCTGTATCTCAAGTAACTCAACAATTTTCGACCATGGGAGTGTCTGGCCAAGACACGAACCC*

*TTGGCAACCCACCGCGAACGAAAAGCCGCCATTACAAACACCCAGTCTTCAACGCGAAGATTCGGGAAACGAAGCCT*

*GGTCAGGCGCAAATCCTCCAAATATCGTTACCTCTTCTGGCTTGTCTCAAAATTCGCAACATCCAGTTTTAGTAGATATT*

*GATGAACCTGAATCTCCAGCATGGGATGAGGATGATTATGACGATGGTGAAGAGGAAGAAGGAACGCCAGTCAGCCC*

*CAAGAAGTCTACGCTACCTACGCACGAAACGCAGGAGATACTAGAAGACCAACATGCATGGGATTCTACTCCTGGTCA*

*AAGTTCGGATCAATCGCAAACAATGCCAGTTCAGTCCTCTGGAAATACACAATATTCGAACCCTCCTACGGAAGGGTG*

*GAATTTGATTGATCATGATCCTATACCGGGGAATTTTCAGCAAAGCGGAGTAGTCGGAGCAGATGGCACAGAGATTTC*

*CAGAATGACCCCTGAAGAAGTTGCTCCAGCACTTCCACCGCGAAACTCTCAAGAACATCCTCCTCCTCAGCCTCCGCG*

*GCCAGTCTTAGTCGCGACAAACACAAGTACAACACCGGCTATGACACCTGATTTATCAGCGGCTGCTCTAAGACAGAA*

*GAAAGAGACGTACGAGATCAAAAAAATATCTTGGCATGACATCAACGCCCAACACAACCCCAGAATTTCACCTGTTCTA*

*GTGCAAAATGCAAATGGACCTTGCCCTCTGTTGGCTCTTGTGAATGCTCTGACTTTATCGACACCCGCAAATGTGGAAA*

*CTGCTTTAGTGGAGACACTCCGGTCGCGAGAGCAGGTAAGCCTCGGGTTACTGCTTGATGCAGTTTTTGATGAACTCA*

-continued

*TGTCCGGGCGACGTGGAGATGCTGCACAAGAGCTTCCAGACGTGGGTGATCTCTATTCCTTTCTCCTAACGCTTCATA*

*CGGGAATGAACGTGAACCCTCTCTTCTTTCCTGTTGATCCTATCCTATCAGTGAATGATCCCAGGAACTCAATGCCACA*

*CATTCATCCTGCGCAGCGTGAGAGCTCACTTCCAGGCACATTTGAGGAGACTCGTGAAATGAAATTATATGGTACTTTC*

*TCTGTGCCTTTGATTCATGGTTGGCTCCCCGAGGAAGAATCGCCTGCATACATGGCACTCAAAAGATCCGCCAAGTCG*

*TATGAAGATGCACAGAACTTGATGTTCCATGAAGAGGTATTGGAAGAGAAGTTAGCCGCTGAAGGCCTCAGTTTCGAG*

*GAACAAGGGATTCTAGAGGACATTTCGACTATAAAAGCGTTTTTTATCTCCGCAGCAACTCAGCTTACAGCTCATGGCT*

*TAGATCTCATAACTAAATCTATGAGTCCAGGTGCTGTAGCCATTCTATTTCGAAATGACCACTTCTCCACAATCTTCAAA*

*CACCCCACAACACTTCAACTATTGCAGCTCGTGACAGATTCTGGTTATGCAGGACATGCAGAAGTTGTATGGGAAGGC*

*CTTATTGATGTTAATGGAGAAAGGGCCGAGTTCTATTCTGGTGACTTTCGTTTAGTCGGCGGATCCTCTACATTACACC*

*AGGGAAATGAAGAAGGCAACTGGACCACAGTCACTGGTCGTAGAAATAATAACCGTGTTGAAAATTCACATGATGCAC*

*CATTAGGGAATCAACAAGAATCGCAGAATCACGAGCAAGGTACGAATGCAGAACAGGAGGATCACGATTTTGCCTTAG*

*CACTGCAACTACAGGAAGAAGAGGACGAGCGGAACCGAAATGAGACCGCCCGAAGGCGAAGAGAATCAGAGCTCTC*

*ACAGCAGTACATCGAGCAACAGGGTAGTAGCAACGACACTGGTAATGCCCCTGTCAGTCAGCGAGGCGGCAATGGAC*

*GAGGTAGTACCAGAGGCCGTGGAGTCAATGTACCAGTTCGAGGAGGGTCAATTCGTGGTAGTGCTAGTACCCGAGGT*

*CGTCCCGCGATTCCACCTCGCAACAATAATGTTGCCACTCCTGCCGCCGACCCAGAAGCAGGCATCGATGCACCGCC*

*TCCTACATACGAGCAAGCCGCTACTGAACCGGCTTACCAACCTCCAGATAATCATCCTGCACATCCAAACGCAGATCC*

*AAGTCGGAGAACAAGTGCTTACACGGCAACCGCTAATAGTCAACAACGTCCTCCAGCTAATGCCGCAGGTCGCCGTA*

*ATACGACTTCCCATAGTGGCATTGGAAGGGGCAGTCAGACACTCATAGATCAGGTTCCTGGGCGCAGGATCCAAGCC*

*CCAAATCAAGGGCTACCGAACTCCCAGCAGCCAGAAAGGCAGAAGGATTGTATTGTTATGTGATTATTGCGTTTTATGA*

*ATATATGGCAACGATGGATATGCAATTGGGGCACATTAGTTGAGCGGAATTTGAAGCTAGGCGTTTAGGCAATGGGTA*

*TATTGATTTATAAGAAGAAACATATCACGAGCTACGGTCGATGAGGGGACTTTTCATCATGTACTCATACGCTTTTTTCA*

*AATGGTTAATTTGCGGGCGATAAATAGGAGGATAGACTTGGAGGGTGGTTTGGTGGTTAATAATCAATTTATTAGTATA*

*CTTTGAAATTTATGGACTTCATTTTATGGCAGTATGCCTCTCTCCTGTTCAGACCATATCTTTAATTGATCGAGATTGGC*

*AAATCAGACGTATTCCTTCCA*

BC1G_11528

SEQ ID NO: 39

*GCTCTTACTTCTCAAATTATTTGTTTAGTACATTAATTATCATTATGGTAGATTCCACGGACTTTTCTCATTACCATCTTAC*

*AGGATGGAATATAGACGACGACTCCTTATCTTATATTGATCATGATTATTGGGAAGGCGTGCTAAATCAAATAGTCGAA*

*TCAGAAATGGGTAGAAAATTATCGGATCTGGATCGAGACAAACTGTTCCACAAAGGCTTTGGCCTCATCAACAACCCA*

*CCGCATGGCGATCGTTCAGGACTAAGACGTTACAGCAAATACTCAGAGAGTCGAAGGTTCAAATTTGTGATAAAATGTT*

*TATGGGATATCACTGCTGGTCGGGATCGTGGTTGTACATTAGACCTTGAAGGTAAGAGACGTAAGACTCGCGATTCAG*

*CAGATAATACACCATGTGGAAAGGATTTCGGCAACACCATATGCAACATGCCGGTTTCTACTAGGGGTTTCTTTTCCTT*

*TGTAGTGGCAACATTACACGCTGCCAAAGAATACGCGTCGAAGCGCAGTCAAATTCCAGCTCTTCATCAGTCAATTGA*

*AGTTGATTCAGAAGAAAGACTATCAAAAGAGACTTCTCCACCTCTGCTAAAAGAAACCTCGAGCAACCAGGAAGAACC*

*AACAATGGATCAACCAATGTCCAGTTCATCAAATGGATTAGACCATTCAAGTGTGGAACAATCAGATGACGATCTTTCA*

*GCGTCGATATCAATTGCATCTGAACAGTCGGAACATTCGACTGGGCAGGGGGAAGTTGTTGAACCGTTAGCAAATTCA*

*TCATGTGGATTGGGACACCTGGGTGAAGAACAGTTAGAAGTCGATCGTCCAGCATCAATGTCAATTGCATCGGACTCT*

*TCGGAAAATCCAGATGTTGGTCATCCAGAGACAATAGCAGTTACACCAGGCTCGTCAGAAAAAATCAGACAGTGATCGT*

*TCAGCGACAATATCAATTGCATCGAACCCTTCGGAACAATCAAACAGTGTTCGTCCAGCACCAGTGTCAATTGAATCAG*

*ACTCATCGGAACATTCAATTCAGTCGGAGGAAGTTACTGATCTGATAGCACTTGCACCAAACGGATTGGGTCATTCAAT*

*TGGGCCTTACCATCCACCACTAGTTGGCATTGATATTACAGGTCATGGAAGTCTCCTTATCAAGAAAGCCTTCTTAGAC*

-continued

*AAAAGGACGGAATCGCAAAATGCCCTTCGAGTTTCTTTGAACGTTCTTTGTACACAGTCCAAGGACTACATCCTATGTG*

*GACTAAGATCTTGGGAGGAAGGAGGCCATGTCGAGGGCCAATTGGCTCTTGATATTGTTGGCGTGTGGCTTGAGAAA*

*TCAATGCGTCAATATTCTTGTCAAACCTTCATATGTTTCATACACGACCTCGGTGCAGGACAACAATTGGATTTGGAGC*

*AACTTTATAGGGCTGCTGGTGGATTTTCCCTTGTGGCTAGCCGAAGTAAATTCGATTTAGTTCCAAAAGACGCAGTAGT*

*TTCAAACCAGTCTCAGAACGTTTCGCATAATTCTTCTTCTCATCGGCACGTATTGCAAATTACGAACCAGAACGTTACTA*

*GTAAGTTCATTGGTCATGACGGAGCCAGCGCAAGAGAAGTCGAGGAAATTCTAGGATTATCCATGTCTATCGAGCATT*

*TTGATGGAAAAGAGTACATTGTGTGTAAGCCACACGCAAATCAAATTCTTGATCGACAGGAACATGTCAATCATGAAAG*

*GTGCCGGATTGGGTTGGAAATTATTAGTATATGGCTTTGGGAACATTGGGACGCAAAAAATGACTACATAGATTTGCCG*

*GGGTTCCTTGTTTGTCTGAAAGCATCAAACGATAAGATGGCTTTGGAGGAAATCTATGAAGCCGCAATACAGTCTATGA*

*GGCGAACAAGGCTGCCATATACCCAAAAAGCTTTCTTCAATTCAAATTATACCATAGAAGCAGAATCAGGAGCTTAGAA*

*AGATGGATATTTGAATCAATGTCAATCAGGTGGAGCAAGCAACTCATCAGTGATGTATCTTTTGGACATGCCCAATATT*

*AGAAAAGCATGACAATCATCACAAGGAAAAGAATCAATGGCCGAATAAACTTTGAACTGTGGCGCTTGAGA*

BC1G_04218

SEQ ID NO: 40

*GAGAAAGCATTGAATTTCATAACAAAATATACTTTTACAAGAGAAGGTTATATTTCAGAAGAACGATTATCCTGTCACTA*

*CGGCGATGGAAAACAAATTAGGTTAGTGTCTACTACGCTTTTTGTTACCCTGTACTGCCGTATCAAAGAAATTACAAGG*

*TATCATAGAAATGCATCCACAAACCTTTGATCTGCTCCGGATGGAGACTAGTCTTCGCAAAATGCAACTATTCGAGCCT*

*CACGATCCTGTCGTCATCGGCGTCGACCACAATTTGGATCCTTATTTCAAATCCCAGCATTCATTTTGCCTCTTTCCCA*

*GATTCCCGCCGGAGCTTCAGCTTATGATCTGGGCTGCGGCTGCCGATGATCGACAGATTGTTCGGATTAAACCTTGC*

*GCCGAGGATGGATCAGGAGAGGAAGGGTTCCGGGGTGATTATACCATGCCGGTGGCTCTGCGCGTTTGTCGCGACT*

*CTAGAAAAGAAGCGCTTAAAAGATACACGGTTATATTCAAAGGTATCCTTCGCAATCCTATTTATTTCAATTATCAGCAA*

*GATTACCTGAGTCTTGTTGGTAGTAGCGCACATGAGCATTTCCAAATTCTATCTGGAGAAGACCATATCATTTCAGAAG*

*AGATCCAAAAGGTCGAAAATGTGTTTTCGATGATTGCTGGTTGTGGAAGTGGTGAGAGCGAGGAAGATGTTTTGACTG*

*AGATATTGGGCATCTGGGATGGTATCAAGCGTCTAGTCATTGCAGAAAGATCGCCAACCTGGTGGGGCACATTCAAG*

*GAGATCTGGTCCGACAAGGAGGTGAAGAGGCTTGCTCGAGACGCCAAAGCTGACCGTATCAGGGAAGGAACTGCGA*

*CTCCAGAATTCCCTCAAGTTCGCATTGTCAAGTTTGATGATGTTCTAGATGCCGTAGCACGAGGTGAGCAACAATCAAT*

*GAGCAGTACGAACGCGACGCTTTCTTTTTTCGACTCGATATTTGAAGCAGATTCTACATATAACATTAAGAAACAGTCTA*

*AGAAAGCTTTGGAATCAGCATAGGCAAAGAAACAATGTAGCTTGCTTTGGTAACTGTTGGAATAATGCTTTATTCATAGA*

*AACCCATGGAAATAGATGGCGGTGTCAATGAAAGGAAGGTTGAAGCTCTAGTTATCTCATGTGTGGGGCATTGGATGG*

*CTTTTGGTTCAAGAATTATGTAACATAGATCAGCTTTCATTTCAAAGGTTGTCTACATATCATGTATTTTCATGATAATGA*

*AATTACCTCTATATTTCAAGGTTCCAGGCGGTCTTCCGTGTAATCGAAAAAAAAAAAATTCTACACATCA*

BC1G_00860

SEQ ID NO: 41

*GCTTCTATTTCCACCACCATCATATTTCACGATCTATAATACTGCGTTCGCTGATTCTATTCAATCTTCCAACTTTGCGAT*

*CAAACTGTCAGATACGATTTCCAAAACAACCCCGCAGCCTTGGAGATTACAACAATATGGGCTCTTCAAATATAGCTCG*

*AAAGGAGCGGCGCAAAAAACAAACACGCTTGACATTCGATCCGATCTCCACCGAAGTGCCTTCAGATTTAGATTTACC*

*TGCCAAAAGCCAAGGACCGTCGCCTGCGAAGGTTAGATATGAGAGAACAAATGACGGCACATCTGCTGGAAGTGGAG*

*GAAGAATTACGCGCAGTGGATTGTCTTCAGGATCGCCCTCGAAAGTAACTTTGGATAGGAAAGGAAAATCTGGGGGCA*

*AAGGAAAGAATGCGAGAGATGGAAAAATCGATTTTGGAACATTACCAACGCCTGCGAAAAGCTCGCAGAAAGAGGATA*

*TTATTGTTGCAGATGCAGAAGTGACTAGCGGATCACGTCGAAGCACACGAAGTTCAAAAACGACTCCATCGAAGACTA*

*CGCCAAAGAAAAGATCGGTAACTTTATCGGATACAAGTGATGATGGCGTATTCACATCAAACTCAAGACCTTCACAACG*

*CTCTGGCCTATTTAGTCAGAAATCAGCTGCGCCAATAGAAAGTAGTGATGAATCTGGCGAGGAAGCTGACGAAGATTC*

*TGAGGATGATATACTGCCATCTTCTACTACGCGTCGACAAGCAACACGGATCGTTCCGCAAGTTGCACTTGAGATTGA*

-continued

*TTCCGAAGACCCGGATGATGAGCCTCCAACCTCACCCATGAAGAGAAAGCGACCCACCATAATTTCTGACGATGAGGA*

*TAGCGTTGTTAGGTCGCCTGCAAAGAGAGCGAGGGTTGTGGATGAGAGTGATTCGGATGATGATTTGCCGCATATGA*

*CTAAGCTATCTAAGACCACCCCCCCTGAATCTGATAGCCCAGCTCCTTCCCCACAAGTTAAACGAAAAGGACCGCCTA*

*GGAAGCACAGAACTGCTAAGCAGAAGCAATTAGAGATTCTCAAACGCAAGCGTGCTGGAGAAAGTAACCCCATTCTTA*

*CAGAATCCGAGTCTGATGAAGAAGAGGTTGGCGGTTTATATGATTCGGGTAGTGATGCATTGACTACATTTGAGGATG*

*AAGAAGAGGAGGAGGTGGAAGAGGAGGTTCAAGAAACGCGCAAACGAAAATCGCCAAAGAAGACTGTACGAGAGAAT*

*GAGGATGAGTACGATTCGGACTTTGTTGATGACGACGATGTTGGCCTTCTTGGAGTACCGGATTATGCTATGATTCCC*

*CTACATCTCACGGCCGCAGCCCACAAACCTCTCAGAGAACACTTTGTCGAAGCGGTTGAATGGTGTGTTCAAAACAAG*

*ATCAATCCAGGTTTCAACCAAAATCTCATGCCCATTTACAAGGCGGCGTGGAATAAGCTCGAAGACGCATACAGTGGA*

*TTATCTGGTAGCAAATTTGTTTCTACTTCATGGACTCGTGATTTTACCAAAGGCCTTTATGCCCGTCCCGAATTCATCAC*

*CAGGAGACTCGCCCCAGGAGAAGCAATTGATCTATTAGGCGAAGCTAAATGTGAGGCATGTAATCGTAGGAAGCATAT*

*ACCAACTTTTGGTATCACATTAAGGGGATCTGCATACCACAAGGATAGCTTAGCCGAGGTAGAGAAAGATGATAGTGA*

*TACTGAGGAAGACGACGAGGAAGATTCTGATGATGAGAAGGACACGCGGAGTTTGAACAGCAGGGATGAACCTCTAC*

*CACCTCAAGACAAAGAGTACATGGTCGGCTCTGTCTGTAAAGAAAATGCCGAAAACGCACACATTCTTATTCATTTGAA*

*GTATGCACTCAACCAATGGGTCATAGGCAGTCTAGAAAGTCAAGGGCATCTTACGATTGAGAAGCTTGCCAAGAGAGA*

*CAAGATGAGTGCAAAGAAGAGACAGAAGGAAGTCAACGGGATTGTCGATAAGTGGAAGGAGGAGAAAGAAATCAAAG*

*AATTGTATGGCATCTGGAAACAACAATTGGAGACGGCACAGAATGCCAGTACAACGGGAAGACGATAAGATACCACGT*

*GGTAGCTGAAGGTGTGAATTCGGAGACGAACATGAGAGGAATGGGATTTATGGCACATAATGGTAGAGAACTGGGAA*

*GATTTTAATGATGCTGGGTAAAGGATCAGGTATTTGGGAGCGAAATATGGAAGCAGCTAGCGATGATTTTGGAATCAT*

*GACTTTGATTCTTCTTCACTTTATTTCAGAGTCAGTAATTAGGGATGACTGGGAACAGAATTTTATTAAAATCAGAGATA*

*CGGCCTGATTTTAGATTTAGATATATATCCACATCCAATAGCAAATTATTAACAATTCA*

BC1G_04811

SEQ ID NO: 42

*GATCTTTTCAACAAACAAACCACTTTAGGTTCATAATGGTGGCTCTCTGATTAATACGGTTCGCTATCGATTATTCCACT*

*CGAGGAACGCTTGTTGCAGACTTGCGACATCTTACTTTTCTTCTGAACCCCTATTGACCCTACGATATGGATCTCTAAA*

*GTCTTCGCATTACTCTCTGCATATCTAGTGTCTTTATTATAAGGTTGACGAAATTCACCTTTCCGCGCTTTACTATTAGG*

*CCCGAATTGATTTCCATCCGTTCGAAAACAATCCTCTCGATAACACAAATCTTGGAGGGTTTGTGGTTACTCTGATCAA*

*ACAAATCAATCATTGTTCTTTTTTAAACACGTGCACTTCACGTGGGCCATAGATCGAATGCCTCCAATACGTCTTGACGA*

*GAGTGACGACGACTCTGAGCTTTCGGACGTTGACGTAGCTGAGATCGCCAGTGTAGCTCTCTCGGATACCCCAGGAT*

*CTACAGTAATTCCAACTGCCACAGGCTTACCTGGACACGATGAGATGAATAGGAATGTGTCTCCTCCTAGATCTCAGA*

*CCATTGCAGCATCATCAAACCCAGAAGAAGATGGTGGAATGATTGGTCTTGCCACCCGGCCACTGTTCCATGACAAAG*

*GCGATCCACGAAATAGTGTAAAGGCGGAATCTGAGTCTCCCAAACATACTCGATTGACCATACAAAATTCGGGACGTC*

*GAGGCAAGAAGTTATTGTTATCCACCGAACGGGAGTCTGGAAATAATCCATCCGAACAACCACCGAATACCCTGAAGA*

*GAAAATCATTTCCAAGTGACTCTCCTAATAATGCTTCCACGAGTCCCACAGCACACAGACAGCTTCGTCGTTCAGATCT*

*TGTTACGCCAACGCTAAGACAACCTTCCATAGCGACCTCTGAACGTCAGTCCATCCGCCACCACGAATCACCATCCAA*

*TGCCAAGATCCAAGAAGAAACTGCTCATTTAAGGGAAGTTTTATTGCATGTGTCAACTGAAGCGACTCAAGAAATATTG*

*AAGGAGCAGTGGAGAAACTTTCTTTTCACGAATGCAAAAGAGTCACACATCACATTCATTCTTCGAGCTGGATTGAAGA*

*ATGCTACTCCTAATGTTCTTGGACGAATCTACAACGACTCTGGTGTCATGAAAGATGCCTTCTTGGAGACTATCACCTC*

*TAAACAGCCCGTTGTCGCTAGGGTTCTCAAGAGTGCATCTGCAAATCAACTTGCAGATCTTGTGCCCAGTAAAGTTCTG*

*GATCAGGCGTTATCTGAACGGTTAAAGAGTGTTCCAGCAAAAACGCTCATACGATGGCTAGCTGAGGCTGACAGACTT*

*GGTTACAGTCTTGATGACATCCTGGATGAGAGCGATGAGACTGTCGTACCAAACATACCGAGTAGGGCGCAAAGTCAT*

-continued

*GACGCTGATGATGGTGATGATAATGATACAGAAATGATAGATGATGGACAAAAGAAATTGGAAGCCCCTTCTTTGGATC*

*CACTTGTTGCTGAACAGGAACGAATCAGCGCCCTGCAAAAGTCTCAAAACGATGCCCAAGCAAATCCTCCACGCGAGT*

*TAAGATGCCCCACATGCACCTATAAGTTTGATACCGTTAGAGGTCATAATTTCCATCGACAGAAGAATATCTGTACTAG*

*AACTCAGCCTCCGGGATTAAAGTTCTATTGTGGTAATTGTGCTCAAGGCTTTACGACCAAGCAAGGAATGCTATATCAT*

*GAAAAGAAGCGTGTTTGTCTTGGGGAAGAAGGAAGTGCAGACGACGAAACCATTTATCAAGACTACCGAGACGTTGTT*

*TCGAATTCGCCAAATGCTCAATACGGACAGCACCCTGATCACCCACAGACTACATCATTTGGCAATATCCCTCGCCCA*

*CCTCTCCACACTCCAGCATCGCGTTCCAAACATATCGAGGCGATTATTGCTTCATCTCCCTGGGACGGCGAGGCTCGT*

*CATTCACCATCTGAATTGCCACCCGAGAAACGTGCTGCTTTAGAAGATGCTCTTCAGAAAATCGAAGAGAAATATCTCG*

*AGGATCAAAGCAAGATTCCCGAGGACTGGACTCCCGAAAGACGAGAAGCACGTCTTATCTCTCTCAAGAATGGAAACG*

*CATCCCGCAAATCTCAAATCCGCAAACAATTTGGTGTTACTCTTCGTATGCGCGACAGAGATAAAGAGGCAAAGAAGAT*

*TCGCGAGGTTTTGGGAGCTAACTCTCCAATGGTGCCTACTGGCATGAACCGAGCTGAATACCGTAATTCACCAACGGT*

*TGCTGGCTATCCAGTAAATCCTCAGCAGCAAATGCAACCGAATCAAACACCGGCCAGCATAAGAATGGAGATGGTGGA*

*TGTGAGACCTGCTACAGGATTTCTCGCCAATCAATGCCCCGCCGCAAAACCAGCAACACCAGCAACATCAGCAACACC*

*AGCAATATCCGCAAGCACCACCAGGTCACCACCCAATGCAATATTCAGGTCCACCTCAAGCTCAAGGTTTCCAACAAA*

*GTATTCCGCCTGTATCACAACTTCTGTCGCAGCAACGACCTAGCCAGGACCACCAAATGAGCCCCCTTGGGTATCAAG*

*GAGCTCCGGAGCAAGCATACAGAGGACCAGAAGATCACGCAAACAAAAGACTCAAGCGTGGATCAAGTGCAGGACTG*

*TCACGATCAGATGAAGAAAGAAGTAGGCATTTTGCATCAGCTGATTCGACTCCAATGGGTGTGAATGAGACAAGGGTT*

*TCAGGGGGAAGAACTCAGGCTTATAACGGTGCGGGAATGCTCTCTGTGGAAAATCAAAGATCTGTTTCTGCAGGAGCA*

*AATGGTGCTATGATTGAAGGTGAGAGTAGACCAAACTCTGCAGGCTCAAGTACTGTGCGAAAGAGGGTGCCAGTTGG*

*TGCGTTGCAGAGGCAATGGGAAGCGTTGAATGGCAAGGGGCCGGGTAGGAAGTCGGAGGTTGAAAATAAGGCGGG*

*GAATGTATTAATGAGTAGTGTGGACGGGAATGAGAAAGCAAATGGACGGGCTGAGGGTGGAAAGTTGGTTATGGGTG*

*GTAAAGGTAAGGAGCCAATGCACGAGGGAGTTAGGAATGTGGTCGATTTGATTAGTGATGATAGTTCGAGTGAGCGT*

*GGAATTAGGAGACCCAGTGGAGGAGGAAAATAGACTCCTGGGAGGGGCAGTGAGATCCTGAAGAGATCATACATTTG*

*TTCGATGGAAGCATGGATTTTCATTTTCATTCAAGGCTACTTGCCTTTTCTTTTATACCTGTTTTTGTCACACAAGCTTTT*

*TTTTTTCTTTCTTCATTCGGAGACCAAGCAAAGGAAAAGAAACAGCGAGATAGGAGACTTATTGGAATCTACATTACAG*

*AAATGGATAGATGGGAGAAGTGTCAAGAAACGTATTGTATTCTAAATACCTCGGTCTGCTTTTTTCCCTTTTTCTTTTTTT*

*CAAAACAGTTTTGATGCGACTCGATGCGATTCGATAAAATACAATACGATAGTTGATGATGTCCTTGGCCTACAAGATC*

*GTGGCTTTAAATATCGTATTTTGATGAAGATGCAGAAGAAGAAGATGATGATGATGATTACTTAGTTAGTTAATACGATG*

*AAATTACTGGATGTTGATTTTCGAGAACATTACAGGAGTTTTTATTGGATGGATGGATGGATGGATGGATGGATTGTATT*

*TGATAGTGTAGGTAGTGTATAATAGGTCATTAGATAGTACCTACCTAGGTAGGTTGATTGATTAATTGATCACCTCTTCC*

*ACCA*

BC1G_05162

SEQ ID NO: 43

*CAGGAACTATGCATCTTATCGGTGACTTCATTCAGTAAGAAATCCGAGAATGAAATGATTTTGAGCCTCATGAATTGTGT*

*ATTAATGGTGATTCCGTTTGCCGCGCCGTAATCAATATTTAGTCATTTTAAGTCGTTGAGTTTATCATGGACAAATTTTTA*

*TTCGACCAACATTTGCGAGATTGCACCATAGTGCAAGAAAAAACAACATGCTTCGAAACTTTTCTCTATGCTGATCCAG*

*AATACCGAACCACAGTGACCGAAGAGACCCTTCTTGAGGCCGAAGAGTTTGATGATTTTTTGAATCAAAAGGGCAGAT*

*TCGAAAACAGAAATCAAGGGTGCATCGGAGGAATTAGACTTATCTTACAAAGAAATGCAATCCATCCCCATACATTCGA*

*ACCCAAGTTTTTATCTTTACCTAATGGCTTTCATAAAAAGATTGTGGACGCAATGCATCTCCCTCACTCATGGATTGAGA*

*CTCTAAGCGCAGTGGGCCCATTTTACTGGTCTGGATATGAGCAAAACGATAACGATCTTTATCTTCAGATAATATACCG*

*CAAGAGCGACGTAAAAAAGCCATCCAATGCTCGAAACTGGGAATTGGTTCTTTCACACTCCCTCAAGACTGGTATCAC*

*GAATGCCTTTTTCAAGGGTACGCCTCGGGCTGATGTTACTCAATGTATTACATGTCTTCGTCAATGCATCAGTGAGATC*

-continued

*GATCACCCTTTATTCCTGCCTGCTCTGGTCTTTTCTTGTGACATTGATTTTGGAGAAGATAAACGTCACCGAGACAATC*

*GAGAGCGAGTCCGGATCTTAGAAAAACAAGTAGTCGATGCATCCCACATATATGCACATCCAGACTTTACCAAGCGAG*

*ATAAAGTCAACCTTTCACAAATCAATAGTGACTTGGTAGATTGCCATAAGAATGTGTTGTGGAAGCGGCCGGAAGGGT*

*ATATCACTATTGTACAAAAAATGGAGAAAACATTATACGAGTTCAAAACTTTGTGGCCGGTTGAAAGAAAGGAAAGATTA*

*AAAAAGCTTCAAACAATGATGGAAGGGAGGCTTGAACTGCTTCAGTCTAAGCTTCAGGGAATAAGCACCCATCGTGAA*

*GTTACAATCTCGAGATTGAAGTTAATTGGGGAGGTGTTGGAAAATTTGGTCTCGCTGGATATCTACAAGCAAGAGAAAC*

*AGCGGCAATTCAGTAAATTGCTGAGTCGAAAAACGGCACTTCTAGAGGAAACAAAACAAGAAGAGAGAAGAGAAATGG*

*AGAAAACACAGAGAGATCTAGAAGTAATGCTAGAAACAAGGAAACAGACGACTATGTCATTACTAGGCATTTTGTTTCT*

*ACCTGGTACATTTTTTGCAGCAATTTTCAGTACCACATTCTTCAACTTCCAACATGGTGATTATGCGGGAATCGTCTCTA*

*AGAAATTTTATATTTACTGGGCAGCTACGGTTCCGACCACTGTAACTTTGTTAGGCATGTGGCTCCTCTGGCAAAGAAG*

*AACTAAGAAAATGCTAGAGAAGAGAGATGATAAATTTCGGGACCTTGAAGCAAAGAGCAAGAAGGCACGAAACGATAT*

*CTTTAAAGAGGAAGAAAAACATTTTAGACCAGTTTGATTCCACAGCTCTTGAATATGTATTTTTCAACTTGGGGTTTTGTT*

*TGCTATAATTTGAAGAAGCGGGTCGCGATTCGTCCAAACACATAGTCGGTGTCGAAGAAAGATAGCATTACACCCGAT*

*GTAACAGCTTTTGGGGATTGTGGGAAAGATAGTCCAATACATGATCTTTCGCTGGAAAATTGCAGTACTGACTACACGC*

*AAAGTTGACGATGGTTCATGAGTTGTAACAGGAACTTATTAAAATGATCGAGCCCA*

BC1G_06835

SEQ ID NO: 44

*GGCCTCAATCTCTCCTTTTCACATATCGTGTCTTGTCTTCTGTTGAAAGTCGGCATTCACAATTTTTTTGGTTCAATCAAC*

*TTTTGGTTAATACATGCATGCATGTAATAGCTGTATCACGCATTTAATTTCGATTCATTCAAAATTACCTCCTTTTGTAAG*

*CATTCCATAAAGGACATGCTCCGTCGAAATAGTTCTAGTCGACCTGTTCGAAGCAAATCAACATTATCAACCTATCCAA*

*AACACGATTTTGTCGACCCTGAAGAGTCTCGTATGCATGCTCATGCTGCAGCAATGCATGCTTTCAATAGGGCCCAAG*

*AGAGGAATGGCACTAGTTATGGAAACAGGAACGGTCTTTCACGAAGCAACACTACAAGTCAAGAAAGTCAATGGCGGC*

*CGAGTCAACAAAATAGTTCTACAAGTCTTGATAACCCAGGGCTCAAGCGTCAGCAGAGTGTTCGATTTGCAGGCCCAA*

*ATGCGGTAAAGAGGCGCCAATCAGCGGGGAAAAGGACGGACCCGCCAGCACTGAACCAGAAACTAAGTACTGCTACT*

*TTGGGACCTGTTGTGATGACCACAAATACTCCAGTCCCAGCAGTGTATCGTCCACCCAGTCGTTCTTCTTCAATTGGCA*

*AAGCTTCACTTAACAAATCAGTCGTTCGAGACTACTCTGCTCATAATTACGTTACCAACTTAGATTTCGATGAATACTAT*

*ACGCAAGAGAACGATGTGGCCTCGACGCCATCTTCATATCGGCGAATCAGAAAGTCGAGGTCTATGTTCAGCCCCTTG*

*TCAGCGCCAACCAACATCTTCTACAGCAATGGCAGCCCTGATCGCACCAATTGTTCATCCACTCCGCGGACGCTAGAG*

*AATAATGCTCCATTACGGGCTCCAAAATCAATGAGCTTCCTCCGAGGGGGGCGGGACTATTTCAAATCTACATCGTCTT*

*GCGAAAGAAATGACGATGCCGTCCAAATGGCCAGAGATAGATTTTTTGTTCAAGCCAATCAACAAAGACTTCGGGAGC*

*AGCCATCTTTTCTCTTCAGATCGAAGGCACAACGGCAAGAGAAGCCTTTTCGAAAGTCGGTTCGAAGCAGCAGCGGAA*

*AGTCTGCAGCGACATATGATTCGGCCGAATCTATGAGAGAGGGTGGCCTAAGAGCCAAAGCTCGCAAGGTATCCCAA*

*GGATTAAAGAGCAAACTCCGAAAAGTTTTTGGCCGCAGCAAAGACGAACCCGTCGCTATCCCTAATCAACAGGTGGAT*

*GCCATTGAAACTCACGTTCGAGAATACGCTGGACAATTAGCGTCAGATCATGAGTCGTTCGATGATATTCCTATACCCG*

*ATGAGGCCGCATTTGCTCATGTGGCAGCTAGAGTCCCATCATTACGTGCTATTGCTTCAAGCCAGAGACTCAGATCAC*

*AAAGTGGTAGTATTCGTAGCTTACGAAGTGATCATAGTGATGAAAAGTCCAGAGTAACAAGCTGGACCAATAGTACAG*

*CTAACAATACTGTTACCAGTCAAGGATTGCGTCCTCCGCCTAGCAGAGACCAAAGACTTTCTATAATCAATGAATCAGG*

*CACGCATATCTCTAAAGCAGCATTTCATCGCCCAAATGTAAAGAATCAACATCCAGCTTATCCTGCATTTCATCGTCCTG*

*GCTATATCCAATCAATTCGACCAGGAGGTGTAGATAGCGCCAGACTTTGCTCTGCTTTGATGAAGCGTCTCGACGAGA*

*ATAGCCCAGAAGCAATACTCGCAAAGTCAAAGAAAGCCAGCACTGAAACTCTCGGACTTGAGAAAGTACCTAGACAAA*

*GTAGCTCCTTTACCAATACTCTTTCACGGCCCAAGCCATGGATTAGACAGGTACCTCCTGACTGTGACCCAGGAAATC*

-continued

*AGAGCCAAAATCAACTTCCTAACGTATACTGTTCGAACAACGCTGGCCCAATACCCGTCACGAGCGGCGAGGAACTAC*

*CTGGTCAGGCAATCGACTCTGAGTATCAATTCAAATCTGCAGGTTTACCATTACATAATCCACAACTTCAAAGCCAAGA*

*CGATGTGTTTTCCTCACTCCCAGGATCTAGTCATGGCAACTCCTTTCACCACGGTAGCTCATTTCATGAAGACAACTCA*

*TTTCATCAACGTGCTCACCAGCGTAATTCAAAGTCTGCACACAGACGCCACTTATCCGATATTGATGCCGCATATGACC*

*CTGTGCAAGACCCTTCAGGTCTCACTCCGCAGCAAGTCGCACAGCGGGACGATCCTATAGTTCCCAAACCAAAAGTTA*

*TCCGCGAGGCAAGGTCTGCATTTTTCGGAGGCACGACATTTGCAATTGACAGAGTCGGAAATACAAGTCCGTATCGTC*

*GCGCTTTGGCGGAAAGCGACAATTCTGCTGCCTACAACGAAGTGAGTATGGCACCGGTAAATGATGACGTTTATAGTG*

*AGAGTGTTTACTCTCGAAGTATTGGCCGTAATCTTTCGGAGGCTATGAGTAGTGATACATCGGTACCGCTCCCAAATGT*

*CCGTATGCCGTCATTGCCCGTCGATGGCTCAACTCCCAATGGTGGCGCTGTCATTATCAACAGCACAACCTATCGTCC*

*AACTCATCCAAGACAGCGAGGTGACAATTCCGGTGGTTCTATTGAGTGGCAAACATGGATGTCGTCTGAAGTGGCAAA*

*GTTGGAAAGACCATCTGAAAACGATCGCGTAAGCGTCAGCAACATCGAACAATCACTATCACCCACGCCTACGATGTC*

*AAACTCCTTTCACATTGTGCACAGAAGAGAAAAGGCTCAGATGGCTGATGATGATACGGATATCGCTCAGAAGAAACTT*

*CCTGCTGGTAAACAGCCGCTTGGTCTCATTCAACAGAATCTTAATGCCCAAGTTCTTCTGAAGCCGATTTTGAAAAATC*

*GCTCGACGACATCTTTGCCTGAAGATGATTTCATTGATAACTCTAAGCCGTTTAATATTCCTTCTGCACCACCACTTCCT*

*CTTAGATCGATATTAAGACCAGCACAAAGCAAAACGAGTCTGAAAAGTACCTCGAACTCTCAACACGCACCAACCCCA*

*AATCCCGTCACTCAAACCCAGAATCCAAATACCAGCGCTCGCAACGTCTTGCGCAAACGTCTCTCATCTACAACCCTAA*

*GAAGCGCACCAACAACACCTAATCATGGTGTAGAAAAACAATCCCCGAGTACGCGTAATGTACTCCACAAACGAAACG*

*TATCGGAAGCCACGATGAAAAGCGGCAAGAGTATTAGAAGCGTGAAGAGTTTCGATACGAGTGGAAGTCAAAGCCGT*

*AGCTTTACCACTAGTCCGGCGAAATTGGTCAAGAGGAGTGGGAGACCGGTGTATAATTTTACGCCGCAGAGTAGTCC*

*GGGTACGGGTATTGGGGCCGCGGTGGAGAGACAGTTTGGGAGTGCGAACGCGAAGCCGAATGCGAATACGAGTGG*

*AGGTTTGTATGGAACGGGGAGATCGAGAGTGAGGGCTGGGGGCAGGGAAAATGAAAGGGTCGGTGGAGGCGGCAC*

*GGATGATGTTTATGGGGTTGAGGGAAGTGGGGTGGGGGATTCGAATGGGTTGGGGTTGGGGTTGGATCAACAACAG*

*GTGGGTAGTAAACAGATGGTGGATATGTTTTTGAGTAGTAGACGAAAGAGAATTGCTAGTGTAGGGACGATCGCGGG*

*GGGGAGTATGGGGGGTGATGGGGGTGGGAGGAGTGATGGTGGAATGGATGATGGTGCGGTGTTTCTTTAGGCGTG*

*GGGATTGGTGTATGAGTATTGGGAATAGATGAGAGGGTAACGAAGTCATGACTTATGGATTTGGGTGCTTGAGACCAG*

*GATTAGGATTAGGATTATGTATATATTTTTAGCGGGTATATCATGTATTATACTTGGTGACTCGGTTACTGGGGATTGGA*

*GAATAGAACAATAAAGCGCTTGTGAGAGGGCTGATATAGTATGGATTAGGGTCGATGACATTACTTTTGCTTTTCTTTTC*

*TTTTTTAGAAAATTAGAGTTTAGTGTAAGTAGACAGCTGGTAGAGTAGTGTAGTGTAGTGCCAGTATGAATGGTAGTTG*

*AGGTATGGAAAATATTAG*

BC1G_10526

SEQ ID NO: 45

*GTTTCCAAGTACAGTACAGTACCACTTCAAGTACATAAACTCAGCGCTCTTCTTGAGATAAAAGGTTAAAGGGTTGCAA*

*GATTTCTTTGATACATATCATTGGAAATAAAGTATTCCGGATTACATTAGAGGAAGCTCACTGTAACAGGTTTCTGCTTT*

*GTTGTTCATGGACATGATGGCAGCAACTCCAGACATTTCTTTGACCTGGTCATCAGTCTATAAAGTCGCCCCAAAAGAC*

*AACGTCTCGCTGCCCGGGGACAAGATACTACTACCTCAATCAGCGCTGGAACAACTACTATCGGCATCTACAGTTACG*

*GTGAATTCTAACACTCGCCCCAGCAATGTTGCATTTGATCCATTCAATCCATATTCATTGGCAGCCGCTCGCATAGAAC*

*AGTCGCAATGGAGAGATACCCAACAACAACTGCCCCATCCTCTCACCTTTAGGCTGGTCAACTCGAAGAACGGAAATG*

*TAGTATATGCAGGAATTCGAGAGTTCTCGGCAGATGAAGGAGAAGTTGTCTTAAGCCCATTTTTGCTAGAGGCATTAG*

*GGATCACTGCGCCCTTACGAAATCCAACACCACCAAGTTCAAAGGTTGAAAGCAGGAGAGGGTCGCCGGATACGCCT*

*ATAGATCTTACAGATAACCCTGCAATCGATCTTACGGGTGACGAGATGATAGACCTTACAGACGAAACCGAAGAACCG*

*GCGCAGATCACTGTACATGCGAAACAATTACCTAAAGGCACATACGTGAGGCTAAGGCCATTGGAGGCTGGTTATAAT*

*CCCGAGGATTGGAAATCATTGCTCGAAAAACACATGCGAGAAAATTTCACAACTTTAACGAAAGGAGAAATATTGACGG*

-continued

*TTCGAGGTTCAAAGTCGGAGGAATTCCGATTTCTGATTGATAAGTTTGCACCGGAAGGAGATGCAGTTTGCGTTGTTG*

*ATACAGATCTAGAGGTCGATATTGAGGCTTTGAATGAAGAGCAGGCTCGGGAAACCTTGAAGCAAATCATGTCAAAGG*

*CACAAAAAGCTCCAGGAACGGCTCAAGGGAGTTCAATTGGCGGAGAATTAGATCTTTGGAATGCTTTGCAGGGACAG*

*GTCGCAGAAGGTGATTATGTCGACTATACTTTACCTTCATGGGATCGATCAAATGGTCTTGATATTGAGCTTTCACTTGA*

*GGACGATGGTGATGGTGATGTGGAGATATTCATTAGTCCTCAATCAGCCCATCAAAGAGCAAAACCACGGGAGGATGA*

*ACATGTTCTCGGAGATTTCTCAAGTGACAAAATCAAGAGAATAACCATACAACAATCAAATGTGGAATTAGACGGAGCT*

*GATGCTATATTAATTTCTTTATACTGTCGAGGAACTGGAGCAGGCTCTGAGCCACCACATGGACCACGGAAGTATTCCA*

*TTAGAGTAAAATCGCTTGAAAAGGGGGCAAGCAATGGGGCCCCAAGCAACCCAATCTCGCTCGAAGAAGATGCCGAA*

*ATGCATGGATCTGATGAGGAGCAATGTAAAAATTGTCATCAATGGGTGCCAAAGCGGACAATGATGCTTCATGAGAAC*

*TTTTGTCTCCGCAATAATATCTCATGCCCTCATTGCAATGGCGTCTTTCAGAAGAAATCTTCAGAATGGCTGAATCATTG*

*GCATTGTCCTCATGATTCAGCCCATGGAAATTCCTCAGAAAGCAAAACTAAACACGACTCTATTTTTCACGAAGCTCGA*

*CAATGTCCCAATTGCCCTTACGAAGCAACAAATATGAGGGATCTTGCCACTCACCGTACGTCTATTTGTCCTGGCAAGA*

*TCATTCTATGTCAATTTTGCCATCTTGAAGTTCCTCAAGAGGGCGACCCCTTCGATCCGTCTCCAGAAAGTCTTATTTCC*

*GGACTTACAGCACACGAGCTTGCAGATGGGGCTCGAACTACGGAATGTCACCTGTGCAGCAAAATTGTTCGACTTCG*

*GGATATGACCACCCATCTTAAACATCACGAACTCGAAAAGAATAGCCGATTTAAACCAGCCATCTGTAGAAATGCAATC*

*TGCGGTAGAACTCTGGAGGGCGTTGGTAAGAATGGGGAAGTGGGCGCTGGATCGAGAATGGGCCAAGGACCTGGTA*

*ATGATTTGGGTCTTTGCAGTATCTGCTTCGGTCCACTATACGCTAGTATGCACGACCCATTAGGAAAAGCAATGAAACG*

*CCGCGTGGAACGAAGGTATCTGAGCCAGATGATCACGGGATGCGGCAAGAAATGGTGTACAAACATCTATTGCAAGA*

*CTGCAAGGGCGAAAGAAGCGAATGGGCCTCAGGCAATACTAGCGATGAAAGATGCCCTTCCTCTTATTCAGCCATTAG*

*TAGCCCAAGTAGAGGATAAGACCGAACCGATGCATTTCTGTGTCGATGAAGGAAACCAGAAGAGAAGAAATCTGGCTG*

*AAATGTTAGCTATGGAGCCTGGAGGTTGGGAATTGGAGTGGTGTGTTGCGGCTTGTGAAGCAGAAGGTGCAAATCTT*

*GATAAGGCCAGGACATGGTTATCTAATTGGGCTCCCAAGAAAGCTTGATGTGGTTCAGATCTGGAAGATATTTTGGTAT*

*GGATGAAAGGGATGGAGCATGGCGTGGTACCGATTGCATAAGTAAGGGAGTTCTGGTGGCTGATGACGATATGATAT*

*GATATGATACCAATTTATAGACCCGATTTTGTTGTGCGTACATAAATATACATGGTTGGCGTCGCATTAGCTAGAGATAG*

*ATCGAACAGATTAAGAATTTACTGCTAATACATAAACATATATACATTCTTCA*

BC1G_03606

SEQ ID NO: 46

*GGATCGCAACTAACTCTTCTGGAAGGTTCTTGTGGCAATATCAACCACATGGATCTTCAGTACCACCGCCGTCAAATTG*

*GCTGTGCTTGGGTTATATATGCGAATCTTCACCACGCCCGTTTTCAAGCGATGGGCCGTCTCTTTGATGACCATAGAC*

*GTTTGTTTCGGTATCACCTTCTTCGTCGTGTTTTTAACTCATTGCAACCCAGTCTCTCAAGAATGGAACCCTGTTCCACG*

*GGGTTCATGCAGATCTCTAACATTGTCCGAGTTTTCCTCCATCGCTCTCAATCTGGCTCTCGACACGGCAATCATCATT*

*CTCCCTATGCCATGGCTATACAAGCTTCAAATCGCATTAAATCACAAGCTTTTTGTGATGGTCATGTTCAGTTTCGGCTT*

*TGCAACTATTGCCATCATGTGCTATCGTCTTGAATTGACAGCCCGAAGCCCTTCTGATCCCATGATTGCCATTGCAAGA*

*GTCGGAGTGCTGAGCAATCTCGAGCTTTGGATTGGTATTATTGTTGCCTGCTTACCTACTATGAAACCTTTTGTTAGAG*

*TATATCTCAGACCCAGCCTATCAAAGCTCTCCCAAAAACTTTATGGCAGCCCCACAGTGTCAACAAAAGACGAAAATCC*

*ACAACTTCAGCTAAGGAACTTCGGGGGTTCCGGACCTTCACGCCCCCAAAAAAAACAGTAACTACACTGAACTTTCTG*

*AAGCTCCATCTGTGCAGACAGATACTGACGAGTTGCATCTCGTTCCAAATGAATCATCCAATTTTGATGCAAATTGTGA*

*ATCTAGCAACA*

BC1G_04443

SEQ ID NO: 47

*GCACGGTTGGCTTGCCAAGACTTTCCCACCCACAGAAAGTGCGATACTGGAGAATACCCCTGTCAGAGGTACCTCCG*

*GAACCGGGCAGGAAAATTTCCTAGCTACTGTTGCCCACAACAAAAAGACGAAGAGTCACATCTACAACTTTTTGATTTA*

-continued

*AACCTCAAAATACCCATCTGTTATTCTTCCTTTTTTTTTGAACTCCACTCACTTCTTCCTTCAAAATGGCCGCCCGTACAT*

*TTTCCAGAGTCGCTAGACCAGTTGCACGTCAATTGACTGCACCAGCACGCAGAACTTTTGTCTCTGCTATCAATGCCTC*

*AGCCAGACCTTCCGCTGCTCGTGCTGTTGTTGGAGCTTCCCAACAAGTCAGAGGTGTAAAGACCATTGACTTTGCTGG*

*CACAAAGGAGAAGGTTTACGAGAGAGCCGACTGGCCAGTTGAGAGACTCCAGGAATACTTCAAGAATGACACAATGG*

*CCATTATTGGTTACGGTTCCCAAGGACATGCTCAATCTTTGAACATGCGTGATAACGGTCTTAACGTCGTGGTCGGTGT*

*ACGAAAGAACGGTCAATCATGGAAGGATGCTCAACAAGATGGTTGGGTTCCAGGAAAGAACCTCTTCGAGGTCGATG*

*AGGCTATCTCAAAGGGTACCATCATCATGAACTTGCTTTCTGATGCTGCTCAAAGTGAAACTTGGCCAGCACTTAAGCC*

*CCAGATCACCAAGGGAAAGACTCTTTACTTCTCCCACGGTTTCTCCCCAGTCTTCAAGGACCAAACCAAGGTCGATGT*

*CCCAACTGACGTTGATGTCATCCTCGTTGCACCAAAGGGATCTGGACGTACCGTCCGAACTCTCTTCCGTGAGGGTC*

*GTGGTATCAACTCTTCCATCGCCGTTTTCCAAGATGTTACCGGTAAGGCACAAGAGAAGGCTATCGCTCTCGGTGTCG*

*GTGTTGGATCTGGATACCTCTACGAGACCACCTTCGAGAAGGAGGTTTACTCCGACTTGTACGGTGAGCGTGGTTGCT*

*TGATGGGTGGTATCCACGGCATGTTCCTCGCACAATACGAGGTTCTCCGTGAGCAAGGTCACAGCCCAAGTGAAGCT*

*TTCAACGAGACTGTTGAGGAGGCTACTCAATCTTTGTACCCATTGATTGGTGCCAACGGTATGGACTGGATGTACGAG*

*GCTTGCTCTACCACTGCTCGTCGTGGTGCTATCGATTGGTCCGGAAAGTTCAAGGATGCTTTGAAGCCAGTCTTCAAC*

*GACTTGTATGACTCCGTCAAGACCGGAAAGGAGACTCAAAGATCCCTTGAGTTCAACTCCCAAAAGGATTACCGTGAG*

*AAGTATGAGGCTGAGATGAAGGAGATCCGTGATTTGGAGATCTGGAGAGCAGGAAAGGCTGTCCGTTCCCTCCGTCC*

*TGAAAACAACTAAGTGGATAGTTAATGGGGCCTTTGGGGCTGGAGTTGCATATTTGAAATTGGGCCAATTGTATCATAC*

*TCTCATGACTTTCCGTTTTTTTAATCAACGGTATCTGGAATTAAAAGTTTAAGCCATTGAATTCAAAAAAATTATATTTCCA*

*ATTGTTTTTATAATTGAC*

BC1G_12479

SEQ ID NO: 48

*GAGCACACCCACTTTCAAAATTTCTTCCAAGTTTTGGATACCTCGAAGTTACATTTCTGGTTATTCTAATAAGTATGGCG*

*CCTTCTCCGGTGACAGTAAGTCTAAAAGATTTGCAAAGTGGCAATGTTTCCTTCTCAACACTCGAAGAGGCTTTTGGCC*

CCGAGTCTTTAGGTATTATACTCGTCAAAGATGTTCCAGAGCCATTCGTAGAGTTAAGACATAGTCTACTCTCATATTCA

*TCTTATCTTGGAAACTTGCCTGAAGCCAGACTAGAGAAAATCGAAAACGCGGCTGCAAAATATCTTACCGGCTGGTCT*

*CGTGGTAAAGAAACTCTAAAAAATGGCCAAGTGGACACACTCAAAGGATCATACTATGCGAATTGTGCCTTCTACGTCG*

*ACCCATCTTTAGCATGTGCGATTCCTACTCCTGACTTTTCACCCGAAAATTTTCCCGAATATCTCAGTCCAAATTTATGG*

*CCTGGAGAAATCGTGTTGCCTGGCTTCAAGAGCACATTTGAGAGATTGTGTCGAATTATTATTGACACCGGAGTACTG*

*GTCGCTCGGGCTTGTGACAGATATGCAGAGAAGGAGATTCCAGACTACAAACCTGGATATCTTGAGCACGTTGTAAAA*

*ACTTCGACAACCACTAAAGCACGATTGCTACATTATTTTCCAGCAGAAGCCAAGGACTCTTCTGATGCTCTAGACGATG*

*ATTGGTGTGCAACCCATTTGGATCATGGCTGCTTAACTGGACTCACATCAGCTATGTTCATTAACGAGACTCGCAATCC*

*ACCCGTGATTCCAGTATCCTACTCATACCGTCCAACTACCCTTAGCCCTCTTAAGGAGCTTCCTACATCTCCGGACCCA*

*ACTGCGGGACTTTACATTCAATCTCGGAGTGGCGAGACTGTTCAAGTTAAAATTCCCAAAGACTGCATTGCTTTCCAAA*

*CGGGGGAGGCCCTCGAGAGAATCACCAAAGGTAAATTCAAGGCAGTTCCTCACTATGTGAGAGGTGTACGACCAGGA*

*GTTGCAGATGGCGAGAATGAAGGAGGAAGGATTGCGAGAAATACTATTGCCGTCTTTACTCAACCCAACTTGGACGAG*

*ATTGTAGACTCAGAGATGGGGATTACTTTTGGAGAGTTCGCGAGAGGGGTAGTTGCGAAAAATACAACGAAGTGAGGT*

*TATTCTAACAAATTATTCACAAGTTCATACAAAATACCCAGTACAGCTTTGTTTTTATCTAAATATATTTCATGATGCTCAA*

*TGTTTTAGCGAGGGGGTATTGGGGGAAATATTGAGGTGGCGAAGCGCATAACTTTCCAGTATCTCAGCCCAAAGGCC*

*CCCATTTGCCCCCCCAATTTATTGTATCGGATTGGAATTCTTCCGTCCGAGTGAAAAAAAAAGCAATAACATCCAAGGA*

*TGGCGGCGGTACGGGGACATTGGAAGGACGTTCCAAGACTAGGATCTTTATTTTATTCTGGTGGCAATAACCCCTA*

-continued

BC1G_06676

SEQ ID NO: 49

*GCTTGTCTTATCTGATCGATTGATCGGATTTCATTGGTTTTCATTCGACAATAGCCATGCGGTCCCGGATGTGACAACT*

*ATTTTCGAAGTGTGAGTTCGTATGAAAAGGTGGGCAGGCATGGTATGAAGTAACTGTGCTCCGTATCTATGGGGAAGG*

*ACGAGGCGTAGAGGTGGTCCGTTCTTTCTTGTCATATCCTGATATAAATATGTACTCCACGGAAGTCGTGATATGTAGT*

*CTTTGAATACTTTGCCATTCGGTGTGTTCTTTTCCATTTTGGCTAACGTTGCACATCTCTTTCTTTCTCTTGGAACTTTGA*

*GATTCGTTTTGATTTTACTGTATTCGTACAAACAGTCGGGAACACAATTCGCTTGACTTAAGAAGATCAGTGTCTTCCAA*

*TTCCCCAAACTATGGCTCCCTCCATCGCAGAACTTCCGTCTTCCCCCTCGACTACTGTCAAGGAAGCTCCTATATCTAC*

*CACTTCTGGGCGCGGCATCTTCAATGCAGAAGTACAACCTCCGGAAGCCTCTGCAGTTCCAATATGGCAATCCATCGC*

*TACTCGTCGCCAGCAAGAAATCAACTCTTCTATTCCTTCGGAATGGCTTCTTCCAACAGGCCTCCTCCAATCTAAACGT*

*CCTCTCGATCTAGTAAAAACATGCGGTTTGTTGGATGAAAGAGAGGTGAAGATTGTGTACAGTGCTGCTGTGGATTTG*

*CTCGAGAAAATGAGAACGAGAGAGTATACAGCTGTGGAAGTTACAACGGCGTTTTGTAAAGCGAGCGCTGTTGCCCAT*

*CAAGCGACAAACTGTCTCGCTTGGACGATGTACCCCAGCGCCCTCTCCCACGCCGCCAAACTCGACGCTCACATGTC*

*CCTAACCGGGACTCCCATCGGGCCCCTCCATGGTCTTCCCATCTCCGTAAAAGAACACGTCTACCTCATCGACACACC*

*TTCCACATCTGGTTTCGTAGGCTGGGCCGATAACTTCTGTACTTCCTCTGCCCAAGAAGGAATGTGCATCCAAGTCCT*

*CCGCGACAGCGGCGCAGTCTTTCACGTCAAGACTACTAATCCCCAAGGGCTCATGGCTCTCGAAACACAATCAAATCT*

*CTATTCAACCACTACCAATCCTCTCAATACCTTCCTCTCCCCAGGTGGTTCATCAGGTGGTGAATCCGCCCTGGTAGC*

*CATGCACGGGTCGATTCTCGGAATTGGCACCGACATCGGAGGGAGCATTCGAAATCCCGCCCTGAGTTGCGGTATCT*

*ACGGACTCAAACCCAGTGTGGCGCGACTTCCACATTCCGGACTCTCCGGCGCACACGACGGAATGGAAAGTGTGATT*

*GGGGTTGTGGGACCCATTGCTACATGTTTGGCAGATATGGAACTGTTTTGCAAAACGCTCTTGGATGCGCAGCCCTGG*

*AGACAGGAAGTTGGATTACTACCCATTCCATGGGGAAGTCGCGAAGCTATCGCTGCCGAGAAAGAAGAGAACAGGAA*

*ATTGAAAATCGGTATCATATACACTGATGGAGTACATACTCCTCATCCACCCATTACCCGTGTTCTGCACTCTACGGAG*

*TCAGCACTCAAAGATGCAGGACATGAAATCATTCCCTTCCCAACACATCTGCACTCTCCTATCGTCTCTACTGTCAATG*

*CATTATACCTCCTAGACAGCGGCGCCGAATATCTTTCCCACCTCTCTCTAACCTCTGAGCCTCCCACCTCATTACTCCA*

*ATGGCTTTTAGAAGAAGAGACCACGAAAAATCGTAGCATTCCCGAACAATGGAAGTTACATAAGGAGAGAAACAGGCT*

*TCAAGACGCATATGCGAAATTGATGTTGGAAACGGGTGTAGATTGTATCATAGCGCCAGGGGGTGTGACGGTAGCGA*

*ATGCACATGAAGAGGCGAAGTACTGGGGATACACGAATGTGTATAACGGGTTAGATCTACCGGTTGCCTGTTTGCCTG*

*CTGGAGAGGTGGAGGAGGGAGATGCGTGGGGCGATGAAAATGAAAATAAAATTGCAAAAACGCATATGGAAGCTCTG*

*TGGGGCCCTGGAAAAGAAGGAGCGCAAAAATATGAAGGAGGAAGTGTAGGATTACAGATTGTTGGAAGGAGGTTGGA*

*GGAGGAAAAGCTATTGAAGATGACCAAAATAATTGAGAGGGACTTGGGATTATCTGGGCCCAACTAGAAGAAAGAACT*

*CGAAGGTAATGTGAAAATGAAGATTAGAGATCAAATCTGAGATATCGAAGTGATTCAGATTTTTTTAGAAGAACA*

BC1G_12472

SEQ ID NO: 50

*GGCCCCGAATCTTTCATCTTTTTCCTGCAGGTTCCAAGTTTTAAGGTTCTGTCGAATCAAACGCGGTTTAATTATACAGC*

*CGTGAGATTTTGGTTAATCAGCCATAATCCATTATCCTTCACCCATTCATTACCCATCATCCCCATCCCCATCCCCATCC*

*CCATCGCCATTCAGAGCCTTTCATTACCGGGCCGTTATTTCGTACTTACTGCGCACCGGTGGTTGATTGATTGATTGAT*

*TGTGTACAGCGCTGGTTACAATCTCCATTTTCTGTTCCATCACAGCCACGGCCACGTCTTTTTTCCCATCGTTGTATTAT*

*TAGATATCGTACCGGATCCTCACATCGCCATCACCACTCTCACCACTCACCACTCACCACTCAGCTACACTCGGGTCA*

*AAGAATACAACATTTAAACCGTCCATTCTTTTCAACTGCCTCGAGTTTCTCCACCTATCGACCGTTCACTCTCGAGCCCA*

*TACCTACCGACCTACATATCCATATACACACGCCTACATATATTGGTACACCATCGTCCCAAACGCCATACATAGGTCC*

*CATACCACAGCCTTCAATTACGAAAAGAATTGCCACGATCGTTGCCAATGAGATCACAGTGTGTCTGATAAAACGAAAA*

*GAGGATCATCCCATAACCCCATAAACCCATTTTGGTCTTTCCAAGTGCAAAAGGTACAAACGAAAGAGACAATAAAGTT*

-continued

TGATTGATTTGGAGAGATATCTTACTTTTTCTCGACTCGACCACCACGCATCTCGTCACCCATCTCGGCATTTCCCTCG

CAGAACGGATTACCTCTTGTATACTACTTATATCATCACCTTGCCTGTCTCCTTTCATTACATTTGTTTGTTTGTTTATTTA

CCAACCAAGCACTGACTGGTATAAAAAGAAGTGAAGCACGAAGTGAAAGAAGAAGTGATCTTATTATTATTATTATCATT

ATTATTACTATTACTATTACTGTAGCTCTGCTGAAGCTTGTTAGCGCAATCCAATCTCGCTAATTCAAAGGTCCTGAATG

TCCCATCCTATTATCGACACTCATCTCGTCCAATCTTCATTCAAAAGTCATTCTTTCAATTTCTCTCCTTCAGGAGCGTC

GAGATTTGTTGATTGGACATCAACTTAAATCATTCGACGCGTTTTGAAGATAAAAGTCCTTGGATTCGATTCGACAGATC

TTTATAAAGATTTAGTCCTCTGATAATCTTGTTTTTTCTTAATCAATATCGAATTGCCCTCGATGAGTAATGAGGTAGCTC

AGCCGACTGAGCAAGATCCTAGCCGCTCAACTTCATTGGAAGGAACGAAAGGAGCCAAACCACCTACCCTCGACACT

TCCAACTTCACCGCAGTTTCCCAACCACCCAGCTCATCTACACAGCAGTCAACTACCCAAAACACTTTGACAGGAGATT

CCGATAACGGTTTGAATTCGACCACAAACGTTGATAACGATCAAGGACGAACCAGCGAAACTTTGACTGAAACTCCCA

AGAAGAATAAAGACCTACTTAAAGTTCCATCGAGATCCTCTTCCAACAAAATTCAGCATTCGCCAACTTCTACAGGTTTG

AGTGGAGCGACGGCGAGCGAGGGAAGAGAGAGCATAGGTGGGCGATCCAAGGAATCGAAGGGTAGTTTTCTTGGGC

GAAGGCGGAATGGGAGTGCAGCAAGCAGCAAAATGTCGATAAAATCACCTGGAAATCCCACGGGCGCTGCAGGTGC

TTCGCAACCAGCAGTTCCAGACGCACCTTCAGTTCGTCAGCCGAAAAAGAAGAAGAGCTTTCTCTCTCTCCTTTGTTGC

GGTACTCCGGACCACGCCAATTCTTTGGATGCACCTGTTCCGGCCAACAAGGTCTCAAAATTTAGTTTAAGTCGCCCT

ACAACAGCTAAGCAACCCGACGCGAGTAAGATGGGACAACAAGCCAGTGTTCCCGCGGTACCACAAGTGGAGAAAGA

GAATTTGCTGCAACCACAACAGGCGCCTCAAGTCGAGAGTGGAGAGGAGAAGCATGACGCAACAAGCTCTCAAGAAA

CCGCCAAGGCTACCTCTTCTTCGGATGCCAATGGGGAGCTGAATCGTCCAATCAGCAACGCTCGCGATCAACCTTTG

CCAGACTTGCCCACTGTCGTAGAATCAGAGCCCACGCTACCCGAGACCGCAAACCCAACAGTATCTGTTGACACCCC

AGCGCAATCTGAAACGGCAATTGGAGCTGTATCTCCAAGTTCGGATCTGGGACAGCAAGATGGTGGGGATGAGAAGA

TCGCAAACTTGGATCCAGGAACTACGGAAATCGAAGAGGCCCCATTACCACTCCCAAAAGACGAACCATTGGCTGGTC

AAACTCTCCCCCCTCCTCCGCCCGTTCCTCAAATTCCAACTACCGAGGATGATGCCGAAGTAGAATCGATAGATCAAA

AACAACAATGGCTCTTACCACCAATTGCACCAAGATTCAAAGGGAAAAAATGTCTGGTTCTTGATCTCGACGAGACTTT

GGTACATAGTAGTTTTAAGATCTTGCACCAAGCAGATTTCACCATTCCTGTGGAGATTGAAGGGCAATTTCACAACGTA

TACGTGATCAAGCGTCCTGGTGTTGATCAATTTATGAAGCGAGTCGGGGAGCTCTACGAGGTTGTGGTCTTCACAGCT

TCAGTTTCCAAGTATGGTGACCCACTTCTCGACCAACTAGACATTCATCACGTTGTTCACCATAGACTTTTCCGTGAAA

GTTGTTACAACCATCAAGGAAATTACGTAAAGGATCTTTCTCAAGTCGGTCGCGATTTGAGAGAAACCATCATCATTGA

CAATTCACCAACCTCTTACATCTTCCACCCGCAACATGCTGTTCCTATCAGCAGTTGGTTCTCAGATGCTCACGACAAT

GAGCTTTTGGATCTAATCCCAGTTCTTGAGGACTTGGCCGGCTCGCAGGTCCGAGATGTCAGTTTAGTTCTTGATGTT

GCGCTCTAAGAAGGGGGCAAAATCTTCTTGCAATTCGCTTGATATCATAGCGGAAGGCGTTTCGGTTGATACCTTTGG

TTTCGTTGTAGAGTGTACTGTTTAATCTATATAATGGGCCAGCGTGCTGGGTCAGCCTTGGTGCAGGAAGGTATGCGA

GTGGGAGTGATGGAGGAAAATTGCTAGAAGGCGCGAGATTGAATAAGACCAACGGGTCAAAATCTCCGCGATTGAGA

TGTGAAAAAAATCACATCATCTCAGTGGAACAACGAACAGCAAAACAGCAAGCATCATACGATGCACACCGTACAACAA

CAGATCGGCCTGTCACATTCTTTTCCTGCCCAGCAAGATCTGAGGCACTTTGGGCAGACGCTTATCCGACATTTTCATT

TGTCCAACTCTTTTTTTTTTACTTTCCTACTTTATTAAAACTTCTCGGGGCTTTGCGCATGGCGCAGACTCTTCATGTATC

AAACACTCTATCCACCGTCTGTGAATGCTTTGGAGATAGCATTCATCAAATACCAAAAATGAAACGATTCCATACGACCT

TCTACTTTACTTACACTCCAATTACACCTTTCTTGTAAATAATTACTGGGTAAATAAAAACTTAATAATAATACTAAGATGC

ATTTTTGGGTGGCTATTTCTTATTGGTTTCCA

BC1G_02471

SEQ ID NO: 51

GAGCATTCGACAATCTGGAATTTCTACCTATTCTACAACTTTATTTAACATCTTCCATTTTGTCAATGAAATATCGGTAGT

AATTGTGGAAGCTCTAGGGATTCTGAAATCATCCTCTAGCAGCAACAAAAATCATGTCTAAATCCAAACATGCGGTTGA

-continued

*GCTTTGCTCACTGCTAGTTGATGATATTTATGGCGAACTATCGTCTCGCATTTTTACTATTTTGCTCAGACGGGGAAGG*

*TTACCTATGAATGCGCTCAAACGACACACTCAACTCACAACGCGACAATTGAAGCTTGGATTAACGGTCTTAGTACGAC*

*AAAATTTGGTTTACCATAACTCAGAAGGCAGTGACACCCATTATGAAGCGAATATCGATGCCGCATATGCGTTGGTTAG*

*ATCTGGGAAAATCTTAGAAATTGCGGAAGAACGATTTGGGTCTGTTGCGGCCGAGATTATGGGACAATTGGTACTTTT*

*GGGCCACGCCAAAATATCCGACATAATCGCAGAGTTAAACAAGAACCATGAACCACACGCCAATGGCAACAGCAACG*

*AAACCAACGGCGCGACAAATGGCAATGGTGTTCATTCATATCCCTCAGGGCAATTGAACCATACATTGATCCAATTATT*

*GGAGGAAGGATTTATTCAACCTGTTGGCCAGAATATGTTTCGAAGTCCGACAGATAGTTATAACGCGGTTGAAAAGGC*

*GCTTCTTCAAGATAGTTATGGGGGAGCCACGAGAGGCACGAAGCAAAAAGACGAGTTGAGGATGAGAATCCGAGGAC*

*AGCTCCAAGAACTGAGAGCTCAGGTTCCAAATTGGAAACCTGTCGGTTACAATCGCTCATCTACCAATGGCCATACGA*

*ACGACATTGCCTCGAAACGAAGAAGACTCTCTCACAGCGGGGGTGCAACTAATGGGTATGACTTTGGCGACGACGAA*

*AGTAGCAAGCTTGACGGAAATTTGGTTTTACGAATCAACCATGAGAAATGCACTGTCTTTATGAGAAATCGACGACTTG*

*TTGAGCTTGCAAATTCCCGGATTGGCGTAACCACATCGTATATCTATGCGGAGCTTCTTCGACTCATGGCAGAGCAAAT*

*TCCTAGGTGTCGACCCGATCCTAGAATTGACGATGCTGTGGACGACGCTGATGGGCCTTCAATCATAATAACAACACA*

*AGAGTTGACTGATGCTTTAAGTAAGACAATCAACGTATCCACTGGAATCGGCAAAGCTACGAGCCAAAAGATCGACAC*

*TTCCAGACTTGACAAACTGCAGAACGGCAGAAAGAGAAAGGCTCAGGATGAAGCAGAAGTAGAAGGTGTGGCAAGTT*

*CTGACGAGGAGTCAGAAGATGATCACAAGCCTTTCACGAATGGAAACGGCCATGCAATGGATGTTGACGAAGATGATC*

*CATTTTCGGATCAACCCGGGGCTAACACCAGCAAACGAGCCGTCACTTTTAAAGACCGGGACAGAACTCCTCCTCCAA*

*CAGAGAGTCGCCAGGCCCGAATGATGCATGTAATGAGCCATCTCCAGTTGTTAGCCGCTGATGATTGCCAACTACTAC*

*GAAAGTGCGGTGCTCGGCAAATGGGCGAGTGGACGGTAGATTTTGAGCGTGTGATTGACCGACTTCGAGAATCCGAA*

*CTTGACTCCATCATTTATGAGAATTTTGGCCAAATTGGTCATCGACTTGTACGAGTCATGAGGAAGATGGGGAAGCTTG*

*AAGAAAAGCATATTGCCAAGCTGGCGTTGATCAAGCAGCAGGACTCCCGTACTACACTTGTGAACATGCAAATGCATG*

*GTATGGTTGATATCCAGGAAGTCCCCAGGGATACTGGTCGTATGATTGTGCGTACTATACACTTGTGGTTTTGTGATGA*

*AGACCGGGTTACCTCACTTTTGTTGGATCGAACTTACAAGGCCATGTCAAGATGTCTCCAGCGACTCGATGTAGAGAA*

*GCGACGCAAAGCAAATATCATTGCATTGTCAGAGCGTACAGATGTTCAAGGTCAAGAAGAGGCTTTTCTTCGACCAGA*

*ACAGATGAACCAGTTGCGTGAGATCCGGGCGAAGGAGGAAGATTTATTAGGACAGATTTGTAGACTCGACGAATTGGT*

*CGGCATATTTCAAGATTATTAACTCATATGGAGGGAAGGTTTTGGTTCGGGGCTTTAGCGTTCTTGATTTTTCACACTG*

*GGGCGGCGCCATCTACTGCATAAAGAAAGGCGTTCTAGTATAGTCGAGCAGCAATGGTTATTTCCAGTTGACTCATTA*

*CTTTGAGATACCATAGGTTTATTTCGTAGCCTAGATTAGTTGCTCAGGCAAATATTCTCCAAATTTACAGATTGTAAAGT*

*AGGTATGAAGCTTTTAATGCCATTGTTTCGCTTCTGATTATCTCCCCTTGAATAGATACAATATTACTTAATTACCTAATA*

*TTCTCCAGTCAATACATAAAACTCA*

BC1G_03511

SEQ ID NO: 52

*GACATATAAGACGACCACATGCACTTACAGCAGTCCAGATTATGAGGATCGACCTGCATGATCCAAAATGGATTCAAA*

*GATTTCGACTTTGAATGACCCTCCAAGACTTTTGTCCGGGCCACAACTTCTACATGATTTGATCCGATGGAATGAATAC*

*GAAAATTCTTGTGCAATTGACTTCACTAGTCACGATAGACGAGAGAGGTACCGTTATCGAGACATACAAGCTTGTGTGA*

*CATCTCTCGTTACACGAATCCAATCAACGATTAAAGTTTGTCAAACATCTCAACAGCAGCACATTGTCCCAATATTGTTA*

*CCGCAATGTCCTGGGTTATATATCTCTCAAATCGCAATCCTGCAGTCGGGAGGGGCCTTCTGCCCTATCAACCTCGAT*

*GCGCCGAGAGATAGGATACGATTCGTCGTGGGCGACGTTTCTGCGAGTATCATAATTACGACATCGGAGTTTCGAGA*

*CTCGGTTTCTTGGGAAAATGGACCCAGAGTTATTGTCGTCGACGAATTTCCCATTGCCCCCACGGAACTGGATGAATC*

*AACTGAATCACGTGAACCTACTAGCAATGATCTTGCATATGTTATGTATACTTCTGGTTCAAGCGGAACCCCAAAAGGA*

*GTTGCAGTCAGTCATCTCGCTGCTTCACAGTCTCTCTTGGCTCACGAGAGTCTTATTCCCAAATTTAAACGATTTCTCCA*

-continued

GTTTGCCGCACCATCTTTCGATGTCTCCGTATTCGAGATTTTCTTCCCTCTGACTAGAGGTCAAACATTGGTTGGATGT

GATCGTAGTCAGCTACTTAACGATTTACCAGGCATGATCAACAATTTGGATATTGATGCTGCCGAACTTACTCCAACCG

TTGTGGGCGCTTTATTACAGAAGAGATCCTATGTTCCTAAATTAAGATTGCTGATGACGATTGGTGAAATGATGACGAG

GCCAATCGTGGAGGAATTTGGTGGATCTGATACAAAAGAGAGCATTCTTTATGGGATGTATGGACCGACTGAAGCAGC

CATTCATTGCACAATTCACCCCAAAATGGAAGCAAGTGCTAAGCCGGGTAATATTGGAGTACCCTTTGAGACAGTATCT

GCGTTCATAGCGGAAGCGGCTTCTGGGTCTGAAAATGAGCAGGATCTCAAATTTCTCCCACAGGGCGAGCTCGGAGA

GCTTATTTTAGGAGGCCCGCAACTAGCAAATGGTTATCTTAACAGAGAAGAGCAGAACAGGGCTGCTTTTCTGGCAGT

GGCAGATAAAAACTACTATAGGACTGGTGATAAAGGTCGGATTCTTGAAGATGGAAGTATAGAAATCCATGGCCGTAT

GAGCGGTGGACAAGTTAAACTACGTGGCCAACGTGTCGAACTTGGAGAGATAGAAGATGCTGTCTACAAACATCCGG

GGATCAGAGCTGTTGTAGCAGTCGTGATACGCGGGGTACTGGTTGTGTTCGCTCTCACAAGTGAAGAAGAAACTCATT

CCGAACAAGTTCTGAATACTTGCTCACAGTGGCTTCCGAGTTTCATGGTACCCAGTGAGATCATTATCCTGCAAGAGTT

TCCTTATCTACCGTCTGGAAAGGTAGATAAAAGGAAGTTGGAAGCGGGCTACCAGCAAGAATGTGAAGAAGGGGACG

AGCAATCAGACTTTACACAAAATGAAGTAATAGTGAGAGAGTTACTGCGCGAGATACTTGGTCCATTTCCCCCAAATAT

ACGTTTGGCAGCTGCAGGTCTTGACTCGCTCGTTTCTATCAAAGTATCTAGAGAACTTCGATTGCGAGGATTTAACGTT

GCGACTTTAGATGTTTTGAAAGCCGAAACATTAACGTCGCTTGCGAGGCTTTGTGAAAATTGCCCCGAGGTTTCAAGTT

CAGCCAAGGCTCAATTGGGCCCTACCAAGTCAGAAATGCACGCTATGCTGAATGGCAATGCACATGCCGTTGAAAGTT

CTTTCCCTTGCACTCCGCTTCAAAATGCAATGCTTGCTGAAACTGCCCTCGACGGGAGAGCTTACCGCAACTGGATCG

AGTTAGATTTACCTGGACTTAGCGACACCGAAAATCTTCGTACGAAGCTACACGACCTCGCTGATTGCAATCCAATCTT

GAGAACTGGCTTTGCAGAGTCTTCTGATAATAGCGGATATATGCAGTTTGTATGGAAATCATTTCCCGACTCGAACATT

AAAATTGTGGACGTATTGACCTACGATCTCGAAGTTGAAAATGCATCACTTCATCGCCCGATTGTTTTCGAGATTCTAC

CTACTAAGCCCTGCCTAAAACTCTTGATTCACATCCATCACGCTCTGTATGATGCCTGGTCGTTAGATCTTCTGCTTGAT

GATTTGAATTGTCTGTTGCAAGATGAGATTCCAATTCCACGTCCCTCATTTGCGGATGTTGTGGGGGGTTATCTCGACG

GCAGCATCTCTTCTGATTCTCGAGTCTCTAAAGATTACTGGAAAGATCATATGGCAAACCTCGAGCTTAGACATTTACC

TAATTTTCACACAAGCAACGTTGCTTCCGCTAGATTGGCTGTGGCGCATCACTCGACTCAGCTCTCAACTTTAGATGTT

GAAGTAGCCGCGAAACAATTAGCTTCGAGTTCGCAAGCTATTTTTCAAGCGGCATATGCTCTAATCTTATCCTCTTACTT

AGGAACAACAGACGTTTGCTTTGGCACTGTTTTTTCTGGCAGAACCATCCCCATTGTTGGAATAGAAGAAATTATCGGA

CCATGTCTCTCAACCTTGCCGATTCGTATAGATACCTCCATAGCCTCTACTCTCCAAGATCTTGTAGAAGAATTAAACAG

TATAAATAGGAAACATCTCAATCATAGCACCCTCCCACTTCGCGAGATCAAATCGGTCAATGGTTTCGAGCCTCGACAG

CCATTATTTGATACACTTCTGATATGGCAACAAACTCTCCATAGTTATGACCAGAGCAGAAGCAACGTCCTTCTTATCGA

CCAGCTTGATCAACTGGAGTTTAATCTAACTCTTGAAATAACTCCTACATCTAATACCATTCAATTCAAAGCAAATTATCA

ACAGTCGATATTCCCCGAAAGCCAGATAAACATGCTTCTGTGTCAAATTGAAGATGTCGCGAAAACAATCATCCAGCAT

GCAGGATCTTCACCTATAAATGTCTTCAATGAAAGTATCTCTGAATTATTATCTTTGGAGAACCATACACCTAGCGTTGC

CCTTGGACCCGAGACTCTGATATCTTCAGTGGAACAGATCGCAGAAGAAGATCCCGATCGTCCGGCAATTGCGTTTGC

TAGCAGAATCGAAGACGTCAGTTCAGACATTCGATACATGAGTTATGGTACTTTGAATAGTCGTGCAAACCAGCTGGG

ACACTATCTATCCAGTAATGGTGTTCTGCCGAATGATATTGTTTGCGTTTGTCTAGAAAAAAGTCATGATTTTTATGCCT

CAGTATTGGCTATCACGAAACTCGGTGCAGGCTATCTCCCAGTAACCCCTGATATTCCACATAGCCGGTTGCACCATA

TCTTGATGGAAGCCAAGGTAAAGGTATTGGTTGGACATTCTTCATCCCGGAAACTGCTGGAACAATTTACGGAACAAAA

AGTTGTTCAAATCGATGAGACTGAACTGGGTCAACAATCTACGAAAAACCTTTCTATTGCCTTCAAGCCAGAAAATATCT

CATATTGTGTGTTCACTTCGGGGAGCACTGGAACTCCAAAAGGAGTGCTTGTCACACAAGGCAATCTTCTAAGTAACCT

CGACGTGTTAGTAGAGATCTATCCAGCAACCAGCGATTCTAGACTTCTCCAGTCATGTTCACAGGCCTTTGACGTATCT

GTCTTCGAAATTTTCTTCACTTGGAGAATTGGGGGATGCCTGTGTTCTGCCGTGAAAGACGTTTTGTTTCGAGACATAG

-continued

*AACTTGCGATTCGTGTTCTGGAAGTGACTCATCTCAGCTTGACACCTACTGTTGCTGCTCTTATCGATCCACTTAATGTA*

*CCTAAAGTAAAGTTCTTGGTCACTGCCGGAGAGGCTGTGACACAAAAGGTTTTCAACACATGGGCTGGCCATGGGCTT*

*TACCAGGGTTATGGTCCCAGTGAGACAACCAATATTTGCACTGTCAAGTCACAGGTCACCCTAGATGATCGTATTGACA*

*ATATTGGTCCTCCTTTCAAGAATACGTCAGCTTTTGTAATTGCTCGCAACTCAGAATTCTCCTTGGTACCAAGAGGTGG*

*CGAGGGTGAGTTTTGCTTTGGTGGCTCTCAGGTCTTCAGAGGGTACATGAATCGAGCTCAAGATGAGGGAAAGATTAT*

*TAATCATCCCGAATATGGGCGTCTATATAAAAGTGGCGACTTTGGGCGTCTGATGTCAGACGGATCCCTTGTTTTTACA*

*GGACGAAAAGATGACCAAGTCAAGGTCAGGGGCCAACGAGTTGAACTTGGCGAAATCAACAATATCTTGATCTCTTTA*

*CCAGATGTCGAAGATTGTGTAACAATGGTTATCAATGGACAAGGAAGTTCGCAACGCCTAGTTTGCTTTTTCACGCCAC*

*AGTCATTAACATCTGGAAATATTCTTCCTCTTCAAGTTGATCCAATTATTATTAGCGAACTCTATCGAATACTGGAGTCG*

*AAGCTCCCGAGCTATATGGTACCTTCAAATCTCATTCCGGTTTCAAACCTTCCATCGACATCGCAAGGCAAGATTGACA*

*AGCGTCGACTAATTAGCTTGTATGAAAACTTTGAGCTTGCGTATCTTGACTCTACTACTAAATCTTCAACGTCTTCTGTA*

*GATCATCAGTGGACAGAACTTGAGCTTGAGATCCGCTCCTCATTGAGTGAAATCTCAAAAGTTTCAGTAGATGATATCG*

*GTCCAGATACATCATTCTTTAGCTTTGGTATCGACTCGATTTCGGCAATTGCATTCTCCCGGAAGCTACGTCAAACAATT*

*GCAAAACCAATTGATATTTCTGATATTTTGAAGCATACTTCTGTAGTCAGACTTGCAGAACATTTATCAAGATCCGATGA*

*GCTTAGAAACGACGACATCTCGATGGTTGATACAAACTTAGGACTCAGCGATGAATTTTTAGAGTCTACTTTGTCTCAG*

*TTTACCACCCCGGAAAAAGTTGCGATAAGCGTTTCACCTTGTACGCCTTTACAAGAAGCTATGCTGTCCGCGGTTGAG*

*TCTTCCTCGGGCGTATCATATAACAACCATGTCATGTTCAATATATTTGGTGATCTCGAACGAATTCGTGGCTGTTGGC*

*AAGAAATGGTCCGGAGACATGAAATTCTTCGAACTTGTTTTCTTGCTACTGAAATGCAAAAACACCCTTACGTCCAAGT*

*CGTGTTTCAAGAATTTGAACTCAAATTCGGCTCTCTTGATTCTAACACTCTGGAGGCTGCCATTCTTGAAGTAGAGACA*

*AATTTAACACACAACGATGATAGCCCGCCTTACAAGGTTAACGTTTTGCACTTCAATGGCCAGCAGCATCTTTTGGTCT*

*CAATGCATCACGCACTTTATGATGGAGTCGCCCTGGCAATTCTTTACGATGAAATTGAAAGGCTGTACAATGATTTGCC*

*TCTACTTCCCCAGGTTTCCTTTACTCCATTTCTAGAGCACATAAGCTCAATGAATCTTGATTCTTCTGATAAATTTTGGG*

*GATCTACCTTACGAGGATATTATCCACTTCACTTCGAAGATATGCCAAATTTGACTAGCCAAGTTGAAGTGGACAGCAC*

*CCGCATTCAGAAGCTGATATCGAAAATTCCTCTTAGTAGCGTCGAAAATAATATCAAGAAGCATAGTACCACCCCTCTC*

*GCTGCGCTTCATGCGGTCTGGGCTGGCATCATTTCTGAACTTTTCAAAAGCACTGATATTTGTTTTGGCAATGTAGTCA*

*GTGGTCGCACTGCCCCAGTTAATGGTATAGAAAGACTGGTCGCGCCATGTTTCAACACGGTTCCAATCCGTTTGGAAA*

*ACATTCACAAGTCCACTTACCTCGAGGCATTCAGAAAATTACAAAATGCAAATGCCAACTCCTTGCCATACCAATTTACT*

*CCTTTACGACGACTTCAGTCAAAGTTCAGTCCTGATGGAACTCGTCTATTTGATACCCTTTTCATTTTACAACAGCCGTC*

*GAAGGAACTCGACTCTTCTATATGGTCCATTGCGGAAGAAAACGGTGCCATGGATTTTCCTTTAGTCTGCGAAATTATA*

*CCCAAACCAAGCAACGATACCCTTGAAATTGTTCTTCATACATCTACTTTAATGTTTTCCGATTACGATGCAAATAATTTA*

*ATTCAGAGATTCGAGGATTTACTACAAGTCGCCCTGGAGAACCCTCGGCGCCAGATTATTTCCTCTTCGGCAAGAGCG*

*CAGATCCTCGCTGTTGACGAGGAAAGAGAGAGAAAAAGGGTGCGAATTTTGGACCCGGAACACCAGGACAAAACCAT*

*GAGTCCATTGGAACTAGAAATTCGAAATATAGTTGCAGGATTTACAGACGTTCCCCCAGACAAGATCTCTCGGGATACC*

*AGTATTTTCAGGTTGGGTCTCGATAGTATCAGTACAGTTCAGGTTGCTTCTCGCTTGAGAGCTCAAGGGCATAACCTCC*

*TTGCGAGTGATATCCTACAGCACCCTACCATCGCTCAAGTTGCTTTGCATCTTGAACAAAATAAGTCTTCAGTGAAACA*

*AAAAAGCGTTCAGTATGATTTCGCTGCTTTTGACCAAAAACATCGCGAGCCAATCTGTTCGAAAATTGGAGTTTTATCTC*

*ATAATGTTGAAGCTATCAGACCTTGCACAGCTGTACAACAAGGCATGCTTGCTCAAAGTTTGCATTCTGGAGGTCATGA*

*ATATATCAACAGCGTGTCTCTGGAGATTTTACCCGATCACTCGTTGGAAGAAATTAAACATTCTTGGACTAAAGTCTGTA*

*AAGTTCATGACATGCTTCGTACAGCATTTGCTCAGATTGAAGACCCAAAGCATCCGTTCGCAATGATAACATTCACAGA*

ACACTCCTTTGTTCTCCCGTGGTTTGAAAGTGGCGTCCAAACATTCTCTGAGGATAATGATCGTCTCCGAAACCCATGG

-continued

GACATGACGATGTACAAGAACGGGGACGGAACTATACTCACTTTCACTGCACATCATGCACTTTACGATGCTCAATCTA

TGGAAATGATATTTTCGGACTTTACAAAGTTATATCATCGTCAAGAATTGGCCAGTCGACCTAGCATGAACACATTGTTG

GGTTCAGTTCTTCAAGCATCCGAAGGAGCCCAAGATGAGAAGAAGACATTTTGGCAACTGCCTGAAAATCGAATTGTG

GTCAATAAGTTCCCTGATTTGACTCCCCTCCGTGTCGCAGCACCTAGTAATGCAGTTCGTGAGATAAAATCTTCTGCTT

CACTGAAAGACCTTGAGAATAGATGTCGAGAACTTGGAGTCACTATGCAAGCAGCTGGGCAAGCTACTTGGGCGAGG

TTGTTGATGGCATATACTGGAGAGAACGCTACGACTTTTGGAATGACCCTCTCTGGTCGATCTGTTCGTGATGATGCCA

ATTTAGTCGCCTTTCCAACTATCGTCACACTTCCGGTTAATTGCAACGTGATGGGCAGTAACGGCGATCTGTTGTCCAG

GACTATGTCAACCAATGCACAACTTCATAATCATCAATTTACGCCGCTGACATCAATTCAAAAGTGGTCTGGGTACCCC

GAGGGACGGATATTCGACACTTTATTTGCGTATCAAAAACTACCTGAAGATGGAGAAACTCTGAATTCTCCATGGAAAG

TAGTCAAAGAGGAGGCTACAGTGGACTACGTCATATCTCTAGAAGTCCAACCCTCATCATCGGGTGAAATCACAATTC

GATTATCATTCAGAGAAGATGTCGTACCCGCAGCTCATGCTGAGCTAATTGTCAAACAATTTGATGCGCTACTGCTGGA

TACGCTCCAAAACCCAGATCATCCCTGCAATGTAGCGCCTGATATTGGAGTTGAGTTGCTGTCCATTACTCCTGCACA

GGATCCTGTTCTTCCGGACTCCGTAGCCCTTCTGCATCAATACGTCGAAAGAGGGGCCAAGACATGGCCAGATAAGG

TCGCATTAGAGTTTGCAACTTGCCTTCAACCAGGCAATTATCAAAGCCAAAAATGGACATACCTACAATTGGACGAAGA

ATCCAACAGGGTGGCTCAGATGCTCCATGCACGTGGAACTACTCCGGGTGAGATAATTGCAGTTTGTTTTGACAAGTG

TGCCGAGGCTTCTTTCGCAATTATTGGTATCATGAAGGCTGGCTGTGGTTATGTTGCACTGGATCCTAATGCTCCTGCC

GATCGCTTAAAGTTTATCGTGGAGGATTCTGCTGCGAGATTAACCATCAGTGCAGGAAGCCCAGCCCAGAATTTGAAA

ACTTTCGTAGACGGGAAGATTATCGATCTGACTGATCCGACCACACTTCGCGAATTTGCCCCTGAAGCCCCGGAACTT

TCCAGAGAAATCACCCCTGACGACATATCCTATTGTTTGTACACGTCTGGAACAACAGGAACACCGAAAGGATGCCTG

CTTACTCATGAAAATGCGATTCAAGCGATGCTTGCATTTCAAAGACTGTTCTCTGGACATTGGACCACCGACTCGAAGT

GGCTACAGTTTGCTTCTTTTCACTTTGACGTGAGCGTCTTGGAACAATTTTGGAGTTGGAGTGTTGGAATTTGTGTAGC

TACAGCTCCTCGAGATCTGATATTTGAGGATATTCCAGTTGCGATTCAACAACTAGGTATCACGCACATTGATTTAACAC

CGAGTCTTGCACGCTTGTTACACCCAGACGACGTCCCGTCATTATGCAAAGGTGTTTTCATTACGGGTGGTGAACAAC

TAAAGCAAGAAATTCTTGATGTATGGGGCGAGCATGCTTGCATTTACAATGGATATGGGCCAACCGAAGCTACTATTG

GTGTGACTATGTATCCTCGAGTACCGAGAAATGGCAAACCTTCCAACATTGGTCCTCAGTTTGACAACGTCGGATCGTT

CGTTCTGAAGCCAGGAACTGAGCTACCCGTTCTAAGAGGAGGCATTGGTGAACTTTGCGTTTCTGGAAAACTAGTCGG

AAAAGGATATCTCAATCGCTCAGAACTTACGACTGAGAAATTCCCTACGCTTACTAATTTCAATGAGCGAGTGTATCGC

ACCGGAGATCTTGTTCGAATCTTGCACGATGGCACCTTCCTCTTTCTTGGTCGTGCTGATGACCAAGTCAAACTTCGTG

GACAACGTTTGGAGTTAAGCGAAATCAATGAGGTAATCAAGAAAAGCAGAAACGATCTAGAAGAGGTAGTCACATTAG

TTCTAAAACACAAAGCACAAGCTAAAGAGCAGCTCGTCACGTTTTTTGTCGTGTCAGGAAAGAGCCAGTTGAAAGATAG

TGAAGTAATTCCCTTCATCAGAGATGCCTGCAGCTCGCGACTTCCAGGATATATGGTCCCAACACATTTCATCCCCATC

AAAGCACTTCCTCTCAACGCAAACAACAAAGCGGATTCGAAACAACTCGCAGCAAAATTCGACGATTTGAGTATGGAG

GATCTTCAAAACATGAGTATTCAGGTGCAGAACCATGCGGAATGGACAAACAGAGAGGAGAAGGTGGTAGATACCATC

GTTAAGGTATTTCCCATCGATGTTCCCGAGTTAACGCGCAGCTCGAATATTTTCCAACTCGGTCTCGACTCCATTACCA

TGACTGCCTTTTCAAGCTCCTTGAGAACTGCGGGATACAATAACGCCACCAATGCCACCGTCAGAAGCAATCCCACGA

TCGGGAAGTTGGTTGAAGCACTTCTTGCTGCCAAAATGAATGATACCAGAGAAAACTCATATCTTGTTACAGCTCAACT

GAGAATTGCCGGCTTTTCACAGCAGCATACAGTCACCATTTGCAAAGACTTAGCGGTTTCACCCGAGCATATTGAGAG

CATCGCACCTTGCACTCCTGTGCAGGAAGCAATGATCTACAGGTTACTTGAGAGTGATGGAAGATTGTATTATAATCAC

TTCGAGTACAAATTGGCACCCGGAGTTAATTCTAAACACGTTTCCGATGCGTGGGATCGTGTAGTTTCTAATCTTCAGA

TCTTGCGAACCAGATTTGCCTTGACAGACGATGGCTATGCCCAGGTGGTTCTCAAACCCCAGGCATCTTCGAAGCATT

GGGAGTCGGGCATCGTATTAGAAACCTTGGAAATTCTCAATAACCCGTGGTGTTTCGATATCAAACATCATGGAGACG

-continued

*AAGATACCGTATCGTTAAATATTTTTCATGGCCTTTATGATGGGAGCAGTCTAGGAATGATCTTGAATCATCTTTGCGAC*

GAATCTCGCCAATTACCGAACATTCAGTATGGACCGGCTTTCCATTCATCGTTGGCTTATGGGCCGCTGTCGATAGTTC

*CCGGAAAGGAGGAATTCTGGAAATCCCATCTAAAGACATGGACTCCCTATTATTTACCTCATGACTACGCAGATCCGG*

*GAACTCGGATATTTTCTCGTACACTTGACCTGCAAGATTTTGAAATCAGACGGAAAGCCTTATCTGTTGCGCCGCAGGC*

*CATAATCCAAGCAGCATGGATCTCAGCCATTCAAAAGATCATTTCTACCAAATTGACCACAATTGGCATTGTCACATCC*

*GGCAGAGCAATTGATTTCGAAGGAGTAGAAAAAGTTGTTGGACCCCTTTTCAACACCGTGCCCTTCCATCTTCCTGTAC*

*AGGCTGGCATTCAAATTTCCTCAATAATAAAGGAGTGCCACCGAATAAATATGGAAATGCAAGAATTCCAACACACGCC*

*ATTGAATGATATAAATAAATTAGTTTCTGCTGCAGTCACAGGTCCGCTCTTCGAGGCACTATTCGTGTTCCAACGTCCG*

*GATGCTAACGAAGAGCAATTATCGGATCTAATGGGAAATATTATCTCTCCTGAGGAGGATAGGAATGCAGATTATCCTA*

*TAGCACTCGAAGCTACTCTGAGCCACGATAGTACTAAGCTTATTTTGGAGATGGTCGTGAAGAGCTCAGCTGTGACGG*

*AAGAAATGGCACGCCTTGTGCTCATTGAGATGAATAATACCCTTAGAACTATTCTTCCCGGTAACGACAATGCGACAAG*

*AACAGTTGGGATTGATCTTCACCATCAAGCCCACTCAAGACTTCTCCCAAACCCCTTTCACTGGCTGAACTTAATTGAC*

*GATTCAAGTCACCTAAAGCAATCTTCGGGAGCTTTACATCAATCTGCGCGCTCAGGCCAAATACCTCTAACCAAAGAAA*

*AGGGTGATGTTGTTTGCAAGGAGGTTGCAAATTTGGCCAAAATTGACAAAATAGATATTGATGATCATAGATCTATCTTC*

*GAACTTGGACTTGATAGCATCGATGTGATCAAGTTGTCTTCACGTCTGCGGAAGAACGAGATTGTGATATCTGTCAGC*

*GAAATTATCAAATGTCAAACGATCACTAAGATTGTAGAAGCCGCGACACTCTCCAAAGAAATTGTATCCGACGCATTGT*

*CTACCAAGAAACTCGCGAGACTTAGTCACAAGCTTCACGGGTATCTAAAGCCTAGGCTTCCTGCAGACTTCGAATCCA*

*TTCTACCGGCTACACCTTTACAAGAGAGCATGTTAAAAGAAATGGTTGATTCCAATTTCAAAAGCTATTTGACCCTCCAG*

*GTTTTCGAACTGAGTGAAAACACCCAGGAGGGAAGATTGTTGGATGCTGTGGATATGGTTATCGAAAATTCGCCAATTT*

*TAAGAACCACCTTCCTTGAAGTTCAAGACCCGCAATCTCCCGTCAACTATGCACAGATTGTTCACAAAAAATGGAACAG*

*GGTGGCCGGAAAGTATCTACCTAATTTTGATGATCATGGGTGCCCCGAAGACCTTTTACAATTAGCAGAAAACAAACTA*

*AGAGCGGACATGTCGTCGATAGAGAGCCAATTGTTTGGAATACTTCCTGTACATTTCGAAAACAGGAGATTTATCGTAA*

*TGGGAATTTCACATGCTCTTTACGATGGGAAATCACTGCCGATGATACACGACGATATCAGCAAAGCTTATAGGTACCA*

*AACAATTGCTAGTCGTCCAGACTATAGACCGTGCCTTGCAGAGATCTTCAATTCTGATACTCATGAAGCGAATGACTTC*

*TGGAAAGCTACCCTGTGGAACTCGCCACCTGCAATATTTCCAAAGCAGGAACCATCATCAATTGGCGAGACTACGACG*

*TACCGATATGAGAAGCATTCTGAGTTCTCTCTAAAAAAAATCAGGAGCTTCTGCCGCTCTTCCAACATTACACTACAAAC*

*TCTGGGACAAGCATGCTGGGCTTTAGTTCTCGCAGAACTCATGGGCCAATTTGATGTTGTGTTTGGAACTGTACTTGC*

*CTGTCGTGATACAGGTGACACAGCCAATGAAGTAAACTTCCCACTGTTCAATACTGTGGCAGTTCGATCAGTACTTCGC*

*GGAACTGTGGGTCAAATGCTTCGAGATATGCAAGAGAAGAGCGATATGATTCGTCAATTTCAACAATTCCCCCTTAGGA*

*AAGCTCAAGCCCTCGCACTTGGCTCTCGAGACCATTCAACCAAAGATACCACATTGTTCGACACATTGTTCACATATCA*

*AGGCTCTCGACCTGAGAAGGAATCTGATCCATTATATTTGTCATTTGGTGGTTCTTCGGATGTTCAGTTCGCAATCTGT*

*GTCGAGATGGAGGTTGAAGATAAATCTGATCGTCTTTACTGGACAACAGCTTGTAAATCTGTGGCTAGAAATCACTTCC*

*AAACCAACGAAATTCTTGAAAAATTAGACAAGGTTCTTGGGAAAATCATGGCAGACAAAGAGGAACAGATCATTAAAAT*

*TTACAGCGACGGAGTCTCTGTATGCGGATCTCCCAAATTTCAACTTCGAGAAAGTCCCCATCAGAAAAACTTCCAAGTA*

*CCTTCTCCTTGTGAAAGTTGGTCTAAAACAGAAATGGAGATTCGAAAATCAATATCATTCATTTCAGGTGTCCCAGAGAA*

*AGATATCCTCAAAGACTCCACAATCTTTCAATTGGGCTTGGATTCAGTTACAGTCCTCAAGCTTCCAGCACATCTCAAAA*

*ACTACAACCTTCATCTGACTGTTTCGGAAATCATGAGACATCTCACAATTCAGGATATGGCTGATCATTTAGCTGAGAAA*

*CAAGACTCACAGTCGAATACTCCTGCCAACGTCGACGTTGACGTCGATGTTGATCTCATCCTGGCTCAATCTACACCAT*

*CGATTGATGAGACCCAGATCAAGCAATTGAATGAATCTTTTGGCGAGATAGACTACATTATGCCCGCAACTGCAGGAC*

*AAATGTATATGATTAGACATTGGCAAAACTCTCAAGGATCTCTCTTCCAAGCAACTTTTGAGTTCAGATTATCCAGCGGT*

-continued

TACGACCCACAACTACTCGATTTTGCTTGGTATAATTTGCTACTTCAGCACGACATTCTACGAACTGGTTTCATTGACTT

GGACTCAACTATCGTTCAAGTTGTTTACAAAGAACCAACAAGTATGGTAAAATATGTTGAGGAGCTACCTAATCTTCAAC

AAGAATGTAGCCTTCAAGATCCACCAATAAGTCTTTTTGTCATCACGCCACAGAACACTTCAAAACAGGTCGATATGCA

TCTTGTTATTCACCATGCTCTTTACGATGGAATCAGCATCTCTTTGTTGCTTAAGGAATTGATGGCTTGGTATAATGACC

CGAACACCATGGCCAAGTCCACGTCTACAATCGCCAAAAATGAATGGAAGAAATTTGTTGCGACGACAATCGAGGAAA

AGAATAAACCGTCCGTGAGGGATCAATGGATTGAGTATCTTGGCACTGTTCCCTCTAAACAATCAAGCCCTGATTCAAA

TGTCGAATTCGAAGTAATAGGACCGGGAATCAGGAAGCCTAATCGAGTCGAAGTTTTCGAACCCAATGTGCCAGCAAA

AGGTGTAAAAAAATATGCACGAAATACAGGTGTTTCTATTGACCACATACTTATCGTTTTGGCATCGACAGTCTTGGGT

GATCAACAATTTAAGAATGTTGTGGATCTTGATGGAAATTTCATCGTTGGCCTGTATCTAGCCAATCGCTTTCCATTTTC

ACAGGACCTTTCTTCCATGATGGCACCTACGCTCAACATATTGCCAATCAGAATCGGGCCAAGTAATCGGAATGAAGA

TGATGGTTTTGCGATACCAGAGTTGGCCAAGAATGTGCAGAAGGGTTTGGCTAAGATTGGTAGAGGCGGAATGGCTA

ACGCGGGGCTGGACGAAATCTATCAGTGGACTGGCGTGAAAGTACATGGATGTATCAATATTGTTAAAGAGGTTTCTG

ATCATAGTGAGAAGATGGATGAGGCAAGCTCCGAGGAGATATCGGATTGGGAAGTTGTTGAAGACTTGAACGGAGAT

ACGGCGAAGGAGCATAAGAAACCTCGCGAGGAGGTCGGTTTACAGCCTGTGAAGAATGAGGAAAAGGATACGACCAA

GCGAGTTCTTTTCGAATCGTTGGAAGATATGAAAGGATATGCGAGAGTGGTGAAGCCGAAGAGGGATCAGACTATGTT

TGTTAGGAAGGATTCGGGCGCGTATCCTTCGTCAATCGATATAGAAATTCGCTATCATCCTGAGAGTGAAACCATCGAT

GTTGGCATTTTCGGGCCGGATGATATGTTGAGTCTTGAGGAGGCTGAGGAATCGATTAGAATGCTTAAAAGTTTTTGCT

TCTGAAAGGAGGTGATGGAATTTTTTATTGTCGTTGGGGAAATAACGGAGCGAGGGATTCTGTTCA

BC1G_03981

SEQ ID NO: 53

GATTTACTTATTCAATTAAACTAAGCTCACCTTCCGCAGTGACTGCGGGCAGTCTAAACCATGGGAAAGATAGCAACAA

AACTACGGGAGATCAAGGAAGGAATCAGAAACGATGAAAACTTAACTCGAGGAAGAAAGGGATTTGTTCGAGGAATAA

AAGGGTTACCGTCATCAACAGGGAAATATTTGGTTCGGAAGATTCCTTTCGTACATTGGTTCCCGAACTATGCTCCAAG

ATGGCTTGTGGACGATATGATTGCTGGGGTAACAGTCGCATTGGTCTTGATTCCCCAGGCTCTGGCATCTGCAGCGCT

AGCTGGCATACCATTGCAGCAAGGACTCTTTGCTAGCTGGCTACCATCGGTTATATACTTCTTCATGGGTACATCGAAA

GATATTGCTACAGGACCCACAACATCTTTGAGTCTACTTACCAATGCCGTTGTGTTATCGATTACTGCCGAAGGATTTC

CAGTACCACCAGCTCTCATTGCCTCCGGTCTCTCTTTCTCGATAGGTACCTTTTCTCTATTATTCGGACTCCTGAACCTT

GGATGGATCTTGAACTTCGTCACTGTTCCTATGCTAGTTGGGTTCCAAATGTCAGCCGCGTTGATCATTGTTCAAGGTC

AGATTCCATTAATTTTAGGAGAATCGGGCGTGGGCCAAAACTTTACGCTACAAGGGATGCAAATACCCAAAAACATTGC

AACTACTCAACCGTTGTCTTTGGCTGTTGGCGTAGCTTCAATAGTGATTATCATTTTATTGAAGCTCATGGGCAAAAAGT

GGGGGCACAAGAGTAGCATCATCAGGATCTTATCAAATTTACGGAACGCTTTTGTGATTGCTATTTCCACTACGATATC

CTTTATTATCAACAAAGATCTCGTCATTCCACAATTCCCCATTGCTGGGACGGTAGCATTAACCCTACAATCTCCACAAC

TTCCGACTAAACTTGTTCTACTTGTCGCCAAGAAATCCTTCCCCGTTTTTATAGCTGCCATAGCTCAGCATTTGATATTC

GCCAAGTCATTTGCTCGTGAGCACAACTATGAAATTGATGAATCGCAAGAACTTGTTTTTTTGGGTACCGCAAATATCG

TGAATAGCTTTTTTGGTGGGATGCCAGTATCCGGATCTCTTTCTCTATCGGCAGTAAATTCAACAACTGGAGTGAGATC

ACCACTTAGTGGACTTTTCTCTGCCGGGTTTGTTTTTCTTGCCATCAATATGTTGACGGAAACATTCCAGTGGATACCAA

CTGCAGCAACCAGTGCGATTATACTAGTCGCTGTAGGAGAAACATTACCTCCAAACAGTATTCCACTCACATACTGGAA

GGGATCATTTGCCGATTTCATAGGCTTTTTTGTTGTCATGAATGTGGCGTTAGTTACAAGTCTAGAGCTTGCTCTTGGA

CTTGGGATAGTCTACATAGCGCTCTACACTCTCCTACGCACATTGTTCTCCTCAATTAGTCCACTAAAGCCCCATGATA

TCGAAAACAGATACAGCTTTGAAAGTGTAAACAGAATGAGCATACCTCTTCAGGGAGGGCGCCTAGTACCCCAAGGCA

CGCAACTCATTACGTTAGAAACTCCCCTCATCTACTTGAACGCCGAGAGAGTTAAGAAAGATATCTTAGAAGCTATTTG

GACCTATCATGAGCCAACTCCGTATGGGCCGACGGAACGAAATGGATGGAGCGACTACCGAGTTCGAAGAACTGCCG

-continued

*CTCTCCGTCGCAGGAGTAACATTAATACACCAACTAGATTCCTTCCAAGGCTTGAAGTTATCGTATTCAATTTCACACGA*

*GTCACATTTATCGATACCACCGGACTCACCTATCTTCAAGATCTCAAAGACGAAATTATGGCATATAGTGGTGACGCTG*

*TAGAGTTACGTTTCGTAGGTATGATTGACTCTGTACAGAAGAAATTCAAAAGAGTAGGATGGCCGTTGGGCACTTATCA*

*AGAATCACAAATCGGCCTAGTCGCGGGAATTGATATTATATTCGAAGATCTACACGATGCAGTTGCAGCACCTCGAAG*

*TGTAAGAGCATCTATGAATGGACTGGATTTTGGGTTTGCAAATCCAAGGAATGATATGGAACAATTTGGAGATGAGGAG*

*GCTTTTGAAAAGGGCAGGATGAATGTCATAGTTACGAATGTTGTAACAAAGGATGGGAGGGCATATAAGGAGAAAATG*

*TAAATATACCTTTGGGTGCTTTGGAGTATTTTGGGAGCGATCTTTGCTGTCTTTATTGGGAGAATAAGAATTGTACAAAT*

*ATATATGCGGAGAATCAATGCGGGAGGATGCTTTCTTGGACTGCATAGTCAAAACGATGAAAGGCGTTGAGACAGTCA*

*CCATATCAACTCACAAATTCCAACCGAAACA*

BC1G_14507

SEQ ID NO: 54

*GGGTGTGGGTGTAGATGAATTAAATGAAGAACATCAGCGTTCCAAGGTAATCCGTATCCATCATATCACATCACATCTC*

*TTCACATCACTCCAATATTCTCTCTTCTATCCTCTCTCTCTCTCTCTCCCTCTCCCTCTCTGTCTTCCTCCCCCTCGC*

*CGTCGTCGCTTCATTGTAGGAGACCTCTTTCTCGTCGCTCCATACCAGTCCCGCAAATCGATAGCTTCTTCCATTTGCC*

*TGCTAATTACCATTCCATATTACATTATTTATATGCGTAATTAGCAACCTTTTGCCTCCTTCCCCTTGCATTAGCACCACG*

*AAACATCGAGAACCAGACAGCTCCATTCCCTCAAACAACCTCCTATTCGATCGATCATTCCTTCTTCAACAAGACTTTG*

*GAACAACTACTGCACTTCAATATGTCTCAACAACCTGAAGCTGTAAATAATATGCATAATTTGACTACGCTCATAAAACG*

*ACTCGAAGCCGCAACCTCTCGTCTTGAAGATATAGCTTCCTCTACCATTCCACCACCTGCTTCATCATCCATCCCTCTA*

*ATTTCTCCTCCGGCCGAAGCTGCGAAAACAAATGGCACAACTCCGCCGCCGCCAACGATCCAAACACCAGATATCAAA*

*AAGATCATCGAGGATCCAATCCCAGGAGTAGTCTCAGAGTTCGATAATTTTATTCAGGGGGCGGTTAAGAAATATGTTA*

*ACTTGAGTGATGAGATTGGAGGGGTTGTTGCGCAGCAGGCATCTAGTGTATTGAAGGCATATGTCGGACAACGAAGAT*

*ATATTTTGATCACTACAAAGTCAAAGAAACCTGGCATGCAAGATGAACCATTCCAAAAGCTCATCAAACCTCTTCAGGAT*

*TCATTTACTGCCGTTGATGATATCCGAAAGTCCAATCGTGCATCTCCATTCTTCAATCATCTCAGTGCTGTTTCTGAAAG*

*TATTGGTGTACTTGCCTGGGTTACAATGGACAACAAACCATTTAAACATGTCGATGAATCATTGGGATCTGCTCAATATT*

*ACGGAAACAGAGTATTGAAGGAATTTAAGGAGAAAGACCCAAAACAAGTCGAATGGATTCAAGCATTCTATCAAATCTT*

*TAAAGATCTCAGCGAATATGCTAAGGATAACTTCCCAAACGGTATTCCATGGAATCCAAAGGGTGAAGATTTGGAAGTT*

*GCGATTAAGGATGTAGATGAAAAGGCTCCAGCCCCTCCTGCTCCTCATCCAAAGGCTGCAACTGCTGGAGGTGCCGC*

*ACCACCACCACCCCCTCCACCTCCTCCTCCACCAGTCTTCGATGACATTCCATCAAAGCCAGCACCAAACCAAGCAGA*

*TTCAGGTGCTGGACTAGGAGCCGTTTTCTCTGAACTGAATAAAGGAGCAGACGTTACAAAAGGATTGCGCAAAGTGAA*

*TGCTGATCAAATGACACATAAAAATCCTTCTTTGAGAGCAGGTGCTACAGTTCCCACCAGAAGTGATAGTCAATCCAGT*

*ATTAATTCGAACCGAGGAAAGAGTCCTGCTCCTGGTAAAAAGCCCAAGCCAGAGAGTATGAGAACTAAGAAACCCCCT*

*GTTAAAAAATTGGAGGGTAACAAGTGGTTTATTGAAAACTACGAAAACGAGTCTGAGCCAATCACAATTGAAGCATCTA*

*TTTCACACTCGATCCTCATTTCCCGCTGCTCAAAAACCACTATTATCATTAAAGGAAAAGCAAACGCTATTTCTATTGAC*

*AACTCCCCTCGTCTTGCCTTGGTAATTGATAGTCTCGTCTCATCGATTGATGTTATCAAAGCACCAAACTTCGCACTTCA*

*AGTACTGGGCACATTGCCAACGATTATGATGGATCAAGTTGATGGTGCTCAAATTTACTTGGGGAAGGAGAGTTTGAA*

*CACGGAAGTCTTCACGAGTAAATGTAGTAGTGTCAATGTGCTACTTCCAGATTTGGAGAGTGCAGACGGGGAAGGAGA*

*TTACAAGGAGGTGCCGTTGCCCGAACAGTTGAGGACTTGGGTGGAGAATGGAAAGGTCAAGAGTGAGATTGTTGAAC*

*ATGCTGGATAGATTGGTTGAGATGGATTGTGGAGTTTGGGGAGAGGCTCTGGCGAAAACTTGTTGGGGGTGAGGGGT*

*AATGAGATGTGATGGAGAATCTGGGTAGATTTGATATTATAGAGATAGTTGAGTGAAGTTTTATATCATCGCATGTTAGT*

TGAAGTTTTCAGGCAGAGTAGAAGTCAAAGTTGAATTGTACATATCTATGTATATGTATATCCGAGGCTTGTCTCGCTTT

GTTGTTTAGTAGATTTCAAACCGAAGATTTTCTACTCATCATATCGTGCCGTGTGTTTTATATTGGGCGATGTGTCGTTG

TGCTTTTTCTCTCTCTATCTCTTTTACTTTCAGGGAAATAAATATA

BC1G_09414

SEQ ID NO: 55

GGCTTCAATTGACGTTGAAACATGAATGCTGAATGATGATACGATACACTTTACTTCAGCCCCTTTAACATTTTGTCGCA

AAATCGGTGAAACTTGGGTTGTATGTATTTGTATATTAAAGATCGCTAAGCCCAGCCTCTATGGTAACAGATTACCTGA

GCTTCGTCATTTCGACCCCCGGACCGTGATCTTCTACCAACCTCGAACCCATTCCTTCAAATAAATGTCACAAATCTAT

CTTTCTTCATACCTATTTCTTTTTTGTTCATACTCATAATGTTTTCGGGTTCGAACTCGTACCTTGGTGGTAACACCGGC

CGCCAACCACCACAGCAACCGCAACAACAATATGGTGGTTTCCAGCCAAACCAAGGTTTCCAACCACAGCAGACTGGT

TTCCAGCCACAACAGACTGGTTTTCAACCTCAACCCACAGGATATGGTAATGCGGCTCCTTTACAACCCAATTTCACCG

GTTATCCACTTCAACCACAGCCTACGGGATATTCTCAGCCCTCTCAAGCAGGCTTCCCTGGAGGCCAGCAGCAACAG

CAGCAGTTCAACAATGCTCCTCAACAGCAGAACTTCCAAACGGGAGCTCCCCCAATCCCGCAGATTCCGCAGCAATTC

CAGCAGCCTCAACAAACGCAACAGGCTCAACCACCTCCTGCACCTCCTGTGCAGCAACCGCAAGCGACCGGATTTGC

TGCAATGGCAGATTCATTTAAACCTGCTGCTGCAGAGCCATCGAAGCCAAGAGGACGCAGAGCCTCCAAGGGGGGAG

CAAAGATACCTAGTATACGACTTTCCTTCATTACAGCCCAAGATCAAGCAAAGTTCGAAACTCTTTTCAAATCCGCTGTT

GGGGATGGGCAAACACTTTCTGGGGAGAAATCGAGGGATCTTTTACTACGCTCAAAACTAGACGGGAACTCACTGTC

GCAAATATGGACGCTCGCAGACACTACAAGATCTGGACAGCTACATTTTCCCGAATTCGCATTGGCTATGTACCTCTGT

AATCTCAAGCTAGTCGGCAAGCAGTTACCATCCGTGCTTCCCGATGTTATCAAAAATGAAGTTTCTAGCATGGTGGATA

TCATAAACTTCGCTATAGATGATGATGCACCAGCGGCAACGAATGCGCCCAGTTTTGATGGTCGACAAAACACCGCGA

CACCTCCGACTATCCAACAACCACAGCCAATGGCGTCTAATTCCGCCCTTCTCACTGCGCAAATGACAGGTTACCCTG

GACAGCAGAATAACTTTTCGGGTGGATTTCAACCACAACAAACAGGCTTCCAGGGCCAAATGCAAACTGGCTTTTCTG

GACAGCAAGGCGGATTGCAACCTCAGCCAACTGGATATAATCAGATGTCAAACCCTCAAGCAACGGGCTATAATGGAC

CGCGCCCTCCAATGCCTCCTATGCCATCTAACTTCAGTTCTCATTTATCTCCGGCTCAGACGGGTATGCAAGGTGGAA

TGATCGCGCCATTGAATAGCCAGCCTACAGGAGTCGATGGCCAATGGGGCTTGGTAAATGCGCCAGCCCCCAATATC

GATCTATTACATTCCCGGATGATGCCGCAACAGGGTCGAGAACAAGGCAACTTCACCACGGCTGGTATAACAGGCAAT

GCTGAAATTCCATGGGGAATTACGAAAGACGAGAAGACCAGATATGATTCCGTTTTCAAAGCTTGGGATGGGTTTGGT

AAAGGATATATTAGCGGTGATGTCGCTATTGAAGTTTTTGGGCAGAGTGGTCTCCCGAAGCCTGACCTGGAGCGCGTA

TGGACCTTAGCAGATCACGGCAACAAGGGAAAGCTCAACATGGATGAATTCGCGGTTGCCATGCATTTGATTTATCGA

AAGCTTAATGGATATCCTCTACCAGCCCAACTACCTCCGGCGCTCATACCCCCTTCCACTCGTAACTTCAATGATTCGA

TTGGGGCTGTCAAATCTTTACTTCATCAAGAATCTAATTTCCGCAAGAACTCTGGTGCTACCCTTTTGCCACAAAAGACT

GGAGTGAGCTACCTCAAAAATCATTCTTTCCGTGGTGATGCTACCCCAGGTCGCACAGGCCGTAAAGACGCTACAGTA

TACAAAAATAACGACGATGATGTTGGGTATAAATCTAGTGCTCGTCGCAGACTCGGGGCCTCTTCTCCACGACCTTCG

TCTCCGGGATCAACAACTTCCAACGATGACCTTTCACTAGACCAGCTTAGAAAGAAAATCGCGGAGAGACAAGTGATA

CTGGATGCAATTGATTTCAAGGCCGAAAATGCTGCAGATGAAGATGATGCTCTTGATCGTAAAGATCGTCGTGAAGCA

GAGGATCTTTATCACCGCATTCGTCGTATTCAAGAGGATATCGATGCGCATCCAGACGCATCGTTGCGTAATGTTGATT

CCGGCGCCGAGCGTCGTGCTTTGAAAAGACAGTTGCAGACATTGACAGATAAACTTCCAGATATTGCTTCGCGTGTCC

GAAGAACGGAAAGAAGCATTGCTGATGCCAAGCTTGAACTATTCCGTCTAAAGGATGCCAAAGCTCACCCTGGAAGTG

CCTCTAGCATTGTTGGAACTGGTCCTGGCGGCGCTATCACCGAATCAGATAGACTCAAAGCAAGAGCCAAGGCTATGA

TGCAACAACGTTCTGCTGCTCTCACTGGTAAGAAGATTGAGGCGAGTAATGATGACTTGGATGCGCCAAAACGCCTCG

AAGAAGAAAATCTCAAGATTCGAACTGAGAAGGAAAACAACGAGCGCATGGTTCAAGATGTTGAAGAGAGTGTCCGTG

-continued

ACTTTTCACGAGGACTGGAGGATAGTCTCAAAGATGGTGGTGAGAGCTCGTCCAGTGAGCATGAGAAGAGACGTTGG

GAGGATGGGCTAGGTGTTGAGGATGAAGTGAAGGACTTCATCTTCGATTTGCAAAGGAGCAGCAGGAGTGCCAGAGT

TCGAACTGATGATCGCAGCAGAGAGACTCCTCGTACTGAAGCGTCTCATGCTAGCCCTGCTCCAGCAGCTCGTAGCG

AAACTCCATCGTCACAGCCATCATCTACACCAACCCCTGCTGGAGGTTCATACTCACAATACAAGACTCCTGAAGATAG

AGCAGCTTATATCAAGCAACAGGCCGAGAAGCGCATGGCTGAACGTCTAGCTGCTCTTGGTATCAAGGCACCATCTAA

ATCTGGAGAAACAACACAACAGAGACTGGAACGTGAAAAGAATGAGCGTGCAGCCAAACTCAGACAAGCAGAAGAGG

AAGATGCTAAACGTGAAGCTGAGAGGCAAGCTAGGATCGCTGAAGAGCAGGGTGCACCACCACCTGCCCCCGAGCA

ACCAAAGGAAACCGCGAAAAAGCCACCTCCACCCCCTTCAAGGAAGGCCGCAAGAAGTGACGCTAGTGAGCGCAAG

GCCGAAGAGGAGAGAATCATTAACGAGCAAAAGGCACAAATTATTGCCACAAATGAGCTAGAGGACGATGCTCAACGA

CAAGAGGCCGAGCTTGCAAAGGAACGCGAGGCGGCTCAGGCTCGTGTCAAGGCCTTGGAAGACCAAATGAAGGCCG

GGAAATTGAAGAAAGAAGAGGAGAAAAAGAAGAGAAAGGCTCTCCAAGCTGAGACCAAACAACAAGAAGCTCGTCTC

GCAGCTCAACGCGCAGAGATTGAAGCCGCACAAGCACGTGAGCGAGAATTGCAACGTCAACTTGAAGCTATTGACGA

TTCAGATTCATCTGATGATGACGAAGGTCCTGAGCAAGTTACCCCTCAAGCATCAACGCCCACTCAAGGAAGTCAAGA

GCTTGAGCGCAAAGAACCTTCTCCACCACCTCCTCCACCTTCAATTCCAGTTGTTGTATCACCAGTCCCTGCTATTGCA

ACAACAACTAGTCTTCCATCACCAACCCCACAAGTTACTAGCCCTGTTGTCAGCCCTCCAGTCGATACAGAGACCCGC

AATCCTTTCTTGAAGAAAATGGCCCAATCCGGTGACGCATCTACCGCATCTACTGCATCTAACAATCCATTCCATCGTC

TTCCTGCTCAAGAGCTTTCTACACCTGCACCAATTCAAGTTCAACCAACAGGTAACAGGCCATCTCGTGTTCGTCCAGA

AGAAGATGATTGGGATGTCGTCGGATCTGACAAAGAGGATGATTCCTCTGACGATGAAGGACCAGGTGCAGGTGGTG

CGCGTCATTTGGCATCGATCCTTTTCGGAACCATGGCACCTCCTCGCCCATTGTCATCCATGGGTAACGAAGCTACAT

CTGCGCCTGAATCTCCTGCTGTAGCATCTCCACCAGCGGCAACCCCCCCACCTCCACCAGTACCTAACTTCAATGCAC

CGCCACCTCCTCCAATGCCATCAGCCGGTGCGCCAGGTGGTCCTCCACCACCACCTCCTCCTCCACCAGGGATGGG

TGCTCCACCTCCACCACCAATGCCACCAATGGGAGGCGCTCCTGCTCCACCAGCAGGTGTACGACCAGCTGGTCTCT

TGGGTGAAATCCAGATGGGGCGATCGTTGAAAAAGACACAAACTAAAGACAAGAGTTCAGCTGCTGTTGCTGGAAGG

GTTTTGGATTAAATACCTTTCAAATCATTGAGAAGAGACAAGATGAAATGGAGGTTTGTGGTTAGCGAGCCTAAGAACA

TGGATTGTATTATAAATTACTTTTGGTTCATAGTATTGGGCAAGGGGGCTTAGGTGTGGAAGGTGCGAAACAGGAAAG

ATAAGAGACGAGCATAATTTGTAGTCGAAGTAGCAATTTGAAAATATTCGTTCGTTTTGATAGTCATTTGATGCACTTAT

CACCA

BC1G_04258

SEQ ID NO: 56

GATATTGTACACGAGCCTCTTCCTGCATTGATTGATTGATTGCTCTTACACATATCCAGTTCATCTCCCACAAAATACCA

AGCGGCCGCATTTGGATGCAACATACATACTCACTACCTTCCACTTCACCTACCTACCTACTGACTTAATATACCTTCTT

GTCATCTTTGATGGCACTGAATAAAGTACCTTCCTATTAAAACTACCTCAACCAGTCCAGTCATTACTACCCACCTTACA

TCTCGAGAAGCCTCCTTCCTCGATATACATTCTTCTCTTATATTAATGCAAAGATGTCGGAGCACGAACATCAAAAACAT

CTTTCCGATTCTGAAGAAGATTCCATAATGGAAGAGAGAGAGGAGAAAAAGGGAAAAGACGAGATAGAGGAGAAAGA

CAAAAAAGACGAGAAAGACGAGATAGAGGAGAAAGAGGAGAAAGAGGAGAAGGAGAAAGACAAAAAAGACGAGGAA

GAGAGAGAGGAGAGAGAGGAGAGAGAAGAGAGAGAAGAGAGAGAGGATACAGTTGATCAGAGTTCTGATCATGAGA

GTGACACCTTCGAGGATGCCAATGATGTTGAAGACATTGCAGACACTCTTACCTCCCCAGTTGAAAGGACAAGATCTTT

AACGAAACGAAGATCATCATCCATTAAGAGCAATACACAAGACCTCAGTACCGATATCCCATCGGTCCCAACAGTACCA

CTTCCAGAAACGAATGGCGAAACGAATGACGAACAAATAGAATCCGATAATCCACTACCTAAATCTCCCCTTTTAACAT

CTCATCGCATGTCCACTACATCCCTACATAATGTGAATCTCGAAGACGGTGATGATTTTGGATCACCTCCACCACCTCC

TCCCGTTTCGAAAGTAGCACCAGAAGATCAACCACCCGAATTACCTCCAAAGCCCAATACAATAATTCCAATGCAGGG

CCTTTCTGGAGCCCTTCCAGATGTGCCATTCTCACCGCCCCCTCCTCCTCCTCCCGCTCCTCCCGCTCCTGCAAACCT

-continued

*CGCTGCGCCAGCACCTGTCACCAGAAAATTAACCAGCCCATTCTCATGGCTGTCGAGAAATACCTCGGCTCCAAAAGA*

*GAACGTCAAGTCACCGCCATTACCTTCATCTCACGCAACCGAGCGTAGACATACCGCTTCTTCGATAGCGACCATTAG*

*CAGCAATCCTGAAATGATGGTAAACAAATTGGAGGAGGGTAATGATACAGATGCCGCGAATGGAGTTAGACGACCTG*

*GGAGGAATAGTTTACGGGACAGGTTTAAGCTCGTGAGAATGCGAGAAGAGGCTGGAATAACAGAATTGCCTGAAGAA*

*AAGGATGAAGCAGGCAACACAGCATTTGGGGGTCTCATTAGGCAGAGTACAAGTCTTGGTTTGGGATTTACCGCCTCA*

*AATGATGACAAAGACCCTTCTCCCGTATCTCCTGGTCCGCCTACGAGTCCCAACCCAATTAGTGTCAACCCTGCATTA*

*GCCCCCGGTACGGCATCTGGAGTTTCTGCAGGCCCTTCTGCATTGGGTGAATCAGAAGCACCAGTCGATTGGGATTT*

*GTGGCAAAATGTCGTCTGGGAAGGACCAGCTGCGGTAGCAAGAACAAGTGCAGAAGAGCTGAATCACGCTATTGCAA*

*CTGGTATACCACATGCTATCAGAGGCGTGGTATGGCAAGTATTGGCGGAGAGTAAGAATGAAGAGCTCGAGGTTGTC*

*TATCGGAATTTGGTCAATCGGGGCACAGACAAGGACAAGGACAGGATGAGTACATCTAGTGGGACACAAAGCAATGG*

*ATCAATCAAGGAGATTGTGGTTTCATCAGCATCATCAATACATTCAGAGAAATCTACACCCGCTACGACAATCACCAAT*

*GGAATGAGATCTCCTTCTCCCCCTAGTGAAAAGGATGTAGCCCAGTCTTTGGCTGAAAAGATGAAAGCTAAGGAG*

*GATGCGGCGGCATTGACAAAACTCGAGAGAGCCATAAAGCGGGACTTGGGTGCTCGAACAAGTTATTCAAAATTCGCT*

*GCAAGTGCTGGACTACAAGATGGATTATTCGGTTTATGCAAAGCATATGCTCTTTATGATGAAGGTGTTGGTTATGCAC*

*AAGGCATGAATTTCTTAGTTATGCCTTTGCTTTTCAACATGCCCGAAGAAGAAGCATTCTGTCTATTAGTACGACTTATG*

*AATCAGTATCACCTTCGAGATCTTTTTATTCAGGATATGCCAGGTCTACATAAACATCTTTATCAGTTTGAGAGATTATTA*

*GAAGATTTTGAACCAGCATTGTATTGTCATCTCCATCGACGTCAGGTCACACCTCACTTATATGCTACGCAATGGTTCC*

*TAACTCTTTTCGCCTATCGATTTCCATTACAGCTTGTGCTTCGAATTTACGATCTCATTTTAAGCGAGGGTCTCGAGGCT*

*ATTCTCAAATTTGGAATTGTACTCATGCAAAAGAATGCAGCTCATCTACTCACCCTCCATGATATGGCTGCATTGACTAC*

GTTCCTGAAAGATCGACTTTTCGATGTTTACATTGATGCTTCACCTTCAGCAGGATCAATTCTAGAATCTGGTTTCTTTG

*GAAATTCAGGAGCGACTATCGATAAGGAAGTTTATCGAGCAGATCATATGATTCAAGATGCTTGTGCCGTCAAAATTAC*

*ACCCAAAATGCTGGAAACTTACGCATTAGAATGGGAGGAAAAGACCAAGATAGAAAAGGATCGTGAAGCAGAATTAGA*

*ACACTTGAAATCAACAAATGTCGCCCTTACACACAAAGTTCGACGTCTGGAAGAAAGAGTCGAATCTCACGATACGGA*

*GCACGCAGCTTTGGCAACTGAACTTGTTCGGACTAAGGTCGAAAATCAAGAGATTCATGAAGAAACAGAAGTTCTTAAA*

*GAACAAGTTAAAGAACTGAAAAAAGTAATTGATAAGCTACCGGAAGAAATTGAAGCGAAATTACAGAGTGAGATGGATA*

*GATTGATGAAGAGAAATCAAGAAGTTCATGAAGAAAATCAAAAATTGGAGGATGAAATGAATGAAATGGAACAAAACTT*

*GGTGGAAACAAAAATGAAATATGCTGAGATGAATGCGGCCCATGAAGCTCTAACTCGTAAATGGACGGATTTGAGAAA*

*AGCTTTGGGTGATTAATATCGTTACTTTGAGATATCCTAAATTATTAAATACGACTTGTACAGTTCTTCTCAATTGATACC*

*GATGCCTTTGAAGTTTTTGGGGGGTAGGGGAGAGAGGCGTAAATGCCTATATTGGGGAACGAAGGAACAATGCTCTC*

*GTTTGGAAGCTTGCTGGATTTCTTGCTAGGTGGAGGGGATGATTGGGAATCAATCAGATTATACAGGTACTGCTGCAT*

*TGGTACGCAAATGGTATAGGAATTGGCGTGGGTTGTAAAAGTACCGGAGAAATACTTTGGGTGCTTGCTTGTCTTGTTT*

*CTCTCTCTTTTTTTTAGTCGTTTTAGCGAGTTGTGATGTTGGTAGGAAAGAAATTAAGAAATTATGGACGGGTAGGGGG*

*AGTGGAGAGAGGAAGGGAGGGGGTGAAAGAGGGTGGGGGGAGGGGAAGAAATAAAAATTAAGAATAAATGATCA*

BC1G_03372

SEQ ID NO: 57

*GAAGCTTTAAAACATACGATTATTTGATCCTGTTTGAACACGTTTTCTTGAAATTTCAAGCTTGAATGAAACACAACACCA*

*AGTCTATCGGCCAAAGGACCCCTTTGAGATTGCATTGAGCGTTGTCCCATCTCAAGATTTAACAACTGTTATTCACGAA*

*ATCATGCCTCCACCACCACCACCTCCTCCTCCGCCGCCTCCTCCGCCTGGAGGAGCTCCAGGAGGTATGCCATCCAG*

*ACCACCTGCGAAAGTTGCTGCAAATAGAGGCGCACTTTTGTCGGATATCACGAAGGGAAGAGCACTCAAGAAAGCTGT*

*AACTAACGATCGATCGGCACCGGTAGTAGGCAAAGTATCTAATGGTTCTGGACCTGCGCCAATAGGAGGTGCTCCTC*

*CAGTACCGGGAATGGCAAAACCTCCCGGTGGATTTGGCGCACCGCCAGTACCAGGAGGAAATAGAGCTCGAAGTGAT*

-continued

AGTAACCAAGGGAGCAATAATGCGGTTTCGGGGATGGAACAAGCTCCACAGTTAGGAGGAATATTCGCAGGCGGCAT

GCCCAAGTTGAAGAAACGAGGTGGAGGAGTAGATACTGGCGCAAACCGCGACTCATCGACTGCATCGGAACCAGAAT

TCTCTGCTCCCAGACCGCCAGGTATGGCTGCTCCCAGACCTCCAACAAATGCAGCTCCGCCTTTGCCATCAGTCCGG

CCTCCTCCTCAACCTAGCGCTAGTACTCCCGCATTTGCGCCCTCGGTTGCAAATCTGAGAAAGACCGGCGGGCCATC

TATTTCTCGTCCTGCATCCTCAACCTCTCTCAAGGGGCCACCACCCCCTATTGGCAAAAAACCTCCTCCACCCCCTGG

AACTCGAAAGCCATCATCAGCGCTATCAACCCCACCACCACCACCGCCTCCAGCATTCGCCCCTCCACCTCCTTCTTC

AGCACCTCCGCCACCTGTTGCACCTCCACCACCACCTTCCCCAGCTCCACGCCCTCCGAGTAACCCACCTCGATCAC

ATGCACCACCGCCACCACCACCACCACCACCACCAACATCTCCACCTTCGACTAACGGAGGTAACCCAAGTCTTGCTA

TACAAGCAACAATTCGTGCTGCTGGCCAAGCATCACCAATGGGTGCACCACCACCACCACCACCGCCTCCTCCTCCAT

CTAATGGGCCTCCCTCTCTCTCGTCGCACAGAACGCCATCTCCGCCCGCGGCACCCCCAGCGGCACCCCCAGCGGC

ACCAATATCAAGAAGTCAAAGTCAACAAGGAAGAACTCACACAATGGATTCCAGTTCTTATACCCTTTCATCAAACGGC

AGTTTACCGCAAGCCTCTAGTTCTAGCAGAAGAATCATGATCAATGATCCTCGATGGAAATTTACAGATGAATCGGTAT

TCCCAAAACCTCGAGATTTTATTGGTGGGCCCAAAAAATACCGGGCTGGTCGTGGAAGTAGTGTTCCGTTGGATCTGA

GTGCTTACCATTAAGAATTTCGCTTACCAAAAAGAATATAACTCTTCGGATCGTATTCATGTGTTACCATTATGATTTAAG

GCGTTATAGCGGGATATCATTTAGAATCCGGTAAGGCGGCATCAAGCTATCTGAATTGGGAGTTATACATCAGGACAC

TAAAGATCGTCAAAAAATTTCCCCTGAATCGCGAGATGGAGATTGACGAGAGACATCAGCTCACTACCCAGGGTACCG

AGGAGGAAATCGCAGCTATAAATATCACGGGTGATGGGCAAATTCCACAGTGGAACCTTAAAAGAATGAGTACGGAGA

ATATTAAACTTTTGAGATTTATCTTTCTCTTCCTGTGATTTTAACCA

BC1G_14667

SEQ ID NO: 58

GGTAAGATTAATTGTAAGGCAACTCTCTAATATTATTTCTTGAACGTCAATCGTCCCAAGTGTTCATCTTTAAGTTTATTT

CGTTCGTTTTACCATTTGTTTAATTTTTTCAATGCCAGTTAATCTTCAACCTTCTGTTGGTACTTCTGGTAGTCTCAGGAA

AGAAAATTCAAGAGGAGAGGGCACGAGAAGGATGCCGACCAATTCGCGACCTCCCCTATCGCATCGGATACGGGCAT

CATTTGAAGGAAGGAAATCTCATGATTCTACCAGTCCTAAACATGCGAGCTTCTCCGGTAGCAGTCCAACAGATCCGG

AACTCCTCCGACGGATAATCGATGAAGCTATCTCTGGAGAGGTCTTCCAGGCTGGACTTGCTTCACATATAGCCAAATT

GCTCAAGCCCGAGATCAAAACGGCTTTAGATACAATTGAGCCAGTTGTCAATGCAGTTCTACAACATGAGCTACTCTTG

AAGAGAACCAACAACAGCGTGGATCATGTTTTATTGAAGTTGGAGTCAATGGCAGATGACGAGGGAGCAATGACTCCA

GGCCAAGCACGACTTAGTTTTCACGGCGCCCTGACTTCACACCCGATAGCAGAAGAAGGGTCACTGCCAATATCAGA

GAATTCGGTCTCTGGAACTGGTACACCTGTTTCCGTTTCCAATCAGGAATCAAGACCCCTCTTCAACCGAGGCCTCAC

ATACACAGCCGGAAAATTAAATGAAATATCGGACTCTTTGGACTTGAATAACCATAAACTAGGGAAGGTGGTCGAAGGA

ATAGCGGAAATAAATAATCTATTGACATCGAACGAACGCTTGGATAGTTTGAAGGAAAGCTCAGACAAGAATGATACCA

AGACTTCGGTAATACAAACGCAAATAGATCAACTGCAGGAGAATGTTAGGGTAGTCATTACTCGAATTGGTCCGGATCT

AGGAATAAATGTAAAGGCTATCAATGATCATCTGACTGGAGAAACGACGATTCAAGAGACGAGGGCGGTGGCTTCCAA

TGGCAGTGGGGGTGATGTTGAGCTTCTTCAAGCCATATCTTCCAAATTAGAAGCCTTGAAGGATAGCTTGGAGACAGG

AACTTCGTCACATAATGATAACTTGGGACTATTGAAGGAACAAATCAATGCTCTACAGTCAACACTCGACGCGCAGAAA

GAGATATTAGGGGAGATTAAGGAAGCTGATAATAGCACTGAAGTTTTGGCTGGTATACACAAATCAAACGAGTCACATG

AAGCGCATGCCACAATTTTGGGCGAGCTCAAAGAGAGAAGTACAACACTTGCGGATTTATCAACTCAACCGGCTCCCA

CATCAGCAGACGCGGAAACACTCCAAACAATCTTGATAGAAGTACAGAAATCCAACGAGGCACATGAGAAACATACAG

CTGCGCTCGAGAGTTTGAAGGAATCGGATACAAATGCAGTCATATTAGCGGAAGTTCAAAAGTCGAACGACTTGCATC

TTTCGCATGCATCTGCTCTAGAAAGTCTCAAAAGTTCCACTCCACCACTAGAACAAACCACCGCAATCGATCTAGGAAG

TTTCGAAACTAAGATGGGCAGCTTAATAGAAACAAGCACAGCAATTCTTACGGAAGTTCAAAAATCAAACGAGTCACAT

GTTTCACACGCAGCTGCATTGGAAAATATCAAGGCCCTACCAACTCCACCTTCTGAAACTGAAACTGCAAGTGCAAGT

-continued

*GTTGATTTGGGAGGCTTGGAGAAGGATATGGGAACTATTATTGAAAAGTTGGACTTGCACGCTGCTGTTCTAGAAGAA*

*ATCAAGACAAAGGATACTCCCGGAGCCGGAGTGATTGATGCTACTGCCTTTGATGGCCATTTTGGTTCCATTAATACTC*

*TCTTGGAAAGACACACAGCGGCATTGGATGAGATTAAATCGATAGATGCAGGAGGTAGTACGGATTTTAGTCCAATAA*

*CTGCCTTGTTAGAAGCTCACAGCGCAACATTGGAGGATATCAAATCGAGAGATTTAAAACCTGCTGATTTTGGTCCAAT*

*CGTATCGATGCTTGAAGCACATACTGTGGCTTTGGAAGAAATCAAGTCGAAAGATCCGGGATGTAATCCAGATTTCAGT*

*CCAATAAGTGCCTTGTTGGAAGCTCATACTGCAACCTTAGATGAAATCAAGGCCAAGGAAACTACAAACAGTATTGATT*

*TAAGTCCAATAACTGCATTGCTAGACGCTCATACTGCCAGCTTGGATGAAATCAAATCGAAAGATATGACAGCTGCTGA*

*TTTCAGCCCAATAACTGCATTGTTGGAAGCTCATACTACAACCTTGGAGGATATCAAGGCCAAGGACAGTGCAAACAA*

*CGTTGATTTAAGTCCAATTACTTCGACTCTGGATTCTCACCGTGCAGTTTTAGATGAGATTGTATCAAAGGATGTCCAAT*

*CTAGTGGTGTACCTGCGACAATCAACATGGATGCCTTCGATACACATTTCGGTTCAATCACAGGTATACTAGCAGCACA*

*CACAGCCGCATTGGACGAGATCAAGTCCAAAGATAGTCCTTCCAATGCTTCGCTGCCTGCAGAAAATACCATTGAAAT*

*CCTCGACAAACATTTTGGTTCTATCATTAACATGTTGGAAGCACACACTGCAGCACTGGAAGAAATTAAGGCAAAGGAT*

*TGCACGGCGACTACAGGACAAACGGAGTTGAACACAGCAGCATTTGATGATCACTTTAGTTCTCTGGCACGCATGCTA*

*GATTCACACACAGAAGCTTTGGATGAAATCAAATCAAAGAACAATGATTCCACTCCGCCTACAATATCAAGAGATAATAT*

*TGGCCTCGAATCATTCGAACCACATGTTACGGCGATTAAGAGTGCACTCGATGCTCATATGGTTGTGCTGCAAGACAT*

*AAAGTCCGAGGCCCTTGCCAAAAATGATATGGATGCAATGGTGGTAGACAATTTGCTGGAACCACACATCATAGCTAT*

*CAAAAATACATTGAATGCACACACAGAAACTCTGGAAGAACTTAAATCCAAAATTCCTACTAACACCACAAATTCATTCG*

*AAATTGCCAACGATGCTTTACCTAGGATCTTGGATACCCTTAATAGCCACACCGATCTACTCACAGAAATCAAGAATTC*

*AGATGTTAGTGACGAGATTTTGACAGCATTGCATGAGCTGCAGGAAGGCAATTCTTCAGCTTTCAATACCCTCAAGGAA*

*TCAGATGTCAGTGATGAGATACTTACTGCGTTGCATACATGCAATGATTCACAAGAAAAGCTGGATAGATCACTACTTG*

*AACTCCAAACAGTAGTGAATAACTCTATTTCCTCCGAACAGAATAGGAACAAGTCCATTGATACTGCTGAAGTAGTCCA*

*AGCACCGATTGCTGCTGTAGATTTGAGTGGATTGGAGACTCAGATTAGTGCCATTATTGCAACTCTCGAAGGCCAAAAT*

*GTGGTTTTAGGTGAGATCAAGGATACTACTAATGCTGGAATGGAAGCACATGGCTTGCATATCACGACTCTAGGTGAG*

*ATCAAGGATGCCACTAGTGCCTCAAATGATTCTCACGCAGCCCATGTGGCAGCTCTTGGAGAAATCAGAGATGCAGCT*

*AATGCTTCAAACGAATCCCATGACGCCCATACTTCTACACTAGGAGTCATCAGAGATGCAGCAGCCTCCTTGAGTACT*

GCACATGCCGCCCAAATTGCTGCTTTGATTGAATTGAAGCAAGCAATAAACGCCTCTAATGAATCTCACAATACTCACA

*CCAGTACCTTAGCAACGATACGAGATGCAGCAGTCAGCTCGAATGACGCAATTCTCTCTCACACGACTACTCTTAGTG*

*AGCTCAAAGAAGCAATCAATGCATCGAATGACTCTCACACTTCTCACGCCGCCGCTTTGACAGATCTGAAATCCATTCA*

*TCCAACACAGTCACCGCCAGATGATACGTCTGAGTCGACATCACCACCATTCCTTGATACAAGTGCACTAGACACCCA*

*GCTCACAACTATCATTACAACGCTTGAATCTCAAAATTCTACTCTGGGAGAGATGAAAGGTGCTCATGAATCTCACACA*

*ACAACTTTGAATGAAATCAAGGACGCAACAGCAGCATCAAACGTGTCACATACTTCACACACGACAATTTTGAGCGAAA*

*TCAAAGAAACAATTGCTCCTATTCGTGGCATCAATGAGGTCATAAGCACACACACAGGTCTATTGGAAGGTCTGAAAGA*

*AGACACTGGATCACAACATAATGAGGTGAGAAGTGATATCGATGGTTTAAGGAACCTTGTAGACGAAAATTCCAATAAA*

*CACGAGGAAAGTCTGTCAAAATTTGGGGATTTAATCAGGGAGCATGGCGACTTGGTTAAAGACAGCCATGATGGGTTG*

*AAGGGAACGATCGCCGGACTTGCTTTGGGTGGAATTGCCGGAGCGGGGATCATGAAAGCTGTGGATGATGGGGAAG*

*ATAACGATGGCGAGGTAAGTGATGTAGTAGAGCGGGATGTGAAAGTGCCGGAAGCTCCAGTCGAAGAAGACAAGGTT*

*ATTGAGGAAGAATCACCAGCATTGGAGCCCGAAGCACCTGCGGTGGAAGATCCAGCTCCAGAGTCTACAGAACAAAC*

*TCCGGAACTTCCAGTCGAAGAACAAGTTCTGCCTGAACCAGAAGCACAGTTAGAGCCCGAAGTGTCTATGGAAGAAGA*

*GAAGACCGCCAGTGAGGAAACGCTAGTAGAGCCAGAGCTAGAACCGAAAGTTATCTTGCCAGATCCTGAGGAGACGG*

*TCGACGTCAACGAAGATTCGGACCCTGCACCAGTAGACCAGGAACCGGGGCCAGAAGCTATTGACAAGGAATTTCCA*

-continued

GCCGAGGAGCCGACACCAATCGAAACGGAGGCTCCAACGCAGGAGGCTGTCGTTGAAGAGCTGATTCCAACAGAGG

AAAAGCCGGAACCAGCTACCTTGGAAACCACGGAAGAAACACCAGCTATCGAATCCCAATATACTGAAAAAGATCTCC

CTGGCGAAGAAACAATCCCTCAAGGGGAAGCTGAGCCCATAGCAACCCCCGAAGATTCCTCTGAACCAAACCAAGGA

ATTGAAGTTCCAGCAAGTATTGAAAATCGGGAGCCCGAAGCTCTTGAGAAGGAACAAGAAATTGAAGTTACCACGCCA

AATTCGGTTGAACAATCGGATTTGGTCCAAGATACTACCGAAGAGGAAGCGCCTCAAATACAAGAAATAGAAGGAGAA

CCAATACCTGGAGAGGACGATGTCACAGAACTGTCTAAGGACGAATTGGATCCCGAAAGAGAGCTTGCCGTTGAGGA

GATACCTGGTGAGGAAGAGGCTGTTGCGATGGAAGGGTCTGAGGAGGAAGCAGTTGATGAGGGCGAGAGAGCTAAA

GTACAGGAAATTGAAGATCTAGGCGATGATGATTTGAAATCCACTGAAGAAATAGTGCCGGATGCTGTGGAGGAAGAG

AAATCAACAGAAGACATAGCTCCAGAAAATGTAGTCGAGTATGTGAACCCAAGCGAGGAAGCTCTACAGGCCGGAGA

AGATAAACCTGTCGATGAACCAATTTCACAGGAGTCAGATGTGAATTTGACTACCGACTTACAACATACACTTCCTGCA

GACGAAGAAGAAAAGCTGCCCGAAATCAAGGAATCTAATGAGCCAAGTTTGGAGGAAACAAACATCGAAAATGCTAGC

CCAGAGGTTTTGATAGACAAACCGACGGACTTGGAGGCGACTCCACCTTTGGAAATAAACGAACCTGTTCCGGAGACT

GAGCCAGCCAACGTATCTGGTTTTGCAGATCCGTCAGTGGAAACCGAAGAAATACCCATTGTTCCAGATCACGATGTC

GATAGTCATACTCAAGTACCCGAAGCAAGCGGTGAAGTTTCCGCGGATGACTTAGAAATTCCTACAGATTCTGAAGTC

ATTGAGCCGTTCAATGAAGAGCAAAAAGTTGATGAAGAAACCGAGAATGAACGACTGGCTGAACATCCGATCGATCCC

CAAGAAACAAATCTGAAAAATGAGGATCGAGAGCCTAACAATGAGGATATTCCTATCGAGAACGCGGAGAGTGTTGCT

GAACCATCGAAAGAGGATAAGTCTTCAGAATCAGTTGCGGAGATCGAGACACCGCACTTGGATTCAAACGATCAAAAT

GAAGGTTCTGCCGAGGTAGATACAAAGGATTTGGAAACAGAAGCTTTGTATCCCAGCAAGGAAGAGACACCAGACCA

GACAGAGGAAGCTGTAGAGCTCTCTAATGATCAAAGTAATCCCAGCCCTATTTTTGAAACCGATGTACCCGTTTCGGA

GATAGACGACCAAGATGAAAAGCCTGTTGAAGTTGAGGCGAGGGATTTGGAAATGGAAGATGGGGAACATCACAGCG

ATGAGGTACCTGAAAAATCTGCGGAGAAACCCTCACAAACCTTACAGGAAGAAAGCGATTCTGAACCGGTTGTCGAAA

CCGAGACATATGTTCCTGAATCAAACTCTCATGATCAAAATCCAATTGAAAGCGAAGAGAAACTAGCGGAACTTCCTGT

TAATCAACTTGTCACTGAGGAGATCTCTAGCGAGCCCAGAGAAGACTCTGAGACCTTACAAGGGAAAAACATTTCACA

ATCACCTGTCGAAACTGAGGAACATATTCCCGAGTTGAACACTTACGTCGAACCTTCAGTTGAGAACGAGCAACCCCC

TAAGGAGCCTGAGGACAGCGAATTTGTTGTCAAGGAACCTGAAAACTTCGAAGACTTGACCCGATCTGTCGAAAATGA

AGAAGAGACTTTCGAACCAGAAAACCAGGTATCTAGGAGTGAGAACACACCACTCGAAACCGAACAAACGGTTCCTCG

AGAAAAGACTCCAGTTTTAAATGCTGAATCCGAGATACCGGCGTTTGAGTCAGATGATCAAATGCAAATCCCTGCTGAG

AATGAAGAGAAGTCTATGGAACCCGCTCTTAGTGAGCCAGAAGCCGCAGGTTTGGAAATTACAGAGCCACAAGTGAAT

AATGAAGCTCAGATCACTGAAACATCGCCGCAAGATACTGTTGAGGAGCCGGTGGTTGAGAATCAAATTCCTGTTGTT

CCAGAATTGAGCAATGAGACTAGAGGGGTCACCGAAGATCATGAAACTCTTGAAACAGCAGAGCAACAAGCTGTCGA

GGTACCTGTCGAAAAATCAGTCATTGAGAGCCAACTTGAACTCTCCAACGAAGATAAAAGTATTGAGGACAATGCATCA

ACAGAAAATACCCCCGAGCCAGATGTCGTGGACAAACATATTTCTGATGGGTTTGGATCAAGCGAAGAAGGACAAATC

GTAACCGACCATGGAGACGAACCTCTATCAAATGAGAAAGAGATTCTTGATAATTATCAAGAAGAATCGGTTCCTGAAA

ACGGATCAACTTCTGAGAGTGTAATTCATGAATATTCCAGAGATATCAGAGATGCAGACCAACCAATGGAAATTGATGA

ACAGGTTGCGGATACAAGCGGTCAAGATTCAAATCCTCAAAGCCAACCAACATCAGAGGTAGCCATCTATGAAGATCC

TGAAGATATCAAAGCCCGTGAGGAAATTGCTGCTTTGAACGCGGAGATGGCTAAAATATTAGCTGAAGCTGAGGAGGA

GGAAAGGAGAAATGTTCCGGTAGAGACGGAAACAATTTCCGAGGATGAACCTATGGAGCCGGAGGTCGAATATCATG

TCGAAGAACCTATTGATGTCTCGGATACACAGCCACTGGTCGAAAGCCACGAAATCCCCGAAGACCGAACTGAGAATG

AGCATGCGCAGGAAGAAGTGACTGAACCGGAAGAAGAGCAGAAGTTTGCTGTTACTGATGAGGAGCGCTCAAACGAC

ACTAGCACAGAAGAACCTCTGGAAAGCCATGTTGTGTCCTCTACCGATTCTGAAGAGCATATCATGCCCATATTACCAG

AAACCAACGCCATCGAGTCTACCAATATTTTACCTGCAGATAAATTGCATCACGTCGAGGATACTATTCCGGTCAACTA

-continued

*CGAGGATCTTAACGAGAGCCAAAATCAGATTACAGAGGATGGAAATATAGATGAAAAGCCTTCCGTGTTCTCTTCCGAA*

*GATGAGAATAGATCTTGGAATACCGTCCATAGCCGAGCAACCTGAGATGGAAGTTGTGAGCAATGAAAGTGCACCT*

*ATGCAAGATAAAGCTTTATCTAGAGAAGAAGTAAAAATTCCGGACATGGAATTGCTACCCTCTGAATCTCACATGGAGC*

*CCGAGACGGAAAACCTTGAGGGCGCACACTTAGGTGACCATGTTGTACTTCCTTTGGACAGCGAGGAAGACAAATCTT*

*TGTCTATCCAAACTGAATTTGAATCAGATCCTAGGGAGATAGCACCAGAGGGACAAAATCTGGAGGGAGAAATCAATC*

*CTGAACAATCTTTCGTAGAATCCGAACAGGAAAATCCAAAAGATGAAATGACATTCGAAGATTACCCTGTCGAAGAAAG*

*TTCGATTCCGAAGTTGGATTCCATTAAGGAAAGCACAGAGGATCCAGAAAGTGGAAACGAGGAAATAGAGAATGGCAG*

*TCCTTCAGTAGAGCATCTCGAGGTTGTAGAAACAGAGCCAAGTCCTGAGGAGCACCTAAAAGAGCTCGAATCCATAGA*

*TGACGGAGATTTCTACCCCGTAGAGCCTGAAACTGACCGAGAAGATTTCGAAGACCACAAAGAATTAGAAGCTAATAC*

*TGTGGTTCCTGGAAGTCTTGAATTCGAAACGATCGACAATAGCGAGCCGGATGAAGTACATGATATTTCCGATGGAAG*

*ATTGCAAGAATTAGAGCATGCAGCGGAAGCTCAATCAACTACGTCTAATCACGGAGAAGCTGCAGATACCGAAGAAAA*

*TTATCATGACAGCGAGCCGAGTCAAGAAGAAATCGCTTCCGAGATTCCTCTCCCAGGCCCATCAGTTCAAGAAGGGCA*

*ATCTATCCTAGAGGAAGAGAAAAATCCTGCTATTAAACAACTTCCAGCCCAAAATGACATGGAACCCGAAAGCCATCAA*

*ATGTCTGATGATGTCTTTCCAGTCAATAATGAAGGTGTCAATAACAGCTTCCATGTTCCAGATGAAGATGAGCTAGAGT*

*TGACGGACGAGCCAAACTCTAGAGAAGTTCCAGTTTCGTTTGACACCAAGCACACAACAGAGAATATTGTTCCTTCCG*

*GAGTCACAGATAACTTAAAACTCAAGGATACCGAATCAATCTATTCCCAAGAAAATGAGCCAATGATCGCAACAGGGCA*

*CTACAGACAAGAGAGAGAAGAGTTTTCTGACCCGACAGCCACAGGTCAACATGTGGCTGCCGAGCAAGTAGAACCGG*

*AACAAGAGTTAGAAGCTAGACACTTTGTTCCCGAAACTACCCCAACTCACGAGACCCAGCTCAGTCAGCCAGAAACTT*

*CAGCGGAGCAAAGGTACACAGGTTATGGCTACGACTATGAAGAGCCTACTCTAAATACACAAACTTACTCCGACTCGG*

*AAGATGATATCGAGCCAATTCAGTCGGAACAAACGAGTTCTCGCTATGAATCAAGGGGCTCTTACCCCTACCAAGGAA*

*CCAGCTTTAGTAGATCTATACCACAACCAAGATATTCAAGCTATGAAGAGCCCCCTCACGATTCACGAACTTTCTTCAA*

*CGACCAAGATGACAACCAGTATTTGAGACCAATGCCTACATACTCTAGCTCAAGCTATTCTCAAGAATACCTCTCAGAG*

*TCCCATCCGACTCAAGAAATCCACTATAACGAGTCTGAGCCTCAACCGAATCAACCGAGAACGCCAACGGACCAAACA*

*ACCCATGAGGATACCATCCCACCCACTCCTCCAACAGCTTTAACTACGAAGATGTCTACAGAAACATTCCCTACATATG*

*ACGAGTCCCGATCGGTTTCCCAGGGTCTAAATCTTGGCTTACCGATAAGAGGAGCAGAACGAGTTGGAACAATTCGC*

*GAAAGTCCTGAGCCTACATATCCTTTATACAATGAGCCAATGCGATCTCCCGCACAATCACGACTACCAATCACGAGC*

*CAGAGATCATCGGATAGTATGCGTAGGAGCCATAGTCCTGAATTGAGAAAACAGAGCAGTTATTCTAGATATGCACAT*

*GATGAGCCTGGATTAGGAAAATCTTTGGGATCTTCACAAGGGTTCAATTTTGGTCTTTCACCGACGAAAATTCCAGGTT*

*CTATTGGAAGGTCCAGCAGGATACCTGAGGTCGGAAATGAGTATGGTTATTCAAAGACTACATATGAGGAGCCAGTGC*

*GTTCTTTAGGGACTTCGCAAGGATCTAGATTCAGTCTACAGAGTACGCATTCAGGTAGAGAGCCTTTTGAGGAAATTCC*

AGAACCAGGTAATGGAAAGAGGAGTAGTAATGTGAAAAATCTGTTGAGTCGATTCGAAAGTGGTGAATCCTCATCTTCA

*ACGCCTCCGCAACAAGAGCGTTTCAGTATCCCGACATATCAAGACCGTTTCGGCACTTCTCTTCCTCGACCTGCTGAT*

*AACAGATCGGTCGGGAAACAGCCTCAATACTTGCAAGAAAGCCAACTCGAAGCTGTGATGCCGCTTGATCATGGTAGA*

*TTTGATCTCATGAGTGAGGAAAGTAGTCCGGTGCAAACTCCTCTTGAAGAGAGGGAACTTCAGTTTGAGAGTGAAGGA*

*AGTAGCGCAGTGCAAACGCCTTTGGAAGGGGAATTTGATTTGGATGGGAGTACAGGTGGGAATGTAAATACAGGAGT*

*ACCGAAGAAGAGGAGAAGTAAGAGGGGGAAGAAGAAGGGTAATGGTGGGGGAGGTATTGGTCAGGCTTGAGGGGC*

*AGGAGAAGTAGGATCGAAAAGTTTGAGATGTGGTTAGGGTGGAAATGTGAGTCGGATGACTGATGGAGAATGAAGAA*

*TGATTGATGTTTGATGGTAATGAAAAAGTTGGATAAATATTGGGATTCGCATGAGTTTTTAATAATTTTTGGGGTTTGTTT*

*TTATAAGTAGCGGGTATGCAACTGGGCAGGAGTTTTGATATAATGCTCATAGAGATACTATTAATAGTCCAATTTATATT*

*TTCA*

-continued

BC1G_14204

SEQ ID NO: 59

*ATGGACATTCCTATGCGTGGCCAAAAGCCGAGCTTCAGCACACCCTTACCAGAAATCCACGTACAAGACTCACACCAC*

*CCCGATCGATATACCGATAGATACTCAGATCAACACAAATACCATTCTTCCAACTCTTCAAGGGCTGCGCCTGGACCAA*

*TGTCTATACCTCACGCGAGAGAGTCTCCTCCTCCTCCTCTACCACCACCTAAATACGTTCCCGATACAGATAACGGGG*

*GAGATCTTGGGTGGCATTTCGCAAATCAAAACCGGGAACCCGATTGGGCAAGAAATATCCCATCGGTTCCCGCCGGC*

*TCGAGTTTGTATGGGAGCTACAGTCGCAGTAGCATATCAGATGAGCGACCGGACATTGGACGTCGAGGAAGCTCCAA*

*CGCCACTATCACTGTTCATCCGTCGAAAGATGCGAGCAGCCATGCAATTGCACTGCCAAAAGACGAAGGCTATTCGAG*

*CCTTTCTGCTTCCAACGCAAGCATTGGGTCGACACAGTGA*

BC1G_10316

SEQ ID NO: 60

*GCTCATTGATTCTCCATCTTCTACGCTCCTACCTACCCCAAAAACTCTTTCAAACCCCCCCATAACGAGTTACAATGGA*

*CCCATATCAGAATCAAGGTTACGGCGGTAACCAGGGCTGGACTGGTGGTGCATGGAACCCTGCCCAACATGGGTACA*

*ATCCAAACAACAACTGGCCACCACAACCTCCACAGCCCCCACAGCAACTACTCCCTCCTCCTCCTCAGTACAATACGC*

*AAGTTGCTTCTTCTCTTTTCTGCTGCGAGAACTGCCAGCGTGTTGCTGCTCCAACTCAGCCAAGCGTTCATGCATATAC*

*CACTCGTTTGGCGTTTTTTACGGCACACATCTTGCATCCCACTGTGGCTTCCTACACCCAGGTACCTAACCGCAATCAA*

*CACCCGAATTGCTTTGCTAGTGATGTACCTCAATCTCAAACAATTGCCCCTACTGGGGGTCATGGGGGTCATGGGGGT*

*CATGGTCAAGGTACCAATGCCCAGCAGATTGCACAGCAAGTCATCCAGCAGCAAGGTGGCCAGCAACAGCATGGTTT*

*CATGCAACAAGCTCCAACCGGACCTGCTGCAGGTGCTGGTACTCATTACACTGCTGTTACTGGTAGCAGTCATCAATC*

*TGGCTTTAATCAGCAAGGAAACTACCAAGCTGGTGGTGGTTATGCTCAAAACAATGCTGCACAACAACATCCTCGCCC*

*AAATGGCCCTCCTAGCAACACCTCGATGGCTATAATCGGTCCTATTATGCATGCTGGCTCATCTTACAGCATCGATCCG*

*AACACCGCCATCCCTCTTCCACGATTTCCTCGTCCTACTTTCCAGCTAAATGTCAAGTTTCGTCTTGAACGCTTCCGTC*

*CAGATCCTCCACAGCAGCCTTTTCAGTATGGAATGCCAAATTATCAAGGCTTCAATGCCTACCAATACCCATCGTACAT*

*GAATCCCTATCCTAACACTGCCGTCTCCACCTCCACTGGTGGCCCTAAATCCAGGGACAACATGGAGCTTATATGGTA*

*CTACTGGCCAGTTCAGCTCGAGGTTCCTCTCTGGGCTAGAGGTCAGAATACTTTGACTTCCGCACCAGATATTGGTGC*

*TCAACTCATTCGAGAGGGCATGCAGATCATCAATGGAGAGCGTTGGGGCTTCATCCAGCACCAAGAGAATCCAGAGG*

*GCTTGTGGCACAAGCGACGATCTTACAAGATCCTCGAGTGTCCTGTTCATGGGATGTACTGGAAGGTCACTGTCTTCG*

*TTCGTCGTGGTTATTAGGGTATTTTAGAAGGCATTGGGTCAATTTTAAGCCTTGA*

BC1G_05030

SEQ ID NO: 61

*GAAAGAGTCAGCTTGTGTTGGCGCTTGTTTGGGCTTTGCGCAACATTGCCAGTGTTATACTTCTCATAGCAAATAGCGC*

*AGGTATCAGTTCTGTGAAACCCATCATTCCATAACACTACGGACTGCTTTCTTACTTCTCAAGATGGATATAGAGGCTA*

*CTAACAAGCCAGCTTCTCTACCCGCCGCTACGATGCCACCAAGTTTACAATATATACCTGCAGAAATTCGGAGAAAGAT*

*ATTTATATGTCTGTTGGTTAGTACTGAGCTAGGAGAGGCGTCTTCCATTGACCAACTTGAGGGATATGGAGCCGATGC*

*GAAATATGGCTTGAGCCCACAGATACTACTCGTCTGCCGCCTTTTCCATGAAGAAGGTATGGAGATTCTTTATGGCTTG*

*AACCAATTCATTATCGAATCACTACCGAGTATACGCATTAAAAGAATGGATGTACTTCATCCGTTCACCATATGCAGTCC*

*TTTGACTCGCTGGGACAACCAACCCACCACGGATCTCCCAACCCACTCCATTCAAAAGACTCTATTACACAGGAATCAA*

*GCTATTAAATTCGTCAGAAAATGGAGAATAATTTTAAGCGCCAGGCTCTATGAGCCCAGAAGTCGAGATGGACTTGTTG*

AATTGTGCCGTTTACTGTGCGAGCTGCAGACACTTTCAGGAGGGTCATTACTGAGGGAGTTAGAAGTATGCATCATTC

*CCAAGGGTGTCGAAGTCAAATATGGCTACATGAACATGAACGAAATGCGCGAAAGTCTTGTGCCACTGGAGCTGCTAC*

*GAAATATACCTATAGTGTCGATTCGAACAGCCAGCATTGATGAGATACCAGACTTTGCATATAGGCATAAGTGGCTTGA*

*TACACCACTCGTAACACCGTCAATGCTACCTACCGCATCCTATCGCCGCCTCCTCATCCACCTCATCCGTGGAAATTCA*

*GAAGTCGAATTGAGTACCAAGATGTTCACTTCTCTTTTGGAGTACACGCAAGCCTTTGAAAGAGATGCCCAATTCAAGA*

*ACGCGATGTCCTTGAGCTCCCAAGAGGTAGCCGCTTTGATGCCGAAGCTGCCTGCACTAAGCGAGAATCCGTTCCTC*

-continued

*AACAAAGAGTTTCACTCAAAAGAATTGGCTCACACTATCGAGACTGGTCTACAAAGAGCACGATATATGACCGAGATCG*

*AAAGTGGAGATATTACCAAGACCACCCAGTTCAAGGAAGAGCGATCTGTTATCCTGAAATACTTGGAACGTCAGTTCTG*

*CAGGATAAGCCACGCATCCCACGAGCTCATCGACTTTCTCAAATTACAAAAGAGAAAGTGGGGCGTTTTTGATCCTGC*

*TTGTACAAAAAAATACAACGGTTTTGATATGGCGATTTATACTGAGGCCATGGTTCTACTTGAGGACTACGCCGCGTCA*

*TTTATCCGAGAATTAGACGCATCAACGAAAAGAGCAGTGCGCGCGCAATTTGGTCTTTTTGAGCATCGCTACGAGTTAA*

*TGGCAAGGGAAGTCAAACTTCAAAAATGTAGGATAGCTTACAACAGAAGAGACCCCATCACGTTTAGAGCAAACTTCC*

*AAGAAGCGGTGAGCGATATGGAGTTGCAGTATCATACCATACTCACGACTAGATCTAAGCTATACGATTGGGACGCTG*

*GTAGCAGTATTCCCGATATCAATATCGCACCGTTGAGCTCATTCGAGGACTGGCAAATTAGATGGGAGATAGAGGAAC*

*CAGCAATCACCGCTATAACAGAGGTAGAAGCGCAAAGGATTCAACAAGATCTTCGCCGCCAGATTGCCCAGAAATGTT*

*TTCTTGCACAGGAGGCAGAAAACAAAGCTCCCGGGGACAACCAGGATTTGGATGCAGCGAATTGTGATGAGGCTCAT*

*GACCAGAGCGGGAGCACTACTGAAAAGGAACTCGAACTTGATATCGCCAATTGGGAGTCTCTACCATATCATGAAGAT*

*GACGAAGTCTCTAAGCTTATCTTACATCTGGATGAAGAACAGCCTCCACTACCATCTACTGTCGAAGCCCTCATGAATT*

*CTGACAATGATTCAGAAAATGATTTCTACGAAGAGCTTTTCAGAGATCGCCCGGAAGACGATAGCTTTTGTTTGGAATC*

*CGAAGACGACATTGAAGTCGGCGATGACTGTATCGATAGGGACAGGTCTACCCTTCACGACCTACCTTACCCCGGGG*

*ACTCTGGAGGTTCTCTATCACATGTGTTCCCGTGGATGACACTCTCTGAGCTATAATTGCCCAAGTCTTATCGAGGTTG*

*TTATATTTGACCAGAGTTATCTCCGATAATGCTTCTGTAGTCGTATCATCTAAGCCCTTGGTGGATTTATGGGATTATAT*

*CCGTTACCACTATGGTTGTAGTAGACCTTAACGGTCCTAGTTGTCCTAATTGATGAACTATGACTCTGTACACTGGATT*

*CTAGAGGATTTGATGAAGCTGATGGGTGCACCAGTGGGTGCATAGACTGGCGGGACACTTCTCAAATTTCAAACGTTT*

*TAACA*

BC1G_00624

SEQ ID NO: 62

*GGTATCGAGGGTCCAAAGTGTGGTCCGTCCGGGTGATGATTATTTTTTTGGCTCTGCCTCATATTAACACTTCCTGCTT*

*CTGTTCGAGCCCACCATTTGTCTTTCTCGAATTCCTTGCAAAGCATCTCTCTCATCCATCGAGCGATGTTCTGATAACCT*

*CTTGTGCCTCATTCATCAAGAGCGATATAAAAACGAGGGAGCAAGAAAAAGAGTTTGATGTTTGATACTTGAATTGAAT*

*ACCTACCAATCTACCTCCCTCCTCCCAAGCTTACATCTCGACTACGATATCATACCCGAAGTACATATATACCAACGGA*

*CCCATCCAATTTCTCCCTCAAATCTTGAAATTTTATCCTTCGAGCCGGTATCACACATATCCTTCCTAATCAAAAGATCG*

*ACAATATCAAAAATGTTTACGACGAGTATCTTAACGCTTTTGGCGATAACGACGAGTGTTTTGGTCCAGGCACATACGG*

*TGATTACATACCCGGGATGGAGAGGTGATAATTTGATTACGAATGAGACTTTTCCTTATGGAATGCAGTGGATGTATCC*

*TTGCGGCGGCATGCCTACTACCACCAACCGCACTCTCTGGCCCATCCACGGCGGCGCCATCTCCGTTCAACCCGGCT*

*GGTTTCAAGGTCACGCCACCGCCTTCTTCTACTTTAATCTCGGATTCGGCACCGATGGCCCCGACAATGGTCCCCAGA*

*ACATGTCTTTCCCCATGACCTCCGTCATGCAAATCGTCGGCCCTAGCAAAAATCCTTACCCGGGAACCTTCTGTTTGCC*

*TCAGGTGCCATTGCCCGCAAATACGACGGTTAATGTAGGAGATAATGCGACGATTCAGGTCGTGGAGACGGCGATTC*

*ATGGGGCTGCTTTGTATTCTTGCGTAGACATAACCTTCGCACTCCCCGAAGACGTCGCCGAAGTAAACACCTCGAACT*

*GCTTCAACTCCTCCGACATCTCCTTTGCAAACGTCTACACCATCAACGATGCCTCAGCCCCCGGAACTTCCTCCTCCG*

*CCTCCTCCTCCGCATCTCCTTCGCGCTCGCTCTGGGCTGCTAGTCTCGCGAGCGTGCTGGGCATCGCTATGTGGAGT*

*TTCTTGTAGGAGATGCGAGATGGAAAATGATCGGAGAGAAATTTGTAATTTCTGGGAGATTACAAACGAAAGATGGGG*

*AGGGGAGGGGAAGAGAAAAGATGAAAGATAATCAGAAGGAAATTCAAGGAAGCAGAAACAGGCAGCATTGTAGATAT*

*GATAAAATATGATATGATACCACGGGCAGATGATAGACGGACACATCAAGTGAGTGTCCCTGCCTCTATACCCAACAA*

*ATCGAGATCGAAATCTCAAACCATGGGAACTGGGAACCGGGAACCGGGAATTGAAGCAGAGCATTCAAGTACCCAAC*

-continued

GAGGAGCTACTTTGCATGTATGTATGAGCACTCAGGCGTTTTATGGCGAGGATTGTGATTGGAAGGAATGATTTTTTTA

*TTAATTTCATTTTAATTCTCGAGTTTCGAGTTTCGAGTTTCGATATTCAATTTCTATCTCAATACAATCCAATTCAATACAA*

*TCATATCCTTTACTGCGCA*

BC1G_15490

SEQ ID NO: 63

*GATTTACACGGGATGTGTTGCCCTTCTCCACGACGTCAACAGTTTTCTCGACAAGTAGACAGAAAATCATGACTGAGAT*

*CATCCCAATTCCTGAGCCCAAGGGCTGGCCCATTATCAATCATTTGGTAGGGGTCATTGATAACGAGAATCCGACTGA*

*GTCTTTCAAACATCTAGCAGAGCAGTTAGGGAGGATTTACAGGCTTCGTCTGATTAATATACCCATCACATTTGTTTCTA*

*GCTACAAATATATAAATGAGCTATGTAATGAGAAGAAGTTTCGGAAAGTCCCTGGAGGGATATTTAAGGAATTGCGAGA*

*TGCAGCCAACGATGGATTGATCACGGCATATCTTGATGAAGAGAATTGGGGTATCGCCCATCGAGTGCTCATGCCTGC*

*ATTTGGACCCTCTGCTGTTCACGGCATGTTCGATGATATGCATGATATTGCCGCCCAGCTCACCATGAAATGGGCCAG*

*GTTAGGCAAGTATGAATCATTTGTCCCAGCTGAGGACTTCACACGTCTCGCGATGGATACTCTGGCATTATGTTCCATG*

*GATTATAGATTCAACAGCTTTTACGGGCGCGAGACACATCCTTTCCTTGAGGCGATGGCTAGAACACTTCTAAGGTCG*

*CGTTATCGTGCTCGACGCTTAAATATTCCCATTGTTAAGTTTTTCTATCAACAAGAGACGAAGCAGTGGTATGAAGACAT*

*CGCACTCCTGCGGGAAGTTTCGGATAGCATCATACGTCATCGAATTAAACATCCCAGTCCTCGAAAGGATTTAGTCGC*

*TGCTATGTTAACGCACAAGGACCCAATGACAGGAAAGGTCATGACAGAAAAGAGCACGACTGACAACGCCTTGAGTTT*

*TCTTGTCGCTGGACACGAGACAACTGCGGGACTGCTCTCTTTTACACTGTACTATCTGCTCAAAGATCCTCGGGTCTA*

*CAATAAGGCTCGGGAGGATATCGATAATGTAGTTGGAGAAGGCCGCATTCGAGTAGAGCATCTTTCGAAATTACCCTA*

*CATCGAAGCAATACTCCGCGAGGTCCTCCGGCTGGAACCACCACTGCCGGTATTTTCGGTCCGTCCTTACGAAGATA*

*CCTTGGTCGATGGTCGCTTTCTCGTAAAGAAGGATGAAGGTTGCGTTCTCCTCCTCAAGCATGCTCATCGCGATAAGG*

*AAGTGTACGGTGAGGATGCGGATGAGTTCCGACCCGAACGTATGCTCGACGAACACTTCAACAAACTCCCACCCGGG*

*GCCTTCAAACCCTTTGGAAATGGACAAAGAGCATGTATTGGCCGAAACTTCGCTCTCCAAGAAGCAAACCTGATGCTC*

*GTCATGCTTCTCCAGAACTTTGACCTCGCTTTGGATGATCCATCATACGAACTGCAAATCAAACAGACCTTGACCATGA*

*AGCCCAAGAACTTTAAGATTCGGGCTAATTTACGAGATGGATTGACTCCGATTACACTGCAGCAGCGATTACTCTATGG*

*GACTTCGACTTTAACAGCAACTCAAGAAGCTCGCAAGGAATTGCGAAATGTTGCTGCAACGGCTCAATTCAAGCCCTT*

*GACAGTTCTCTATGGATCGAATGCCGGCACTTGTGCACAACTGGCACAACTTCTAGGATCACATGCTCGTTCCCACGG*

*TTTCAACGCCGTGACTATCGAAACTCTCGACGCCGCAGTGGAAAAAGTACCCAATGACCATCCTGTCATTTTCATCACC*

*ACATCCTACGAGGGTCAACCCACAGACAACGCCAAGCGATTTTTCTCTTGGCTAGAGACGTCCTCGGGAAAATTTCTT*

*GACGGTATCAGTTATGCCGTTTATGGTCTTGGACATCATGATTGGGTTTCCACGTTTCACAAAATTCCTAAGGCCCTGG*

*ACGCTCGATTGGAGCAAGCTGGTGGAGAGCGTCTGCTTCCACTCCAACTTGATGATGTTGGTGACTCTGATATTTTTC*

*CGCCTTTGATACATGGGAGGAAGATGTGTTCTGGCCAACATTGGAGAAGCAGTATGGTGTTATCAACGCGAATCATGA*

*GAGTCATGATGTTGATGAACTTGATACTAAGCTAGTGAGCCTTCGAAAAACGACCTTGAGCTACTTTGTCTCCGAAGCC*

*CAAGTTGTCAGCTCCAAAATCTTGACTGCCCCTGGTGAGCCAGTCAAGAAACACCTCGAGATTAAGTTGCCAGCCAAC*

*ATGCCATATCAAGTCGGGGATTATCTTCTTACATTACCGAAAAATCCCCCTGAGACAGTCGAACGAGTGTTGAAGCATT*

*TTCAAATCTCTCGCGATACTCAGAACAATACATTTCCTAGGATTGAATCCTATACTCTCACCACCGTGGAATCAATCGAG*

*TCGTATGTAGAGCTGAGCCATCCCGCCTCGAAAAAGGCCATGGCAGTACTAGTTGACGCTACAAAGAACGAGCAAGT*

*CAAACAAAAGCTACAAGAGATGGCTATGGAACTGTACTCATCTGAGATTGAGAGCAAATACATTTCTGTTCTGGATTTG*

*CTCGAGGCGTTCCCTGGCATTGAATTATCATTAAATTCATTCTTGGCACTCCTTCCACCACTCAAACTTCGTCAATATTC*

*CATTTCGTCCTCTCCATTGTGGAAACCAAATCACGCCACCTTAACTTTTTCCCTCTTGGATGCGCCGTCACTGGCACAC*

*CAAGGACGACATCATGGTGTAGCAACTTCGTATCTCAACTCCTTGCAGAATGGAGATTCCGTCCGCGTTGCCGTCCGA*

*CCGTGTCACGATGCTTTCCGACCCCCACTTATCACGGAAGATACTCCTATTATCATGATCGGCGCCGGTTCCGGCCTT*

-continued

GCACCCTTCCGCGGCTTTATTCAACAACGATCACTTCTCACTCTCAATGGCGCCAAACTCCCAAAAGCATATCTATTTC

AAGGCTGTCGGGAACCTGGAAACGATGATATCTATGCTGATGATTTATCAACGTGGGAGGATGAAGGGGTTGTCAAAA

TTCATCGTGCGTATAGTCGCACACCTGAGAAAGCGGGTGGATATAAGTATGTACAGGATGTGGTTCTGGGAGAGAGTA

TGAAGATTGTTGAGTTGTGGAAGGAGGGGGCGAAGTTGTATATTTGTGGGTCACATAAAATGGGGGAGACTGTCGCA

GAAGCGGTGCAGAAGATTCTTTCTGAGGCTGATCTTGTGGAGGGGGAGAATGTGAAGTGGTGGTGGGAGAAGATGA

GGAATGACAGGTATGCAGTTGATGTATTTGATTAGATTATCAGTCGGTATATCCCAAGATAATACTGCATGTAGGCTGG

GAAATTTTGATGAACA

BC1G_14979

SEQ ID NO: 64

GGGTAAGCAGCCCACATAATGAGCATCGTAAATAGACAAATAAATAATGCCGCATTCAAATGGCTCGCATTGCCGTCA

ACAGTAATGGAGACAACCCTCCAGATGCCAACTCTCTTCCTAACCCCCCACGCTTCAACGTCGAACTACCACCTATATC

GTGCTTCATTGAAGACAAAAATGGTAGCCCCACGAGAAAGTTTTTCACGACCCCAGATGAACTCACAAATCACTTGGA

GCGCACCACGCATCACAAGGAGAGGAAATTGTATGTTTTGGAAGGGTTGCCGATTGAATACGTACAGGTGTTAGGGTT

ACACTTCAACATAGATGTGGATATTTTTGATTCTCATGCGATGAGAAAGAGTGGGCAATTGAATAAGCTGGAATTTCCA

ACCAAAATAGGGAATGAGAAAAAAGTTCGAACTTTTGCTCTGGACCATCCTGAAATTACGACAAACATTACCCCGCCGC

CTGAAGCCAGTGGAGGAGTTGCTGGTGATTTCATGATACCGTGTAAAACGATAGACATATCAGATGAAAGCTGGAATG

GAATCAGTGTAAAATTATGTCACGTGACTTTGGTGTGCTTTCCCGGGGAAAATGGGAGTGAAACTTTACTATTGCTTCT

CGAAAACCAGTCGTGGGCGAGAAGAGGCGCCCAATTTCAAACTGCGGGTTACCACAGTATTCTTGCAAATGCCCTCAA

AAGTCTTCCAGAGGGAAAGCAGAAATGGAAACCATCCCGAAAACATGACCCGGCTTTGACTCTAGCAGACGAGATATT

CAATTCTATAGAATTGCCGGGTGGCATCCTGGCTTGGGATGACCTCACAGAGATACTTGCTGATATCGTACTCAGACA

ATGGAAATTTGCCTTGGGCGAGGTAATCGAACATGCATGTGCATCTAGATCGATTCCTTATCACGAAATTCATCAGGTA

TGTGATCTGATAGAATCTAATATCTGGACTTTGGATCGTACTGAGGCTCTCTGGGGCCCTCATTATGTTGTAAGAGTGG

AAGGGTTTAAAAGACTTTTAAAGAAAGCAAAGCGTTATGCACATTTATTTGTGTGGGGACAAATTGTGGAGGAGGGTCT

TGAGACAAAGGCCAAAAATGAGAGTGCGACTGACAATGAGGATGATGACGATACCAGCTCCAGTGCTTCTTCTAAGTC

GGGAGTGCATATTCGTGGAGGAGAGACCTTAGATTTGGAAACCCGCCAAAGCATCAATAGAGTGACCTACCTTGGCG

GTGTATTACTCCCGTTCTCCATAATCGCGGCAATATTTTCAATGGGTGGGAATTTTCAGCCTGGTGGAGATCAGTTTTT

CATATTTTGGGTCATCGCTATTCCAGTATGTATGCTTACAACGGTTTTAATATATGCGGATAGTATTCGGCGAATGACCT

TGGAGCAATTTGCTCAACAGTACGGGTCTGATGCAGTGACGGCAGAAGCTGATGATATGGTTACTTCATCAATTTCTG

GCAGTGAGATCATTTCATACAAAGTGGGTATTAAAGAACGTCTTAGGTCGCGTATCCCAGGTGTCTGGAATTCACGCA

GGGCTGGTTCTTCCTCCAGTGTTGGCTATACAGATAGCGATGACAATTCATCCTCTACAGACAGTACTCAGTTACCTCC

AGGTCTATCCATAGATGGCGATTTGTTAGTTCGCAGGAAAAGGAAAAAGGTGTCAAGATCATGGATTTGGCGATTTTG

GAGACGGAAACCTCTGGGTCGAAAATCAGATCCGGAGAATGTCTTGCCATCTCCTAGACATTCGGATCACAATGTATC

TTCACCTTCTGCACCTCCTCCGACTTCTCCACCATCCGCGTTTCACCCTATTCGATCTTCACCACAAATTACACCGGTG

AAGCCCATACTTGTTGGAAATGACCGTCCAGAGTCTCTTACTTCTGATAACTCTCCGACGGCCGGGCCAGCCCCGCCA

GAAACACCCCCAGCTAGTCCTCCGTTACCCGACCCTGACCTATCCATTCCTGACCAAATTATCCCTGAGCCAATAGTTC

TTGACCCAGGCTGGAATTTTGGGGGAACCCCTTCAAAGAAATCTAAAAAAGGCAAAAAGACAAGACAACACAGGATTG

GATACCTAAATGATGAATTCGATATCCCAACCCGTCCGAATCCAGCCACTTCTCCACCACATCCGTCTACACCAGACCC

CGCGGGGATACCACTACCTCCATTGGATTCGGATTCTGATGACTGGCGAGAGCGAGACAGTTCTGAGGGAATACATC

CTGAAAGATCTCCATCTCCAGGTCGTGCAGACTCGGATTATGCCACAGATCGTGAACGCCGTTCTTTGGAAAGACGAA

TGAGAGAAAATGACGACCGAGCACTGACCAGAAGAGGAAGTAGAGAATATCTAGGCATTGGAGATGAATATGAGCGC

ATTGTTGAGCGAGAAATCATTTATCGACGCCGGCGCCGATCCGAGCATTCTGTGAAGTCTGAGAGAAAACATGTAATA

GAAAAAACGACTGAAAAGCTTGTTGAAGAGCAGGAAAGAAAACATGCGACAGATGATATCGTGAAAGATGATGATGAT

-continued

GTTCCGGAAGACCGAGGAAGACAACGAAAACGATCTACAGTACGATGGGCACACCGTGGAACTTATTATGATTATCCA

AGGCGGCCAACACCCAACACTGATCCTACTGAGATACCATTGCCACCATCCCCAGAAGAACTATCAGAGGAAGAACG

AATTAGAATGAAACTAGAGAGAGAGAAACTAGAATACCTTGAGAAGTTGAAGCAAAAAGAACGACATAGGAGAATGGC

GGAGATGGAAGAGGAACACGCAAAAAAGCGAGCGGAAGAGGAATATGCAAGAAGAATAGCCGAAGAAGAATACAAGA

AAAAGGCGGCAGAAAGTAGAGCTGCCAAGGGAAAAGATCGAGCCTACTCCCCTGTGGAATCCGATAACAAGGGATTA

AAACCAGCGATAAAGTTCAAGGACGCTGTGGGAAGGAAATTCACGTTCCCATTCCATTTAGTGTCTACATGGGCTGGA

ATGGAAGAATTAGTGAAACAAGCCTTCCTTCATGTCGATGTCATTGGGCCTCACGTCAATGAGGGTCACTACGATCTC

CTTGGCCCCACAGGCGAAATCATCCTCCCTCAAGTATGGGAATCAGTTATTGAGCCTGGTTGGTTAATAACTATGCACA

TGTGGCCAATGCCGGAGCCGCGAAGGCAAGCACCCGCTCCTATGCCTCCTAAACCAGGGCATCCCGGTAACTTTCCA

CCTCCTCCTCCTCCACCTGGATTCACAGCACCCCAGCCCGGCGGCCTAATTAGTGGGCCTACTCCGAGAATGAAGAA

ATCTACGCAGACTGGAGCTTGGGACTGGGTGGAAGGAGCACGTCACTCGAAATCTCGCAAGAAACAAAAGTCGGCAC

CGATACGACTTGGGCCTCCTCTACCGCCTTCATTTCCTAGGCCCCCTCCGCCGCCACCGGCATCTGGAAGACGAGAA

TCTGATACAGTCGTCATAATAGAGGATCTGCCGCCAAAAGTTCACAGAAGACAAACGGGTATGAGCGACAGACATAGA

CACGGAGCAAGCGGCGGTGGCATAATTGGAGGAGCAGCAAAGCCTAATGAGGAGTTGGGGTGGGTAAGAGCCCTGG

GAACCATTGTTGGTGTGAAGCCGGGGATACAGGTGAAAAAACGCAGTGGTGGAAGTAGTTCATCGTCGAGTGTTTGAT

GGGTCGTTGATGAGATGACTGACTGCTCGTAAATTTGAGAAGCTAAGGTATCAATGGTTGAATGTGTGCCTGCA

BC1G_12936

SEQ ID NO: 65

GAAGTATTAATCTCCAACTTTCAGACCATGTGAGGCTTCACGGAACAACACCTTCGGGTACAAGATTAATACAATGGCA

GCCACAGCTTTATCAGCGTTATTCTCTTTGGAGGGGCAAACCGCACTCGTTACTGGTGGTACTCGAGGCATTGGACAA

GCTGTTTGCTTAGCACTTGCTGAAGCAGGAGCAGATTTGATCTTGATACAGCGTAGTCGTGAGAATCTCGAGACTCAG

AAAGCCGTCGAGGCTCTGGGAAGGAAAGCTCCTATATACACCGCGGACCTGGCATCGCAGGAAGAGGTCGCCGGCA

TCACATCTACTATCCTGAAAGATGGACACTCGATACACATCTTGGTAAATTGTGCTGGGATTCAAAGGCGCCATCCGAG

CCACGAGTTTCCGGATAAAGACTGGAATGAGGTGATCCAAGTCAACCTCAATACTGTCTTTACCCTCTGTCGCGATGTT

GGCGCACACATGTTGAAGCTCGAACCATCTGCTATTACTGGCCGAAGAGGTAGCATCATCAATTTTGCTAGTCTTCTTA

CCTTTCAAGGTGGTCTTACTGTTCCAGCATATTCCGCATCGAAAGGCGCGGTGGGACAGCTTACCAAAGCTTTATCGA

ACGAATGGGCATCGAAAGGAATTAATGTCAATGCGATTGCTCCGGGGTATATTGAGACGGAGATGAATACCGCCTTGT

TGGCCAACCCAGAACGATTGAGGAGTATTAGTGAAAGAATACCGGCGGGTCGATGGGGTTCCCCAGATGATTTCAAG

GCGAGTGTTGTTTTCTTGGCAAGCAAGGGAAGTGCATATATCTCTGGAGATATTCTCACGGTAGATGGTGGCTGGATG

GGTAGATAAACACTTGTCAGGTTAAAATAATACATTTCTAATTCTAATTCGACGCTCTTTGACTTTCTGCCGATTTCCTCA

ATTCTCACGGTCATCCAAATATTCAGACTCTCCCA

BC1G_04424

SEQ ID NO: 66

GTAACAATCAACAAATTTCATCAACCACCAACCCACCACATCCATTCTACAGGTTTGGGGGATTTCTATATCACGTACC

GAGACCCCTGGACGCGTCTTGAGCCATATCTGCTTTTCTGCTTGGTCAAGGCCCTTTGACAACAAGTACATATAACAAT

GGTTCTCTTCAAGAGGAAACCAGTGCAATATGCACCCAAGCCACATGTCGAAAATGAAGACACAGAGGTCTGGGTAAT

TCCTGCTACTGGAGAGTATTTCTTAGAGTATGAACAATACTTAAGCCGAATGGATTTCTATAGACAGCATAAATTCATTT

GCCAGATTTCAGGTCATTCTCAGTTAACATTCTTCGACGCACTCAAGAGTGAGTTGGCAGGCGCACAAGAAGTCGAAG

AGGCATTCCCGAATCCATTGAAGCAACCAGTTCTAAGACGTGTACAATTCTCAACTATTTCCCGAATCGATACCTTGGT

GGACATTATTTTCGAAGAGTTCAGATCCGATTATTTCCCCGGCGAGGTTGTTACAGTTCATGTGATTACGGGCGATCGA

CTTACTGGTACCGTAAGAGAAAAAACGCACTTCGGAAGCAAAGTTCTGCCAGATGGCTCACTAAGCGCACCTTTCTCG

AGATATTTCGTTAGTCTGGATGGCCGACCAAATGAAGAGGCAGTGGTGGATGACCAGCATATTACTCGTGATCGCAAG

-continued

ATATTCACAAAGCAAGTTCTGCGATCTTTTATTAAGAAAACCGTTACAAGAGAGGCATGGACCGGCGCGCCTTGGCTG

GTGAAGCACGACGTGGCCGCCATTTACAATATCGATACCAGGATTCCTCCACATCTTCGATATGAGAGTAAAGCTGCA

GAAAGAAAACAAAATCAATCTCAGAAAAAATCGGGAGGGACTGATTTTGATAATATGATTGGTAGCTTTCATGGAGGAA

ATGGACCACAAGCTAGACTCCCGGAGTTGAAGCCAGCACCCAAAAGCCATAAAAGCAAGCAGCAACAATCCCAACTA

GCAAAGGGTAAGCAGCAGCCATTTTTAGAGCAAGCTCCTTTAAATTTCATCCCTGCACATTTCCCTCCCCATCATTTCTA

CCCCCAACCCCACCCCAACTACAATCCACCACAAATTCCATACAATTCTCACCCTCCTCATCCTCCTCAACCCCACCCC

AATTACAATCCCCCTCCTCAAATTCCATTCAATCCTCATCCTCAAACTCCTCCCTTCATGTCTCACACCTTTCAAGTCAAT

GGACAATCACAACAAGCGGGACCCCACTTCCAGAATTTTCACAATTCTAGCTTTGCGCTTGCGCCTCTTGCATCGCTTC

CTCCGGCTCCTCCTCCACCGCCTCCTATCAAATACCCAATTGAGGATTTGGAAGTTCCTCCCCGAGTTGATGGACCGA

AACGACCCGATATCAAATACTTTTCGCAAGATAATCCAATGATGGTGGGAAAACCAAAGGCCGAGGGTAATGGCATTC

ACATGTCATCGATTGGACAGTTACTGGAGACCTGGGACACTTTGAATGTTTACTGTCAAATCTTCAAGTTGGACTCATT

CACTTTTGATGACTTTGTCGAAGCCTTACAATTTACATCTGAAGATGTAGACTGCGAACTGTTCGTCGAAATTCATTGCG

CTGTTTTGAAAATCTTGGTTAATTCTGAAGCCGATGATGGAGAGATGCAAATTCGGTTACGAGAAATAGAGGAGTCAGA

TGACGAAGAAGAGTCCGATGACGAGGCTAGCGTTGCACCATCACCTACACCAGAGCCAGAGCCAAAACCCAAAGGGC

GCGCTACCAGAAGTAGTCTCGCAAAAGCCGAGGCAGAAGCTTTACAAAAAGCCGCCGAACAACCTCCCGAAGAGCCC

GCTGGACCAGTCAACACTCATCGCGCAGCCGAGATGGAAGATAGTCTTGAGTGGGCCCAGAAGCTAAGAAAACGTGA

TTTCAAGAATGGTGGCTGGGAAGCTATTATGGTCGGCCTTTTGTATCAACTTTCGAAATACGAGAGATACTTTGCCGCC

TGTGAATCACTCCTTGTTGAACTCGCCCCCCTCGATTCGGAGCCAACGCAGGAAACCGCTCGCCTACAGTACGCTAAA

CTTGACGTTAACCTTCGTATCAAGGCACTGCAAATTATTTGCATGCTTACGATGGAGACTAAAGCAATTCGTGGTTACA

TGGAAGAGAGTAGTGAACACATGACGGAGCTCCGAAAGGAAAAAATAAAGTACCAGCGTGATAAGAAGGATGCTCAT

GATGCTCTCAAAAAGCTCAATGAAACGCGCAAAGCACTCGAACCACCACCCGAGCCAAGTCCAGCGCCAGCTACAGA

GAAGCCTGCAGAGAAAGAAGCTTCAGCCAGCGTCAACGGAGATGTGACTATGGTCGACGCCGAGGATGAAGTTCAG

GACTCTCATGGTGATGAAATTATGGACTCAGATGGAGAGGCTCCCCCAACTCGATCATTACGCCGCGGATTAGATCGA

GCAGCAGAACGAAAGCGTAAGCGTGAGGCCGAGCAGGAGAAGAAAGCAAAAGCAGAAGCTGAGCCTAAGGCCCCCA

AACAATCTAAGGCCCTCACGAAAGTTCTCAAAGACATCCAAAAATTGCATGATGAGATCAAGCATTGCGAGGAAGAGAT

TGCCATTCTCGATAATGACCTCCGAGAGGCTGATTGCCCTCGCACTCGTGTACTTGGCAAGGATCGATTCTGGAATCG

CTATTATTGGTTTGAGCGCAATGGTATGCCATATAGTGGTCTTCCTACCAGCTCTACTGCTGAGGCTGGATATGCCAAC

GGATGTATCTGGATTCAAGGACCGGATGATCTTGAGCGCGAAGGTTATATTGAGATGCGACCTGAGTGGCAAGATGA

GTATCGATATAAATTCAACCTGACTGTGCCGGAAAGAAAGGTTATGGAGGAAGGAAATACTCATGTATTCAATTCTCGT

GAATGGGGATACTATGATGATCCTGAGTCAGTCGAAGGCCTGCTTAATTGGCTTGACGCCCGTGGAAACAACGAGTTG

AAACTTCGAAAAGAACTCCAACTTTACAAGGACAAGATCATCACTCACATGGAAAAGCGCAAGGAGTATCTCAACCCTA

GTGATGAAAAGAGTATCGATTCTAGTCACAAGCGAATGTCCACTCGTGGAAAACAACAACCTCATGTTGATCATACAGC

TCATCGATGCCTATCCTGGCACAACAATACGGCAATTGAAGAATTAGGTCACTTGCATTCCGATCCACCACGAAATCGT

AAGCAAACTAAGAAGGCGGCTCCTATTTTACCACCGGCAATTGAAGAAGAGAGACAAACTAGGAGCGAAGCGGCTAA

GAGACAGAGAAAGCGTTAAGTTTTCGGTGTTTTACAGCTTTGAGAATGATAGATCACGAGCGCTCGCAAAATTTACTGG

TGCGTTTTGTTCATGGCTATTTCATATAGAAAATCTTGAACGCGCATGGAGTTCATTGGTTCTATGTATTTGAATTTGGC

CTTGGGAGGAGTTTATGGGTTTATGGGCTTCAAAAACACATTTGAAGTTGGGAAATAAGGAAATCACAAAAGTCATGGG

AGTGCGTGCATATATGGTATTTTACAAAATGGATTGGTTTGTATTTAGACGGTCTGTGGTGAGGGAAAGCATTGCTTGC

GTTGCATTTGGATGGTGTTGGCTGGATTGTGTTTTGATGGTTAGTTAGCACTGAGAGGGAGCACTGAAGAGAGGAGAG

ACTGGAGATCTGTTTGTATGGAATGTTATTTGCTTCATGAGGGAGCGAGCGAAGAGAGCAGTAGTATAGTGAGTGATG

CGAATACCCAAAATACATATCAAATT

-continued

BC1G_14463

SEQ ID NO: 67

*GGAACTGTGGGCTTATTCGAGGTCTGCCTCTCTTGCAATTTTCTCTCTTCTCTTTATAACTTTTTGATCTAAATTTTCACA*

*TCAGCTCTATTCAAACTACATAATTCTCAGGCCACGTGCTACTCTTCATAACTATTATATCCTATTGGGGGGCGCTGGT*

*CGTCACACTAGTCAAGGTATATTAGTCTTCTTTCTAAAATCTTGATACTATAAGCCTGTCGCCTCACTTTCCACAATGCA*

*ACAACAACCACATAGTATCACCAGAATCAGGATCCAATAAACTTAGCTCCCTTATCCTTTTCGGCTTCCAGTTACCCTTA*

*TACTTCATCACTTCATATCTACATCACTGACGCTTTCATCTTTCAACAATCTTCTGAAGAATTTGATGTCGAAAATGGAGC*

*TTGACGATACATGGGATCCTGATCCCTTGCCAAGTGGTAGTTCTAGGAACCAATCTCAGCCTCGATTCAAGAGAGAAA*

*CATCTCATCACTCTAAGGCACAACCGGACCCGCAGCATCAATACTACGAACAACCAAAAACATCTCATTCACAACTCAG*

*AGGTCTGATCGCGCCCATGAAGCTTTATCAAGACTTTTCAGACGATGGAAGCTCATCTGATGAATATCCTGTCGTCTTG*

*CAACAACCACAGATTAATAATAAAAGGGTGACAAGTCCCGCTCAACCTGCGAAGGACAGACGGAAGCGACATCAGAG*

*TGAACACCCAAATCGAATTGAACGTGGCCGCACAACAAACGTAGAGGAGGTTATATATGATCACATCTCAGCGATCCC*

*GCGGTCTCGCAATGAATCCGTTGCCCGCAATGACGCTCGATATAAGAGTGTTGCAAATGATGTTTTCGAAGAGTATGA*

*AAGTTTCAAAAACACCTCAGCAGTTAGCAGAACATCGGTCGCCCGTAGTCATTCGCTTGCAAGAGACTTGTATGAGGA*

*CCAAGGTTATGTTACAATGAAAGATTACAACCGGCAGTTCGACAAAGAGCCAAGTGTCTTTTCACCTAACAATGCTCAA*

ACTAAGAGGCGCATGAGGGAGGAGTCAACCTACGGATCTATGTCATCTGGTACAGATGCTCATAGAACAGCTGGCCG

*AAGTCGTCAAGAAAGTTCAAGCCAATCGCGAACTAGTCGGTGCACCCAAGAAAAAAAAACGTCATAGTTATTCTCGT*

*GCACAAAGTCTAGCCCCAAGAATCTCAAACGACAATAGCGATGTTCAATATCTGGGCACTGAAAATGGTATGTACAGT*

*GTCAGAATTCAAAAGCAGGGAAAGAAGCCCCAACTTCGCTCGCCATTATGGCCAAGCTTTGAATCTGCTGTACCCAAA*

*CCTTACTCTGCTAACAGATTGAAAGGGAGAATTGATAAATCTGCCTCGATGAAGCCACTCCCACATATGCCAAAGAATC*

*AACCAGTTAGAATCAGATCAGTTGCGTCTGATCGCATACAGAACTATTCAAGTCAAGCCCGAACGGTTGATTATGGTCT*

*CATTGATGACGACGATGTTTATGACACACCATTGGAAAATGATCTTCGCCGCAGATCTAAGTCTCAAGTGAGAGCTCAT*

*AATGCTCCCATGAACTTCATAAATGCTCTACCAAAGTCTAGTGTATTTCGAAGGAAAAACTCCGAAGTCGCAGAACAGG*

*TTCATCAGACTCCATCCAGAGACTCAAATAGATCTAACAATCCGGGCGTCACTATTGATCTCGTTACTCCAGAAAGTAC*

*TGTTTATGCCCGCAGTGCAATGCCTTTTATACCTCAGCACTGGACTCCAACAAGGAGAGGCCCAATGAAAGTATCGGC*

*TCCAATGGAGATCTCTGAGCAGGATGGTCTTGGCACTAAAACTGGACAACAACCTGGTCAAAATACTCATCAGCACCA*

*AGTCATTAAATCTAGTCCTAATAATGGACAACAAACTGAAGAAAACATACGACAACGACAAGCAGCCGAGAAGATCATC*

*CGACAAGAACTCAATGCAGATAATGAGGCTTTGCAAGCGGAGCTTTTCGGAGAAGTTATTGGTGAAACTGAGGAAGAA*

*ATGAGAGAGCGTGAAGAAGCTAAACGTTTGGAAGCTCAAAGAGTGCGGGAACAAAAAGAGAAGCAAGATCTCATTGAT*

*GCTGAGAGGAAGCGAAAGAAGAATGAAGCAAGAGCCAAGAAAGAGAACGAGAGGAAAGCGGCTGAGCAGGCCGAGA*

*AGGAGAAAGAAGCAGCAGCAAAAAAAGCCAAACGTGATGCCGAACGCCATCATCAATCATTGAAGGAGCAACAGAAT*

*GCAGACGAGAGACGTAAGGCGGCAAACAAGTTACTACAAGAGAAGAAAGAAAGAGATTTGGCTGCATCCAAGGTCAT*

*CGAGGAAAATGTCCAAGCTGCAGAAAAAGAAAGAAAAGAGAATGAAGCTAAGTTTGAGCGAATGAAACGACAATTGGA*

*AAAACTTGAGGCGCAAGTTAAAGCAAAATCGATTGCGGAATTGAAGCCTGCGAGAAAGTCTACGGCTTTGGACGGTAT*

*CTCGAACAGAGTCAACTCTCAGCCTCCTCAAGTCAGGCTTTCAACAAGCATGGAAATTGACGATGAAAGTTCATTGCC*

*CACTACACAGACCCAAATAACACCTGTAAACGGTACTGATACTTCACATACAGCAAATACTTCATCTACTCAAGCCACA*

*CCTTCAATAATCACCGAAGTCGAGGATGAAGATTCACTGTTCGTTTCAGACAATCGAAAGACAGTTGTGGAAGCCACTC*

*CAGAACAGCAAATTTCGAATGATCTTCAAAATTTCACTGGGAGCTTTAGTAGTGACTCGACAATTGTTCAGTCCATAGA*

*GCATGATCGACCTCCTACTAGTATAACTGAGATCTTTGCCAAGACAATTCACAATCCAAGTGGTGACAAGACTCTCGAA*

*GATAGGGACGCGGAGCGAGAAGCCATTCGAAAAAAAAGAGCAAACGAGAATGCAGCTGCCAAGCAAAAACGAGCAAA*

*TTCCATACCCGCAGAGCCAAACCCCGAAATATTTGCTCAAAAGGTTGCTCCACGGGAAGTTTCTAAAGCACCATCGAA*

-continued

*AAGCACGCCAAAGAAAAAACGTATCCAGCCGCTAACAAAGGCATTAGGAGATTCCATATTCAGTGTTAAATTACAGCCT*

*CTAGCCGGACATGAGCCCGAAGGATACGTTCCTCGTGAACAGTCAGAAGGTTTTCAGAATTTCACTGAGAACTCTTCC*

*ACAGACCTTACAGTCTTGAAACCCCGCCCACTTCCATTGACTTTACCTCCCCCTCTTCCTCCACCAGTAGCATTTACTA*

*CTACTTCAATTAGACCAGAAACTCGTCTGATTTCACAAGCAGAGCGAGAGGAAATTGAAGCTAATCGCCAAAGAGTCC*

*AGGCTGCGGCACAGGCTCGGAAGGAAAATTCGAACAGGGCAAGATTGGAGGGGAGAAAAGCTGCATCTGCGAAGAA*

*GAGAACAGTTGAGTATCGCAAGAGGAAAGAGAAAGAACTCATCGAAGAGGCTCATAAAGAGGGTAGGATATTAGGTAA*

*TTCTGAGCTGGAAGCTAGACTTGACAAGTTGATGGAGAAGCGAGAGCGTGAGCAAAAACGAAAGAAAAATCGTGCGG*

*GAGAAAAGGCTTCATTTAACGAACATGAACATGAACCTCTTTCTAGAATAAATATACTTAACCATTCTAGCATGCCCGCG*

*GCGCAAATCTCATCCTCCGATACTGCCAGTGATTCTAATCAAATTGAAGAAGATGATGATCCTCCGGCTCTAACTCTGA*

*AAGAGCATAAGATTAAAACGGCCGAAATTATGAAAGAACGGGCTCAATTGCATGCAGCTCAGCGTGCCCAACCACAAC*

*CGAAGAAGAAACTGGAACCAATTTTTGACTCGGACGAGTCTGAGGAGTCTGTAGAAGATCCGATGGACGAAGAGACTA*

*CGGAAATGTACATAGAGCACGCTCGAAAAAACAACACCGAGGCTAAAGAAGATGTCGAAAAGAGTGATGTGGTTCAAT*

*TAGAAACTCGGACTGAGGAAGACATTGCTTTCGAGAAAGAGATAGAAGATTTTCTTGAAGAAGATCCAAATTTCGAAGG*

*AGAGGCTCAAGAAGCAACCACTACACTCAACCCCGATGAACATAGTGCTCAGATCGTCCTACCAATGCCCAATATGAC*

*AAGATACTTTGAGGGACAATCCGCTCCACGGTCTTCCAGTAATCTAGAGACCCAATCAACGTTACTTGCAGGACCGAT*

*TCAAATGGCCAAAAAAATACCTCCCAAACCTCAGCAGCCCGCATCATATGAAATGGTCAATTTATATATGGTCATGACG*

*CAAGTGACACTTCACGAATGTGAAGACGAAGCAATTCTCAAAAAGAAGTTCCTTGATATTGAAAAGGCCAACAAGTACG*

CACAGATGCTTGTCAACGAACACAGAAATAAAATGTTCAGACAACGGGAAATTCTGGAAAGATGGGATTCAGACCGTA

*TGTATCATGGCCAAATCATTCACGACAAACAGAAGACTACCAAGATTTTTGTTGAATTTAAGCCAATGAACACCGAAGAT*

*ATTGACAAATATGATCCAACACTGGTACGACCGATGTTTGCTACTCAATACTACATGGTTCGATTTGAGAAAGTCGTTG*

*AAGAAATTGACCCCAAAACCCAGAAAGTCTGTATGAAAAACCATACTATTGGATTTGCAGACTCGGGCAAGCTATACAC*

*GGTATTAGAAATGGCAAATCATGCTGCTTCCGAATACCTCCTCAAGGAAATCAAACCCAAGGAAGAAGTTGAGGAGCA*

*TCATACTACTTACGAACAAATTCTCCTCCCGGAAGTGAGAGCAGGAAGAGATGATGCCAACCAAACAGATCAAATGTTC*

*AATTGCGAGTTTACTTGCGAAGGAGCTCCCTGGGTAGATTTCAAATCGTTCGAAGTTGGCGTGGAAATGTATAAGACT*

*GAGGGCCCGGTCAACTGAAAAGGAAAGTGATGAATGTGCTTGCCTCGTCATCTTCTATCATCAATACAAATTGTTTACT*

*GAAACCATCACTGCTCTGTTTCTTACAACACCACTCTTATTTTCATCAAACGACACTTCTTGGCCGCCAAGTTTGCACAT*

*TTTCAGATAATTACACCATATCCATTTCAGCATCACATACATTCACTATAAATAATATCGACGGTTTCAACAACACCTCCA*

*CACTTTGCATCACCCCCGAAATGCCATCATATTTCATTCATGCTTCCCACCAAAATCAGCATAGCATTATTATTCTAGTG*

*TATCAAACTCAACATCAAATCAATCATCATGAAAATCGCAATCGCTCAATCCTCCACAAATTTTCATCGCCACAAAAACA*

*AATAATACAGTCAGAAAAGAAAGTGCAGAAGTCAGTTCAGCCATTAGACGTTCAAGGGTAGTAATGACACGAACAACTC*

*TTGGGGGACTCATCGATGAGTTTATTTCTTGCTGTTTATTAATAGGAAGGGCGTGGGATTTAGGTATTTTATTTTACTTT*

*ATCTGCTTTTTATTACCTTTTACTTTACTCCGGTATTTGTGGTGACAGGTTCCGTAAGCTTTTCAGAGGAAGGGGGGCG*

*GTAGTGGGATCGAATAGGGAGAGAAAGGGGTGAGGCCATAGGCGGGTGGAGAAAAGGGGTGAGTTTGTGCTGAGCT*

*AAGCTGAGCACACGTACTGGGAAAAAGCTACGTGACAGGAGGAAGATTCTCGGAGAGTAGGGAACAAAACATTTTCTT*

*TTGTTGTCGTTGTTTCAATGAAAATTATTGATACTA*

BC1G_10235

SEQ ID NO: 68

*GACTTTTCTGTCTGTTCTGAATGAATGAAGGAAGAAGCCCTCGCGGATTACGACCCTTTCTCCCATTCTCCCATCCATA*

*CACATTAAAATTAACCATCCCATCCATCCCATCCATCCCACCCATCCCTTGTGAACTCTTTTTCCATTTGCTTTTGCTTTG*

*GTGGAAATAATTAGGATCAGACAGGCAGACTGGCACACAGGCACACAGGCACACAGCCAGCCAGCCAGCCAGCCAG*

*AGCGCGACCACAGGCTGAGATTAAGGAGATAATTTACTATTCATTTTGCAAATATTGGCCAATATCGGCGCAACTTTAT*

*ATCGTTTGAACCCTTGGATGGATGGATGTATCTTAGTAAAGTGTCGAATGATTATTGCTTGCGAAGTGCTCTTTTCCCC*

-continued

GTTGGTCAACAGAAGCGTGGGAGCTCTGCTATATTTGCTTCTTGAGGGTTTGTTCACGGCGCAAATCCTGCACGAAAA
AGGAAATCTTTGGAAAGCTGATGTCTTGCTCTACAGTCCCGTTACCCATGGCTTAATGACGATACGATCATCTTTTCGA
GATACCCTCTGCGAATGCGACCTTAGACATTCACGAATCGAAGCGGCCGATTTTTAAAGGACCTGTACACATCGATCA
TCCAACAATAATTTACATCAAATACAATGGCTGATGATGGGCCACCACCTCCTCCTCCCCCTCATGGCACTCCGCCAAA
ATCATCCGGTCTGCCGCCGGGGAATTATGACATTTTTATCATTCCACCGCATGCGTCAGGTTCAGGATTTCTCTATTTA
CCGTCACTGCAACCAAATGTCAATAGTTTCGTAGCGGGGTTTGCCTCAGCGCTTGTGCTTGTCGCACTAACTTTCATAT
TAAAACCATTCATGGATACCATGAAAGGAGGTGGAGGGCCAGCAACCTTGATTCTTATGGTTGCAATTGGGTTGGGAG
CTTGGGCACTAGGGCGGATGCAATCGAACGGTGAGACCAGGCCCGGACCAAGTCAAGGATCGGGTGCACCTCCGCA
TGGTGGATCATATTCAGGTGCCAATGATAACACATACTCCAATGGATCGACTTCAAGTGGTGGGCCACGAACTTCAGG
AACTGGATTTTCACCTGGATCCACATCAGAGGGGGCTGGGGGTCCTCCACCTAATCCGCAGGCCGGATCTGGCGCAA
GAAAAAGATCAAGTGAAGGTTGTGAAGAAACTCCTCCTCCTTCGCCTGATGCCGGTCCAGAGATGCCGGGCGCAACA
CCCAGGTACAGTCCTGGCACAACTCCTGGCGCAAACGATGACGCTCGATCGAAAGAAAATGCTTCGAGGACGGCGTG
GGAAGAGGCTCGAGAAAGGACGAGAAGGAAGGAAGAGGAGAGAAGGAGGGTAGAGGCCGAGAAGAAGCGAAAGGA
GGATTTGGAAAAGAGGTTGAGAGAGTTGCGAGCAAAGGAAGCTCTTGAGCGAGCTGCCCGCGAGAAAAAACAAAGG
GACGAACGCGAAGCTAGGGAACAAAAGGAAAGAGAGGAACGAGAAGCCAAGGAACGAAAGGAAGCAGAGGAACGAG
AAGCCAAGGAACGAAAGGAAGCAGAGGAACGGGAAGCCAAGGAACGAAGAGATAGGGAAGAGCTGGAAGCTCGGG
AGAAGAGAGAACGAGCAGCGCGATGGAAGGAAAGAGAGGAACGTGAAAGGTTGGCAAAATTGGAGAGAGAAGATCA
ACAGGCTCGAGAGAGAAAGGCAAAGGAGGACCGCGAAACTCGAGAACGAATCAAAGCAGAAACAGCGCGAATCAGG
GCAGAAGCAAGAGCAAACTACGATAGGAGACTTAAAGAAGAATTGGCTAAGAGGGAAGCTCTAAGGAAAGAAGAAGA
AGCCAGGAGGGAAGTTTTAAGGAAGGAAGAGGAAGCCAGGAGGGAAGTTTTAAGGAAGGAAGAGGAGGCCATTAAG
AGAGAGCAAGAAAAGTTACGACTAGAAGCTATTGCTAGAGTAGAAGCCGACAAGAAAGCCAGAGCAGACAAAGAAAG
GGCAGAGGCGGAGGCAAAAGCAAAGGCGGAAAAGGCAGAGGCGGAGGCAAAAGCAAAGGCGGAAAAGGCAAGAGC
TGCTGCGAAAGCATGGGCAGATGCTAAAGCCGCGGCAGCAGCAAAACGTGAGGCCAAAGCCAGAGAAGAGCGCGAG
AAGGAAGTAGCGGCGCAAATACGTGAAGTCAAACTTAAGGAGGAGCGCGAGAAAGCAGCCGAAGTAGCAGCTCAAAT
CAGGGAGCTCAAACTCCAGCAAGAGCGTGAAAGGGCAGCCGAGGTAGAAGCGCAAATAAGAGAAGTCAAACTCCGG
GAAGAACGTGAAAAGGCAGCCCTAGCCGCACTCGCAGCGGAACGGAGAAAACCGAATACTTATTCGAATGCTGGAGT
GGGGGAGAGAATAAGCCCGTGGCCAAATGGAAAACCGCCCACAGCAACACCCGCTCCCCCCACTGCCAGCTCGATA
CCCCGACCTCAAGCACAATCCACCGCATCCAAGAAACCCCCGGTCTCAACTGCAAGAACGTATGCAGGTACCGACAA
GGATTCCCAGTCCCACTCACCTTATGCACAATCGCCAAGGCCAACACGAAAAAAGTCACTCAGTTCCTTGTATTCCGAA
TCATCATACGCGGCCTCACAATCGACAAGTAGAACTACCCCACCTCCTTCGACACGAGGAGCATATAGCACCAAGGAT
CCGGACAAGATTGTTATCAAAGGTGTATTCGCATTCAATAACGCATTCCACAAAACCCCCACATCTCAACTTCTATCTG
GTGTCGGTTCTGTTACCGACGGACTAATATTAAGAATCACAACAGAGGGTCTCTTCATTGATGATGATGTACGAGGCGT
CGCTCAACGAGAGTGGGATGTCAAAGCATGGACAATGAAACTCGTAGAGGTATGGTGCCCATCTTTCAGACAAGCATC
GCGTGTTCCTCCCGCTACCACAGCGTTTAAAAATCCCGTTCGACGCCTTTGGGGTCTCGATAAAGAATTGGCAGCAAG
TGAAGAAGAAAAAGATACTCTTCTAGTTAGTATGCTGCAACTCTGTCGGGATAATTGTCGCGCTCGTGCCATTTCTAGT
TCTTCCACTGGGCATTCTGCTAGTGGTTCTGTCTATTCTGCCAGCTCTTATGCTTCATCTGATACTAGATCGTCTGTTTC
ATCTGATTATGCTGATTCCATTGGGTCGTCTAATTCTCCTTATGGTGAGAAATCAAAGAGAACCACTAACCATAATGGC
CAGACTGGTGAGAGTAGAACAGCCGGTCTGCATATTTTGAGGGCGAGCATTAGGGATCAAGAAGGCAAAAAGTATGT
CTTTGTGGTTCAAGAAGGTGAGGCTTGGAAGGTAGCACTAGGATTGCAGAGGTTGAGGAGGGGAACTCAGGTGAGAA
GTTTGGGTGTTAGTGGCATGAGTCCGAATGATGCAAAGGCTACACTGGATAACTTGGGATGGTTTTGAGAGTTGGGG

-continued

GTGATGGGAAGATTTCAGAATCTCTGGAATACGCCATGGAATGTGGAGTTTGGAACGCGGAATCGTATCCCTCGGCG

AAAAGGGATGCGAGGCGAATCATGAGTCCCGAAAGTCAAATCTAGCATTTACAACACAACGGAAGCATCAGCGATGGA

GTTTTTTTTTTTTTTTTTTTTTGTCTTTTTGTTTAAGTTTTTGTGTTTGATACTACAGTATTTTCACTCATCTCAAGGAGTTTA

TGTGTTTGTTTGCGCACGGGAGCTGTCGAGTTTTAGTTGGAACTTTCTTGTGGGAATTTAGAATGGAATTGGGTATCAG

TACCTCTTCAATTTTCTGAGGTGTTTGGTTAGAGAGCGTATTGTATGTATCTTGAATACCCGGTTCTGTGCTAAAGTTTG

TGGTTTGAAGTATGTTTGTGTGGAATGTTTGGTAATGAAATGGGATGGGGAGAGGGGGA

BC1G_12627

SEQ ID NO: 69

ACTCGTGCGTCTACTGCCACTGCCACTGCTGCTACTTTGCTATTCAACTTCGCCTCGCCTTTCAATTAAGAATTGTCAC

TTCGTCGCATCTGAGGCCGGAATGCTAATATCTTCTCGTCATCTTTGAAGCCAATCTCACTCGTTATCCCGTCCAATTC

AGTCGATATATTAAGAGCCTTTGAAGTTCCGATCCAAGAAACCTTTCGTCTATCCATATCGCAAGAGTTCACTTCTTCAC

AATGAAGTTCACCCCAGTTTCTGTTGCGCTTCTCAGCGTGGCCGGCGTTGCGATTGCGCAACCCCACAACCATCAACA

CCGTCATCCAGTTCGAGCAAACAAGGTCGCACGCGACAATGCTGTTGTCTCTGTGACAGAGGTTATGCCAGGTCCAG

TCGAGACAGTCTACATGCTTAACGGAAAGGATATCTCTTTGGCCGAAGTACAAGATGGTTTGAAATCTGGAAAATACGT

TTTGGTGGGAGACGCTGTCGAAGACGCCCCTTCTGCTACTAACTGGTACACTGCACCCGTATCTGTTGCACCCACAAC

ATCTGCCGCTACAACCTCTTCCGCAGCTACCTCCACCAGTTCGATCGTCAAGGCTGCTGCAGAGTTCATTGAGGTCTC

CTCGTCTTCCACCAAAGCTGCGTACACTTGGAAATCAAGCGCTGCATCAAGCGCTGCATCATCCACTTCAGAATCAAG

CTCGGTCGCCTCTGTCTCCTCTACCAGTTCTGCTGCTGCTTCTTCCTCCTCCGCCAGCAGCTCCACTTCCGCCGCAGC

CAGCAGCTCTACTTCCTCCAGCAGCGCCGGCAATTGGGCCGACTTCCCAAGTGGCACAATCCCTTGTTCCACTTTCCC

ATCTGAGTATGGCCCAATCGCTGTCGATTACCTTGGTTTAGATGGCTGGATCGGTATCCAAAGCACCCCTGGCTACAC

CACTTCTGCTTCCTCGATCGTTACCATTAACACACTAACCAGCGGTGGATGTGTGAAAGGCGCTTTCTGCTCGTATGCA

TGCCCAGCGGGATACCAGAAATCTCAATGGCCTAGCGCACAAGGAAGCACTGGTGAATCCATCGGCGGTCTTTACTG

TAACTCCAAGGGAATGCTCGAGTTGTCCCGAACTACCACCAAGCAACTTTGCACTGCTGGATCTGGATCCGTCAAGGT

TGAAAACAAGCTCAGCAGCATTGTTTCTGTTTGCCGTACTGATTACCCTGGTCTCGAGGCTGAAACGGTTCCATTGTCA

ACCTCCCCTGGCCAAACCTATGACTTGACTTGCCCAGATGCCAGTAACTACTACTCATGGGAAGGACTTCCAACTTCC

GCACAATACTACATCAACCCACAAGGAGCTTCTACCTCTGAAGCTTGCGTATGGGGTGAAGCAGGTAAAAACCTTGGT

AACTGGGCTCCTGTCAATGCTGGTGTCGGCAAAGATGCCTCTGGTAACACTTGGTTGTCAATCATCCCTAACACCCCA

ACCAACACATATGGTACCTTGGACTTCACCATCACTATCGAAGGTGATGTCTCCGGAAAATGCTCGTACTCATCTGGAA

CATACTACAACAATGGTGTTGAGTCCTCAACAGGTTGCACCGTCTCTGTTCTCGCAGGCGGAACCGCTACATACGTCT

TCTCATCATAGGCGCTTGAGTCTCGATTTTCCCTTTTACAAAATTTCCGGTGCACATATTGTTGTTTTCTTTCCGCGCGC

ATATCCACAATTGCGGCTTATGATCGTTGTAGTCACTTTTTTTTTTTTTCCTTTACACGCCCTCAAGTTATTCTAAGTCTCG

GATGTTCGAACTCACGCTCGACTTGCAACGTTCAAACAAATTTGTCAATAAGATACCCCCTCCATCCGATCTCTGAATG

TACTTCGTGTGGTAACTTTTCCTTTGTAATAAATGTCGCTAATGTTTTTACATTATTGAAGTGGAAGATATCTGGACGTTG

GAATACTACGTTCCAGATGGTTGTTGTAAGCATGAATGGATTTCTTGAGGGGGTTGGGGCTGTTGGTAGAAAAAAAGG

TTGTGTTCTCGGCAGATGAATGTTCATATGGCGAACGGGAAAGCTCTCTTTCCTTGAAGCGATCACCTTGGTTAACTCT

TCTATGTATTCGTTACTCATTTTGAAGGAGACGTGCTCCTGGTACAGAGTGCCCCTCTATCCCTACGGCCTTTTTATCA

ATTTGCCGCAGGCACTCTTGCATATGTTTTCACACTGGCTACAAATGTTTGGAAGGAGCGCGCACACGAAACAAAAATT

ACCACCATGTCTCTTTTCTGAGGAGATTTGGTAGAGAGCTATAACACCTGTTGTATGTGGATGTGAATGGAAAATTTGA

CGGCAGAGGCTGCAGAATATGGTGCATGTATCAATGTAAAGTAGTCTAGTCGGCACAACACAGACAGGGAAAGGGAG

ATCAGTTACACTCTACTTATTCTACCTTTTCAAGAAGATGTTGAGAAATTTTTGAGAACAGAAAATTCCAAAAAAACAAAA

ACAAAAAAACAAGTAAATGGAGCATTCAGATGAAGTGTGTGGCCTTTTTCGTGTATACAGATTAAAATCTCTTTTCGTAT

CTTATAATTTCTTCATTTTTCTTTCCTGACGATGTTCACATACAACTAACTGTCTTTCTGAATCTGTGAATATGAATA

-continued

BC1G_09656

SEQ ID NO: 70

*GTCCTTTTGTTTCTTCATTCTTTCATTTCAAAATGTATTTTTCTTCTCATTCTCTCATTGCTTCCGTGCTCTTGGTCTCTGC*

*CGTTCAAGCATACCCAGGAGTTCAAGCAGATCTTGTTGTTGATATACTAGCTACAGCGACATCTGCAATTGTTTTAGAG*

*ACCCCTCCACCTTCGGAAGGGCTTCTTGACAATGTAGGGTTGTTCAAATTCTTCGCAAGAGCCGCGAAGAAGACAACA*

*GCAAAAACCACTGCTAAAACCACTGCTAAAACAACAGAGGCTGCACCGACAACCCAGAAAACTACAGCTCCAGCAACA*

*ACGCAAAAAACTACAGCCGTGGTGACTACACCCACAACTACCTCGGTGAAAACCACTGAAACACCTACTACCACTTCA*

*ATCAAGACTACTTCCATCCCGACTACGTCATCTATATCCACGAAACCTACGTCTACGTCTACTTCAACGAGTTCGACTT*

*CGGTTGTAGCACCAAGTAGTACGAGTACTATCTCCAAATCCTTGATTTCAAGCACCAGCTCAATTCCTACCTCGGTGGC*

*TTCAATTCAGACATCTCAAGTCTCATCTTCCACTGTGTCTCCGATCTCTAGCTCGTCAACATCTAGCTCTTTGGTATCCA*

*GTAAAAGTTCTACTTCTGTAGCTACGTCTTCTCAAATATCAACTTCTAAAACTGGTTCATTGTCCAGTGTTAGTGGAGTC*

*TCCGGATCCATTGTCAGCACTGGCTCTTTATCATCCCCTACTGTCTCTACTTCGGCTGGTGGGTCTGTTTCTTCTGGAA*

*TCAATTCAAAGACTAGTGAATCTCTCACCAGTACTGGATCAGCATCAACAAGAACCGGTTCCATAACGAGCACTGCTTC*

*CGCTTCAGCGAGTGGATCCCTTTCATCTGGAACAGGTTCTATCACCAGTGGATCTCTCACCAGCACTGGGCCAGTATC*

*ATCAGGAATCAGTTCGAGCTCGATCTCAGGGAGTGGAACTATAACTTCCTCCTCCCGCATCTCCTCCTCCAGCGGTTC*

*CATCTCTTGTTCCGTCTCCAACACCGTAACAGACATAACCTACTTTGTTTCACCCGCCACCAACACCCTTGGTTCCGTA*

*ACAAAACTTTCCACCATCTCCTCCACCGCCGTCAGAACCATCGGATGTTCTCTCAGCGCCAAAACCGCCACATCCACC*

*GTCTCCTCCTCCGCATCTATCAGTAAAATCGTCATTCCAACCGGCTATGGAGATCCCATCATGAGCGCCGAAGCCAAA*

*AATGCCGCTTTCTACAAAGCCGGCGTGGCGGGATACTCAAGCCAGCTGAGCGTTTACAGCGCAGCCTCGACGAGAAC*

*AAGCGGGATGACCACAATGGCTTCTGCGACGGGGAGTGCGTCGGGCGTGCAAAGCGGTTCGGGTTCATCTAGTGCT*

*TTGAGTGCCCCGAGTAGTCTTGCAAGTGGCACGACGAAGGAAAGTGTAAGTAGTGTTGCTACCACGGATGTTTCGAGT*

*ACTACTAGTGCGCCGGCTACTTCTGAGACGGCTTCCGCCACGGGGTTTGTAGGGGAGATCTCTTCGCTTCTTAATATC*

*TTTTAAGGGGGAGGTGTGGATATATGAGGGGGCTGGATATTAGCATGGGAATAGATTCA*

BC1G_07658

SEQ ID NO: 71

*GGAATTGATTCATGTATGGGTCATCACCCTTTCCAAATCAAAATACCCTTGCGAGCAACAAATATATTACCAGTTACCGC*

*CTTGCATACTTCTTTTGTTCATTCAAAATCATCCACAAACAGATTTGATCCAATCCGATCCAAGCTTTATGACGGGCATA*

*AGCGTTGGATCATGTTTCTAGCCCTTTGGTGAATGCTCCCTTGACTGCCTCCAAAAGCAAAATCTGCTTGTTCGATTCG*

*TGGATGACTGGGATATCTAGTTTCTTGTACACAGATTGAATCTCCACAACTAACCAGTTCATCTAATGGCACAGTGCTA*

*GGTCCCATTCCCCAACTTTTGTATAAGTATCTTTCTCTTGGCCAGTTTGACTTCGAATTCTTCATCGTTCAAGCAAACGT*

*TTCTTTCTTTACCCATCACATTCATTTACACAGTCCTCGGTGACTATCTACATTCATTACTTCATTGATTGAAGCTTATCA*

*ACAACTTTTCAAATCCAACGCTCATTTTTTCCACCTCACGAAAAACTTCCAAACACTTTTTCCATCAAAATCATCAATCTC*

*AAGATTTTATCATCAAAAATGTCTTTCTCCAAGATCGCCGTTGTGGCTGGTGCCGCTTTTATCTCTGGTGTTGCTGCTCA*

*CGGACGTGTCCAAGGTATCACTGCTGATGGTGTTTGGTACGAGGGTTACAACCCAGCTTTCCAATACGAGCAAGTTGC*

*ACCAGTCGTTGCTGGATGGTCCGACCCAACTGATCAATCGAACGGTTTCATTGCACCAGATGCTTATGGTACATCCGA*

*CATCATCTGCCACTTGGCCGCTACCAATGCTCAAGGATACGTTAATGTCACTGCCGGAAGTGAGGTTAACTTGCAATG*

*GACCACCTGGCCCGATTCGCATCACGGTCCAGTCATCGACTACCTTGCTGCCTGTACTGGAGGTGATTGCACAACTGT*

*TGACAAGACCACCCTCGGATTCTTCAAGATCGATGGTGTAGGACTTATCGATGATTCCACCGTCCCAGGTACATGGGC*

*ATCTGATCAGCTCATCGCCAACAACAACTCCTGGTCTGTTACCATCCCAGAGTCCTTGGCACCAGGTGGTTACGTTCT*

*CCGCCACGAGATCATCGCACTCCACTCCGCTGAGCAAGCCGATGGAGCTCAAAACTACCCACAATGTATTAACCTTTG*

*GGTTTCCGGCTCTGGATCTGCTGTTCCAGCTAGCGCAGATACCACTCTCGGTACGGCTCTTTACACCGAGACTGAAGC*

*CGGTGTCAACGTCAACATCTACGCTTCCATTGCTTCATACGATGTCCCAGGTCCTACTCAATGGGCTTCCGCTACTGCT*

-continued

*TCCGTTGCTCAAGGTACTTCCGGAGCAGTTGCCACCGGAGCCGCCGTCGTTTCTTCAGCTGCTTCTTCAGCCGCCGC*

*CGTAGCTACCTCAAGCGCCGCTTCATCGGCCGCTGTTGTCGCCTCTTCCTCCGCTCAAACCAGCGCACAAGTTGCCG*

*CCGTCAGTTCCGCTGCTCCAGTAGCCTCCTCCTCAGCTGTTGCCTCCAGCTCCGTTGCTAGCGTTGCTTCATCAGTTG*

*TTGCCAGTTCCGCTGCATCAGTTGTTACCTCAGCCCCAGCTGTCACCTCGGCACCTTCAAACGTTGTCACTGATATGAT*

*CACCGACTACGTCACTGTTACTGACGTCGTAACTGTCACCGTTACCGCTGCATAAATTCTGAACCTCTTTGGTTTAAAA*

*TCAGCACCTCCTTTTGACTAAAAATCTTTTTGATGATATTTTGATGGTTTATTTTTGGATCTGATTCGGGCTATCGGGCAT*

*AGCTTGGATGGAAAATTTATGAGCCGCATGATGAGTTGGATAGGCTTCATGTCACTTTCTTGTATATATTATGTCCTGTA*

*TAAACAGAATTGAACATTTTTCGA*

BC1G_02429

SEQ ID NO: 72

*GCTTCAAAAAAAGTCGCGTCTCTGCCAAAAAGTTATAAGTTATAAGCTTATTGTAAGCTTTAACTTCCTTTCTCTCCAAG*

*AGCATTAAGCATTAAATTGCGCTCCTTCTTGATTTGCTACTACTCATCATCGAGAGTCTTTCTTTTCCCTTTCAATTTTAT*

*TCCCCTCAGGACCTTGGAACGAATTGAAACCGGTCACAATGTCGCTCTTCGGGAACACGAATCAAAACAAGCCGTCGC*

*TCTTTGGTGCACCGCAGACCACAGGAGCGTCTACAGGTGCTAGCACGGGAGGTCTTTTTGGTGGATTGGGAACGACT*

*GCGACTAGCCAGGCTCCATCAACGGGAGGAATGTTCGGTGGAATGGGTGCTACAAGCCAACCCCAATCGACTGGCG*

*GTCTTTTTGGAGCAACTACAAGCCAACCTCAATCAACCGGAGGCCTTTTTGGAGGAACGACTACAAGCCAACCTCAAT*

*CAACCGGAGGCCTTTTTGGCGGAACAACTACAAGCCAACCTCAATCGACTGGCGGTCTTTTTGGAGCAGCCAAACCTC*

*AACAACAATCAGGGACAGGATCCGGTGGTTTATTTGGAGGACTTGGAGCAACTCCAGCAGCAACCCAACCACAACAAA*

*CAGGCGGTCTTTTTGGTGCGACTACACAACCCCAAACTACAAACAACACAACTGGAGGTCTCTTTGGTAATTCTTTGGC*

*ACAACCACAACAGCAGCCGCAACAAAGTACTGGTGGGCTTTTTGGAAACACAACTACACAACCCAACCCTTCAGGATC*

*AATGTTCGGTCCTACTCCACAAATCCAGCCTCTCTCGCAATCTCGACAACAAAATGGAACCAGCGGTGCCTATTTTGAT*

*GCTATATTGGAGAAGAGTCGTAAGAGGGCACACGATGAGGATTCCTTGGGCTTACAATTAGGTTTGGGGGATATTCGA*

*CAGCGCATGAAGAGGCTGGCTCCTAGTACCCAAGATGGCTCTGTCGATGGAAGAGCTCATTACCTATTGGCAGCTTCT*

*GGCGTGGACCCAGGCGCTGCGCTCAGAGATTTGAATCTATTCACCGCTGCCACAGGAAGACTTGATAGGACAGCACC*

*TGTAGAAGCACCCATTGATGCGGATGTCGAAGCATACCTTACACGTCTGGAAACCCAAACCACAATGAGCATGATATC*

*TGAAGGGTTGGCACGATCCGTTCGAGATTTCGATGATTTCCTCGAGGAGAATGTTGCTATGGAATGGAGTGCACAGCG*

*CAAGAGAATATATGAACATTTTGGAATTAAGCCCAGAAGAGAACAAACAACAGGGCCATCAGTGAGCTTTGCAGCTAC*

*AGCTACAGAACCTATGGGCGGTTTTGGTCGATCAAGACGCGGCAAAGGACTCGCTCCTGGAGCATCTAAAGGGCCTG*

*GAATCCCGCGGGCTAGCGTTTTTGGAAAATCAAGCATGCAGAGATCTGTTATAGGAGCTATTACTCCAGGAGGAACCG*

*CAAACCGCACACTTTTTACTGATATAGAGAAAGCAGATACGAATGGGTCAGCACCAGGTCCAAGTGACCGATTCATTC*

*GCGAGAAGCAGGCTCGATATATCGAGAAAGTCCAGAACCTAAATGGTGCTAGACTAAAGAACCTTCACTACCCAATTG*

*CGAACGAATTCTCAGCTGTTGTAGCCCAAGGTAGCGAACAGCACTCTGCAGATGTTTACAGGGCATACAGATGCTTGA*

*TGGAAATCGTTGGTGAAGATCCTGACCCGGACAGACTACAACTCCCTGGCGCGGTCAAACAGAGACAGTTTGCAGCC*

*GCATACCTGGATGACAATACAAACTCAGCTCAAGCGGCCGATTTGAAAAAGCGGATACTCAGTGGATCACTTCGATTT*

*CTTGAAAAGGAGTTTTTCGAGAATGTAGAAACTATTGTTGCCAAAAACCCCAGGGAAGCACTTGTGGGTGGTAAGCCT*

*AGTCCTCTCACAAAGATCCAGGGTTATGTTCGTCTACGCTCAGCTCGTAAAGACCTTGCTACAGACATCTCCGCTCTAC*

*AAATTGTTAATGACGATTACGTCTGGGCAGTAGTCTTTTATCTTCTGAGATCTGGCCACGTTGAGGAAGCCAATGCTTA*

*TGTCCAAGAGAACAGGGAAGCATTCCGGGTAATTGACCGCAGCTTCATGTTTTACATCGCAGAATATGCCAATAGCCC*

*AGACAGAAAATTAGGACATGACCTTCAAAATCGCATTCAAAGCGAATACAGTCAGCGAAATCGAATTTCCCCTGAGGGT*

*TCTATAGATCCTTTCAGAATGGCATGCTACAAGATAATTGGTCGCTGCGAACTCCACGTTCGCGCTCTGGATCAAAACA*

*TTGTCCAAAACCAGGATGACTTTGTCTGGATACAGTTTGTCCTTGCGCGCGAAGCCAACCGAGTCGATGAAATTGCCA*

*GCGATGCATATGGACTCGCAAATGTACAAAAGACATTCAAAGATATTGGCGCCCGGATGTTTTCCAAGGGAAATGAAA*

-continued

*ATAGTGGACCATTTAGTGTGTACTTTGTGCTGTTGGTACTTTCAGGCCTATTCGAAGACGCAATCGACCTTCTTTATCG*

*CCATAGTATTTCTGATTGTGTTCATTTCGCCACGGCACTTGACTTTTACGGCCTGCTTCGAGTCTCAGATCCAGATGTT*

*GCAGAGGGTGGATTCTTAAGTTACACAATAAGACAACAACCTCAGATAGCATTTGGATTAATGATGGGATTTTACACTG*

*CAGAATTTAGAGCTGCAAATGTCAGCGCTGCCGTGGATTATCTCACCTTGATCTGCCTTAATAGTGACCTCAAAGGCG*

*ATGCTGGCTCAAAACAAGTCGCATTGTGCCACGAAGCTCTCCAAGAGCTGATTTTGGAAAGCAGAGAATTTGCTTTGTT*

*GCTTGGAGATATCAGACAAGACGGAAAGCGCCTAAAGGGAGTTATCGAAGAACGCCTGGAACTCATCAATCTCAGCA*

*GCGCTGATGATTTCATGAGAACAGTGACGATACAGGCAGGAAGTGTCGCGGATGACAATGGGCGAACCACTGATGCA*

*GTCCTACTTTATCATTTAGCAGAAGAGTATGACAACGTCGTTACTATCCTTAACAGAGCCCTTAGCGAAGCTATTGCCG*

*TGCCTGTAGGCCATAGCCCGTTGCGATTACAACCACTCAAGCCAAGGCCTGGAGACAAATCCGGAAGAGAGGCCCAT*

*ACCAGTCTCAGTCTTACCTCAATTGATGATCCTTTCGAATTGGCTACCATCATGACGAAGCTCTACTCAAATAATCGCAT*

*GTATCTCAACAAGATCAAGCAAGAAAACCGCGCAGCTTGTGAGGCTTTGTTAAATATCTGCCGTGCTAAGGAATTTGTT*

*GAAAATAGACAATGGGCTGAAGCATTAGATGTTGTGCAGAATCTTGACATTCTTCCCTTGAGCGCCGAGGGCAACCCA*

*AGTGCAGTACGAAGTTATGCCACCAAATTTTCATCACTCTCCCAAGAGGTCGCAAACACTATCCCTAGTCTTTTGACAT*

*GGACAGTCTTGTGTTGCAACAACCAAAGAACTTCCCTCATGAATGCCCAATACGGAGGTAATGAGGGTACCAGACGAC*

*TGATGATTAATCAATTGAGACAACAAAACATGGACTTAACGACTTATACCAGTCAATTAAGATACAGATTCCCTGCGTCT*

*CTTCATGAAGCTCTTGCGAGGGCTCAATCGGAGTAAGGGATGAACATATGACATGAGCTTATGAGCTTGAATGTATATT*

*AGAACAGCACAGTGGGAAGAGATTAAAAGGGCATTTTGAGTTTTTATCTGGACGGAACGAAATGAAAACATTGGGGGT*

*CTGTCTACTACTTTTGTAGTTGATTTTTACAGTTTCTCATGAACAAGTGCATAGATGAAGAATGTATTGTGTTGTCTATTA*

*GAAGATTAATTATGAGTGGTTAATGAATACAGAATATCGAGATCTCGCTTCCA*

BC1G_09103

SEQ ID NO: 73

*GCAATCAATCATCTAATCGCGACGACAACTTTCAACAATTACCATATTTCAACAATCATTTGGAATCTTCTGCGATATAC*

*ATTGAGGAATAATAACGACCACAGTCTCCGGCTCATGATCGCAAGTAAATCTCAAGATGGCTGATCAACCACCAGCAA*

*TGCAGCATGAGGACTCCATCAGTTCGCAAGATCCTCATTTACATGGCGACAAAGGAAAGACGAAGAGTAGACGGCCA*

*GCAAATACGGCATTTAGACAACAAAGATTGAAGGCATGGCAACCGATCTTAACACCAAAAACCGTACTCCCATTATTCT*

*TCGCCATCGGAATCATTTTCGCGCCAATTGGTGGAGGGTTGTTATATGCTAGTAGTGTGGTCCAAGAAATTGTACTCGA*

*TTATTCGAAATGCCACACAGATGCGCCAATCTGCACGGACTACCTCGATACAGGCTCCCTGATGCCCGATGACAATGT*

*TGAAATGTTTTTCAAAACACCTCACGTATATGATGGAACTCCTCCGCAATGGTGCAGACAAGATATCAACCAAACATAC*

*TACAACGGCAGTGTTGCGCATGCTACTGTTCCCGCTGTACAATGCCGGCTCACATTCCCAATCAAATCCGAAATGGAG*

*CCTCCTGTTTTATTCTATTATAAGCTCACCAACTTCTACCAAAATCATCGACGATATGCTAAGTCCTTCGATTCCGATCA*

*GCTTTCCGGCAAAGCCGTTACCGCAAGTACCATACATTCTGGTGATTGTACGCCACTCACGACTGTAAATGATAATGGT*

*GTCGACAAGCCATATTATCCTTGTGGTCTAGCACCAAACTCTGTGTTCAACGATACATTTTCAAGTCCATTCCTACAAAA*

*TGTCGCAAACAGTACTTCAGGTGGCGTAGTCTATCCTATGAAGAACAACTCGGATGTATCATGGAGTAGTGATAGAGA*

*GCTATATGGTCAAACAAAGTACAACTGGTCGGACGTCATTGTTCCTCCAAATTGGGTTGAGAGATATCCAAACAATTAT*

*AGTGACGATTATCATCCCGATCTCGAGAACGATCAAGCATTCCAAGTTTGGATGAGACTGGCTGGTTTGCCAACATTTA*

*GTAAACTGTTTCAGAGAAATGACGACGATACTATGACGACTGGACAATATCAAGTCAACATCACACATCTTTTCAATGTT*

*ACCGAATATGGCGGTACTAAATCAATCGTTCTTTCAACCCGTACCGTTATGGGTGGTAAGAATCCTTTCCTAGGTATCG*

*CCTATATCGTTGTTGGAGGTTTATGTATCCTACTCGGTGCACTTTTCACCGTCACTCATCTTATAAAACCAAGAAAATTG*

*GGCGATCACACATATTTGAGTTGGAATAACGACAACCCTACAACGGCGACTACCAGTGGACGTGAAATGGGTGCGAG*

*CATGGGATAGACGCTGGATCGATATCGAATCAAAAAAGGGGACGTGTAAAATAGTGATGGATGATGAGATATGAGGCA*

*GGGTTGTTGTATTCGAACATTTTCTTCTACGTTACCAATGGGCAATATGGCGTCTAGGTATTATGAGCTTTTGATCTGTG*

-continued

*CTGCTTTTGAAAAGCATTCTGCGATGCGAGGAAAAGTGGGTGGAGGGAATCTTTGGCTGGACTGGGGAATCAATGGG*

*TGCTATGAATATTTTGTGCTCTTATTTTTTTGAATTAGAAAGAAACTTATAACTTTGAAATATACCACAGATGAAACTTGTA*

*AAGGCGAATGGACTTCTGGTGTTCTCGAATAGCCAAACATA*

BC1G_02638

SEQ ID NO: 74

*GGATGCATTTCAAGATTGGGATTCCATTCCATCTTCTAGGCAACTATTACGTCGACCCACCATATTTCCGGCTTTTTGAT*

*GAGCAAGGTTATGTTTCCCGGTAAGAATATATCATTGCCGTCATGGCACCTCCAGCGAAGAGACGGAAGCGTAGTGC*

*CATTGAATCCTCTCCCCATTCCTCTGAGAACGAGGATAATCAATCAATTCAGGTGAACAAGTTCAAAGGTCGATTGAGC*

*AGTTTGGCACATTCTCCTCCACCAAGATCGAGCTCTTCTGAGCCTGCCCCAAGGTCTATGTCGCAGTCCAGTAATTCTA*

*CGAGATCCTCTTCTTTTTTGAAACCTCCAGCAAAAGCGGCCATTCATCCTCACAATGCTGCCCCGGTCTACTTACCAAA*

*CCACCGTAAGAAGTCCACTACAAAGAGTCCCAGCACAAGTCCAGAGAAACCAAGAAGTAAAGGAAGAGTTGAGGAAA*

*AGCGGCAGAATGCAGATATTCATACGTTGTTTGCAAGACAATCACAGAGGCAGCAAGCACAAACGGAAGGCGAGACG*

*ATACCCAAACAAAGAATCAAGGTTCTTAATTCGAGAGATATTCAGCAGGAGACCGATTTAATAGACGATTTAATATCAGA*

*TGATGACGATGTGGGAGAGGGTCAAGCGCAAGCAATTAGCATTGTTGGGCAGGCCGCCAAACGGGGACTTGGAAAG*

*AACGTATTCATAAATTCAGGTACAAACACACCCAGCGCCAGTCAAAGATTTGTAAGACCGTCTCAGGCTTCTACAATAG*

*AACATATGGTCGAGGAAGAGGATATACGACCTTGGGCTGAACGCTTTGGGCCAAATAATCTGGAAGAGCTTGGGGTT*

*CACAAGAAGAAAGTAATGGATGTTCGAACCTGGCTTGATAATGTTATAGGAGGGCGGATGAGACAACGGTTATTGATC*

*TTAAAGGGTGCTGCCGGAACCGGAAAGACGACAACAGTGCAGCTATTAGCGAAAGATATGGGGTGTGATGTTCTAGA*

*ATGGAGGAACCCTGTTGGATCAATCGATTCCTCAGACGGCTTTCAGTCAATGGCTGCACAATTTGAGGATTTCATGGG*

*GCGGGGTGGAAAGTTTGGTCAACTAGATTTATTTTCCGACGATCATGGAGATATTCCAGCAGAAGCAGAAGTAAAACC*

*GTTGGATCAAAGGAAGCAAATTATACTAGTCGAAGAATTTCCAAACACTTTCACGCGTTCTTCAAGTGCCTTGCAATCAT*

*TTCGATCTGCGATACTTCAATACCTTGCATCTAATACTCCTCTTCTTTCAATGTCACACAATCCTCACTTTAAAAGTGATC*

*CCATCACTCCTGTGGTAATGATTGTATCAGAAACATTGCTCACAACGACATCAGCGTCTGCAGACAGCTTCACTGCTCA*

*TCGTCTTCTTGGGCCAGAGATTCTTCAGCACCCGGGAGTAGGAGTGATAGAATTCAATTCTATTGCCCCGACCATATT*

*GGCAAAAGCTCTCGAGACTGTAGTACAAAAAGAGTCGAGAAAATCAGGCAGGAGAAAGACACCAGGACCCCAGGTAT*

*TGAAAAAGCTTGGGGAGGTGGGCGATATTAGAAGTGCAATTGGCTCTTTGGAGTTTATGTGTCTAAGAGGGGATGTCG*

*ATGACTGGGGAGGCAAAGTTGTTTTCGGCAAGGGAAAGAAAACAAGCAAAGATACATCTTTGACAAAAATGGAAGAGG*

*AATCGCTGGAGCTGATCACTCGCCGCGAAGCTAGCTTGGGAATCTTCCATGCCGTTGGGAAGGTTGTTTACAACAAGC*

*GCGAAGGAAAGGTATCAGGCGATGTGGAATCTTTGCCACACTTTATATCTCATCAATCACGTCCTAAGAAATCTGAAGT*

*AGGCATAAACGAGCTTATCGACGAGACTGGCACCGACACACCAACCTTCATAGCTGCCCTTCATGAAAATTACATCCTT*

*TCATGTGAAGCACCACCCTCTTCCTTCGAATTCTCATCTCTTGATCACGTCAATGGCTGCATCGATGCCCTCTCTGACA*

*GTGACCTCCTCTGTCCCTCTTGGGACGGTTCCATCCAATCCTCCGGCTTCGGTGGTGGCATAACAGGAACCGGAGGC*

*GACATTCTCCGCCAAGACGAAATGTCCTTTCAAATTGCCGTCCGCGGTATCCTTTTCTCACTCCCTCACCCCGTATCTC*

*GTAAAGCACCTGCAGCAGCGGGGTTCAGAACTGGCAAAACAGGCGATGCGCATAAAATGTTCTATCCCACCAGTCTC*

*AAACTCTGGCGCATGAAAGAGGAAATGGAAAGTACACTAGATCTCTGGGTTACACGATTAATAAAAGGAGAAATTGATC*

*CCACGAGTACGCATGCGTCAAGTATTAAATCTGGCGCTGCAGTATTCGCTCGTCCTAAAGCTGGCACAGTCGAAAGCT*

*GGAAAGTGAAAATCGCCGCACCATTGCCCTCGCAATCAAAATCCAAATCCAGCCTCAACACTCCAAAAGAAGAAGACA*

*GCCCACCCCTCCTCACCCTCGGCGTCTCCGCTCGTACAGAAATGCTCCTCGAGCGTCTCCCCTACATGATCCAAATCT*

*CCAAATCCAAATCATCCCACCAATCGCGCAACCCATTTTCTTCCTCCTCCTCCTCCTCCTCTTCCACTTCCGCCATCAC*

*GAACTTCCAAAACAACCCCCTTCTCGCCTCCCTCTCTAAAATAACAACCTTCACTGGCATCGGTCCCGCGCAAACCTC*

*CGACGACCCCGCCTCCCTTTCCGATGACGAATCTCCCAATCCCAATACTGAAAATTGGGCCACCGATAAACCAAACGG*

*TAATGGTATGGATACACCTCGGAAGAAGAAGCAAGGCGGGAATATGGGGGTTTTTATGAAGAAGGGAATTGGTAATCA*

-continued

GAGAGCAATGCCCATGCAGCAGTTGGAGCAGAAATTTGTTTTGAGCGATGATGATATTGAGGATGATTGATTGATGATT

GGAATCTGGATTGGGAGTGGGGCCTCAAACGCTTGATGAATATGGGGGTTTTGGGTGATATGCTTGAGGTGTTCGTG

GATGAAAGGCATGTGTTTTTTATGATCCGGGATGAGATGGTTTGGTATTTACTTCTTTGTATTGTATTTTGAAAATCAAAA

TTAACATCGAGTTTCACCGCGTTTCAATTCTTTTGCGCGTTGTCATTCTACAAAATATCAAACTACTTATTTCTATACACA

BC1G_02869

SEQ ID NO: 75

GAAGCTCAGAAATTCATCTCACAATATTAATATGCCCTTAAATCGGTAACAATGAAGACGGAATTTAAGTTCTCCAATCT

CTTAGGGACTGTTTACAGCCAAGGAAACCTTCTCTTCAGTCCAGATGGATCATGTCTATTTTCTCCAGTAGGGAACAGA

GTCACAGTTTTTGATTTAGTAAATAATAAGTCACATACACTTCCATTCGCACATCGAAAGAATATAGCACGGTTGGGACT

TGCGCCGCGAGGAAACTTATTGCTTTCAGTCGATGAAGATGGCCGCGCGATATTGACCAATGTACCGAGAAGGATTGT

CCTTCACCACTTTTCTTTCAAATCAGCTGTATCCGCCATATCGTTTTCGCCATCTGGGCGCCATTTCGCTGTGGGAGTT

GGACGAATGATCGAAGTATGGCATACACCCTCAACACCGGATACAAATTCAGAAGGGGAGTTAGAGTTTGCGCCATTT

GTTAGACACAGAGTATATACCGGTCACTATGATACTGTTCAAAGCATCGAATGGTCGAGTGATTCTCGTTTTTTCCTTAG

TGCAGCAAAAGATTTGACAGCCCGGATATGGAGCTTGGATCCAGAAGAAACCTTTATACCTACTACATTGGCGGGCCA

CAGAGAAGGTGTTATGGGCGCATGGTTTTCGAAAGATCAGGAGACTATTTACACTTGTAGTAAGGACGGAGCAGTATT

TCAATGGGCGTATATACGGAACCCCAATGCTCCTGAGCCAGAGGATGAGGATGAGGATATGGAAAATCCGGACGACG

ACTCGCACATGCAATGGAGAATTACGGAGCGACATTACTTCCTACAGAACAACGCTAAGGTCAATTGTGTTGCATACCA

TGCCGAAACGAATCTTTTGGTTGCAGGATTCTCGAATGGTGTATTTGGACTCTACGAAATGCCAGAATTCAACATGATC

CATACCTTGAGTATCTCACAAAACGATATTGACTTCGTCACAATTAACAAGTCTGGAGAATGGCTCGCATTTGGAGCCT

CAAAGCTGGGGCAACTCTTAGTTTGGGAATGGCAATCAGAATCATATATCTTGAAGCAACAAGGCCATTTCGATTCAAT

GAATTCCTTGGTTTACTCCCCAGACGGACAAAAGATTATCACCACTGCTGACGACGGAAAGATAAAAGTTTGGGATGT

GAATACTGGTTTCTGTATAGTCACTTTCACAGAACATACCAGTGGAGTCACGGCTTGTGAATTTGCCAAGAGAGGAAAT

GTTCTTTTCACATCAAGTCTTGATGGGTCGATAAGAGCATGGGATTTGATAAGATATCGAAATTTCCGTACTTTTACAGC

GCCCACTAGACTTTCATTCTCATCCTTAGCAGTTGATCCCAGTGGCGAAGTCGTTTGCGCGGGATCTTTAGATTCTTTC

GATATCCATATTTGGTCGGTACAGACTGGTCAATTACTAGATAGATTATCAGGTCACGAGGGACCTGTATCATCACTAG

CTTTTGCGCCAAATGGAGGTGTAGTAGTAAGTGGAAGTTGGGATCATACAGTTAGAATTTGGTCTATTTTTGACCGTAC

ACAAACGAGCGAACCGCTTCAACTTCAAGCGGATGTATTAGATGTCGCATTCCGTCCCGATTCACTACAGCTTGCTGT

CTCAACACTAGATGGACAGTTGACATTCTGGTCCGTTTCAGAAGCTGAACAACAGTCAGGTGTTGATGGCCGAAGAGA

CGTTTCAGGTGGTCGAAAAATAACCGACCGAAGAACCGCCGCTAATGCTGCGGGCAACAAAAGTTTCGGGTCCCTTA

GATATAGCGCAGACGGATCCTGTGTTCTTGCAGGTGGTAACAGTAAATACATATGTTTGTATTCTGTAGACTCCCTCGT

CTTACTGAAGCGATTTACCGTCAGTGTCAACTTATCCCTATCCGGAACGCAAGAGTTCCTCAACAGCAAACTTTTGACC

GAAGGTGGACCAGCCGGTCTTATCGATGAGCAAGGTGAAGCCTCTGACCTCGAAGACCGCATCGATCGATCTCTCCC

CGGATCAACCCGCGGTGGAGATCCTTCCGTCCGCAAAAGACTCCCCGAAGTACGCGTTGCCGGCGTGGCTTTCTCTC

CCACAGGAAGATCCTTCTGCGCAGCCTCAACAGAAGGACTCCTCATCTACAGTCTCGACACTATGCCCCTCTTCGACC

CCATCGATCTCGATCTCGCCGTCACCCCCTCCTCCACTCTCCACGTCCTCAACATCGAAAAAGATTACCTCAAAGCTCT

CGTCATGGCATTCCGTCTCAACGAAGCTCCGCTCCTCCGTCAAGTCTTCGAAGGTATCCCACACCCCAACATCGCGCT

CGTAGTCGCTGAATTACCAGTCGTTTACATTCCTCGTCTGCTGCGTTTTGTAGCCATGCAAACGGAGGAATCCCCTCAT

CTGGAATTTTGCTTACTCTGGGTCCAAGCGATACTCGTTTCCCATGGTCAATGGGTTGGCGAAAATAGAATTCTAGTGG

ACTCAGAACTAAGAATTGTGGGGAGAGCAGTGGGCAGGATTAGAGACGATTTGAGAAGGCTGGCGGATGAAAATGTT

TACATGATTGATTATCTACTTAATCAACCATTAGAAAAGGGAATCGAGGGTACAGATGCAGGGGAGAAGGATGTAGTG

GTCAAAGATGTGGATATTAATGATGATGATGATGAGGCGGAATGGATTGGTCTAGATTAGGTTGTATCATATTATATGG

-continued

AAGGAAAAAAAAATTTAAGCTGGTTTTTGTACTCATTTTTGAAAACTTGGTTGTGTGTATTATTATTGTTGTTCTCGTTGTT

GTTGTCGCCTCCCAATTTTGGAAGATCTTGTATATTCGTTGATCAATTATCAGGATGCATACTCTGTCTGCAAATCAACA

TCAGTCTCGCCAAATTCTCTTTTGCATAAATATTTACATTCCCATCACAATCTTCACCCCTATCTCTATTCGATGCAGATC

CTTCTCTTCTAGAATAAAAGGTCACTCACTATTAAAATATCATCAGCCGCTTTTTCTCATCGCTCACA

BC1G_09169

SEQ ID NO: 76

GAATTCGAGTGTGATCAGTGCGAGAGTGCCGGCACAATGCAGGTGGGTGGGTGGTACGGAAGACGAAAAAGACACG

GCCCGAGGTGAGGCTCATCACGACGCCAACAATTCCATACTGTTGTGAACCTCCAATAGATGTCTGGGCGTTGCGGT

ATCCATACGTCCAACTTGCATCTGCGTACGAAGGAATCACATATGCATGAACATGAACATGAACATGAAGTGGCAAGAT

GGTTGGATCGGGTCAATCAATGGCGCGCATCTATTGACTGTTGCTTGATACAACCGAAAGCCGACATTCTTTAGCGTA

AGGGCTACCAAGGTCTGTGCATTGATGGGTACCTCTGGCCAGTCTCGAGCCAGTCCTCCGCATTGCGAATCCTCGCT

GTGTCAAGTCGTTCATATGTAGACATCCGATGTTAACGTGGACTTGCTGTCGATTGACACAAATATATAAACACCTTGG

ATCATGTGTCGTTCTATCGCCACGCATTTATATCGAGGGGATGTTATTTCCACATCCAAGCTTTGCGGCAGAAAAGAAG

TGCTCCTGGCGCACCGAGTCAAGCGTCAGCAGAGTAAGCAGAGTCAGCAAGCAATGGATTATTCAATGGGAGTCTCG

TGCGACCTTATCGGCTGCCAACTTATGCACGTCTTTTCTTCCGAGCAAATGGTTCGACAGGAGCCTTCCTTTTTGCGGA

GGCGACAGCGAATGGCATTTGGGCGCAGTGTCTGCCTATCTGGTAAGCTGATGAAGACGGAGAGTGCAAGGCTGGA

GAGTGATGGTGATTTAAGCATCCCATCGCCATGGTGATTTGACGTAAGAGATCGTTGCTTTCGTTTGATTATCGTTGGT

CTTTTTTTCTTGCCTTTTCACTTTCGCAGACAATCATCAATCATCAAAGGTATCATGTCTTCTACGGCATCTTCAAGCGAT

TCCGATAACAGTAGAAGACGACGCCGACAGGGTCCAAGACCCTCACCACCACCTCCTCCTCCGCCGTTTCAAGGGAA

CAATAAGAAATCAAAGAAGAGGAACAAATACGTAGCCCCTCAAGATACGATCGATAAACTTTGGTCTCGATTCTCGGTA

TCAAAATTTAGTAAAGCTACAAAAGTTTTACCAAATGCAGCACCTTTTGCGAAGGGCACATCTGCAAAGACCGTTATTGT

TCCTCCACCTGGTCCGCAGAACCAGCTCGTTTCCGAAGACTTTGAAAGAGCGGTTCAAGAATGCAGAGCCAAAGTCAA

GAAACTTGTTAAAGAATGTAGGCGCGTTAATATGCGGTTTCGCGACGCCAGCTTTGATATAGACTGGGACTTGAAATG

GGAGAAAGGAAATTGTCTAAATACACTTGATGAAATAAGATTTGAAGTTTGCAAACAGGCTCTTCTCAATCCTACATCCT

CCGGGCCGAAGGCCGTCAAGAGAGTTCACGAAATATTCGATAAGCCAACATTCTTAGGAGATAAAATTTCTCCTTCGG

ATGTCAAACAAGGAAGTCTTGGGGATTGTTGGTTGATGGCTAGTTTGACAGCATTGGCAAATACAGACGACGGAATTC

AAAGAATATGTGTTGAATGGGACACAAAAATTGGGATATATGGTTTTGTGTTCCATCGTGATGGTGAATGGATCATTTC

GATCATCGATGACAAGCTCTATCTAAAATCGCCAGATTGGGATTCACCCTCGGTCCACAGGCATCTACTCGAGCAAAC

TGACCGAGAGGATGTTGAAAAGGATTATCGAAAAACGTATCAAACCGGATCTCAGTCATTATTCTTCGCTCAATGTAAA

GATCCAAATCAAACATGGCTTCCTCTTCTCGAAAAGGCTTACGCTAAAGCACACGGGGATTTCTTTTCTTTGAGTGGAG

GATGGATAGGGGAGGGTCTTGAAGATTTGACAGGAGGCGTAACTACGGAACTTCTTACTTCGGATATTCTTGATACCG

ATGAATTTTGGCATAATGAAATTCTCAAGGTCAATAAAGAATTCCTTTTTGGTTGCTCTACTGGTCTTCTCGATTACGGTT

ATGGCAATAGAGATGGAATATCTGAAGGCCATGCATACGTTATTATGGAGGCTAGAGAGTTATCTACTGGCGAACGTC

TCCTAAAATTACGGAATCCGTGGGGAAAGATCAAAAAAGGTAATTGGGAAGGTCCATGGTCAGATGGAAGCAAGGAAT

TCACCCCTGAAGCTCAGATAGAGCTCAACCACAAATTTGGAAACGATAGTGTTTTCTGGATTTCATATCAGGATTTACTA

CGCAAATATCAACATTTCGATCGCACTCGGTTGTTCATGGACAGTCCTGATTGGAGATTGACCCAAGACTGGGTCAGT

GTAGAGGTGCCATGGAGATCCGAGTTTGAACAGAAGTTCACCATAACGCTTAAGAAGGAATCACCCATAGTTTTGGTT

ATGAGTCAACTCGACGACAGGTACTTTATTGGTCTACATGGTCAATACAACTTCAGATTGCAGTTTCGGGTTCATGAGA

TTAATTCACCCGATGAAGAAGATTATATCGTCCGAAGCCATGGGAATTATCTTATGAGGCGAAGTGTGGTTGCTGAATT

GAAAAGTCTCTCCGCCGGAACATATACAGTATATATGATGGTCATAGCAGAAAGGGATAAGGATCGACAGAGTGTTGA

AGATGTCGTTAAAGATGAATTGAGTCAAAGGGAAGATAATGAAAAATTAGCTAAAGTTGGTCTAGCTTACGATCTGGCT

CACCAGAAAGGATTGTCTCATATGGAGTTAAGAATTAAATCCAGAAAGGCTCTAGATAAAGCAAAGGCCCGAGAATCC

-continued

```
AGGATTGCTAAACGTAAAGTCCTTTGGGAGAAAAGACACATTGCGCGGGAGATACTAAGGAAGCAAAAGAAGAAGAAT
TATGAGAAACGTGAAGGTAAAGCAGCAAAAGATACTGAGTGGGCAAAGGAACAAGAAGAACGTGAGCTAAAGGATCA
AGGTGTTCAAACGGAAGATATTCCAGAAGTTCAAGTCGAGAAACAAGACAAGTCAATGCAAACCGAAGATCTCAATGA
GGAGTCAATGAACACTACAGTTGATACACAACCCACAAATGAAAGGGACAAAGCAGTACAGACAGAAGGCTTTACACC
ATCTTCTAATGAGTCCCAGACAACTCCCGTAACTCCAAAGAGTAATGGTTCATCTCCACGTTCACCGTATACGATGATC
TCGAGATCCGGATCTAATCGCCGCAAATCACTACCTCCACCTCCAAGCTTTGTTAATCTTCGTAGAAATCCGAGTCGTC
CACCAAATCATGGTCGAGGGCCTCCTCCTCCTTCTTCGAAACCAGGTCTATATGTTACTTCGGAGGGGGAGTCAAGTG
CAAGTCCTCTTTCGGATTATGATATGTATAGTGACGATGATCCGACTCTTAAGCCACGAAATCAGTCAACCGAGCCGAA
ACGCCCAAAGGAAAGGGAGGCTGGTGAAGATGAGCCAGAACCATGGAATGCGGTTTGTATCGTTGGCTTCAGGGTTT
ACAGTAAGGATGAAGGACTAGTGCTTACTGTTTGCGAGGAGGGTATGGAGGAAGTGATTGAGTTGAAAGAGGATAGT
GAAGCTGGTACTGATGGTGATGTGGAAGATGCTGAAGATGAAGATTGCCATGAGAAGAAAGGAGGAAATGGGGAAGA
TTTGAAATTAAAAGATACTGCAGCAGGAAACGACTCAACACTTTCAGATGTCGCAATCAAAATTGAGCCTGACAAAGAT
TTGAATGTCGCTATCTCCAATTCACCTTACGAGATTACTGGAACCTCTTCGTCAGTCAACAATGGCCTTGAAGAAATTC
CTACCGAGAAGCAATCCCAAGAAGCCACCAAAATTTTGGAAATAGAGACAAACGGCGACGCTCAGCAGAAGTCGGCT
CTTGGGATCTCGGAGGGTGCTACAGATGATATCGTGAAGGAATCAGATTCTCAATCCGGCATTGCAACATCAAGCGCT
TCTTCGAACTGCACTTAAAGCTCACACTGATTTTTGTTCAGGTAACATTCAGTGTACAATTCATTCTTCAGATCAGTGCA
CAATGAAAACAATTTCTCGTTTTTGGAAGCCCCATTTTGATCTTTCAAGCGATTCAGGCAGTCTAGGCGGTCTATGCGA
GCTTCTCGGTTTTATCTTCAGCAAAATCTTCGAACCCGCATGTAGTTCTAGTAATTCTAGTGATTACATTCTCATGACTA
ATGAAATTTTTCGTAATATCTGTAGGTAGATACAATGATGTTAGTATTATTCCCATCAATGAATATATTCAGACTACTCAA
TCAACACAATTTTCATTGGCCCTTTCTCA
```

BC1G_07037
SEQ ID NO: 77

```
GATCAACAATATCCATGAACGATATCCATGGAGAAGAGAAGAAAAGAACCTTGCCTCCACCACCACCACCTCCACTCTT
CACATTGACTCCTCTTGAGTCTTGAGAGTCGAGACATGCGAGACATGGTCGGATAGACATTAAGCGAAACACCGATGG
CGAAAAATTTGATTTTCACAAGCAAAAAACTAGTAAAAGTAGAGGGAAAGCCCAGACAAAATCCGAATTCGATCCGACC
CTTTATCTTGAAAATCCTATGCAGAGTAATAGTTATTCCTATCTTACTAACAAATTCCATCTTCCTATAAGTTAACTATCTG
ACTCTCCCTCCTTCTTGATTACTACCAACGAGACATCACACATCATCCTTTTGTTTTGTTTCTGCGATACAAGTACAATA
GATCAATACATCAACACATCCCTACGATATCTTCTTACCCGTTCGAAGCTTCAAAAAAAGGGTCCAAATCTCCAACAAG
CACACGACCAAAGGCACACGATCAAAATGAAGGTCTTTTCTAGCGACTGCAAATTCGATTATTCGTGGGAAGAGGTTT
CGACTGCAAACTGGAGAAAGTACTGTCCATGGAATCATAAATCTACTCACGTTATCGCCGTCGATACATTATCCCGACA
TGTAGATGCTGACACCGGAATTCTACGCACCGAACGTTTAATTACCTGCCAACAATCTGCTCCAAAATGGTTACAATCA
CTCATGGGCGGCAAAGATACATCCCACGTCTTCGAAACCTCATATGTCGATCCGATTACCAAGAAAGTCACAATGACAT
CTACCAATCTCACATTTTCCAACATCATCAATGTGCAAGAAACAGTTGTCTACCAACCCTTATCGGCAAACACAACACAA
TTTGTCCAGGCGGCACAGATTACTGCATTATGTGGTGGATGGCAAAAAGTGAAGAATGCAGTTGAAGACGCGACAGTT
ACTGCGTTTTCGGAAAATGCACGCAAAGGAAAGGAGGGATTCGAAGCAGTTTTGGCGATGAGCAGGAGGGTATTCAG
TGAGGAGAAAATGAGACAACAACAAGCGGCTACCGTTACTGCATAAAGTTCGAAATTTCAAAGGCGTTTTGAAGAGGG
GTTTCCGTGAAGATATTCCGGTTCGGTCCGAGATATACATGATGAGATTCATATCATTTGAATCTCCTCACATCACGACT
GAAACGATTCCTCCCTTGTCCTTTTTCTTCACTTCACTTCAACCATCTCCTCACTTCATTTCGGCATTTACGAGTTTCACA
TCATTTTAGGAGTTTGGGGATTTTTTATTACAAGTTCCGGTATACAAAAAAGTCCACTTTCGGAGTTCTAGAAGGCGAAA
TTCTCGGTTGCGAATTCTATTTTAAGCGCGGCGTTAAAAAAGGATAAATGGGATATTTGGGTTAGGTTGGGTTTTGCTT
CAAAAAGACGATTGTCTTTTGTTGTCTTTGAATGGAAAAGTTATGATATTCAAAGAAACTTTCATCCTCAACGCTGATGT
```

-continued

*GGGTTATTGTTACGATACAGATACCCCTTTTTTCCTTCTTTCTTTTTTTGCGGTGCTTTTTTTTTTTTTCTTCTTTGAAGGGG*

*GAGATAAAAATAGATGGATAGATGGGTTGATTTTATAGATGAGGCTGAATAGGGAGATGATGTAGATAGAGTGAGCGA*

*GTCAGTGGGTGAGAGACTTGAAGAAAATAAATATTAGATTTTACTTTATA*

BC1G_10614

SEQ ID NO: 78

*GATTAGCCTGGATATTTTGGAGTTGAATGCTTGGAGAAACTTGGACCCAAAATTTGACCCCTCCTTCTATCGACTTTTC*

*CAATCACAAATTCACAAATATAAACCATTTCATTGCCAGCTATCGATTTTGTATGTTTAGAAATACAATCAAAATGGCAGA*

*AACAGCAGCAAAAAGACTCAAGACCTCTCCCGTTACCATCGGTACTCATAATGGCCATTTTCACGCAGATGAAGCCTT*

GGCTGTTTACATGCTTCGCCTTCTTCCTACTTATCAATCTTCAGAGCTCATTCGAACTCGGGATCCCAAACTTCTAGAG

*ACTTGCCATACCGTGGTTGATGTGGGAGGTGAATACAACGACGAAACTAAGAGATATGATCACCATCAACGTACTTTC*

*GATACCACATTCCCAAATCGTCCTACCAAGCTCTCTTCTGCGGGGTTAGTGTATATGCACTACGGCAAGGCGATTATC*

*GCACAACATCTAGGTGTCGCCGAAGATGCGGAAGAAGTTGCCGTTATCTGGAGAAAGATTTACGAAAGCTTTATTGAA*

*GCACTTGATGCTCACGATAACGGTATTTCAGTCTACGACCCAAAGGCCATTTCCGCCGCAGGCTTGGAGAAGAAGTTC*

*AGCGACGGAGGTTTCTCATTAGGGGCTATGGTATCCAGATTGAACCCAAACTGGAATGACCCCACTCCATCTGATCCT*

*GTCGAGGCTCAAAAGGCAGAAGATGAGAAATTCTTGGTAGCCAGCACTAGAATGGGTGAAGAATTCTCAAGAGATTTG*

*GATTACTATACAAAATCGTGGTTACCAGCACGATCAATTGTCCAACAAGCATATGCCAAACGCCTACAATACGACTCGA*

*AGGGAAGAATCTTGGTGTTCGACGGTCAATCTGTTCCATGGAAAGATCATCTCTACACACTGGAAGATCAAGAGAACA*

*GCGAGAACAAAGTACTCTACGTTCTCTACCCTGAAAGCCCACGTCCAGATGCGAAATGGAGAATCCAATGTGTACCAG*

*TCACCAAAGACTCTTTCCAAAGCAGAAAGCCATTGCCTGAGGCATGGAGAGGTTTCAGAGATGAGGAATTATCTCAAA*

*TTACTGGTATTCCAGGAGGAGTATTCGTTCATGCAGCGGGATTCATTGGAGGAAACAAGACTTTCGATGGGGCAAGTA*

*AGATGGCAGCAACAGCGGTTGATTTGTGATATCCACTAAAGTCATGAAAAACATTATTATGAGGCGTTGTTCGGTATCA*

*AAAGCCAAAAGGTTAGATAGGTTCAAGAAATATAAAACCCAAATCGATGTGTTCATACACATCGGAATCTCAAAGACA*

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A pathogen-resistant plant comprising:

(a) a heterologous expression construct comprising a promoter operably linked to a first polynucleotide that inhibits expression of a first target gene of a fungal pathogen and a second polynucleotide that inhibits expression of a second target gene of the fungal pathogen; or (b) a first expression construct comprising a first promoter operably linked to the first polynucleotide that inhibits expression of the first target gene of the fungal pathogen; and a second expression construct comprising a second promoter operably linked to the second polynucleotide that inhibits expression of the second target gene of the fungal pathogen;

wherein the first and the second target gene are selected from the following three target genes of the fungal pathogen: a DCTN gene, a VPS51 gene, and a SAC1 gene; and wherein the plant has increased resistance to the fungal pathogen compared to a control plant lacking the expression construct of (a) or the first and second expression constructs of (b).

2. The pathogen-resistant plant of claim 1, wherein the fungal pathogen is *Botrytis, Verticillium*, or *Sclerotinia.*

3. The pathogen-resistant plant of claim 1, wherein the first polynucleotide comprises an antisense nucleic acid or inhibitory RNA (RNAi) that targets the first target gene; and/or the first polynucleotide comprises a nucleic acid having a sequence that is identical or complementary to at least 15 contiguous nucleotides of the first target gene; and the second polynucleotide comprises an antisense nucleic acid or inhibitory RNA (RNAi) that targets the second target gene; and/or the second polynucleotide comprises a nucleic acid having a sequence that is identical or complementary to at least 15 contiguous nucleotides of the second target gene.

4. The pathogen-resistant plant of claim 1, wherein:

the heterologous expression construct of (a) further comprises a third polynucleotide that inhibits expression of a third target gene of the fungal pathogen; or the plant further comprises a third expression construct, wherein the third expression construct comprises a promoter operably linked to the third polynucleotide; and wherein the third target gene is the third of the three target genes.

5. A plurality of pathogen-resistant plants of claim 1.

6. An isolated nucleic acid comprising an expression construct comprising a promoter operably linked to a first polynucleotide that inhibits expression of a first target gene of a fungal pathogen and a second polynucleotide that inhibits expression of a second target gene of the fungal pathogen, wherein the first and the second target genes are selected from the following three target genes: a DCTN gene, a VPS51 gene, and a SAC1 gene.

7. A host cell comprising the nucleic acid of claim 6.

8. A method of making a pathogen-resistant plant, the method comprising:

(a) introducing an expression construct into a plant, wherein the expression construct comprises a promoter operably linked to a first polynucleotide that inhibits expression of a first target gene of a fungal pathogen and a second polynucleotide that inhibits expression of a second target gene of the fungal pathogen, or (b) introducing a first expression construct and a second expression construct into the plant, wherein the first expression construct comprises a promoter operably linked to the first polynucleotide that inhibits expression of the first target gene of the fungal pathogen, and the second expression construction comprises a promoter operably linked to the second polynucleotide that inhibits expression of the second target gene of the fungal pathogen; and wherein the first and the second target genes are selected from the following three target genes: a DCTN gene, a VPS51 gene, and a SAC1 gene, and wherein the plant has increased resistance to the fungal pathogen compared to a control plant lacking the first and the second polynucleotide.

9. The method of claim 8, wherein the fungal pathogen is *Botrytis, Verticillium*, or *Sclerotinia.*

10. The method of claim 8, wherein the first polynucleotide comprises an antisense nucleic acid or inhibitory RNA (RNAi) that targets the first target gene of the fungal pathogen; and/or the first polynucleotide comprises a nucleic acid having a sequence that is identical or complementary to at least 15 contiguous nucleotides of the first target gene of the fungal pathogen; and the second polynucleotide comprises an antisense nucleic acid or inhibitory RNA (RNAi) that targets the second target gene of the fungal pathogen; and/or the second polynucleotide comprises a nucleic acid having a sequence that is identical or complementary to at least 15 contiguous nucleotides of the second target gene of the fungal pathogen.

11. The method of claim 8, wherein the construct of (a) further comprises a third polynucleotide that inhibits expression of the third of the three target genes.

12. The method of claim 8, wherein (b) further comprises introducing into the plant a third construct comprising a promoter operably linked to a third polynucleotide that inhibits expression of the third of the three target genes.

13. A method of increasing pathogen resistance in a plant or a part of a plant, the method comprising:

contacting the plant or the part of the plant with dsRNA or RNA (sRNA) duplexes that target a first gene of a fungal pathogen, and dsRNA or RNA (sRNA) duplexes that target a second gene of the fungal pathogen, wherein the first and the second genes are selected from the following three target genes of the fungal pathogen: a DCTN gene, a VPS51 gene, and a SAC1 gene, and wherein the plant or the part of the plant has increased resistance to the fungal pathogen compared to a control plant or control plant part that has not been contacted with the dsRNAs or sRNA duplexes.

14. The method of claim 13, wherein the fungal pathogen is *Botrytis, Verticillium*, or *Sclerotinia.*

15. The method of claim 13, wherein the dsRNA or sRNA are contained within liposomes.

16. The method of claim 13, wherein the method further comprises contacting the plant or the part of the plant with dsRNA or sRNA duplexes that target the third of the three target genes.

17. The method of claim 13, wherein the method comprises contacting the plant or the part of the plant with dsRNAs or sRNA duplexes that target two or more fungal pathogen genes selected from a DCTN gene, a VPS51 gene, and a SAC1 gene from a first species of fungal pathogen and comprises contacting the plant or the part of the plant with dsRNAs or sRNA duplexes that target two or more target genes selected from a DCTN gene, a VPS51 gene, and a SAC1 gene from a second species of fungal pathogen.

18. The method of claim 13, wherein the dsRNA or sRNA duplexes are sprayed onto the plant or the part of the plant; and/or the part of the plant is a leaf, a root, a stem, a fruit, a vegetable, or a flower.

19. Isolated synthetic liposomes comprising dsRNA, sRNAs or sRNA duplexes that target two or more fungal pathogen genes selected from the following three fungal pathogen genes: a DCTN gene, a VPS51 gene, and a SAC1 gene.

20. The method of claim 16, wherein the method comprises spraying the plant or the part of the plant with dsRNA or sRNA duplexes that targets the third of the three fungal pathogen genes.

21. An isolated nucleic acid of claim 6, further comprising a third polynucleotide that inhibits expression of a third target gene of the fungal pathogen, wherein the third polynucleotide targets the third gene of the three target genes.

22. The isolated nucleic acid of claim 21, wherein the fungal pathogen is *Botrytis, Verticillium*, or *Sclerotinia.*

23. An expression construct comprising the isolated nucleic acid of claim 6, wherein the first and the second polynucleotide are operably linked to the same promoter.

24. An expression construct comprising the isolated nucleic acid of claim 21, wherein the first, the second, and the third polynucleotides are operably linked to the same promoter.

25. A plant comprising the expression construct of claim 23.

26. The isolated synthetic liposomes of claim 19, further comprising dsRNA, sRNAs or sRNA duplexes that target the third of the three fungal pathogen genes.

* * * * *